US007964623B2

(12) United States Patent
Ohrai et al.

(10) Patent No.: US 7,964,623 B2
(45) Date of Patent: Jun. 21, 2011

(54) TRICYCLIC BENZOPYRANE COMPOUND

(75) Inventors: Kazuhiko Ohrai, Funabashi (JP); Yukohiro Shigeta, Funabashi (JP); Osamu Uesugi, Funabashi (JP); Takumi Okada, Funabashi (JP); Tomoyuki Matsuda, Minamisaitama-gun (JP)

(73) Assignee: Nissan Chemical Industries Ltd., Tokyo (JP)

( * ) Notice: Subject to any disclaimer, the term of this patent is extended or adjusted under 35 U.S.C. 154(b) by 54 days.

(21) Appl. No.: 12/591,353

(22) Filed: Nov. 17, 2009

(65) Prior Publication Data

US 2010/0069374 A1 Mar. 18, 2010

Related U.S. Application Data

(62) Division of application No. 10/590,975, filed as application No. PCT/JP2005/006004 on Mar. 23, 2005, now Pat. No. 7,652,008.

(30) Foreign Application Priority Data

Mar. 23, 2004 (JP) ................................ 2004-084605

(51) Int. Cl.
*A61K 31/429* (2006.01)
*C07D 513/06* (2006.01)

(52) U.S. Cl. ........................................ 514/366; 548/151

(58) Field of Classification Search .................. 514/366; 548/151
See application file for complete search history.

(56) References Cited

U.S. PATENT DOCUMENTS

| | | | |
|---|---|---|---|
| 4,900,752 | A | 2/1990 | Seto et al. |
| 5,164,509 | A | 11/1992 | Atwal |
| 5,319,089 | A | 6/1994 | Matsumoto et al. |
| 5,843,989 | A | 12/1998 | Vong et al. |
| 5,919,806 | A | 7/1999 | Seto et al. |

FOREIGN PATENT DOCUMENTS

| | | | |
|---|---|---|---|
| EP | 0 327 127 | A1 | 8/1989 |
| EP | 0 409 165 | A2 | 1/1991 |
| EP | 0 488 107 | A2 | 6/1992 |
| EP | 0 693 283 | A1 | 1/1996 |
| JP | A 58-67683 | | 4/1983 |
| JP | A 2-4791 | | 1/1990 |
| WO | WO 95/34547 | A1 | 12/1995 |
| WO | WO 99/62867 | A1 | 12/1999 |
| WO | WO 00/12492 | A1 | 3/2000 |
| WO | WO 00/58300 | A1 | 10/2000 |
| WO | WO 01/21609 | A1 | 3/2001 |
| WO | WO 01/21610 | A1 | 3/2001 |
| WO | WO 01/25224 | A1 | 4/2001 |
| WO | WO 02/064581 | A1 | 8/2002 |
| WO | WO 03/000675 | A1 | 1/2003 |
| WO | WO 03/014113 | A1 | 2/2003 |

OTHER PUBLICATIONS

Chan, Wai N. et al. "Conformational Preference of the 6-acetyl Group in Novel Anticonvulsant *trans* 4s-benzamido-benzo[b]pyran-3*r*-ols;" *Bioorganic & Medicinal Chemistry Letters*, vol. 7, No. 12, pp. 1573-1576, 1997.

*Primary Examiner* — Taofiq A Solola
(74) *Attorney, Agent, or Firm* — Oliff & Berridge, PLC

(57) ABSTRACT

This invention relates to benzopyran derivatives of formula (I) or (II), or pharmaceutically acceptable salts thereof (I)

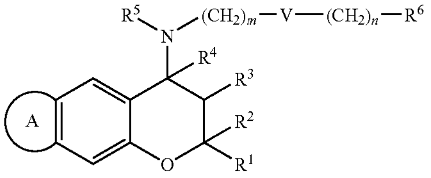

(II)

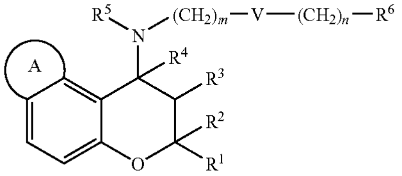

wherein $R^1$ and $R^2$ are independently of each other hydrogen atom, $C_{1-6}$alkyl group or $C_{6-14}$aryl group, $R^3$ is hydrogen atom or $C_{1-6}$alkylcarbonyloxy group, or together with $R^4$ forms a bond, $R^4$ is hydrogen atom, or together with $R^3$ forms a bond, m is an integer of 0 to 4, n is an integer of 0 to 4, V is a single bond, $CR^7R^8$, $NR^9$, O, S, SO or $SO_2$, $R^5$ is hydrogen atom or $C_{1-6}$alkyl group, $R^6$ is hydrogen atom, $C_{1-6}$alkyl group, $C_{3-8}$cycloalkyl group, $C_{3-8}$cycloalkenyl group, amino group, $C_{1-6}$alkylamino group, di-$C_{1-6}$alkylamino group, $C_{6-14}$arylamino group, $C_{2-9}$heteroarylamino group, $C_{6-14}$aryl group, $C_{2-9}$heteroaryl group or $C_{2-9}$heterocyclyl group, A is 5-, 6- or 7-member ring fused with benzene ring, as constituent atom of the ring, oxygen atom, nitrogen atom or sulfur atom may be contained in the number of 1 to 3 alone or in a combination thereof, the number of unsaturated bond in the ring is 1, 2 or 3 including an unsaturated bond of the benzene ring to be fused, carbon atoms constituting the ring may be carbonyl or thiocarbonyl. These compounds are useful as an anti-arrhythmic agent.

40 Claims, No Drawings

TRICYCLIC BENZOPYRANE COMPOUND

RELATED APPLICATIONS

This is a Divisional of application Ser. No. 10/590,975, filed Oct. 27, 2006, which in turn is a U.S. national stage of PCT/JP2005/006004, filed Mar. 23, 2005. The entire disclosures of the prior applications are hereby incorporated by reference herein.

TECHNICAL FIELD

The present invention relates to benzopyran derivatives having the prolongation effect on the refractory period, which are used for the treatment of arrhythmia in mammals including human being.

BACKGROUND ART

As benzopyran derivatives, 4-acylaminobenzopyran derivatives exemplified by Cromakalim have been known (for example, Japanese Patent Laid-open No. Sho 58-67683). These 4-acylaminobenzopyran derivatives exemplified by Cromakalim are known to open ATP sensitive $K^+$ channel so as to be effective for the treatment of hypertension and asthma, but there has not been any mention as to the treatment of arrhythmia based on the prolongation effect on the refractory period.

In addition, it is reported that 4-aminobenzopyran derivatives that have β3-receptor stimulating action and are supposed to be effective for the treatment of obesity (for example, WO 03/014113), but there has not been any mention as to the treatment of arrhythmia based on the prolongation effect on the refractory period this document.

DISCLOSURE OF INVENTION

In the meanwhile, conventional anti-arrhythmic agents having the prolongation effect on the refractory period as a main mechanism (such as Class I drugs of anti-arrhythmic agent classification according to Vaughan Williams, or d-sotalol or dofetilide belonging to Class III) have the therapeutic problems in inducing highly dangerous arrhythmia leading to the sudden death from such as torsades de pointes among others due to prolongation of action potential in ventricular muscle correlated to the prolongation effect on the refractory period. Thus, treating agents with less adverse effect have been highly desired.

The inventors have investigated compounds having the prolongation effect on the refractory period selective for atrium muscle rather than for ventricular muscle in order to solve the problems, and consequently found that the compound of formula (I) or (II) has the prolongation effect on the refractory period selective for atrium muscle without any influence on the refractory period and action potential in ventricular muscle. Thus, the present invention has been accomplished.

That is, the present invention relates to the following aspects:

(1) A benzopyran derivative of formula (I) or (II), or pharmaceutically acceptable salt thereof (I)

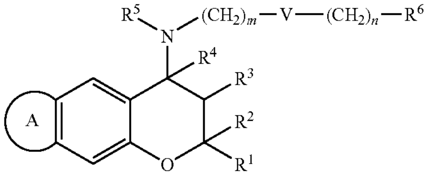

(II)

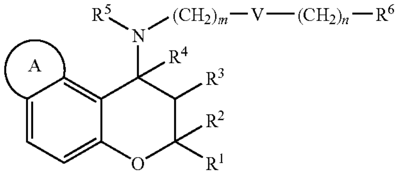

wherein $R^1$ and $R^2$ are independently of each other hydrogen atom, $C_{1-6}$ alkyl group (wherein the alkyl group may be arbitrarily substituted with halogen atom, $C_{1-6}$ alkoxy group (wherein the alkoxy group may be arbitrarily substituted with halogen atom) or hydroxy group), or $C_{6-14}$ aryl group (wherein the aryl group may be arbitrarily substituted with halogen atom, hydroxy group, nitro group, cyano group, $C_{1-6}$ alkyl group (wherein the alkyl group may be arbitrarily substituted with halogen atom, $C_{1-6}$ alkoxy group (wherein the alkoxy group may be arbitrarily substituted with halogen atom) or hydroxy group) or $C_{1-6}$ alkoxy group (wherein the alkoxy group may be arbitrarily substituted with halogen atom));

$R^3$ is hydroxy group or $C_{1-6}$ alkylcarbonyloxy group, or $R^3$ forms a bond together with $R^4$;

$R^4$ is hydrogen atom, or $R^4$ forms a bond together with $R^3$;

m is an integer of 0 to 4;

n is an integer of 0 to 4;

V is a single bond, $CR^7R^8$ wherein $R^7$ is $C_{1-6}$ alkyl group (wherein the alkyl group may be arbitrarily substituted with halogen atom, hydroxy group, $C_{1-6}$ alkoxy group (wherein $C_{1-6}$ alkoxy group may be arbitrarily substituted with halogen atom), $C_{6-14}$ aryl group, $C_{2-9}$ heteroaryl group (wherein each of the aryl group or heteroaryl group may be arbitrarily substituted with 1 to 3 $R^{10}$ wherein $R^{10}$ is halogen atom; hydroxy group; $C_{1-6}$ alkyl group (wherein the alkyl group may be arbitrarily substituted with halogen atom, hydroxy group or $C_{1-6}$ alkoxy group (wherein the alkoxy group may be arbitrarily substituted with halogen atom)); $C_{1-6}$ alkoxy group (wherein the alkoxy group may be arbitrarily substituted with halogen atom); nitro group; cyano group; formyl group; formamide group; sulfonylamino group; sulfonyl group; amino group; $C_{1-6}$ alkylamino group; di-$C_{1-6}$ alkylamino group; $C_{1-6}$ alkylcarbonylamino group; $C_{1-6}$ alkylsulfonylamino group; aminocarbonyl group; $C_{1-6}$ alkylaminocarbonyl group; di-$C_{1-6}$ alkylaminocarbonyl group; $C_{1-6}$ alkylcarbonyl group; $C_{1-6}$ alkoxycarbonyl group; aminosulfonyl group; $C_{1-6}$ alkylsulfonyl group; carboxy group or $C_{6-14}$ arylcarbonyl group, and when a plurality of $R^{10}$ are present, they may be identical or different from each other); $C_{1-6}$ alkylcarbonyloxy group; nitro group; cyano group; formyl group; formamide group; amino group; $C_{1-6}$ alkylamino group; di-$C_{1-6}$ alkylamino group; $C_{1-6}$ alkylcarbonylamino group; $C_{1-6}$ alkylsulfonylamino group; aminocarbonyl group; $C_{1-6}$ alkylaminocarbonyl group; di-$C_{1-6}$ alkylaminocarbonyl group; $C_{1-6}$ alkylcarbonyl group; $C_{1-6}$ alkoxycarbonyl group; aminosulfonyl group; $C_{1-6}$ alkylsulfonyl group; carboxy group or sulfonyl group;

$C_{6-14}$ aryl group, $C_{2-9}$ heteroaryl group (wherein each of the aryl group or heteroaryl group may be arbitrarily substituted with 1 to 3 $R^{10}$ wherein $R^{10}$ has the above-mentioned meaning);

hydroxy group;

$C_{1-6}$ alkoxy group (wherein the alkoxy group may be arbitrarily substituted with halogen atom); or nitro group; cyano group; formyl group; formamide group; sulfonylamino group; sulfonyl group; amino group; $C_{1-6}$ alkylamino group; di-$C_{1-6}$ alkylamino group; $C_{1-6}$ alkylcarbonylamino group; $C_{1-6}$ alkylsulfonylamino group; aminocarbonyl group; $C_{1-6}$ alkylaminocarbonyl group; di-$C_{1-6}$ alkylaminocarbonyl group; $C_{1-6}$ alkylcarbonyl group; $C_{1-6}$ alkoxycarbonyl group; aminosulfonyl group; $C_{1-6}$ alkylsulfonyl group; carboxy group, $C_{6-14}$ arylcarbonyl group or $C_{2-9}$ heteroarylcarbonyl group (wherein each of the arylcarbonyl group or heteroarylcarbonyl group may be arbitrarily substituted with 1 to 3 $R^{10}$ wherein $R^{10}$ has the above-mentioned meaning), and $R^8$ is hydrogen atom, $C_{1-6}$ alkyl group (wherein the $C_{1-6}$ alkyl group may be arbitrarily substituted with halogen atom, hydroxy group, $C_{1-6}$ alkoxy group (wherein the alkoxy group may be arbitrarily substituted with halogen atom), $C_{6-14}$ aryl group, $C_{2-9}$ heteroaryl group (wherein each of the aryl group or heteroaryl group may be arbitrarily substituted with 1 to 3 $R^{17}$ wherein $R^{17}$ has the same meaning as $R^{10}$), $C_{1-6}$ alkylcarbonyloxy group; nitro group; cyano group; formyl group; formamide group; amino group; $C_{1-6}$ alkylamino group; di-$C_{1-6}$ alkylamino group; $C_{1-6}$ alkylcarbonylamino group; $C_{1-6}$ alkylsulfonylamino group; aminocarbonyl group; $C_{1-6}$ alkylaminocarbonyl group; di-$C_{1-6}$ alkylaminocarbonyl group; $C_{1-6}$ alkylcarbonyl group; $C_{1-6}$ alkoxycarbonyl group; aminosulfonyl group; $C_{1-6}$ alkylsulfonyl group; carboxy group or sulfonyl group);

$C_{6-14}$ aryl group, $C_{2-9}$ heteroaryl group (wherein each of the aryl group or heteroaryl group may be arbitrarily substituted with 1 to 3 $R^{17}$ wherein $R^{17}$ has the same meaning as $R^{10}$);

hydroxy group;

$C_{1-6}$ alkoxy group (wherein the alkoxy group may be arbitrarily substituted with halogen atom), or nitro group; cyano group; formyl group; formamide group; sulfonylamino group; sulfonyl group; amino group; $C_{1-6}$ alkylamino group; di-$C_{1-6}$ alkylamino group; $C_{1-6}$ alkylcarbonylamino group; $C_{1-6}$ alkylsulfonylamino group; aminocarbonyl group; $C_{1-6}$ alkylaminocarbonyl group; di-$C_{1-6}$ alkylaminocarbonyl group; $C_{1-6}$ alkylcarbonyl group; $C_{1-6}$ alkoxycarbonyl group; aminosulfonyl group; $C_{1-6}$ alkylsulfonyl group; carboxy group, $C_{6-14}$ arylcarbonyl group or $C_{2-9}$ heteroarylcarbonyl group (wherein each of the arylcarbonyl group or heteroarylcarbonyl group may be arbitrarily substituted with 1 to 3 $R^{17}$ wherein $R^{17}$ has the same meaning as $R^{10}$), or $R^7$ together with $R^8$ may represent =O or =S, or V is $NR^9$ wherein $R^9$ is hydrogen atom or $C_{1-6}$ alkyl group (wherein the alkyl group may be arbitrarily substituted with halogen atom, $C_{1-6}$ alkoxy group (wherein the alkoxy group may be arbitrarily substituted with halogen atom), hydroxy group, $C_{6-14}$ aryl group, $C_{2-9}$ heteroaryl group (wherein each of the aryl group or heteroaryl group may be arbitrarily substituted with 1 to 3 $R^{17}$ wherein $R^{17}$ has the same meaning as $R^{10}$), $C_{1-6}$ alkylaminocarbonyl group, di-$C_{1-6}$ alkylaminocarbonyl group, $C_{1-6}$ alkylcarbonyl group, $C_{3-8}$ cycloalkylcarbonyl group, $C_{1-6}$ alkoxycarbonyl group, $C_{1-6}$ alkylsulfonyl group, carboxy group, $C_{6-14}$ arylsulfonyl group or $C_{2-9}$ heteroarylsulfonyl group), $C_{1-6}$ alkylaminocarbonyl group, di-$C_{1-6}$ alkylaminocarbonyl group, $C_{1-6}$ alkylcarbonyl group, $C_{3-8}$ cycloalkylcarbonyl group, $C_{1-6}$ alkoxycarbonyl group, $C_{1-6}$ alkylsulfonyl group, $C_{6-14}$ arylsulfonyl group, $C_{2-9}$ heteroarylsulfonyl group (wherein each of the arylsulfonyl group or heteroarylsulfonyl group may be arbitrarily substituted with 1 to 3 $R^{17}$ wherein $R^{17}$ has the same meaning as $R^{10}$), carboxy group; $C_{6-14}$ arylcarbonyl group, $C_{2-9}$ heteroarylcarbonyl group (wherein each of the arylcarbonyl group or heteroarylcarbonyl group may be arbitrarily substituted with 1 to 3 $R^{17}$ wherein $R^{17}$ has the same meaning as $R^{10}$); or O, S, SO or $SO_2$;

$R^5$ is hydrogen atom or $C_{1-6}$ alkyl group (wherein the alkyl group may be arbitrarily substituted with halogen atom, $C_{1-6}$ alkoxy group (wherein the alkoxy group may be arbitrarily substituted with halogen atom), or hydroxy group); and $R^6$ is hydrogen atom, $C_{1-6}$ alkyl group (wherein the alkyl group may be arbitrarily substituted with halogen atom, $C_{1-6}$ alkoxy group (wherein the alkoxy group may be arbitrarily substituted with halogen atom), amino group, carboxy group or hydroxy group), $C_{3-8}$ cycloalkyl group, $C_{3-9}$ cycloalkenyl group (wherein the cycloalkyl group or cycloalkenyl group may be arbitrarily substituted with halogen atom, $C_{1-6}$ alkyl group (wherein the alkyl group may be arbitrarily substituted with halogen atom, $C_{1-6}$ alkoxy group (wherein the alkoxy group may be arbitrarily substituted with halogen atom), amino group, carboxy group or hydroxy group), $C_{1-6}$ alkoxy group (wherein the alkoxy group may be arbitrarily substituted with halogen atom), amino, carboxy group or hydroxy group), amino group, $C_{1-6}$ alkylamino group, di-$C_{1-6}$ alkylamino group, $C_{6-14}$ arylamino group, $C_{2-9}$ heteroarylamino group (wherein each of the arylamino group or heteroarylamino group may be arbitrarily substituted with 1 to 3 $R^{18}$ wherein $R^{18}$ has the same meaning as $R^{10}$;

$C_{6-14}$ aryl group, $C_{2-9}$ heteroaryl group (wherein each of the aryl group or heteroaryl group may be arbitrarily substituted with 1 to 3 $R^{18}$ wherein $R^{18}$ has the same meaning as $R^{10}$; or $C_{2-9}$ heterocyclyl group (wherein the heterocyclyl group may be arbitrarily substituted with halogen atom, $C_{1-6}$ alkyl group (wherein the alkyl group may be arbitrarily substituted with halogen atom, $C_{1-6}$ alkoxy group (wherein the alkoxy group may be arbitrarily substituted with halogen atom), amino group, carboxy group or hydroxy group), $C_{1-6}$ alkoxy group (wherein the alkoxy group may be arbitrarily substituted with halogen atom), $C_{6-14}$ aryl group, $C_{2-9}$ heteroaryl group (wherein each of the aryl group or heteroaryl group may be arbitrarily substituted with 1 to 3 $R^{18}$ wherein $R^{18}$ has the same meaning as $R^{10}$), hydroxy group, nitro group, cyano group, formyl group, formamide group, amino group, $C_{1-6}$ alkylamino group, di-$C_{1-6}$ alkylamino group, $C_{1-6}$ alkylcarbonylamino group, $C_{1-6}$ alkylsulfonylamino group, aminocarbonyl group, $C_{1-6}$ alkylaminocarbonyl group, di-$C_{1-6}$ alkylaminocarbonyl group, $C_{1-6}$ alkylcarbonyl group, $C_{1-6}$ alkoxycarbonyl group; aminosulfonyl group, $C_{1-6}$ alkylsulfonyl group, carboxy group or $C_{6-14}$ arylcarbonyl group);

A is 5-, 6- or 7-member ring fused with benzene ring (wherein the 5-, 6- or 7-member ring may be arbitrarily substituted with 1 to 6 $R^{21}$ wherein $R^{21}$ has the same meaning as $R^{10}$, and when a plurality of $R^{21}$ are present, they may be identical or different from each other), as constituent atom of the ring, oxygen atom, nitrogen atom or sulfur atom may be contained in the number of 1 to 3 alone or in a combination thereof, the number of unsaturated bond in the ring is 1, 2 or 3 including an unsaturated bond of the benzene ring to be fused, carbon atoms constituting the ring may be carbonyl or thiocarbonyl;

(2) The benzopyran derivative or pharmaceutically acceptable salt thereof as set forth in (1), wherein A is

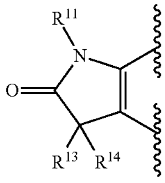
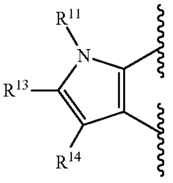
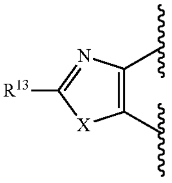
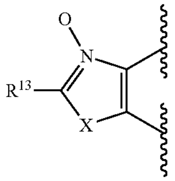
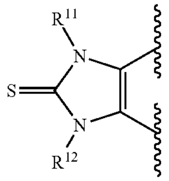
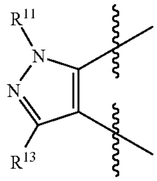
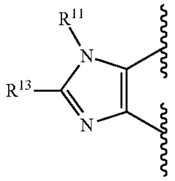
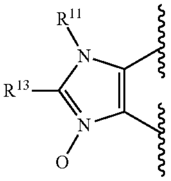
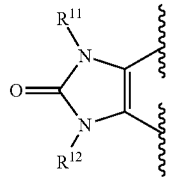
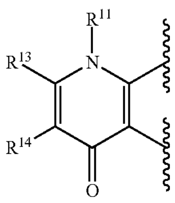
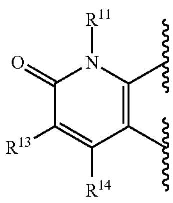
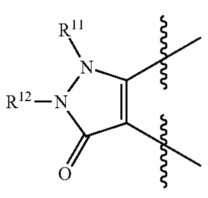
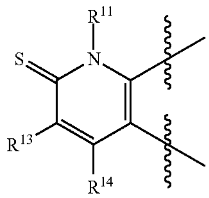
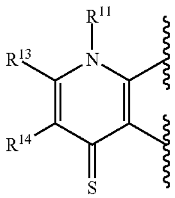
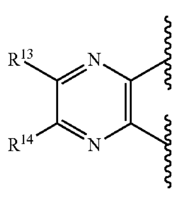
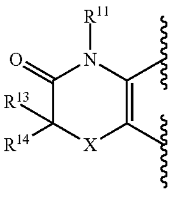

-continued

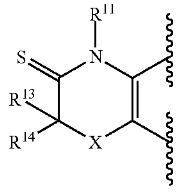
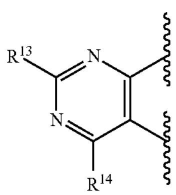
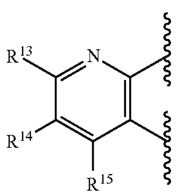
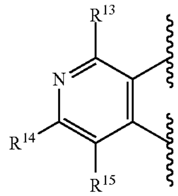
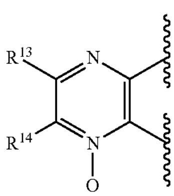
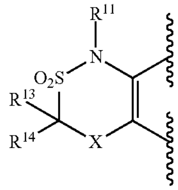
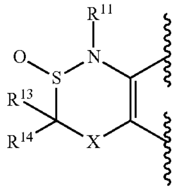
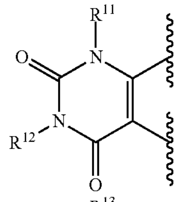
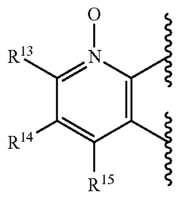
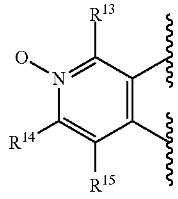
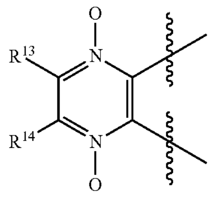
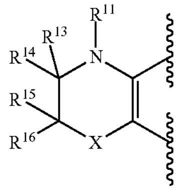
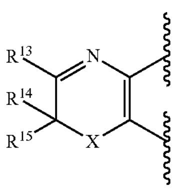
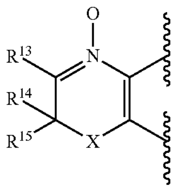
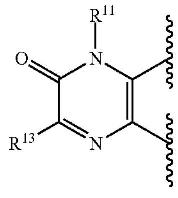
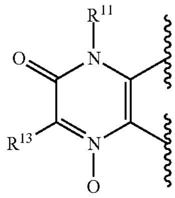

or

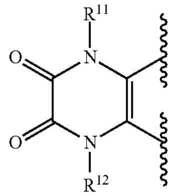

wherein $R^{11}$ and $R^{12}$ are independently of each other hydrogen atom, $C_{1-6}$ alkyl group (wherein the alkyl group may be arbitrarily substituted with halogen atom, $C_{1-6}$ alkoxy group (wherein the alkoxy group may be arbitrarily substituted with halogen atom), hydroxy group, $C_{6-14}$ aryl group, $C_{2-9}$ heteroaryl group (wherein each of the aryl group or heteroaryl group may be arbitrarily substituted with 1 to 3 $R^{19}$ wherein $R^{19}$ has the same meaning as $R^{10}$), $C_{1-6}$ alkylaminocarbonyl group, di-$C_{1-6}$ alkylaminocarbonyl group, $C_{1-6}$ alkylcarbonyl group, $C_{3-8}$ cycloalkylcarbonyl group, $C_{1-6}$ alkoxycarbonyl group, $C_{1-6}$ alkylsulfonyl group, carboxy group, $C_{6-14}$ arylcarbonyl group or $C_{2-9}$ heteroarylcarbonyl group), $C_{6-14}$ aryl group, $C_{2-9}$ heteroaryl group (wherein each of the aryl group or heteroaryl group may be arbitrarily substituted with 1 to 3 $R^{19}$ wherein $R^{19}$ has the same meaning as $R^{10}$), $C_{1-6}$ alkylaminocarbonyl group, di-$C_{1-6}$ alkylaminocarbonyl group, $C_{1-6}$ alkylcarbonyl group, $C_{3-8}$ cycloalkylcarbonyl group, $C_{1-6}$ alkoxycarbonyl group, $C_{1-6}$ alkylsulfonyl group, $C_{6-14}$ arylsulfonyl group, $C_{2-9}$ heteroarylsulfonyl group (wherein each of the arylsulfonyl group or heteroarylsulfonyl group may be arbitrarily substituted with 1 to 3 $R^{19}$ wherein $R^{19}$ has the same meaning as $R^{10}$), carboxy group; $C_{6-14}$ arylcarbonyl group, $C_{2-9}$ heteroarylcarbonyl group (wherein each of the arylcarbonyl group or heteroarylcarbonyl group may be arbitrarily substituted with 1 to 3 $R^{19}$ wherein $R^{19}$ has the same meaning as $R^{10}$), $R^{13}$, $R^{14}$, $R^{15}$ and $R^{16}$ are independently of each other hydrogen atom, halogen atom, $C_{1-6}$ alkyl group (wherein the alkyl group may be arbitrarily substituted with halogen atom, $C_{1-6}$ alkoxy group (wherein the alkoxy group may be arbitrarily substituted with halogen atom), amino group, hydroxy group, $C_{6-14}$ aryl group, $C_{2-9}$ heteroaryl group (wherein each of the aryl group or heteroaryl group may be arbitrarily substituted with 1 to 3 $R^{20}$ wherein $R^{20}$ has the same meaning as $R^{10}$), $C_{1-6}$ alkylaminocarbonyl group, di-$C_{1-6}$ alkylaminocarbonyl group, $C_{1-6}$ alkylcarbonyl group, $C_{3-8}$ cycloalkylcarbonyl group, $C_{1-6}$ alkoxycarbonyl group, $C_{1-6}$ alkylsulfonyl group, carboxy group, $C_{6-14}$ arylcarbonyl group or $C_{2-9}$ heteroarylcarbonyl group), $C_{1-6}$ alkoxy group (wherein the alkoxy group may be arbitrarily substituted with halogen atom, (wherein the alkoxy group may be arbitrarily substituted with halogen atom), carboxy group, amino group, hydroxy group, $C_{6-14}$ aryl group or $C_{2-9}$ heteroaryl group (wherein each of the aryl group or heteroaryl group may be arbitrarily substituted with 1 to 3 $R^{20}$ wherein $R^{20}$ has the same meaning as $R^{10}$), $C_{1-6}$ thioalkoxy group (wherein the thioalkoxy group may be arbitrarily substituted with halogen atom, $C_{1-6}$ alkoxy group (wherein the alkoxy group may be arbitrarily substituted with halogen atom), carboxy group, hydroxy group, $C_{6-14}$ aryl group or $C_{2-9}$ heteroaryl group (wherein each of the aryl group or heteroaryl group may be arbitrarily substituted with 1 to 3 $R^{20}$ wherein $R^{20}$ has the same meaning as $R^{10}$), hydroxy group, $C_{6-14}$ aryl group or $C_{2-9}$ heteroaryl group (wherein each of the aryl group or heteroaryl group may be arbitrarily substituted with 1 to 3 $R^{20}$ wherein $R^{20}$ has the same meaning as $R^{10}$), $C_{1-6}$ alkylcarbonyloxy group, nitro group, cyano group, formyl group, formamide group, amino group, sulfonyl group, $C_{1-6}$ alkylamino group, di-$C_{1-6}$ alkylamino group, $C_{6-14}$ arylamino group, $C_{2-9}$ heteroarylamino group (wherein each of the arylamino group or heteroarylamino group may be arbitrarily substituted with 1 to 3 $R^{20}$ wherein $R^{20}$ has the same meaning as $R^{10}$), $C_{1-6}$ alkylcarbonyloxyamino group, $C_{1-6}$ alkylsulfonylamino group, aminocarbonyl group, $C_{1-6}$ alkylaminocarbonyl group, di-$C_{1-6}$ alkylaminocarbonyl group, $C_{1-6}$ alkylcarbonyl group, $C_{6-14}$ arylcarbonyl group, $C_{2-9}$ heteroarylcarbonyl group (wherein each of the arylcarbonyl group or heteroarylcarbonyl group may be arbitrarily substituted with 1 to 3 $R^{20}$ wherein $R^{20}$ has the same meaning as $R^{10}$), $C_{1-6}$ alkoxycarbonyl group, aminosulfonyl group, $C_{1-6}$ alkylsulfonyl group, $C_{6-14}$ arylsulfonyl group, $C_{2-9}$ heteroarylsulfonyl group (wherein each of the arylsulfonyl group or heteroarylsulfonyl group may be arbitrarily substituted with 1 to 3 $R^{20}$ wherein $R^{20}$ has the same meaning as $R^{10}$), carboxy group, sulfonyl group or $C_{2-9}$ heterocyclyl group (wherein the heterocyclyl group may be arbitrarily substituted with halogen atom, $C_{1-6}$ alkyl group (wherein the alkyl group may be arbitrarily substituted with halogen atom, $C_{1-6}$ alkoxy group (wherein the alkoxy group may be arbitrarily substituted with halogen atom), amino group, carboxy group or hydroxy group), $C_{1-6}$ alkoxy group (wherein the alkoxy group may be arbitrarily substituted with halogen atom), $C_{6-14}$ aryl group, $C_{2-9}$ heteroaryl group (wherein each of the aryl group or heteroaryl group may be arbitrarily substituted with 1 to 3 $R^{20}$ wherein $R^{20}$ has the same meaning as $R^{10}$), hydroxy group, nitro group, cyano group, formyl group, formamide group, amino group, $C_{1-6}$ alkylamino group, di-$C_{1-6}$ alkylamino group, $C_{1-6}$ alkylcarbonylamino group, $C_{1-6}$ alkylsulfonylamino group, aminocarbonyl group, $C_{1-6}$ alkylaminocarbonyl group, di-$C_{1-6}$ alkylaminocarbonyl group, $C_{1-6}$ alkylcarbonyl group, $C_{1-6}$ alkoxycarbonyl group, aminosulfonyl group, $C_{1-6}$ alkylsulfonyl group, carboxy group or $C_{6-14}$ arylcarbonyl group), X is O, S, SO or $SO_2$;

(3) The benzopyran derivative or pharmaceutically acceptable salt thereof as set forth in (2), wherein $R^1$ and $R^2$ are methyl group, $R^3$ is hydroxy group, and $R^4$ is hydrogen atom;

(4) The benzopyran derivative or pharmaceutically acceptable salt thereof as set forth in (3), wherein $R^5$ is hydrogen atom, m is an integer of 0 to 3 and n is an integer of 0 to 2;

(5) The benzopyran derivative or pharmaceutically acceptable salt thereof as set forth in (4), wherein V is a single bond;

(6) The benzopyran derivative or pharmaceutically acceptable salt thereof as set forth in (5), wherein m is an integer of 1 to 3, n is 0, and $R^6$ is $C_{6-14}$ aryl group wherein the aryl group may be arbitrarily substituted with 1 to 3 $R^{18}$ wherein $R^{18}$ has the same meaning as $R^{10}$;

(7) The benzopyran derivative or pharmaceutically acceptable salt thereof as set forth in (6), wherein m is 2;

(8) The benzopyran derivative or pharmaceutically acceptable salt thereof as set forth in (7), wherein $R^6$ is $C_{6-14}$ aryl group wherein the aryl group may be arbitrarily substituted with 1 to 3 halogen atom or amino group, when and when a plurality of substituents are present, they may be identical or different from each other;

(9) The benzopyran derivative or pharmaceutically acceptable salt thereof as set forth in (5), wherein m is an integer of 1 to 3, n is 0, and $R^6$ is $C_{2-9}$ heteroaryl group wherein the heteroaryl group may be arbitrarily substituted with 1 to 3 $R^{18}$ wherein $R^{18}$ has the same meaning as $R^{10}$;

(10) The benzopyran derivative or pharmaceutically acceptable salt thereof as set forth in (9), wherein m is 2;

(11) The benzopyran derivative or pharmaceutically acceptable salt thereof as set forth in (10), wherein $R^6$ is 2-pyridyl group, 3-pyridyl group or 4-pyridyl group;

(12) The benzopyran derivative or pharmaceutically acceptable salt thereof as set forth in (5), wherein m is an integer of 1 to 3, n is 0, and $R^6$ is $C_{2-4}$ alkyl group (wherein the alkyl group may be arbitrarily substituted with halogen atom, $C_{1-6}$ alkoxy group (wherein the alkoxy group may be arbitrarily substituted with halogen atom), amino group, carboxy group or hydroxy group), $C_{1-6}$ alkoxy group (wherein the alkoxy group may be arbitrarily substituted with halogen atom), amino group, carboxy group or hydroxy group), $C_{3-8}$ cycloalkyl group, $C_{3-8}$ cycloalkenyl group (wherein the cycloalkyl group or cycloalkenyl group may be arbitrarily substituted with halogen atom, $C_{1-6}$ alkyl group (wherein the alkyl group may be arbitrarily substituted with halogen atom, $C_{1-6}$ alkoxy group (wherein the alkoxy group may be arbitrarily substituted with halogen atom), amino group, carboxy group or hydroxy group), $C_{1-6}$ alkoxy group (wherein the alkoxy group may be arbitrarily substituted with halogen atom), amino group, carboxy group or hydroxy group), or $C_{2-9}$ heterocyclyl group (wherein the heterocyclyl group may be arbitrarily substituted with halogen atom, $C_{1-6}$ alkyl group (wherein the alkyl group may be arbitrarily substituted with halogen atom, $C_{1-6}$ alkoxy group (wherein the alkoxy group may be arbitrarily substituted with halogen atom), amino group, carboxy group or hydroxy group), $C_{1-6}$ alkoxy group (wherein the alkoxy group may be arbitrarily substituted with halogen atom), hydroxy group or amino group);

(13) The benzopyran derivative or pharmaceutically acceptable salt thereof as set forth in (12), wherein m is 2;

(14) The benzopyran derivative or pharmaceutically acceptable salt thereof as set forth in (13), wherein $R^6$ is n-propyl group, i-propyl group, c-pentyl group, c-hexyl group, 1-c-pentenyl group, 2-c-pentenyl group, 3-c-pentenyl group, 1-c-hexenyl group, 2-c-hexenyl group or 3-c-hexenyl group;

(15) The benzopyran derivative or pharmaceutically acceptable salt thereof as set forth in (4), wherein V is $CR^7R^8$;

(16) The benzopyran derivative or pharmaceutically acceptable salt thereof as set forth in (15), wherein $R^7$ is hydroxy group, $C_{1-6}$ alkyl group (wherein the alkyl group may be arbitrarily substituted with halogen atom, $C_{1-6}$ alkoxy group (wherein the alkoxy group may be arbitrarily substituted with halogen atom), amino group, carboxy group or hydroxy group), $C_{1-6}$ alkoxy group (wherein the alkoxy group may be arbitrarily substituted with halogen atom), $C_{1-6}$ alkylamino group, di-$C_{1-6}$ alkylamino group, or carboxy group, and $R^8$ is hydrogen atom or $C_{1-6}$ alkyl group (wherein the alkyl group may be arbitrarily substituted with halogen atom, $C_{1-6}$ alkoxy group (wherein the alkoxy group may be arbitrarily substituted with halogen atom), amino group, carboxy group or hydroxy group), or $R^7$ and $R^8$ together are =O or =S;

(17) The benzopyran derivative or pharmaceutically acceptable salt thereof as set forth in (16), wherein $R^7$ is hydroxy group, $C_{1-6}$ alkyl group (wherein the alkyl group may be arbitrarily substituted with halogen atom, hydroxy group or carboxy group) or carboxy group, and $R^8$ is hydrogen atom or $C_{1-6}$ alkyl group (wherein the alkyl group may be arbitrarily substituted with halogen atom, hydroxy group or carboxy group), or $R^7$ and $R^8$ together are =O;

(18) The benzopyran derivative or pharmaceutically acceptable salt thereof as set forth in (17), wherein $R^7$ is hydroxy group, and $R^8$ is hydrogen atom;

(19) The benzopyran derivative or pharmaceutically acceptable salt thereof as set forth in (15), wherein m is an integer of 1 to 2, n is 0, and $R^6$ is $C_{6-14}$ aryl group or $C_{2-9}$ heteroaryl wherein each of the aryl group or heteroaryl group may be arbitrarily substituted with 1 to 3 $R^{18}$ wherein $R^{18}$ has the same meaning as $R^{10}$;

(20) The benzopyran derivative or pharmaceutically acceptable salt thereof as set forth in (19), wherein $R^7$ is hydroxy group, $C_{1-6}$ alkyl group (wherein the alkyl group may be arbitrarily substituted with halogen atom, $C_{1-6}$ alkoxy group (wherein the alkoxy group may be arbitrarily substituted with halogen atom), amino group, carboxy group or hydroxy group), $C_{1-6}$ alkoxy group (wherein the alkoxy group may be arbitrarily substituted with halogen atom), $C_{1-6}$ alkylamino group, di-$C_{1-6}$ alkylamino group, or carboxy group, and $R^8$ is hydrogen atom or $C_{1-6}$ alkyl group (wherein the alkyl group may be arbitrarily substituted with halogen atom, $C_{1-6}$ alkoxy group (wherein the alkoxy group may be arbitrarily substituted with halogen atom), amino group, carboxy group or hydroxy group), or $R^7$ and $R^8$ together are =O or =S;

(21) The benzopyran derivative or pharmaceutically acceptable salt thereof as set forth in (20), wherein $R^7$ is hydroxy group, $C_{1-6}$ alkyl group (wherein the alkyl group may be arbitrarily substituted with halogen atom, hydroxy group or carboxy group) or carboxy group, and $R^8$ is hydrogen atom or $C_{1-6}$ alkyl group (wherein the alkyl group may be arbitrarily substituted with halogen atom, hydroxy group or carboxy group), or $R^7$ and $R^8$ together are =O;

(22) The benzopyran derivative or pharmaceutically acceptable salt thereof as set forth in (21), wherein $R^7$ is hydroxy group, and $R^8$ is hydrogen atom;

(23) The benzopyran derivative or pharmaceutically acceptable salt thereof as set forth in (22), wherein m is 1, n is 0, and $R^6$ is $C_{6-14}$ aryl group wherein the aryl group may be arbitrarily substituted with 1 to 3 halogen atom or amino group, when and when a plurality of substituents are present, they may be identical or different from each other;

(24) The benzopyran derivative or pharmaceutically acceptable salt thereof as set forth in (15), wherein m is an integer of 1 to 2, n is 0, and $R^6$ is $C_{1-4}$ alkyl group (wherein the alkyl group may be arbitrarily substituted with halogen atom, $C_{1-6}$ alkoxy group (wherein the alkoxy group may be arbitrarily substituted with halogen atom), amino group, carboxy group or hydroxy group), $C_{3-8}$ cycloalkyl group, $C_{3-8}$ cycloalkenyl group (wherein the cycloalkyl group or cycloalkenyl group may be arbitrarily substituted with halogen atom, $C_{1-6}$ alkyl group (wherein the alkyl group may be arbitrarily substituted with halogen atom, $C_{1-6}$ alkoxy group (wherein the alkoxy group may be arbitrarily substituted with halogen atom), amino group, carboxy group or hydroxy group), $C_{1-6}$ alkoxy group (wherein the alkoxy group may be arbitrarily substituted with halogen atom), amino group, carboxy group or hydroxy group), or $C_{2-9}$ heterocyclyl group (wherein the heterocyclyl group may be arbitrarily substituted with halogen atom, $C_{1-6}$ alkyl group (wherein the alkyl group may be arbitrarily substituted with halogen atom, $C_{1-6}$ alkoxy group (wherein the alkoxy group may be arbitrarily substituted with halogen atom), amino group, carboxy group or hydroxy group), $C_{1-6}$ alkoxy group (wherein the alkoxy group may be arbitrarily substituted with halogen atom), amino group, carboxy group or hydroxy group);

(25) The benzopyran derivative or pharmaceutically acceptable salt thereof as set forth in (24), wherein $R^7$ is hydroxy group, $C_{1-6}$ alkyl group (wherein the alkyl group may be arbitrarily substituted with halogen atom, $C_{1-6}$ alkoxy group (wherein $C_{1-6}$ alkoxy group may be arbitrarily substituted with halogen atom), amino group, carboxy group or hydroxy group), $C_{1-6}$ alkoxy group (wherein $C_{1-6}$ alkoxy group may be arbitrarily substituted with halogen atom), $C_{1-6}$ alkylamino group, di-$C_{1-6}$ alkylamino group, or carboxy group, and $R^8$ is hydrogen atom or $C_{1-6}$ alkyl group (wherein the alkyl group may be arbitrarily substituted with halogen atom, $C_{1-6}$ alkoxy group (wherein $C_{1-6}$ alkoxy group may be arbitrarily substituted with halogen atom), amino group, carboxy group or hydroxy group), or $R^7$ and $R^8$ together are =O or =S;

(26) The benzopyran derivative or pharmaceutically acceptable salt thereof as set forth in (25), wherein $R^7$ is hydroxy group, $C_{1-6}$ alkyl group (wherein the alkyl group may be arbitrarily substituted with halogen atom, hydroxy group or carboxy group) or carboxy group, and $R^8$ is hydrogen atom or $C_{1-6}$ alkyl group (wherein the alkyl group may be arbitrarily substituted with halogen atom, hydroxy group or carboxy group), or $R^7$ and $R^8$ together are =O;

(27) The benzopyran derivative or pharmaceutically acceptable salt thereof as set forth in (26), wherein $R^7$ is hydroxy group, and $R^8$ is hydrogen atom;

(28) The benzopyran derivative or pharmaceutically acceptable salt thereof as set forth in (27), wherein $R^6$ is n-propyl group, i-propyl group, c-pentyl group, c-hexyl group, 1-c-pentenyl group, 2-c-pentenyl group, 3-c-pentenyl group, 1-c-hexenyl group, 2-c-hexenyl group or 3-c-hexenyl group;

(29) The benzopyran derivative or pharmaceutically acceptable salt thereof as set forth in (15), wherein $R^7$ and $R^8$ together are =O or =S, and $R^6$ is amino group, $C_{1-6}$ alkylamino group, di-$C_{1-6}$ alkylamino group, $C_{6-14}$ arylamino group, $C_{2-9}$ heteroarylamino (wherein each of the arylamino group or heteroarylamino group may be arbitrarily substituted with 1 to 3 $R^{18}$ wherein $R^{18}$ has the same meaning as $R^{10}$, or $C_{2-9}$ heterocyclyl group (wherein the heterocyclyl group may be arbitrarily substituted with halogen atom, $C_{1-6}$ alkyl group (wherein the alkyl group may be arbitrarily substituted with halogen atom, $C_{1-6}$ alkoxy group (wherein the alkoxy group may be arbitrarily substituted with halogen atom), amino group, carboxy group or hydroxy group), $C_{1-6}$ alkoxy group (wherein the alkoxy group may be arbitrarily substituted with halogen atom), amino group, carboxy group or hydroxy group);

(30) The benzopyran derivative or pharmaceutically acceptable salt thereof as set forth in (4), wherein V is $NR^9$;

(31) The benzopyran derivative or pharmaceutically acceptable salt thereof as set forth in (30), wherein m is an integer of 1 to 3, n is 0, and $R^6$ is $C_{6-14}$ aryl group or $C_{2-9}$ heteroaryl wherein each of the aryl group or heteroaryl group may be arbitrarily substituted with 1 to 3 $R^{18}$ wherein $R^{18}$ has the same meaning as $R^{10}$;

(32) The benzopyran derivative or pharmaceutically acceptable salt thereof as set forth in (31), wherein m is 2;

(33) The benzopyran derivative or pharmaceutically acceptable salt thereof as set forth in (30), wherein m is an integer of 1 to 3, n is 0 and $R^6$ is hydrogen atom, $C_{2-4}$ alkyl group (wherein the alkyl group may be arbitrarily substituted with halogen atom, $C_{1-6}$ alkoxy group (wherein the alkoxy group may be arbitrarily substituted with halogen atom), amino group, carboxy group or hydroxy group), $C_{3-8}$ cycloalkyl group, $C_{3-8}$ cycloalkenyl group (wherein the cycloalkyl group or cycloalkenyl group may be arbitrarily substituted with halogen atom, $C_{1-6}$ alkyl group (wherein the alkyl group may be arbitrarily substituted with halogen atom, $C_{1-6}$ alkoxy group (wherein the alkoxy group may be arbitrarily substituted with halogen atom), amino group, carboxy group or hydroxy group), $C_{1-6}$ alkoxy group (wherein the alkoxy group may be arbitrarily substituted with halogen atom), amino, carboxy group or hydroxy group), or $C_{2-9}$ heterocyclyl group (wherein the heterocyclyl may be arbitrarily substituted with halogen atom, $C_{1-6}$ alkyl group (wherein the alkyl group may be arbitrarily substituted with halogen atom, $C_{1-6}$ alkoxy group (wherein the alkoxy group may be arbitrarily substituted with halogen atom), amino group, carboxy group or hydroxy group), $C_{1-6}$ alkoxy group (wherein the alkoxy group may be arbitrarily substituted with halogen atom), amino group, carboxy group or hydroxy group);

(34) The benzopyran derivative or pharmaceutically acceptable salt thereof as set forth in (33), wherein m is 2;

(35) The benzopyran derivative or pharmaceutically acceptable salt thereof as set forth in (3), which is the compound of formula (I);

(36) The benzopyran derivative or pharmaceutically acceptable salt thereof as set forth in (3), which is the compound of formula (II);

(37) The benzopyran derivative or pharmaceutically acceptable salt thereof as set forth in (8), (11), (14), (23), (28) or (35), wherein the ring structure of A is

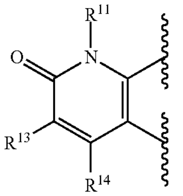

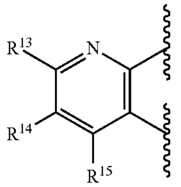

or

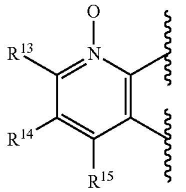

wherein $R^{11}$, $R^{13}$, $R^{14}$ and $R^{15}$ have the above-mentioned meanings;

(38) The benzopyran derivative or pharmaceutically acceptable salt thereof as set forth in (37), wherein $R^{11}$ is hydrogen atom or $C_{1-6}$ alkyl group (wherein the alkyl group may be arbitrarily substituted with halogen atom, $C_{1-6}$ alkoxy group (wherein the alkoxy group may be arbitrarily substituted with halogen atom), amino group or hydroxy group), and $R^{13}$, $R^{14}$ and $R^{15}$ are independently of each other hydrogen atom, halogen atom, $C_{1-6}$ alkyl group (wherein the alkyl group may be arbitrarily substituted with halogen atom, $C_{1-6}$ alkoxy group (wherein the alkoxy group may be arbitrarily substituted with halogen atom) or hydroxy group), $C_{3-8}$ cycloalkyl group (wherein the cycloalkyl group may be arbitrarily substituted with halogen atom, $C_{1-6}$ alkoxy group (wherein the alkoxy group may be arbitrarily substituted with halogen atom), amino group or hydroxy group), $C_{1-6}$ alkoxy group (wherein the alkoxy group may be arbitrarily substituted with halogen atom, amino group, $C_{1-6}$ alkoxy group (wherein the alkoxy group may be arbitrarily substituted with halogen atom) or hydroxy group), $C_{1-6}$ alkylcarbonyl group, aminocarbonyl group, amino group, carboxy group or cyano group;

(39) The benzopyran derivative or pharmaceutically acceptable salt thereof as set forth in (38), wherein $R^{11}$ is hydrogen atom or $C_{1-6}$ alkyl group (wherein the alkyl group may be arbitrarily substituted with halogen atom, amino group or hydroxy group), and $R^{13}$, $R^{14}$ and $R^{15}$ are independently of each other hydrogen atom, halogen atom, $C_{1-6}$ alkyl group (wherein the alkyl group may be arbitrarily substituted with halogen atom, amino group or hydroxy group), carboxy group, amino group or cyano group;

(40) The benzopyran derivative or pharmaceutically acceptable salt thereof as set forth in (39), wherein $R^{11}$ is hydrogen atom, $R^{13}$ is hydrogen atom, halogen atom, carboxy group or $C_{1-6}$ alkyl group (wherein the alkyl group may be arbitrarily substituted with halogen atom, amino group or hydroxy group), $R^{14}$ is hydrogen atom, and $R^{15}$ is hydrogen atom, halogen atom or $C_{1-6}$ alkyl group (wherein the alkyl group may be arbitrarily substituted with halogen atom, amino group or hydroxy group);

(41) The benzopyran derivative or pharmaceutically acceptable salt thereof as set forth in (8), (11), (14), (23), (28) or (35), wherein the ring structure of A is

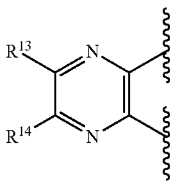
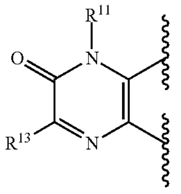
or
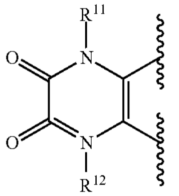

wherein $R^{11}$, $R^{12}$, $R^{13}$ and $R^{14}$ have the above-mentioned meanings;

(42) The benzopyran derivative or pharmaceutically acceptable salt thereof as set forth in (41), wherein $R^{11}$ and $R^{12}$ are independently of each other hydrogen atom or $C_{1-6}$ alkyl group (wherein the alkyl group may be arbitrarily substituted with halogen atom, $C_{1-6}$ alkoxy group (wherein the alkoxy group may be arbitrarily substituted with halogen atom), amino group or hydroxy group), and $R^{13}$ and $R^{14}$ are independently of each other hydrogen atom, halogen atom, $C_{1-6}$ alkyl group (wherein the alkyl group may be arbitrarily substituted with halogen atom, amino group, $C_{1-6}$ alkoxy group (wherein the alkoxy group may be arbitrarily substituted with halogen atom) or hydroxy group), $C_{1-6}$ alkoxy group (wherein the alkoxy group may be arbitrarily substituted with halogen atom, amino group, $C_{1-6}$ alkoxy group (wherein the alkoxy group may be arbitrarily substituted with halogen atom), or hydroxy group), $C_{1-6}$ alkylcarbonyl group, amino group or cyano group;

(43) The benzopyran derivative or pharmaceutically acceptable salt thereof as set forth in (42), wherein $R^{11}$ and $R^{12}$ are independently of each other hydrogen atom or $C_{1-6}$ alkyl group (wherein the alkyl group may be arbitrarily substituted with halogen atom, amino group or hydroxy group), and $R^{13}$ and $R^{14}$ are independently of each other hydrogen atom, halogen atom, $C_{1-6}$ alkyl group (wherein the alkyl group may be arbitrarily substituted with halogen atom, amino group or hydroxy group), amino group or cyano group;

(44) The benzopyran derivative or pharmaceutically acceptable salt thereof as set forth in (43), wherein $R^{11}$, $R^{12}$, $R^{13}$ and $R^{14}$ are hydrogen atom;

(45) The benzopyran derivative or pharmaceutically acceptable salt thereof as set forth in (8), (11), (14), (23), (28) or (35), wherein the ring structure of A is

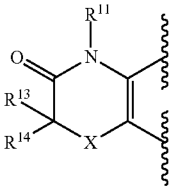
or
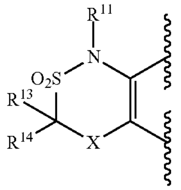

wherein $R^{11}$, $R^{13}$ and $R^{14}$ have the above-mentioned meanings;

(46) The benzopyran derivative or pharmaceutically acceptable salt thereof as set forth in (45), wherein $R^{11}$ is hydrogen atom or $C_{1-6}$ alkyl group (wherein the alkyl group may be arbitrarily substituted with halogen atom, $C_{1-6}$ alkoxy group (wherein the alkoxy group may be arbitrarily substituted with halogen atom), amino group or hydroxy group), $R^{13}$ and $R^{14}$ are independently of each other hydrogen atom, halogen atom, $C_{1-6}$ alkyl group (wherein the alkyl group may be arbitrarily substituted with halogen atom, amino group, $C_{1-6}$ alkoxy group (wherein the alkoxy group may be arbitrarily substituted with halogen atom) or hydroxy group), $C_{1-6}$ alkoxy group (wherein the alkoxy group may be arbitrarily substituted with halogen atom, amino group, $C_{1-6}$ alkoxy group (wherein the alkoxy group may be arbitrarily substituted with halogen atom), or hydroxy group), amino group or cyano group, and X is O, S, SO or $SO_2$;

(47) The benzopyran derivative or pharmaceutically acceptable salt thereof as set forth in (46), wherein $R^{11}$ is hydrogen atom or $C_{1-6}$ alkyl group (wherein the alkyl group may be arbitrarily substituted with halogen atom, amino group or hydroxy group), $R^{13}$ and $R^{14}$ are independently of each other hydrogen atom, halogen atom or $C_{1-6}$ alkyl group (wherein the alkyl group may be arbitrarily substituted with halogen atom, amino group or hydroxy group), and X is O;

(48) The benzopyran derivative or pharmaceutically acceptable salt thereof as set forth in (47), wherein $R^{11}$ is hydrogen atom or $C_{1-6}$ alkyl group (wherein the alkyl group may be arbitrarily substituted with halogen atom, amino group or hydroxy group), $R^{13}$ and $R^{14}$ are hydrogen atom, and X is O;

(49) The benzopyran derivative or pharmaceutically acceptable salt thereof as set forth in (8), (11), (14), (23), (28) or (35), wherein the ring structure of A is

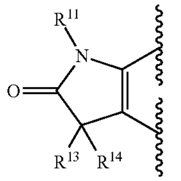
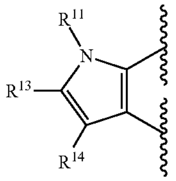
or
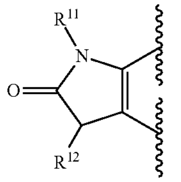

wherein $R^{11}$, $R^{12}$, $R^{13}$ and $R^{14}$ have the above-mentioned meanings;

(50) The benzopyran derivative or pharmaceutically acceptable salt thereof as set forth in (49), wherein $R^{11}$ and $R^{12}$ are independently of each other hydrogen atom or $C_{1-6}$ alkyl group (wherein the alkyl group may be arbitrarily substituted with halogen atom, $C_{1-6}$ alkoxy group (wherein the alkoxy group may be arbitrarily substituted with halogen atom), $C_{1-6}$ aryl group (wherein the aryl group may be arbitrarily substituted with halogen atom, hydroxy group or $C_{1-6}$ alkoxy group (wherein the alkoxy group may be arbitrarily substituted with halogen atom)), amino group or hydroxy group), and $R^{13}$ and $R^{14}$ are independently of each other hydrogen atom, halogen atom, $C_{1-6}$ alkyl group (wherein the alkyl group may be arbitrarily substituted with halogen atom, amino group, $C_{1-6}$ alkoxy group (wherein the alkoxy group may be arbitrarily substituted with halogen atom) or hydroxy group), $C_{1-6}$ alkoxy group (wherein the alkoxy group may be arbitrarily substituted with halogen atom, amino group, $C_{1-6}$ alkoxy group (wherein the alkoxy group may be arbitrarily substituted with halogen atom), or hydroxy group), amino group or cyano group;

(51) The benzopyran derivative or pharmaceutically acceptable salt thereof as set forth in (50), wherein $R^{11}$ and $R^{12}$ are independently of each other hydrogen atom or $C_{1-6}$ alkyl group (wherein the alkyl group may be arbitrarily substituted with halogen atom, amino group or hydroxy group), and $R^{13}$ and $R^{14}$ are hydrogen atom;

(52) A benzopyran derivative or pharmaceutically acceptable salt thereof which is 2,2,7,9-tetramethyl-4-[(2-phenylethyl)amino]-3,4-dihydro-2H-pyrano[2,3-g]quinolin-3-ol,
2,2,7-trimethyl-4-[(2-phenylethyl)amino]-3,4-dihydro-2H-pyrano[2,3-g]quinolin-3-ol,
3-hydroxy-2,2,9-trimethyl-4-[(2-phenylethyl)amino]-3,4-dihydro-2H-pyrano[2,3-g]quinolin-7-carbonitrile,
3-hydroxy-2,2,9-trimethyl-4-[(2-phenylethyl)amino]-3,4-dihydro-2H-pyrano[2,3-g]quinolin-7-carboxamide,
{3-hydroxy-2,2,9-trimethyl-4-[(2-phenylethyl)amino]-3,4-dihydro-2H-pyrano[2,3-g]quinolin-7-yl}ethanone,
3,3-dimethyl-1-[(2-phenylethyl)amino]-2,3-dihydro-1H-pyrano[3,2-f]quinolin-2-ol
7-hydroxymethyl-2,2,9-trimethyl-4-[(2-phenylethyl)amino]-3,4-dihydro-2H-pyrano[2,3-g]quinolin-3-ol,
3-hydroxy-2,2,9-trimethyl-4-[(2-phenylethyl)amino]-3,4-dihydro-2H-pyrano[2,3-g]quinolin-3-carboxylic acid,
7-chloro-2,2,9-trimethyl-4-[(2-phenylethyl)amino]-3,4-dihydro-2H-pyrano[2,3-g]quinolin-3-ol,
4-(benzylamino)-7-chloro-2,2,9-trimethyl-3,4-dihydro-2H-pyrano[2,3-g]quinolin-3-ol,
7-chloro-4-{[2-(1,3-benzodioxol-5-yl)methyl]amino}-2,2,9-trimethyl-3,4-dihydro-2H-pyrano[2,3-g]quinolin-3-ol,
7-chloro-2,2,9-trimethyl-4-[(3-phenylpropyl)amino]-3,4-dihydro-2H-pyrano[2,3-g]quinolin-3-ol,
7-chloro-4-{[2-(4-fluorophenyl)ethyl]amino}-2,2,9-trimethyl-3,4-dihydro-2H-pyrano[2,3-g]quinolin-3-ol,
7-chloro-4-{[2-(2-fluorophenyl)ethyl]amino}-2,2,9-trimethyl-3,4-dihydro-2H-pyrano[2,3-g]quinolin-3-ol,
7-chloro-4-{[2-(4-chlorophenyl)ethyl]amino}-2,2,9-trimethyl-3,4-dihydro-2H-pyrano[2,3-g]quinolin-3-ol,
4-{[2-(4-aminophenyl)ethyl]amino}-7-chloro-2,2,9-trimethyl-3,4-dihydro-2H-pyrano[2,3-g]quinolin-3-ol,
7-chloro-4-[(2-hydroxy-2-phenylethyl)amino]-2,2,9-trimethyl-3,4-dihydro-2H-pyrano[2,3-g]quinolin-3-ol,
7-chloro-4-(2-phenylbutyl)amino}-2,2,9-trimethyl-3,4-dihydro-2H-pyrano[2,3-g]quinolin-3-ol,
7-chloro-4-{([2-(1,3-benzodioxol-5-yl)ethyl]amino}-2,2,9-trimethyl-3,4-dihydro-2H-pyrano[2,3-g]quinolin-3-ol,
7-chloro-2,2,9-trimethyl-4-{[2-(1-piperidinyl)ethyl]amino}-3,4-dihydro-2H-pyrano[2,3-g]quinolin-3-ol,
7-chloro-2,2,9-trimethyl-4-{[2-(1-methyl-2-pyrrolidinyl)ethyl]amino}-3,4-dihydro-2H-pyrano[2,3-g]quinolin-3-ol,
4-[(2-anilinoethyl)amino]-7-chloro-2,2,9-trimethyl-3,4-dihydro-2H-pyrano[2,3-g]quinolin-3-ol,
7-chloro-4-({2-[ethyl(3-methylphenyl)amino]ethyl}amino)-2,2,9-trimethyl-3,4-dihydro-2H-pyrano[2,3-g]quinolin-3-ol,
7-chloro-2,2,9-trimethyl-4-{[(1-ethyl-(R)-2-pyrrolidinyl)methyl]amino}-3,4-dihydro-2H-pyrano[2,3-g]quinolin-3-ol,
7-chloro-2,2,9-trimethyl-4-[(2,2-diethoxyethyl)amino]-3,4-dihydro-2H-pyrano[2,3-g]quinolin-3-ol,
7-chloro-2,2,9-trimethyl-4-{[2-(3-thienyl)ethyl]amino}-3,4-dihydro-2H-pyrano[2,3-g]quinolin-3-ol,
7-chloro-4-[2-(1-pyrazolylethyl)amino]-2,2,9-trimethyl-3,4-dihydro-2H-pyrano[2,3-g]quinolin-3-ol,
7-chloro-4-{([2-(4-methylpyrazol-1-yl)ethylamino]-2,2,9-trimethyl-3,4-dihydro-2H-pyrano[2,3-g]quinolin-3-ol,
7-chloro-4-{([2-(4-chloropyrazol-1-yl)ethyl]amino}-2,2,9-trimethyl-3,4-dihydro-2H-pyrano[2,3-g]quinolin-3-ol,
7-chloro-4-[2-(2-pyridylethyl)amino]-2,2,9-trimethyl-3,4-dihydro-2H-pyrano[2,3-g]quinolin-3-ol,
7-chloro-4-[2-(3-pyridylethyl)amino]-2,2,9-trimethyl-3,4-dihydro-2H-pyrano[2,3-g]quinolin-3-ol,
7-chloro-4-[2-(4-pyridylethyl)amino]-2,2,9-trimethyl-3,4-dihydro-2H-pyrano[2,3-g]quinolin-3-ol,
7-chloro-4-ethylamino-2,2,9-trimethyl-3,4-dihydro-2H-pyrano[2,3-g]quinolin-3-ol,
7-chloro-4-isobutylamino-2,2,9-trimethyl-3,4-dihydro-2H-pyrano[2,3-g]quinolin-3-ol,
7-chloro-4-[(cyclopropylmethyl)amino]-2,2,9-trimethyl-3,4-dihydro-2H-pyrano[2,3-g]quinolin-3-ol,
7-chloro-4-isoamylamino-2,2,9-trimethyl-3,4-dihydro-2H-pyrano[2,3-g]quinolin-3-ol,
7-chloro-4-[2-(cyclopentylethyl)amino]-2,2,9-trimethyl-3,4-dihydro-2H-pyrano[2,3-g]quinolin-3-ol,
7-chloro-4-[2-(1-cyclopentenylethyl)amino]-2,2,9-trimethyl-3,4-dihydro-2H-pyrano[2,3-g]quinolin-3-ol,
7-chloro-2,2,9-trimethyl-4-[(1,4-dimethylpentyl)amino]-3,4-dihydro-2H-pyrano[2,3-g]quinolin-3-ol,
7-chloro-2,2,9-trimethyl-4-(pentylamino)-3,4-dihydro-2H-pyrano[2,3-g]quinolin-3-ol,
7-chloro-4-[(2-cyclohexylethyl)amino]-2,2,9-trimethyl-3,4-dihydro-2H-pyrano[2,3-g]quinolin-3-ol,
7-chloro-2,2,9-trimethyl-4-[(2-tetrahydro-2H-pyran-4-ylethyl)amino]-3,4-dihydro-2H-pyrano[2,3-g]quinolin-3-ol,
7-chloro-2,2,9-trimethyl-4-[(2-tetrahydro-2H-thiopyran-4-ylethyl)amino]-3,4-dihydro-2H-pyrano[2,3-g]quinolin-3-ol,
7-chloro-4-({[6-(4-chlorophenyl)-3-pyridinyl]methyl}amino)-2,2,9-trimethyl-3,4-dihydro-2H-pyrano[2,3-g]quinolin-3-ol,
4-[(2-benzofuranylmethyl)amino]-7-chloro-2,2,9-trimethyl-3,4-dihydro-2H-pyrano[2,3-g]quinolin-3-ol,
7-chloro-4-[(2-hydroxypentyl)amino]-2,2,9-trimethyl-3,4-dihydro-2H-pyrano[2,3-g]quinolin-3-ol,
7,7-dimethyl-9-[(2-phenylethyl)amino]-8,9-dihydro-7H-pyrano[2,3-g]quinoxalin-8-ol,
{[2-(2-fluorophenyl)ethyl]amino}-7,7-dimethyl-8,9-dihydro-7H-pyrano[2,3-g]quinoxalin-8-ol,
{[2-(4-fluorophenyl)ethyl]amino}-7,7-dimethyl-8,9-dihydro-7H-pyrano[2,3-g]quinoxalin-8-ol, 9-[(2-hydroxy-2- phenylethyl)amino]-7,7-dimethyl-8,9-dihydro-7H-pyrano[2,3-g]quinoxalin-8-ol,
7,7-dimethyl-9-(pentylamino)-8,9-dihydro-7H-pyrano[2,3-g]quinoxalin-8-ol,
2,3,7,7-tetramethyl-9-[(2-phenylethyl)amino]-8,9-dihydro-7H-pyrano[2,3-g]quinoxalin-8-ol,
2,3-diethyl-7,7-dimethyl-9-[(2-phenylethyl)amino]-8, 9-dihydro-7H-pyrano[2,3-g]quinoxalin-8-ol,
3,7,7-trimethyl-2-phenyl-9-[(2-phenylethyl)amino]-8, 9-dihydro-7H-pyrano[2,3-g]quinoxalin-8-ol,
2,7,7-trimethyl-3-phenyl-9-[(2-phenylethyl)amino]-8, 9-dihydro-7H-pyrano[2,3-g]quinoxalin-8-ol,
3,7,7-trimethyl-9-[(2-phenylethyl)amino]-8,9-dihydro-7H-pyrano[2,3-g]quinoxalin-8-ol,
9-[(2-cyclohexylethyl)amino]-7,7-dimethyl-8,9-dihydro-7H-pyrano[2,3-g]quinoxalin-8-ol,
6,7-imidazolino-3,4-dihydro-2,2-dimethyl-4-(2'-phenylethylamino)2H-1-benzopyran-3-ol,
7-hydroxy-6,6-dimethyl-8-(2-phenylethylamino)-4,6,7,8-tetrahydro-1,5-dioxa-4-aza-anthracen-3-on,
7-hydroxy-4,6,6-trimethyl-8-(2-phenylethylamino)-4,6,7,8-tetrahydro-1,5-dioxa-4-aza-anthracen-3-on,
6,6-dimethyl-8-(2-phenylethylamino)-2,3,4,6,7,8-hexahydro-1, 5-dioxa-4-aza-anthracen-7-ol,
7-hydroxy-6,6-dimethyl-8-(2-phenylethylamino)-7,8-dihydro-1H,6H-4,5-dioxa-1-aza-anthracen-2-on,
6,6-dimethyl-8-(2-phenylethylamino)-2,3,7,8-tetrahydro-1H,6H-4,5-dioxa-1-aza-anthracen-7-ol,
9-hydroxymethyl-2,2-dimethyl-4-[(2-phenylethyl)amino]-3, 4-dihydro-2H-pyrano[2,3-g]quinolin-3-ol,
2,2,9-trimethyl-4-[(2-phenylethyl)amino]-3,4-dihydro-2H-pyrano[2,3-g]quinoline-3,7-diol,
7-aminomethyl-2,2,9-trimethyl-4-[(2-phenylethyl)amino]-3, 4-dihydro-2H-pyrano[2,3-g]quinolin-3-ol,
7-chloro-2,2,9-trimethyl-5-oxy-4-[(2-phenylethyl)amino]-3, 4-dihydro-2H-pyrano[2,3-g]quinolin-3-ol,
7-chloro-4-{[2-(4-fluorophenyl)ethyl]amino}-2,2, 9-trimethyl-5-oxy-3,4-dihydro-2H-pyrano[2,3-g]quinolin-3-ol,
7-chloro-2,2,9-trimethyl-5-oxy-4-(pentylamino)-3,4-dihydro-2H-pyrano[2,3-g]quinolin-3-ol,
4-{[2-(fluorophenyl)ethyl]amino}-7-hydroxymethyl-2,2, 9-trimethyl-3,4-dihydro-2H-pyrano[2,3-g]quinolin-3-ol or
2,2-dimethyl-4-[(2-phenylethyl)amino]-3,4-dihydro-2H-pyrano[2,3-g]quinolin-3-ol;

(53) The benzopyran derivative or pharmaceutically acceptable salt thereof which is
2,2,7-trimethyl-4-[(2-phenylethyl)amino]-3,4-dihydro-2H-pyrano[2,3-g]quinolin-3-ol,
3,3-dimethyl-1-[(2-phenylethyl)amino]-2,3-dihydro-1H-pyrano[3,2-f]quinolin-2-ol,
7-hydroxymethyl-2,2,9-trimethyl-4-[(2-phenylethyl) amino]-3,4-dihydro-2H-pyrano[2,3-g]quinolin-3-ol,
7-chloro-2,2,9-trimethyl-4-[(2-phenylethyl)amino]-3, 4-dihydro-2H-pyrano[2,3-g]quinolin-3-ol,
7-chloro-4-{[2-(4-fluorophenyl)ethyl]amino}-2,2, 9-trimethyl-3,4-dihydro-2H-pyrano[2,3-g]quinolin-3-ol,
7-chloro-4-{[2-(2-fluorophenyl)ethyl]amino}-2,2, 9-trimethyl-3,4-dihydro-2H-pyrano[2,3-g]quinolin-3-ol,
7-chloro-4-{[2-(4-chlorophenyl)ethyl]amino}-2,2,9-trimethyl-3,4-dihydro-2H-pyrano[2,3-g]quinolin-3-ol,
3-hydroxy-2,2,9-trimethyl-4-[2-(phenylethyl)amino]-3, 4-dihydro-2H-pyrano[2,3-g]quinoline-7carboxylic acid,
4-{([2-(4-aminophenyl)ethyl]amino}-7-chloro-2,2, 9-trimethyl-3,4-dihydro-2H-pyrano[2,3-g]quinolin-3-ol,
7-chloro-4-[(2-hydroxy-2-phenylethyl)amino]-2,2, 9-trimethyl-3,4-dihydro-2H-pyrano[2,3-g]quinolin-3-ol,
7-chloro-2,2,9-trimethyl-4-{[2-(1-piperidinyl)ethyl] amino}-3,4-dihydro-2H-pyrano[2,3-g]quinolin-3-ol,
7-chloro-4-{[2-(4-chloropyrazol-1-yl)ethyl]amino}-2,2,9-trimethyl-3,4-dihydro-2H-pyrano[2,3-g]quinolin-3-ol,
7-chloro-4-[2-(2-pyridylethyl)amino]-2,2,9-trimethyl-3,4-dihydro-2H-pyrano[2,3-g]quinolin-3-ol,
7-chloro-4-[2-(3-pyridylethyl)amino]-2,2,9-trimethyl-3,4-dihydro-2H-pyrano[2,3-g]quinolin-3-ol,
7-chloro-4-[2-(4-pyridylethyl)amino]-2,2,9-trimethyl-3,4-dihydro-2H-pyrano[2,3-g]quinolin-3-ol,
7-chloro-4-isoamylamino-2,2,9-trimethyl-3,4-dihydro-2H-pyrano[2,3-g]quinolin-3-ol,
7-chloro-4-[2-(cyclopentylethyl)amino]-2,2,9-trimethyl-3, 4-dihydro-2H-pyrano[2,3-g]quinolin-3-ol,
7-chloro-4-[2-(1-cyclopentenylethyl)amino]-2,2,9-trimethyl-3,4-dihydro-2H-pyrano[2,3-g]quinolin-3-ol,
7-chloro-2,2,9-trimethyl-4-(pentylamino)-3,4-dihydro-2H-pyrano[2,3-g]quinolin-3-ol,
7-chloro-4-[(2-cyclohexylethyl)amino]-2,2,9-trimethyl-3, 4-dihydro-2H-pyrano[2,3-g]quinolin-3-ol,
7-chloro-4-[(2-hydroxypentyl)amino]-2,2,9-trimethyl-3, 4-dihydro-2H-pyrano[2,3-g]quinolin-3-ol,
7,7-dimethyl-9-[(2-phenylethyl)amino]-8,9-dihydro-7H-pyrano[2,3-g]quinoxalin-8-ol,
{([2-(2-fluorophenyl)ethyl]amino}-7,7-dimethyl-8,9-dihydro-7H-pyrano[2,3-g]quinoxalin-8-ol,
{[2-(4-fluorophenyl)ethyl]amino}-7,7-dimethyl-8,9-dihydro-7H-pyrano[2,3-g]quinoxalin-8-ol, 9-[(2-hydroxy-2-phenylethyl)amino]-7,7-dimethyl-8,9-dihydro-7H-pyrano[2,3-g]quinoxalin-8-ol,
7,7-dimethyl-9-(pentylamino)-8,9-dihydro-7H-pyrano[2,3-g]quinoxalin-8-ol, 9-[(2-cyclohexylethyl)amino]-7,7-dimethyl-8,9-dihydro-7H-pyrano[2,3-g]quinoxalin-8-ol,
7-hydroxy-6,6-dimethyl-8-(2-phenylethylamino)-4,6,7,8-tetrahydro-1,5-dioxa-4-aza-anthracen-3-on,
7-hydroxy-4,6,6-trimethyl-8-(2-phenylethylamino)-4,6,7,8-tetrahydro-1,5-dioxa-4-aza-anthracen-3-one,
7-hydroxy-6,6-dimethyl-8-(2-phenylethylamino)-7,8-dihydro-1H,6H-4,5-dioxa-1-aza-anthracen-2-one,
9-hydroxymethyl-2,2-dimethyl-4-[(2-phenylethyl)amino]-3, 4-dihydro-2H-pyrano[2,3-g]quinolin-3-ol,
2,2,9-trimethyl-4-[(2-phenylethyl)amino]-3,4-dihydro-2H-pyrano[2,3-g]quinoline-3,7-diol,
7-aminomethyl-2,2,9-trimethyl-4-[(2-phenylethyl)amino]-3, 4-dihydro-2H-pyrano[2,3-g]quinolin-3-ol,
7-chloro-2,2,9-trimethyl-5-oxy-4-[(2-phenylethyl)amino]-3, 4-dihydro-2H-pyrano[2,3-g]quinolin-3-ol,
7-chloro-4-{[2-(4-fluorophenyl)ethyl]amino}-2,2, 9-trimethyl-5-oxy-3,4-dihydro-2H-pyrano[2,3-g]quinolin-3-ol,
7-chloro-2,2,9-trimethyl-5-oxy-4-(pentylamino)-3,4-dihydro-2H-pyrano[2,3-g]quinolin-3-ol,
4-{[2-(4-fluorophenyl)ethyl]amino}-7-hydroxymethyl-2,2, 9-trimethyl-3,4-dihydro-2H-pyrano[2,3-g]quinolin-3-ol or
2,2-dimethyl-4-[(2-phenylethyl)amino]-3,4-dihydro-2H-pyrano[2,3-g]quinolin-3-ol;

(54) A pharmaceutical characterized by comprising the benzopyran derivative or pharmaceutically acceptable salt thereof as set forth in any one of (1) to (53) as an active ingredient; and

(55) A pharmaceutical for treating arrhythmia characterized by comprising the benzopyran derivative or pharmaceutically acceptable salt thereof as set forth in any one of (1) to (53) as an active ingredient.

The compound according to the present invention has a strong prolongation effect on the refractory period and it can be used as a drug for treating arrhythmia.

BEST MODE FOR CARRYING OUT THE INVENTION

Respective substituents of compounds (I) or (II) according to the present invention are concretely defined below.

In the meanwhile, "n" means normal, "i" means iso, "s" means secondary, "t" means tertiary, "c" means cyclo, "o" means ortho, "m" means meta, "p" means para, "Ph" means phenyl, "Py" means pyridyl, "Bn" means benzyl, "Me" means methyl, "Et" means ethyl, "Pr" means propyl, "Bu" means butyl, "Pen" means pentyl, "Hex" hexyl, "Ac" means acetyl, "Boc" means tertiary butoxycarbonyl and "MOM" means methoxymethyl in this specification.

Examples of $C_{2-4}$ alkyl group are such as ethyl, n-propyl, i-propyl, n-butyl, i-butyl, s-butyl, t-butyl and the like.

Examples of $C_{1-4}$ alkyl group are such as methyl, ethyl, n-propyl, i-propyl, n-butyl, i-butyl, s-butyl, t-butyl and the like.

Examples of $C_{1-6}$ alkyl group are such as methyl, ethyl, n-propyl, i-propyl, n-butyl, i-butyl, s-butyl, t-butyl, 1-pentyl, 2-pentyl, 3-pentyl, i-pentyl, neopentyl, 2,2-dimethylpropyl, 1-hexyl, 2-hexyl, 3-hexyl, 1-methyl-n-pentyl, 1,1,2-trimethyl-n-propyl, 1,2,2-trimethyl-n-propyl, 3,3-dimethyl-n-butyl and the like.

Preferably, methyl, ethyl, n-propyl, i-propyl, n-butyl, n-pentyl and i-pentyl may be mentioned.

Examples of $C_{3-8}$ cycloalkyl group are such as c-propyl, c-butyl, i-methyl-c-propyl, 2-methyl-c-propyl, c-pentyl, 1-methyl-c-butyl, 2-methyl-c-butyl, 3-methyl-c-butyl, 1,2-dimethyl-c-propyl, 2,3-dimethyl-c-propyl, 1-ethyl-c-propyl, 2-ethyl-c-propyl, c-hexyl, c-heptyl, c-octyl, 1-methyl-c-hexyl, 2-methyl-c-hexyl, 3-methyl-c-hexyl, 1,2-dimethyl-c-hexyl, 1-methyl-c-pentyl, 2-methyl-c-pentyl, 3-methyl-c-pentyl, 1-ethyl-c-butyl, 2-ethyl-c-butyl, 3-ethyl-c-butyl, 1,2-dimethyl-c-butyl, 1,3-dimethyl-c-butyl, 2, 2-dimethyl-c-butyl, 2,3-dimethyl-c-butyl, 2,4-dimethyl-c-butyl, 3,3-dimethyl-c-butyl, 1-n-propyl-c-propyl, 2-n-propyl-c-propyl, 1-i-propyl-c-propyl, 2-i-propyl-c-propyl, 1,2,2-trimethyl-c-propyl, 1,2,3-trimethyl-c-propyl, 2,2,3-trimethyl-c-propyl, 1-ethyl-2-methyl-c-propyl, 2-ethyl-1-methyl-c-propyl, 2-ethyl-2-methyl-c-propyl, 2-ethyl-3-methyl-c-propyl, and the like.

Preferably, c-pentyl and c-hexyl may be mentioned.

Examples of $C_{3-8}$ cycloalkenyl group are such as 1-c-pentenyl, 2-c-pentenyl, 3-c-pentenyl, 1-methyl-2-c-pentenyl, 1-methyl-3-c-pentenyl, 2-methyl-1-c-pentenyl, 2-methyl-3-c-pentenyl, 2-methyl-4-c-pentenyl, 2-methyl-5-c-pentenyl, 2-methylene-c-pentyl, 3-methyl-1-c-pentenyl, 3-methyl-2-c-pentenyl, 3-methyl-3-c-pentenyl, 3-methyl-4-c-pentenyl, 3-methylene-c-pentyl, 1-c-hexenyl, 2-c-hexenyl, 3-c-hexenyl, 2-c-heptynyl, 3-c-heptynyl, 4-c-heptynyl, 1-c-octenynyl, 2-c-octenynyl, 3-c-octenynyl, 4-c-octenynyl, and the like.

Preferably, 1-c-pentenyl, 2-c-pentenyl, 3-c-pentenyl, 1-c-hexenyl 2-c-hexenyl and 3-c-hexenyl may be mentioned.

Examples of halogen atom are fluorine atom, chlorine atom, bromine atom and iodine atom. Preferably, fluorine atom, chlorine atom and bromine atom may be mentioned.

Examples of $C_{1-6}$ alkoxy group are such as methoxy, ethoxy, n-propoxy, i-propoxy, n-butoxy, i-butoxy, s-butoxy, t-butoxy, 1-pentyloxy, 2-pentyloxy, 3-pentyloxy, i-pentyloxy, neopentyloxy, 2,2-dimethylpropoxy, 1-hexyloxy, 2-hexyloxy, 3-hexyloxy, 1-methyl-n-pentyloxy, 1,1,2-trimethyl-n-propoxy, 1,2,2-trimethyl-n-propoxy, 3,3-dimethyl-n-butoxy and the like.

Preferably, methoxy, ethoxy, n-propoxy and i-propoxy may be mentioned.

Examples of $C_{1-6}$ thioalkoxy group are such as methylthio, ethylthio, n-propylthio, i-propylthio, c-propylthio, n-butylthio, i-butylthio, s-butylthio, t-butylthio, n-pentylthio, i-pentylthio, neopentylthi, t-pentylthio, n-hexylthio, c-hexylthio and the like.

Examples of $C_{1-6}$ alkylcarbonyloxy group are such as methylcarbonyloxy, ethylcarbonyloxy, n-propylcarbonyloxy, i-propylcarbonyloxy, n-butylcarbonyloxy, i-butylcarbonyloxy, s-butylcarbonyloxy, t-butylcarbonyloxy, 1-pentylcarbonyloxy, 2-pentylcarbonyloxy, 3-pentylcarbonyloxy, i-pentylcarbonyloxy, neopentylcarbonyloxy, t-pentylcarbonyloxy, 1-hexylcarbonyloxy, 2-hexylcarbonyloxy, 3-hexylcarbonyloxy, 1-methyl-n-pentylcarbonyloxy, 1,1,2-trimethyl-n-propylcarbonyloxy, 1,2,2-trimethyl-n-propylcarbonyloxy, 3,3-dimethyl-n-butylcarbonyloxy and the like.

Preferably, methylcarbonyloxy, ethylcarbonyloxy, n-propylcarbonyloxy, l-propylcarbonyloxy, n-butylcarbonyloxy and t-butylcarbonyloxy may be mentioned.

Examples of $C_{6-14}$ aryl group are such as phenyl, o-biphenylyl, m-biphenylyl, p-biphenylyl, □-naphthyl, □-naphthyl, 1-anthryl, 2-anthryl, 9-anthryl, 1-phenanthryl, 2-phenanthryl, 3-phenanthryl, 4-phenanthryl, 9-phenanthryl and the like.

Preferably, phenyl, o-biphenylyl, m-biphenylyl, p-biphenylyl, □-naphthyl and □-naphthyl may be mentioned.

$C_{2-9}$ heteroaryl group includes $C_{2-6}$ single-ring heterocyclic group with 5- to 7-member ring and $C_{5-9}$ fused double-ring heterocyclic group with member atom number of 8 to 10, which may contain 1 to 3 hetero atoms selected from the group consisting of oxygen atom, nitrogen atom and sulfur atom alone or in a combination.

Examples of the $C_{2-6}$ single-ring heterocyclic group with 5- to 7-member ring are such as 2-thienyl group, 3-thienyl group, 2-furyl group, 3-furyl group, 2-pyranyl group, 3-pyranyl group, 4-pyranyl group, 1-pyrrolyl group, 2-pyrrolyl group, 3-pyrrolyl group, 1-imidazolyl group, 2-imidazolyl group, 4-imidazolyl group, 1-pyrazolyl group, 3-pyrazolyl group, 4-pyrazolyl group, 2-thiazolyl group, 4-thiazolyl group, 5-thiazolyl group, 3-isothiazolyl group, 4-isothiazolyl group, 5-isothiazolyl group, 2-oxazolyl group, 4-oxazolyl group, 5-oxazolyl group, 3-isooxazolyl group, 4-isooxazolyl group, 5-isooxazolyl group, 2-pyridyl group, 3-pyridyl group, 4-pyridyl group, 2-pyradinyl group, 2-pyrimidinyl group, 4-pyrimidinyl group, 5-pyrimidinyl group, 3-pyridazinyl group, 4-pyridazinyl group, 2-1,3,4-oxadiazolyl group, 2-1,3,4-thiadiazolyl group, 3-1,2,4-oxadiazolyl group, 5-1,2,4-oxadiazolyl group, 3-1,2,4-thiadiazolyl group, 5-1,2,4-thiadiazolyl group, 3-1,2,5-oxadiazolyl group, 3-1,2,5-thiadiazolyl group and the like.

Examples of the $C_{5-9}$ fused double-ring heterocyclic group with member atom number of 8 to 10 are 2-benzofuranyl group, 3-benzofuranyl group, 4-benzofuranyl group, 5-benzofuranyl group, 6-benzofuranyl group, 7-benzofuranyl group, 1-isobenzofuranyl group, 4-isobenzofuranyl group, 5-isobenzofuranyl group, 2-benzothienyl group, 3-benzothienyl group, 4-benzothienyl group, 5-benzothienyl group, 6-benzothienyl group, 7-benzothienyl group, 1-isobenzothienyl group, 4-isobenzothienyl group, 5-isobenzothienyl group, 2-chromenyl group, 3-chromenyl group, 4-chromenyl group, 5-chromenyl group, 6-chromenyl group, 7-chromenyl group, 8-chromenyl group, 1-indolizinyl group, 2-indolizinyl group, 3-indolizinyl group, 5-indolizinyl group, 6-indolizinyl group, 7-indolizinyl group, 8-indolizinyl group, 1-isoindolyl group, 2-isoindolyl group, 4-isoindolyl group, 5-isoindolyl group, 1-indolyl group, 2-indolyl group, 3-indolyl group, 4-indolyl group, 5-indolyl group, 6-indolyl group, 7-indolyl group, 1-indazolyl group, 2-indazolyl group, 3-indazolyl group, 4-indazolyl group, 5-indazolyl group, 6-indazolyl group, 7-indazolyl group, 1-purinyl group, 2-purinyl group, 3-purinyl group, 6-purinyl group, 7-purinyl group, 8-purinyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 1-phthalazinyl group, 5-phthalazinyl group, 6-phthalazinyl group, 1-2,7-naphthyridinyl group, 3-2,7-naphthyridinyl group, 4-2,7-naphthyridinyl group, 1-2,6-naphthyridinyl group, 3-2,6-naphthyridinyl group, 4-2,6-naphthyridinyl group, 2-1,8-naphthyridinyl group, 3-1,8-naphthyridinyl group, 4-1,8-naphthyridinyl group, 2-1,7-naphthyridinyl group, 3-1,7-naphthyridinyl group, 4-1,7-naphthyridinyl group, 5-1,7-naphthyridinyl group, 6-1,7-naphthyridinyl group, 8-1,7-naphthyridinyl group, 2-1,6-naphthyridinyl group, 3-1,6-naphthyridinyl group, 4-1,6-naphthyridinyl group, 5-1,6-naphthyridinyl group, 7-1,6-naphthyridinyl group, 8-1,6-naphthyridinyl group, 2-1,5-naphthyridinyl group, 3-1,5-naphthyridinyl group, 4-1,5-naphthyridinyl group, 6-1,5-naphthyridinyl group, 7-1,5-naphthyridinyl group, 8-1,5-naphthyridinyl group, 2-quinoxalinyl group, 5-quinoxalinyl group, 6-quinoxalinyl group, 2-quinazolinyl group, 4-quinazolinyl group, 5-quinazolinyl group, 6-quinazolinyl group, 7-quinazolinyl group, 8-quinazolinyl group, 3-cinnolinyl group, 4-cinnolinyl group, 5-cinnolinyl group, 6-cinnolinyl group, 7-cinnolinyl group, 8-cinnolinyl group, 2-pteridinyl group, 4-pteridinyl group, 6-pteridinyl group, 7-pteridinyl group, and the like.

Preferably, 2-pyridyl group, 3-pyridyl group and 4-pyridyl group may be mentioned.

$C_{2-9}$ heterocyclyl group includes single-ring or fused double-ring heterocyclic group composed of 1 or more atoms freely selected from nitrogen atom, oxygen atom and sulfur atom and 2 to 9 carbon atoms, and concretely includes the following groups:

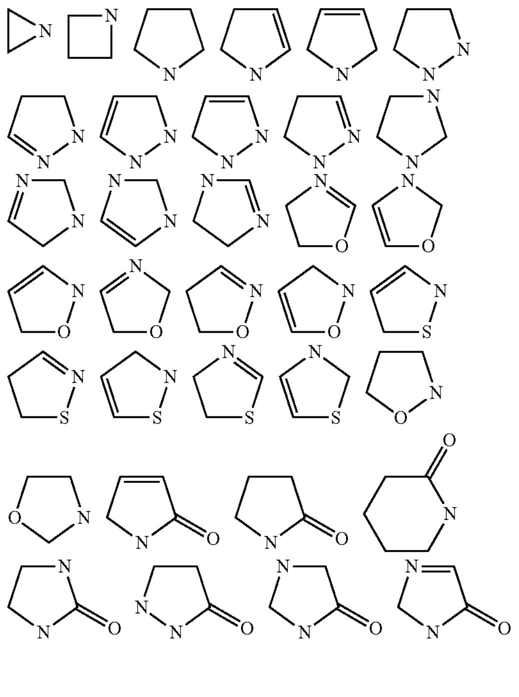

-continued

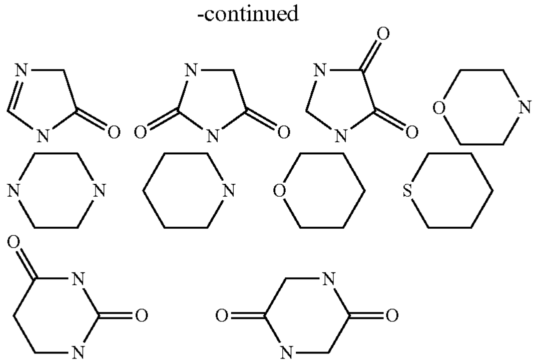

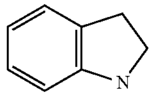

and

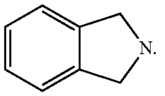

Examples of $C_{1-6}$ alkylamino group are such as methylamino, ethylamino, n-propylamino, i-propylamino, c-propylamino, n-butylamino, i-butylamino, s-butylamino, t-butylamino, c-butylamino, 1-pentylamino, 2-pentylamino, 3-pentylamino, i-pentylamino, neopentylamino, t-pentylamino, c-pentylamino, 1-hexylamino, 2-hexylamino, 3-hexylamino, c-hexylamino, 1-methyl-n-pentylamino, 1,1,2-trimethyl-n-propylamino, 1,2,2-trimethyl-n-propylamino, 3,3-dimethyl-n-butylamino and the like.

Preferably, methylamino, ethylamino, n-propylamino, i-propylamino and n-butylamino may be mentioned.

Examples of di-$C_{1-6}$ alkylamino group are such as dimethylamino, diethylamino, di-n-propylamino, di-i-propylamino, di-c-propylamino, di-n-butylamino, di-i-butylamino, di-s-butylamino, di-t-butylamino, di-c-butylamino, di-i-pentylamino, di-2-pentylamino, di-3-pentylamino, di-i-pentylamino, di-neopentylamino, di-t-pentylamino, di-c-pentylamino, di-i-hexylamino, di-2-hexylamino, di-3-hexylamino, di-c-hexylamino, di-(1-methyl-n-pentyl)amino, di-(1,1,2-trimethyl-n-propyl)amino, di-(1,2,2-trimethyl-n-propyl)amino, di-(3,3-dimethyl-n-butyl)amino, methyl(ethyl)amino, methyl(n-propyl)amino, methyl(i-propyl)amino, methyl(c-propyl)amino, methyl(n-butyl)amino, methyl(i-butyl)amino, methyl(s-butyl)amino, methyl(t-butyl)amino, methyl(c-butyl)amino, ethyl(n-propyl)amino, ethyl(i-propyl)amino, ethyl(c-propyl)amino, ethyl(n-butyl)amino, ethyl(i-butyl)amino, ethyl(s-butyl)amino, ethyl(t-butyl)amino, ethyl(c-butyl)amino, n-propyl(i-propyl)amino, n-propyl(c-propyl)amino, n-propyl(n-butyl)amino, n-propyl(i-butyl)amino, n-propyl(s-butyl)amino, n-propyl(t-butyl)amino, n-propyl(c-butyl)amino, i-propyl(c-propyl)amino, i-propyl(n-butyl)amino, i-propyl(i-butyl)amino, i-propyl(s-butyl)amino, i-propyl(t-butyl)amino, i-propyl(c-butyl)amino, c-propyl(n-butyl)amino, c-propyl(i-butyl)amino, c-propyl(s-butyl)amino, c-propyl(t-butyl)amino, c-propyl(c-butyl)amino, n-butyl(i-butyl)amino, n-butyl(s-butyl)amino, n-butyl(t-butyl)amino, n-butyl(c-butyl)amino, i-butyl(s-butyl)amino, i-butyl(t-butyl)amino, i-butyl(c-butyl)amino, s-butyl(t-butyl)amino, s-butyl(c-butyl)amino, t-butyl(c-butyl)amino and the like.

Preferably, dimethylamino, diethylamino, di-n-propylamino, di-i-propylamino and di-n-butylamino may be mentioned.

Examples of $C_{1-6}$ alkylcarbonylamino group are such as methylcarbonylamino, ethylcarbonylamino, n-propylcarbonylamino, i-propylcarbonylamino, n-butylcarbonylamino, i-butylcarbonylamino, s-butylcarbonylamino, t-butylcarbonylamino, 1-pentylcarbonylamino, 2-pentylcarbonylamino, 3-penylcarbonylamino, i-pentylcarbonylamino, neopentylcarbonylamino, t-pentylcarbonylamino, 1-hexylcarbonylamino, 2-hexylcarbonylamino, 3-hexylcarbonylamino and the like.

Preferably, methylcarbonylamino, ethylcarbonylamino, n-propylcarbonylamino, i-propylcarbonylamino and n-butylcarbonylamino may be mentioned.

Examples of $C_{1-6}$ alkylsulfonylamino group are such as methylsulfonylamino, ethylsulfonylamino, n-propylsulfonylamino, i-propylsulfonylamino, n-butylsulfonylamino, i-butylsulfonylamino, s-butylsulfonylamino, t-butylsulfonylamino, 1-pentylsulfonylamino, 2-pentylsulfonylamino, 3-pentylsulfonylamino, i-pentylsulfonylamino, neopentylsulfonylamino, t-pentylsulfonylamino, 1-hexylsulfonylamino, 2-hexylsulfonylamino, 3-hexylsulfonylamino and the like.

Preferably, methylsulfonylamino, ethylsulfonylamino, n-propylsulfonylamino, i-propylsulfonylamino and n-butylsulfonylamino may be mentioned.

Examples of $C_{1-6}$ alkylaminocarbonyl group are such as methylaminocarbonyl, ethylaminocarbonyl, n-propylaminocarbonyl, i-propyl-aminocarbonyl, n-butylaminocarbonyl, i-butylaminocarbonyl, s-butylaminocarbonyl, t-butylaminocarbonyl, 1-pentylaminocarbonyl, 2-pentylaminocarbonyl, 3-pentyl-aminocarbonyl, i-pentylaminocarbonyl, neopentylaminocarbonyl, t-pentylamino-carbonyl, 1-hexylaminocarbonyl, 2-hexylaminocarbonyl, 3-hexylaminocarbonyl and the like.

Preferably, methylaminocarbonyl, ethylaminocarbonyl, n-propylaminocarbonyl, i-propylaminocarbonyl and n-butylaminocarbonyl may be mentioned.

Examples of di-$C_{1-6}$ alkylaminocarbonyl group are such as dimethylaminocarbonyl, diethylaminocarbonyl, di-n-propylaminocarbonyl, di-i-propylaminocarbonyl, di-c-propylaminocarbonyl, di-n-butylaminocarbonyl, di-i-butylaminocarbonyl, di-s-butylaminocarbonyl, di-t-butylaminocarbonyl, di-c-butylaminocarbonyl, di-i-pentylaminocarbonyl, di-2-pentylaminocarbonyl, di-3-pentylaminocarbonyl, di-i-pentylaminocarbonyl, di-neopentylaminocarbonyl, di-t-pentylaminocarbonyl, di-c-pentylaminocarbonyl, di-i-hexylaminocarbonyl, di-2-hexylaminocarbonyl, di-3-hexylaminocarbonyl, di-c-hexylaminocarbonyl, di-(1-methyl-n-pentyl)aminocarbonyl, di-(1,1,2-trimethyl-n-propyl)aminocarbonyl, di-(1,2,2-trimethyl-n-propyl)aminocarbonyl, di-(3,3-dimethyl-n-butyl)aminocarbonyl, methyl(ethyl)aminocarbonyl, methyl(n-propyl)aminocarbonyl, methyl(i-propyl)aminocarbonyl, methyl(c-propyl)aminocarbonyl, methyl(n-butyl)aminocarbonyl, methyl(i-butyl)aminocarbonyl, methyl(s-butyl)aminocarbonyl, methyl(t-butyl)aminocarbonyl, methyl(c-butyl)aminocarbonyl, ethyl(n-propyl)aminocarbonyl, ethyl(i-propyl)aminocarbonyl, ethyl(c-propyl)aminocarbonyl, ethyl(n-butyl)aminocarbonyl, ethyl(i-butyl)aminocarbonyl, ethyl(s-butyl)aminocarbonyl, ethyl(t-butyl)aminocarbonyl, ethyl(c-butyl)aminocarbonyl, n-propyl(i-propyl)aminocarbonyl, n-propyl(c-propyl)aminocarbonyl, n-propyl(n-butyl)aminocarbonyl, n-propyl(i-butyl)aminocarbonyl, n-propyl(s-butyl)aminocarbonyl, n-propyl(t-butyl)aminocarbonyl, n-propyl(c-butyl)aminocarbonyl, i-propyl(c-propyl)aminocarbonyl, i-propyl(n-butyl)aminocarbonyl, i-propyl(i-butyl)aminocarbonyl, i-propyl(s-butyl)aminocarbonyl, i-propyl(t-butyl)aminocarbonyl, i-propyl(c-butyl)aminocarbonyl, c-propyl(n-butyl)aminocarbonyl, c-propyl(i-butyl)aminocarbonyl, c-propyl(s-butyl)aminocarbonyl, c-propyl(t-butyl)aminocarbonyl, c-propyl(c-butyl)aminocarbonyl, n-butyl(i-butyl)aminocarbonyl, n-butyl(s-butyl)aminocarbonyl, n-butyl(t-butyl)aminocarbonyl, n-butyl(c-butyl)aminocarbonyl, i-butyl(s-butyl)aminocarbonyl, i-butyl(t-butyl)aminocarbonyl, i-butyl(c-butyl)aminocarbonyl, i-butyl(c-butyl)aminocarbonyl, s-butyl(t-butyl)aminocarbonyl, s-butyl(c-butyl)aminocarbonyl, t-butyl(c-butyl)aminocarbonyl, and the like.

Preferably, dimethylaminocarbonyl, diethylaminocarbonyl, di-n-propylaminocarbonyl, di-i-propylaminocarbonyl, di-c-propylaminocarbonyl and di-n-butylaminocarbonyl may be mentioned.

Examples of $C_{1-6}$ alkylcarbonyl group are such as methylcarbonyl, ethylcarbonyl, n-propylcarbonyl, i-propylcarbonyl, n-butylcarbonyl, i-butylcarbonyl, s-butylcarbonyl, t-butylcarbonyl, 1-pentylcarbonyl, 2-pentylcarbonyl, 3-pentylcarbonyl, i-pentylcarbonyl, neopentylcarbonyl, t-pentylcarbonyl, 1-hexylcarbonyl, 2-hexylcarbonyl, 3-hexylcarbonyl and the like.

Preferably, methylcarbonyl, ethylcarbonyl, n-propylcarbonyl, i-propylcarbonyl and n-butylcarbonyl may be mentioned.

Examples of $C_{3-8}$ cycloalkylcarbonyl group are such as c-propylcarbonyl, c-butylcarbonyl, i-methyl-c-propylcarbonyl, 2-methyl-c-propylcarbonyl, c-pentylcarbonyl, 1-methyl-c-butylcarbonyl, 2-methyl-c-butylcarbonyl, 3-methyl-c-butylcarbonyl, 1,2-dimethyl-c-propylcarbonyl, 2,3-dimethyl-c-propylcarbonyl, 1-ethyl-c-propylcarbonyl, 2-ethyl-c-propylcarbonyl, c-hexylcarbonyl, c-heptylcarbonyl, c-octylcarbonyl, 1-methyl-c-hexylcarbonyl, 2-methyl-c-hexylcarbonyl, 3-methyl-c-hexylcarbonyl, 1,2-dimethyl-c-hexylcarbonyl, 2,3-dimethyl-c-propylcarbonyl, 1-ethyl-c-propylcarbonyl, 1-methyl-c-pentylcarbonyl, 2-methyl-c-pentylcarbonyl, 3-methyl-c-pentylcarbonyl, 1-ethyl-c-butylcarbonyl, 2-ethyl-c-butylcarbonyl, 3-ethyl-c-butylcarbonyl, 1,2-dimethyl-c-butylcarbonyl, 1,3-dimethyl-c-butylcarbonyl, 2,2-dimethyl-c-butylcarbonyl, 2,3-dimethyl-c-butylcarbonyl, 2,4-dimethyl-c-butylcarbonyl, 3,3-dimethyl-c-butylcarbonyl, 1-n-propyl-c-propylcarbonyl, 2-n-propyl-c-propylcarbonyl, 1-i-propyl-c-propylcarbonyl, 2-i-propyl-c-propylcarbonyl, 1,2,2-trimethyl-c-propylcarbonyl, 1,2,3-trimethyl-c-propylcarbonyl, 2,2,3-trimethyl-c-propylcarbonyl, 1-ethyl-2-methyl-c-propylcarbonyl, 2-ethyl-1-methyl-c-propylcarbonyl, 2-ethyl-2-methyl-c-propylcarbonyl, 2-ethyl-3-methyl-c-propylcarbonyl, and the like.

Preferably, c-pentylcarbonyl and c-hexylcarbonyl may be mentioned.

Examples of $C_{1-6}$ alkoxycarbonyl group are such as methoxycarbonyl, ethoxycarbonyl, n-propoxycarbonyl, i-propoxycarbonyl, n-butoxycarbonyl, i-butoxycarbonyl, s-butoxycarbonyl, t-butoxycarbonyl, 1-pentyloxycarbonyl, 2-pentyloxycarbonyl, 3-pentyloxycarbonyl, i-pentyloxycarbonyl, neopentyloxycarbonyl, t-pentyloxycarbonyl, 1-hexyloxycarbonyl, 2-hexyloxycarbonyl, 3-hexyloxycarbonyl and the like.

Preferably, methoxycarbonyl, ethoxycarbonyl, n-propoxycarbonyl, i-propoxycarbonyl, n-butoxycarbonyl, i-butoxycarbonyl, s-butoxycarbonyl and t-butoxycarbonyl may be mentioned.

Examples of $C_{1-6}$ alkylsulfonyl group are such as methanesulfonyl, ethanesulfonyl and the like.

Examples of $C_{6-14}$ arylcarbonyl group are such as phenylcarbonyl, o-biphenylylcarbonyl, m-biphenylylcarbonyl, p-biphenylylcarbonyl, □-naphthylcarbonyl, □-naphthylcarbonyl, 1-anthrylcarbonyl, 2-anthrylcarbonyl, 9-anthrylcarbonyl, 1-phenanthrylcarbonyl, 2-phenanthrylcarbonyl, 3-phenanthrylcarbonyl, 4-phenanthrylcarbonyl, 9-phenanthrylcarbonyl and the like.

Preferably, phenylcarbonyl, o-biphenylylcarbonyl, m-biphenylylcarbonyl, p-biphenylylcarbonyl, □-naphthylcarbonyl and □-naphthylcarbonyl may be mentioned.

$C_{2-9}$ heteroarylcarbonyl group includes $C_{2-6}$ single-ring heterocyclic carbonyl group with 5- to 7-member ring and $C_{5-9}$ fused double-ring heterocyclic carbonyl group with member atom number of 8 to 10, which may contain 1 to 3 hetero atoms selected from the group consisting of oxygen atom, nitrogen atom and sulfur atom alone or in a combination.

Examples of the $C_{2-6}$ single-ring heterocyclic carbonyl group with 5- to 7-member ring are such as 2-thienylcarbonyl group, 3-thienylcarbonyl group, 2-furylcarbonyl group, 3-furylcarbonyl group, 2-pyranylcarbonyl group, 3-pyranylcarbonyl group, 4-pyranylcarbonyl group, 1-pyrrolylcarbonyl group, 2-pyrrolylcarbonyl group, 3-pyrrolylcarbonyl group, 1-imidazolylcarbonyl group, 2-imidazolylcarbonyl group, 4-imidazolylcarbonyl group, 1-pyrazolylcarbonyl group, 3-pyrazolylcarbonyl group, 4-pyrazolylcarbonyl group, 2-thiazolylcarbonyl group, 4-thiazolylcarbonyl group, 5-thiazolylcarbonyl group, 3-isothiazolylcarbonyl group, 4-isothiazolylcarbonyl group, 5-isothiazolylcarbonyl group, 2-oxazolylcarbonyl group, 4-oxazolylcarbonyl group, 5-oxazolylcarbonyl group, 3-isooxazolylcarbonyl group, 4-isooxazolylcarbonyl group, 5-isooxazolylcarbonyl group, 2-pyridylcarbonyl group, 3-pyridylcarbonyl group, 4-pyridylcarbonyl group, 2-pyradinylcarbonyl group, 2-pyrimidinylcarbonyl group, 4-pyrimidinylcarbonyl group, 5-pyrimidinylcarbonyl group, 3-pyridazinylcarbonyl group, 4-pyridazinylcarbonyl group, 2-1,3,4-oxadiazolylcarbonyl group, 2-1,3,4-thiadiazolylcarbonyl group, 3-1,2,4-oxadiazolylcarbonyl group, 5-1,2,4-oxadiazolylcarbonyl group, 3-1,2,4-thiadiazolylcarbonyl group, 5-1,2,4-thiadiazolylcarbonyl group, 3-1,2,5-oxadiazolylcarbonyl group, 3-1,2,5-thiadiazolylcarbonyl group and the like.

Examples of the $C_{5-9}$ fused double-ring heterocyclic carbonyl group with member atom number of 8 to 10 are 2-benzofuranylcarbonyl group, 3-benzofuranylcarbonyl group, 4-benzofuranylcarbonyl group, 5-benzofuranylcarbonyl group, 6-benzofuranylcarbonyl group, 7-benzofuranylcarbonyl group, 1-isobenzofuranylcarbonyl group, 4-isobenzofuranylcarbonyl group, 5-isobenzofuranylcarbonyl group, 2-benzothienylcarbonyl group, 3-benzothienylcarbonyl group, 4-benzothienylcarbonyl group, 5-benzothienylcarbonyl group, 6-benzothienylcarbonyl group, 7-benzothienylcarbonyl group, 1-isobenzothienylcarbonyl group, 4-isobenzothienylcarbonyl group, 5-isobenzothienylcarbonyl group, 2-chromenylcarbonyl group, 3-chromenylcarbonyl group, 4-chromenylcarbonyl group, 5-chromenylcarbonyl group, 6-chromenylcarbonyl group, 7-chromenylcarbonyl group, 8-chromenylcarbonyl group, 1-indolizinylcarbonyl group, 2-indolizinylcarbonyl group, 3-indolizinylcarbonyl group, 5-indolizinylcarbonyl group, 6-indolizinylcarbonyl group, 7-indolizinylcarbonyl group, 8-indolizinylcarbonyl group, 1-isoindolylcarbonyl group, 2-isoindolylcarbonyl group, 4-isoindolylcarbonyl group, 5-isoindolylcarbonyl group, 1-indolylcarbonyl group, 2-indolylcarbonyl group, 3-indolylcarbonyl group, 4-indolylcarbonyl group, 5-indolylcarbonyl group, 6-indolylcarbonyl group, 7-indolylcarbonyl group, 1-indazolylcarbonyl group, 2-indazolylcarbonyl group, 3-indazolylcarbonyl group, 4-indazolylcarbonyl group, 5-indazolylcarbonyl group, 6-indazolylcarbonyl group, 7-indazolylcarbonyl group, 1-purinylcarbonyl group, 2-purinylcarbonyl group, 3-purinylcarbonyl group, 6-purinylcarbonyl group, 7-purinylcarbonyl group, 8-purinylcarbonyl group, 2-quinolylcarbonyl group, 3-quinolylcarbonyl group, 4-quinolylcarbonyl group, 5-quinolylcarbonyl group, 6-quinolylcarbonyl group, 7-quinolylcarbonyl group, 8-quinolylcarbonyl group, 1-isoquinolylcarbonyl group, 3-isoquinolylcarbonyl group, 4-isoquinolylcarbonyl group, 5-isoquinolylcarbonyl group, 6-isoquinolylcarbonyl group, 7-isoquinolylcarbonyl group, 8-isoquinolylcarbonyl group, 1-phthalazinylcarbonyl group, 5-phthalazinylcarbonyl group, 6-phthalazinylcarbonyl group, 1-2,7-naphthyridinylcarbonyl group, 3-2,7-naphthyridinylcarbonyl group, 4-2,7-naphthyridinylcarbonyl group, 1-2,6-naphthyridinylcarbonyl group, 3-2,6-naphthyridinylcarbonyl group, 4-2,6-naphthyridinylcarbonyl group, 2-1,8-naphthyridinylcarbonyl group, 3-1,8-naphthyridinylcarbonyl group, 4-1,8-naphthyridinylcarbonyl group, 2-1,7-naphthyridinylcarbonyl group, 3-1,7-naphthyridinylcarbonyl group, 4-1,7-naphthyridinylcarbonyl group, 5-1,7-naphthyridinylcarbonyl group, 6-1,7-naphthyridinylcarbonyl group, 8-1,7-naphthyridinylcarbonyl group, 2-1,6-naphthyridinylcarbonyl group, 3-1,6-naphthyridinylcarbonyl group, 4-1,6-naphthyridinylcarbonyl group, 5-1,6-naphthyridinylcarbonyl group, 7-1,6-naphthyridinylcarbonyl group, 8-1,6-naphthyridinylcarbonyl group, 2-1,5-naphthyridinylcarbonyl group, 3-1,5-naphthyridinylcarbonyl group, 4-1,5-naphthyridinylcarbonyl group, 6-1,5-naphthyridinylcarbonyl group, 7-1,5-naphthyridinylcarbonyl group, 8-1,5-naphthyridinylcarbonyl group, 2-quinoxalinylcarbonyl group, 5-quinoxalinylcarbonyl group, 6-quinoxalinylcarbonyl group, 2-quinazolinylcarbonyl group, 4-quinazolinylcarbonyl group, 5-quinazolinylcarbonyl group, 6-quinazolinylcarbonyl group, 7-quinazolinylcarbonyl group, 8-quinazolinylcarbonyl group, 3-cinnolinylcarbonyl group, 4-cinnolinylcarbonyl group, 5-cinnolinylcarbonyl group, 6-cinnolinylcarbonyl group, 7-cinnolinylcarbonyl group, 8-cinnolinylcarbonyl group, 2-pteridinylcarbonyl group, 4-pteridinylcarbonyl group, 6-pteridinylcarbonyl group, 7-pteridinylcarbonyl group, and the like.

Preferably, 2-pyridylcarbonyl group, 3-pyridylcarbonyl group and 4-pyridylcarbonyl group may be mentioned.

Examples of $C_{6-14}$ arylsulfonyl group are such as phenylsulfonyl, o-biphenylylsulfonyl, m-biphenylylsulfonyl, p-biphenylylsulfonyl, □-naphthylsulfonyl, □-naphthylsulfonyl, 1-anthrylsulfonyl, 2-anthrylsulfonyl, 9-anthrylsulfonyl, 1-phenanthrylsulfonyl, 2-phenanthrylsulfonyl, 3-phenanthrylsulfonyl, 4-phenanthrylsulfonyl, 9-phenanthrylsulfonyl and the like.

Preferably, phenylsulfonyl, o-biphenylylsulfonyl, m-biphenylylsulfonyl, p-biphenylylsulfonyl, □-naphthylsulfonyl and □-naphthylsulfonyl may be mentioned.

$C_{2-9}$ heteroarylsulfonyl group includes $C_{2-6}$ single-ring heterocyclic sulfonyl group with 5- to 7-member ring and $C_{5-9}$ fused double-ring heterocyclic sulfonyl group with member atom number of 8 to 10, which may contain 1 to 3 hetero atoms selected from the group consisting of oxygen atom, nitrogen atom and sulfur atom alone or in a combination.

Examples of the $C_{2-6}$ single-ring heterocyclic sulfonyl group with 5- to 7-member ring are such as 2-thienylsulfonyl group, 3-thienylsulfonyl group, 2-furylsulfonyl group, 3-furylsulfonyl group, 2-pyranylsulfonyl group, 3-pyranylsulfonyl group, 4-pyranylsulfonyl group, 1-pyrrolylsulfonyl group, 2-pyrrolylsulfonyl group, 3-pyrrolylsulfonyl group, 1-imidazolylsulfonyl group, 2-imidazolylsulfonyl group, 4-imidazolylsulfonyl group, 1-pyrazolylsulfonyl group, 3-pyrazolylsulfonyl group, 4-pyrazolylsulfonyl group, 2-thiazolylsulfonyl group, 4-thiazolylsulfonyl group, 5-thiazolylsulfonyl group, 3-isothiazolylsulfonyl group, 4-isothiazolylsulfonyl group, 5-isothiazolylsulfonyl group, 2-oxazolylsulfonyl group, 4-oxazolylsulfonyl group, 5-oxazolylsulfonyl group, 3-isooxazolylsulfonyl group, 4-isooxazolylsulfonyl group, 5-isooxazolylsulfonyl group, 2-pyridylsulfonyl group, 3-pyridylsulfonyl group, 4-pyridylsulfonyl group, 2-pyradinylsulfonyl group, 2-pyrimidinylsulfonyl group, 4-pyrimidinylsulfonyl group, 5-pyrimidinylsulfonyl group, 3-pyridazinylsulfonyl group, 4-pyridazinylsulfonyl group, 2-1,3,4-oxadiazolylsulfonyl group, 2-1,3,4-thiadiazolylsulfonyl group, 3-1,2,4-oxadiazolylsulfonyl group, 5-1,2,4-oxadiazolylsulfonyl group, 3-1,2,4-thiadiazolylsulfonyl group, 5-1,2,4-thiadiazolylsulfonyl group, 3-1,2,5-oxadiazolylsulfonyl group, 3-1,2,5-thiadiazolylsulfonyl group and the like.

Examples of the $C_{5-9}$ fused double-ring heterocyclic sulfonyl group with member atom number of 8 to 10 are 2-benzofuranylsulfonyl group, 3-benzofuranylsulfonyl group, 4-benzofuranylsulfonyl group, 5-benzofuranylsulfonyl group, 6-benzofuranylsulfonyl group, 7-benzofuranylsulfonyl group, 1-isobenzofuranylsulfonyl group, 4-isobenzofuranylsulfonyl group, 5-isobenzofuranylsulfonyl group, 2-benzothienylsulfonyl group, 3-benzothienylsulfonyl group, 4-benzothienylsulfonyl group, 5-benzothienylsulfonyl group, 6-benzothienylsulfonyl group, 7-benzothienylsulfonyl group, 1-isobenzothienylsulfonyl group, 4-isobenzothienylsulfonyl group, 5-isobenzothienylsulfonyl group, 2-chromenylsulfonyl group, 3-chromenylsulfonyl group, 4-chromenylsulfonyl group, 5-chromenylsulfonyl group, 6-chromenylsulfonyl group, 7-chromenylsulfonyl group, 8-chromenylsulfonyl group, 1-indolizinylsulfonyl group, 2-indolizinylsulfonyl group, 3-indolizinylsulfonyl group, 5-indolizinylsulfonyl group, 6-indolizinylsulfonyl group, 7-indolizinylsulfonyl group, 8-indolizinylsulfonyl group, 1-isoindolylsulfonyl group, 2-isoindolylsulfonyl group, 4-isoindolylsulfonyl group, 5-isoindolylsulfonyl group, 1-indolylsulfonyl group, 2-indolylsulfonyl group, 3-indolylsulfonyl group, 4-indolylsulfonyl group, 5-indolylsulfonyl group, 6-indolylsulfonyl group, 7-indolylsulfonyl group, 1-indazolylsulfonyl group, 2-indazolylsulfonyl group, 3-indazolylsulfonyl group, 4-indazolylsulfonyl group, 5-indazolylsulfonyl group, 6-indazolylsulfonyl group, 7-indazolylsulfonyl group, 1-purinylsulfonyl group, 2-purinylsulfonyl group, 3-purinylsulfonyl group, 6-purinylsulfonyl group, 7-purinylsulfonyl group, 8-purinylsulfonyl group, 2-quinolylsulfonyl group, 3-quinolylsulfonyl group, 4-quinolylsulfonyl group, 5-quinolylsulfonyl group, 6-quinolylsulfonyl group, 7-quinolylsulfonyl group, 8-quinolylsulfonyl group, 1-isoquinolylsulfonyl group, 3-isoquinolylsulfonyl group, 4-isoquinolylsulfonyl group, 5-isoquinolylsulfonyl group, 6-isoquinolylsulfonyl group, 7-isoquinolylsulfonyl group, 8-isoquinolylsulfonyl group, 1-phthalazinylsulfonyl group, 5-phthalazinylsulfonyl group, 6-phthalazinylsulfonyl group, 1-2,7-naphthyridinylsulfonyl group, 3-2,7-naphthyridinylsulfonyl group, 4-2,7-naphthyridinylsulfonyl group, 1-2,6-naphthyridinylsulfonyl group, 3-2,6-naphthyridinylsulfonyl group, 4-2,6-naphthyridinylsulfonyl group, 2-1,8-naphthyridinylsulfonyl group, 3-1,8-naphthyridinylsulfonyl group, 4-1,8-naphthyridinylsulfonyl group, 2-1,7-naphthyridinylsulfonyl group, 3-1,7-naphthyridinylsulfonyl group, 4-1,7-naphthyridinylsulfonyl group, 5-1,7-naphthyridinylsulfonyl group, 6-1,7-naphthyridinylsulfonyl group, 8-1,7-naphthyridinylsulfonyl group, 2-1,6-naphthyridinylsulfonyl group, 3-1,6-naphthyridinylsulfonyl group, 4-1,6-naphthyridinylsulfonyl group, 5-1,6-naphthyridinylsulfonyl group, 7-1,6-naphthyridinylsulfonyl group, 8-1,6-naphthyridinylsulfonyl group, 2-1,5-naphthyridinylsulfonyl group, 3-1,5-naphthyridinylsulfonyl group, 4-1,5-naphthyridinylsulfonyl group, 6-1,5-naphthyridinylsulfonyl group, 7-1,5-naphthyridinylsulfonyl group, 8-1,5-naphthyridinylsulfonyl group, 2-quinoxalinylsulfonyl group, 5-quinoxalinylsulfonyl group, 6-quinoxalinylsulfonyl group, 2-quinazolinylsulfonyl group, 4-quinazolinylsulfonyl group, 5-quinazolinylsulfonyl group, 6-quinazolinylsulfonyl group, 7-quinazolinylsulfonyl group, 8-quinazolinylsulfonyl group, 3-cinnolinylsulfonyl group, 4-cinnolinylsulfonyl group, 5-cinnolinylsulfonyl group, 6-cinnolinylsulfonyl group, 7-cinnolinylsulfonyl group, 8-cinnolinylsulfonyl group, 2-pteridinylsulfonyl group, 4-pteridinylsulfonyl group, 6-pteridinylsulfonyl group, 7-pteridinylsulfonyl group, and the like.

Preferably, 2-pyridylsulfonyl group, 3-pyridylsulfonyl group and 4-pyridylsulfonyl group may be mentioned.

Examples of $C_{6-14}$ arylamino group are such as phenylamino, o-biphenylylamino, m-biphenylylamino, p-biphenylylamino, □-naphthylamino, □-naphthylamino, 1-anthrylamino, 2-anthrylamino, 9-anthrylamino, 1-phenanthrylamino, 2-phenanthrylamino, 3-phenanthrylamino, 4-phenanthrylamino, 9-phenanthrylamino and the like.

Preferably, phenylamino, o-biphenylylamino, m-biphenylylamino, p-biphenylylamino, □-naphthylamino and □-naphthylamino may be mentioned.

$C_{2-9}$ heteroarylamino group includes $C_{2-6}$ single-ring heterocyclic amino group with 5- to 7-member ring and $C_{5-9}$ fused double-ring heterocyclic amino group with member atom number of 8 to 10, which may contain 1 to 3 hetero atoms selected from the group consisting of oxygen atom, nitrogen atom and sulfur atom alone or in a combination.

Examples of the $C_{2-6}$ single-ring heterocyclic amino group with 5- to 7-member ring are such as 2-thienylamino group, 3-thienylamino group, 2-furylamino group, 3-furylamino group, 2-pyranylamino group, 3-pyranylamino group, 4-pyranylamino group, 1-pyrrolylamino group, 2-pyrrolylamino group, 3-pyrrolylamino group, 1-imidazolylamino group, 2-imidazolylamino group, 4-imidazolylamino group, 1-pyrazolylamino group, 3-pyrazolylamino group, 4-pyrazolylamino group, 2-thiazolylamino group, 4-thiazolylamino group, 5-thiazolylamino group, 3-isothiazolylamino group, 4-isothiazolylamino group, 5-isothiazolylamino group, 2-oxazolylamino group, 4-oxazolylamino group, 5-oxazolylamino group, 3-isooxazolylamino group, 4-isooxazolylamino group, 5-isooxazolylamino group, 2-pyridylamino group, 3-pyridylamino group, 4-pyridylamino group, 2-pyradinylamino group, 2-pyrimidinylamino group, 4-pyrimidinylamino group, 5-pyrimidinylamino group, 3-pyridazinylamino group, 4-pyridazinylamino group, 2-1,3,4-oxadiazolylamino group, 2-1,3,4-thiadiazolylamino group, 3-1,2,4-oxadiazolylamino group, 5-1,2,4-oxadiazolylamino group, 3-1,2,4-thiadiazolylamino group, 5-1,2,4-thiadiazolylamino group, 3-1,2,5-oxadiazolylamino group, 3-1,2,5-thiadiazolylamino group and the like.

Examples of the $C_{5-9}$ fused double-ring heterocyclic amino group with member atom number of 8 to 10 are 2-benzofuranylamino group, 3-benzofuranylamino group, 4-benzofuranylamino group, 5-benzofuranylamino group, 6-benzofuranylamino group, 7-benzofuranylamino group, 1-isobenzofuranylamino group, 4-isobenzofuranylamino group, 5-isobenzofuranylamino group, 2-benzothienylamino group, 3-benzothienylamino group, 4-benzothienylamino group, 5-benzothienylamino group, 6-benzothienylamino group, 7-benzothienylamino group, 1-isobenzothienylamino group, 4-isobenzothienylamino group, 5-isobenzothienylamino group, 2-chromenylamino group, 3-chromenylamino group, 4-chromenylamino group, 5-chromenylamino group, 6-chromenylamino group, 7-chromenylamino group, 8-chromenylamino group, 1-indolizinylamino group, 2-indolizinylamino group, 3-indolizinylamino group, 5-indolizinylamino group, 6-indolizinylamino group, 7-indolizinylamino group, 8-indolizinylamino group, 1-isoindolylamino group, 2-isoindolylamino group, 4-isoindolylamino group, 5-isoindolylamino group, 1-indolylamino group, 2-indolylamino group, 3-indolylamino group, 4-indolylamino group, 5-indolylamino group, 6-indolylamino group, 7-indolylamino group, 1-indazolylamino group, 2-indazolylamino group, 3-indazolylamino group, 4-indazolylamino group, 5-indazolylamino group, 6-indazolylamino group, 7-indazolylamino group, 1-purinylamino group, 2-purinylamino group, 3-purinylamino group, 6-purinylamino group, 7-purinylamino group, 8-purinylamino group, 2-quinolylamino group, 3-quinolylamino group, 4-quinolylamino group, 5-quinolylamino group, 6-quinolylamino group, 7-quinolylamino group, 8-quinolylamino group, 1-isoquinolylamino group, 3-isoquinolylamino group, 4-isoquinolylamino group, 5-isoquinolylamino group, 6-isoquinolylamino group, 7-isoquinolylamino group, 8-isoquinolylamino group, 1-phthalazinylamino group, 5-phthalazinylamino group, 6-phthalazinylamino group, 1-2,7-naphthyridinylamino group, 3-2,7-naphthyridinylamino group, 4-2,7-naphthyridinylamino group, 1-2,6-naphthyridinylamino group, 3-2,6-naphthyridinylamino group, 4-2,6-naphthyridinylamino group, 2-1,8-naphthyridinylamino group, 3-1,8-naphthyridinylamino group, 4-1,8-naphthyridinylamino group, 2-1,7-naphthyridinylamino group, 3-1,7-naphthyridinylamino group, 4-1,7-naphthyridinylamino group, 5-1,7-naphthyridinylamino group, 6-1,7-naphthyridinylamino group, 8-1,7-naphthyridinylamino group, 2-1,6-naphthyridinylamino group, 3-1,6-naphthyridinylamino group, 4-1,6-naphthyridinylamino group, 5-1,6-naphthyridinylamino group, 7-1,6-naphthyridinylamino group, 8-1,6-naphthyridinylamino group, 2-1,5-naphthyridinylamino group, 3-1,5-naphthyridinylamino group, 4-1,5-naphthyridinylamino group, 6-1,5-naphthyridinylamino group, 7-1,5-naphthyridinylamino group, 8-1,5-naphthyridinylamino group, 2-quinoxalinylamino group, 5-quinoxalinylamino group, 6-quinoxalinylamino group, 2-quinazolinylamino group, 4-quinazolinylamino group, 5-quinazolinylamino group, 6-quinazolinylamino group, 7-quinazolinylamino group, 8-quinazolinylamino group, 3-cinnolinylamino group, 4-cinnolinylamino group, 5-cinnolinylamino group, 6-cinnolinylamino group, 7-cinnolinylamino group, 8-cinnolinylamino group, 2-pteridinylamino group, 4-pteridinylamino group, 6-pteridinylamino group, 7-pteridinylamino group, and the like.

Preferably, 2-pyridylamino group, 3-pyridylamino group and 4-pyridylamino group may be mentioned.

Concrete examples of substituents on the compounds used in the present invention are as follows.

Concrete examples of $R^1$ and $R^2$ are preferably methyl.

Concrete examples of $R^3$ are preferably hydroxy group.

Concrete examples of $R^4$ are preferably hydrogen atom.

Concrete examples of $R^5$ are preferably hydrogen atom.

Concrete examples of $-N-(CH_2)_m-V-(CH_2)_n-R^6$ are preferably the following 1) to 4).

1)

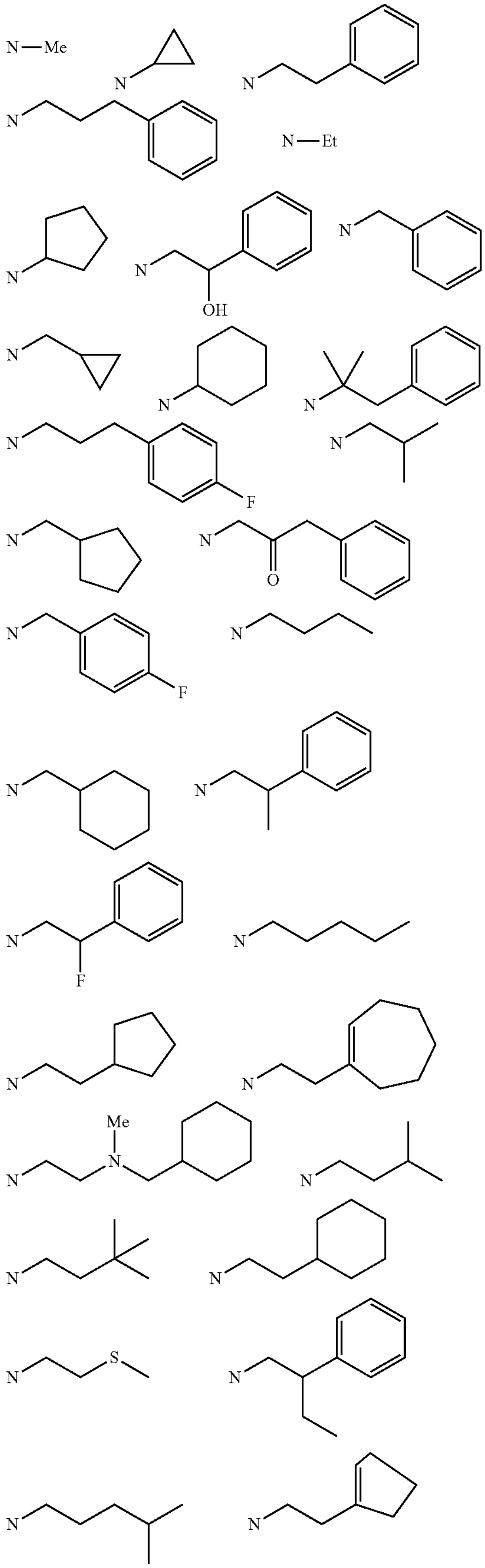

-continued
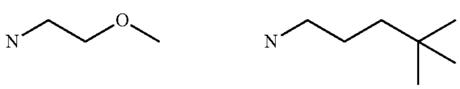
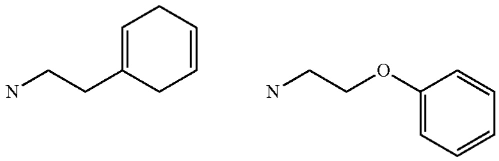
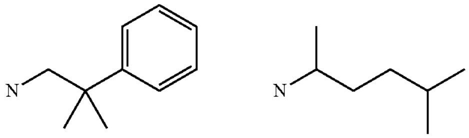
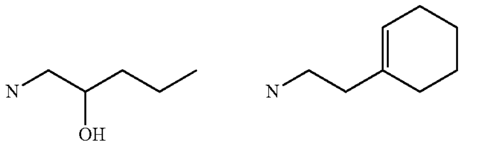
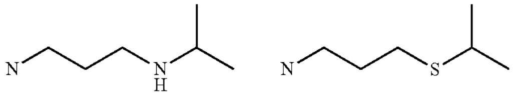
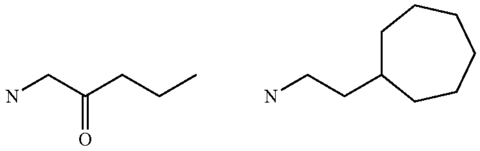
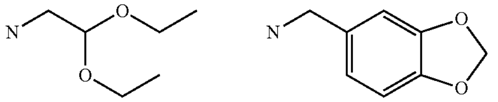
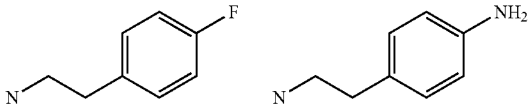
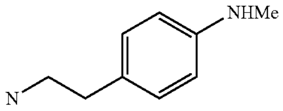
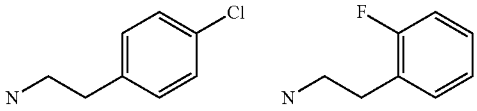
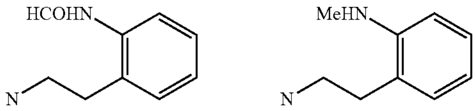
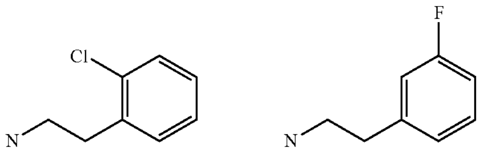
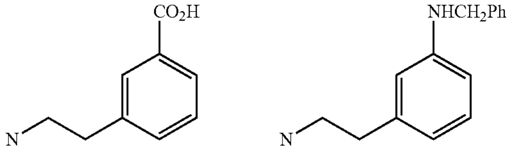
-continued
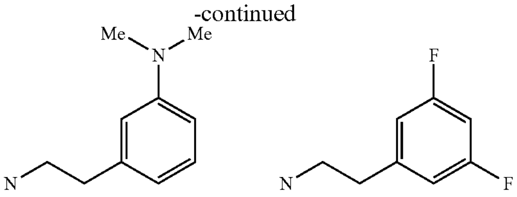
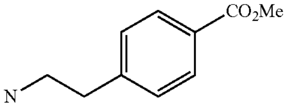
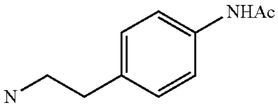
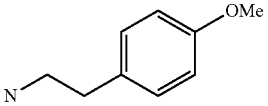
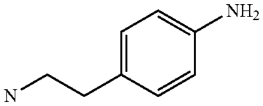
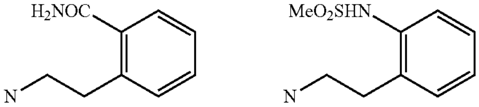
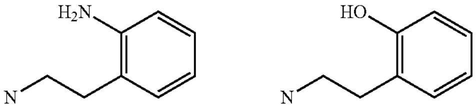
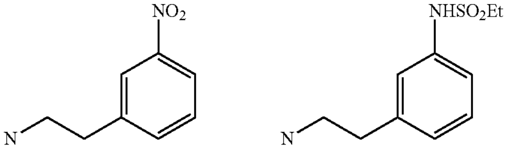
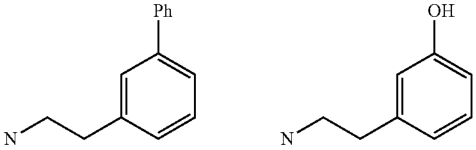
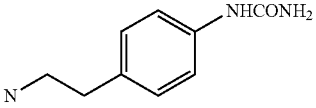
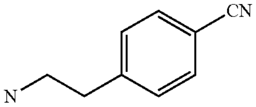
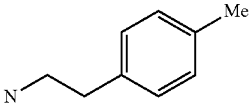
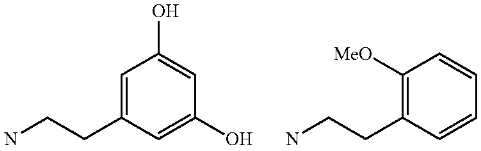
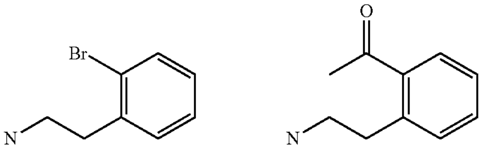

-continued
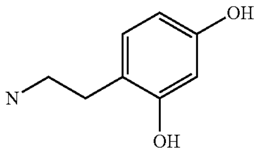
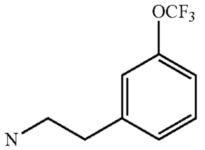
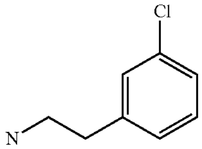
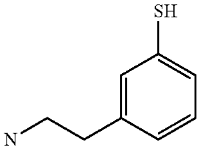
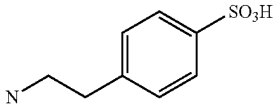
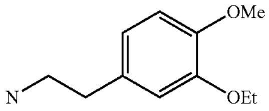
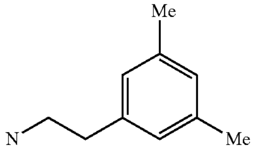
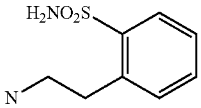
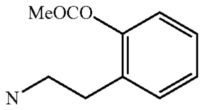
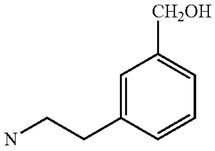
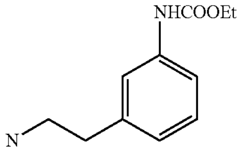
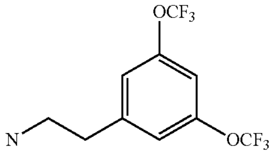
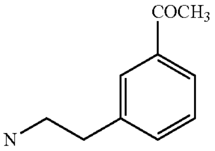
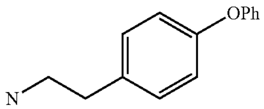
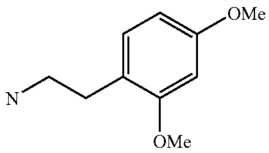
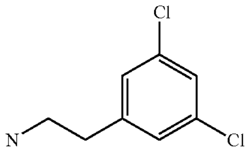
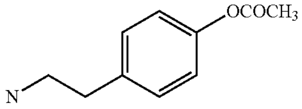
-continued
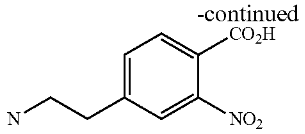
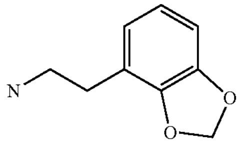
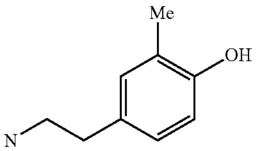
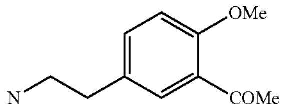
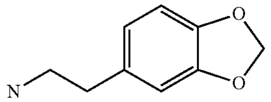
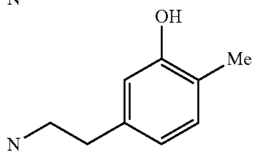
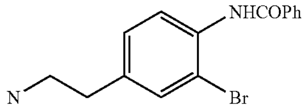
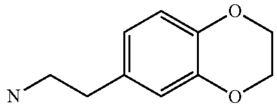
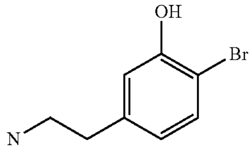
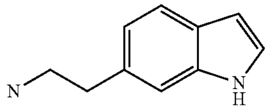
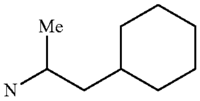
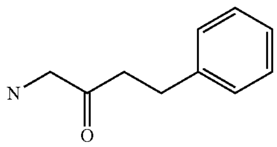
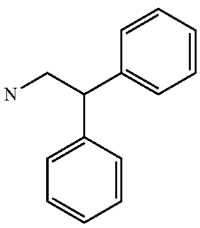
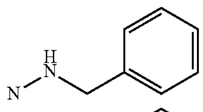
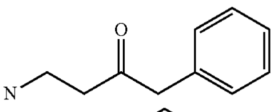
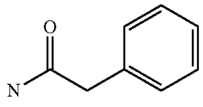
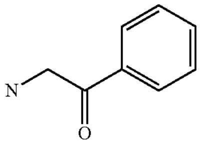
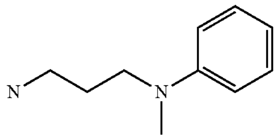

-continued
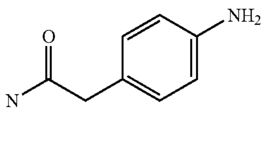
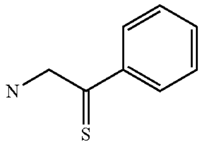
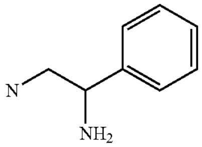
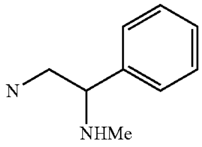
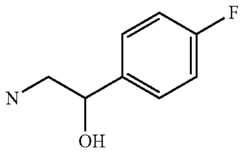
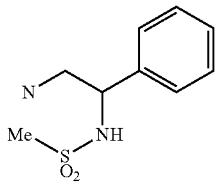
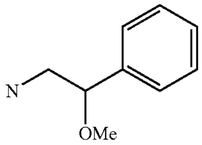
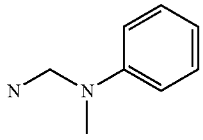
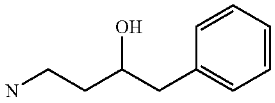
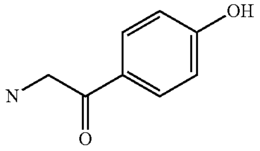
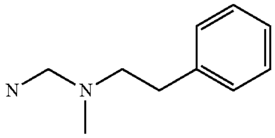
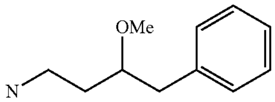
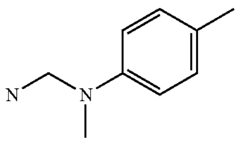
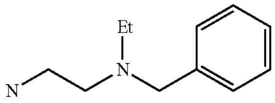
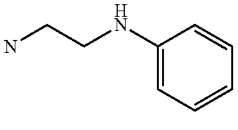
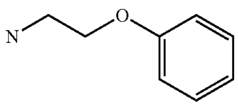
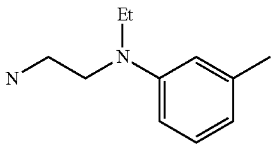
-continued
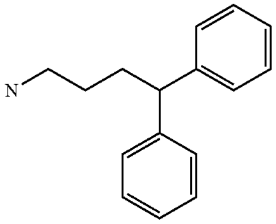
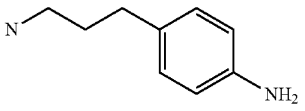
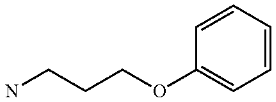
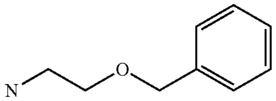
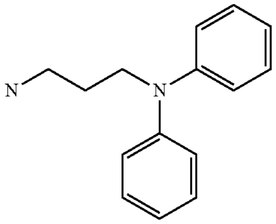
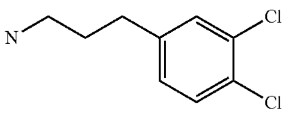
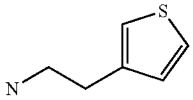
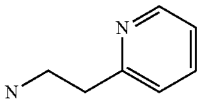
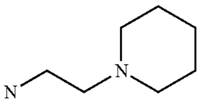
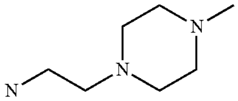
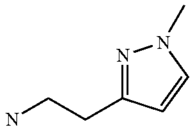
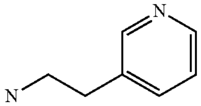
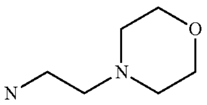
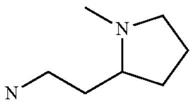
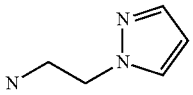
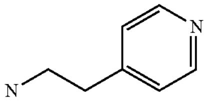
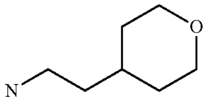
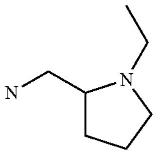
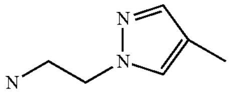
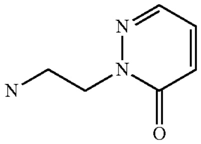
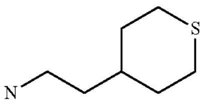

-continued
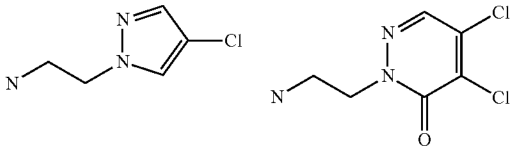
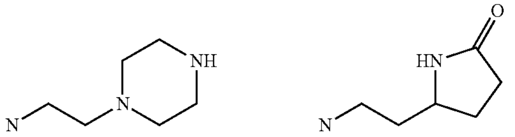
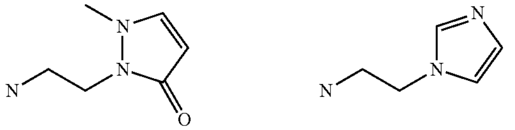
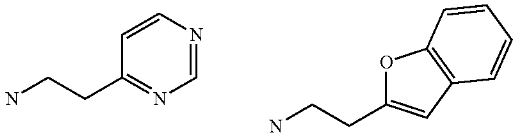
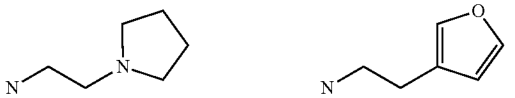
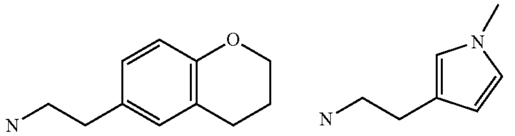
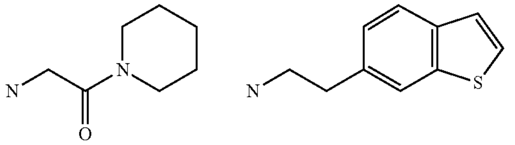
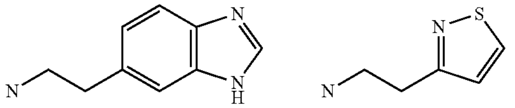
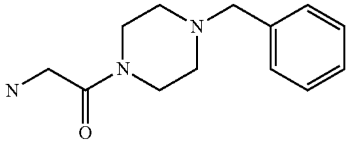
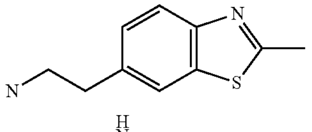
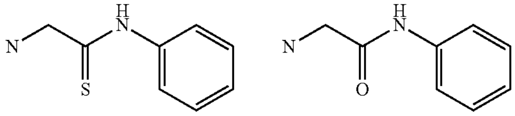
2)
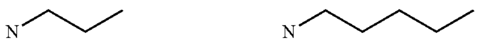
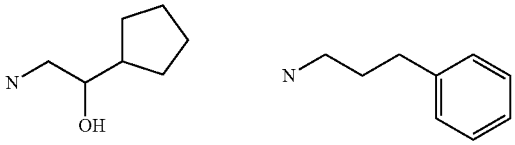
-continued
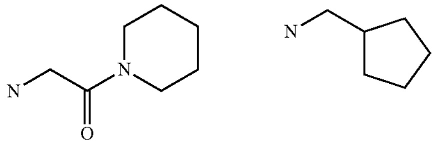
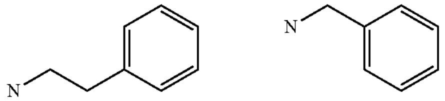
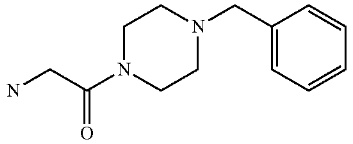
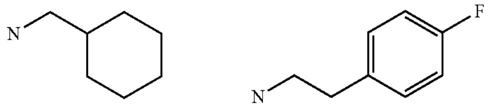
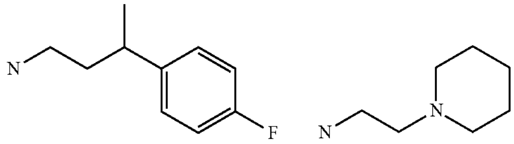
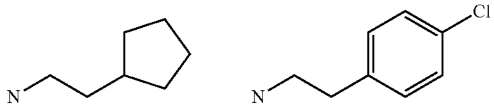
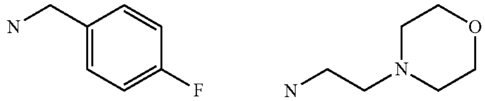
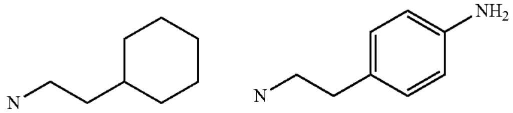
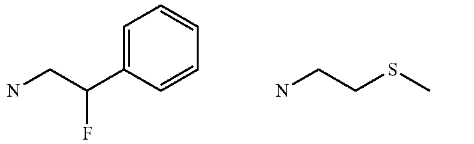
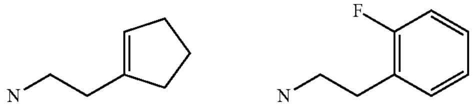
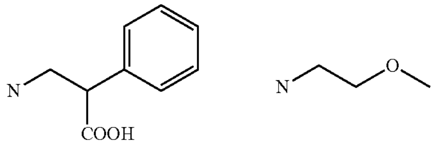
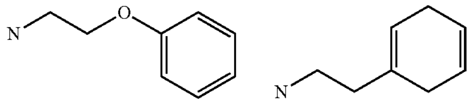
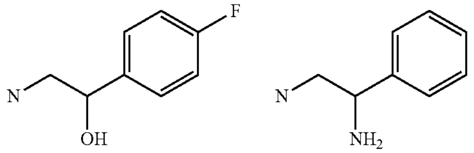
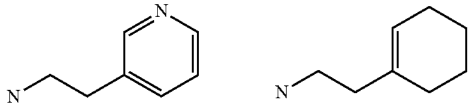

-continued
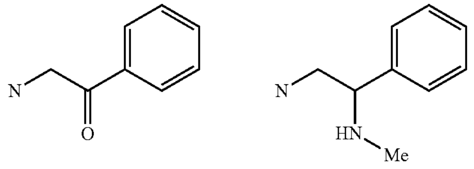
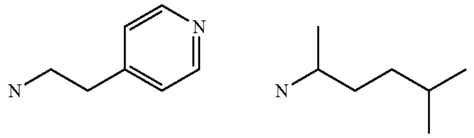
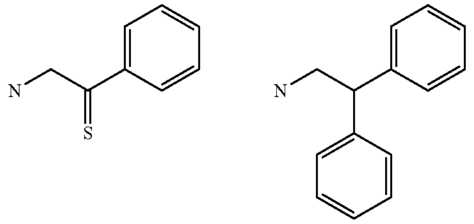
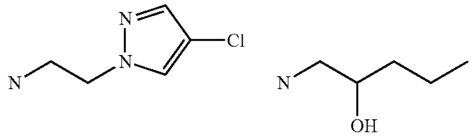
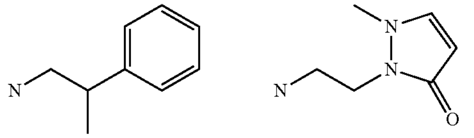
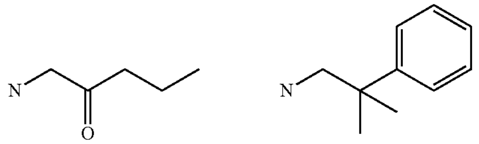
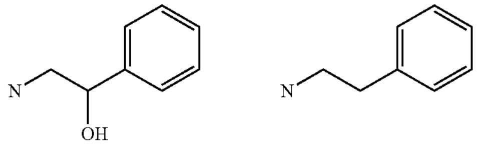
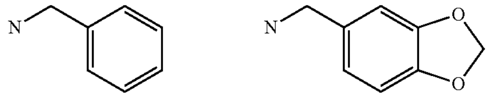
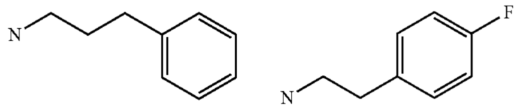
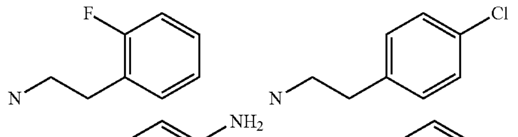
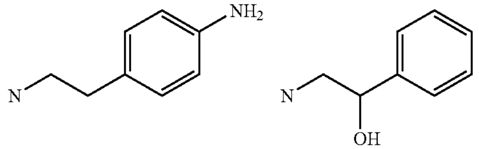
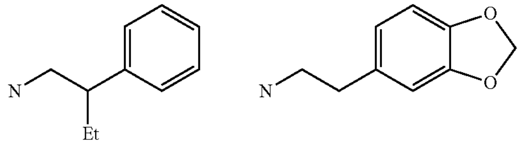
-continued
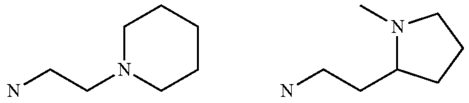
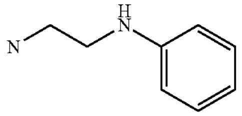
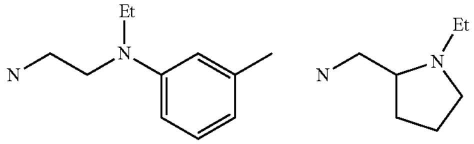
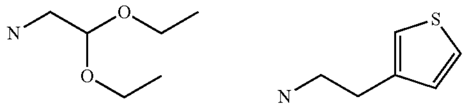
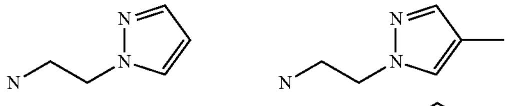
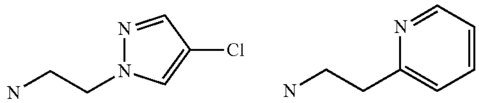
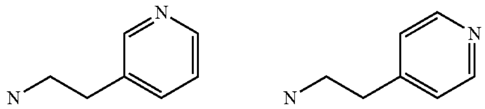
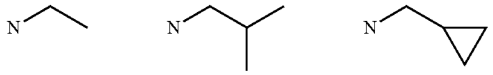
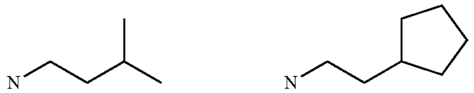
3)
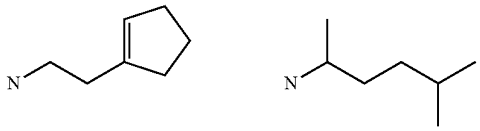
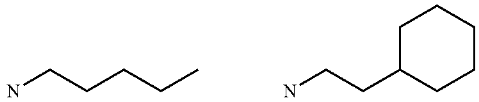
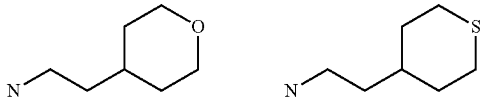
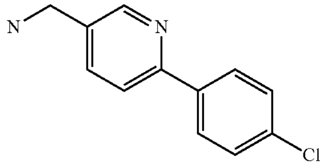
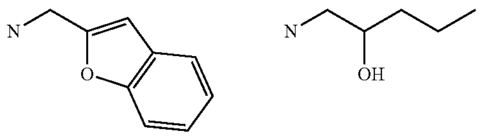
4)
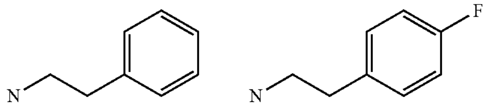

-continued
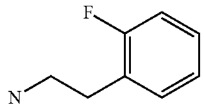
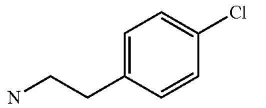
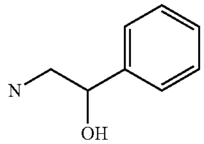
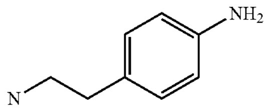
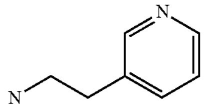
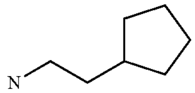
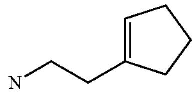
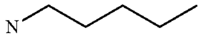
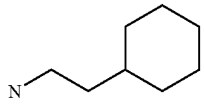
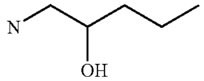
Concrete examples of A are preferably the following 1) and 2).
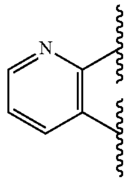
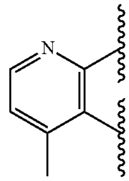
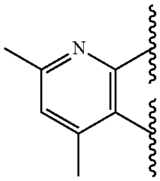
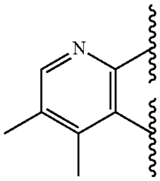
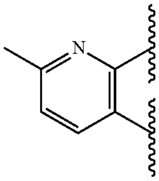
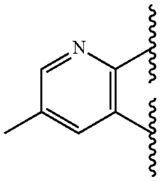
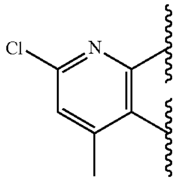
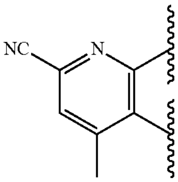
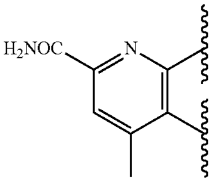
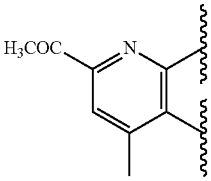
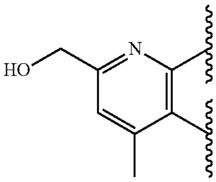
-continued
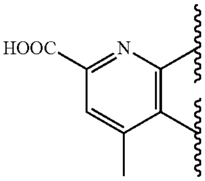
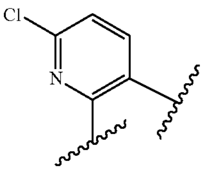
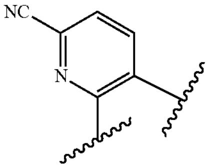
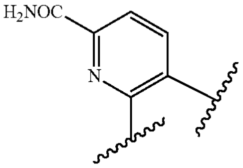
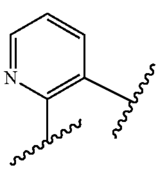
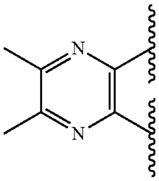
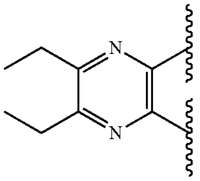
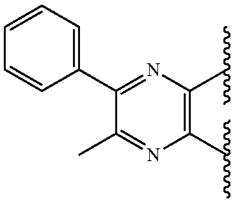
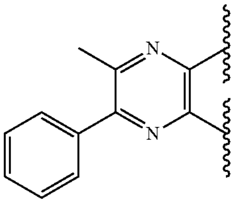
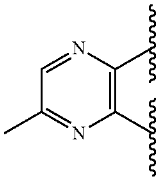
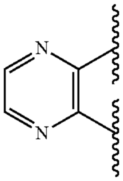
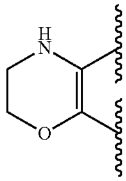
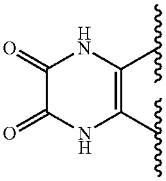
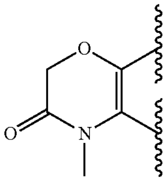
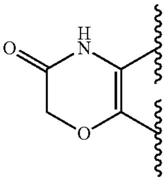
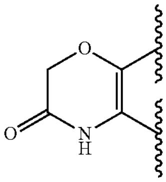
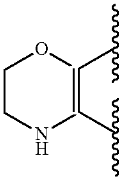
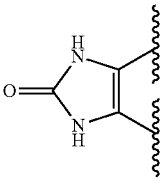

-continued

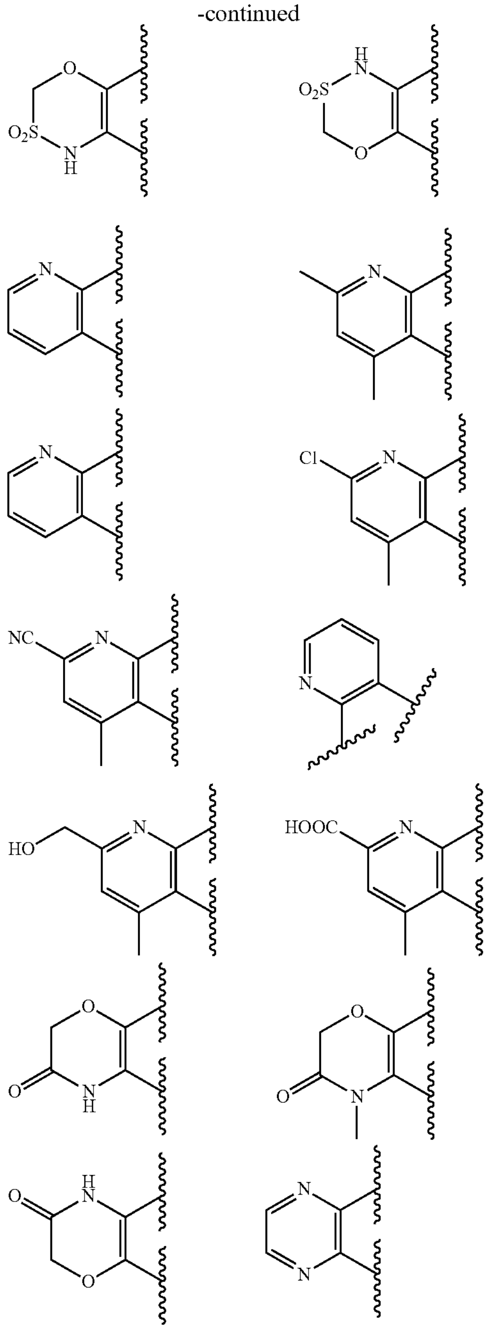

The preferable compounds used in the present invention include the followings:

(1) A benzopyran derivative of formula (I) or (II), or pharmaceutically acceptable salt thereof, wherein both $R^1$ and $R^2$ are methyl, $R^3$ is hydroxy group, and $R^4$ is hydrogen atom;

(2) The benzopyran derivative or pharmaceutically acceptable salt thereof as set forth in (1), which is the compound of formula (I);

(3) The benzopyran derivative or pharmaceutically acceptable salt thereof as set forth in (2), wherein V is a bond, m is an integer of 1 to 3, n is 0 or 1 and $R^6$ is benzene ring;

(4) The benzopyran derivative or pharmaceutically acceptable salt thereof as set forth in (3), wherein V is $CR^7R^8$ wherein $R^7$ is hydroxy group and $R^8$ is hydrogen atom, and m is 0 or 1;

(5) The benzopyran derivative or pharmaceutically acceptable salt thereof as set forth in (3), wherein $R^6$ is alkyl group, cycloalkyl group or cycloalkenyl ring;

(6) The benzopyran derivative or pharmaceutically acceptable salt thereof as set forth in (5), wherein V is $CR^7R^8$ wherein $R^7$ is hydroxy group and $R^8$ is hydrogen atom, and m is 0 or 1;

(7) The benzopyran derivative or pharmaceutically acceptable salt thereof as set forth in (3), wherein A is the group of formula (VIII)

Formula (VIII)

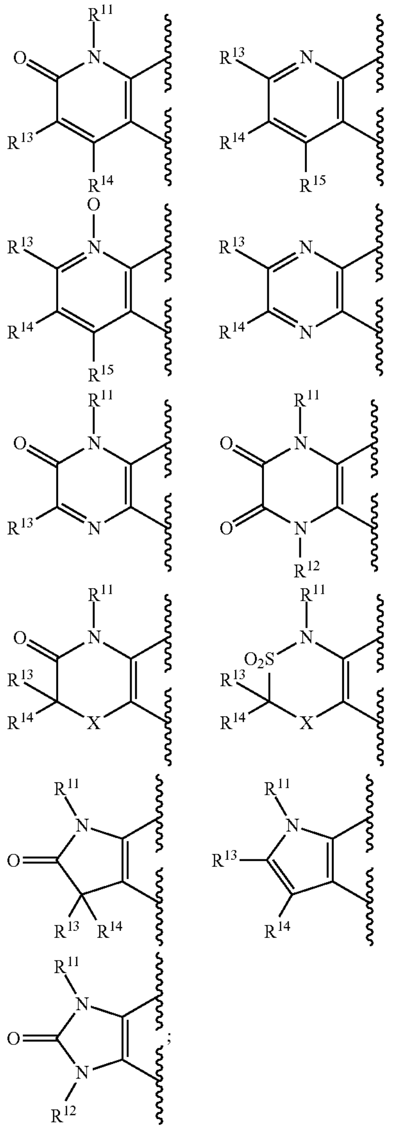

;

(8) The benzopyran derivative or pharmaceutically acceptable salt thereof as set forth in (4), wherein A is the group of formula (VIII);

(9) The benzopyran derivative or pharmaceutically acceptable salt thereof as set forth in (5), wherein A is the group of formula (VIII);

(10) The benzopyran derivative or pharmaceutically acceptable salt thereof as set forth in (6), wherein A is the group of formula (VIII);

Hereinafter, concrete examples of the compounds that can be used in the present invention are shown, but the present invention is not limited thereto. In the meanwhile, "Me" means methyl, "Et" means ethyl, "Pr" means propyl, "Bu" means butyl, "Ac" means acetyl ($COCH_3$), and "-" means a bond.

| $R^{11}$ | $R^{13}$ | $R^{14}$ | $R^{11}$ | $R^{13}$ | $R^{14}$ | $R^{11}$ | $R^{13}$ | $R^{14}$ |
|---|---|---|---|---|---|---|---|---|
| 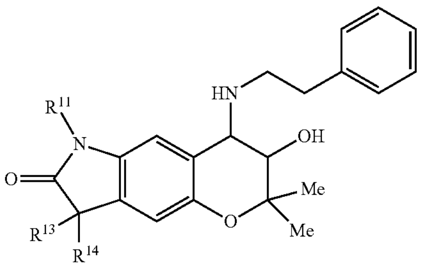 | | | | | | | | |
| H | H | Et | H | $NO_2$ | H | H | H | $NO_2$ |
| H | H | iPr | H | CHO | H | H | H | CHO |
| H | H | nPr | H | $SO_3H$ | H | H | H | $SO_3H$ |
| H | H | nBu | H | Cl | H | H | H | Cl |
| H | H | tBu | H | Br | H | H | H | Br |
| Me | H | Ph | Me | $CH_2OH$ | H | Me | H | $CH_2OH$ |
| Me | Et | Ph | Me | $CH_2NH_2$ | H | Me | H | $CH_2NH_2$ |
| Me | iPr | H | Me | $CH_2NHMe$ | H | Me | H | $CH_2NHMe$ |
| Me | nPr | H | Me | $CH_2Ph$ | H | Me | H | $CH_2Ph$ |
| Me | nBu | H | Me | COMe | H | Me | H | COMe |
| Me | tBu | H | Me | COOH | H | Me | H | COOH |
| Et | Ph | H | Et | $CONH_2$ | H | Et | H | $CONH_2$ |
| Et | H | Et | Et | CONHMe | Et | Et | Et | CONHMe |
| Et | H | iPr | Et | CONHMs | iPr | Et | iPr | CONHMs |
| iPr | H | nPr | iPr | NHMs | nPr | iPr | nPr | NHMs |
| nPr | H | nBu | nPr | NHCOMe | nBu | nPr | nBu | NHCOMe |
| nBu | H | tBu | nBu | $NO_2$ | tBu | nBu | tBu | $NO_2$ |
| tBu | H | Ph | tBu | CHO | Ph | tBu | Ph | H |
| Ph | Cl | Et | Ph | $SO_3H$ | Et | Ph | Et | H |
| $CH_2OH$ | Cl | nPr | $CH_2OH$ | $SO_2NHMe$ | nPr | $CH_2OH$ | nPr | H |
| $CH_2OH$ | Cl | Ph | $CH_2OH$ | OH | Ph | $CH_2OH$ | Ph | H |
| $CH_2OMe$ | Et | Cl | $CH_2OMe$ | COMe | Cl | $CH_2OMe$ | Cl | Cl |
| $CH_2OMe$ | nPr | Cl | $CH_2OMe$ | COOH | Cl | $CH_2OMe$ | Cl | Cl |
| $CH_2NH_2$ | Ph | Cl | $CH_2NH_2$ | $CONH_2$ | Cl | $CH_2NH_2$ | Cl | Cl |
| $CH_2NH_2$ | H | Et | $CH_2NH_2$ | CONHMe | Et | $CH_2NH_2$ | Et | H |
| $CH_2NH_2$ | H | nPr | $CH_2NH_2$ | CONHMs | nPr | $CH_2NH_2$ | nPr | H |
| $CH_2NH_2$ | H | Ph | $CH_2NH_2$ | NHMs | Ph | $CH_2NH_2$ | Ph | H |
| $CH_2NHMe$ | Me | Me | $CH_2NHMe$ | $NO_2$ | Me | $CH_2NHMe$ | Me | H |
| $CH_2Ph$ | Et | Et | $CH_2Ph$ | OH | Et | $CH_2Ph$ | Et | H |
| $CH_2Ph$ | nPr | nPr | $CH_2Ph$ | COMe | nPr | $CH_2Ph$ | nPr | H |
| $CH_2CH_2Ph$ | Ph | Ph | $CH_2CH_2Ph$ | COOH | Ph | $CH_2CH_2Ph$ | Ph | H |
| 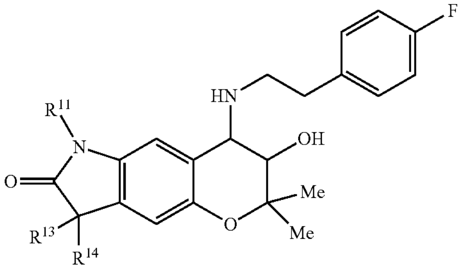 | | | | | | | | |
| H | H | Et | H | $NO_2$ | H | H | H | $NO_2$ |
| H | H | iPr | H | CHO | H | H | H | CHO |
| H | H | nPr | H | $SO_3H$ | H | H | H | $SO_3H$ |
| H | H | nBu | H | Cl | H | H | H | Cl |
| H | H | tBu | H | Br | H | H | H | Br |
| Me | H | Ph | Me | $CH_2OH$ | H | Me | H | $CH_2OH$ |
| Me | Et | Ph | Me | $CH_2NH_2$ | H | Me | H | $CH_2NH_2$ |
| Me | iPr | H | Me | $CH_2NHMe$ | H | Me | H | $CH_2NHMe$ |
| Me | nPr | H | Me | $CH_2Ph$ | H | Me | H | $CH_2Ph$ |
| Me | nBu | H | Me | COMe | H | Me | H | COMe |
| Me | tBu | H | Me | COOH | H | Me | H | COOH |
| Et | Ph | H | Et | $CONH_2$ | H | Et | H | $CONH_2$ |
| Et | H | Et | Et | CONHMe | Et | Et | Et | CONHMe |

-continued

| $R^{11}$ | $R^{13}$ | $R^{14}$ | $R^{11}$ | $R^{13}$ | $R^{14}$ | $R^{11}$ | $R^{13}$ | $R^{14}$ |
|---|---|---|---|---|---|---|---|---|
| Et | H | iPr | Et | CONHMs | iPr | Et | iPr | CONHMs |
| iPr | H | nPr | iPr | NHMs | nPr | iPr | nPr | NHMs |
| nPr | H | nBu | nPr | NHCOMe | nBu | nPr | nBu | NHCOMe |
| nBu | H | tBu | nBu | $NO_2$ | tBu | nBu | tBu | $NO_2$ |
| tBu | H | Ph | tBu | CHO | Ph | tBu | Ph | H |
| Ph | Cl | Et | Ph | $SO_3H$ | Et | Ph | Et | H |
| $CH_2OH$ | Cl | nPr | $CH_2OH$ | $SO_2NHMe$ | nPr | $CH_2OH$ | nPr | H |
| $CH_2OH$ | Cl | Ph | $CH_2OH$ | OH | Ph | $CH_2OH$ | Ph | H |
| $CH_2OMe$ | Et | Cl | $CH_2OMe$ | COMe | Cl | $CH_2OMe$ | Cl | Cl |
| $CH_2OMe$ | nPr | Cl | $CH_2OMe$ | COOH | Cl | $CH_2OMe$ | Cl | Cl |
| $CH_2NH_2$ | Ph | Cl | $CH_2NH_2$ | $CONH_2$ | Cl | $CH_2NH_2$ | Cl | Cl |
| $CH_2NH_2$ | H | Et | $CH_2NH_2$ | CONHMe | Et | $CH_2NH_2$ | Et | H |
| $CH_2NH_2$ | H | nPr | $CH_2NH_2$ | CONHMs | nPr | $CH_2NH_2$ | nPr | H |
| $CH_2NH_2$ | H | Ph | $CH_2NH_2$ | NHMs | Ph | $CH_2NH_2$ | Ph | H |
| $CH_2NHMe$ | Me | Me | $CH_2NHMe$ | $NO_2$ | Me | $CH_2NHMe$ | Me | H |
| $CH_2Ph$ | Et | Et | $CH_2Ph$ | OH | Et | $CH_2Ph$ | Et | H |
| $CH_2Ph$ | nPr | nPr | $CH_2Ph$ | COMe | nPr | $CH_2Ph$ | H | H |
| $CH_2CH_2Ph$ | Ph | Ph | $CH_2CH_2Ph$ | COOH | Ph | $CH_2CH_2Ph$ | Ph | H |

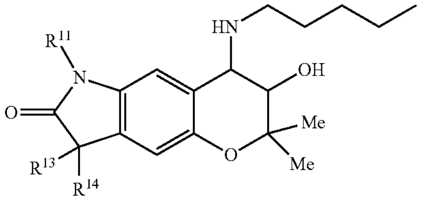

| | | | | | | | | |
|---|---|---|---|---|---|---|---|---|
| H | H | Et | H | $NO_2$ | H | H | H | $NO_2$ |
| H | H | iPr | H | CHO | H | H | H | CHO |
| H | H | nPr | H | $SO_3H$ | H | H | H | $SO_3H$ |
| H | H | nBu | H | Cl | H | H | H | Cl |
| H | H | tBu | H | Br | H | H | H | Br |
| Me | H | Ph | Me | $CH_2OH$ | H | Me | H | $CH_2OH$ |
| Me | Et | Ph | Me | $CH_2NH_2$ | H | Me | H | $CH_2NH_2$ |
| Me | iPr | H | Me | $CH_2NHMe$ | H | Me | H | $CH_2NHMe$ |
| Me | nPr | H | Me | $CH_2Ph$ | H | Me | H | $CH_2Ph$ |
| Me | nBu | H | Me | COMe | H | Me | H | COMe |
| Me | tBu | H | Me | COOH | H | Me | H | COOH |
| Et | Ph | H | Et | $CONH_2$ | H | Et | H | $CONH_2$ |
| Et | H | Et | Et | CONHMe | Et | Et | Et | CONHMe |
| Et | H | iPr | Et | CONHMs | iPr | Et | iPr | CONHMs |
| iPr | H | nPr | iPr | NHMs | nPr | iPr | nPr | NHMs |
| nPr | H | nBu | nPr | NHCOMe | nBu | nPr | nBu | NHCOMe |
| nBu | H | tBu | nBu | $NO_2$ | tBu | nBu | tBu | $NO_2$ |
| tBu | H | Ph | tBu | CHO | Ph | tBu | Ph | H |
| Ph | Cl | Et | Ph | $SO_3H$ | Et | Ph | Et | H |
| $CH_2OH$ | Cl | nPr | $CH_2OH$ | $SO_2NHMe$ | nPr | $CH_2OH$ | nPr | H |
| $CH_2OH$ | Cl | Ph | $CH_2OH$ | OH | Ph | $CH_2OH$ | Ph | H |
| $CH_2OMe$ | Et | Cl | $CH_2OMe$ | COMe | Cl | $CH_2OMe$ | Cl | Cl |
| $CH_2OMe$ | nPr | Cl | $CH_2OMe$ | COOH | Cl | $CH_2OMe$ | Cl | Cl |
| $CH_2NH_2$ | Ph | Cl | $CH_2NH_2$ | $CONH_2$ | Cl | $CH_2NH_2$ | Cl | Cl |
| $CH_2NH_2$ | H | Et | $CH_2NH_2$ | CONHMe | Et | $CH_2NH_2$ | Et | H |
| $CH_2NH_2$ | H | nPr | $CH_2NH_2$ | CONHMs | nPr | $CH_2NH_2$ | nPr | H |
| $CH_2NH_2$ | H | Ph | $CH_2NH_2$ | NHMs | Ph | $CH_2NH_2$ | Ph | H |
| $CH_2NHMe$ | Me | Me | $CH_2NHMe$ | $NO_2$ | Me | $CH_2NHMe$ | Me | H |
| $CH_2Ph$ | Et | Et | $CH_2Ph$ | OH | Et | $CH_2Ph$ | Et | H |
| $CH_2Ph$ | nPr | nPr | $CH_2Ph$ | COMe | nPr | $CH_2Ph$ | H | H |
| $CH_2CH_2Ph$ | Ph | Ph | $CH_2CH_2Ph$ | COOH | Ph | $CH_2CH_2Ph$ | Ph | H |

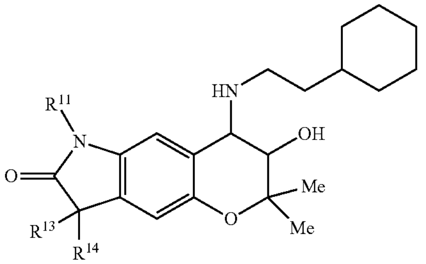

| | | | | | | | | |
|---|---|---|---|---|---|---|---|---|
| H | H | Et | H | $NO_2$ | H | H | H | $NO_2$ |
| H | H | iPr | H | CHO | H | H | H | CHO |
| H | H | nPr | H | $SO_3H$ | H | H | H | $SO_3H$ |

-continued

| $R^{11}$ | $R^{13}$ | $R^{14}$ | $R^{11}$ | $R^{13}$ | $R^{14}$ | $R^{11}$ | $R^{13}$ | $R^{14}$ |
|---|---|---|---|---|---|---|---|---|
| H | H | nBu | H | Cl | H | H | H | Cl |
| H | H | tBu | H | Br | H | H | H | Br |
| Me | H | Ph | Me | $CH_2OH$ | H | Me | H | $CH_2OH$ |
| Me | Et | Ph | Me | $CH_2NH_2$ | H | Me | H | $CH_2NH_2$ |
| Me | iPr | H | Me | $CH_2NHMe$ | H | Me | H | $CH_2NHMe$ |
| Me | nPr | H | Me | $CH_2Ph$ | H | Me | H | $CH_2Ph$ |
| Me | nBu | H | Me | COMe | H | Me | H | COMe |
| Me | tBu | H | Me | COOH | H | Me | H | COOH |
| Et | Ph | H | Et | $CONH_2$ | H | Et | H | $CONH_2$ |
| Et | H | Et | Et | CONHMe | Et | Et | Et | CONHMe |
| Et | H | iPr | Et | CONHMs | iPr | Et | iPr | CONHMs |
| iPr | H | nPr | iPr | NHMs | nPr | iPr | nPr | NHMs |
| nPr | H | nBu | nPr | NHCOMe | nBu | nPr | nBu | NHCOMe |
| nBu | H | tBu | nBu | $NO_2$ | tBu | nBu | tBu | $NO_2$ |
| tBu | H | Ph | tBu | CHO | Ph | tBu | Ph | H |
| Ph | Cl | Et | Ph | $SO_3H$ | Et | Ph | Et | H |
| $CH_2OH$ | Cl | nPr | $CH_2OH$ | $SO_2NHMe$ | nPr | $CH_2OH$ | nPr | H |
| $CH_2OH$ | Cl | Ph | $CH_2OH$ | OH | Ph | $CH_2OH$ | Ph | H |
| $CH_2OMe$ | Et | Cl | $CH_2OMe$ | COMe | Cl | $CH_2OMe$ | Cl | Cl |
| $CH_2OMe$ | nPr | Cl | $CH_2OMe$ | COOH | Cl | $CH_2OMe$ | Cl | Cl |
| $CH_2NH_2$ | Ph | Cl | $CH_2NH_2$ | $CONH_2$ | Cl | $CH_2NH_2$ | Cl | Cl |
| $CH_2NH_2$ | H | Et | $CH_2NH_2$ | CONHMe | Et | $CH_2NH_2$ | Et | H |
| $CH_2NH_2$ | H | nPr | $CH_2NH_2$ | CONHMs | nPr | $CH_2NH_2$ | nPr | H |
| $CH_2NH_2$ | H | Ph | $CH_2NH_2$ | NHMs | Ph | $CH_2NH_2$ | Ph | H |
| $CH_2NHMe$ | Me | Me | $CH_2NHMe$ | $NO_2$ | Me | $CH_2NHMe$ | Me | H |
| $CH_2Ph$ | Et | Et | $CH_2Ph$ | OH | Et | $CH_2Ph$ | Et | H |
| $CH_2Ph$ | nPr | nPr | $CH_2Ph$ | COMe | nPr | $CH_2Ph$ | H | H |
| $CH_2CH_2Ph$ | Ph | Ph | $CH_2CH_2Ph$ | COOH | Ph | $CH_2CH_2Ph$ | Ph | H |

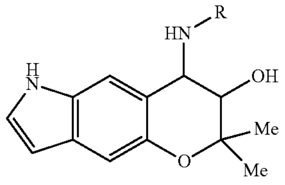

HN—R

| | | |
|---|---|---|
| 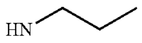 | 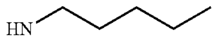 | 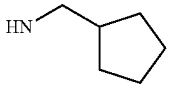 |
| 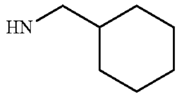 | 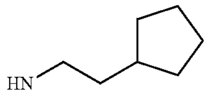 | 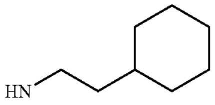 |
| 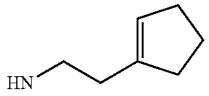 | 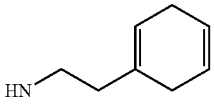 | 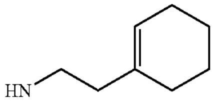 |
| 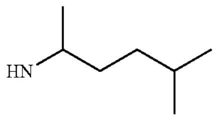 | 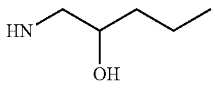 | 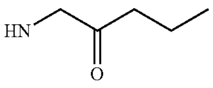 |
| 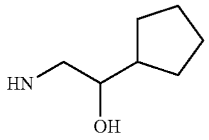 | 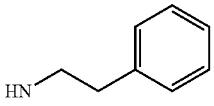 | 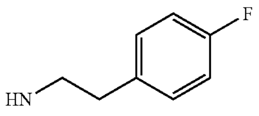 |

-continued
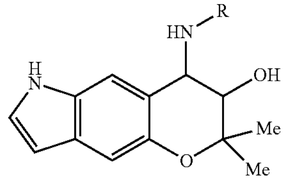
HN—R
| | | |
|---|---|---|
| 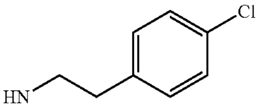 | 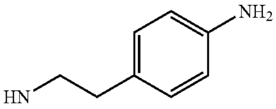 | 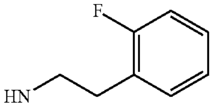 |
| 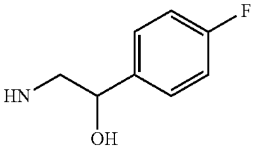 | 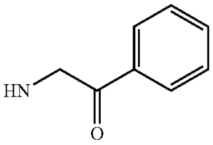 | 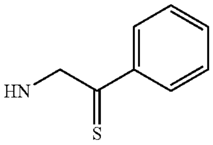 |
| 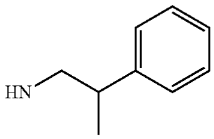 | 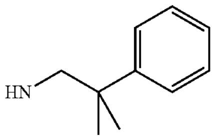 | 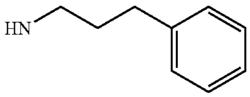 |
| 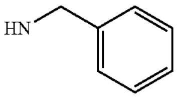 | 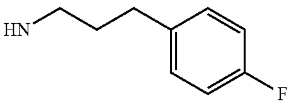 | 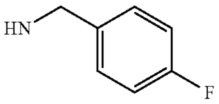 |
| 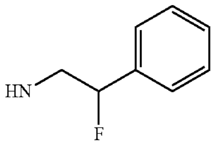 | 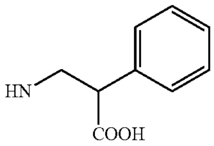 | 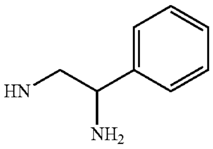 |
| 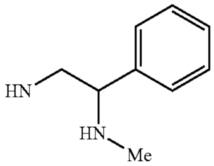 | 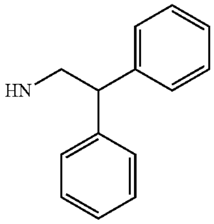 | 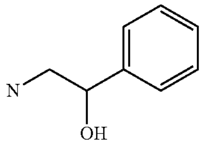 |
| 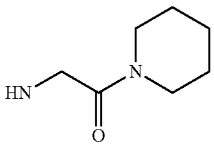 | 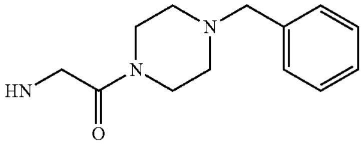 | 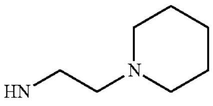 |
| 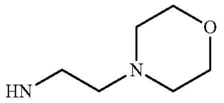 | 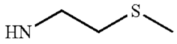 | 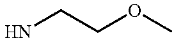 |
| 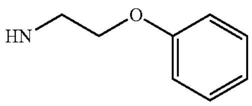 | 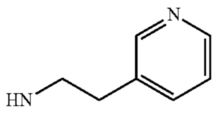 | 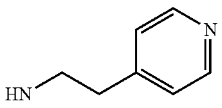 |

-continued

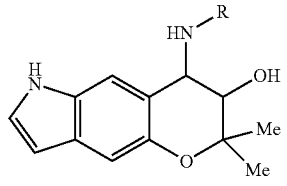

HN—R

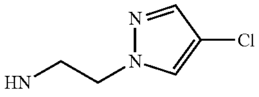 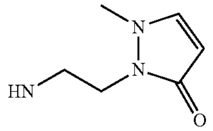

| $R^{11}$ | $R^{13}$ | $R^{14}$ | $R^{11}$ | $R^{13}$ | $R^{14}$ | $R^{11}$ | $R^{13}$ | $R^{14}$ |
|---|---|---|---|---|---|---|---|---|
| 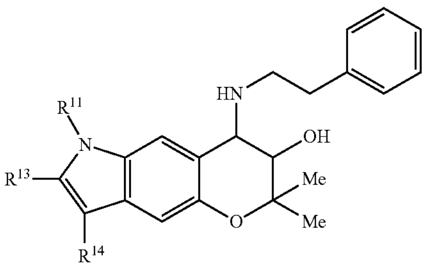 | | | | | | | | |
| H | H | Et | H | $NO_2$ | H | H | H | $NO_2$ |
| H | H | iPr | H | CHO | H | H | H | CHO |
| H | H | nPr | H | $SO_3H$ | H | H | H | $SO_3H$ |
| H | H | nBu | H | Cl | H | H | H | Cl |
| H | H | tBu | H | Br | H | H | H | Br |
| Me | H | Ph | Me | $CH_2OH$ | H | Me | H | $CH_2OH$ |
| Me | Et | Ph | Me | $CH_2NH_2$ | H | Me | H | $CH_2NH_2$ |
| Me | iPr | H | Me | $CH_2NHMe$ | H | Me | H | $CH_2NHMe$ |
| Me | nPr | H | Me | $CH_2Ph$ | H | Me | H | $CH_2Ph$ |
| Me | nBu | H | Me | COMe | H | Me | H | COMe |
| Me | tBu | H | Me | COOH | H | Me | H | COOH |
| Et | Ph | H | Et | $CONH_2$ | H | Et | H | $CONH_2$ |
| Et | H | Et | Et | CONHMe | Et | Et | Et | CONHMe |
| Et | H | iPr | Et | CONHMs | iPr | Et | iPr | CONHMs |
| iPr | H | nPr | iPr | NHMs | nPr | iPr | nPr | NHMs |
| nPr | H | nBu | nPr | NHCOMe | nBu | nPr | nBu | NHCOMe |
| nBu | H | tBu | nBu | $NO_2$ | tBu | nBu | tBu | $NO_2$ |
| tBu | H | Ph | tBu | CHO | Ph | tBu | Ph | H |
| Ph | Cl | Et | Ph | $SO_3H$ | Et | Ph | Et | H |
| $CH_2OH$ | Cl | nPr | $CH_2OH$ | $SO_2NHMe$ | nPr | $CH_2OH$ | nPr | H |
| $CH_2OH$ | Cl | Ph | $CH_2OH$ | OH | Ph | $CH_2OH$ | Ph | H |
| $CH_2OMe$ | Et | Cl | $CH_2OMe$ | COMe | Cl | $CH_2OMe$ | Cl | Cl |
| $CH_2OMe$ | nPr | Cl | $CH_2OMe$ | COOH | Cl | $CH_2OMe$ | Cl | Cl |
| $CH_2NH_2$ | Ph | Cl | $CH_2NH_2$ | $CONH_2$ | Cl | $CH_2NH_2$ | Cl | Cl |
| $CH_2NH_2$ | H | Et | $CH_2NH_2$ | CONHMe | Et | $CH_2NH_2$ | Et | H |
| $CH_2NH_2$ | H | nPr | $CH_2NH_2$ | CONHMs | nPr | $CH_2NH_2$ | nPr | H |
| $CH_2NH_2$ | H | Ph | $CH_2NH_2$ | NHMs | Ph | $CH_2NH_2$ | Ph | H |
| $CH_2NHMe$ | Me | Me | $CH_2NHMe$ | $NO_2$ | Me | $CH_2NHMe$ | Me | H |
| $CH_2Ph$ | Et | Et | $CH_2Ph$ | OH | Et | $CH_2Ph$ | Et | H |
| $CH_2Ph$ | nPr | nPr | $CH_2Ph$ | COMe | nPr | $CH_2Ph$ | nPr | H |
| $CH_2CH_2Ph$ | Ph | Ph | $CH_2CH_2Ph$ | COOH | Ph | $CH_2CH_2Ph$ | Ph | H |

-continued

| $R^{11}$ | $R^{13}$ | $R^{14}$ | $R^{11}$ | $R^{13}$ | $R^{14}$ | $R^{11}$ | $R^{13}$ | $R^{14}$ |
|---|---|---|---|---|---|---|---|---|

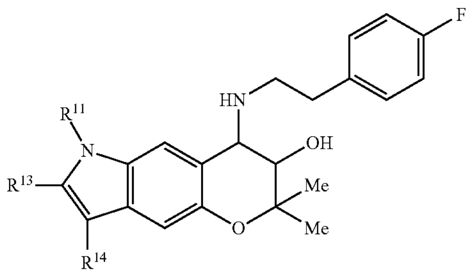

| | | | | | | | | |
|---|---|---|---|---|---|---|---|---|
| H | H | Et | H | $NO_2$ | H | H | H | $NO_2$ |
| H | H | iPr | H | CHO | H | H | H | CHO |
| H | H | nPr | H | $SO_3H$ | H | H | H | $SO_3H$ |
| H | H | nBu | H | Cl | H | H | H | Cl |
| H | H | tBu | H | Br | H | H | H | Br |
| Me | H | Ph | Me | $CH_2OH$ | H | Me | H | $CH_2OH$ |
| Me | Et | Ph | Me | $CH_2NH_2$ | H | Me | H | $CH_2NH_2$ |
| Me | iPr | H | Me | $CH_2NHMe$ | H | Me | H | $CH_2NHMe$ |
| Me | nPr | H | Me | $CH_2Ph$ | H | Me | H | $CH_2Ph$ |
| Me | nBu | H | Me | COMe | H | Me | H | COMe |
| Me | tBu | H | Me | COOH | H | Me | H | COOH |
| Et | Ph | H | Et | $CONH_2$ | H | Et | H | $CONH_2$ |
| Et | H | Et | Et | CONHMe | Et | Et | Et | CONHMe |
| Et | H | iPr | Et | CONHMs | iPr | Et | iPr | CONHMs |
| iPr | H | nPr | iPr | NHMs | nPr | iPr | nPr | NHMs |
| nPr | H | nBu | nPr | NHCOMe | nBu | nPr | nBu | NHCOMe |
| nBu | H | tBu | nBu | $NO_2$ | tBu | nBu | tBu | $NO_2$ |
| tBu | H | Ph | tBu | CHO | Ph | tBu | Ph | H |
| Ph | Cl | Et | Ph | $SO_3H$ | Et | Ph | Et | H |
| $CH_2OH$ | Cl | nPr | $CH_2OH$ | $SO_2NHMe$ | nPr | $CH_2OH$ | nPr | H |
| $CH_2OH$ | Cl | Ph | $CH_2OH$ | OH | Ph | $CH_2OH$ | Ph | H |
| $CH_2OMe$ | Et | Cl | $CH_2OMe$ | COMe | Cl | $CH_2OMe$ | Cl | Cl |
| $CH_2OMe$ | nPr | Cl | $CH_2OMe$ | COOH | Cl | $CH_2OMe$ | Cl | Cl |
| $CH_2NH_2$ | Ph | Cl | $CH_2NH_2$ | $CONH_2$ | Cl | $CH_2NH_2$ | Cl | Cl |
| $CH_2NH_2$ | H | Et | $CH_2NH_2$ | CONHMe | Et | $CH_2NH_2$ | Et | H |
| $CH_2NH_2$ | H | nPr | $CH_2NH_2$ | CONHMs | nPr | $CH_2NH_2$ | nPr | H |
| $CH_2NH_2$ | H | Ph | $CH_2NH_2$ | NHMs | Ph | $CH_2NH_2$ | Ph | H |
| $CH_2NHMe$ | Me | Me | $CH_2NHMe$ | $NO_2$ | Me | $CH_2NHMe$ | Me | H |
| $CH_2Ph$ | Et | Et | $CH_2Ph$ | OH | Et | $CH_2Ph$ | Et | H |
| $CH_2Ph$ | nPr | nPr | $CH_2Ph$ | COMe | nPr | $CH_2Ph$ | nPr | H |
| $CH_2CH_2Ph$ | Ph | Ph | $CH_2CH_2Ph$ | COOH | Ph | $CH_2CH_2Ph$ | Ph | H |

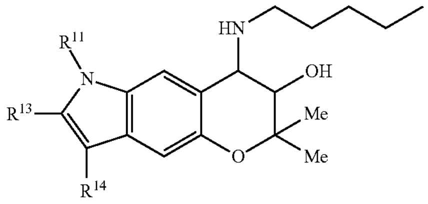

| | | | | | | | | |
|---|---|---|---|---|---|---|---|---|
| H | H | Et | H | $NO_2$ | H | H | H | $NO_2$ |
| H | H | iPr | H | CHO | H | H | H | CHO |
| H | H | nPr | H | $SO_3H$ | H | H | H | $SO_3H$ |
| H | H | nBu | H | Cl | H | H | H | Cl |
| H | H | tBu | H | Br | H | H | H | Br |
| Me | H | Ph | Me | $CH_2OH$ | H | Me | H | $CH_2OH$ |
| Me | Et | Ph | Me | $CH_2NH_2$ | H | Me | H | $CH_2NH_2$ |
| Me | iPr | H | Me | $CH_2NHMe$ | H | Me | H | $CH_2NHMe$ |
| Me | nPr | H | Me | $CH_2Ph$ | H | Me | H | $CH_2Ph$ |
| Me | nBu | H | Me | COMe | H | Me | H | COMe |
| Me | tBu | H | Me | COOH | H | Me | H | COOH |
| Et | Ph | H | Et | $CONH_2$ | H | Et | H | $CONH_2$ |
| Et | H | Et | Et | CONHMe | Et | Et | Et | CONHMe |
| Et | H | iPr | Et | CONHMs | iPr | Et | iPr | CONHMs |
| iPr | H | nPr | iPr | NHMs | nPr | iPr | nPr | NHMs |
| nPr | H | nBu | nPr | NHCOMe | nBu | nPr | nBu | NHCOMe |
| nBu | H | tBu | nBu | $NO_2$ | tBu | nBu | tBu | $NO_2$ |
| tBu | H | Ph | tBu | CHO | Ph | tBu | Ph | H |
| Ph | Cl | Et | Ph | $SO_3H$ | Et | Ph | Et | H |
| $CH_2OH$ | Cl | nPr | $CH_2OH$ | $SO_2NHMe$ | nPr | $CH_2OH$ | nPr | H |
| $CH_2OH$ | Cl | Ph | $CH_2OH$ | OH | Ph | $CH_2OH$ | Ph | H |
| $CH_2OMe$ | Et | Cl | $CH_2OMe$ | COMe | Cl | $CH_2OMe$ | Cl | Cl |

-continued

| $R^{11}$ | $R^{13}$ | $R^{14}$ | $R^{11}$ | $R^{13}$ | $R^{14}$ | $R^{11}$ | $R^{13}$ | $R^{14}$ |
|---|---|---|---|---|---|---|---|---|
| $CH_2OMe$ | nPr | Cl | $CH_2OMe$ | COOH | Cl | $CH_2OMe$ | Cl | Cl |
| $CH_2NH_2$ | Ph | Cl | $CH_2NH_2$ | $CONH_2$ | Cl | $CH_2NH_2$ | Cl | Cl |
| $CH_2NH_2$ | H | Et | $CH_2NH_2$ | CONHMe | Et | $CH_2NH_2$ | Et | H |
| $CH_2NH_2$ | H | nPr | $CH_2NH_2$ | CONHMs | nPr | $CH_2NH_2$ | nPr | H |
| $CH_2NH_2$ | H | Ph | $CH_2NH_2$ | NHMs | Ph | $CH_2NH_2$ | Ph | H |
| $CH_2NHMe$ | Me | Me | $CH_2NHMe$ | $NO_2$ | Me | $CH_2NHMe$ | Me | H |
| $CH_2Ph$ | Et | Et | $CH_2Ph$ | OH | Et | $CH_2Ph$ | Et | H |
| $CH_2Ph$ | nPr | nPr | $CH_2Ph$ | COMe | nPr | $CH_2Ph$ | nPr | H |
| $CH_2CH_2Ph$ | Ph | Ph | $CH_2CH_2Ph$ | COOH | Ph | $CH_2CH_2Ph$ | Ph | H |

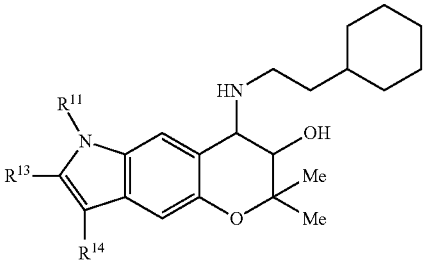

| | | | | | | | | |
|---|---|---|---|---|---|---|---|---|
| H | H | Et | H | $NO_2$ | H | H | H | $NO_2$ |
| H | H | iPr | H | CHO | H | H | H | CHO |
| H | H | nPr | H | $SO_3H$ | H | H | H | $SO_3H$ |
| H | H | nBu | H | Cl | H | H | H | Cl |
| H | H | tBu | H | Br | H | H | H | Br |
| Me | H | Ph | Me | $CH_2OH$ | H | Me | H | $CH_2OH$ |
| Me | Et | Ph | Me | $CH_2NH_2$ | H | Me | H | $CH_2NH_2$ |
| Me | iPr | H | Me | $CH_2NHMe$ | H | Me | H | $CH_2NHMe$ |
| Me | nPr | H | Me | $CH_2Ph$ | H | Me | H | $CH_2Ph$ |
| Me | nBu | H | Me | COMe | H | Me | H | COMe |
| Me | tBu | H | Me | COOH | H | Me | H | COOH |
| Et | Ph | H | Et | $CONH_2$ | H | Et | H | $CONH_2$ |
| Et | H | Et | Et | CONHMe | Et | Et | Et | CONHMe |
| Et | H | iPr | Et | CONHMs | iPr | Et | iPr | CONHMs |
| iPr | H | nPr | iPr | NHMs | nPr | iPr | nPr | NHMs |
| nPr | H | nBu | nPr | NHCOMe | nBu | nPr | nBu | NHCOMe |
| nBu | H | tBu | nBu | $NO_2$ | tBu | nBu | tBu | $NO_2$ |
| tBu | H | Ph | tBu | CHO | Ph | tBu | Ph | H |
| Ph | Cl | Et | Ph | $SO_3H$ | Et | Ph | Et | H |
| $CH_2OH$ | Cl | nPr | $CH_2OH$ | $SO_2NHMe$ | nPr | $CH_2OH$ | nPr | H |
| $CH_2OH$ | Cl | Ph | $CH_2OH$ | OH | Ph | $CH_2OH$ | Ph | H |
| $CH_2OMe$ | Et | Cl | $CH_2OMe$ | COMe | Cl | $CH_2OMe$ | Cl | Cl |
| $CH_2OMe$ | nPr | Cl | $CH_2OMe$ | COOH | Cl | $CH_2OMe$ | Cl | Cl |
| $CH_2NH_2$ | Ph | Cl | $CH_2NH_2$ | $CONH_2$ | Cl | $CH_2NH_2$ | Cl | Cl |
| $CH_2NH_2$ | H | Et | $CH_2NH_2$ | CONHMe | Et | $CH_2NH_2$ | Et | H |
| $CH_2NH_2$ | H | nPr | $CH_2NH_2$ | CONHMs | nPr | $CH_2NH_2$ | nPr | H |
| $CH_2NH_2$ | H | Ph | $CH_2NH_2$ | NHMs | Ph | $CH_2NH_2$ | Ph | H |
| $CH_2NHMe$ | Me | Me | $CH_2NHMe$ | $NO_2$ | Me | $CH_2NHMe$ | Me | H |
| $CH_2Ph$ | Et | Et | $CH_2Ph$ | OH | Et | $CH_2Ph$ | Et | H |
| $CH_2Ph$ | nPr | nPr | $CH_2Ph$ | COMe | nPr | $CH_2Ph$ | nPr | H |
| $CH_2CH_2Ph$ | Ph | Ph | $CH_2CH_2Ph$ | COOH | Ph | $CH_2CH_2Ph$ | Ph | H |

| HN—R | | |
|---|---|---|
| | 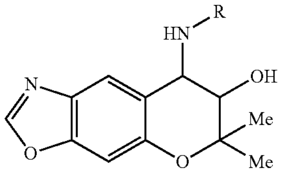 | |
| 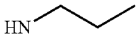 | 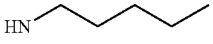 | 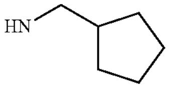 |

-continued
| HN—R | | |
|---|---|---|
| 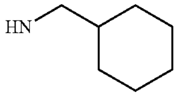 | 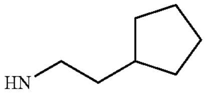 | 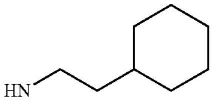 |
| 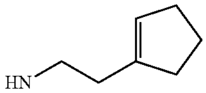 | 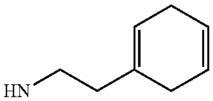 | 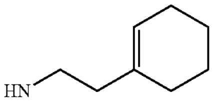 |
| 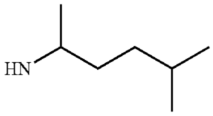 | 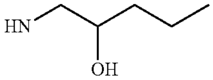 | 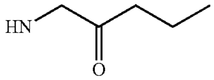 |
| 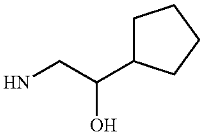 | 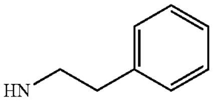 | 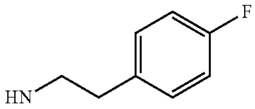 |
| 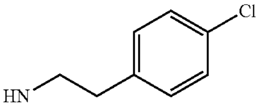 | 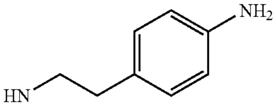 | 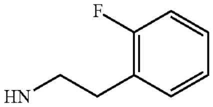 |
| 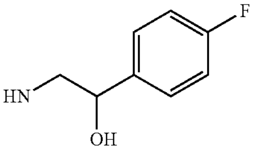 | 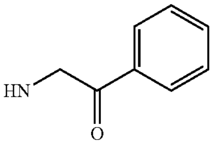 | 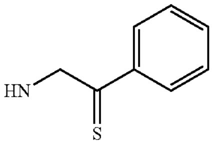 |
| 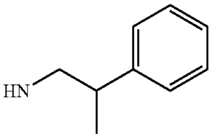 | 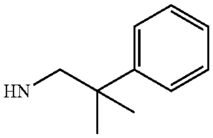 | 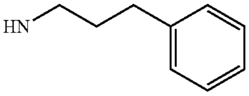 |
| 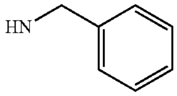 | 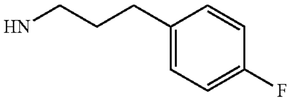 | 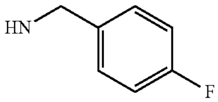 |
| 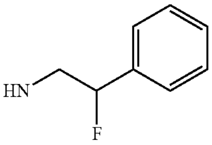 | 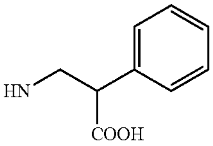 | 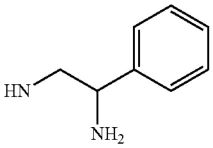 |
| 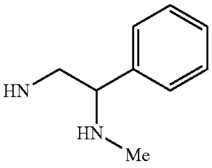 | 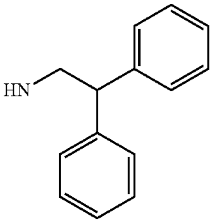 | 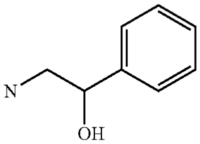 |

-continued
| HN—R | | |
|---|---|---|
| 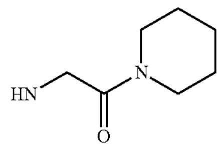 | 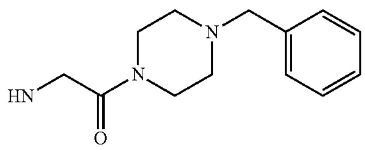 | 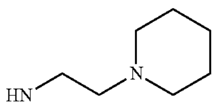 |
| 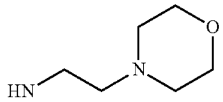 | 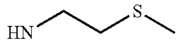 | 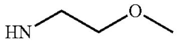 |
| 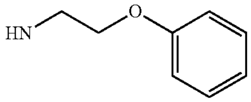 | 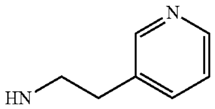 | 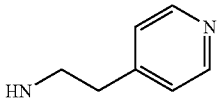 |
| 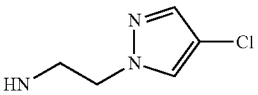 | 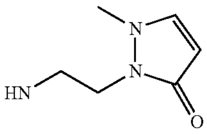 | |
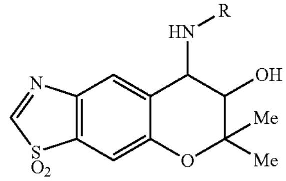
| | | |
|---|---|---|
| 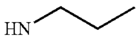 | 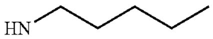 | 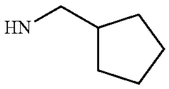 |
| 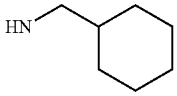 | 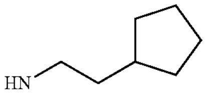 | 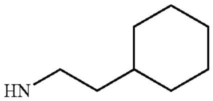 |
| 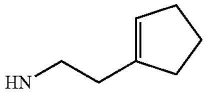 | 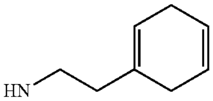 | 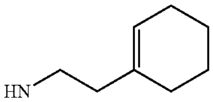 |
| 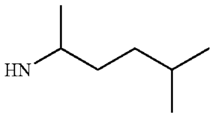 | 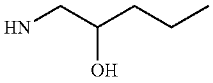 | 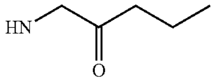 |
| 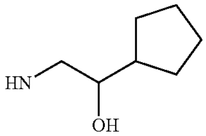 | 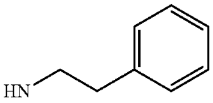 | 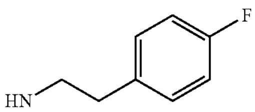 |
| 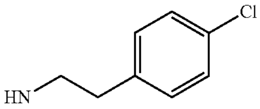 | 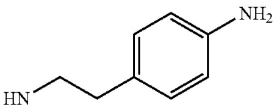 | 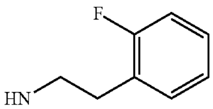 |

-continued
| HN—R | | |
|---|---|---|
| 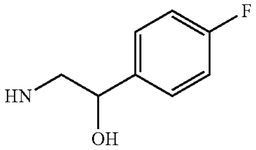 | 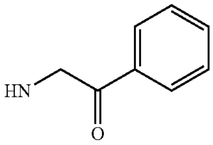 | 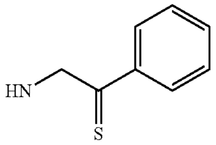 |
| 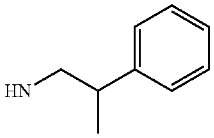 | 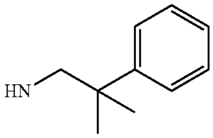 | 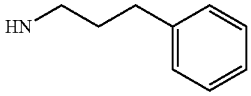 |
| 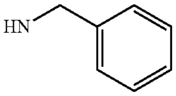 | 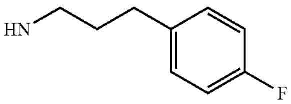 | 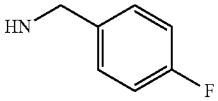 |
| 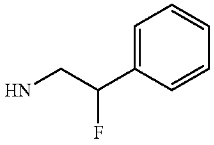 | 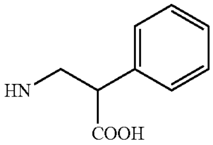 | 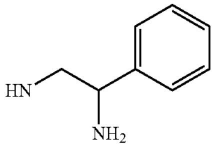 |
| 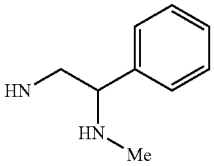 | 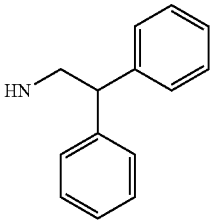 | 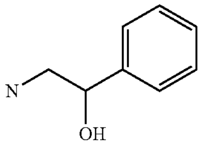 |
| 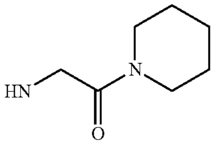 | 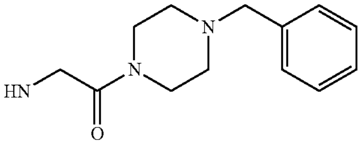 | 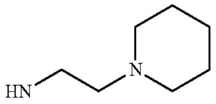 |
| 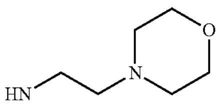 | 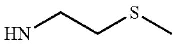 | 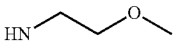 |
| 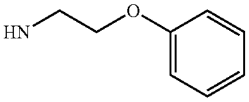 | 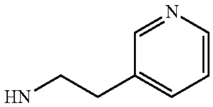 | 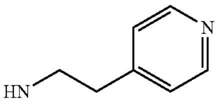 |
| 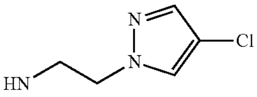 | 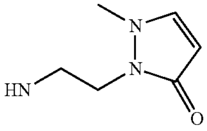 | |

-continued
| HN—R | | |
|---|---|---|
| | 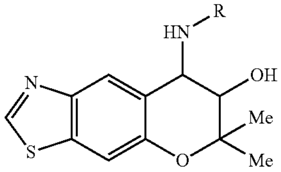 | |
| 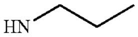 | 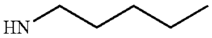 | 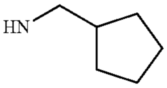 |
| 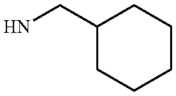 | 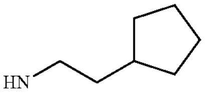 | 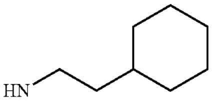 |
| 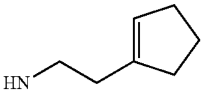 | 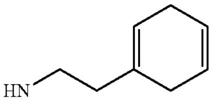 | 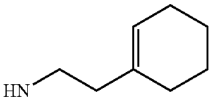 |
| 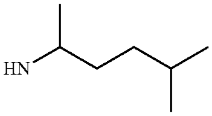 | 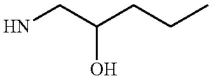 | 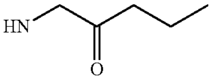 |
| 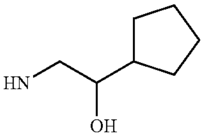 | 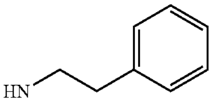 | 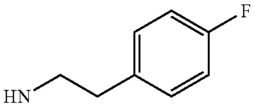 |
| 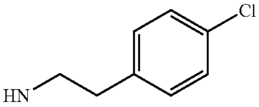 | 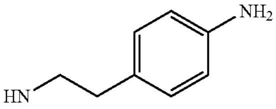 | 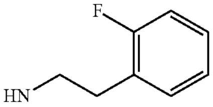 |
| 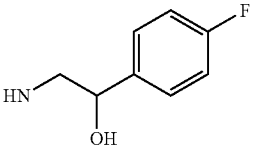 | 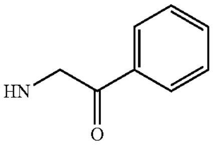 | 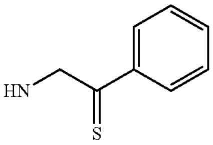 |
| 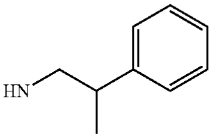 | 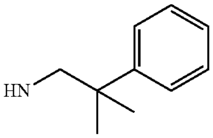 | 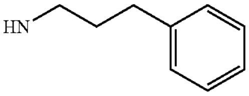 |
| 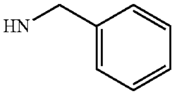 | 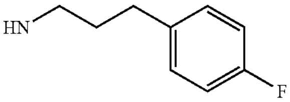 | 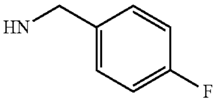 |
| 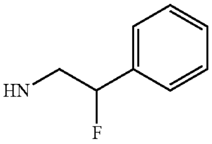 | 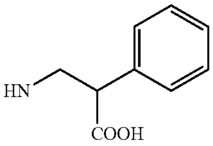 | 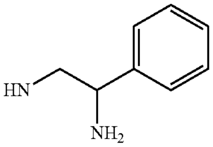 |

-continued

| HN—R | | |
|---|---|---|
| 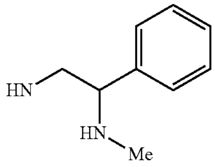 | 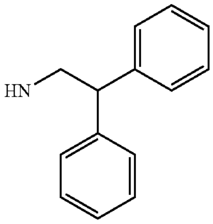 | 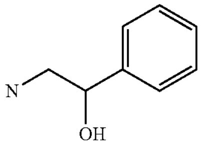 |
| 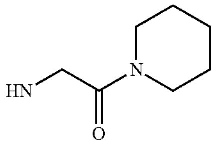 | 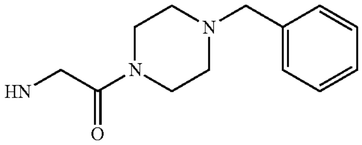 | 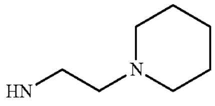 |
| 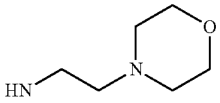 | 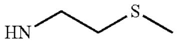 | 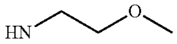 |
| 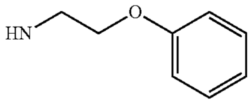 | 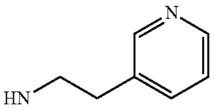 | 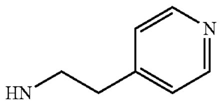 |
| 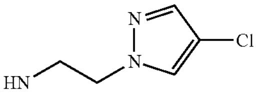 | 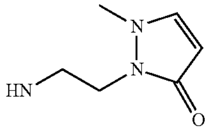 | |

| $R^{13}$ | X | $R^{13}$ | X |
|---|---|---|---|
| 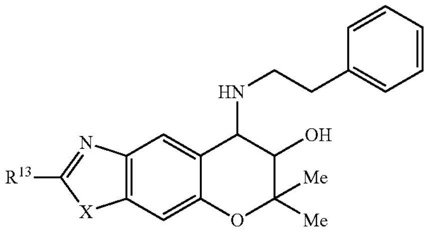 | | | |
| $NO_2$ | O | Me | O |
| CHO | O | Et | O |
| $SO_3H$ | O | iPr | O |
| Cl | O | nPr | O |
| Br | O | nBu | O |
| $CH_2OH$ | O | tBu | O |
| $CH_2NH_2$ | O | Ph | O |
| $CH_2NHMe$ | O | $CH_2Ph$ | O |
| $CH_2Ph$ | SO | $CH_2CH_2Ph$ | O |
| COMe | SO | Me | S |
| COOH | SO | Et | S |
| $CONH_2$ | SO | iPr | S |
| CONHMe | SO | nPr | S |
| CONHMs | SO | nBu | S |
| NHMs | SO | tBu | S |
| NHCOMe | SO | Ph | S |
| $NO_2$ | $SO_2$ | $CH_2Ph$ | S |
| CHO | S | $CH_2CH_2Ph$ | S |
| $SO_3H$ | S | Me | $SO_2$ |
| $SO_2NHMe$ | $SO_2$ | Et | $SO_2$ |
| OH | SO | iPr | $SO_2$ |
| COMe | O | nPr | $SO_2$ |

-continued

| $R^{13}$ | X | $R^{13}$ | X |
|---|---|---|---|
| COOH | O | nBu | $SO_2$ |
| $CONH_2$ | O | tBu | $SO_2$ |
| CONHMe | O | Ph | $SO_2$ |
| CONHMs | O | $CH_2Ph$ | $SO_2$ |
| NHMs | $SO_2$ | $CH_2CH_2Ph$ | $SO_2$ |
| $NO_2$ | $SO_2$ | Me | SO |
| OH | $SO_2$ | Et | SO |
| COMe | $SO_2$ | iPr | SO |
| COOH | $SO_2$ | nPr | SO |

| $R^{13}$ | X | $R^{13}$ | X |
|---|---|---|---|
| 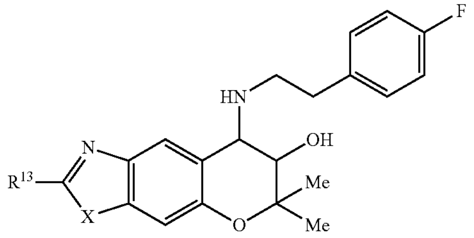 | | | |
| $NO_2$ | O | Me | O |
| CHO | O | Et | O |
| $SO_3H$ | O | iPr | O |
| Cl | O | nPr | O |
| Br | O | nBu | O |
| $CH_2OH$ | O | tBu | O |
| $CH_2NH_2$ | O | Ph | O |
| $CH_2NHMe$ | O | $CH_2Ph$ | O |
| $CH_2Ph$ | SO | $CH_2CH_2Ph$ | O |
| COMe | SO | Me | S |
| COOH | SO | Et | S |

-continued

| $R^{13}$ | X | $R^{13}$ | X |
|---|---|---|---|
| $CONH_2$ | SO | iPr | S |
| CONHMe | SO | nPr | S |
| CONHMs | SO | nBu | S |
| NHMs | SO | tBu | S |
| NHCOMe | SO | Ph | S |
| $NO_2$ | $SO_2$ | $CH_2Ph$ | S |
| CHO | S | $CH_2CH_2Ph$ | S |
| $SO_3H$ | S | Me | $SO_2$ |
| $SO_2NHMe$ | $SO_2$ | Et | $SO_2$ |
| OH | SO | iPr | $SO_2$ |
| COMe | O | nPr | $SO_2$ |
| COOH | O | nBu | $SO_2$ |
| $CONH_2$ | O | tBu | $SO_2$ |
| CONHMe | O | Ph | $SO_2$ |
| CONHMs | O | $CH_2Ph$ | $SO_2$ |
| NHMs | $SO_2$ | $CH_2CH_2Ph$ | $SO_2$ |
| $NO_2$ | $SO_2$ | Me | SO |
| OH | $SO_2$ | Et | SO |
| COMe | $SO_2$ | iPr | SO |
| COOH | $SO_2$ | nPr | SO |

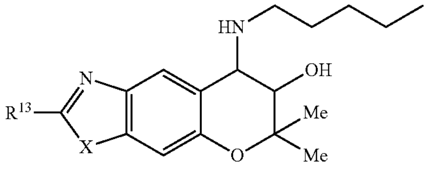

| $R^{13}$ | X | $R^{13}$ | X |
|---|---|---|---|
| $NO_2$ | O | Me | O |
| CHO | O | Et | O |
| $SO_3H$ | O | iPr | O |
| Cl | O | nPr | O |
| Br | O | nBu | O |
| $CH_2OH$ | O | tBu | O |
| $CH_2NH_2$ | O | Ph | O |
| $CH_2NHMe$ | O | $CH_2Ph$ | O |
| $CH_2Ph$ | SO | $CH_2CH_2Ph$ | O |
| COMe | SO | Me | S |
| COOH | SO | Et | S |
| $CONH_2$ | SO | iPr | S |
| CONHMe | SO | nPr | S |
| CONHMs | SO | nBu | S |
| NHMs | SO | tBu | S |
| NHCOMe | SO | Ph | S |
| $NO_2$ | $SO_2$ | $CH_2Ph$ | S |
| CHO | S | $CH_2CH_2Ph$ | S |
| $SO_3H$ | S | Me | $SO_2$ |
| $SO_2NHMe$ | $SO_2$ | Et | $SO_2$ |
| OH | SO | iPr | $SO_2$ |
| COMe | O | nPr | $SO_2$ |
| COOH | O | nBu | $SO_2$ |

-continued

| $R^{13}$ | X | $R^{13}$ | X |
|---|---|---|---|
| $CONH_2$ | O | tBu | $SO_2$ |
| CONHMe | O | Ph | $SO_2$ |
| CONHMs | O | $CH_2Ph$ | $SO_2$ |
| NHMs | $SO_2$ | $CH_2CH_2Ph$ | $SO_2$ |
| $NO_2$ | $SO_2$ | Me | SO |
| OH | $SO_2$ | Et | SO |
| COMe | $SO_2$ | iPr | SO |
| COOH | $SO_2$ | nPr | SO |

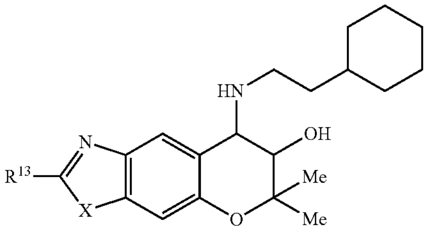

| $R^{13}$ | X | $R^{13}$ | X |
|---|---|---|---|
| $NO_2$ | O | Me | O |
| CHO | O | Et | O |
| $SO_3H$ | O | iPr | O |
| Cl | O | nPr | O |
| Br | O | nBu | O |
| $CH_2OH$ | O | tBu | O |
| $CH_2NH_2$ | O | Ph | O |
| $CH_2NHMe$ | O | $CH_2Ph$ | O |
| $CH_2Ph$ | SO | $CH_2CH_2Ph$ | O |
| COMe | SO | Me | S |
| COOH | SO | Et | S |
| $CONH_2$ | SO | iPr | S |
| CONHMe | SO | nPr | S |
| CONHMs | SO | nBu | S |
| NHMs | SO | tBu | S |
| NHCOMe | SO | Ph | S |
| $NO_2$ | $SO_2$ | $CH_2Ph$ | S |
| CHO | S | $CH_2CH_2Ph$ | S |
| $SO_3H$ | S | Me | $SO_2$ |
| $SO_2NHMe$ | $SO_2$ | Et | $SO_2$ |
| OH | SO | iPr | $SO_2$ |
| COMe | O | nPr | $SO_2$ |
| COOH | O | nBu | $SO_2$ |
| $CONH_2$ | O | tBu | $SO_2$ |
| CONHMe | O | Ph | $SO_2$ |
| CONHMs | O | $CH_2Ph$ | $SO_2$ |
| NHMs | $SO_2$ | $CH_2CH_2Ph$ | $SO_2$ |
| $NO_2$ | $SO_2$ | Me | SO |
| OH | $SO_2$ | Et | SO |
| COMe | $SO_2$ | iPr | SO |
| COOH | $SO_2$ | nPr | SO |

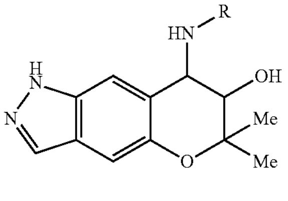

HN—R

| | | |
|---|---|---|
| 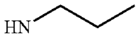 | 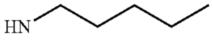 | 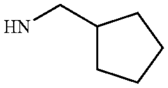 |
| 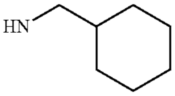 | 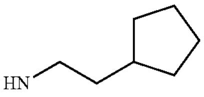 | 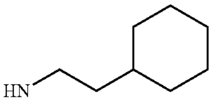 |

-continued
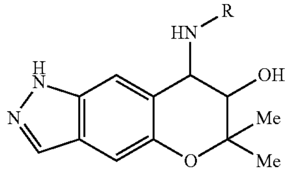
HN—R
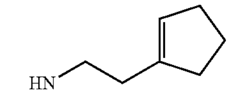 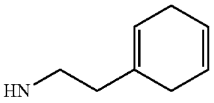 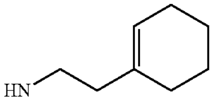
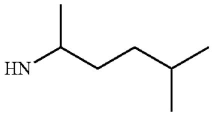 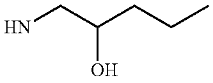 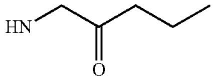
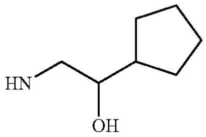 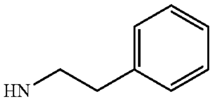 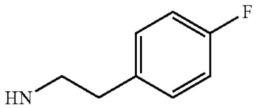
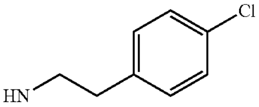 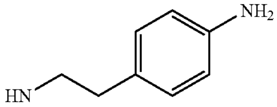 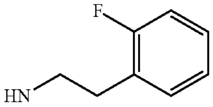
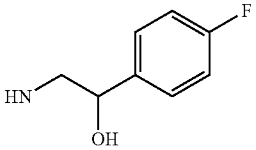 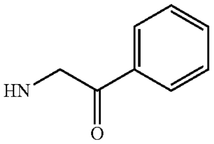 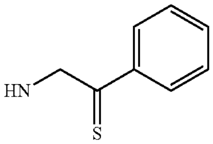
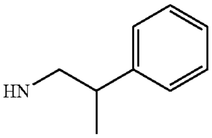 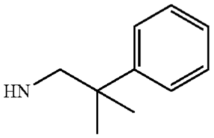 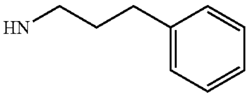
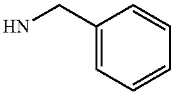 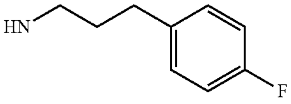 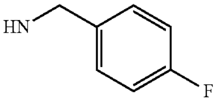
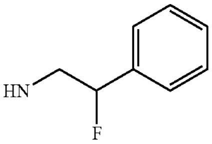 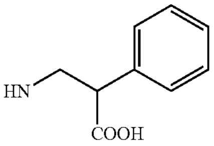 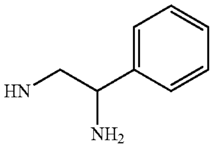
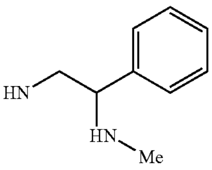 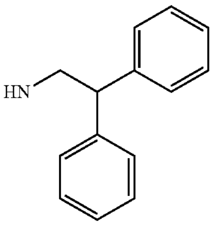 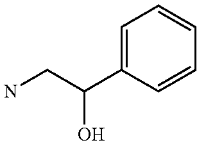

-continued

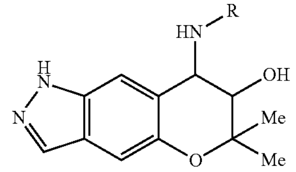

HN—R

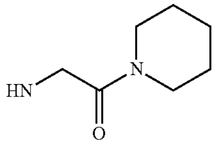
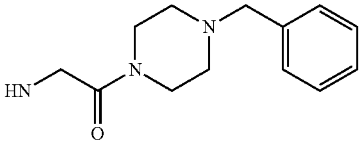
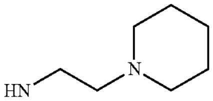

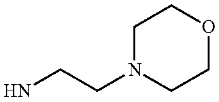
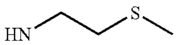
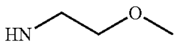

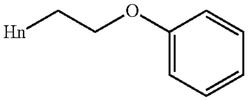
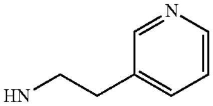
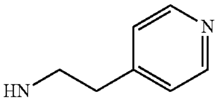

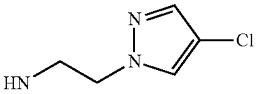
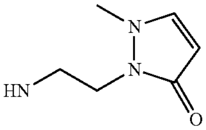

| $R^{11}$ | $R^{13}$ |
|---|---|
| 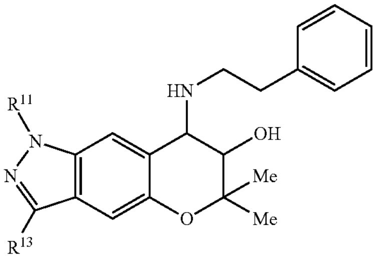 | |
| H | Et |
| H | iPr |
| H | nPr |
| H | nBu |
| H | tBu |
| Me | Ph |
| Me | $NO_2$ |
| Me | CHO |
| Me | $SO_3H$ |
| Me | Cl |
| Me | Br |
| Et | $CH_2OH$ |
| Et | $CH_2NH_2$ |
| Et | $CH_2NHMe$ |
| iPr | $CH_2Ph$ |
| nPr | COMe |
| nBu | COOH |
| tBu | $CONH_2$ |
| Ph | CONHMe |
| $CH_2OH$ | CONHMs |
| $CH_2OH$ | NHMs |
| $CH_2OMe$ | NHCOMe |
| $CH_2OMe$ | $NO_2$ |

-continued

| $R^{11}$ | $R^{13}$ |
|---|---|
| $CH_2NH_2$ | CHO |
| $CH_2NH_2$ | nPr |
| $CH_2NH_2$ | Cl |
| $CH_2NH_2$ | F |
| $CH_2NHMe$ | Cl |
| $CH_2Ph$ | Et |
| $CH_2Ph$ | nPr |
| $CH_2CH_2Ph$ | Ph |
| 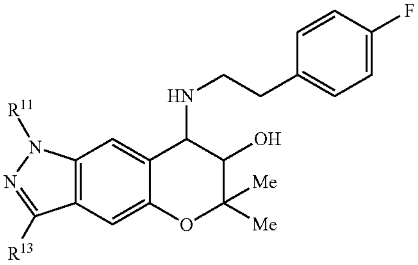 | |
| H | Et |
| H | iPr |
| H | nPr |
| H | nBu |
| H | tBu |
| Me | Ph |
| Me | $NO_2$ |
| Me | CHO |
| Me | $SO_3H$ |
| Me | Cl |
| Me | Br |
| Et | $CH_2OH$ |
| Et | $CH_2NH_2$ |

-continued

| $R^{11}$ | $R^{13}$ |
|---|---|
| Et | $CH_2NHMe$ |
| iPr | $CH_2Ph$ |
| nPr | COMe |
| nBu | COOH |
| tBu | $CONH_2$ |
| Ph | CONHMe |
| $CH_2OH$ | CONHMs |
| $CH_2OH$ | NHMs |
| $CH_2OMe$ | NHCOMe |
| $CH_2OMe$ | $NO_2$ |
| $CH_2NH_2$ | CHO |
| $CH_2NH_2$ | nPr |
| $CH_2NH_2$ | Cl |
| $CH_2NH_2$ | F |
| $CH_2NHMe$ | Cl |
| $CH_2Ph$ | Et |
| $CH_2Ph$ | nPr |
| $CH_2CH_2Ph$ | Ph |

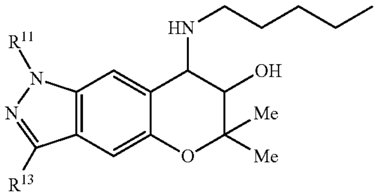

| | |
|---|---|
| H | Et |
| H | iPr |
| H | nPr |
| H | nBu |
| H | tBu |
| Me | Ph |
| Me | $NO_2$ |
| Me | CHO |
| Me | $SO_3H$ |
| Me | Cl |
| Me | Br |
| Et | $CH_2OH$ |
| Et | $CH_2NH_2$ |
| Et | $CH_2NHMe$ |
| iPr | $CH_2Ph$ |
| nPr | COMe |
| nBu | COOH |
| tBu | $CONH_2$ |
| Ph | CONHMe |
| $CH_2OH$ | CONHMs |
| $CH_2OH$ | NHMs |
| $CH_2OMe$ | NHCOMe |
| $CH_2OMe$ | $NO_2$ |
| $CH_2NH_2$ | CHO |

-continued

| $R^{11}$ | $R^{13}$ |
|---|---|
| $CH_2NH_2$ | nPr |
| $CH_2NH_2$ | Cl |
| $CH_2NH_2$ | F |
| $CH_2NHMe$ | Cl |
| $CH_2Ph$ | Et |
| $CH_2Ph$ | nPr |
| $CH_2CH_2Ph$ | Ph |

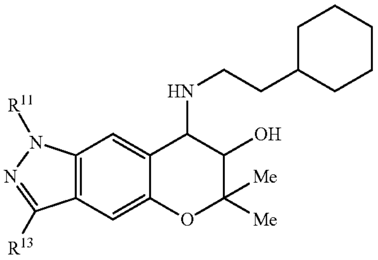

| | |
|---|---|
| H | Et |
| H | iPr |
| H | nPr |
| H | nBu |
| H | tBu |
| Me | Ph |
| Me | $NO_2$ |
| Me | CHO |
| Me | $SO_3H$ |
| Me | Cl |
| Me | Br |
| Et | $CH_2OH$ |
| Et | $CH_2NH_2$ |
| Et | $CH_2NHMe$ |
| iPr | $CH_2Ph$ |
| nPr | COMe |
| nBu | COOH |
| tBu | $CONH_2$ |
| Ph | CONHMe |
| $CH_2OH$ | CONHMs |
| $CH_2OH$ | NHMs |
| $CH_2OMe$ | NHCOMe |
| $CH_2OMe$ | $NO_2$ |
| $CH_2NH_2$ | CHO |
| $CH_2NH_2$ | nPr |
| $CH_2NH_2$ | Cl |
| $CH_2NH_2$ | F |
| $CH_2NHMe$ | Cl |
| $CH_2Ph$ | Et |
| $CH_2Ph$ | nPr |
| $CH_2CH_2Ph$ | Ph |

| HN—R | | |
|---|---|---|
| 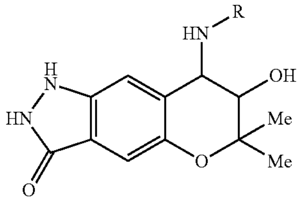 | | |
| 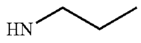 | 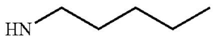 | 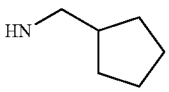 |

-continued
| HN—R | | |
|---|---|---|
| 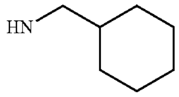 | 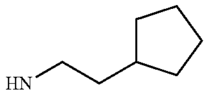 | 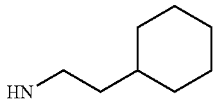 |
| 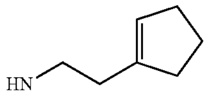 | 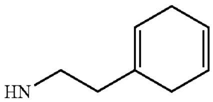 | 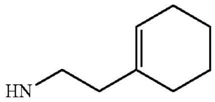 |
| 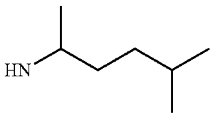 | 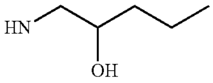 | 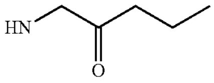 |
| 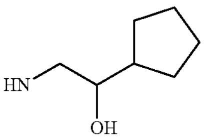 | 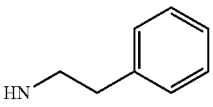 | 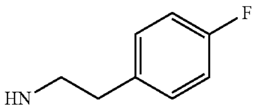 |
| 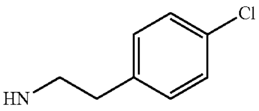 | 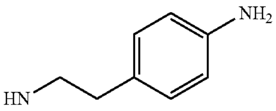 | 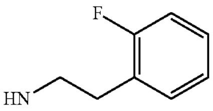 |
| 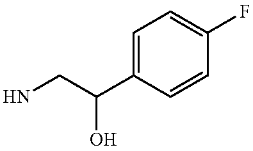 | 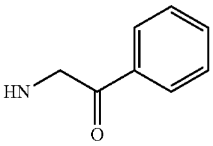 | 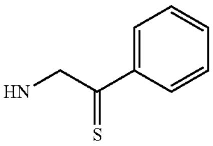 |
| 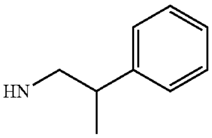 | 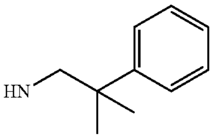 | 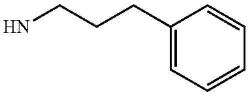 |
| 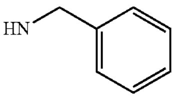 | 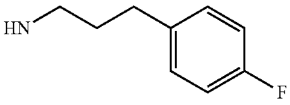 | 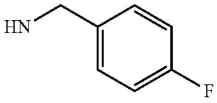 |
| 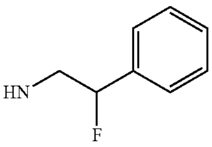 | 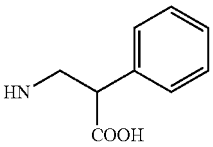 | 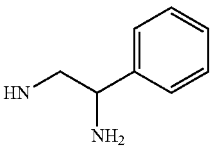 |
| 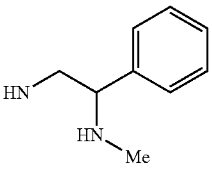 | 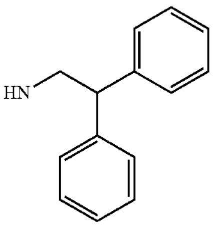 | 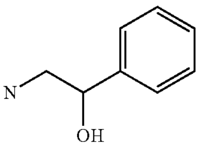 |

-continued
| HN—R | | |
|---|---|---|
| 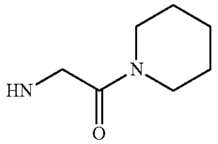 | 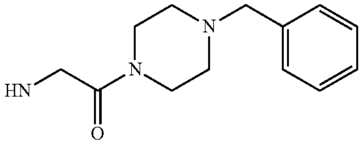 | 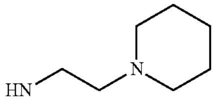 |
| 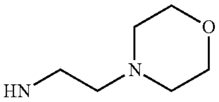 | 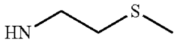 | 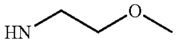 |
| 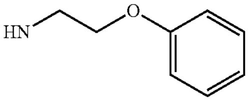 | 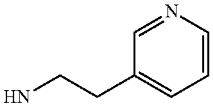 | 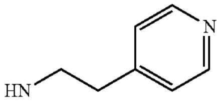 |
| 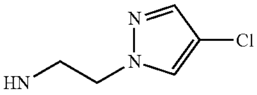 | 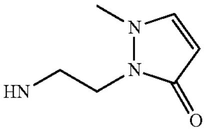 | |
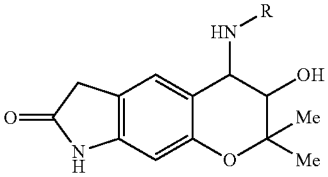
| | | |
|---|---|---|
| 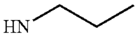 | 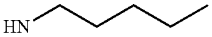 | 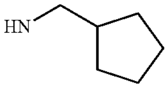 |
| 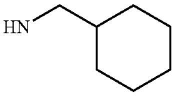 | 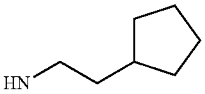 | 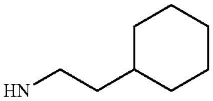 |
| 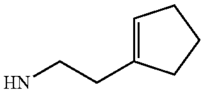 | 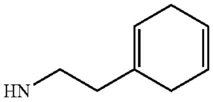 | 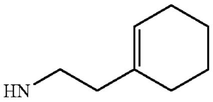 |
| 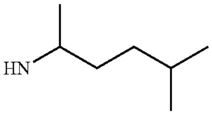 | 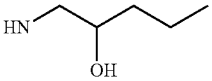 | 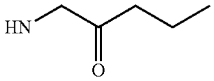 |
| 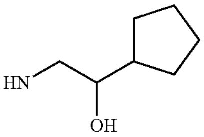 | 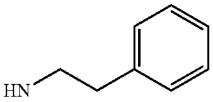 | 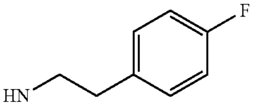 |
| 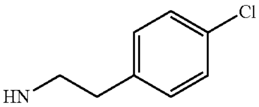 | 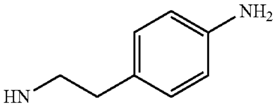 | 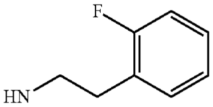 |

-continued
| HN—R | | |
|---|---|---|
| 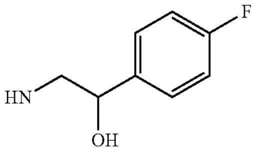 | 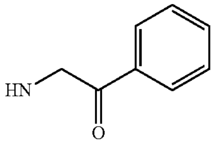 | 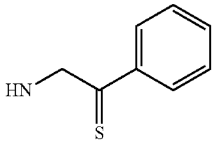 |
| 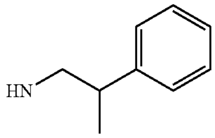 | 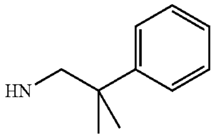 | 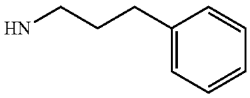 |
| 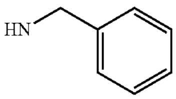 | 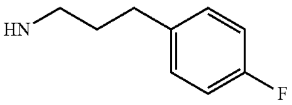 | 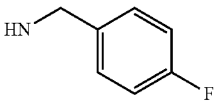 |
| 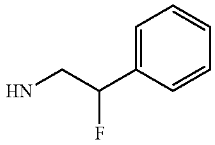 | 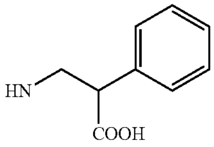 | 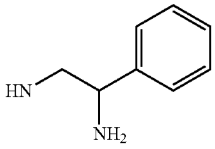 |
| 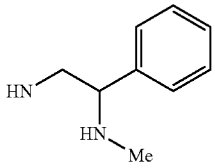 | 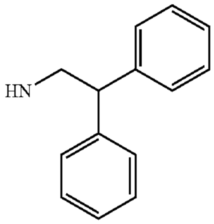 | 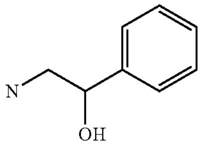 |
| 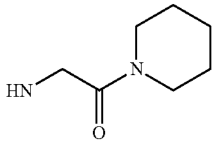 | 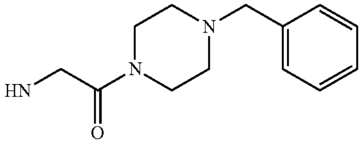 | 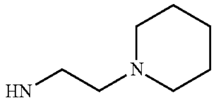 |
| 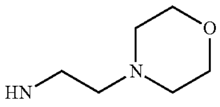 | 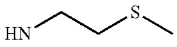 | 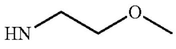 |
| 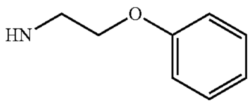 | 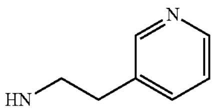 | 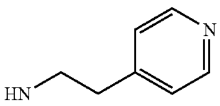 |
| 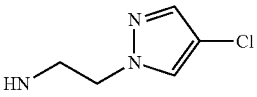 | 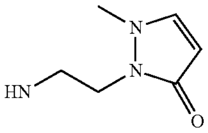 | |

-continued
| | HN—R | |
|---|---|---|
| | 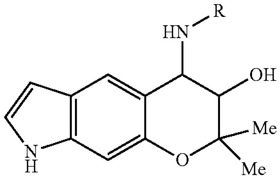 | |
| 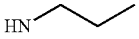 | 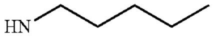 | 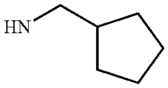 |
| 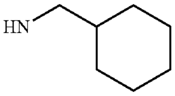 | 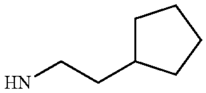 | 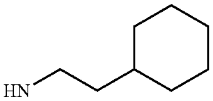 |
| 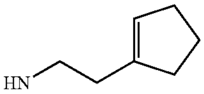 | 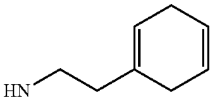 | 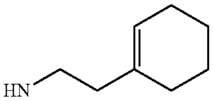 |
| 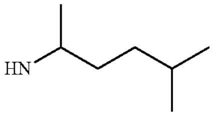 | 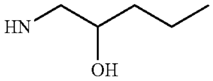 | 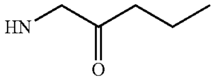 |
| 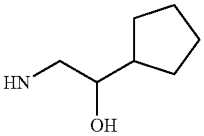 | 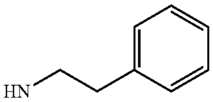 | 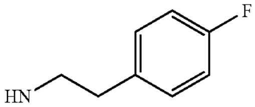 |
| 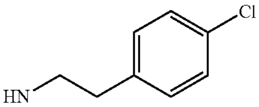 | 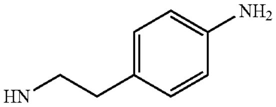 | 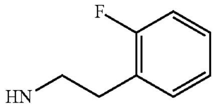 |
| 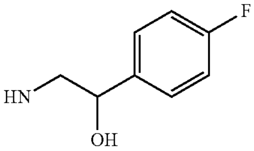 | 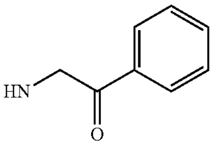 | 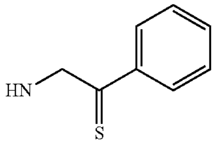 |
| 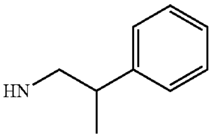 | 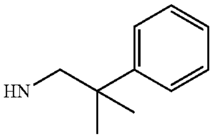 | 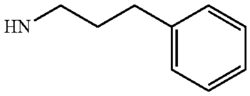 |
| 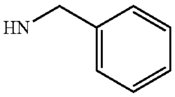 | 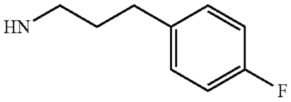 | 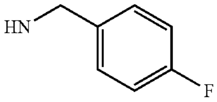 |
| 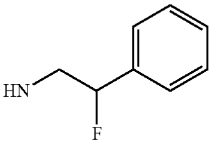 | 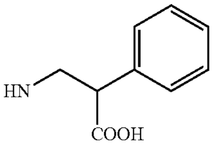 | 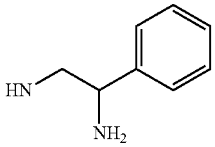 |

-continued
| HN—R | | |
|---|---|---|
| 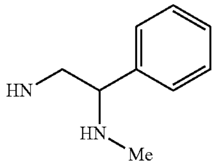 | 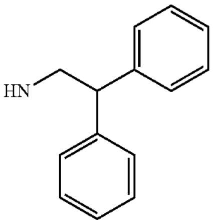 | 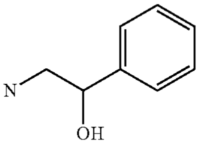 |
| 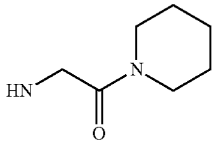 | 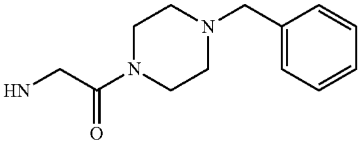 | 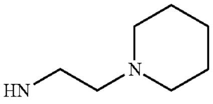 |
| 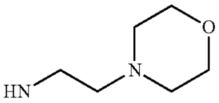 | 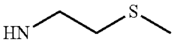 | 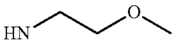 |
| 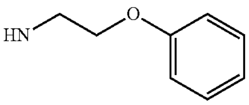 | 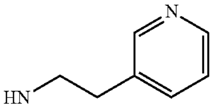 | 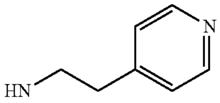 |
| 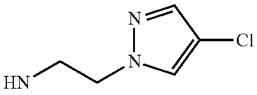 | 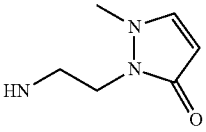 | |
| | 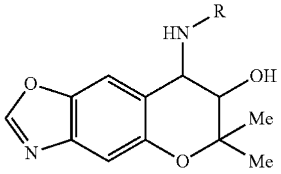 | |
|---|---|---|
| 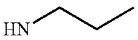 | 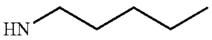 | 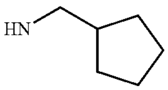 |
| 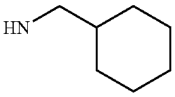 | 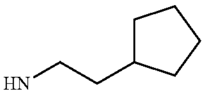 | 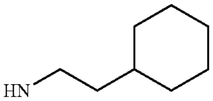 |
| 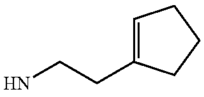 | 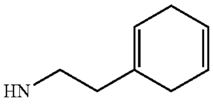 | 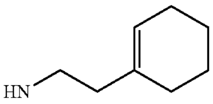 |
| 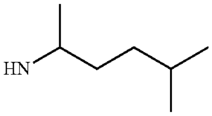 | 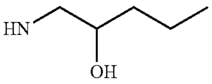 | 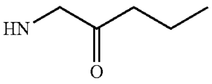 |
| 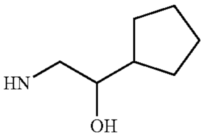 | 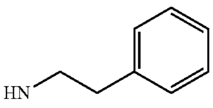 | 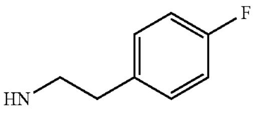 |

-continued
| HN—R | | |
|---|---|---|
| 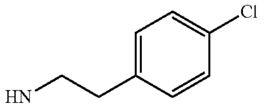 | 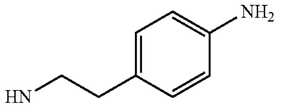 | 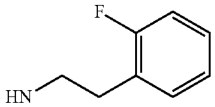 |
| 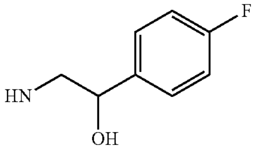 | 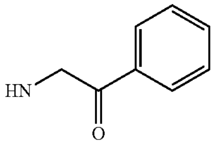 | 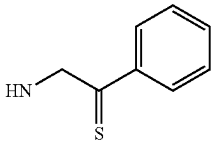 |
| 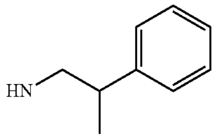 | 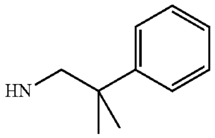 | 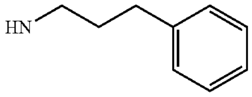 |
| 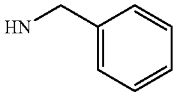 | 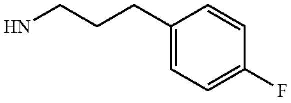 | 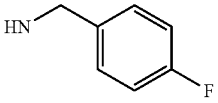 |
| 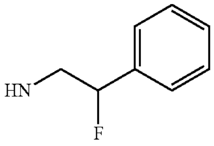 | 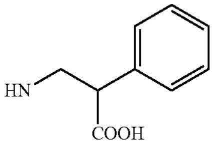 | 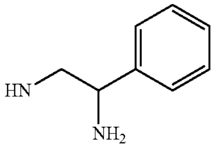 |
| 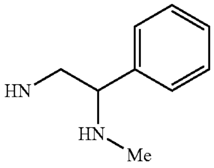 | 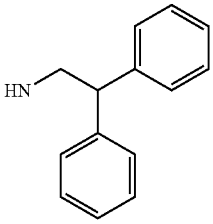 | 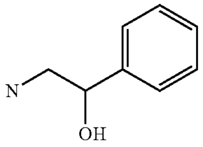 |
| 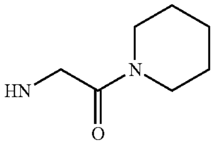 | 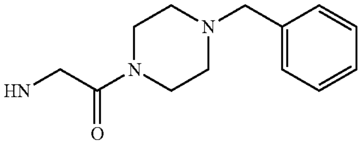 | 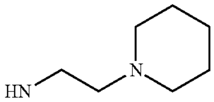 |
| 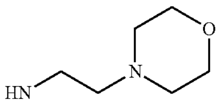 | 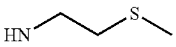 | 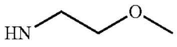 |
| 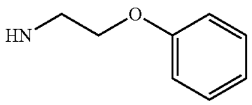 | 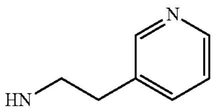 | 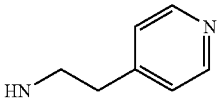 |
| 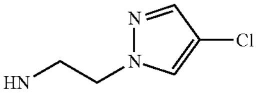 | 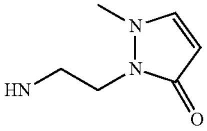 | |

-continued
| | HN—R | |
|---|---|---|
| | 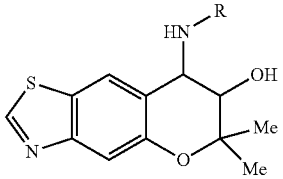 | |
| 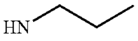 | 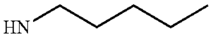 | 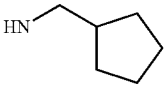 |
| 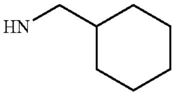 | 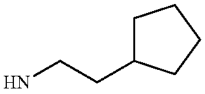 | 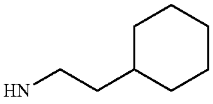 |
| 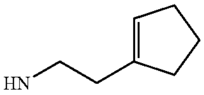 | 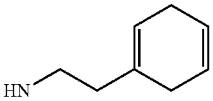 | 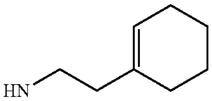 |
| 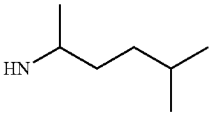 | 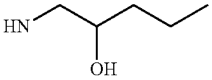 | 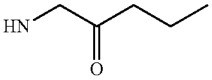 |
| 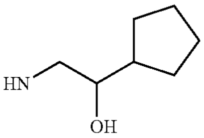 | 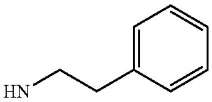 | 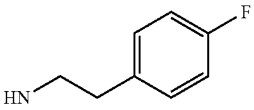 |
| 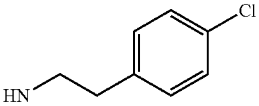 | 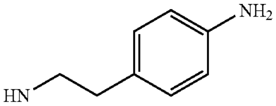 | 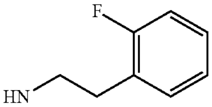 |
| 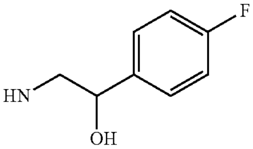 | 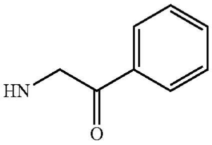 | 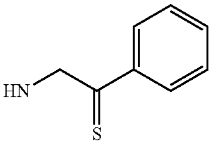 |
| 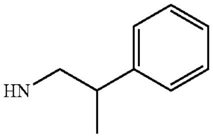 | 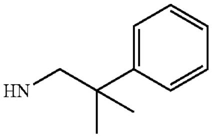 | 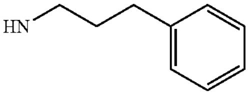 |
| 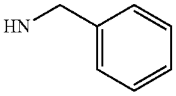 | 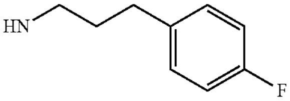 | 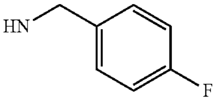 |
| 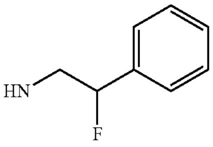 | 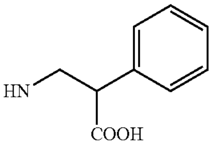 | 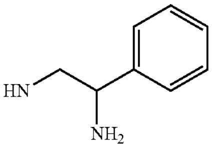 |

-continued
| HN—R | | |
|---|---|---|
| 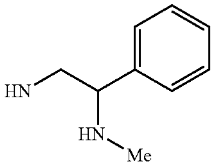 | 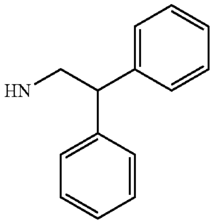 | 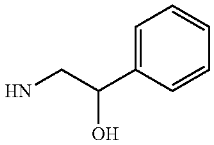 |
| 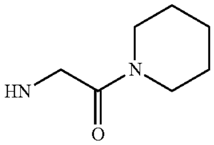 | 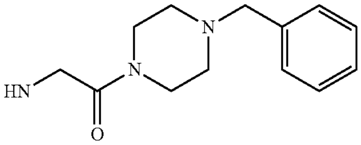 | 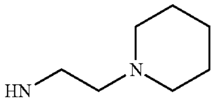 |
| 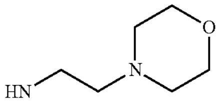 | 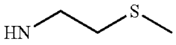 | 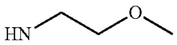 |
| 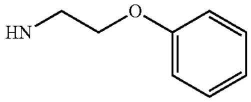 | 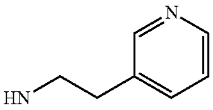 | 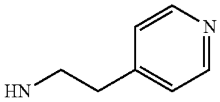 |
| 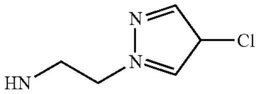 | 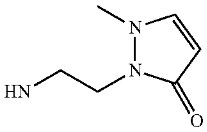 | |
| 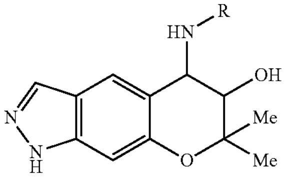 | | |
|---|---|---|
| 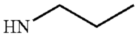 | 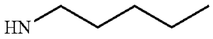 | 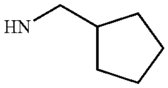 |
| 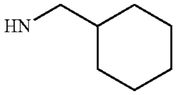 | 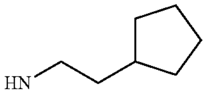 | 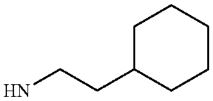 |
| 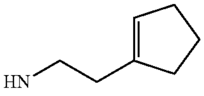 | 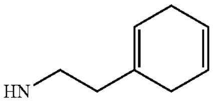 | 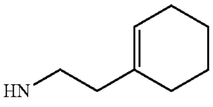 |
| 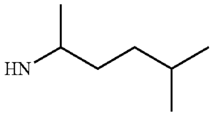 | 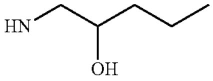 | 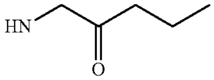 |
| 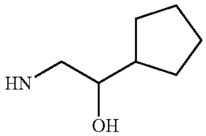 | 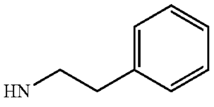 | 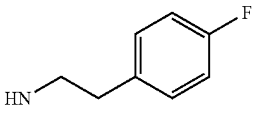 |

-continued
| HN—R | | |
|---|---|---|
| 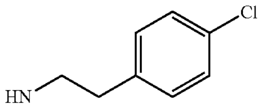 | 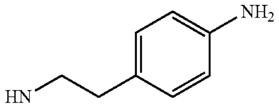 | 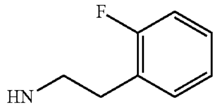 |
| 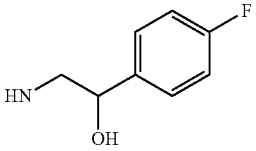 | 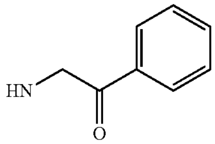 | 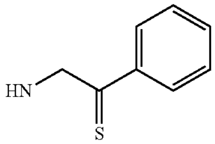 |
| 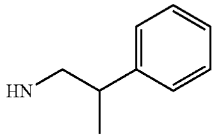 | 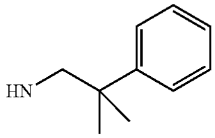 | 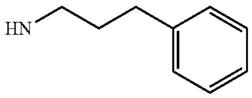 |
| 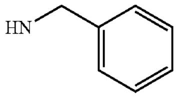 | 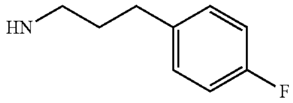 | 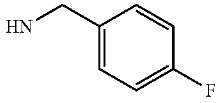 |
| 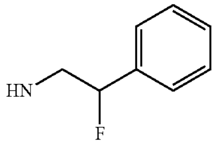 | 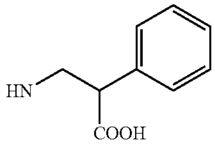 | 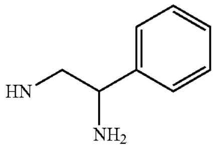 |
| 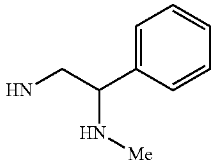 | 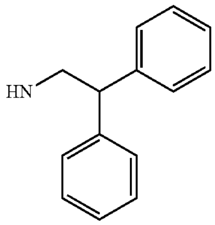 | 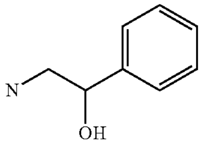 |
| 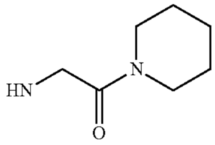 | 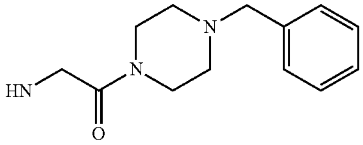 | 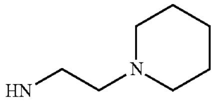 |
| 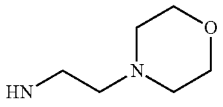 | 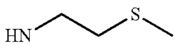 | 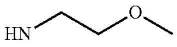 |
| 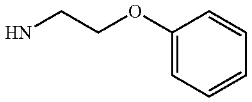 | 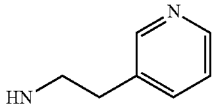 | 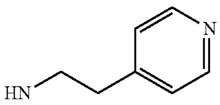 |
| 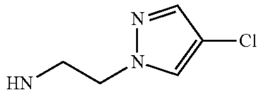 | 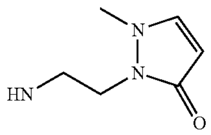 | |

-continued
| | HN—R | |
|---|---|---|
| | 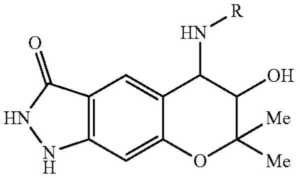 | |
| 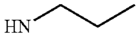 | 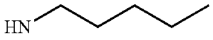 | 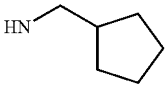 |
| 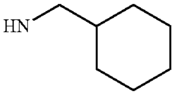 | 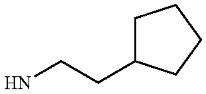 | 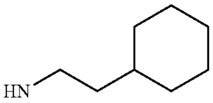 |
| 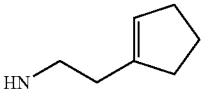 | 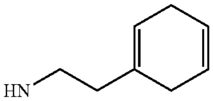 | 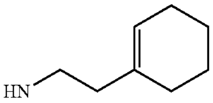 |
| 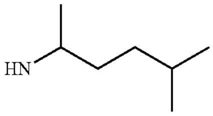 | 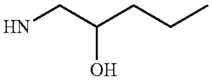 | 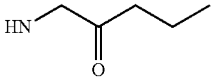 |
| 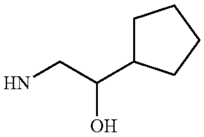 | 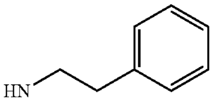 | 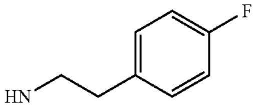 |
| 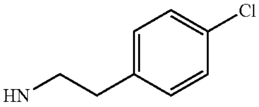 | 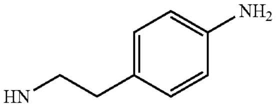 | 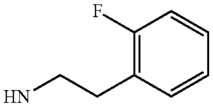 |
| 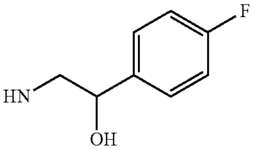 | 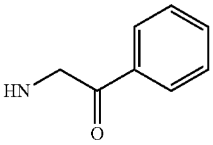 | 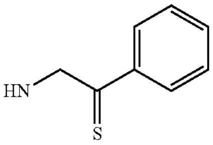 |
| 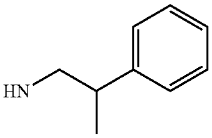 | 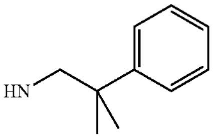 | 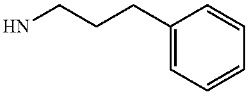 |
| 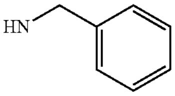 | 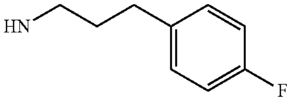 | 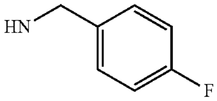 |
| 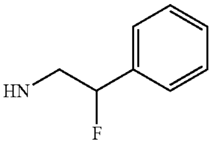 | 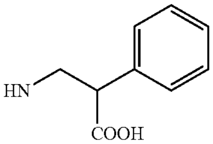 | 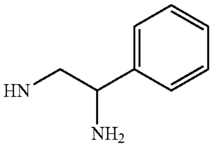 |

-continued
| HN—R | | |
|---|---|---|
| 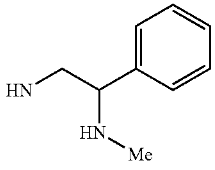 | 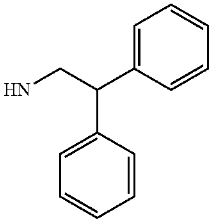 | 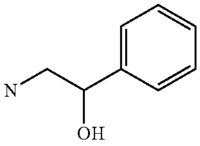 |
| 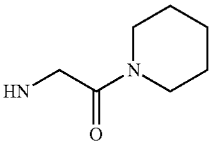 | 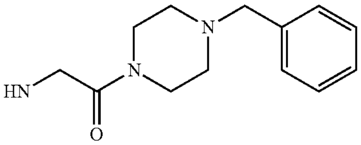 | 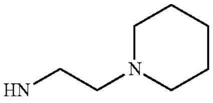 |
| 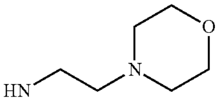 | 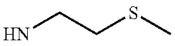 | 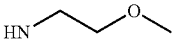 |
| 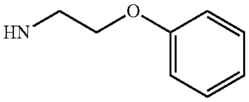 | 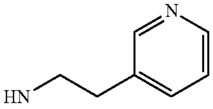 | 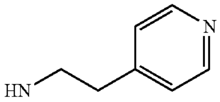 |
| 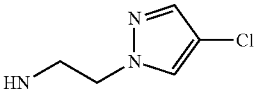 | 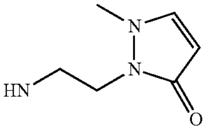 | |
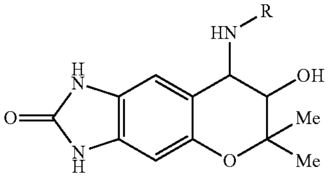
| | | |
|---|---|---|
| 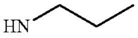 | 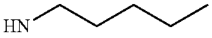 | 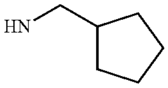 |
| 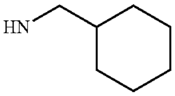 | 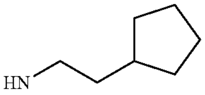 | 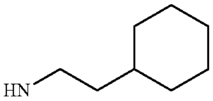 |
| 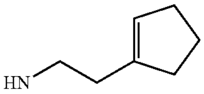 | 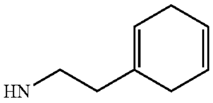 | 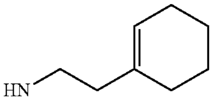 |
| 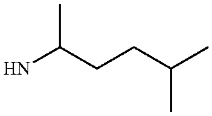 | 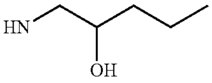 | 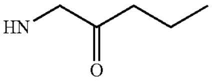 |
| 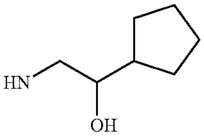 | 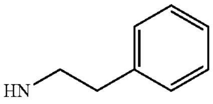 | 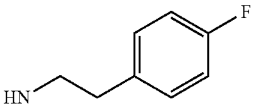 |

-continued
| HN—R | | |
|---|---|---|
| 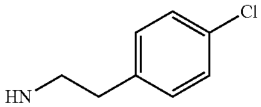 | 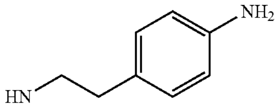 | 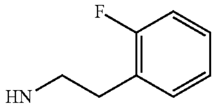 |
| 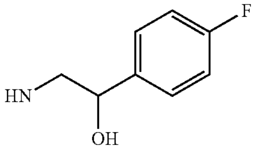 | 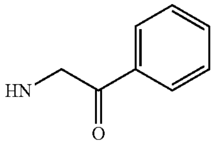 | 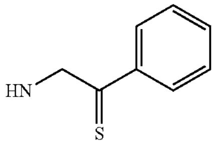 |
| 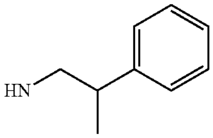 | 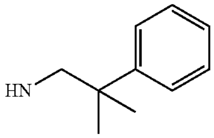 | 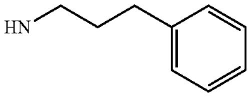 |
| 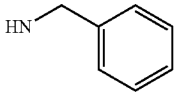 | 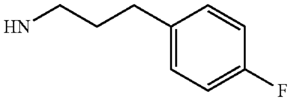 | 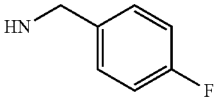 |
| 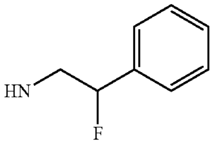 | 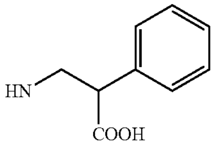 | 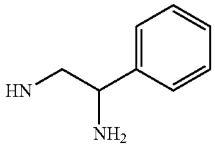 |
| 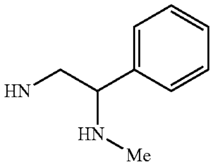 | 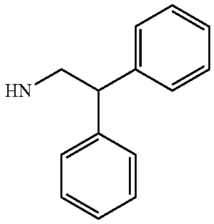 | 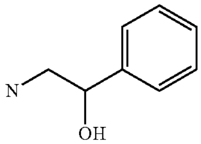 |
| 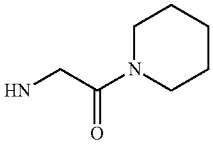 | 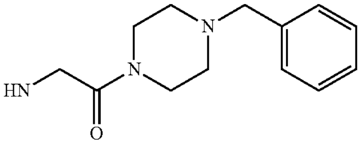 | 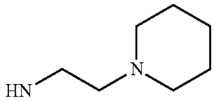 |
| 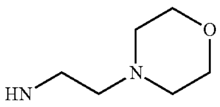 | 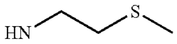 | 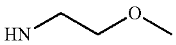 |
| 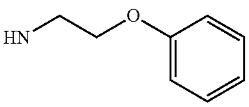 | 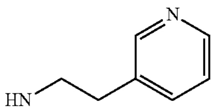 | 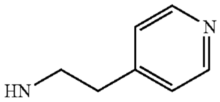 |
| 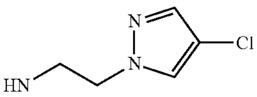 | 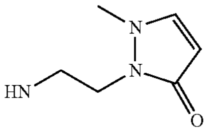 | |

| $R^{11}$ | $R^{12}$ |
|---|---|

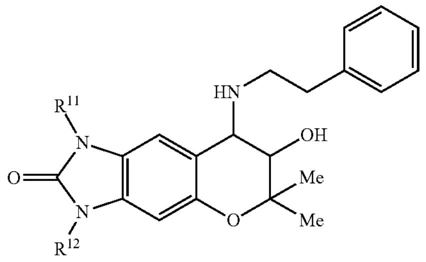

| | |
|---|---|
| H | Me |
| H | Et |
| H | iPr |
| H | nPr |
| H | nBu |
| Me | tBu |
| Me | Ph |
| Me | $CH_2OH$ |
| Me | $CH_2OMe$ |
| Me | $CH_2NH_2$ |
| Me | Me |
| Et | $CH_2NH_2$ |
| Et | $CH_2NHMe$ |
| Et | $CH_2Ph$ |
| iPr | $CH_2Ph$ |
| nPr | $CH_2CH_2Ph$ |
| nBu | H |
| tBu | Me |
| Ph | H |
| $CH_2OH$ | Me |
| $CH_2OH$ | Et |
| $CH_2OMe$ | nPr |
| $CH_2OMe$ | Ph |
| $CH_2NH_2$ | H |
| $CH_2NH_2$ | nPr |
| $CH_2NH_2$ | Ph |
| $CH_2NH_2$ | Me |
| $CH_2NHMe$ | Et |
| $CH_2Ph$ | nPr |
| $CH_2Ph$ | Ph |
| $CH_2CH_2Ph$ | $CH_2Ph$ |

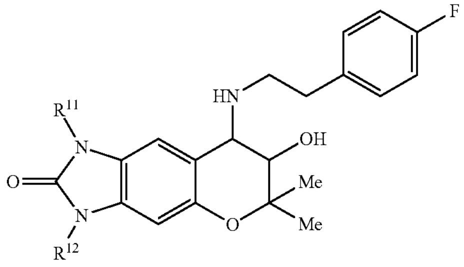

| | |
|---|---|
| H | Me |
| H | Et |
| H | iPr |
| H | nPr |
| H | nBu |
| Me | tBu |
| Me | Ph |
| Me | $CH_2OH$ |
| Me | $CH_2OMe$ |
| Me | $CH_2NH_2$ |
| Me | Me |
| Et | $CH_2NH_2$ |
| Et | $CH_2NHMe$ |
| Et | $CH_2Ph$ |
| iPr | $CH_2Ph$ |
| nPr | $CH_2CH_2Ph$ |
| nBu | H |
| tBu | Me |
| Ph | H |

-continued

| $R^{11}$ | $R^{12}$ |
|---|---|
| $CH_2OH$ | Me |
| $CH_2OH$ | Et |
| $CH_2OMe$ | nPr |
| $CH_2OMe$ | Ph |
| $CH_2NH_2$ | H |
| $CH_2NH_2$ | nPr |
| $CH_2NH_2$ | Ph |
| $CH_2NH_2$ | Me |
| $CH_2NHMe$ | Et |
| $CH_2Ph$ | nPr |
| $CH_2Ph$ | Ph |
| $CH_2CH_2Ph$ | $CH_2Ph$ |

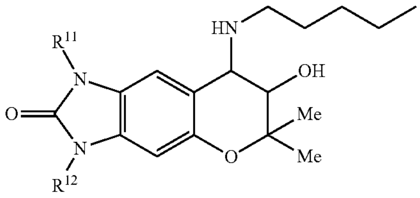

| | |
|---|---|
| H | Me |
| H | Et |
| H | iPr |
| H | nPr |
| H | nBu |
| Me | tBu |
| Me | Ph |
| Me | $CH_2OH$ |
| Me | $CH_2OMe$ |
| Me | $CH_2NH_2$ |
| Me | Me |
| Et | $CH_2NH_2$ |
| Et | $CH_2NHMe$ |
| Et | $CH_2Ph$ |
| iPr | $CH_2Ph$ |
| nPr | $CH_2CH_2Ph$ |
| nBu | H |
| tBu | Me |
| Ph | H |
| $CH_2OH$ | Me |
| $CH_2OH$ | Et |
| $CH_2OMe$ | nPr |
| $CH_2OMe$ | Ph |
| $CH_2NH_2$ | H |
| $CH_2NH_2$ | nPr |
| $CH_2NH_2$ | Ph |
| $CH_2NH_2$ | Me |
| $CH_2NHMe$ | Et |
| $CH_2Ph$ | nPr |
| $CH_2Ph$ | Ph |
| $CH_2CH_2Ph$ | $CH_2Ph$ |

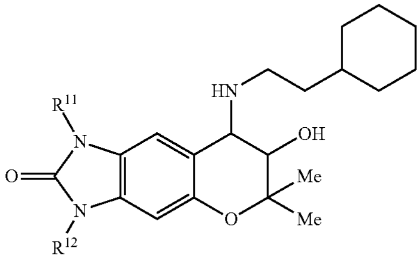

| | |
|---|---|
| H | Me |
| H | Et |
| H | iPr |
| H | nPr |
| H | nBu |
| Me | tBu |
| Me | Ph |
| Me | $CH_2OH$ |
| Me | $CH_2OMe$ |

-continued
| $R^{11}$ | $R^{12}$ |
|---|---|
| Me | $CH_2NH_2$ |
| Me | Me |
| Et | $CH_2NH_2$ |
| Et | $CH_2NHMe$ |
| Et | $CH_2Ph$ |
| iPr | $CH_2Ph$ |
| nPr | $CH_2CH_2Ph$ |
| nBu | H |
| tBu | Me |
| Ph | H |
| $CH_2OH$ | Me |
| $CH_2OH$ | Et |
-continued
| $R^{11}$ | $R^{12}$ |
|---|---|
| $CH_2OMe$ | nPr |
| $CH_2OMe$ | Ph |
| $CH_2NH_2$ | H |
| $CH_2NH_2$ | nPr |
| $CH_2NH_2$ | Ph |
| $CH_2NH_2$ | Me |
| $CH_2NHMe$ | Et |
| $CH_2Ph$ | nPr |
| $CH_2Ph$ | Ph |
| $CH_2CH_2Ph$ | $CH_2Ph$ |
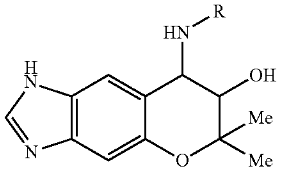
HN—R
| | | |
|---|---|---|
| 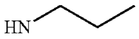 | 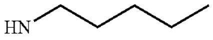 | 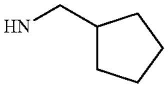 |
| 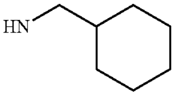 | 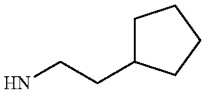 | 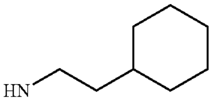 |
| 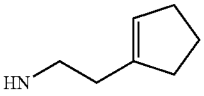 | 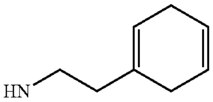 | 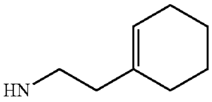 |
| 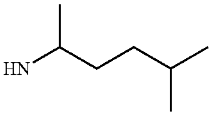 | 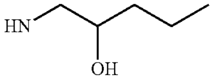 | 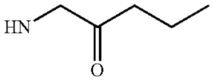 |
| 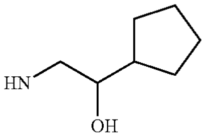 | 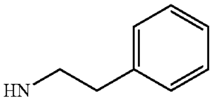 | 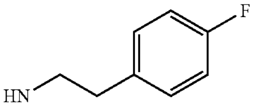 |
| 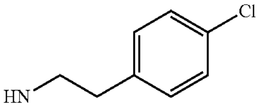 | 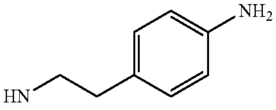 | 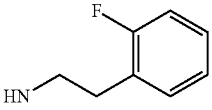 |
| 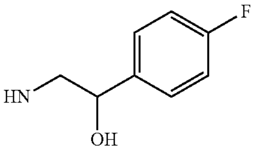 | 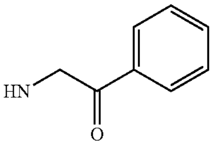 | 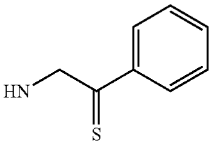 |
| 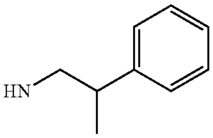 | 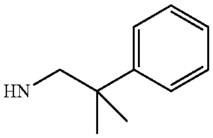 | 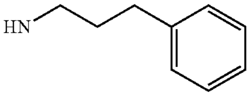 |

-continued

| | | |
|---|---|---|
| 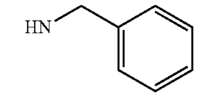 | 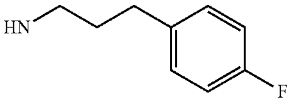 | 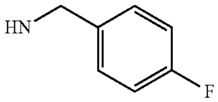 |
| 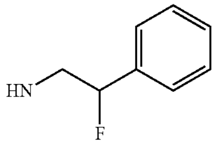 | 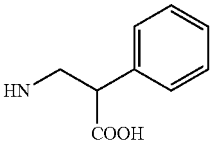 | 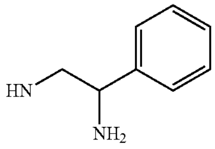 |
| 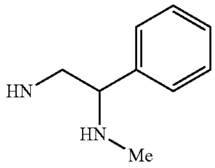 | 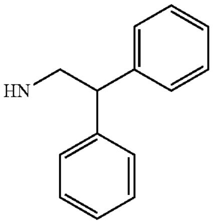 | 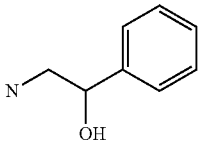 |
| 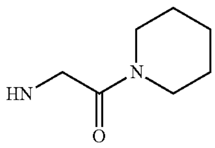 | 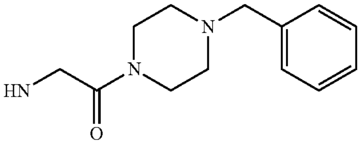 | 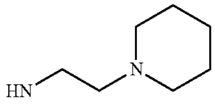 |
| 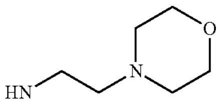 | 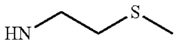 | 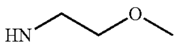 |
| 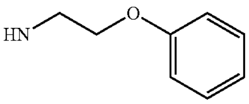 | 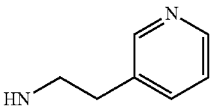 | 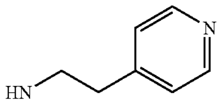 |
| 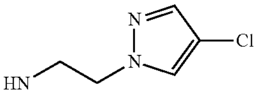 | 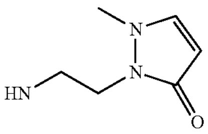 | |

| $R^{11}$ | $R^{13}$ | $R^{11}$ | $R^{13}$ |
|---|---|---|---|
| 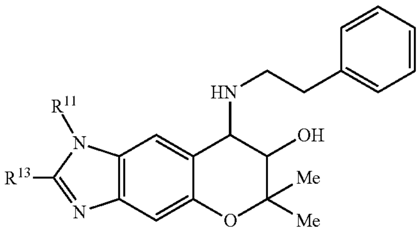 | | | |
| H | Me | H | $NO_2$ |
| H | Et | H | CHO |
| H | iPr | H | $SO_3H$ |
| H | nPr | H | Cl |
| H | nBu | H | Br |
| H | tBu | Me | $CH_2OH$ |
| H | Ph | Me | $CH_2NH_2$ |
| Me | Me | Me | $CH_2NHMe$ |
| Me | Et | Me | $CH_2Ph$ |

-continued

| $R^{11}$ | $R^{13}$ | $R^{11}$ | $R^{13}$ |
|---|---|---|---|
| Et | iPr | Me | COMe |
| Et | nPr | Me | COOH |
| iPr | nBu | Et | $CONH_2$ |
| nPr | tBu | Et | CONHMe |
| nBu | Ph | Et | CONHMs |
| tBu | iPr | iPr | NHMs |
| Ph | nPr | nPr | NHCOMe |
| $CH_2OH$ | nBu | nBu | $NO_2$ |
| $CH_2OH$ | tBu | tBu | CHO |
| $CH_2OMe$ | Ph | Ph | $SO_3H$ |
| $CH_2OMe$ | Et | $CH_2OH$ | $SO_2NHMe$ |
| $CH_2NH_2$ | nPr | $CH_2OH$ | OH |
| $CH_2NH_2$ | Ph | $CH_2OMe$ | COMe |
| $CH_2NH_2$ | Cl | $CH_2OMe$ | COOH |
| $CH_2NH_2$ | F | $CH_2NH_2$ | $CONH_2$ |
| $CH_2NHMe$ | Cl | $CH_2NH_2$ | CONHMe |
| $CH_2Ph$ | Et | $CH_2NH_2$ | CONHMs |
| $CH_2Ph$ | nPr | $CH_2NH_2$ | NHMs |
| $CH_2Ph$ | Ph | $CH_2NHMe$ | $NO_2$ |
| $CH_2CH_2Ph$ | Me | $CH_2Ph$ | OH |
| H | $CH_2Ph$ | $CH_2Ph$ | COMe |

-continued

| $R^{11}$ | $R^{13}$ | $R^{11}$ | $R^{13}$ |
|---|---|---|---|
| Me | $CH_2Ph$ | $CH_2CH_2Ph$ | COOH |

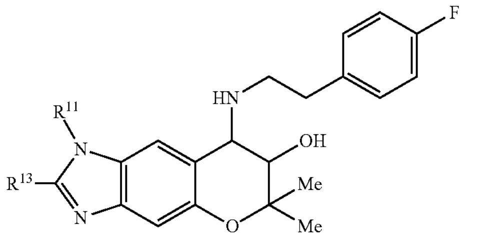

| | | | |
|---|---|---|---|
| H | Me | H | $NO_2$ |
| H | Et | H | CHO |
| H | iPr | H | $SO_3H$ |
| H | nPr | H | Cl |
| H | nBu | H | Br |
| H | tBu | Me | $CH_2OH$ |
| H | Ph | Me | $CH_2NH_2$ |
| Me | Me | Me | $CH_2NHMe$ |
| Me | Et | Me | $CH_2Ph$ |
| Et | iPr | Me | COMe |
| Et | nPr | Me | COON |
| iPr | nBu | Et | $CONH_2$ |
| nPr | tBu | Et | CONHMe |
| nBu | Ph | Et | CONHMs |
| tBu | iPr | iPr | NHMs |
| Ph | nPr | nPr | NHCOMe |
| $CH_2OH$ | nBu | nBu | $NO_2$ |
| $CH_2OH$ | tBu | tBu | CHO |
| $CH_2OMe$ | Ph | Ph | $SO_3H$ |
| $CH_2OMe$ | Et | $CH_2OH$ | $SO_2NHMe$ |
| $CH_2NH_2$ | nPr | $CH_2OH$ | OH |
| $CH_2NH_2$ | Ph | $CH_2OMe$ | COMe |
| $CH_2NH_2$ | Cl | $CH_2OMe$ | COOH |
| $CH_2NH_2$ | F | $CH_2NH_2$ | $CONH_2$ |
| $CH_2NHMe$ | Cl | $CH_2NH_2$ | CONHMe |
| $CH_2Ph$ | Et | $CH_2NH_2$ | CONHMs |
| $CH_2Ph$ | nPr | $CH_2NH_2$ | NHMs |
| $CH_2Ph$ | Ph | $CH_2NHMe$ | $NO_2$ |
| $CH_2CH_2Ph$ | Me | $CH_2Ph$ | OH |
| H | $CH_2Ph$ | $CH_2Ph$ | COMe |
| Me | $CH_2Ph$ | $CH_2CH_2Ph$ | COOH |

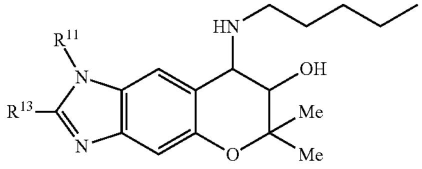

| | | | |
|---|---|---|---|
| H | Me | H | $NO_2$ |
| H | Et | H | CHO |
| H | iPr | H | $SO_3H$ |
| H | nPr | H | Cl |
| H | nBu | H | Br |
| H | tBu | Me | $CH_2OH$ |
| H | Ph | Me | $CH_2NH_2$ |
| Me | Me | Me | $CH_2NHMe$ |
| Me | Et | Me | $CH_2Ph$ |
| Et | iPr | Me | COMe |
| Et | nPr | Me | COOH |
| iPr | nBu | Et | $CONH_2$ |
| nPr | tBu | Et | CONHMe |
| nBu | Ph | Et | CONHMs |
| tBu | iPr | iPr | NHMs |
| Ph | nPr | nPr | NHCOMe |
| $CH_2OH$ | nBu | nBu | $NO_2$ |
| $CH_2OH$ | tBu | tBu | CHO |
| $CH_2OMe$ | Ph | Ph | $SO_3H$ |
| $CH_2OMe$ | Et | $CH_2OH$ | $SO_2NHMe$ |
| $CH_2NH_2$ | nPr | $CH_2OH$ | OH |

-continued

| $R^{11}$ | $R^{13}$ | $R^{11}$ | $R^{13}$ |
|---|---|---|---|
| $CH_2NH_2$ | Ph | $CH_2OMe$ | COMe |
| $CH_2NH_2$ | Cl | $CH_2OMe$ | COOH |
| $CH_2NH_2$ | F | $CH_2NH_2$ | $CONH_2$ |
| $CH_2NHMe$ | Cl | $CH_2NH_2$ | CONHMe |
| $CH_2Ph$ | Et | $CH_2NH_2$ | CONHMs |
| $CH_2Ph$ | nPr | $CH_2NH_2$ | NHMs |
| $CH_2Ph$ | Ph | $CH_2NHMe$ | $NO_2$ |
| $CH_2CH_2Ph$ | Me | $CH_2Ph$ | OH |
| H | $CH_2Ph$ | $CH_2Ph$ | COMe |
| Me | $CH_2Ph$ | $CH_2CH_2Ph$ | COOH |

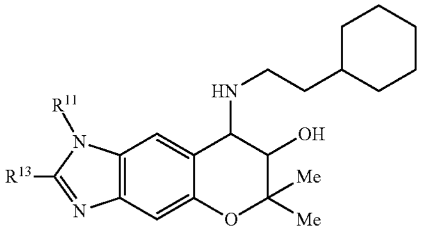

| | | | |
|---|---|---|---|
| H | Me | H | $NO_2$ |
| H | Et | H | CHO |
| H | iPr | H | $SO_3H$ |
| H | nPr | H | Cl |
| H | nBu | H | Br |
| H | tBu | Me | $CH_2OH$ |
| H | Ph | Me | $CH_2NH_2$ |
| Me | Me | Me | $CH_2NHMe$ |
| Me | Et | Me | $CH_2Ph$ |
| Et | iPr | Me | COMe |
| Et | nPr | Me | COOH |
| iPr | nBu | Et | $CONH_2$ |
| nPr | tBu | Et | CONHMe |
| nBu | Ph | Et | CONHMs |
| tBu | iPr | iPr | NHMs |
| Ph | nPr | nPr | NHCOMe |
| $CH_2OH$ | nBu | nBu | $NO_2$ |
| $CH_2OH$ | tBu | tBu | CHO |
| $CH_2OMe$ | Ph | Ph | $SO_3H$ |
| $CH_2OMe$ | Et | $CH_2OH$ | $SO_2NHMe$ |
| $CH_2NH_2$ | nPr | $CH_2OH$ | OH |
| $CH_2NH_2$ | Ph | $CH_2OMe$ | COMe |
| $CH_2NH_2$ | Cl | $CH_2OMe$ | COOH |
| $CH_2NH_2$ | F | $CH_2NH_2$ | $CONH_2$ |
| $CH_2NHMe$ | Cl | $CH_2NH_2$ | CONHMe |
| $CH_2Ph$ | Et | $CH_2NH_2$ | CONHMs |
| $CH_2Ph$ | nPr | $CH_2NH_2$ | NHMs |
| $CH_2Ph$ | Ph | $CH_2NHMe$ | $NO_2$ |
| $CH_2CH_2Ph$ | Me | $CH_2Ph$ | OH |
| H | $CH_2Ph$ | $CH_2Ph$ | COMe |
| Me | $CH_2Ph$ | $CH_2CH_2Ph$ | COOH |

| | HN—R | |
|---|---|---|
| | 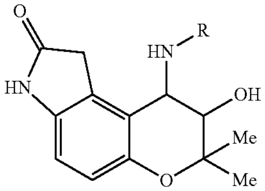 | |
| 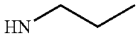 | 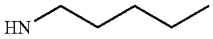 | 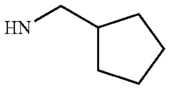 |
| 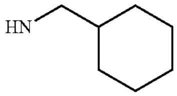 | 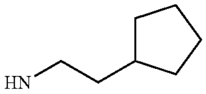 | 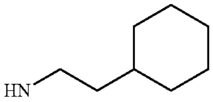 |
| 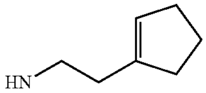 | 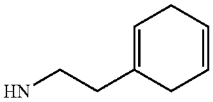 | 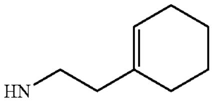 |
| 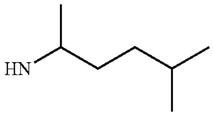 | 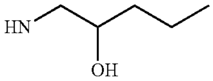 | 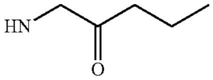 |
| 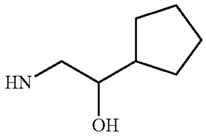 | 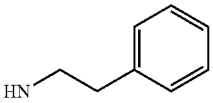 | 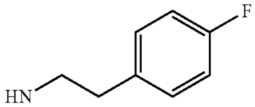 |
| 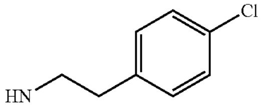 | 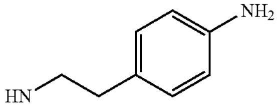 | 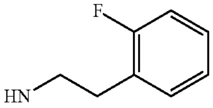 |
| 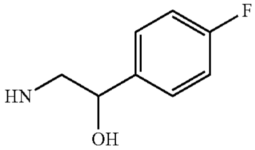 | 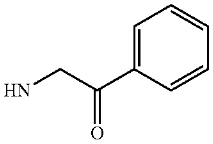 | 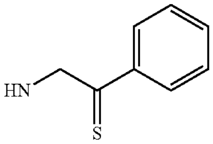 |
| 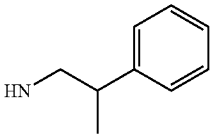 | 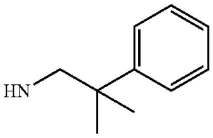 | 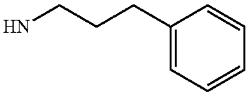 |
| 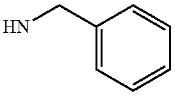 | 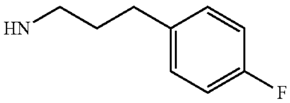 | 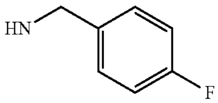 |
| 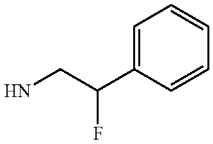 | 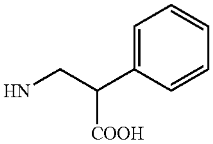 | 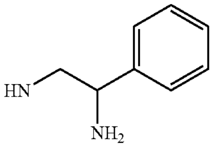 |

-continued
| HN—R | | |
|---|---|---|
| 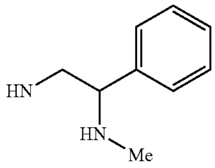 | 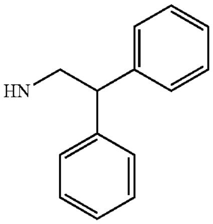 | 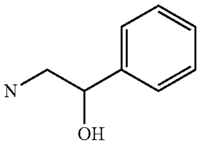 |
| 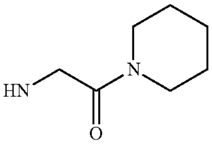 | 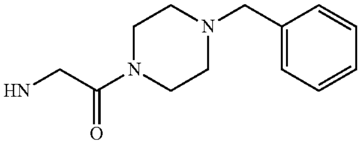 | 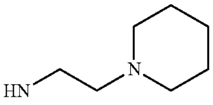 |
| 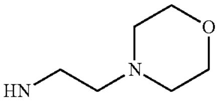 | 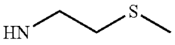 | 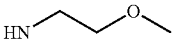 |
| 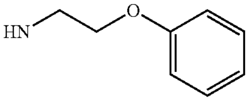 | 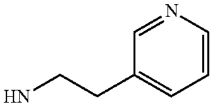 | 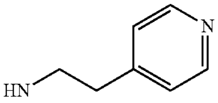 |
| 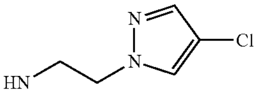 | 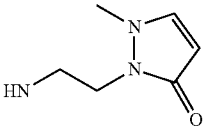 | |
| | 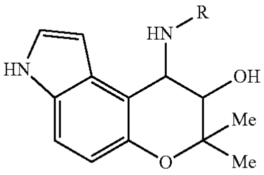 | |
|---|---|---|
| 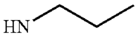 | 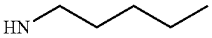 | 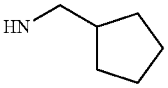 |
| 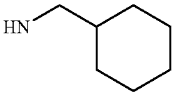 | 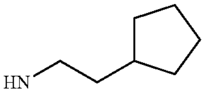 | 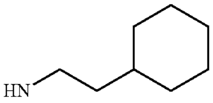 |
| 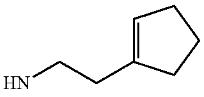 | 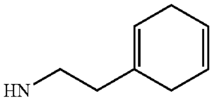 | 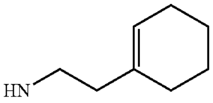 |
| 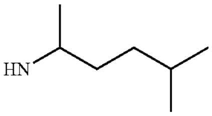 | 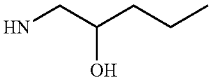 | 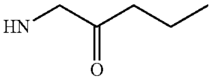 |
| 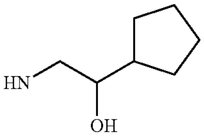 | 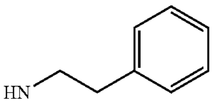 | 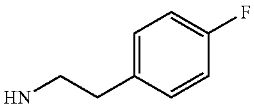 |

-continued
| HN—R | | |
|---|---|---|
| 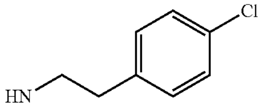 | 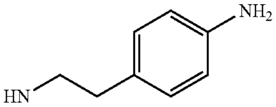 | 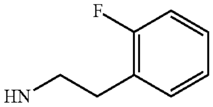 |
| 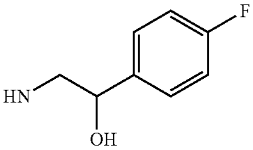 | 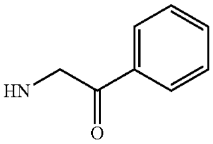 | 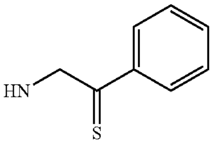 |
| 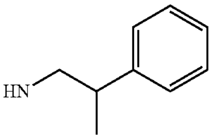 | 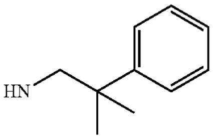 | 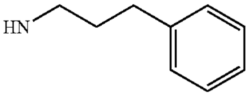 |
| 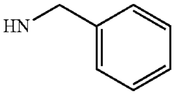 | 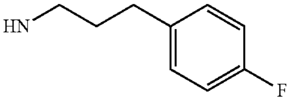 | 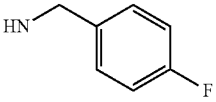 |
| 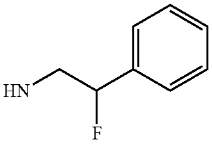 | 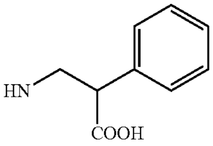 | 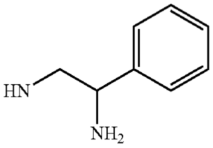 |
| 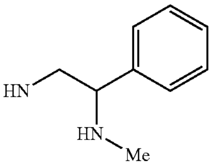 | 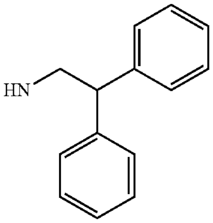 | 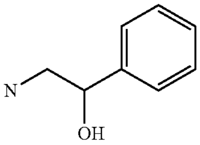 |
| 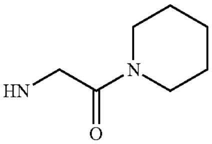 | 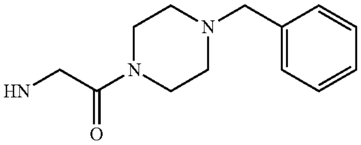 | 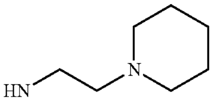 |
| 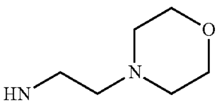 | 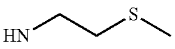 | 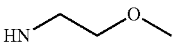 |
| 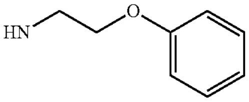 | 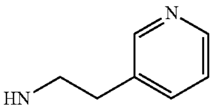 | 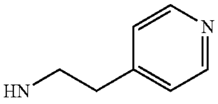 |
| 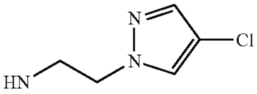 | 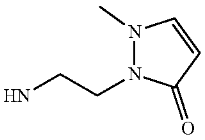 | |

-continued
| | HN—R | |
|---|---|---|
| | 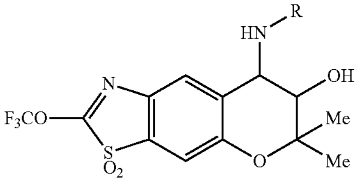 | |
| 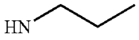 | 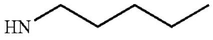 | 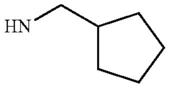 |
| 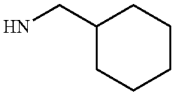 | 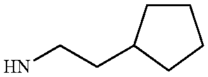 | 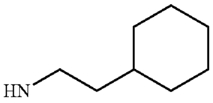 |
| 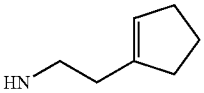 | 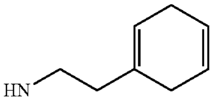 | 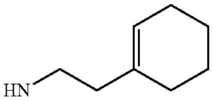 |
| 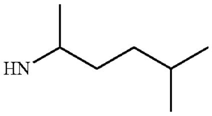 | 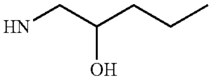 | 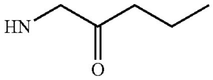 |
| 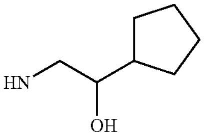 | 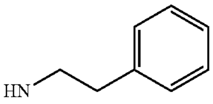 | 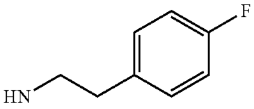 |
| 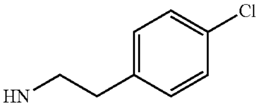 | 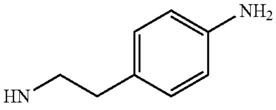 | 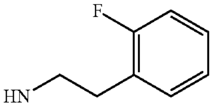 |
| 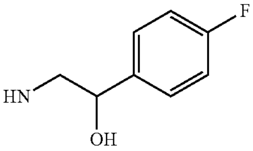 | 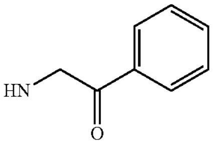 | 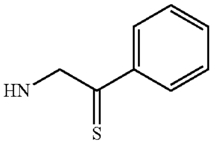 |
| 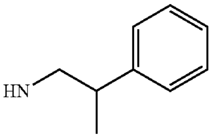 | 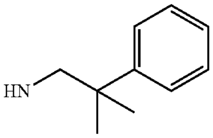 | 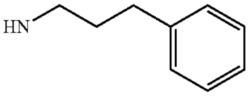 |
| 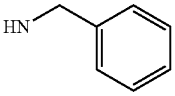 | 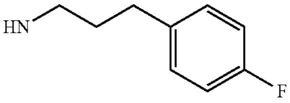 | 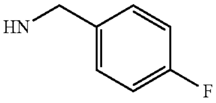 |
| 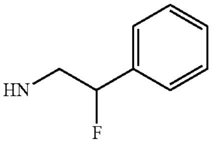 | 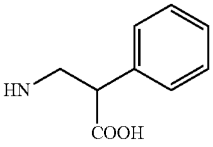 | 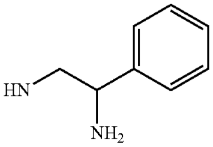 |

-continued
| HN—R | | |
|---|---|---|
| 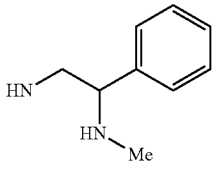 | 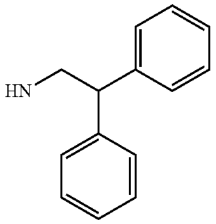 | 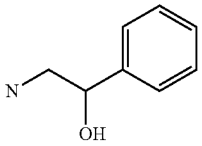 |
| 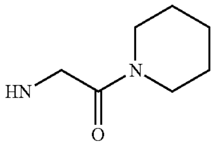 | 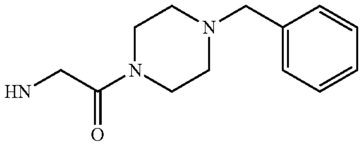 | 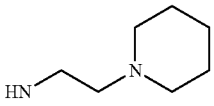 |
| 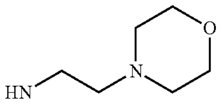 | 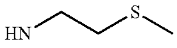 | 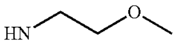 |
| 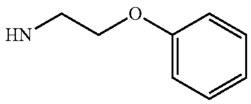 | 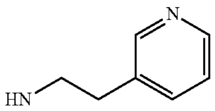 | 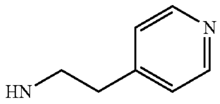 |
| 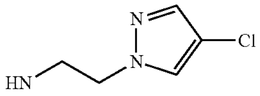 | 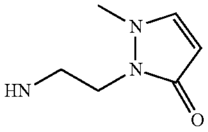 | |
| | 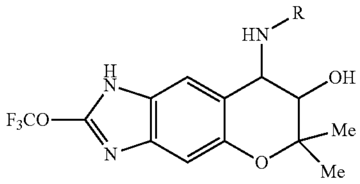 | |
| 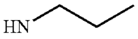 | 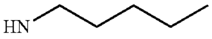 | 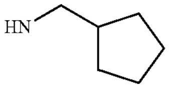 |
| 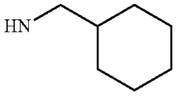 | 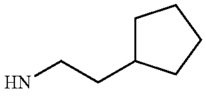 | 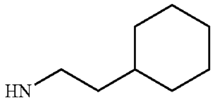 |
| 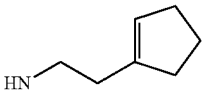 | 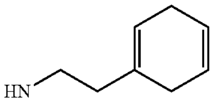 | 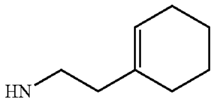 |
| 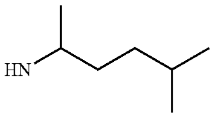 | 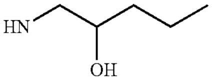 | 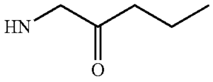 |
| 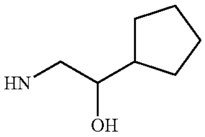 | 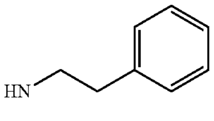 | 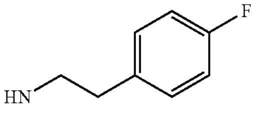 |

-continued
| HN—R | | |
|---|---|---|
| 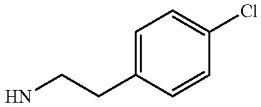 | 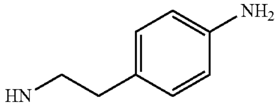 | 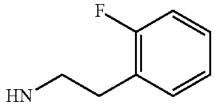 |
| 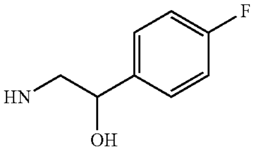 | 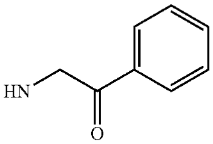 | 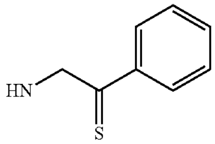 |
| 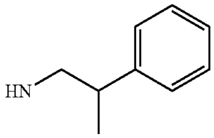 | 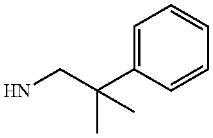 | 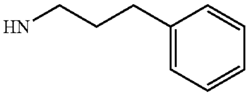 |
| 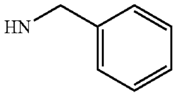 | 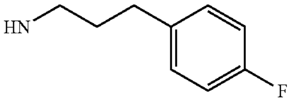 | 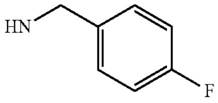 |
| 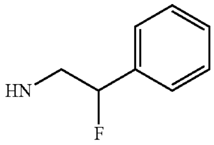 | 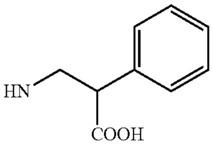 | 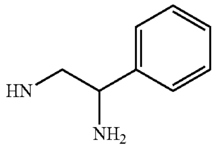 |
| 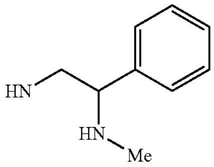 | 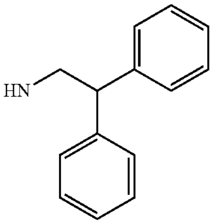 | 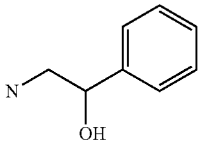 |
| 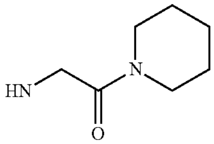 | 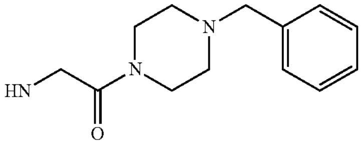 | 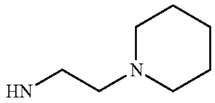 |
| 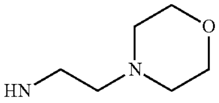 | 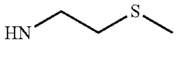 | 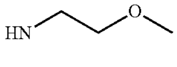 |
| 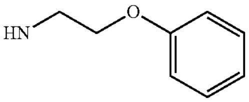 | 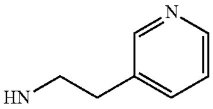 | 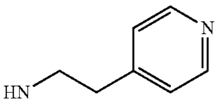 |
| 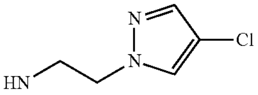 | 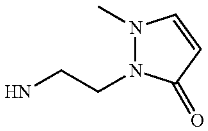 | |

| $R^{11}$ | $R^{13}$ | $R^{14}$ | $R^{11}$ | $R^{13}$ | $R^{14}$ | $R^{11}$ | $R^{13}$ | $R^{14}$ |
|---|---|---|---|---|---|---|---|---|
| 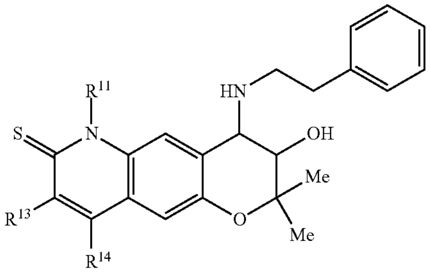 | | | | | | | | |
| H | H | Et | H | $NO_2$ | H | H | H | $NO_2$ |
| H | H | iPr | H | CHO | H | H | H | CHO |
| H | H | nPr | H | $SO_3H$ | H | H | H | $SO_3H$ |
| H | H | nBu | H | Cl | H | H | H | Cl |
| H | H | tBu | H | Br | H | H | H | Br |
| Me | H | H | Me | $CH_2OH$ | H | Me | H | $CH_2OH$ |
| Me | Et | Ph | Me | $CH_2NH_2$ | H | Me | H | $CH_2NH_2$ |
| Me | iPr | H | Me | $CH_2NHMe$ | H | Me | H | $CH_2NHMe$ |
| Me | nPr | H | Me | $CH_2Ph$ | H | Me | H | $CH_2Ph$ |
| Me | nBu | H | Me | COMe | H | Me | H | COMe |
| Me | tBu | H | Me | COOH | H | Me | H | COON |
| Et | Ph | H | Et | $CONH_2$ | H | Et | H | $CONH_2$ |
| Et | H | Et | Et | CONHMe | Et | Et | Et | CONHMe |
| Et | H | iPr | Et | CONHMs | iPr | Et | iPr | CONHMs |
| iPr | H | nPr | iPr | NHMs | nPr | iPr | nPr | NHMs |
| nPr | H | nBu | nPr | NHCOMe | nBu | nPr | nBu | NHCOMe |
| nBu | H | tBu | nBu | $NO_2$ | tBu | nBu | tBu | $NO_2H$ |
| tBu | H | Ph | tBu | CHO | Ph | tBu | Ph | H |
| Ph | Cl | Et | Ph | $SO_3H$ | Et | Ph | Et | H |
| $CH_2OH$ | Cl | nPr | $CH_2OH$ | $SO_2NMe$ | nPr | $CH_2OH$ | nPr | H |
| $CH_2OH$ | Cl | Ph | $CH_2OH$ | OH | Ph | $CH_2OH$ | Ph | H |
| $CH_2OMe$ | Et | Cl | $CH_2OMe$ | COMe | Cl | $CH_2OMe$ | Cl | Cl |
| $CH_2OMe$ | nPr | Cl | $CH_2OMe$ | COOH | Cl | $CH_2OMe$ | Cl | Cl |
| $CH_2NH_2$ | Ph | Cl | $CH_2NH_2$ | $CONH_2$ | Cl | $CH_2NH_2$ | Cl | Cl |
| $CH_2NH_2$ | H | Et | $CH_2NH_2$ | CONHMe | Et | $CH_2NH_2$ | Et | H |
| $CH_2NH_2$ | H | nPr | $CH_2NH_2$ | CONHMs | nPr | $CH_2NH_2$ | nPr | H |
| $CH_2NH_2$ | H | Ph | $CH_2NH_2$ | NHMs | Ph | $CH_2NH_2$ | Ph | H |
| $CH_2NHMe$ | Me | Me | $CH_2NHMe$ | $NO_2$ | Me | $CH_2NHMe$ | Me | H |
| $CH_2Ph$ | Et | Et | $CH_2Ph$ | OH | Et | $CH_2Ph$ | Et | H |
| $CH_2Ph$ | nPr | nPr | $CH_2Ph$ | COMe | nPr | $CH_2Ph$ | nPr | H |
| $CH_2CH_2Ph$ | Ph | Ph | $CH_2CH_2Ph$ | COOH | Ph | $CH_2CH_2Ph$ | Ph | H |
| 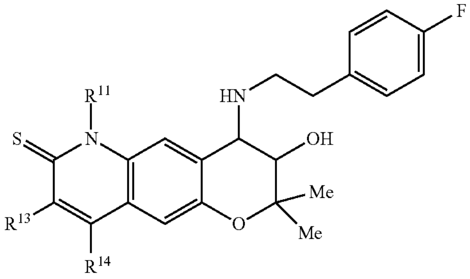 | | | | | | | | |
| H | H | Et | H | $NO_2$ | H | H | H | $NO_2$ |
| H | H | iPr | H | CHO | H | H | H | CHO |
| H | H | nPr | H | $SO_3H$ | H | H | H | $SO_3H$ |
| H | H | nBu | H | Cl | H | H | H | Cl |
| H | H | tBu | H | Br | H | H | H | Br |
| Me | H | H | Me | $CH_2OH$ | H | Me | H | $CH_2OH$ |
| Me | Et | Ph | Me | $CH_2NH_2$ | H | Me | H | $CH_2NH_2$ |
| Me | iPr | H | Me | $CH_2NHMe$ | H | Me | H | $CH_2NHMe$ |
| Me | nPr | H | Me | $CH_2Ph$ | H | Me | H | $CH_2Ph$ |
| Me | nBu | H | Me | COMe | H | Me | H | COMe |
| Me | tBu | H | Me | COOH | H | Me | H | COOH |
| Et | Ph | H | Et | $CONH_2$ | H | Et | H | $CONH_2$ |
| Et | H | Et | Et | CONHMe | Et | Et | Et | CONHMe |
| Et | H | iPr | Et | CONHMs | iPr | Et | iPr | CONHMs |
| iPr | H | nPr | iPr | NHMs | nPr | iPr | nPr | NHMs |
| nPr | H | nBu | nPr | NHCOMe | nBu | nPr | nBu | NHCOMe |
| nBu | H | tBu | nBu | $NO_2$ | tBu | nBu | tBu | NO2H |
| tBu | H | Ph | tBu | CHO | Ph | tBu | Ph | H |

-continued

| $R^{11}$ | $R^{13}$ | $R^{14}$ | $R^{11}$ | $R^{13}$ | $R^{14}$ | $R^{11}$ | $R^{13}$ | $R^{14}$ |
|---|---|---|---|---|---|---|---|---|
| Ph | Cl | Et | Ph | $SO_3H$ | Et | Ph | Et | H |
| $CH_2OH$ | Cl | nPr | $CH_2OH$ | $SO_2NMe$ | nPr | $CH_2OH$ | nPr | H |
| $CH_2OH$ | Cl | Ph | $CH_2OH$ | OH | Ph | $CH_2OH$ | Ph | H |
| $CH_2OMe$ | Et | Cl | $CH_2OMe$ | COMe | Cl | $CH_2OMe$ | Cl | Cl |
| $CH_2OMe$ | nPr | Cl | $CH_2OMe$ | COOH | Cl | $CH_2OMe$ | Cl | Cl |
| $CH_2NH_2$ | Ph | Cl | $CH_2NH_2$ | $CONH_2$ | Cl | $CH_2NH_2$ | Cl | Cl |
| $CH_2NH_2$ | H | Et | $CH_2NH_2$ | CONHMe | Et | $CH_2NH_2$ | Et | H |
| $CH_2NH_2$ | H | nPr | $CH_2NH_2$ | CONHMs | nPr | $CH_2NH_2$ | nPr | H |
| $CH_2NH_2$ | H | Ph | $CH_2NH_2$ | NHMs | Ph | $CH_2NH_2$ | Ph | H |
| $CH_2NHMe$ | Me | Me | $CH_2NHMe$ | $NO_2$ | Me | $CH_2NHMe$ | Me | H |
| $CH_2Ph$ | Et | Et | $CH_2Ph$ | OH | Et | $CH_2Ph$ | Et | H |
| $CH_2Ph$ | nPr | nPr | $CH_2Ph$ | COMe | nPr | $CH_2Ph$ | nPr | H |
| $CH_2CH_2Ph$ | Ph | Ph | $CH_2CH_2Ph$ | COOH | Ph | $CH_2CH_2Ph$ | Ph | H |

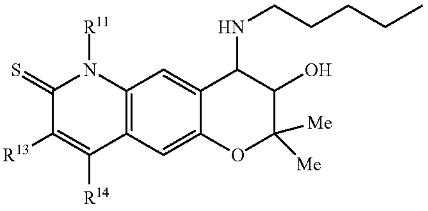

| | | | | | | | | |
|---|---|---|---|---|---|---|---|---|
| H | H | Et | H | $NO_2$ | H | H | H | $NO_2$ |
| H | H | iPr | H | CHO | H | H | H | CHO |
| H | H | nPr | H | $SO_3H$ | H | H | H | $SO_3H$ |
| H | H | nBu | H | Cl | H | H | H | Cl |
| H | H | tBu | H | Br | H | H | H | Br |
| Me | H | H | Me | $CH_2OH$ | H | Me | H | $CH_2OH$ |
| Me | Et | Ph | Me | $CH_2NH_2$ | H | Me | H | $CH_2NH_2$ |
| Me | iPr | H | Me | $CH_2NHMe$ | H | Me | H | $CH_2NHMe$ |
| Me | nPr | H | Me | $CH_2Ph$ | H | Me | H | $CH_2Ph$ |
| Me | nBu | H | Me | COMe | H | Me | H | COMe |
| Me | tBu | H | Me | COOH | H | Me | H | COOH |
| Et | Ph | H | Et | $CONH_2$ | H | Et | H | $CONH_2$ |
| Et | H | Et | Et | CONHMe | Et | Et | Et | CONHMe |
| Et | H | iPr | Et | CONHMs | iPr | Et | iPr | CONHMs |
| iPr | H | nPr | iPr | NHMs | nPr | iPr | nPr | NHMs |
| nPr | H | nBu | nPr | NHCOMe | nBu | nPr | nBu | NHCOMe |
| nBu | H | tBu | nBu | $NO_2$ | tBu | nBu | tBu | $NO_2$ |
| tBu | H | Ph | tBu | CHO | Ph | tBu | Ph | H |
| Ph | Cl | Et | Ph | $SO_3H$ | Et | Ph | Et | H |
| $CH_2OH$ | Cl | nPr | $CH_2OH$ | $SO_2NHMe$ | nPr | $CH_2OH$ | nPr | H |
| $CH_2OH$ | Cl | Ph | $CH_2OH$ | OH | Ph | $CH_2OH$ | Ph | H |
| $CH_2OMe$ | Et | Cl | $CH_2OMe$ | COMe | Cl | $CH_2OMe$ | Cl | Cl |
| $CH_2OMe$ | nPr | Cl | $CH_2OMe$ | COOH | Cl | $CH_2OMe$ | Cl | Cl |
| $CH_2NH_2$ | Ph | Cl | $CH_2NH_2$ | $CONH_2$ | Cl | $CH_2NH_2$ | Cl | Cl |
| $CH_2NH_2$ | H | Et | $CH_2NH_2$ | CONHMe | Et | $CH_2NH_2$ | Et | H |
| $CH_2NH_2$ | H | nPr | $CH_2NH_2$ | CONHMs | nPr | $CH_2NH_2$ | nPr | H |
| $CH_2NH_2$ | H | Ph | $CH_2NH_2$ | NHMs | Ph | $CH_2NH_2$ | Ph | H |
| $CH_2NHMe$ | Me | Me | $CH_2NHMe$ | $NO_2$ | Me | $CH_2NHMe$ | Me | H |
| $CH_2Ph$ | Et | Et | $CH_2Ph$ | OH | Et | $CH_2Ph$ | Et | H |
| $CH_2Ph$ | nPr | nPr | $CH_2Ph$ | COMe | nPr | $CH_2Ph$ | nPr | H |
| $CH_2CH_2Ph$ | Ph | Ph | $CH_2CH_2Ph$ | COON | Ph | $CH_2CH_2Ph$ | Ph | H |

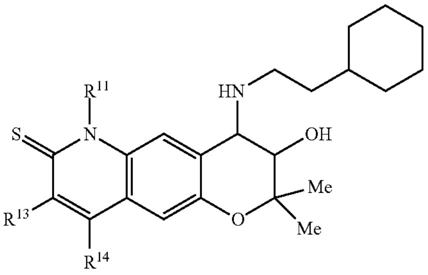

| | | | | | | | | |
|---|---|---|---|---|---|---|---|---|
| H | H | Et | H | $NO_2$ | H | H | H | $NO_2$ |
| H | H | iPr | H | CHO | H | H | H | CHO |
| H | H | nPr | H | $SO_3H$ | H | H | H | $SO_3H$ |
| H | H | nBu | H | Cl | H | H | H | Cl |
| H | H | tBu | H | Br | H | H | H | Br |
| Me | H | H | Me | $CH_2OH$ | H | Me | H | $CH_2OH$ |
| Me | Et | Ph | Me | $CH_2NH_2$ | H | Me | H | $CH_2NH_2$ |

-continued

| $R^{11}$ | $R^{13}$ | $R^{14}$ | $R^{11}$ | $R^{13}$ | $R^{14}$ | $R^{11}$ | $R^{13}$ | $R^{14}$ |
|---|---|---|---|---|---|---|---|---|
| Me | iPr | H | Me | $CH_2NHMe$ | H | Me | H | $CH_2NHMe$ |
| Me | nPr | H | Me | $CH_2Ph$ | H | Me | H | $CH_2Ph$ |
| Me | nBu | H | Me | COMe | H | Me | H | COMe |
| Me | tBu | H | Me | COOH | H | Me | H | COOH |
| Et | Ph | H | Et | $CONH_2$ | H | Et | H | $CONH_2$ |
| Et | H | Et | Et | CONHMe | Et | Et | Et | CONHMe |
| Et | H | iPr | Et | CONHMs | iPr | Et | iPr | CONHMs |
| iPr | H | nPr | iPr | NHMs | nPr | iPr | nPr | NHMs |
| nPr | H | nBu | nPr | NHCOMe | nBu | nPr | nBu | NHCOMe |
| nBu | H | tBu | nBu | $NO_2$ | tBu | nBu | tBu | $NO_2$ |
| tBu | H | Ph | tBu | CHO | Ph | tBu | Ph | H |
| Ph | Cl | Et | Ph | $SO_3H$ | Et | Ph | Et | H |
| $CH_2OH$ | Cl | nPr | $CH_2OH$ | $SO_2NHMe$ | nPr | $CH_2OH$ | nPr | H |
| $CH_2OH$ | Cl | Ph | $CH_2OH$ | OH | Ph | $CH_2OH$ | Ph | H |
| $CH_2OMe$ | Et | Cl | $CH_2OMe$ | COMe | Cl | $CH_2OMe$ | Cl | Cl |
| $CH_2OMe$ | nPr | Cl | $CH_2OMe$ | COOH | Cl | $CH_2OMe$ | Cl | Cl |
| $CH_2NH_2$ | Ph | Cl | $CH_2NH_2$ | $CONH_2$ | Cl | $CH_2NH_2$ | Cl | Cl |
| $CH_2NH_2$ | H | Et | $CH_2NH_2$ | CONHMe | Et | $CH_2NH_2$ | Et | H |
| $CH_2NH_2$ | H | nPr | $CH_2NH_2$ | CONHMs | nPr | $CH_2NH_2$ | nPr | H |
| $CH_2NH_2$ | H | Ph | $CH_2NH_2$ | NHMs | Ph | $CH_2NH_2$ | Ph | H |
| $CH_2NHMe$ | Me | Me | $CH_2NHMe$ | $NO_2$ | Me | $CH_2NHMe$ | Me | H |
| $CH_2Ph$ | Et | Et | $CH_2Ph$ | OH | Et | $CH_2Ph$ | Et | H |
| $CH_2Ph$ | nPr | nPr | $CH_2Ph$ | COMe | nPr | $CH_2Ph$ | nPr | H |
| $CH_2CH_2Ph$ | Ph | Ph | $CH_2CH_2Ph$ | COOH | Ph | $CH_2CH_2Ph$ | Ph | H |

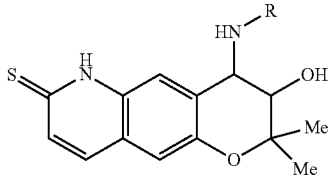

HN—R

| | | |
|---|---|---|
| 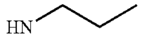 | 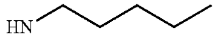 | 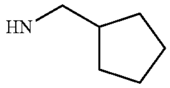 |
| 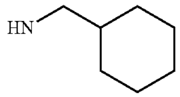 | 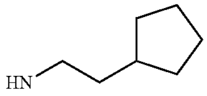 | 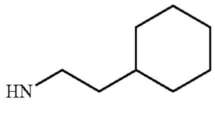 |
| 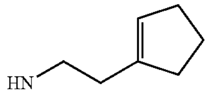 | 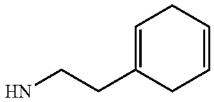 | 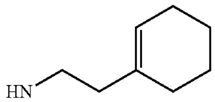 |
| 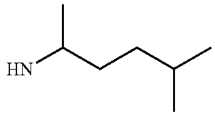 | 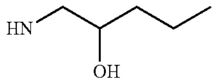 | 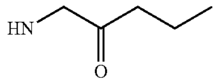 |
| 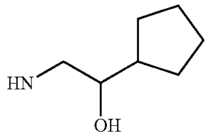 | 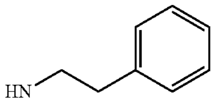 | 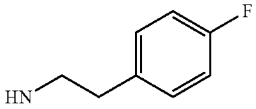 |
| 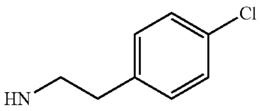 | 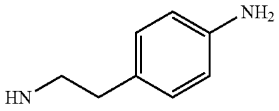 | 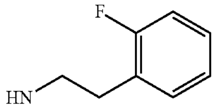 |

-continued
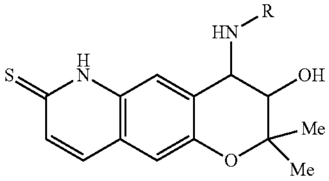
HN—R
| | | |
|---|---|---|
| 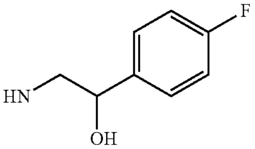 | 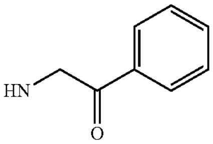 | 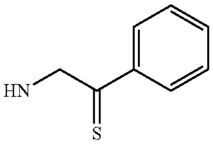 |
| 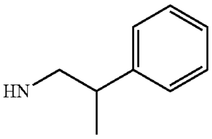 | 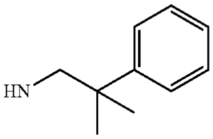 | 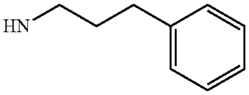 |
| 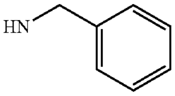 | 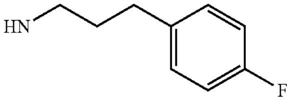 | 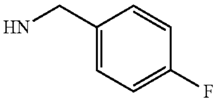 |
| 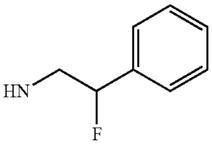 | 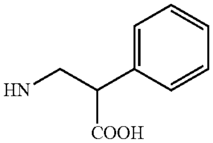 | 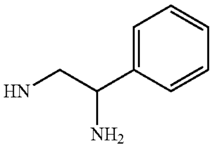 |
| 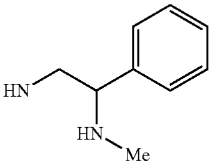 | 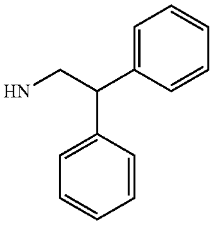 | 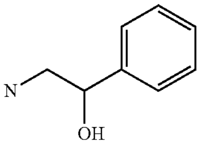 |
| 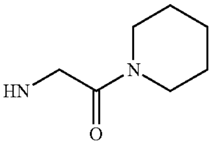 | 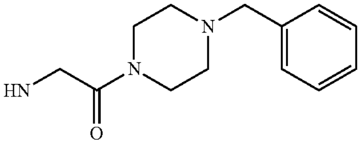 | 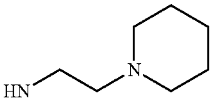 |
| 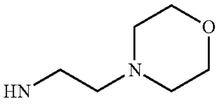 | 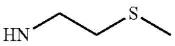 | 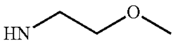 |
| 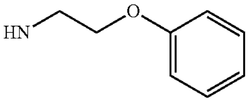 | 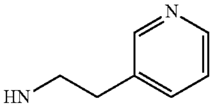 | 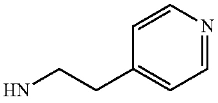 |
| 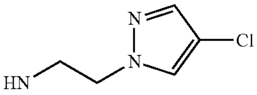 | 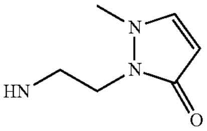 | |

| $R^{13}$ | $R^{14}$ | $R^{15}$ | $R^{13}$ | $R^{14}$ | $R^{15}$ | $R^{13}$ | $R^{14}$ | $R^{15}$ |
|---|---|---|---|---|---|---|---|---|
| 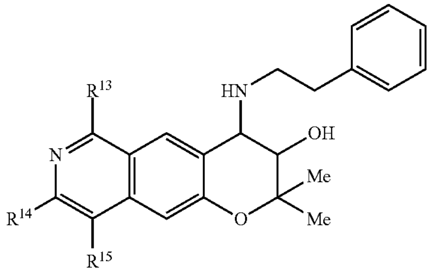 | | | | | | | | |
| H | H | Et | $NO_2$ | H | Et | H | $NO_2$ | Et |
| H | H | iPr | CHO | H | iPr | H | CHO | iPr |
| H | H | nPr | $SO_3H$ | H | nPr | H | $SO_3H$ | nPr |
| H | H | nBu | Cl | H | nBu | H | Cl | nBu |
| H | H | tBu | Br | H | tBu | H | Br | tBu |
| H | H | Ph | $CH_2OH$ | H | Ph | H | $CH_2OH$ | Ph |
| Et | H | H | $CH_2NH_2$ | H | H | H | $CH_2NH_2$ | H |
| iPr | H | H | $CH_2NHMe$ | H | H | H | $CH_2NHMe$ | H |
| nPr | H | H | $CH_2Ph$ | H | H | H | $CH_2Ph$ | H |
| nBu | H | H | COMe | H | H | H | COMe | H |
| tBu | H | H | COON | H | H | H | COOH | H |
| Ph | H | H | $CONH_2$ | H | H | H | $CONH_2$ | H |
| H | Et | H | CONHMe | Et | H | Et | CONHMe | H |
| H | iPr | H | CONHMs | iPr | H | iPr | CONHMe | H |
| H | nPr | H | NHMs | nPr | H | nPr | NHMe | H |
| H | nBu | H | NHCOMe | nBu | H | nBu | NHCOMe | H |
| H | tBu | H | $NO_2$ | tBu | H | tBu | $NO_2$ | H |
| H | Ph | H | CHO | Ph | H | Ph | H | $SO_3H$ |
| Cl | Et | H | $SO_3H$ | Et | H | Et | H | $SO_2NHMe$ |
| Cl | nPr | H | $SO_2NHMe$ | nPr | H | nPr | H | OH |
| Cl | Ph | H | OH | Ph | H | Ph | H | COMe |
| Et | Cl | H | COMe | Cl | H | Cl | Cl | COOH |
| nPr | Cl | H | COOH | Cl | H | Cl | Cl | CONH2 |
| Ph | Cl | H | $CONH_2$ | Cl | H | Cl | Cl | CONHMe |
| H | Et | Cl | CONHMe | Et | Cl | Et | H | CONHMe |
| H | nPr | Cl | CONHMs | nPr | Cl | nPr | H | NHMe |
| H | Ph | Cl | NHMs | Ph | Cl | Ph | H | $NO_2$ |
| Me | Me | H | $NO_2$ | Me | H | Me | H | OH |
| Et | Et | H | OH | Et | H | Et | H | COMe |
| nPr | nPr | H | COMe | nPr | H | nPr | H | COOH |
| Ph | Ph | H | COOH | Ph | H | Ph | H | $NO_2$ |
| 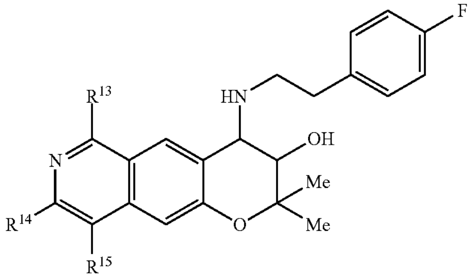 | | | | | | | | |
| H | H | Et | $NO_2$ | H | Et | H | $NO_2$ | Et |
| H | H | iPr | CHO | H | iPr | H | CHO | iPr |
| H | H | nPr | $SO_3H$ | H | nPr | H | $SO_3H$ | nPr |
| H | H | nBu | Cl | H | nBu | H | Cl | nBu |
| H | H | tBu | Br | H | tBu | H | Br | tBu |
| H | H | Ph | $CH_2OH$ | H | Ph | H | $CH_2OH$ | Ph |
| Et | H | H | $CH_2NH_2$ | H | H | H | $CH_2NH_2$ | H |
| iPr | H | H | $CH_2NHMe$ | H | H | H | $CH_2NHMe$ | H |
| nPr | H | H | $CH_2Ph$ | H | H | H | $CH_2Ph$ | H |
| nBu | H | H | COMe | H | H | H | COMe | H |
| tBu | H | H | COOH | H | H | H | COOH | H |
| Ph | H | H | $CONH_2$ | H | H | H | $CONH_2$ | H |
| H | Et | H | CONHMe | Et | H | Et | CONHMe | H |
| H | iPr | H | CONHMs | iPr | H | iPr | CONHMs | H |
| H | nPr | H | NHMs | nPr | H | nPr | NHMs | H |
| H | nBu | H | NHCOMe | nBu | H | nBu | NHCOMe | H |
| H | tBu | H | $NO_2$ | tBu | H | tBu | $NO_2$ | H |
| H | Ph | H | CHO | Ph | H | Ph | H | $SO_3H$ |

-continued

| $R^{13}$ | $R^{14}$ | $R^{15}$ | $R^{13}$ | $R^{14}$ | $R^{15}$ | $R^{13}$ | $R^{14}$ | $R^{15}$ |
|---|---|---|---|---|---|---|---|---|
| Cl | Et | H | $SO_3H$ | Et | H | Et | H | $SO_2NHMe$ |
| Cl | nPr | H | $SO_2NHMe$ | nPr | H | nPr | H | OH |
| Cl | Ph | H | OH | Ph | H | Ph | H | COMe |
| Et | Cl | H | COMe | Cl | H | Cl | Cl | COOH |
| nPr | Cl | H | COOH | Cl | H | Cl | Cl | CONH2 |
| Ph | Cl | H | $CONH_2$ | Cl | H | Cl | Cl | CONHMe |
| H | Et | Cl | CONHMe | Et | Cl | Et | H | CONHMs |
| H | nPr | Cl | CONHMs | nPr | Cl | nPr | H | NHMs |
| H | Ph | Cl | NHMs | Ph | Cl | Ph | H | $NO_2$ |
| Me | Me | H | $NO_2$ | Me | H | Me | H | OH |
| Et | Et | H | OH | Et | H | Et | H | COMe |
| nPr | nPr | H | COMe | nPr | H | nPr | H | COOH |
| Ph | Ph | H | COOH | Ph | H | Ph | H | $NO_2$ |

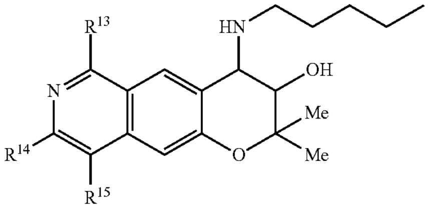

| | | | | | | | | |
|---|---|---|---|---|---|---|---|---|
| H | H | Et | $NO_2$ | H | Et | H | $NO_2$ | Et |
| H | H | iPr | CHO | H | iPr | H | CHO | iPr |
| H | H | nPr | $SO_3H$ | H | nPr | H | $SO_3H$ | nPr |
| H | H | nBu | Cl | H | nBu | H | Cl | nBu |
| H | H | tBu | Br | H | tBu | H | Br | tBu |
| H | H | Ph | $CH_2OH$ | H | Ph | H | $CH_2OH$ | Ph |
| Et | H | H | $CH_2NH_2$ | H | H | H | $CH_2NH_2$ | H |
| iPr | H | H | $CH_2NHMe$ | H | H | H | $CH_2NHMe$ | H |
| nPr | H | H | $CH_2Ph$ | H | H | H | $CH_2Ph$ | H |
| nBu | H | H | COMe | H | H | H | COMe | H |
| tBu | H | H | COOH | H | H | H | COOH | H |
| Ph | H | H | $CONH_2$ | H | H | H | $CONH_2$ | H |
| H | Et | H | CONHMe | Et | H | Et | CONHMe | H |
| H | iPr | H | CONHMs | iPr | H | iPr | CONHMe | H |
| H | nPr | H | NHMs | nPr | H | nPr | NHMe | H |
| H | nBu | H | NHCOMe | nBu | H | nBu | NHCOMe | H |
| H | tBu | H | $NO_2$ | tBu | H | tBu | $NO_2H$ | H |
| H | Ph | H | CHO | Ph | H | Ph | H | $SO_3H$ |
| Cl | Et | H | $SO_3H$ | Et | H | Et | H | $SO_2NHMe$ |
| Cl | nPr | H | $SO_2NHMe$ | nPr | H | nPr | H | OH |
| Cl | Ph | H | OH | Ph | H | Ph | H | COMe |
| Et | Cl | H | COMe | Cl | H | Cl | Cl | COOH |
| nPr | Cl | H | COOH | Cl | H | Cl | Cl | $CONH_2$ |
| Ph | Cl | H | $CONH_2$ | Cl | H | Cl | Cl | CONHMe |
| H | Et | Cl | CONHMe | Et | Cl | Et | H | CONHMs |
| H | nPr | Cl | CONHMs | nPr | Cl | nPr | H | NHMs |
| H | Ph | Cl | NHMe | Ph | Cl | Ph | H | $NO_2$ |
| Me | Me | H | $NO_2$ | Me | H | Me | H | OH |
| Et | Et | H | OH | Et | H | Et | H | COMe |
| nPr | nPr | H | COMe | nPr | H | nPr | H | COOH |
| Ph | Ph | H | COOH | Ph | H | Ph | H | $NO_2$ |

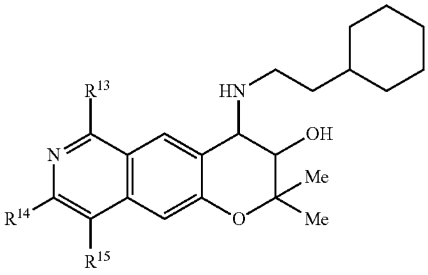

| | | | | | | | | |
|---|---|---|---|---|---|---|---|---|
| H | H | Et | $NO_2$ | H | Et | H | $NO_2$ | Et |
| H | H | iPr | CHO | H | iPr | H | CHO | iPr |
| H | H | nPr | $SO_3H$ | H | nPr | H | $SO_3H$ | nPr |
| H | H | nBu | Cl | H | nBu | H | Cl | nBu |
| H | H | tBu | Br | H | tBu | H | Br | tBu |
| H | H | Ph | $CH_2OH$ | H | Ph | H | $CH_2OH$ | Ph |
| Et | H | H | $CH_2NH_2$ | H | H | H | $CH_2NH_2$ | H |

-continued

| $R^{13}$ | $R^{14}$ | $R^{15}$ | $R^{13}$ | $R^{14}$ | $R^{15}$ | $R^{13}$ | $R^{14}$ | $R^{15}$ |
|---|---|---|---|---|---|---|---|---|
| iPr | H | H | $CH_2NHMe$ | H | H | H | $CH_2NHMe$ | H |
| nPr | H | H | $CH_2Ph$ | H | H | H | $CH_2Ph$ | H |
| nBu | H | H | COMe | H | H | H | COMe | H |
| tBu | H | H | COOH | H | H | H | COOH | H |
| Ph | H | H | $CONH_2$ | H | H | H | $CONH_2$ | H |
| H | Et | H | CONHMe | Et | H | Et | CONHMe | H |
| H | iPr | H | CONHMs | iPr | H | iPr | CONHMs | H |
| H | nPr | H | NHMs | nPr | H | nPr | NHMs | H |
| H | nBu | H | NHCOMe | nBu | H | nBu | NHCOMe | H |
| H | tBu | H | $NO_2$ | tBu | H | tBu | $NO_2H$ | H |
| H | Ph | H | CHO | Ph | H | Ph | H | $SO_3H$ |
| Cl | Et | H | $SO_3H$ | Et | H | Et | H | $SO_2NHMe$ |
| Cl | nPr | H | $SO_2NHMe$ | nPr | H | nPr | H | OH |
| Cl | Ph | H | OH | Ph | H | Ph | H | COMe |
| Et | Cl | H | COMe | Cl | H | Cl | Cl | COOH |
| nPr | Cl | H | COOH | Cl | H | Cl | Cl | CONH2 |
| Ph | Cl | H | $CONH_2$ | Cl | H | Cl | Cl | CONHMe |
| H | Et | Cl | CONHMe | Et | Cl | Et | H | CONHMs |
| H | nPr | Cl | CONHMs | nPr | Cl | nPr | H | NHMs |
| H | Ph | Cl | NHMs | Ph | Cl | Ph | H | $NO_2$ |
| Me | Me | H | $NO_2$ | Me | H | Me | H | OH |
| Et | Et | H | OH | Et | H | Et | H | COMe |
| nPr | nPr | H | COMe | nPr | H | nPr | H | COOH |
| Ph | Ph | H | COOH | Ph | H | Ph | H | $NO_2$ |

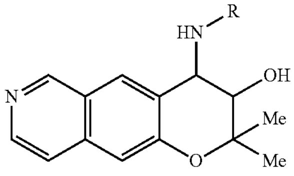

| HN—R | | |
|---|---|---|
| 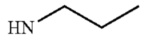 | 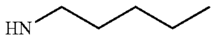 | 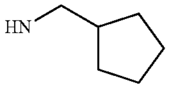 |
| 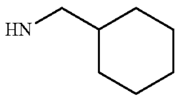 | 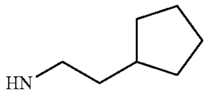 | 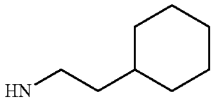 |
| 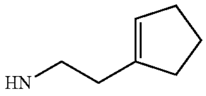 | 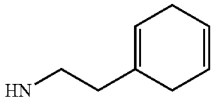 | 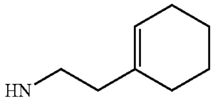 |
| 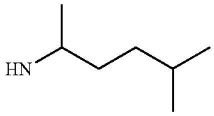 | 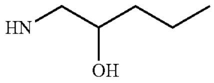 | 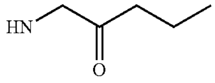 |
| 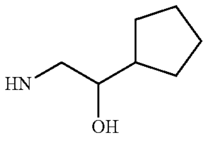 | 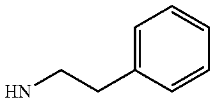 | 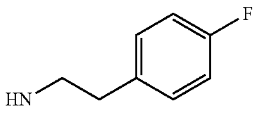 |
| 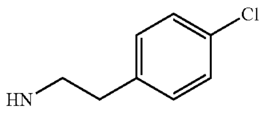 | 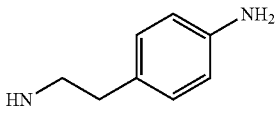 | 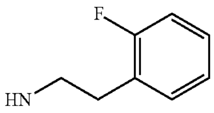 |

-continued
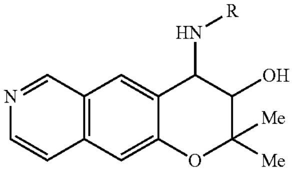
HN—R
| | | |
|---|---|---|
| 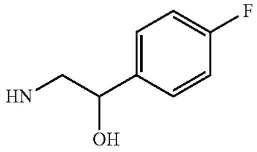 | 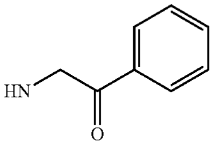 | 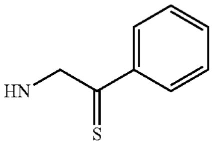 |
| 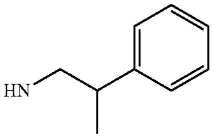 | 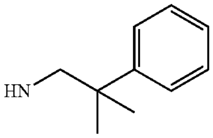 | 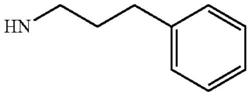 |
| 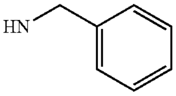 | 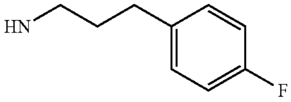 | 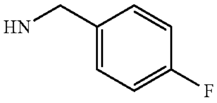 |
| 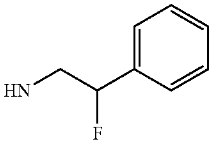 | 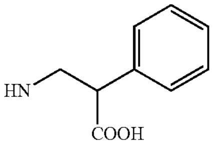 | 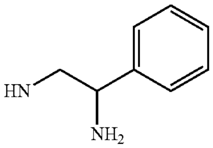 |
| 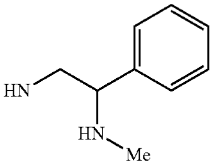 | 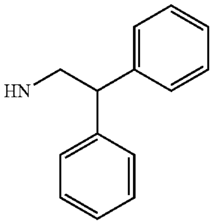 | 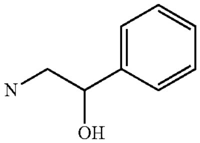 |
| 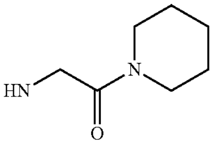 | 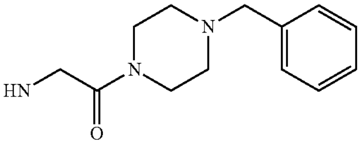 | 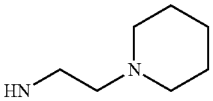 |
| 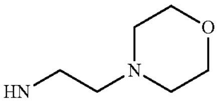 | 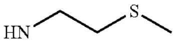 | 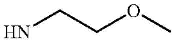 |
| 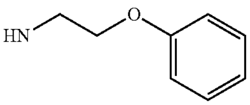 | 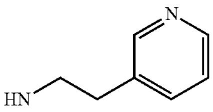 | 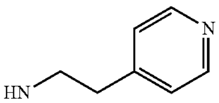 |
| 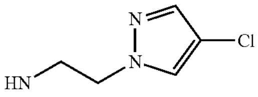 | 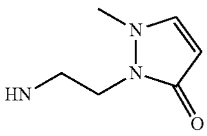 | |

| $R^{13}$ | $R^{14}$ | $R^{15}$ | $R^{13}$ | $R^{14}$ | $R^{15}$ | $R^{13}$ | $R^{14}$ | $R^{15}$ |
|---|---|---|---|---|---|---|---|---|
| 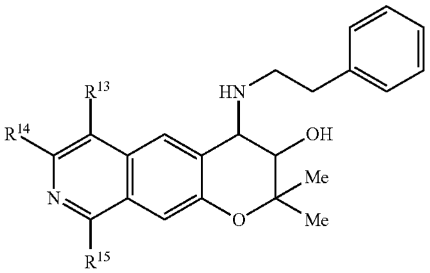 | | | | | | | | |
| H | H | Et | $NO_2$ | H | Et | H | $NO_2$ | Et |
| H | H | iPr | CHO | H | iPr | H | CHO | iPr |
| H | H | nPr | $SO_3H$ | H | nPr | H | $SO_3H$ | nPr |
| H | H | nBu | Cl | H | nBu | H | Cl | nBu |
| H | H | tBu | Br | H | tBu | H | Br | tBu |
| H | H | Ph | $CH_2OH$ | H | Ph | H | $CH_2OH$ | Ph |
| Et | H | H | $CH_2NH_2$ | H | H | H | $CH_2NH_2$ | H |
| iPr | H | H | $CH_2NHMe$ | H | H | H | $CH_2NHMe$ | H |
| nPr | H | H | $CH_2Ph$ | H | H | H | $CH_2Ph$ | H |
| nBu | H | H | COMe | H | H | H | COMe | H |
| tBu | H | H | COOH | H | H | H | COOH | H |
| Ph | H | H | $CONH_2$ | H | H | H | $CONH_2$ | H |
| H | Et | H | CONHMe | Et | H | Et | CONHMe | H |
| H | iPr | H | CONHMs | iPr | H | iPr | CONHMs | H |
| H | nPr | H | NHMs | nPr | H | nPr | NHMs | H |
| H | nBu | H | NHCOMe | nBu | H | nBu | NHCOMe | H |
| H | tBu | H | $NO_2$ | tBu | H | tBu | $NO_2$ | H |
| H | Ph | H | CHO | Ph | H | Ph | H | $SO_3H$ |
| Cl | Et | H | $SO_3H$ | Et | H | Et | H | $SO_2NHMe$ |
| Cl | nPr | H | $SO_2NHMe$ | nPr | H | nPr | H | OH |
| Cl | Ph | H | OH | Ph | H | Ph | H | COMe |
| Et | Cl | H | COMe | Cl | H | Cl | Cl | COOH |
| nPr | Cl | H | COOH | Cl | H | Cl | Cl | $CONH_2$ |
| Ph | Cl | H | $CONH_2$ | Cl | H | Cl | Cl | CONHMe |
| H | Et | Cl | CONHMe | Et | Cl | Et | H | CONHMs |
| H | nPr | Cl | CONHMs | nPr | Cl | nPr | H | NHMs |
| H | Ph | Cl | NHMs | Ph | Cl | Ph | H | $NO_2$ |
| Me | Me | H | $NO_2$ | Me | H | Me | H | OH |
| Et | Et | H | OH | Et | H | Et | H | COMe |
| nPr | nPr | H | COMe | nPr | H | nPr | H | COOH |
| Ph | Ph | H | COOH | Ph | H | Ph | H | $NO_2$ |
| 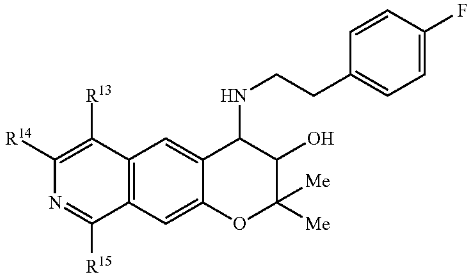 | | | | | | | | |
| H | H | Et | $NO_2$ | H | Et | H | $NO_2$ | Et |
| H | H | iPr | CHO | H | iPr | H | CHO | iPr |
| H | H | nPr | $SO_3H$ | H | nPr | H | $SO_3H$ | nPr |
| H | H | nBu | Cl | H | nBu | H | Cl | nBu |
| H | H | tBu | Br | H | tBu | H | Br | tBu |
| H | H | Ph | $CH_2OH$ | H | Ph | H | $CH_2OH$ | Ph |
| Et | H | H | $CH_2NH_2$ | H | H | H | $CH_2NH_2$ | H |
| iPr | H | H | $CH_2NHMe$ | H | H | H | $CH_2NHMe$ | H |
| nPr | H | H | $CH_2Ph$ | H | H | H | $CH_2Ph$ | H |
| nBu | H | H | COMe | H | H | H | COMe | H |
| tBu | H | H | COOH | H | H | H | COOH | H |
| Ph | H | H | $CONH_2$ | H | H | H | $CONH_2$ | H |
| H | Et | H | CONHMe | Et | H | Et | CONHMe | H |
| H | iPr | H | CONHMs | iPr | H | iPr | CONHMs | H |
| H | nPr | H | NHMs | nPr | H | nPr | NHMs | H |
| H | nBu | H | NHCOMe | nBu | H | nBu | NHCOMe | H |
| H | tBu | H | $NO_2$ | tBu | H | tBu | $NO_2$ | H |
| H | Ph | H | CHO | Ph | H | Ph | H | $SO_3H$ |

-continued

| R13 | R14 | R15 | R13 | R14 | R15 | R13 | R14 | R15 |
|---|---|---|---|---|---|---|---|---|
| Cl | Et | H | $SO_3H$ | Et | H | Et | H | $SO_2NHMe$ |
| Cl | nPr | H | $SO_2NHMe$ | nPr | H | nPr | H | OH |
| Cl | Ph | H | OH | Ph | H | Ph | H | COMe |
| Et | Cl | H | COMe | Cl | H | Cl | Cl | COOH |
| nPr | Cl | H | COOH | Cl | H | Cl | Cl | $CONH_2$ |
| Ph | Cl | H | $CONH_2$ | Cl | H | Cl | Cl | CONHMe |
| H | Et | Cl | CONHMe | Et | Cl | Et | H | CONHMs |
| H | nPr | Cl | CONHMs | nPr | Cl | nPr | H | NHMs |
| H | Ph | Cl | NHMs | Ph | Cl | Ph | H | $NO_2$ |
| Me | Me | H | $NO_2$ | Me | H | Me | H | OH |
| Et | Et | H | OH | Et | H | Et | H | COMe |
| nPr | nPr | H | COMe | nPr | H | nPr | H | COOH |
| Ph | Ph | H | COOH | Ph | H | Ph | H | $NO_2$ |

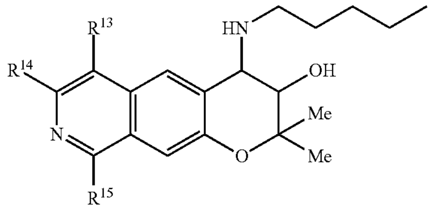

| | | | | | | | | |
|---|---|---|---|---|---|---|---|---|
| H | H | Et | $NO_2$ | H | Et | H | $NO_2$ | Et |
| H | H | iPr | CHO | H | iPr | H | CHO | iPr |
| H | H | nPr | $SO_3H$ | H | nPr | H | $SO_3H$ | nPr |
| H | H | nBu | Cl | H | nBu | H | Cl | nBu |
| H | H | tBu | Br | H | tBu | H | Br | tBu |
| H | H | Ph | $CH_2OH$ | H | Ph | H | $CH_2OH$ | Ph |
| Et | H | H | $CH_2NH_2$ | H | H | H | $CH_2NH_2$ | H |
| iPr | H | H | $CH_2NHMe$ | H | H | H | $CH_2NHMe$ | H |
| nPr | H | H | $CH_2Ph$ | H | H | H | $CH_2Ph$ | H |
| nBu | H | H | COMe | H | H | H | COMe | H |
| tBu | H | H | COOH | H | H | H | COOH | H |
| Ph | H | H | $CONH_2$ | H | H | H | $CONH_2$ | H |
| H | Et | H | CONHMe | Et | H | Et | CONHMe | H |
| H | iPr | H | CONHMs | iPr | H | iPr | CONHMs | H |
| H | nPr | H | NHMs | nPr | H | nPr | NHMs | H |
| H | nBu | H | NHCOMe | nBu | H | nBu | NHCOMe | H |
| H | tBu | H | $NO_2$ | tBu | H | tBu | $NO_2$ | H |
| H | Ph | H | CHO | Ph | H | Ph | H | $SO_3H$ |
| Cl | Et | H | $SO_3H$ | Et | H | Et | H | $SO_2NHMe$ |
| Cl | nPr | H | $SO_2NHMe$ | nPr | H | nPr | H | OH |
| Cl | Ph | H | OH | Ph | H | Ph | H | COMe |
| Et | Cl | H | COMe | Cl | H | Cl | Cl | COOH |
| nPr | Cl | H | COOH | Cl | H | Cl | Cl | $CONH_2$ |
| Ph | Cl | H | $CONH_2$ | Cl | H | Cl | Cl | CONHMe |
| H | Et | Cl | CONHMe | Et | Cl | Et | H | CONHMs |
| H | nPr | Cl | CONHMs | nPr | Cl | nPr | H | NHMs |
| H | Ph | Cl | NHMs | Ph | Cl | Ph | H | $NO_2$ |
| Me | Me | H | $NO_2$ | Me | H | Me | H | OH |
| Et | Et | H | OH | Et | H | Et | H | COMe |
| nPr | nPr | H | COMe | nPr | H | nPr | H | COOH |
| Ph | Ph | H | COOH | Ph | H | Ph | H | $NO_2$ |

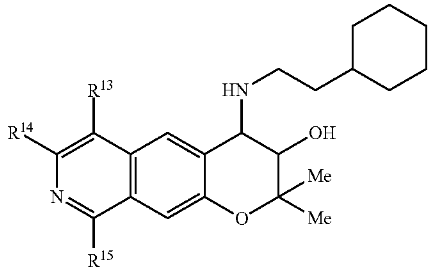

| | | | | | | | | |
|---|---|---|---|---|---|---|---|---|
| H | H | Et | $NO_2$ | H | Et | H | $NO_2$ | Et |
| H | H | iPr | CHO | H | iPr | H | CHO | iPr |
| H | H | nPr | $SO_3H$ | H | nPr | H | $SO_3H$ | nPr |
| H | H | nBu | Cl | H | nBu | H | Cl | nBu |
| H | H | tBu | Br | H | tBu | H | Br | tBu |
| H | H | Ph | $CH_2OH$ | H | Ph | H | $CH_2OH$ | Ph |
| Et | H | H | $CH_2NH_2$ | H | H | H | $CH_2NH_2$ | H |

-continued

| $R^{13}$ | $R^{14}$ | $R^{15}$ | $R^{13}$ | $R^{14}$ | $R^{15}$ | $R^{13}$ | $R^{14}$ | $R^{15}$ |
|---|---|---|---|---|---|---|---|---|
| iPr | H | H | $CH_2NHMe$ | H | H | H | $CH_2NHMe$ | H |
| nPr | H | H | $CH_2Ph$ | H | H | H | $CH_2Ph$ | H |
| nBu | H | H | COMe | H | H | H | COMe | H |
| tBu | H | H | COOH | H | H | H | COOH | H |
| Ph | H | H | $CONH_2$ | H | H | H | $CONH_2$ | H |
| H | Et | H | CONHMe | Et | H | Et | CONHMe | H |
| H | iPr | H | CONHMs | iPr | H | iPr | CONHMs | H |
| H | nPr | H | NHMs | nPr | H | nPr | NHMs | H |
| H | nBu | H | NHCOMe | nBu | H | nBu | NHCOMe | H |
| H | tBu | H | $NO_2$ | tBu | H | tBu | $NO_2$ | H |
| H | Ph | H | CHO | Ph | H | Ph | H | $SO_3H$ |
| Cl | Et | H | $SO_3H$ | Et | H | Et | H | $SO_2NHMe$ |
| Cl | nPr | H | $SO_2NHMe$ | nPr | H | nPr | H | OH |
| Cl | Ph | H | OH | Ph | H | Ph | H | COMe |
| Et | Cl | H | COMe | Cl | H | Cl | Cl | COOH |
| nPr | Cl | H | COOH | Cl | H | Cl | Cl | $CONH_2$ |
| Ph | Cl | H | $CONH_2$ | Cl | H | Cl | Cl | CONHMe |
| H | Et | Cl | CONHMe | Et | Cl | Et | H | CONHMs |
| H | nPr | Cl | CONHMs | nPr | Cl | nPr | H | NHMs |
| H | Ph | Cl | NHMs | Ph | Cl | Ph | H | $NO_2$ |
| Me | Me | H | $NO_2$ | Me | H | Me | H | OH |
| Et | Et | H | OH | Et | H | Et | H | COMe |
| nPr | nPr | H | COMe | nPr | H | nPr | H | COOH |
| Ph | Ph | H | COOH | Ph | H | Ph | H | $NO_2$ |

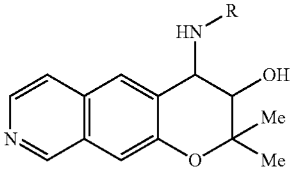

| HN—R | | |
|---|---|---|
| 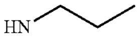 | 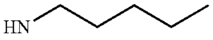 | 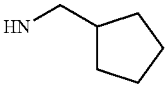 |
| 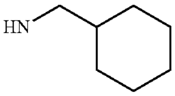 | 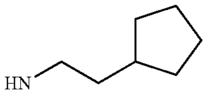 | 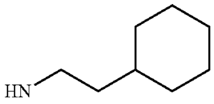 |
| 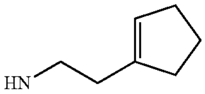 | 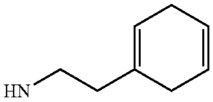 | 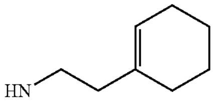 |
| 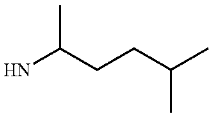 | 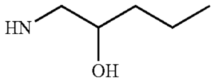 | 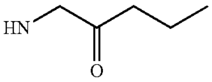 |
| 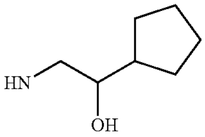 | 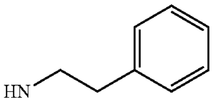 | 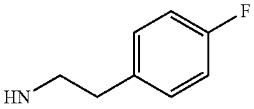 |
| 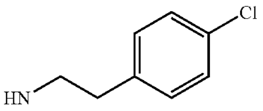 | 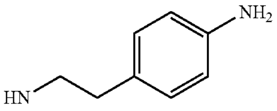 | 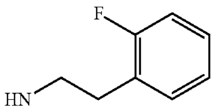 |

-continued
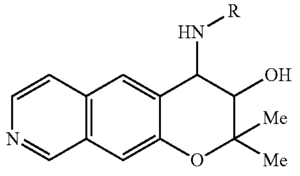
HN—R
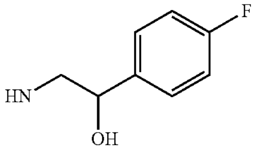 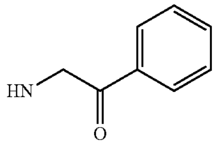 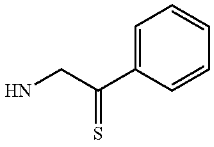
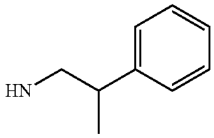 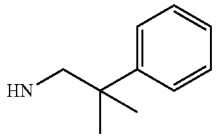 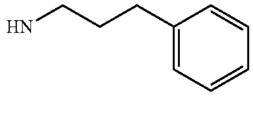
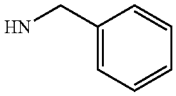 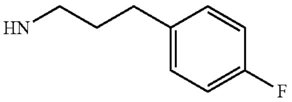 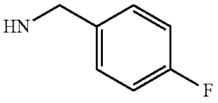
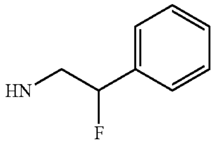 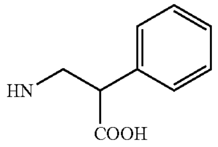 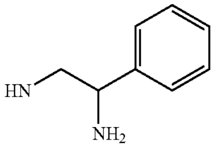
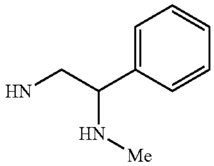 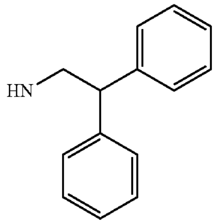 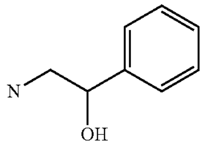
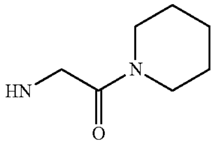 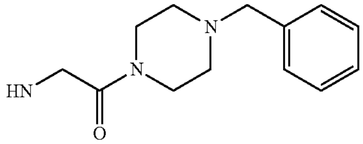 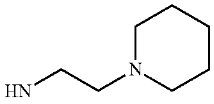
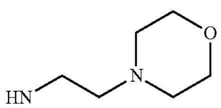 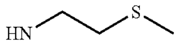 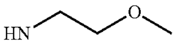
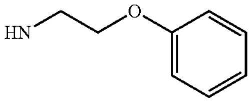 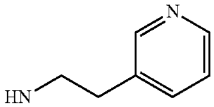 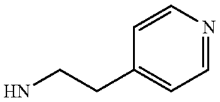
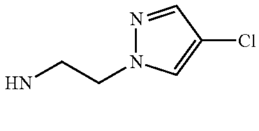 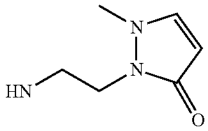

| $R^{11}$ | $R^{13}$ | $R^{14}$ | $R^{11}$ | $R^{13}$ | $R^{14}$ | $R^{11}$ | $R^{13}$ | $R^{14}$ |
|---|---|---|---|---|---|---|---|---|
| 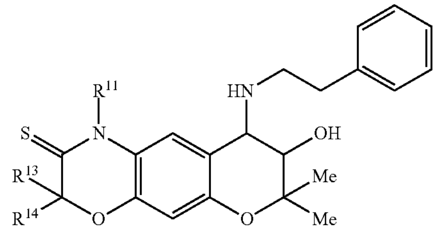 | | | | | | | | |
| H | H | Et | H | $NO_2$ | H | H | H | $NO_2$ |
| H | H | iPr | H | CHO | H | H | H | CHO |
| H | H | nPr | H | $SO_3H$ | H | H | H | $SO_3H$ |
| H | H | nBu | H | Cl | H | H | H | Cl |
| H | H | tBu | H | Br | H | H | H | Br |
| Me | H | Ph | Me | $CH_2OH$ | H | Me | H | $CH_2OH$ |
| Me | Et | Ph | Me | $CH_2NH_2$ | H | Me | H | $CH_2NH_2$ |
| Me | iPr | H | Me | $CH_2NHMe$ | H | Me | H | $CH_2NHMe$ |
| Me | nPr | H | Me | $CH_2Ph$ | H | Me | H | $CH_2Ph$ |
| Me | nBu | H | Me | COMe | H | Me | H | COMe |
| Me | tBu | H | Me | COOH | H | Me | H | COOH |
| Et | Ph | H | Et | $CONH_2$ | H | Et | H | $CONH_2$ |
| Et | H | Et | Et | CONHMe | Et | Et | Et | CONHMe |
| Et | H | iPr | Et | CONHMs | iPr | Et | iPr | CONHMs |
| iPr | H | nPr | iPr | NHMs | nPr | iPr | nPr | NHMs |
| nPr | H | nBu | nPr | NHCOMe | nBu | nPr | nBu | NHCOMe |
| nBu | H | tBu | nBu | $NO_2$ | tBu | nBu | tBu | $NO_2$ |
| tBu | H | Ph | tBu | CHO | Ph | tBu | Ph | H |
| Ph | Cl | Et | Ph | $SO_3H$ | Et | Ph | Et | H |
| $CH_2OH$ | Cl | nPr | $CH_2OH$ | $SO_2NHMe$ | nPr | $CH_2OH$ | nPr | H |
| $CH_2OH$ | Cl | Ph | $CH_2OH$ | OH | Ph | $CH_2OH$ | Ph | H |
| $CH_2OMe$ | Et | Cl | $CH_2OMe$ | COMe | Cl | $CH_2OMe$ | Cl | Cl |
| $CH_2OMe$ | nPr | Cl | $CH_2OMe$ | COOH | Cl | $CH_2OMe$ | Cl | Cl |
| $CH_2NH_2$ | Ph | Cl | $CH_2NH_2$ | $CONH_2$ | Cl | $CH_2NH_2$ | Cl | Cl |
| $CH_2NH_2$ | H | Et | $CH_2NH_2$ | CONHMe | Et | $CH_2NH_2$ | Et | H |
| $CH_2NH_2$ | H | nPr | $CH_2NH_2$ | CONHMs | nPr | $CH_2NH_2$ | nPr | H |
| $CH_2NH_2$ | H | Ph | $CH_2 2NH_2$ | NHMs | Ph | $CH_2 2NH_2$ | Ph | H |
| $CH_2NHMe$ | Me | Me | $CH_2NHMe$ | $NO_2$ | Me | $CH_2NHMe$ | Me | H |
| $CH_2Ph$ | Et | Et | $CH_2Ph$ | OH | Et | $CH_2Ph$ | Et | H |
| $CH_2Ph$ | nPr | nPr | $CH_2Ph$ | COMe | nPr | $CH_2Ph$ | nPr | H |
| $CH_2CH_2Ph$ | Ph | Ph | $CH_2CH_2Ph$ | COOH | Ph | $CH_2CH_2Ph$ | Ph | H |
| 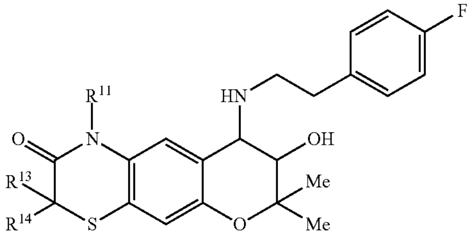 | | | | | | | | |
| H | H | Et | H | $NO_2$ | H | H | H | $NO_2$ |
| H | H | iPr | H | CHO | H | H | H | CHO |
| H | H | nPr | H | $SO_3H$ | H | H | H | $SO_3H$ |
| H | H | nBu | H | Cl | H | H | H | Cl |
| H | H | tBu | H | Br | H | H | H | Br |
| Me | H | Ph | Me | $CH_2OH$ | H | Me | H | $CH_2OH$ |
| Me | Et | Ph | Me | $CH_2NH_2$ | H | Me | H | $CH_2NH_2$ |
| Me | iPr | H | Me | $CH_2NHMe$ | H | Me | H | $CH_2NHMe$ |
| Me | nPr | H | Me | $CH_2Ph$ | H | Me | H | $CH_2Ph$ |
| Me | nBu | H | Me | COMe | H | Me | H | COMe |
| Me | tBu | H | Me | COOH | H | Me | H | COOH |
| Et | Ph | H | Et | $CONH_2$ | H | Et | H | $CONH_2$ |
| Et | H | Et | Et | CONHMe | Et | Et | Et | CONHMe |
| Et | H | iPr | Et | CONHMs | iPr | Et | iPr | CONHMs |
| iPr | H | nPr | iPr | NHMs | nPr | iPr | nPr | NHMs |
| nPr | H | nBu | nPr | NHCOMe | nBu | nPr | nBu | NHCOMe |
| nBu | H | tBu | nBu | $NO_2$ | tBu | nBu | tBu | $NO_2$ |
| tBu | H | Ph | tBu | CHO | Ph | tBu | Ph | H |
| Ph | Cl | Et | Ph | $SO_3H$ | Et | Ph | Et | H |
| $CH_2OH$ | Cl | nPr | $CH_2OH$ | $SO_2NHMe$ | nPr | $CH_2OH$ | nPr | H |
| $CH_2OH$ | Cl | Ph | $CH_2OH$ | OH | Ph | $CH_2OH$ | Ph | H |
| $CH_2OMe$ | Et | Cl | $CH_2OMe$ | COMe | Cl | $CH_2OMe$ | Cl | Cl |

-continued

| $R^{11}$ | $R^{13}$ | $R^{14}$ | $R^{11}$ | $R^{13}$ | $R^{14}$ | $R^{11}$ | $R^{13}$ | $R^{14}$ |
|---|---|---|---|---|---|---|---|---|
| $CH_2OMe$ | nPr | Cl | $CH_2OMe$ | COOH | Cl | $CH_2OMe$ | Cl | Cl |
| $CH_2NH_2$ | Ph | Cl | $CH_2NH_2$ | $CONH_2$ | Cl | $CH_2NH_2$ | Cl | Cl |
| $CH_2NH_2$ | H | Et | $CH_2NH_2$ | CONHMe | Et | $CH_2NH_2$ | Et | H |
| $CH_2NH_2$ | H | nPr | $CH_2NH_2$ | CONHMs | nPr | $CH_2NH_2$ | nPr | H |
| $CH_22NH_2$ | Ph | nPr | $CH_2NH_2$ | NHMs | Ph | $CH_22NH_2$ | Ph | H |
| $CH_2NHMe$ | Me | Me | $CH_2NHMe$ | $NO_2$ | Me | $CH_2NHMe$ | Me | H |
| $CH_2Ph$ | Et | Et | $CH_2Ph$ | OH | Et | $CH_2Ph$ | Et | H |
| $CH_2Ph$ | nPr | nPr | $CH_2Ph$ | COMe | nPr | $CH_2Ph$ | nPr | H |
| $CH_2CH_2Ph$ | Ph | Ph | $CH_2CH_2Ph$ | COOH | Ph | $CH_2CH_2Ph$ | Ph | H |

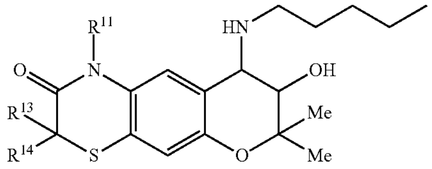

| | | | | | | | | |
|---|---|---|---|---|---|---|---|---|
| H | H | Et | H | $NO_2$ | H | H | H | $NO_2$ |
| H | H | iPr | H | CHO | H | H | H | CHO |
| H | H | nPr | H | $SO_3H$ | H | H | H | $SO_3H$ |
| H | H | nBu | H | Cl | H | H | H | Cl |
| H | H | tBu | H | Br | H | H | H | Br |
| Me | H | Ph | Me | $CH_2OH$ | H | Me | H | $CH_2OH$ |
| Me | Et | Ph | Me | $CH_2NH_2$ | H | Me | H | $CH_2NH_2$ |
| Me | iPr | H | Me | $CH_2NHMe$ | H | Me | H | $CH_2NHMe$ |
| Me | nPr | H | Me | $CH_2Ph$ | H | Me | H | $CH_2Ph$ |
| Me | nBu | H | Me | COMe | H | Me | H | COMe |
| Me | tBu | H | Me | COOH | H | Me | H | COOH |
| Et | Ph | H | Et | $CONH_2$ | H | Et | H | $CONH_2$ |
| Et | H | Et | Et | CONHMe | Et | Et | Et | CONHMe |
| Et | H | iPr | Et | CONHMs | iPr | Et | iPr | CONHMs |
| iPr | H | nPr | iPr | NHMs | nPr | iPr | nPr | NHMs |
| nPr | H | nBu | nPr | NHCOMe | nBu | nPr | nBu | NHCOMe |
| nBu | H | tBu | nBu | $NO_2$ | tBu | nBu | tBu | $NO_2$ |
| tBu | H | Ph | tBu | CHO | Ph | tBu | Ph | H |
| Ph | Cl | Et | Ph | $SO_3H$ | Et | Ph | Et | H |
| $CH_2OH$ | Cl | nPr | $CH_2OH$ | $SO_2NHMe$ | nPr | $CH_2OH$ | nPr | H |
| $CH_2OH$ | Cl | Ph | $CH_2OH$ | OH | Ph | $CH_2OH$ | Ph | H |
| $CH_2OMe$ | Et | Cl | $CH_2OMe$ | COMe | Cl | $CH_2OMe$ | Cl | Cl |
| $CH_2OMe$ | nPr | Cl | $CH_2OMe$ | COOH | Cl | $CH_2OMe$ | Cl | Cl |
| $CH_2NH_2$ | Ph | Cl | $CH_2NH_2$ | CONH2 | Cl | $CH_2NH_2$ | Cl | Cl |
| $CH_2NH_2$ | H | Et | $CH_2NH_2$ | CONHMe | Et | $CH_2NH_2$ | Et | H |
| $CH_2NH_2$ | H | nPr | $CH_2NH_2$ | CONHMs | nPr | $CH_2NH_2$ | nPr | H |
| $CH_2NH_2$ | H | Ph | $CH_22NH_2$ | NHMs | Ph | $CH_22NH_2$ | Ph | H |
| $CH_2NHMe$ | Me | Me | $CH_2NHMe$ | $NO_2$ | Me | $CH_2NHMe$ | Me | H |
| $CH_2Ph$ | Et | Et | $CH_2Ph$ | OH | Et | $CH_2Ph$ | Et | H |
| $CH_2Ph$ | nPr | nPr | $CH_2Ph$ | COMe | nPr | $CH_2Ph$ | nPr | H |
| $CH_2CH_2Ph$ | Ph | Ph | $CH_2CH_2Ph$ | COON | Ph | $CH_2CH_2Ph$ | Ph | H |

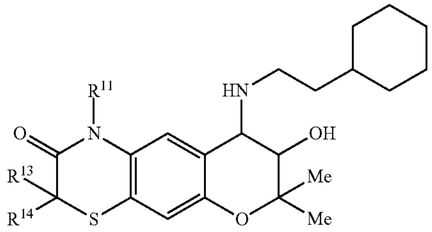

| | | | | | | | | |
|---|---|---|---|---|---|---|---|---|
| H | H | Et | H | $NO_2$ | H | H | H | $NO_2$ |
| H | H | iPr | H | CHO | H | H | H | CHO |
| H | H | nPr | H | $SO_3H$ | H | H | H | $SO_3H$ |
| H | H | nBu | H | Cl | H | H | H | Cl |
| H | H | tBu | H | Br | H | H | H | Br |
| Me | H | Ph | Me | $CH_2OH$ | H | Me | H | $CH_2OH$ |
| Me | Et | Ph | Me | $CH_2NH_2$ | H | Me | H | $CH_2NH_2$ |
| Me | iPr | H | Me | $CH_2NHMe$ | H | Me | H | $CH_2NHMe$ |
| Me | nPr | H | Me | $CH_2Ph$ | H | Me | H | $CH_2Ph$ |
| Me | nBu | H | Me | COMe | H | Me | H | COMe |
| Me | tBu | H | Me | COOH | H | Me | H | COOH |
| Et | Ph | H | Et | $CONH_2$ | H | Et | H | $CONH_2$ |
| Et | H | Et | Et | CONHMe | Et | Et | Et | CONHMe |
| Et | H | iPr | Et | CONHMs | iPr | Et | iPr | CONHMs |
| iPr | H | nPr | iPr | NHMs | nPr | iPr | nPr | NHMs |

-continued

| $R^{11}$ | $R^{13}$ | $R^{14}$ | $R^{11}$ | $R^{13}$ | $R^{14}$ | $R^{11}$ | $R^{13}$ | $R^{14}$ |
|---|---|---|---|---|---|---|---|---|
| nPr | H | nBu | nPr | NHCOMe | nBu | nPr | nBu | NHCOMe |
| nBu | H | tBu | nBu | $NO_2$ | tBu | nBu | tBu | $NO_2$ |
| tBu | H | Ph | tBu | CHO | Ph | tBu | Ph | H |
| Ph | Cl | Et | Ph | $SO_3H$ | Et | Ph | Et | H |
| $CH_2OH$ | Cl | nPr | $CH_2OH$ | $SO_2NHMe$ | nPr | $CH_2OH$ | nPr | H |
| $CH_2OH$ | Cl | Ph | $CH_2OH$ | OH | Ph | $CH_2OH$ | Ph | H |
| $CH_2OMe$ | Et | Cl | $CH_2OMe$ | COMe | Cl | $CH_2OMe$ | Cl | Cl |
| $CH_2OMe$ | nPr | Cl | $CH_2OMe$ | COOH | Cl | $CH_2OMe$ | Cl | Cl |
| $CH_2NH_2$ | Ph | Cl | $CH_2NH_2$ | CONH2 | Cl | $CH_2NH_2$ | Cl | Cl |
| $CH_2NH_2$ | H | Et | $CH_2NH_2$ | CONHMe | Et | $CH_2NH_2$ | Et | H |
| $CH_2NH_2$ | H | nPr | $CH_2NH_2$ | CONHMs | nPr | $CH_2NH_2$ | nPr | H |
| $CH_2NH_2$ | H | Ph | $CH_22NH_2$ | NHMs | Ph | $CH_2NH_2$ | Ph | H |
| $CH_2NHMe$ | Me | Me | $CH_2NHMe$ | $NO_2$ | Me | $CH_2NHMe$ | Me | H |
| $CH_2Ph$ | Et | Et | $CH_2Ph$ | OH | Et | $CH_2Ph$ | Et | H |
| $CH_2Ph$ | nPr | nPr | $CH_2Ph$ | COMe | nPr | $CH_2Ph$ | nPr | H |
| $CH_2CH_2Ph$ | Ph | Ph | $CH_2CH_2Ph$ | COOH | Ph | $CH_2CH_2Ph$ | Ph | H |

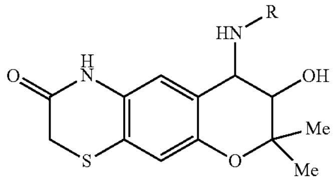

HN—R

| | | |
|---|---|---|
| 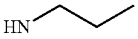 | 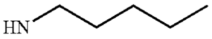 | 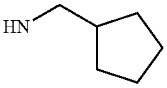 |
| 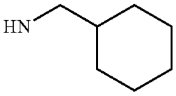 | 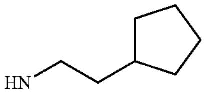 | 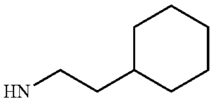 |
| 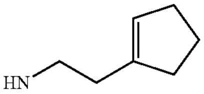 | 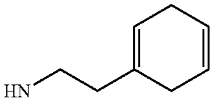 | 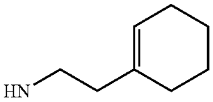 |
| 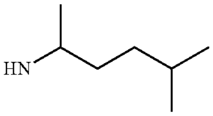 | 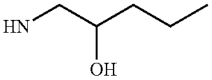 | 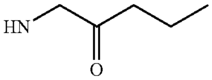 |
| 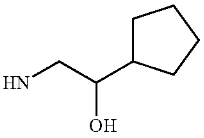 | 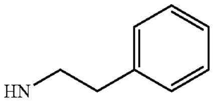 | 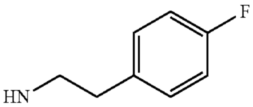 |
| 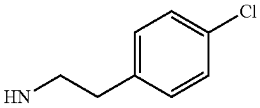 | 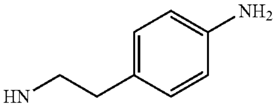 | 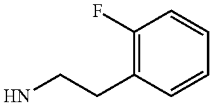 |
| 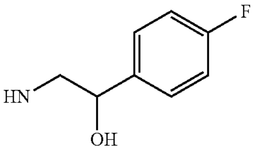 | 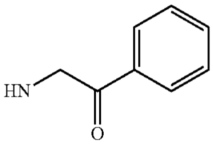 | 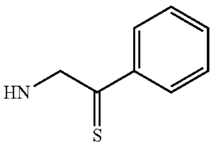 |

-continued
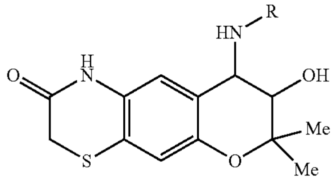
HN—R
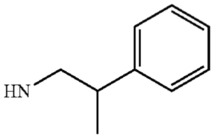
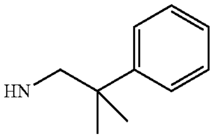
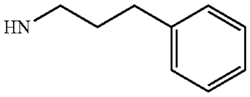
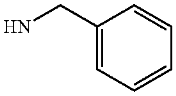
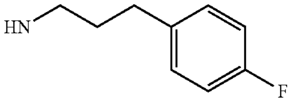
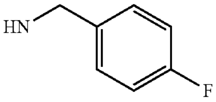
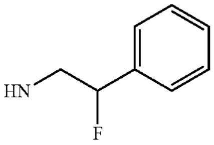
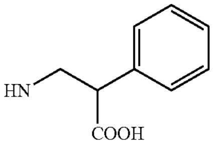
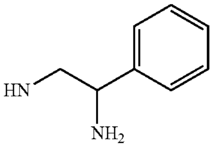
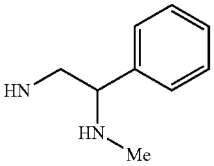
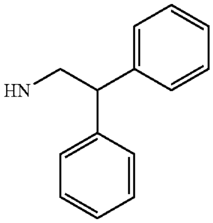
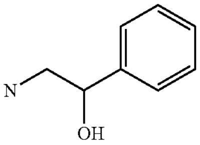
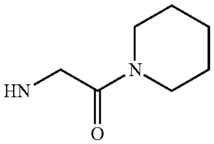
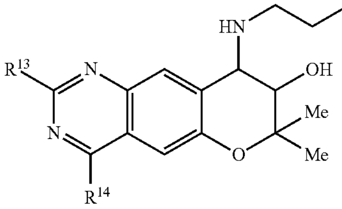
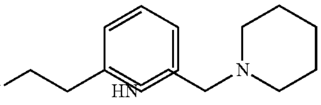
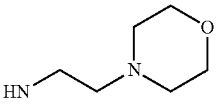
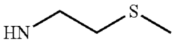
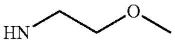
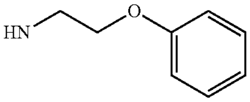
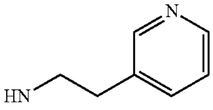
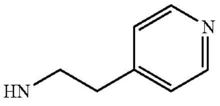
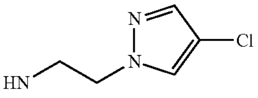
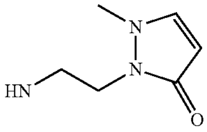

| $R^{13}$ | $R^{14}$ | $R^{13}$ | $R^{14}$ | $R^{13}$ | $R^{14}$ |
|---|---|---|---|---|---|

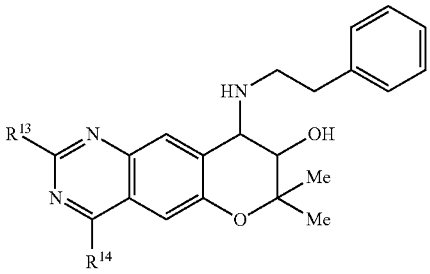

| | | | | | |
|---|---|---|---|---|---|
| H | Me | $NO_2$ | H | OMe | H |
| H | Et | CHO | H | OEt | H |
| H | iPr | $SO_3H$ | H | OiPr | H |
| H | nPr | Cl | H | OnPr | H |
| H | nBu | Br | H | OBn | H |
| H | tBu | $CH_2OH$ | H | OPh | H |
| H | Ph | $CH_2NH_2$ | H | SMe | H |
| Me | H | $CH_2NHMe$ | H | SEt | H |
| Et | H | $CH_2Ph$ | H | SiPr | H |
| iPr | H | COMe | H | SnPr | H |
| nPr | H | COOH | H | $OCH_2CH_2Ph$ | H |
| nBu | H | $CONH_2$ | H | $SCH_2CH_2Ph$ | H |
| tBu | H | CONHMe | Et | H | OMe |
| Ph | $NO_2$ | CONHMs | iPr | H | OEt |
| H | CHO | NHMs | nPr | Cl | OiPr |
| H | $SO_3H$ | NHCOMe | nBu | Me | OnPr |
| H | Cl | $NO_2$ | tBu | Et | OBn |
| H | Br | CHO | Ph | nPr | OPh |
| H | $CH_2OH$ | $SO_3H$ | Et | Ph | SMe |
| H | $CH_2NH_2$ | $SO_2NHMe$ | nPr | Me | SEt |
| Cl | $CH_2NHMe$ | OH | Ph | Et | SiPr |
| Cl | $CH_2Ph$ | COMe | Cl | nPr | SnPr |
| Cl | COMe | COOH | Cl | Ph | $OCH_2CH_2Ph$ |
| Et | COOH | CONH2 | Cl | $NO_2$ | SCOMe |
| nPr | $CONH_2$ | CONHMe | Et | CHO | OMe |
| Ph | CONHMe | CONHMs | nPr | $SO_3H$ | OEt |
| H | CONHMs | NHMs | Ph | Cl | OnPr |
| H | NHMs | $NO_2$ | Me | Br | SMe |
| H | NHCOMe | OH | Et | $CH_2OH$ | SEt |
| Me | $CO_2H$ | COMe | nPr | $CH_2NH_2$ | SiPr |
| Et | H | COON | Ph | F | SPh |

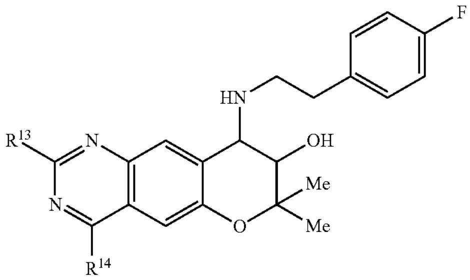

| | | | | | |
|---|---|---|---|---|---|
| H | Me | $NO_2$ | H | OMe | H |
| H | Et | CHO | H | OEt | H |
| H | iPr | $SO_3H$ | H | OiPr | H |
| H | nPr | Cl | H | OnPr | H |
| H | nBu | Br | H | OBn | H |
| H | tBu | $CH_2OH$ | H | OPh | H |
| H | Ph | $CH_2NH_2$ | H | SMe | H |
| Me | H | $CH_2NHMe$ | H | SEt | H |
| Et | H | $CH_2Ph$ | H | SiPr | H |
| iPr | H | COMe | H | SnPr | H |
| nPr | H | COOH | H | $OCH_2CH_2Ph$ | H |
| nBu | H | $CONH_2$ | H | $SCH_2CH_2Ph$ | H |
| tBu | H | CONHMe | Et | H | OMe |
| Ph | $NO_2$ | CONHMs | iPr | H | OEt |
| H | CHO | NHMs | nPr | Cl | OiPr |
| H | $SO_3H$ | NHCOMe | nBu | Me | OnPr |
| H | Cl | $NO_2$ | tBu | Et | OBn |
| H | Br | CHO | Ph | nPr | OPh |

-continued

| $R^{13}$ | $R^{14}$ | $R^{13}$ | $R^{14}$ | $R^{13}$ | $R^{14}$ |
|---|---|---|---|---|---|
| H | $CH_2OH$ | $SO_3H$ | Et | Ph | SMe |
| H | $CH_2NH_2$ | $SO_2NHMe$ | nPr | Me | SEt |
| Cl | $CH_2NHMe$ | OH | Ph | Et | SiPr |
| Cl | $CH_2Ph$ | COMe | Cl | nPr | SnPr |
| Cl | COMe | COOH | Cl | Ph | $OCH_2CH_2Ph$ |
| Et | COOH | $CONH_2$ | Cl | $NO_2$ | SCOMe |
| nPr | $CONH_2$ | CONHMe | Et | CHO | OMe |
| Ph | CONHMe | CONHMs | nPr | $SO_3H$ | OEt |
| H | CONHMs | NHMs | Ph | Cl | OnPr |
| H | NHMs | $NO_2$ | Me | Br | SMe |
| H | NHCOMe | OH | Et | $CH_2OH$ | SEt |
| Me | $CO_2H$ | COMe | nPr | $CH_2NH_2$ | SiPr |
| Et | H | COOH | Ph | F | SPh |

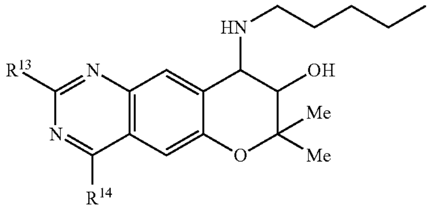

| | | | | | |
|---|---|---|---|---|---|
| H | Me | $NO_2$ | H | OMe | H |
| H | Et | CHO | H | OEt | H |
| H | iPr | $SO_3H$ | H | OiPr | H |
| H | nPr | Cl | H | OnPr | H |
| H | nBu | Br | H | OBn | H |
| H | tBu | $CH_2OH$ | H | OPh | H |
| H | Ph | $CH_2NH_2$ | H | SMe | H |
| Me | H | $CH_2NHMe$ | H | SEt | H |
| Et | H | $CH_2Ph$ | H | SiPr | H |
| iPr | H | COMe | H | SnPr | H |
| nPr | H | COOH | H | $OCH_2CH_2Ph$ | H |
| nBu | H | $CONH_2$ | H | $SCH_2CH_2Ph$ | H |
| tBu | H | CONHMe | Et | H | OMe |
| Ph | $NO_2$ | CONHMs | iPr | H | OEt |
| H | CHO | NHMs | nPr | Cl | OiPr |
| H | $SO_3H$ | NHCOMe | nBu | Me | OnPr |
| H | Cl | $NO_2$ | tBu | Et | OBn |
| H | Br | CHO | Ph | nPr | OPh |
| H | $CH_2OH$ | $SO_3H$ | Et | Ph | SMe |
| H | $CH_2NH_2$ | $SO_2NHMe$ | nPr | Me | SEt |
| Cl | $CH_2NHMe$ | OH | Ph | Et | SiPr |
| Cl | $CH_2Ph$ | COMe | Cl | nPr | SnPr |
| Cl | COMe | COON | Cl | Ph | $OCH_2CH_2Ph$ |
| Et | COOH | $CONH_2$ | Cl | $NO_2$ | SCOMe |
| nPr | $CONH_2$ | CONHMe | Et | CHO | OMe |
| Ph | CONHMe | CONHMs | nPr | $SO_3H$ | OEt |
| H | CONHMs | NHMs | Ph | Cl | OnPr |
| H | NHMs | $NO_2$ | Me | Br | SMe |
| H | NHCOMe | OH | Et | $CH_2OH$ | SEt |
| Me | $CO_2H$ | COMe | nPr | $CH_2NH_2$ | SiPr |
| Et | H | COOH | Ph | F | SPh |

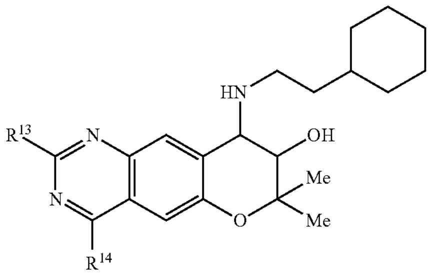

| | | | | | |
|---|---|---|---|---|---|
| H | Me | $NO_2$ | H | OMe | H |
| H | Et | CHO | H | OEt | H |
| H | iPr | $SO_3H$ | H | OiPr | H |
| H | nPr | Cl | H | OnPr | H |
| H | nBu | Br | H | OBn | H |
| H | tBu | $CH_2OH$ | H | OPh | H |
| H | Ph | $CH_2NH_2$ | H | SMe | H |

-continued

| $R^{13}$ | $R^{14}$ | $R^{13}$ | $R^{14}$ | $R^{13}$ | $R^{14}$ |
|---|---|---|---|---|---|
| Me | H | $CH_2NHMe$ | H | SEt | H |
| Et | H | $CH_2Ph$ | H | SiPr | H |
| iPr | H | COMe | H | SnPr | H |
| nPr | H | COOH | H | $OCH_2CH_2Ph$ | H |
| nBu | H | $CONH_2$ | H | $SCH_2CH_2Ph$ | H |
| tBu | H | CONHMe | Et | H | OMe |
| Ph | $NO_2$ | CONHMs | iPr | H | OEt |
| H | CHO | NHMs | nPr | Cl | OiPr |
| H | $SO_3H$ | NHCOMe | nBu | Me | OnPr |
| H | Cl | $NO_2$ | tBu | Et | OBn |
| H | Br | CHO | Ph | nPr | OPh |
| H | $CH_2OH$ | $SO_3H$ | Et | Ph | SMe |
| H | $CH_2NH_2$ | $SO_2NHMe$ | nPr | Me | SEt |

-continued

| $R^{13}$ | $R^{14}$ | $R^{13}$ | $R^{14}$ | $R^{13}$ | $R^{14}$ |
|---|---|---|---|---|---|
| Cl | $CH_2NHMe$ | OH | Ph | Et | SiPr |
| Cl | $CH_2Ph$ | COMe | Cl | nPr | SnPr |
| Cl | COMe | COOH | Cl | Ph | $OCH_2CH_2Ph$ |
| Et | COOH | $CONH_2$ | Cl | $NO_2$ | SCOMe |
| nPr | $CONH_2$ | CONHMe | Et | CHO | OMe |
| Ph | CONHMe | CONHMs | nPr | $SO_3H$ | OEt |
| H | CONHMs | NHMs | Ph | Cl | OnPr |
| H | NHMs | $NO_2$ | Me | Br | SMe |
| H | NHCOMe | OH | Et | $CH_2OH$ | SEt |
| Me | $CO_2H$ | COMe | nPr | $CH_2NH_2$ | SiPr |
| Et | H | COOH | Ph | F | SPh |

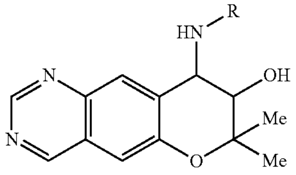

| HN—R | | |
|---|---|---|
| 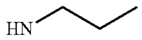 | 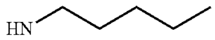 | 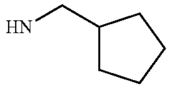 |
| 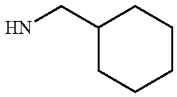 | 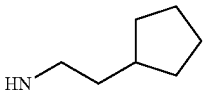 | 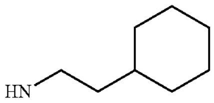 |
| 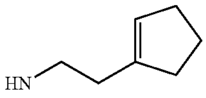 | 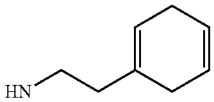 | 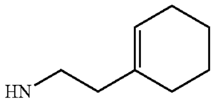 |
| 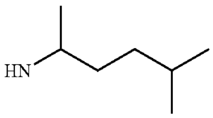 | 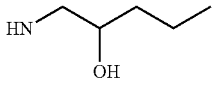 | 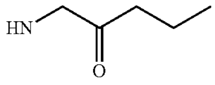 |
| 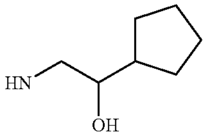 | 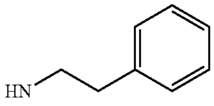 | 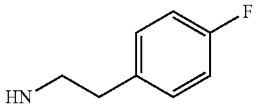 |
| 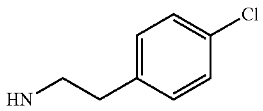 | 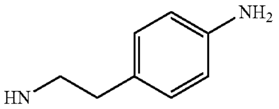 | 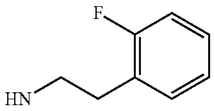 |
| 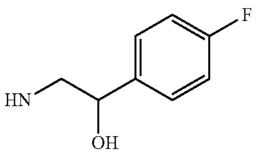 | 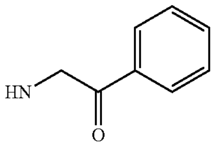 | 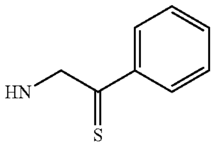 |

-continued
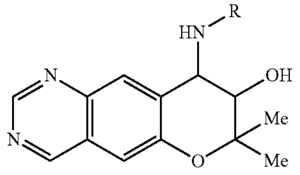
HN—R
| | | |
|---|---|---|
| 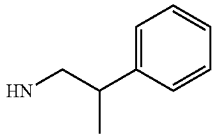 | 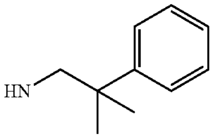 | 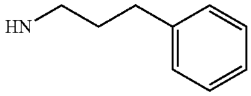 |
| 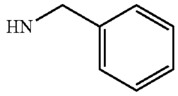 | 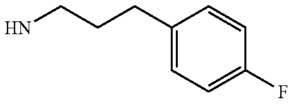 | 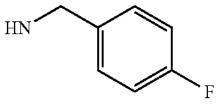 |
| 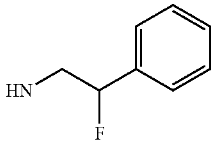 | 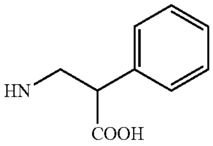 | 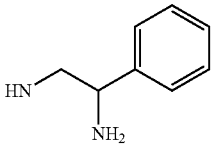 |
| 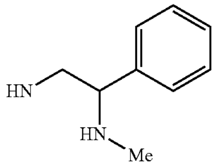 | 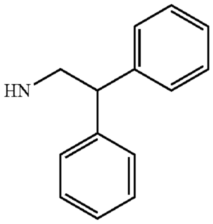 | 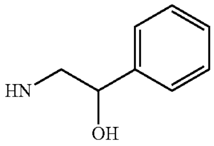 |
| 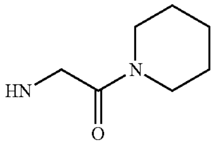 | 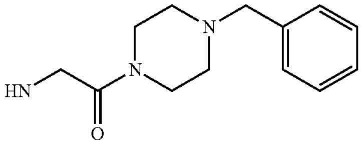 | 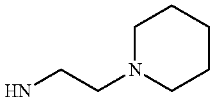 |
| 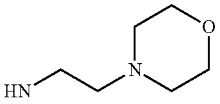 | 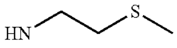 | 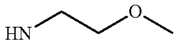 |
| 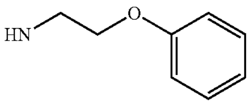 | 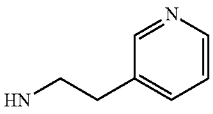 | 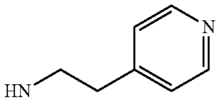 |
| 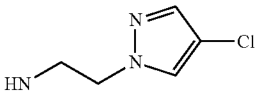 | 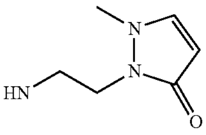 | |

| $R^{11}$ | $R^{12}$ |
|---|---|
| 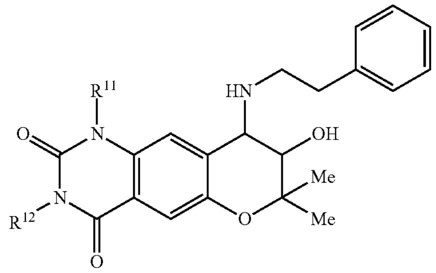 | |
| H | Me |
| H | Et |
| H | iPr |
| H | nPr |
| H | nBu |
| Me | tBu |
| Me | Ph |
| Me | $CH_2OH$ |
| Me | $CH_2OMe$ |
| Me | $CH_2NH_2$ |
| Me | Me |
| Et | $CH_2NH_2$ |
| Et | $CH_2NHMe$ |
| Et | $CH_2Ph$ |
| iPr | $CH_2Ph$ |
| nPr | $CH_2CH_2Ph$ |
| nBu | H |
| tBu | Me |
| Ph | H |
| $CH_2OH$ | Me |
| $CH_2OH$ | Et |
| $CH_2OMe$ | nPr |
| $CH_2OMe$ | Ph |
| $CH_2NH_2$ | H |
| $CH_2NH_2$ | nPr |
| $CH_2NH_2$ | Ph |
| $CH_2NH_2$ | Me |
| $CH_2NHMe$ | Et |
| $CH_2Ph$ | nPr |
| $CH_2Ph$ | Ph |
| $CH_2CH_2Ph$ | $CH_2Ph$ |
| 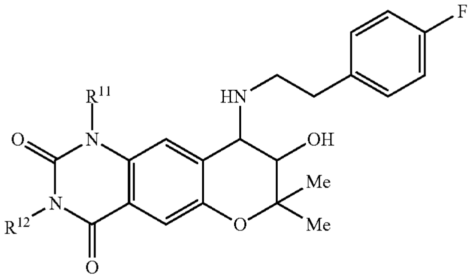 | |
| H | Me |
| H | Et |
| H | iPr |
| H | nPr |
| H | nBu |
| Me | tBu |
| Me | Ph |
| Me | $CH_2OH$ |
| Me | $CH_2OMe$ |
| Me | $CH_2NH_2$ |
| Me | Me |
| Et | $CH_2NH_2$ |
| Et | $CH_2NHMe$ |
| Et | $CH_2Ph$ |
| iPr | $CH_2Ph$ |
| nPr | $CH_2CH_2Ph$ |
| nBu | H |
| tBu | Me |

-continued

| $R^{11}$ | $R^{12}$ |
|---|---|
| Ph | H |
| $CH_2OH$ | Me |
| $CH_2OH$ | Et |
| $CH_2OMe$ | nPr |
| $CH_2OMe$ | Ph |
| $CH_2NH_2$ | H |
| $CH_2NH_2$ | nPr |
| $CH_2NH_2$ | Ph |
| $CH_2NH_2$ | Me |
| $CH_2NHMe$ | Et |
| $CH_2Ph$ | nPr |
| $CH_2Ph$ | Ph |
| $CH_2CH_2Ph$ | $CH_2Ph$ |
| 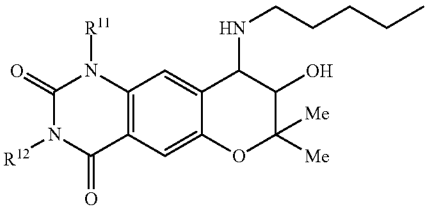 | |
| H | Me |
| H | Et |
| H | iPr |
| H | nPr |
| H | nBu |
| Me | tBu |
| Me | Ph |
| Me | $CH_2OH$ |
| Me | $CH_2OMe$ |
| Me | $CH_2NH_2$ |
| Me | Me |
| Et | $CH_2NH_2$ |
| Et | $CH_2NHMe$ |
| Et | $CH_2Ph$ |
| iPr | $CH_2Ph$ |
| nPr | $CH_2CH_2Ph$ |
| nBu | H |
| tBu | Me |
| Ph | H |
| $CH_2OH$ | Me |
| $CH_2OH$ | Et |
| $CH_2OMe$ | nPr |
| $CH_2OMe$ | Ph |
| $CH_2NH_2$ | H |
| $CH_2NH_2$ | nPr |
| $CH_2NH_2$ | Ph |
| $CH_2NH_2$ | Me |
| $CH_2NHMe$ | Et |
| $CH_2Ph$ | nPr |
| $CH_2Ph$ | Ph |
| $CH_2CH_2Ph$ | $CH_2Ph$ |
| 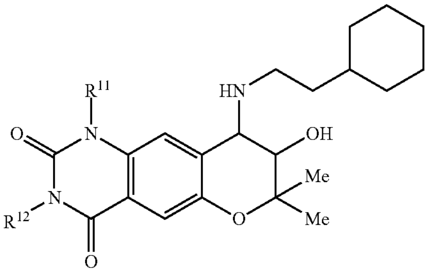 | |
| H | Me |
| H | Et |
| H | iPr |
| H | nPr |
| H | nBu |
| Me | tBu |
| Me | Ph |

-continued
| $R^{11}$ | $R^{12}$ |
|---|---|
| Me | $CH_2OH$ |
| Me | $CH_2OMe$ |
| Me | $CH_2NH_2$ |
| Me | Me |
| Et | $CH_2NH_2$ |
| Et | $CH_2NHMe$ |
| Et | $CH_2Ph$ |
| iPr | $CH_2Ph$ |
| nPr | $CH_2CH_2Ph$ |
| nBu | H |
| tBu | Me |
| Ph | H |
| $CH_2OH$ | Me |
-continued
| $R^{11}$ | $R^{12}$ |
|---|---|
| $CH_2OH$ | Et |
| $CH_2OMe$ | nPr |
| $CH_2OMe$ | Ph |
| $CH_2NH_2$ | H |
| $CH_2NH_2$ | nPr |
| $CH_2NH_2$ | Ph |
| $CH_2NH_2$ | Me |
| $CH_2NHMe$ | Et |
| $CH_2Ph$ | nPr |
| $CH_2Ph$ | Ph |
| $CH_2CH_2Ph$ | $CH_2Ph$ |
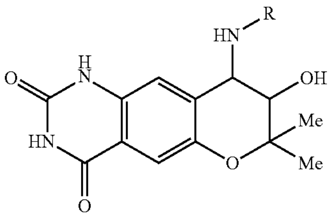
| HN—R | | |
|---|---|---|
| 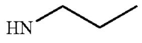 | 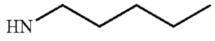 | 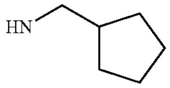 |
| 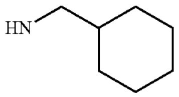 | 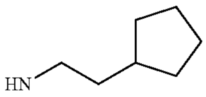 | 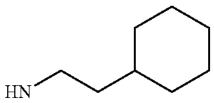 |
| 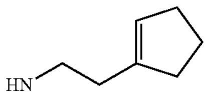 | 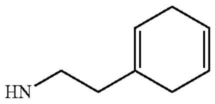 | 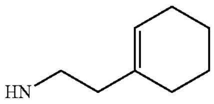 |
| 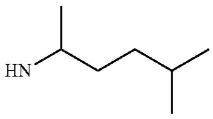 | 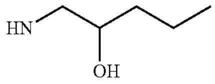 | 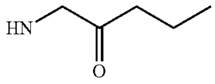 |
| 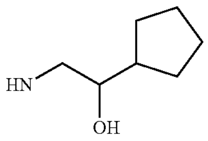 | 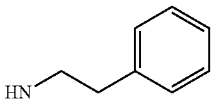 | 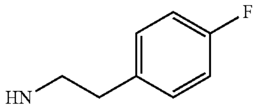 |
| 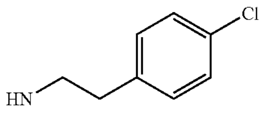 | 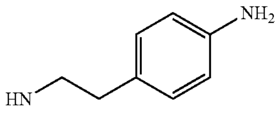 | 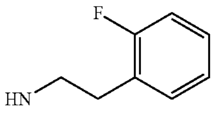 |
| 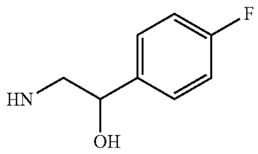 | 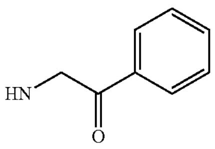 | 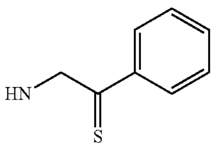 |

-continued
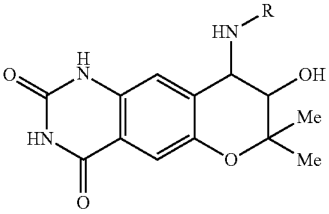
| HN—R | | |
|---|---|---|
| 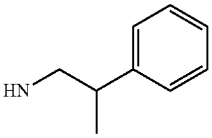 | 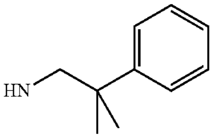 | 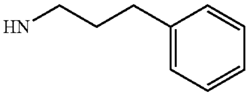 |
| 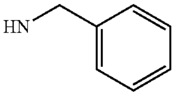 | 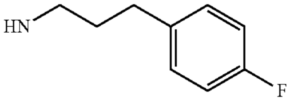 | 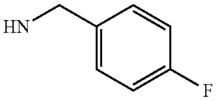 |
| 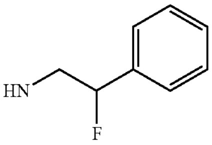 | 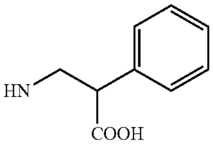 | 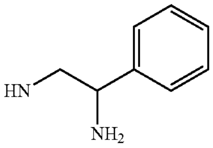 |
| 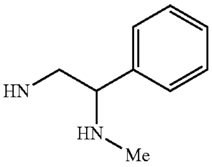 | 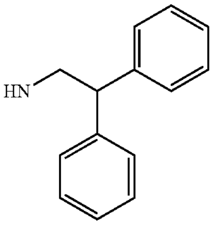 | 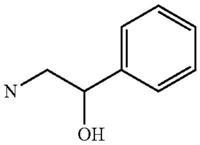 |
| 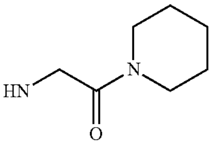 | 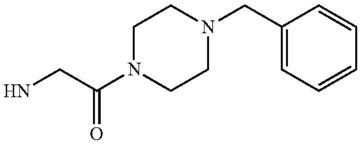 | 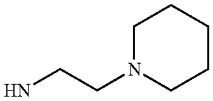 |
| 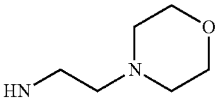 | 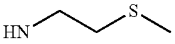 | 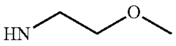 |
| 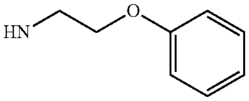 | 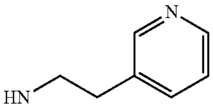 | 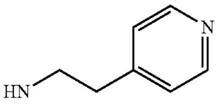 |
| 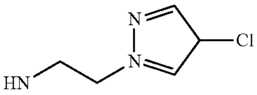 | 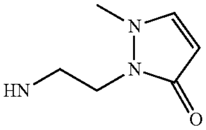 | |

| $R^{11}$ | $R^{12}$ |
|---|---|

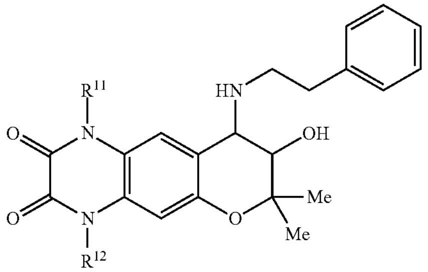

| | |
|---|---|
| H | Me |
| H | Et |
| H | iPr |
| H | nPr |
| H | nBu |
| Me | tBu |
| Me | Ph |
| Me | $CH_2OH$ |
| Me | $CH_2OMe$ |
| Me | $CH_2NH_2$ |
| Me | Me |
| Et | $CH_2NH_2$ |
| Et | $CH_2NHMe$ |
| Et | $CH_2Ph$ |
| iPr | $CH_2Ph$ |
| nPr | $CH_2CH_2Ph$ |
| nBu | H |
| tBu | Me |
| Ph | H |
| $CH_2OH$ | Me |
| $CH_2OH$ | Et |
| $CH_2OMe$ | nPr |
| $CH_2OMe$ | Ph |
| $CH_2NH_2$ | H |
| $CH_2NH_2$ | nPr |
| $CH_2NH_2$ | Ph |
| $CH_2NH_2$ | Me |
| $CH_2NHMe$ | Et |
| $CH_2Ph$ | nPr |
| $CH_2Ph$ | Ph |
| $CH_2CH_2Ph$ | $CH_2Ph$ |

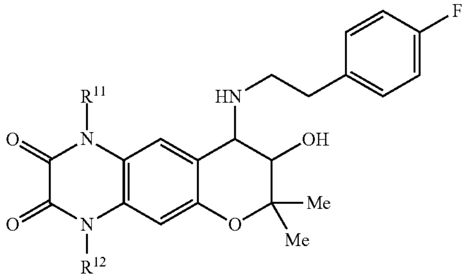

| | |
|---|---|
| H | Me |
| H | Et |
| H | iPr |
| H | nPr |
| H | nBu |
| Me | tBu |
| Me | Ph |
| Me | $CH_2OH$ |
| Me | $CH_2OMe$ |
| Me | $CH_2NH_2$ |
| Me | Me |
| Et | $CH_2NH_2$ |
| Et | $CH_2NHMe$ |
| Et | $CH_2Ph$ |
| iPr | $CH_2Ph$ |
| nPr | $CH_2CH_2Ph$ |
| nBu | H |
| tBu | Me |

-continued

| $R^{11}$ | $R^{12}$ |
|---|---|
| Ph | H |
| $CH_2OH$ | Me |
| $CH_2OH$ | Et |
| $CH_2OMe$ | nPr |
| $CH_2OMe$ | Ph |
| $CH_2NH_2$ | H |
| $CH_2NH_2$ | nPr |
| $CH_2NH_2$ | Ph |
| $CH_2NH_2$ | Me |
| $CH_2NHMe$ | Et |
| $CH_2Ph$ | nPr |
| $CH_2Ph$ | Ph |
| $CH_2CH_2Ph$ | $CH_2Ph$ |

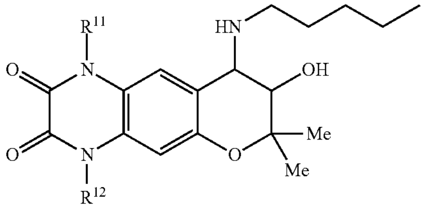

| | |
|---|---|
| H | Me |
| H | Et |
| H | iPr |
| H | nPr |
| H | nBu |
| Me | tBu |
| Me | Ph |
| Me | $CH_2OH$ |
| Me | $CH_2OMe$ |
| Me | $CH_2NH_2$ |
| Me | Me |
| Et | $CH_2NH_2$ |
| Et | $CH_2NHMe$ |
| Et | $CH_2Ph$ |
| iPr | $CH_2Ph$ |
| nPr | $CH_2CH_2Ph$ |
| nBu | H |
| tBu | Me |
| Ph | H |
| $CH_2OH$ | Me |
| $CH_2OH$ | Et |
| $CH_2OMe$ | nPr |
| $CH_2OMe$ | Ph |
| $CH_2NH_2$ | H |
| $CH_2NH_2$ | nPr |
| $CH_2NH_2$ | Ph |
| $CH_2NH_2$ | Me |
| $CH_2NHMe$ | Et |
| $CH_2Ph$ | nPr |
| $CH_2Ph$ | Ph |
| $CH_2CH_2Ph$ | $CH_2Ph$ |

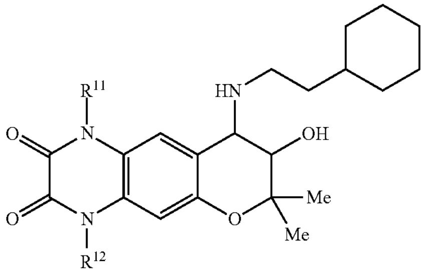

| | |
|---|---|
| H | Me |
| H | Et |
| H | iPr |
| H | nPr |
| H | nBu |
| Me | tBu |
| Me | Ph |

-continued
| $R^{11}$ | $R^{12}$ |
|---|---|
| Me | $CH_2OH$ |
| Me | $CH_2OMe$ |
| Me | $CH_2NH_2$ |
| Me | Me |
| Et | $CH_2NH_2$ |
| Et | $CH_2NHMe$ |
| Et | $CH_2Ph$ |
| iPr | $CH_2Ph$ |
| nPr | $CH_2CH_2Ph$ |
| nBu | H |
| tBu | Me |
| Ph | H |
| $CH_2OH$ | Me |
-continued
| $R^{11}$ | $R^{12}$ |
|---|---|
| $CH_2OH$ | Et |
| $CH_2OMe$ | nPr |
| $CH_2OMe$ | Ph |
| $CH_2NH_2$ | H |
| $CH_2NH_2$ | nPr |
| $CH_2NH_2$ | Ph |
| $CH_2NH_2$ | Me |
| $CH_2NHMe$ | Et |
| $CH_2Ph$ | nPr |
| $CH_2Ph$ | Ph |
| $CH_2CH_2Ph$ | $CH_2Ph$ |
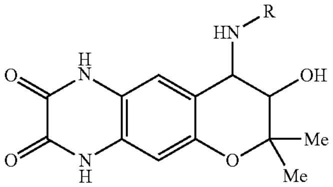
HN—R
| | | |
|---|---|---|
| 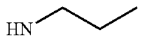 | 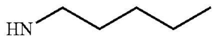 | 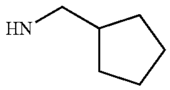 |
| 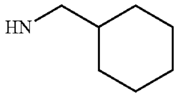 | 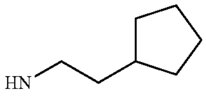 | 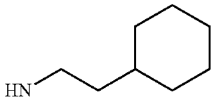 |
| 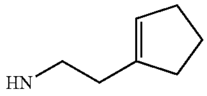 | 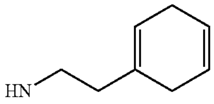 | 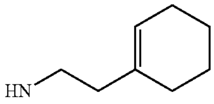 |
| 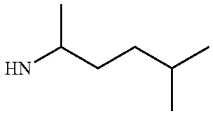 | 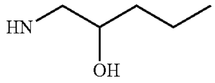 | 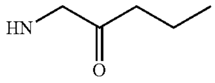 |
| 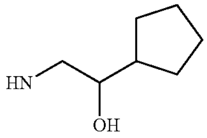 | 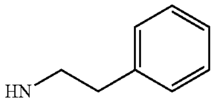 | 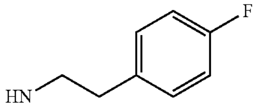 |
| 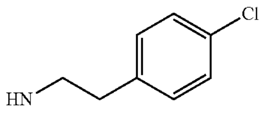 | 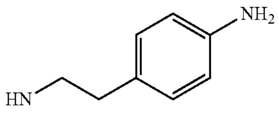 | 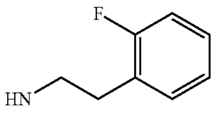 |
| 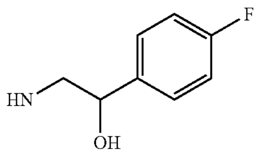 | 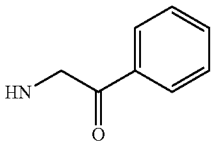 | 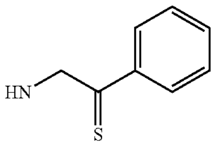 |

-continued
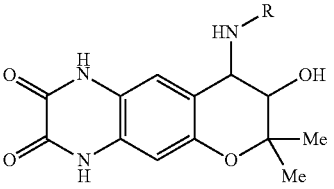
HN—R
| | | |
|---|---|---|
| 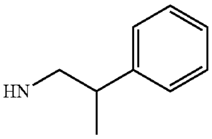 | 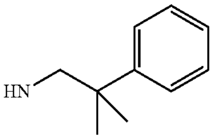 | 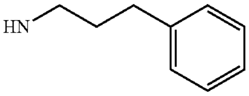 |
| 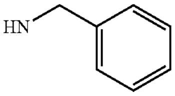 | 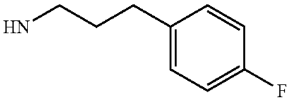 | 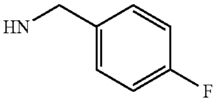 |
| 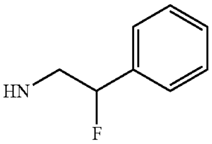 | 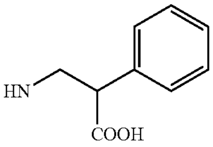 | 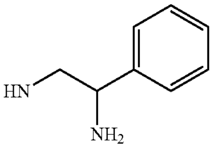 |
| 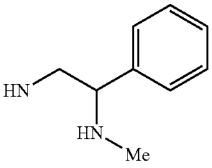 | 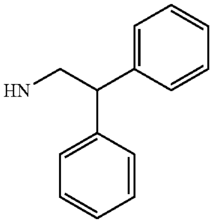 | 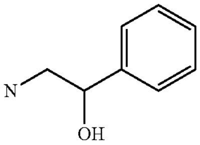 |
| 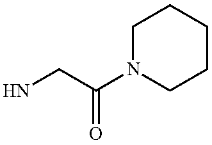 | 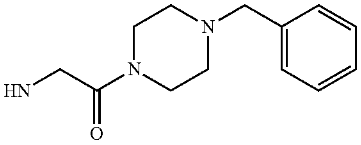 | 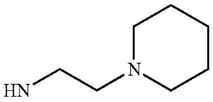 |
| 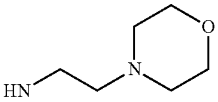 | 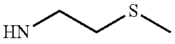 | 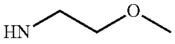 |
| 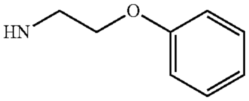 | 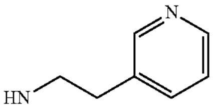 | 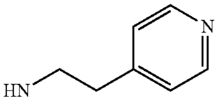 |
| 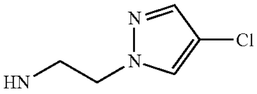 | 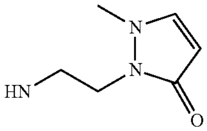 | |

| $R^{11}$ | $R^{13}$ | $R^{14}$ | $R^{11}$ | $R^{13}$ | $R^{14}$ | $R^{11}$ | $R^{13}$ | $R^{14}$ |
|---|---|---|---|---|---|---|---|---|
| 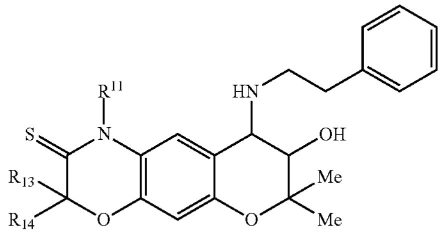 | | | | | | | | |
| H | H | Et | H | $NO_2$ | H | H | H | $NO_2$ |
| H | H | iPr | H | CHO | H | H | H | CHO |
| H | H | nPr | H | $SO_3H$ | H | H | H | $SO_3H$ |
| H | H | nBu | H | Cl | H | H | H | Cl |
| H | H | tBu | H | Br | H | H | H | Br |
| Me | H | H | Me | $CH_2OH$ | H | Me | H | $CH_2OH$ |
| Me | Et | Ph | Me | $CH_2NH_2$ | H | Me | H | $CH_2NH_2$ |
| Me | iPr | H | Me | $CH_2NHMe$ | H | Me | H | $CH_2NHMe$ |
| Me | nPr | H | Me | $CH_2Ph$ | H | Me | H | $CH_2Ph$ |
| Me | nBu | H | Me | COMe | H | Me | H | COMe |
| Me | tBu | H | Me | COOH | H | Me | H | COOH |
| Et | Ph | H | Et | $CONH_2$ | H | Et | H | $CONH_2$ |
| Et | H | Et | Et | CONHMe | Et | Et | Et | CONHMe |
| Et | H | iPr | Et | CONHMs | iPr | Et | iPr | CONHMs |
| iPr | H | nPr | iPr | NHMs | nPr | iPr | nPr | NHMs |
| nPr | H | nBu | nPr | NHCOMe | nBu | nPr | nBu | NHCOMe |
| nBu | H | tBu | nBu | $NO_2$ | tBu | nBu | tBu | $NO_2$ |
| tBu | H | Ph | tBu | CHO | Ph | tBu | Ph | H |
| Ph | Cl | Et | Ph | $SO_3H$ | Et | Ph | Et | H |
| $CH_2OH$ | Cl | nPr | $CH_2OH$ | $SO_2NHMe$ | nPr | $CH_2OH$ | nPr | H |
| $CH_2OH$ | Cl | Ph | $CH_2OH$ | OH | Ph | $CH_2OH$ | Ph | H |
| $CH_2OMe$ | Et | Cl | $CH_2OMe$ | COMe | Cl | $CH_2OMe$ | Cl | Cl |
| $CH_2OMe$ | nPr | Cl | $CH_2OMe$ | COOH | Cl | $CH_2OMe$ | Cl | Cl |
| $CH_2NH_2$ | Ph | Cl | $CH_2NH_2$ | $CONH_2$ | Cl | $CH_2NH_2$ | Cl | Cl |
| $CH_2NH_2$ | H | Et | $CH_2NH_2$ | CONHMe | Et | $CH_2NH_2$ | Et | H |
| $CH_2NH_2$ | H | nPr | $CH_2NH_2$ | CONHMs | nPr | $CH_2NH_2$ | nPr | H |
| $CH_2NH_2$ | H | Ph | $CH_2NH_2$ | NHMs | Ph | $CH_2NH_2$ | Ph | H |
| $CH_2NHMe$ | Me | Me | $CH_2NHMe$ | $NO_2$ | Me | $CH_2NHMe$ | Me | H |
| $CH_2Ph$ | Et | Et | $CH_2Ph$ | OH | Et | $CH_2Ph$ | Et | H |
| $CH_2Ph$ | nPr | nPr | $CH_2Ph$ | COMe | nPr | $CH_2Ph$ | nPr | H |
| $CH_2CH_2Ph$ | Ph | Ph | $CH_2CH_2Ph$ | COOH | Ph | $CH_2CH_2Ph$ | Ph | H |
| 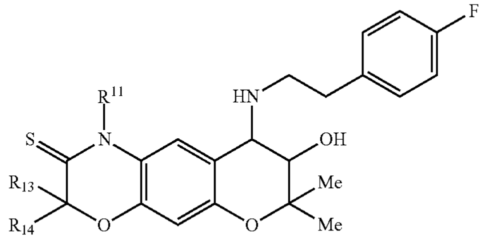 | | | | | | | | |
| H | H | Et | H | $NO_2$ | H | H | H | $NO_2$ |
| H | H | iPr | H | CHO | H | H | H | CHO |
| H | H | nPr | H | $SO_3H$ | H | H | H | $SO_3H$ |
| H | H | nBu | H | Cl | H | H | H | Cl |
| H | H | tBu | H | Br | H | H | H | Br |
| Me | H | H | Me | $CH_2OH$ | H | Me | H | $CH_2OH$ |
| Me | Et | Ph | Me | $CH_2NH_2$ | H | Me | H | $CH_2NH_2$ |
| Me | iPr | H | Me | $CH_2NHMe$ | H | Me | H | $CH_2NHMe$ |
| Me | nPr | H | Me | $CH_2Ph$ | H | Me | H | $CH_2Ph$ |
| Me | nBu | H | Me | COMe | H | Me | H | COMe |
| Me | tBu | H | Me | COOH | H | Me | H | COOH |
| Et | Ph | H | Et | $CONH_2$ | H | Et | H | $CONH_2$ |
| Et | H | Et | Et | CONHMe | Et | Et | Et | CONHMe |
| Et | H | iPr | Et | CONHMs | iPr | Et | iPr | CONHMs |
| iPr | H | nPr | iPr | NHMs | nPr | iPr | nPr | NHMs |
| nPr | H | nBu | nPr | NHCOMe | nBu | nPr | nBu | NHCOMe |
| nBu | H | tBu | nBu | $NO_2$ | tBu | nBu | tBu | $NO_2$ |
| tBu | H | Ph | tBu | CHO | Ph | tBu | Ph | H |
| Ph | Cl | Et | Ph | $SO_3H$ | Et | Ph | Et | H |
| $CH_2OH$ | Cl | nPr | $CH_2OH$ | $SO_2NHMe$ | nPr | $CH_2OH$ | nPr | H |
| $CH_2OH$ | Cl | Ph | $CH_2OH$ | OH | Ph | $CH_2OH$ | Ph | H |
| $CH_2OMe$ | Et | Cl | $CH_2OMe$ | COMe | Cl | $CH_2OMe$ | Cl | Cl |

-continued

| $R^{11}$ | $R^{13}$ | $R^{14}$ | $R^{11}$ | $R^{13}$ | $R^{14}$ | $R^{11}$ | $R^{13}$ | $R^{14}$ |
|---|---|---|---|---|---|---|---|---|
| $CH_2OMe$ | nPr | Cl | $CH_2OMe$ | COOH | Cl | $CH_2OMe$ | Cl | Cl |
| $CH_2NH_2$ | Ph | Cl | $CH_2NH_2$ | $CONH_2$ | Cl | $CH_2NH_2$ | Cl | Cl |
| $CH_2NH_2$ | H | Et | $CH_2NH_2$ | CONHMe | Et | $CH_2NH_2$ | Et | H |
| $CH_2NH_2$ | H | nPr | $CH_2NH_2$ | CONHMs | nPr | $CH_2NH_2$ | nPr | H |
| $CH_2NH_2$ | H | Ph | $CH_2NH_2$ | NHMs | Ph | $CH_2NH_2$ | Ph | H |
| $CH_2NHMe$ | Me | Me | $CH_2NHMe$ | $NO_2$ | Me | $CH_2NHMe$ | Me | H |
| $CH_2Ph$ | Et | Et | $CH_2Ph$ | OH | Et | $CH_2Ph$ | Et | H |
| $CH_2Ph$ | nPr | nPr | $CH_2Ph$ | COMe | nPr | $CH_2Ph$ | nPr | H |
| $CH_2CH_2Ph$ | Ph | Ph | $CH_2CH_2Ph$ | COOH | Ph | $CH_2CH_2Ph$ | Ph | H |

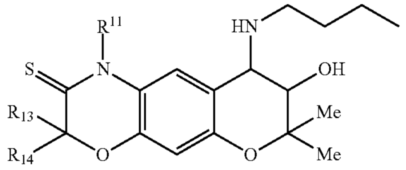

| | | | | | | | | |
|---|---|---|---|---|---|---|---|---|
| H | H | Et | H | $NO_2$ | H | H | H | $NO_2$ |
| H | H | iPr | H | CHO | H | H | H | CHO |
| H | H | nPr | H | $SO_3H$ | H | H | H | $SO_3H$ |
| H | H | nBu | H | Cl | H | H | H | Cl |
| H | H | tBu | H | Br | H | H | H | Br |
| Me | H | H | Me | $CH_2OH$ | H | Me | H | $CH_2OH$ |
| Me | Et | Ph | Me | $CH_2NH_2$ | H | Me | H | $CH_2NH_2$ |
| Me | iPr | H | Me | $CH_2NHMe$ | H | Me | H | $CH_2NHMe$ |
| Me | nPr | H | Me | $CH_2Ph$ | H | Me | H | $CH_2Ph$ |
| Me | nBu | H | Me | COMe | H | Me | H | COMe |
| Me | tBu | H | Me | COOH | H | Me | H | COOH |
| Et | Ph | H | Et | $CONH_2$ | H | Et | H | $CONH_2$ |
| Et | H | Et | Et | CONHMe | Et | Et | Et | CONHMe |
| Et | H | iPr | Et | CONHMs | iPr | Et | iPr | CONHMs |
| iPr | H | nPr | iPr | NHMs | nPr | iPr | nPr | NHMs |
| nPr | H | nBu | nPr | NHCOMe | nBu | nPr | nBu | NHCOMe |
| nBu | H | tBu | nBu | $NO_2$ | tBu | nBu | tBu | $NO_2$ |
| tBu | H | Ph | tBu | CHO | Ph | tBu | Ph | H |
| Ph | Cl | Et | Ph | $SO_3H$ | Et | Ph | Et | H |
| $CH_2OH$ | Cl | nPr | $CH_2OH$ | $SO_2NHMe$ | nPr | $CH_2OH$ | nPr | H |
| $CH_2OH$ | Cl | Ph | $CH_2OH$ | OH | Ph | $CH_2OH$ | Ph | H |
| $CH_2OMe$ | Et | Cl | $CH_2OMe$ | COMe | Cl | $CH_2OMe$ | Cl | Cl |
| $CH_2OMe$ | nPr | Cl | $CH_2OMe$ | COOH | Cl | $CH_2OMe$ | Cl | Cl |
| $CH_2NH_2$ | Ph | Cl | $CH_2NH_2$ | $CONH_2$ | Cl | $CH_2NH_2$ | Cl | Cl |
| $CH_2NH_2$ | H | Et | $CH_2NH_2$ | CONHMe | Et | $CH_2NH_2$ | Et | H |
| $CH_2NH_2$ | H | nPr | $CH_2NH_2$ | CONHMs | nPr | $CH_2NH_2$ | nPr | H |
| $CH_2NH_2$ | H | Ph | $CH_2NH_2$ | NHMs | Ph | $CH_2NH_2$ | Ph | H |
| $CH_2NHMe$ | Me | Me | $CH_2NHMe$ | $NO_2$ | Me | $CH_2NHMe$ | Me | H |
| $CH_2Ph$ | Et | Et | $CH_2Ph$ | OH | Et | $CH_2Ph$ | Et | H |
| $CH_2Ph$ | nPr | nPr | $CH_2Ph$ | COMe | nPr | $CH_2Ph$ | nPr | H |
| $CH_2CH_2Ph$ | Ph | Ph | $CH_2CH_2Ph$ | COOH | Ph | $CH_2CH_2Ph$ | Ph | H |

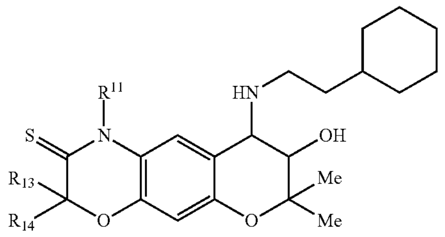

| | | | | | | | | |
|---|---|---|---|---|---|---|---|---|
| H | H | Et | H | $NO_2$ | H | H | H | $NO_2$ |
| H | H | iPr | H | CHO | H | H | H | CHO |
| H | H | nPr | H | $SO_3H$ | H | H | H | $SO_3H$ |
| H | H | nBu | H | Cl | H | H | H | Cl |
| H | H | tBu | H | Br | H | H | H | Br |
| Me | H | H | Me | $CH_2OH$ | H | Me | H | $CH_2OH$ |
| Me | Et | Ph | Me | $CH_2NH_2$ | H | Me | H | $CH_2NH_2$ |
| Me | iPr | H | Me | $CH_2NHMe$ | H | Me | H | $CH_2NHMe$ |
| Me | nPr | H | Me | $CH_2Ph$ | H | Me | H | $CH_2Ph$ |
| Me | nBu | H | Me | COMe | H | Me | H | COMe |
| Me | tBu | H | Me | COOH | H | Me | H | COOH |
| Et | Ph | H | Et | $CONH_2$ | H | Et | H | $CONH_2$ |
| Et | H | Et | Et | CONHMe | Et | Et | Et | CONHMe |
| Et | H | iPr | Et | CONHMs | iPr | Et | iPr | CONHMs |
| iPr | H | nPr | iPr | NHMs | nPr | iPr | nPr | NHMs |

-continued

| $R^{11}$ | $R^{13}$ | $R^{14}$ | $R^{11}$ | $R^{13}$ | $R^{14}$ | $R^{11}$ | $R^{13}$ | $R^{14}$ |
|---|---|---|---|---|---|---|---|---|
| nPr | H | nBu | nPr | NHCOMe | nBu | nPr | nBu | NHCOMe |
| nBu | H | tBu | nBu | $NO_2$ | tBu | nBu | tBu | $NO_2$ |
| tBu | H | Ph | tBu | CHO | Ph | tBu | Ph | H |
| Ph | Cl | Et | Ph | $SO_3H$ | Et | Ph | Et | H |
| $CH_2OH$ | Cl | nPr | $CH_2OH$ | $SO_2NHMe$ | nPr | $CH_2OH$ | nPr | H |
| $CH_2OH$ | Cl | Ph | $CH_2OH$ | OH | Ph | $CH_2OH$ | Ph | H |
| $CH_2OMe$ | Et | Cl | $CH_2OMe$ | COMe | Cl | $CH_2OMe$ | Cl | Cl |
| $CH_2OMe$ | nPr | Cl | $CH_2OMe$ | COOH | Cl | $CH_2OMe$ | Cl | Cl |
| $CH_2NH_2$ | Ph | Cl | $CH_2NH_2$ | $CONH_2$ | Cl | $CH_2NH_2$ | Cl | Cl |
| $CH_2NH_2$ | H | Et | $CH_2NH_2$ | CONHMe | Et | $CH_2NH_2$ | Et | H |
| $CH_2NH_2$ | H | nPr | $CH_2NH_2$ | CONHMs | nPr | $CH_2NH_2$ | nPr | H |
| $CH_2NH_2$ | H | Ph | $CH_2NH_2$ | NHMs | Ph | $CH_2NH_2$ | Ph | H |
| $CH_2NHMe$ | Me | Me | $CH_2NHMe$ | $NO_2$ | Me | $CH_2NHMe$ | Me | H |
| $CH_2Ph$ | Et | Et | $CH_2Ph$ | OH | Et | $CH_2Ph$ | Et | H |
| $CH_2Ph$ | nPr | nPr | $CH_2Ph$ | COMe | nPr | $CH_2Ph$ | nPr | H |
| $CH_2CH_2Ph$ | Ph | Ph | $CH_2CH_2Ph$ | COOH | Ph | $CH_2CH_2Ph$ | Ph | H |

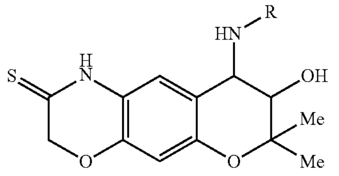

HN—R

| | | |
|---|---|---|
| 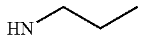 | 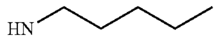 | 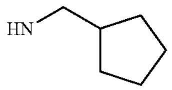 |
| 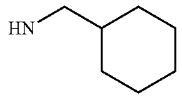 | 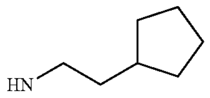 | 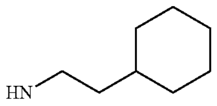 |
| 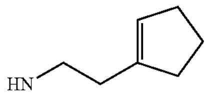 | 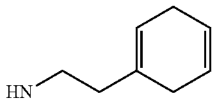 | 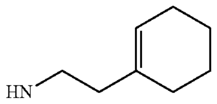 |
| 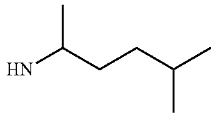 | 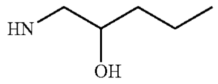 | 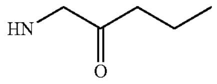 |
| 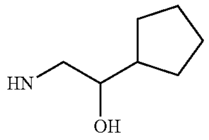 | 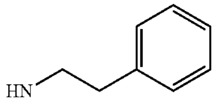 | 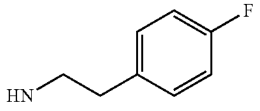 |
| 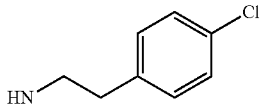 | 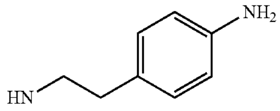 | 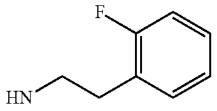 |
| 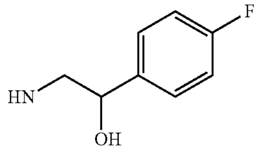 | 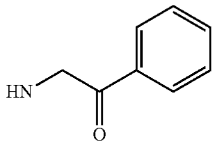 | 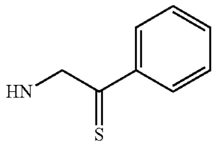 |

-continued
| | | |
|---|---|---|
| | 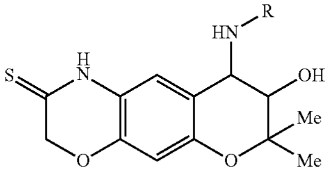<br>HN—R | |
| 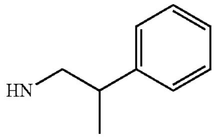 | 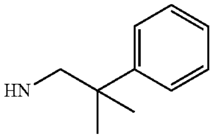 | 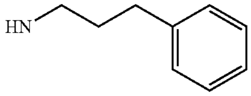 |
| 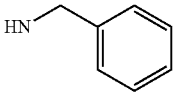 | 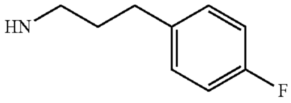 | 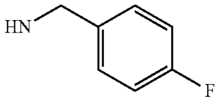 |
| 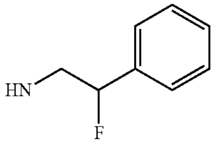 | 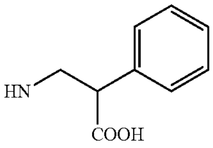 | 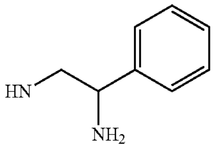 |
| 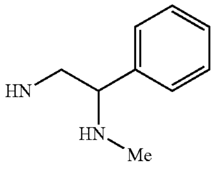 | 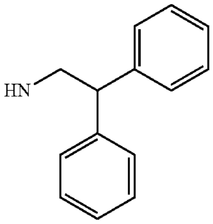 | 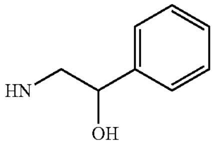 |
| 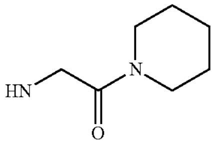 | 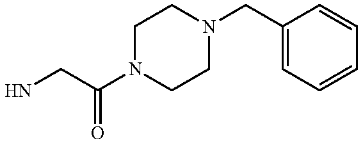 | 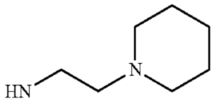 |
| 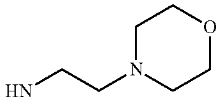 | 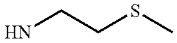 | 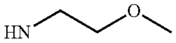 |
| 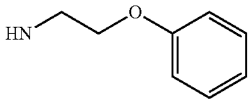 | 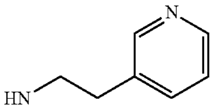 | 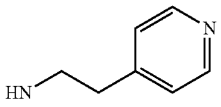 |
| 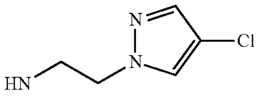 | 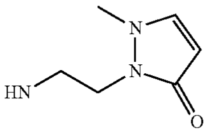 | |

| $R^{11}$ | $R^{13}$ | $R^{14}$ | $R^{11}$ | $R^{13}$ | $R^{14}$ | $R^{11}$ | $R^{13}$ | $R^{14}$ |
|---|---|---|---|---|---|---|---|---|
| 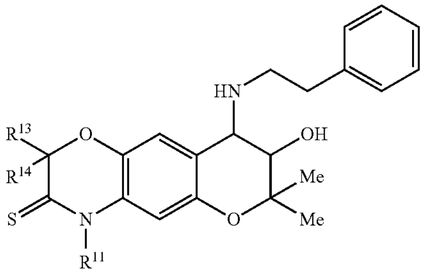 | | | | | | | | |
| H | H | Et | H | $NO_2$ | H | H | H | $NO_2$ |
| H | H | iPr | H | CHO | H | H | H | CHO |
| H | H | nPr | H | $SO_3H$ | H | H | H | $SO_3H$ |
| H | H | nBu | H | Cl | H | H | H | Cl |
| H | H | tBu | H | Br | H | H | H | Br |
| Me | H | H | Me | $CH_2OH$ | H | Me | H | $CH_2OH$ |
| Me | Et | Ph | Me | $CH_2NH_2$ | H | Me | H | $CH_2NH_2$ |
| Me | iPr | H | Me | $CH_2NHMe$ | H | Me | H | $CH_2NHMe$ |
| Me | nPr | H | Me | $CH_2Ph$ | H | Me | H | $CH_2Ph$ |
| Me | nBu | H | Me | COMe | H | Me | H | COMe |
| Me | tBu | H | Me | COOH | H | Me | H | COOH |
| Et | Ph | H | Et | $CONH_2$ | H | Et | H | $CONH_2$ |
| Et | H | Et | Et | CONHMe | Et | Et | Et | CONHMe |
| Et | H | iPr | Et | CONHMs | iPr | Et | iPr | CONHMs |
| iPr | H | nPr | iPr | NHMs | nPr | iPr | nPr | NHMs |
| nPr | H | nBu | nPr | NHCOMe | nBu | nPr | nBu | NHCOMe |
| nBu | H | tBu | nBu | $NO_2$ | tBu | nBu | tBu | $NO_2$ |
| tBu | H | Ph | tBu | CHO | Ph | tBu | Ph | H |
| Ph | Cl | Et | Ph | $SO_3H$ | Et | Ph | Et | H |
| $CH_2OH$ | Cl | nPr | $CH_2OH$ | $SO_2NHMe$ | nPr | $CH_2OH$ | nPr | H |
| $CH_2OH$ | Cl | Ph | $CH_2OH$ | OH | Ph | $CH_2OH$ | Ph | H |
| $CH_2OMe$ | Et | Cl | $CH_2OMe$ | COMe | Cl | $CH_2OMe$ | Cl | Cl |
| $CH_2OMe$ | nPr | Cl | $CH_2OMe$ | COOH | Cl | $CH_2OMe$ | Cl | Cl |
| $CH_2NH_2$ | Ph | Cl | $CH_2NH_2$ | $CONH_2$ | Cl | $CH_2NH_2$ | Cl | Cl |
| $CH_2NH_2$ | H | Et | $CH_2NH_2$ | CONHMe | Et | $CH_2NH_2$ | Et | H |
| $CH_2NH_2$ | H | nPr | $CH_2NH_2$ | CONHMs | nPr | $CH_2NH_2$ | nPr | H |
| $CH_2NH_2$ | H | Ph | $CH_2NH_2$ | NHMs | Ph | $CH_2NH_2$ | Ph | H |
| $CH_2NHMe$ | Me | Me | $CH_2NHMe$ | $NO_2$ | Me | $CH_2NHMe$ | Me | H |
| $CH_2Ph$ | Et | Et | $CH_2Ph$ | OH | Et | $CH_2Ph$ | Et | H |
| $CH_2Ph$ | nPr | nPr | $CH_2Ph$ | COMe | nPr | $CH_2Ph$ | nPr | H |
| $CH_2CH_2Ph$ | Ph | Ph | $CH_2CH_2Ph$ | COOH | Ph | $CH_2CH_2Ph$ | Ph | H |
| 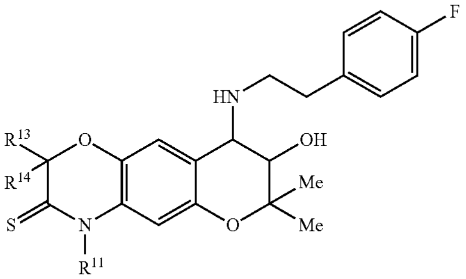 | | | | | | | | |
| H | H | Et | H | $NO_2$ | H | H | H | $NO_2$ |
| H | H | iPr | H | CHO | H | H | H | CHO |
| H | H | nPr | H | $SO_3H$ | H | H | H | $SO_3H$ |
| H | H | nBu | H | Cl | H | H | H | Cl |
| H | H | tBu | H | Br | H | H | H | Br |
| Me | H | H | Me | $CH_2OH$ | H | Me | H | $CH_2OH$ |
| Me | Et | Ph | Me | $CH_2NH_2$ | H | Me | H | $CH_2NH_2$ |
| Me | iPr | H | Me | $CH_2NHMe$ | H | Me | H | $CH_2NHMe$ |
| Me | nPr | H | Me | $CH_2Ph$ | H | Me | H | $CH_2Ph$ |
| Me | nBu | H | Me | COMe | H | Me | H | COMe |
| Me | tBu | H | Me | COOH | H | Me | H | COOH |
| Et | Ph | H | Et | $CONH_2$ | H | Et | H | $CONH_2$ |
| Et | H | Et | Et | CONHMe | Et | Et | Et | CONHMe |
| Et | H | iPr | Et | CONHMs | iPr | Et | iPr | CONHMs |
| iPr | H | nPr | iPr | NHMs | nPr | iPr | nPr | NHMs |
| nPr | H | nBu | nPr | NHCOMe | nBu | nPr | nBu | NHCOMe |
| nBu | H | tBu | nBu | $NO_2$ | tBu | nBu | tBu | $NO_2$ |
| tBu | H | Ph | tBu | CHO | Ph | tBu | Ph | H |

-continued

| $R^{11}$ | $R^{13}$ | $R^{14}$ | $R^{11}$ | $R^{13}$ | $R^{14}$ | $R^{11}$ | $R^{13}$ | $R^{14}$ |
|---|---|---|---|---|---|---|---|---|
| Ph | Cl | Et | Ph | $SO_3H$ | Et | Ph | Et | H |
| $CH_2OH$ | Cl | nPr | $CH_2OH$ | $SO_2NHMe$ | nPr | $CH_2OH$ | nPr | H |
| $CH_2OH$ | Cl | Ph | $CH_2OH$ | OH | Ph | $CH_2OH$ | Ph | H |
| $CH_2OMe$ | Et | Cl | $CH_2OMe$ | COMe | Cl | $CH_2OMe$ | Cl | Cl |
| $CH_2OMe$ | nPr | Cl | $CH_2OMe$ | COOH | Cl | $CH_2OMe$ | Cl | Cl |
| $CH_2NH_2$ | Ph | Cl | $CH_2NH_2$ | $CONH_2$ | Cl | $CH_2NH_2$ | Cl | Cl |
| $CH_2NH_2$ | H | Et | $CH_2NH_2$ | CONHMe | Et | $CH_2NH_2$ | Et | H |
| $CH_2NH_2$ | H | nPr | $CH_2NH_2$ | CONHMe | nPr | $CH_2NH_2$ | nPr | H |
| $CH_2NH_2$ | H | Ph | $CH_2NH_2$ | NHMs | Ph | $CH_2NH_2$ | Ph | H |
| $CH_2NHMe$ | Me | Me | $CH_2NHMe$ | $NO_2$ | Me | $CH_2NHMe$ | Me | H |
| $CH_2Ph$ | Et | Et | $CH_2Ph$ | OH | Et | $CH_2Ph$ | Et | H |
| $CH_2Ph$ | nPr | nPr | $CH_2Ph$ | COMe | nPr | $CH_2Ph$ | nPr | H |
| $CH_2CH_2Ph$ | Ph | Ph | $CH_2CH_2Ph$ | COOH | Ph | $CH_2CH_2Ph$ | Ph | H |

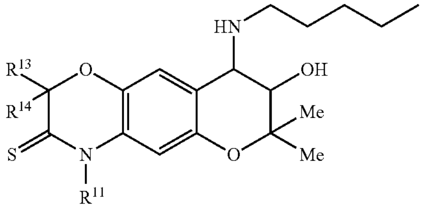

| | | | | | | | | |
|---|---|---|---|---|---|---|---|---|
| H | H | Et | H | $NO_2$ | H | H | H | $NO_2$ |
| H | H | iPr | H | CHO | H | H | H | CHO |
| H | H | nPr | H | $SO_3H$ | H | H | H | $SO_3H$ |
| H | H | nBu | H | Cl | H | H | H | Cl |
| H | H | tBu | H | Br | H | H | H | Br |
| Me | H | H | Me | $CH_2OH$ | H | Me | H | $CH_2OH$ |
| Me | Et | Ph | Me | $CH_2NH_2$ | H | Me | H | $CH_2NH_2$ |
| Me | iPr | H | Me | $CH_2NHMe$ | H | Me | H | $CH_2NHMe$ |
| Me | nPr | H | Me | $CH_2Ph$ | H | Me | H | $CH_2Ph$ |
| Me | nBu | H | Me | COMe | H | Me | H | COMe |
| Me | tBu | H | Me | COOH | H | Me | H | COOH |
| Et | Ph | H | Et | $CONH_2$ | H | Et | H | $CONH_2$ |
| Et | H | Et | Et | CONHMe | Et | Et | Et | CONHMe |
| Et | H | iPr | Et | CONHMs | iPr | Et | iPr | CONHMs |
| iPr | H | nPr | iPr | NHMs | nPr | iPr | nPr | NHMs |
| nPr | H | nBu | nPr | NHCOMe | nBu | nPr | nBu | NHCOMe |
| nBu | H | tBu | nBu | $NO_2$ | tBu | nBu | tBu | $NO_2$ |
| tBu | H | Ph | tBu | CHO | Ph | tBu | Ph | H |
| Ph | Cl | Et | Ph | $SO_3H$ | Et | Ph | Et | H |
| $CH_2OH$ | Cl | nPr | $CH_2OH$ | $SO_2NHMe$ | nPr | $CH_2OH$ | nPr | H |
| $CH_2OH$ | Cl | Ph | $CH_2OH$ | OH | Ph | $CH_2OH$ | Ph | H |
| $CH_2OMe$ | Et | Cl | $CH_2OMe$ | COMe | Cl | $CH_2OMe$ | Cl | Cl |
| $CH_2OMe$ | nPr | Cl | $CH_2OMe$ | COOH | Cl | $CH_2OMe$ | Cl | Cl |
| $CH_2NH_2$ | Ph | Cl | $CH_2NH_2$ | $CONH_2$ | Cl | $CH_2NH_2$ | Cl | Cl |
| $CH_2NH_2$ | H | Et | $CH_2NH_2$ | CONHMe | Et | $CH_2NH_2$ | Et | H |
| $CH_2NH_2$ | H | nPr | $CH_2NH_2$ | CONHMs | nPr | $CH_2NH_2$ | nPr | H |
| $CH_2NH_2$ | H | Ph | $CH_2NH_2$ | NHMs | Ph | $CH_2NH_2$ | Ph | H |
| $CH_2NHMe$ | Me | Me | $CH_2NHMe$ | $NO_2$ | Me | $CH_2NHMe$ | Me | H |
| $CH_2Ph$ | Et | Et | $CH_2Ph$ | OH | Et | $CH_2Ph$ | Et | H |
| $CH_2Ph$ | nPr | nPr | $CH_2Ph$ | COMe | nPr | $CH_2Ph$ | nPr | H |
| $CH_2CH_2Ph$ | Ph | Ph | $CH_2CH_2Ph$ | COOH | Ph | $CH_2CH_2Ph$ | Ph | H |

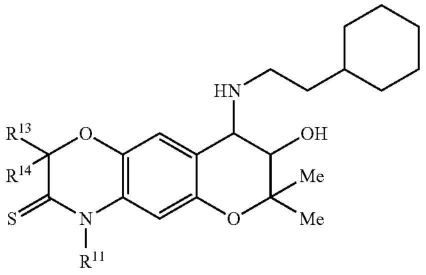

| | | | | | | | | |
|---|---|---|---|---|---|---|---|---|
| H | H | Et | H | $NO_2$ | H | H | H | $NO_2$ |
| H | H | iPr | H | CHO | H | H | H | CHO |
| H | H | nPr | H | $SO_3H$ | H | H | H | $SO_3H$ |
| H | H | nBu | H | Cl | H | H | H | Cl |
| H | H | tBu | H | Br | H | H | H | Br |
| Me | H | H | Me | $CH_2OH$ | H | Me | H | $CH_2OH$ |
| Me | Et | Ph | Me | $CH_2NH_2$ | H | Me | H | $CH_2NH_2$ |

-continued

| $R^{11}$ | $R^{13}$ | $R^{14}$ | $R^{11}$ | $R^{13}$ | $R^{14}$ | $R^{11}$ | $R^{13}$ | $R^{14}$ |
|---|---|---|---|---|---|---|---|---|
| Me | iPr | H | Me | $CH_2NHMe$ | H | Me | H | $CH_2NHMe$ |
| Me | nPr | H | Me | $CH_2Ph$ | H | Me | H | $CH_2Ph$ |
| Me | nBu | H | Me | COMe | H | Me | H | COMe |
| Me | tBu | H | Me | COOH | H | Me | H | COOH |
| Et | Ph | H | Et | $CONH_2$ | H | Et | H | $CONH_2$ |
| Et | H | Et | Et | CONHMe | Et | Et | Et | CONHMe |
| Et | H | iPr | Et | CONHMs | iPr | Et | iPr | CONHMs |
| iPr | H | nPr | iPr | NHMs | nPr | iPr | nPr | NHMs |
| nPr | H | nBu | nPr | NHCOMe | nBu | nPr | nBu | NHCOMe |
| nBu | H | tBu | nBu | $NO_2$ | tBu | nBu | tBu | $NO_2$ |
| tBu | H | Ph | tBu | CHO | Ph | tBu | Ph | H |
| Ph | Cl | Et | Ph | $SO_3H$ | Et | Ph | Et | H |
| $CH_2OH$ | Cl | nPr | $CH_2OH$ | $SO_2NHMe$ | nPr | $CH_2OH$ | nPr | H |
| $CH_2OH$ | Cl | Ph | $CH_2OH$ | OH | Ph | $CH_2OH$ | Ph | H |
| $CH_2OMe$ | Et | Cl | $CH_2OMe$ | COMe | Cl | $CH_2OMe$ | Cl | Cl |
| $CH_2OMe$ | nPr | Cl | $CH_2OMe$ | COOH | Cl | $CH_2OMe$ | Cl | Cl |
| $CH_2NH_2$ | Ph | Cl | $CH_2NH_2$ | $CONH_2$ | Cl | $CH_2NH_2$ | Cl | Cl |
| $CH_2NH_2$ | H | Et | $CH_2NH_2$ | CONHMe | Et | $CH_2NH_2$ | Et | H |
| $CH_2NH_2$ | H | nPr | $CH_2NH_2$ | CONHMs | nPr | $CH_2NH_2$ | nPr | H |
| $CH_2NH_2$ | H | Ph | $CH_2NH_2$ | NHMs | Ph | $CH_2NH_2$ | Ph | H |
| $CH_2NHMe$ | Me | Me | $CH_2NHMe$ | $NO_2$ | Me | $CH_2NHMe$ | Me | H |
| $CH_2Ph$ | Et | Et | $CH_2Ph$ | OH | Et | $CH_2Ph$ | Et | H |
| $CH_2Ph$ | nPr | nPr | $CH_2Ph$ | COMe | nPr | $CH_2Ph$ | nPr | H |
| $CH_2CH_2Ph$ | Ph | Ph | $CH_2CH_2Ph$ | COOH | Ph | $CH_2CH_2Ph$ | Ph | H |

| HN—R | | |
|---|---|---|
| | 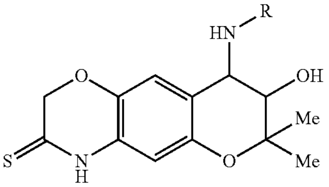 | |
| 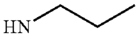 | 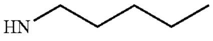 | 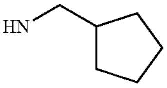 |
| 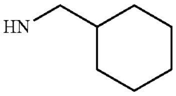 | 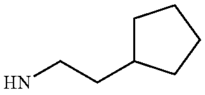 | 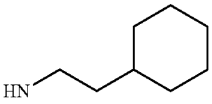 |
| 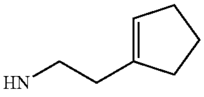 | 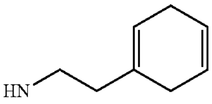 | 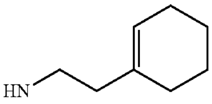 |
| 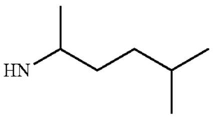 | 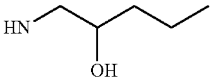 | 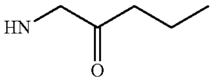 |
| 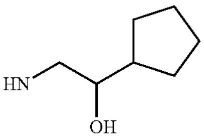 | 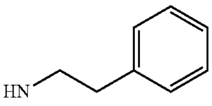 | 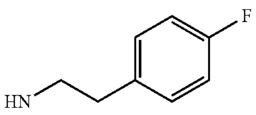 |
| 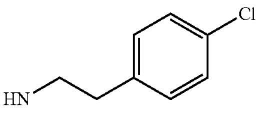 | 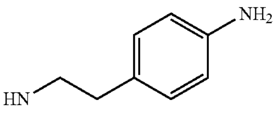 | 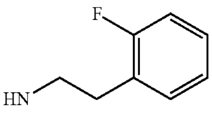 |

-continued
| HN—R | | |
|---|---|---|
| 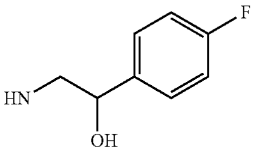 | 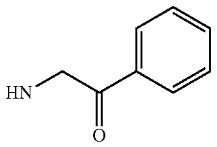 | 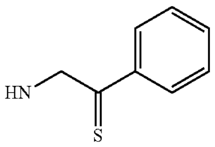 |
| 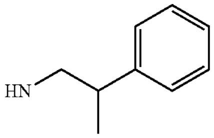 | 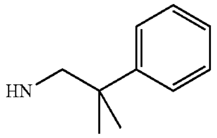 | 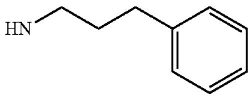 |
| 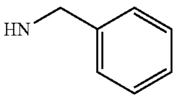 | 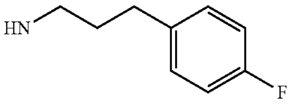 | 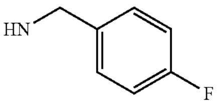 |
| 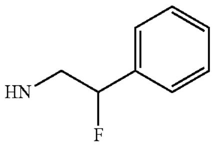 | 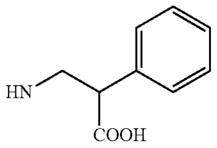 | 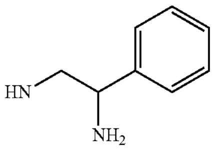 |
| 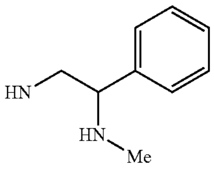 | 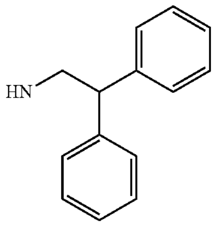 | 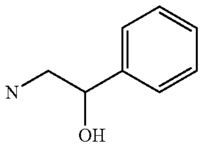 |
| 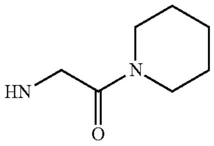 | 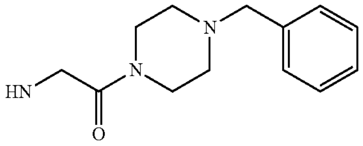 | 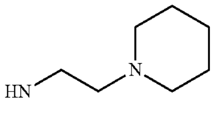 |
| 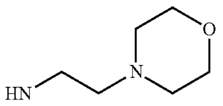 | 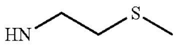 | 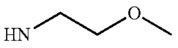 |
| 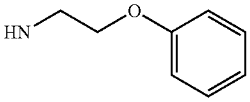 | 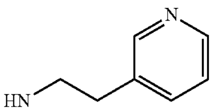 | 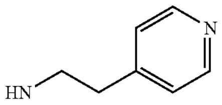 |
| 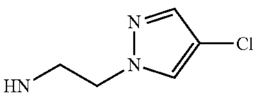 | 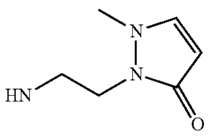 | |

-continued
| | HN—R | |
|---|---|---|
| | 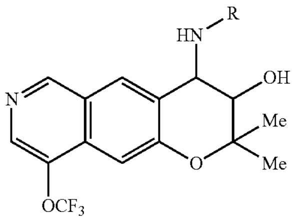 | |
| 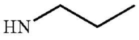 | 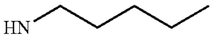 | 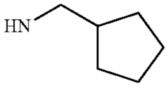 |
| 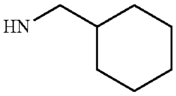 | 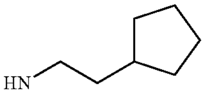 | 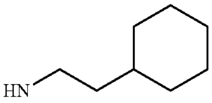 |
| 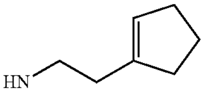 | 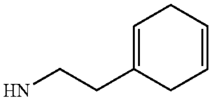 | 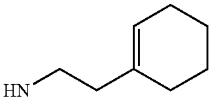 |
| 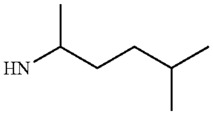 | 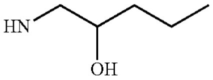 | 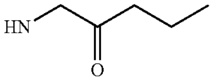 |
| 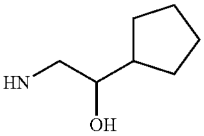 | 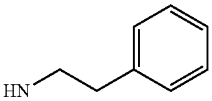 | 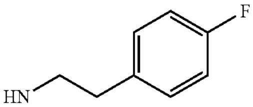 |
| 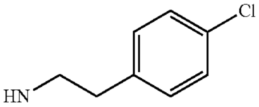 | 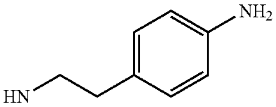 | 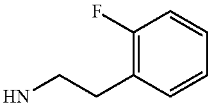 |
| 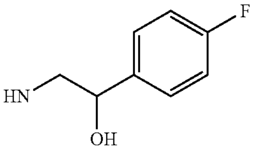 | 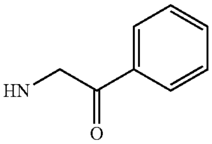 | 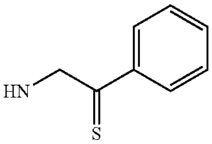 |
| 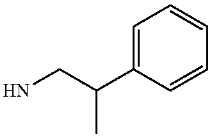 | 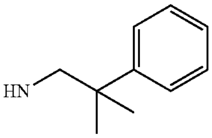 | 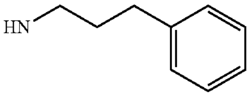 |
| 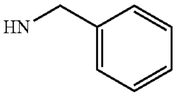 | 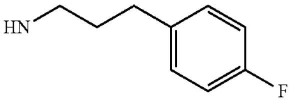 | 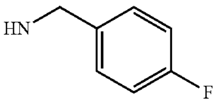 |
| 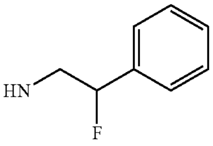 | 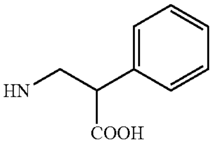 | 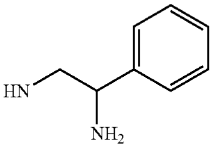 |

-continued
| HN—R | | |
|---|---|---|
| 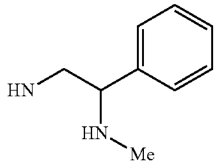 | 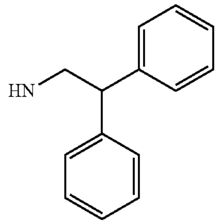 | 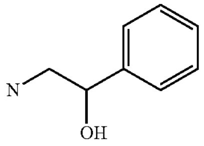 |
| 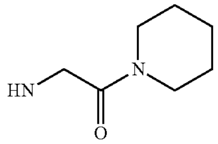 | 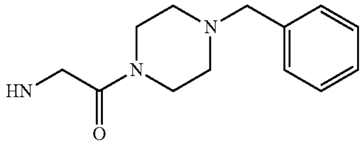 | 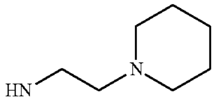 |
| 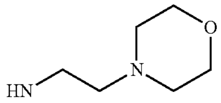 | 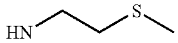 | 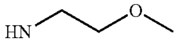 |
| 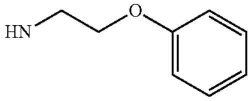 | 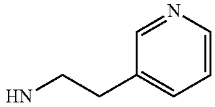 | 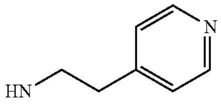 |
| 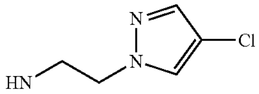 | 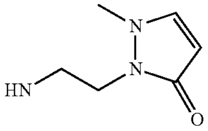 | |
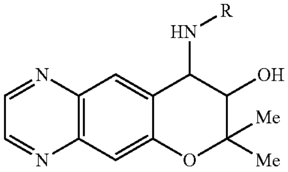
| | | |
|---|---|---|
| HN—Me | HN—Et | 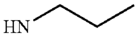 |
| 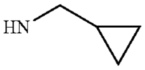 | 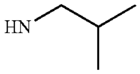 | 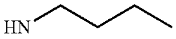 |
| 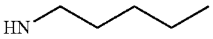 | 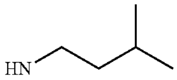 | 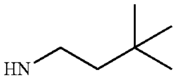 |
| 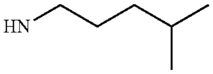 | 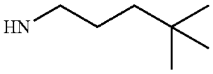 | 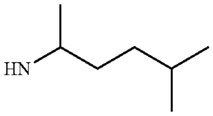 |
| 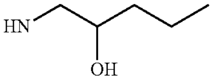 | 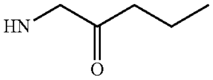 | 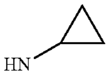 |
| 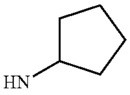 | 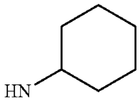 | 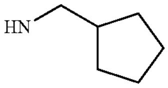 |

-continued
| HN—R | | |
|---|---|---|
| 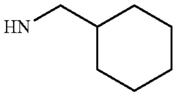 | 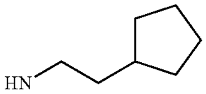 | 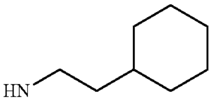 |
| 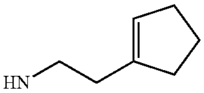 | 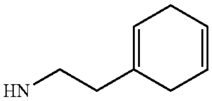 | 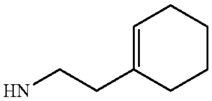 |
| 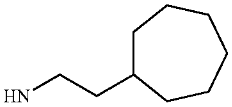 | 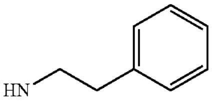 | 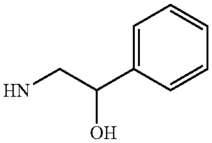 |
| 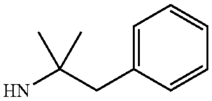 | 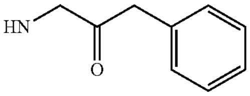 | 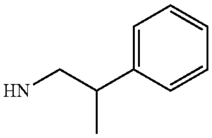 |
| 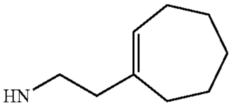 | 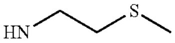 | 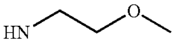 |
| 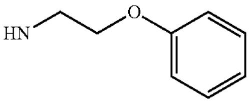 | 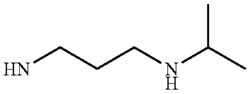 | 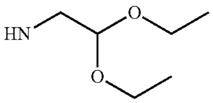 |
| 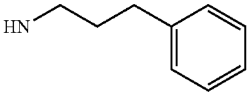 | 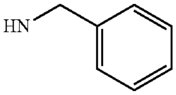 | 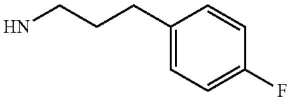 |
| 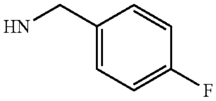 | 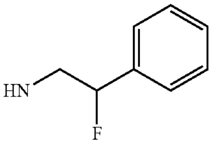 | 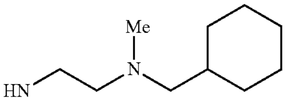 |
| 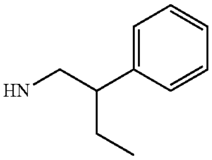 | 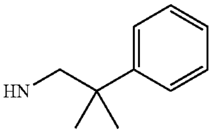 | 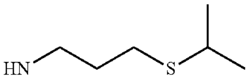 |
| 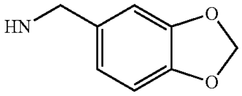 | | |

-continued
| HN—R | | |
|---|---|---|
| 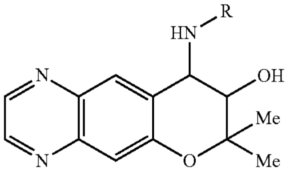 | | |
| 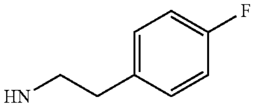 | 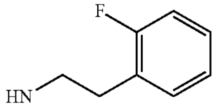 | 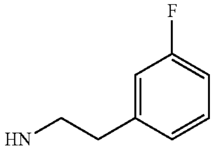 |
| 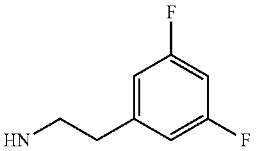 | 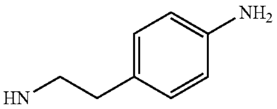 | 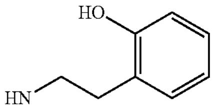 |
| 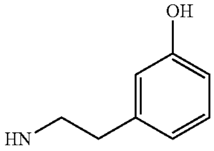 | 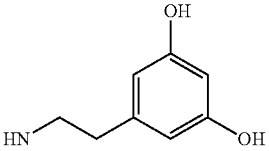 | 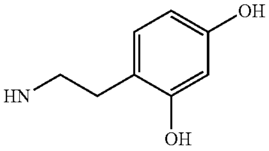 |
| 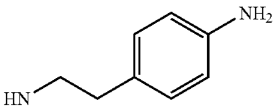 | 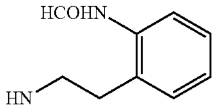 | 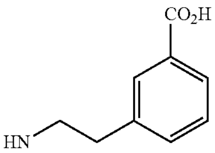 |
| 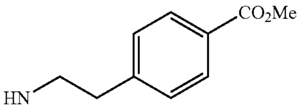 | 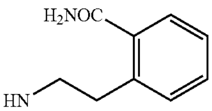 | 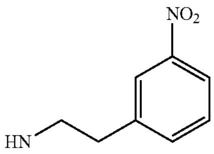 |
| 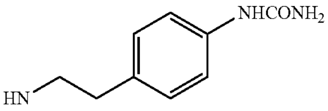 | 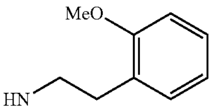 | 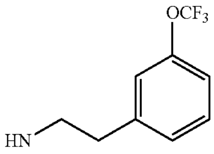 |
| 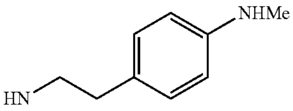 | 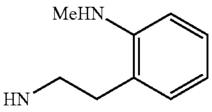 | 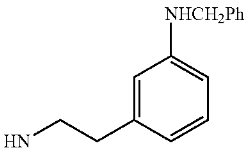 |
| 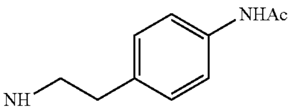 | 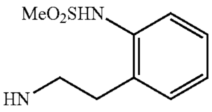 | 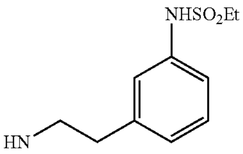 |

-continued
| HN—R | | |
|---|---|---|
| 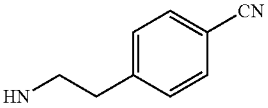 | 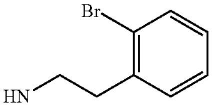 | 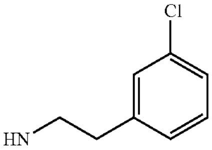 |
| 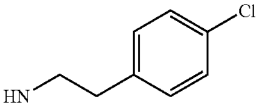 | 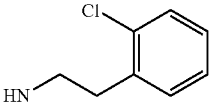 | 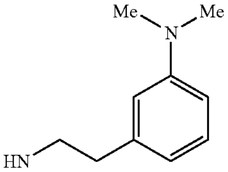 |
| 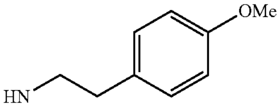 | 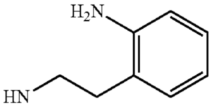 | 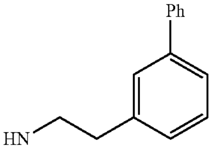 |
| 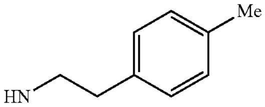 | 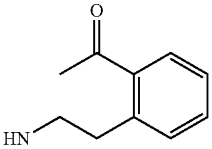 | 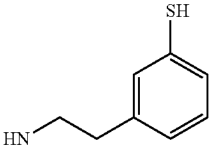 |
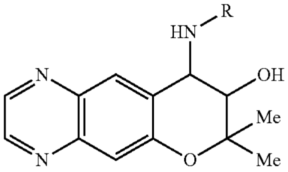
| HN—R | | |
|---|---|---|
| 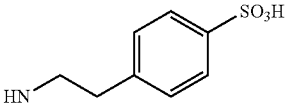 | 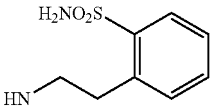 | 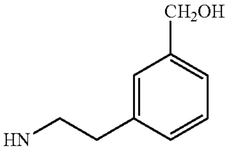 |
| 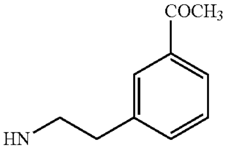 | 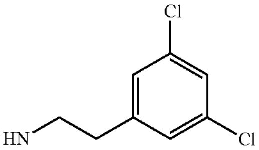 | 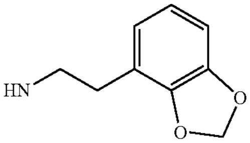 |
| 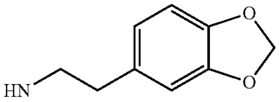 | 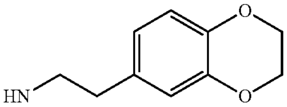 | 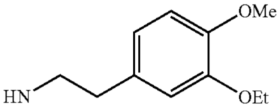 |

-continued
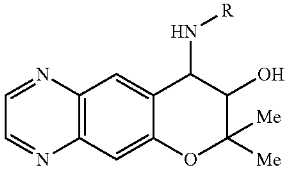
HN—R
| | | |
|---|---|---|
| 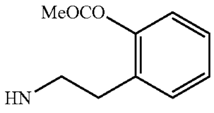 | 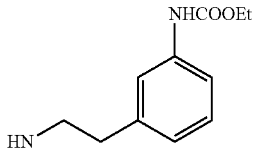 | 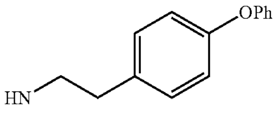 |
| 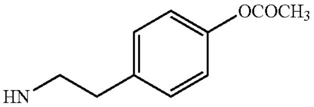 | 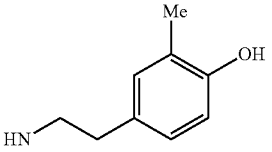 | 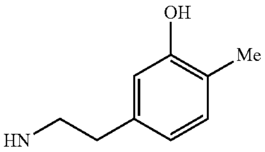 |
| 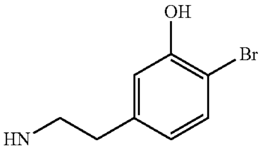 | 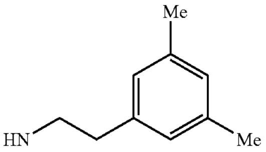 | 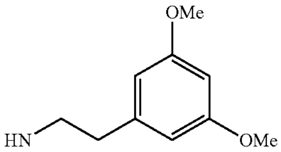 |
| 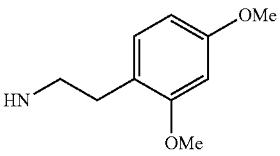 | 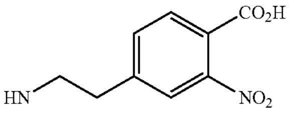 | 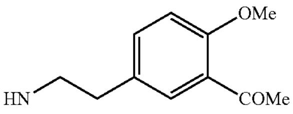 |
| 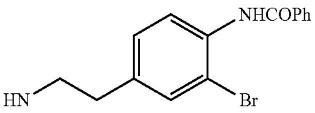 | 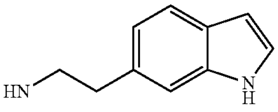 | 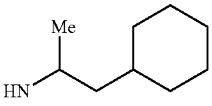 |
| 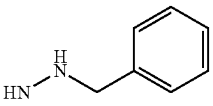 | 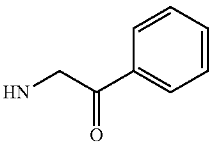 | 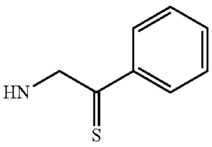 |
| 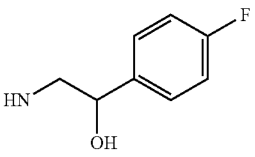 | 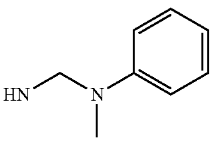 | 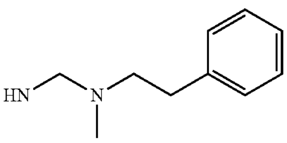 |
| 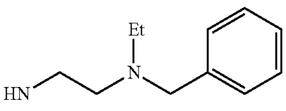 | 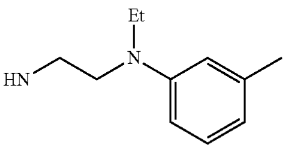 | 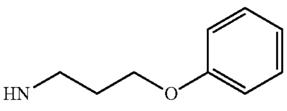 |
| 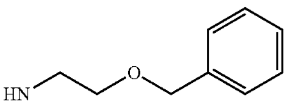 | 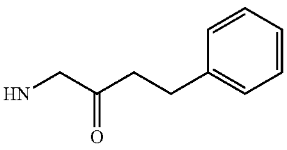 | 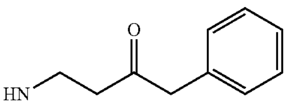 |

-continued
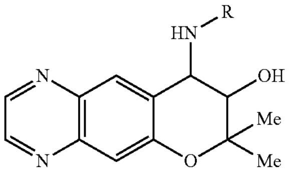
HN—R
| | | |
|---|---|---|
| 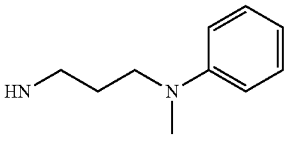 | 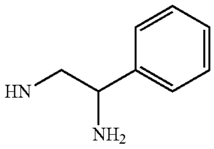 | 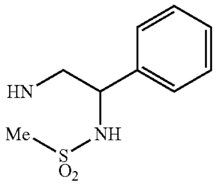 |
| 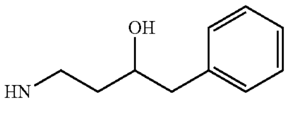 | 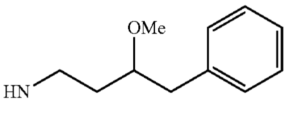 | 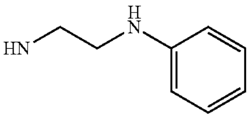 |
| 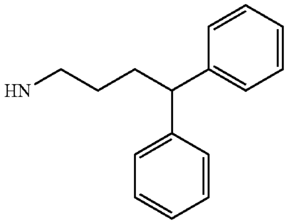 | 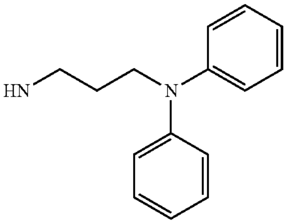 | 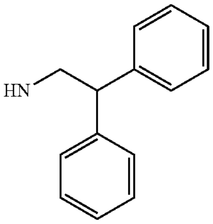 |
| 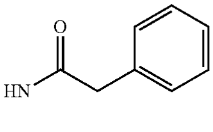 | 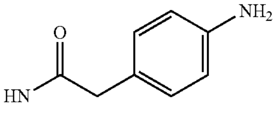 | 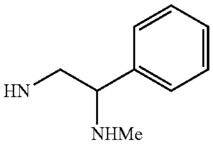 |
| 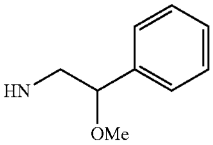 | 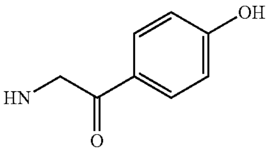 | 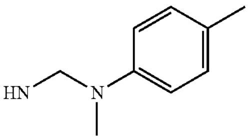 |
| 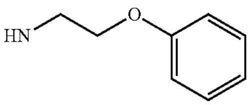 | 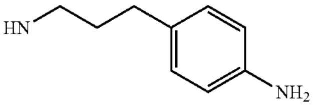 | 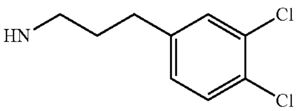 |

| | HN—R | |
|---|---|---|
| | 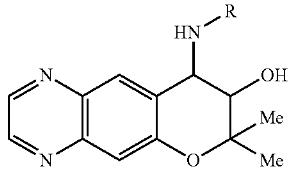 | |
| 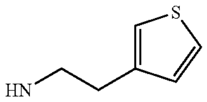 | 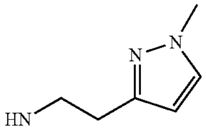 | 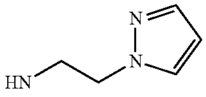 |
| 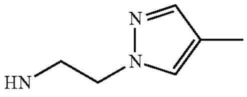 | 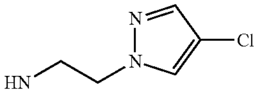 | 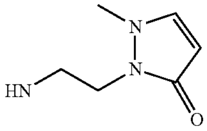 |
| 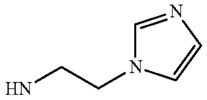 | 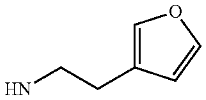 | 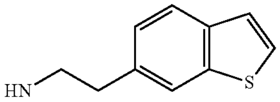 |
| 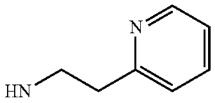 | 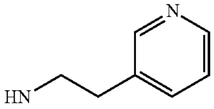 | 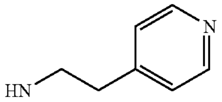 |
| 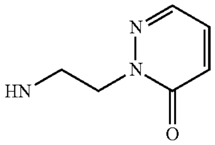 | 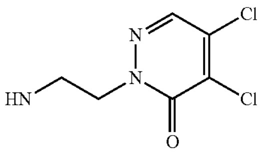 | 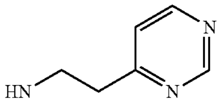 |
| 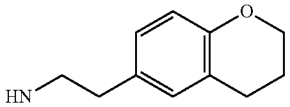 | 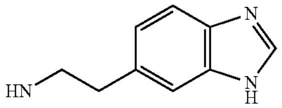 | 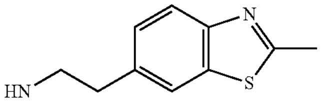 |
| 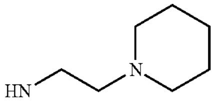 | 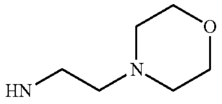 | 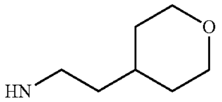 |
| 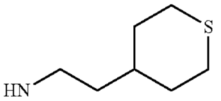 | 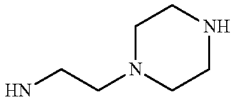 | 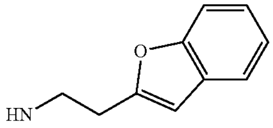 |
| 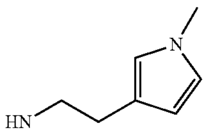 | 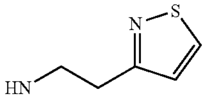 | 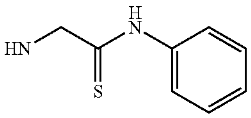 |
| 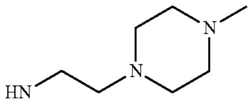 | 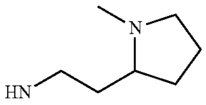 | 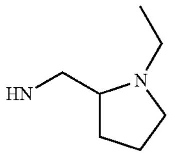 |

-continued
| HN—R | | |
|---|---|---|
| 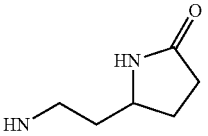 | 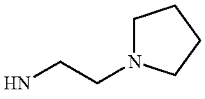 | 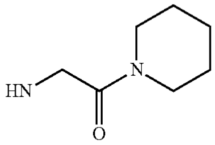 |
| 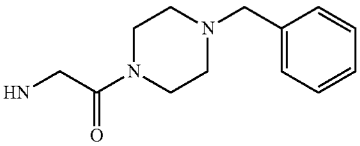 | 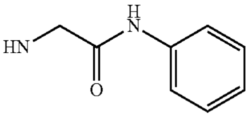 | |
| 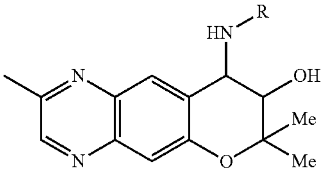 | | |
|---|---|---|
| 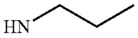 | 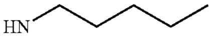 | 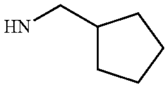 |
| 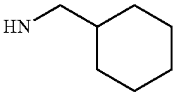 | 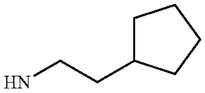 | 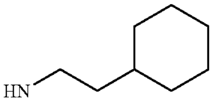 |
| 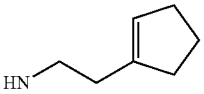 | 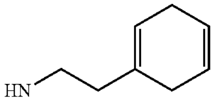 | 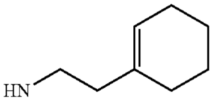 |
| 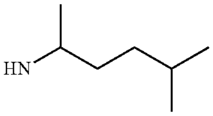 | 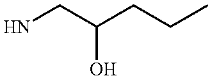 | 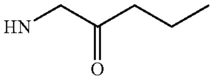 |
| 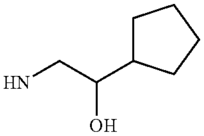 | 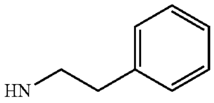 | 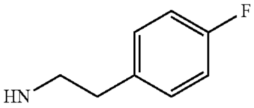 |
| 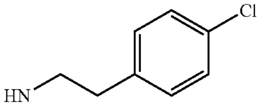 | 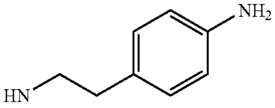 | 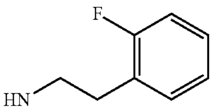 |
| 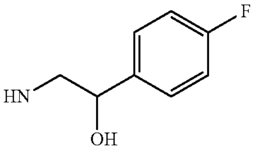 | 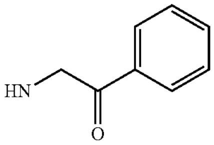 | 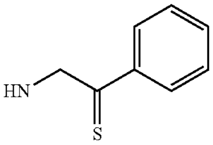 |
| 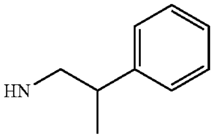 | 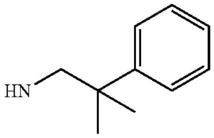 | 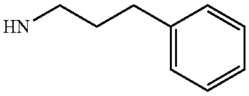 |

-continued
| HN—R | | |
|---|---|---|
| 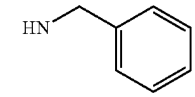 | 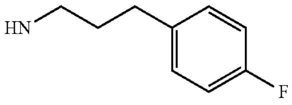 | 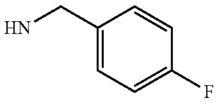 |
| 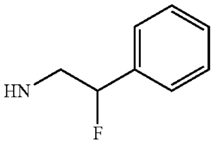 | 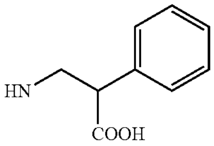 | 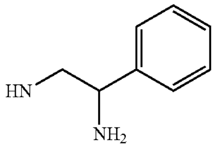 |
| 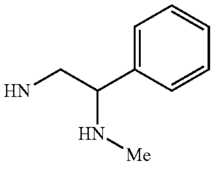 | 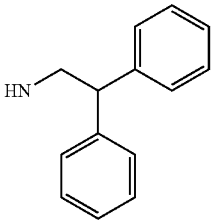 | 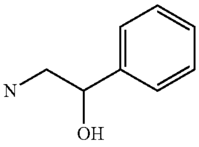 |
| 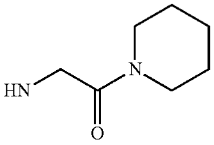 | 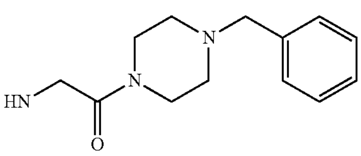 | 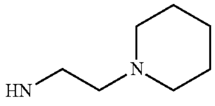 |
| 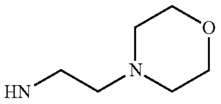 | 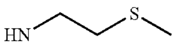 | 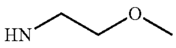 |
| 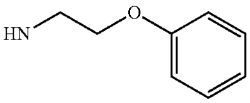 | 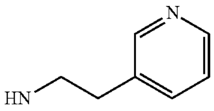 | 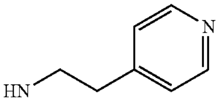 |
| 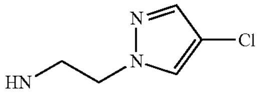 | 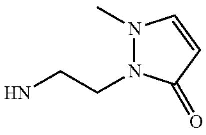 | |
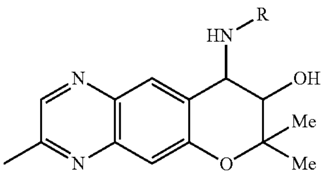
| | | |
|---|---|---|
| 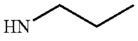 | 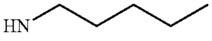 | 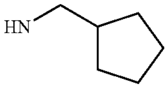 |
| 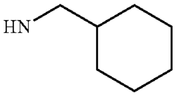 | 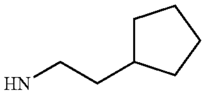 | 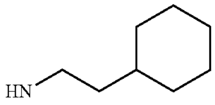 |
| 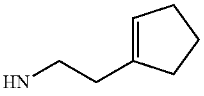 | 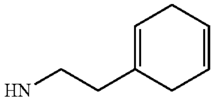 | 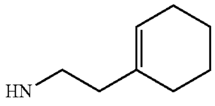 |

-continued
| | HN—R | |
|---|---|---|
| 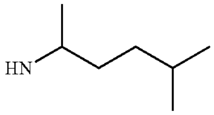 | 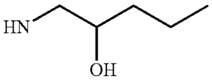 | 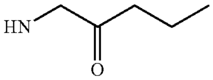 |
| 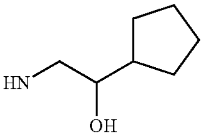 | 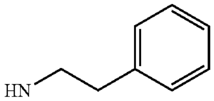 | 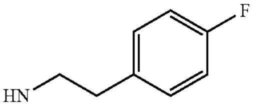 |
| 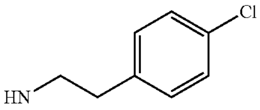 | 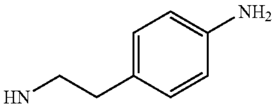 | 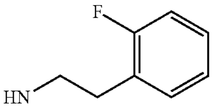 |
| 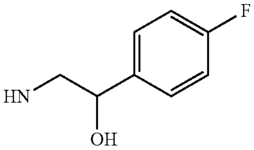 | 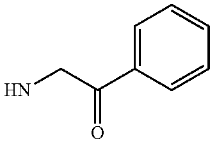 | 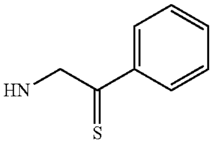 |
| 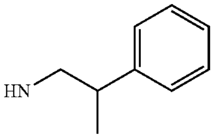 | 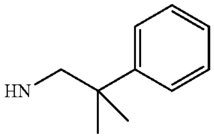 | 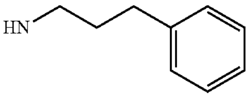 |
| 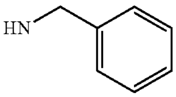 | 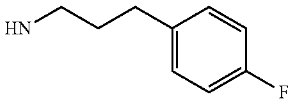 | 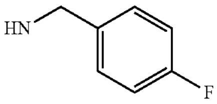 |
| 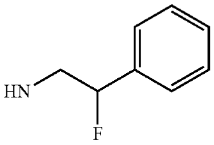 | 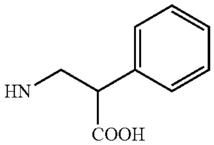 | 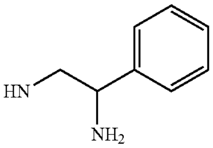 |
| 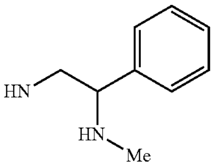 | 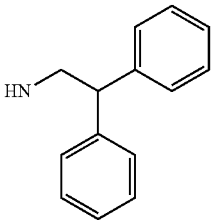 | 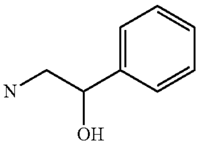 |
| 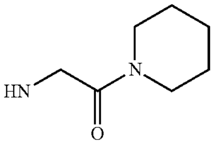 | 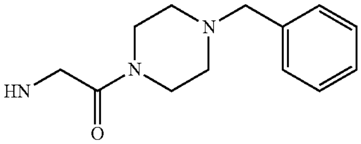 | 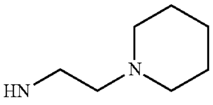 |
| 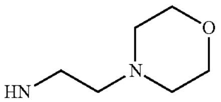 | 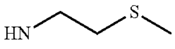 | 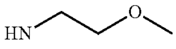 |

-continued
| | | |
|---|---|---|
| HN—R | | |
| 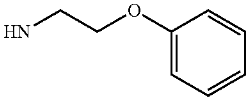 | 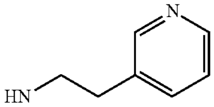 | 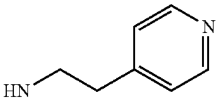 |
| 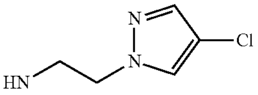 | 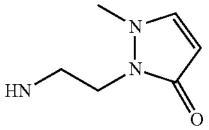 | |
| 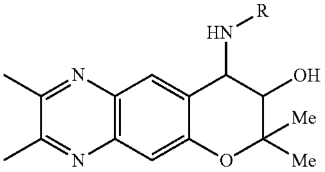 | | |
| 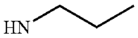 | 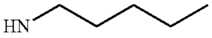 | 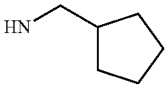 |
| 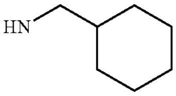 | 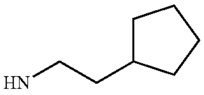 | 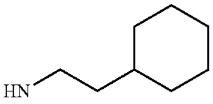 |
| 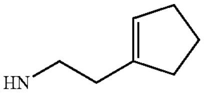 | 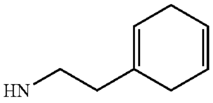 | 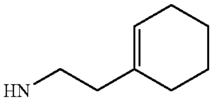 |
| 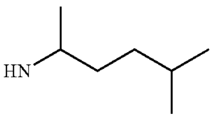 | 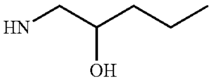 | 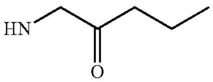 |
| 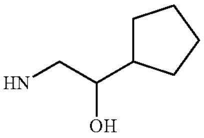 | 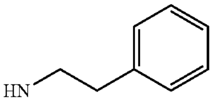 | 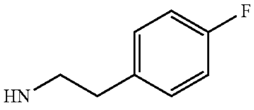 |
| 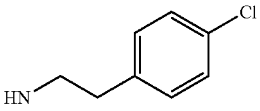 | 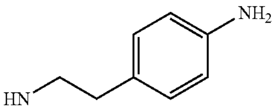 | 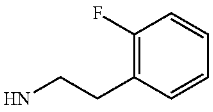 |
| 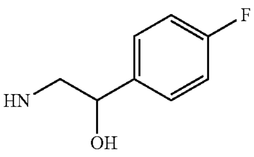 | 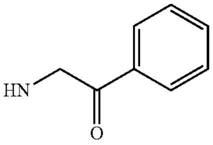 | 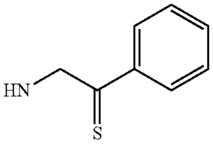 |
| 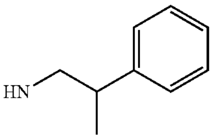 | 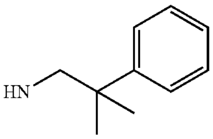 | 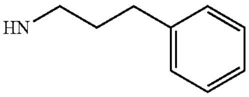 |

-continued
| HN—R | | |
|---|---|---|
| 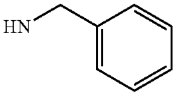 | 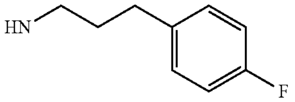 | 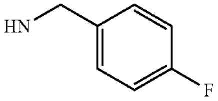 |
| 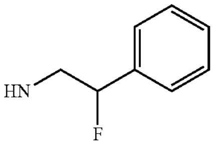 | 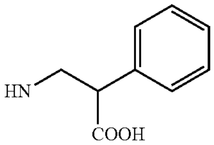 | 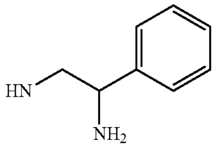 |
| 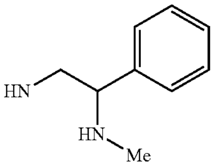 | 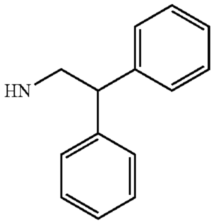 | 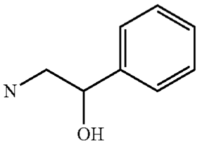 |
| 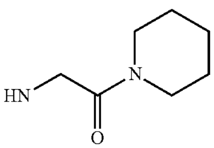 | 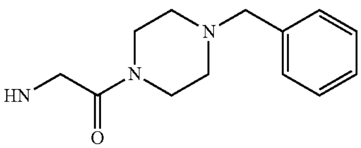 | 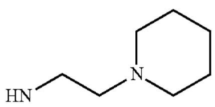 |
| 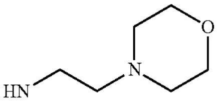 | 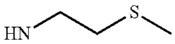 | 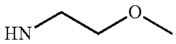 |
| 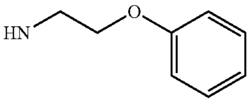 | 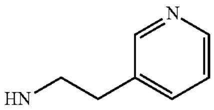 | 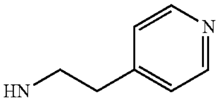 |
| 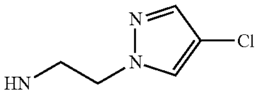 | 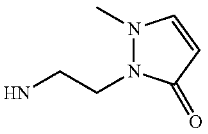 | |
| 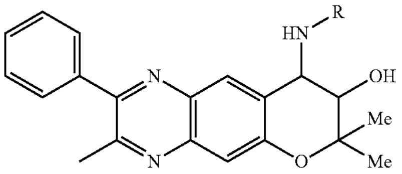 | | |
|---|---|---|
| 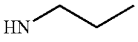 | 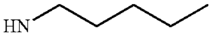 | 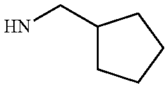 |
| 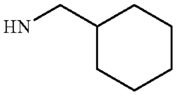 | 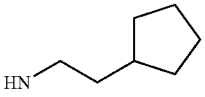 | 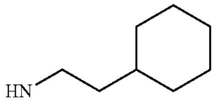 |
| 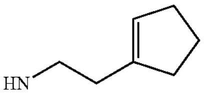 | 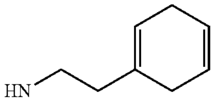 | 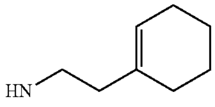 |

-continued
| HN—R | | |
|---|---|---|
| 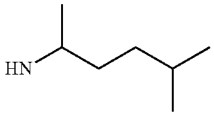 | 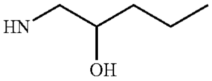 | 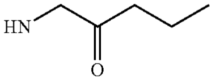 |
| 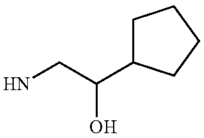 | 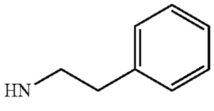 | 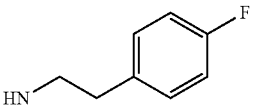 |
| 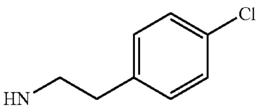 | 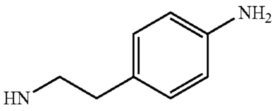 | 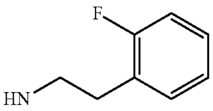 |
| 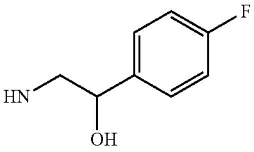 | 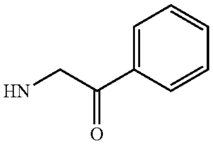 | 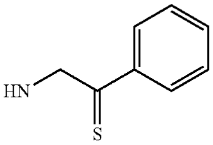 |
| 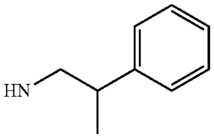 | 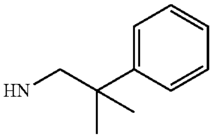 | 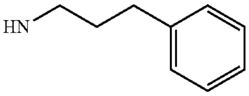 |
| 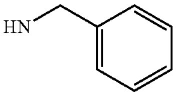 | 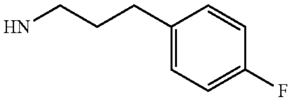 | 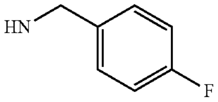 |
| 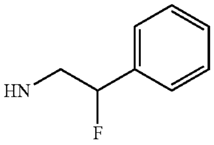 | 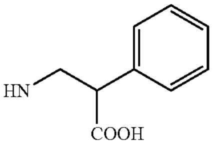 | 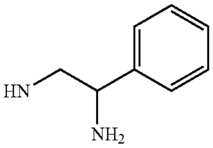 |
| 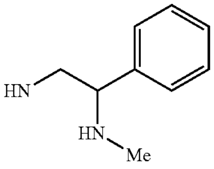 | 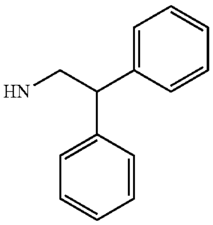 | 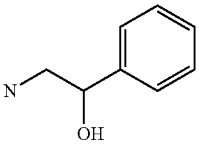 |
| 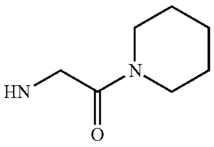 | 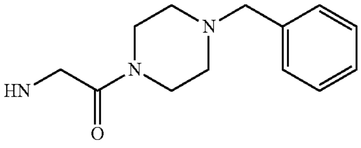 | 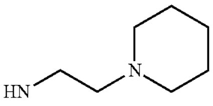 |
| 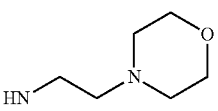 | 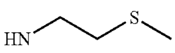 | 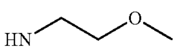 |

-continued
| | HN—R | |
|---|---|---|
| 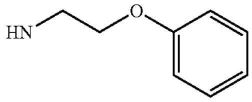 | 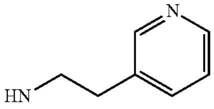 | 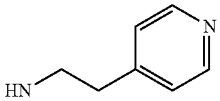 |
| 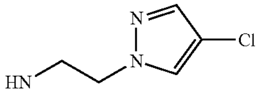 | 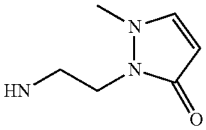 | |
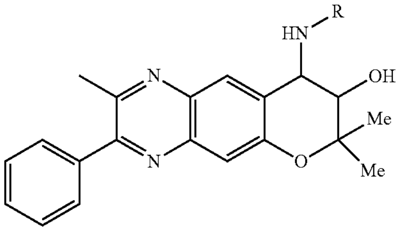
| | | |
|---|---|---|
| 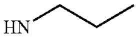 | 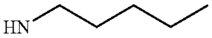 | 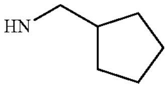 |
| 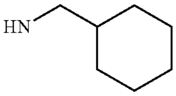 | 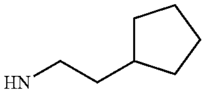 | 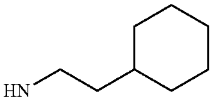 |
| 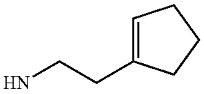 | 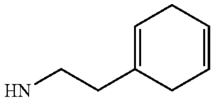 | 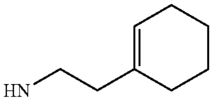 |
| 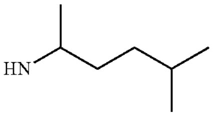 | 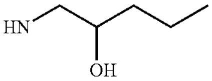 | 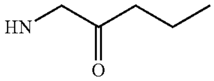 |
| 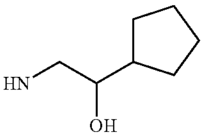 | 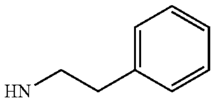 | 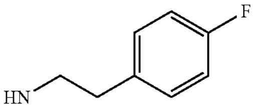 |
| 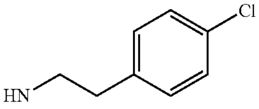 | 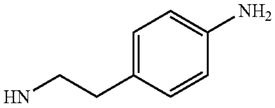 | 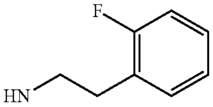 |
| 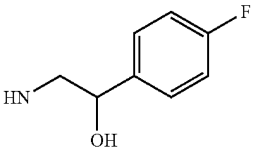 | 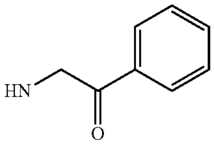 | 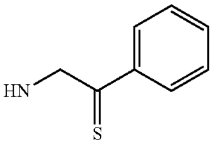 |
| 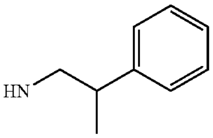 | 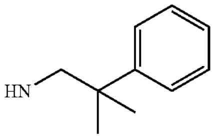 | 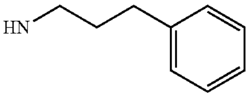 |

-continued
| | HN—R | |
|---|---|---|
| 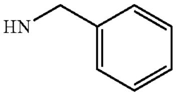 | 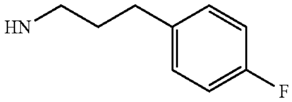 | 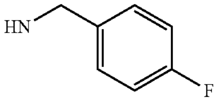 |
| 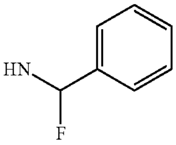 | 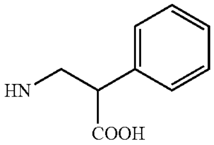 | 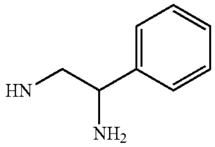 |
| 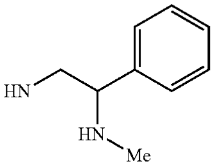 | 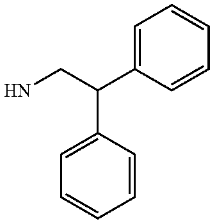 | 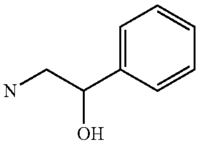 |
| 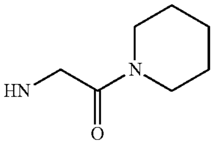 | 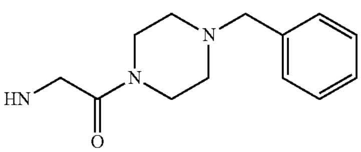 | 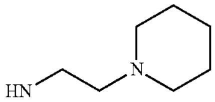 |
| 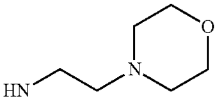 | 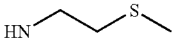 | 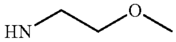 |
| 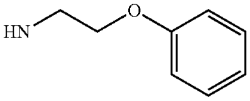 | 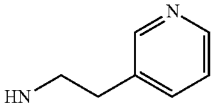 | 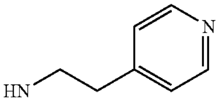 |
| 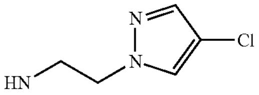 | 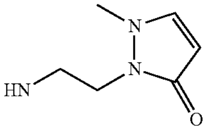 | |
| | 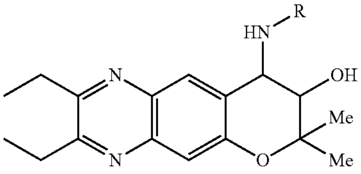 | |
|---|---|---|
| 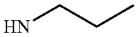 | 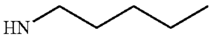 | 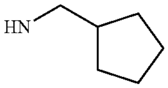 |
| 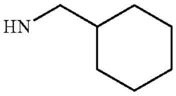 | 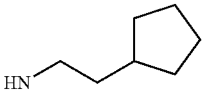 | 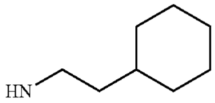 |
| 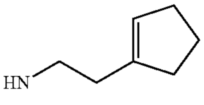 | 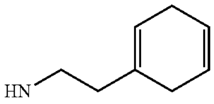 | 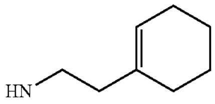 |

-continued
| HN—R | | |
|---|---|---|
| 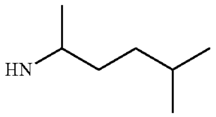 | 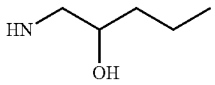 | 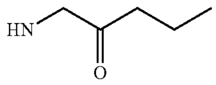 |
| 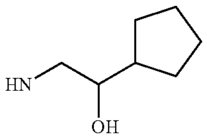 | 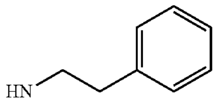 | 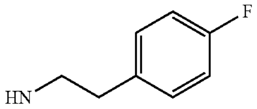 |
| 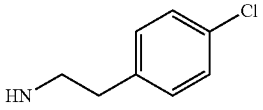 | 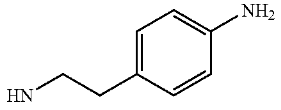 | 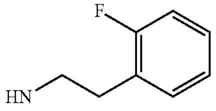 |
| 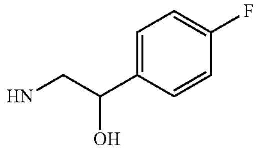 | 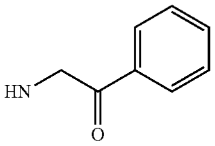 | 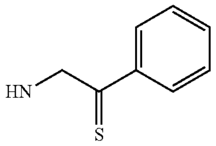 |
| 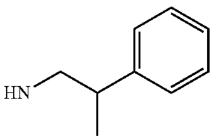 | 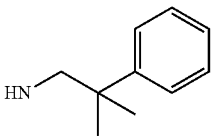 | 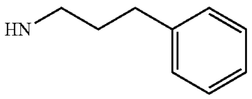 |
| 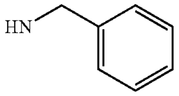 | 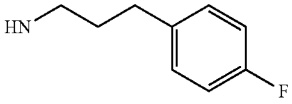 | 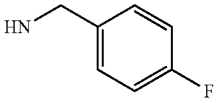 |
| 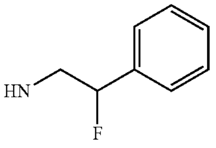 | 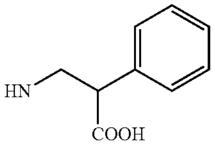 | 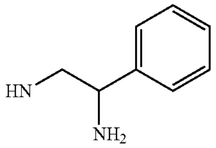 |
| 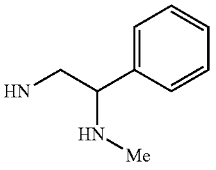 | 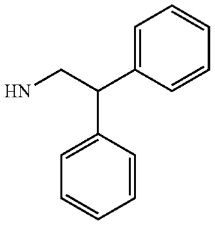 | 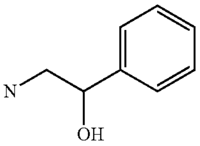 |
| 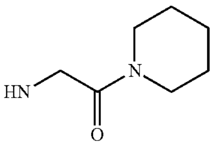 | 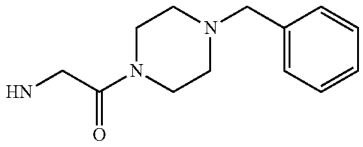 | 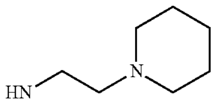 |
| 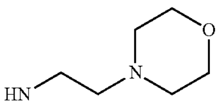 | 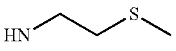 | 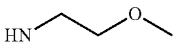 |

-continued
| | HN—R | |
|---|---|---|
| 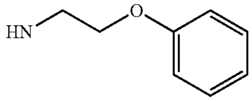 | 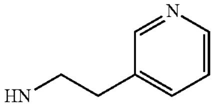 | 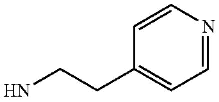 |
| 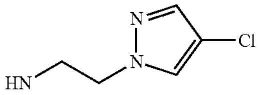 | 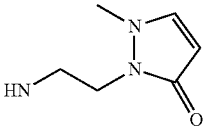 | |
| | 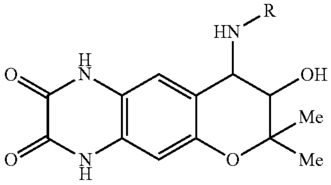 | |
| 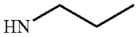 | 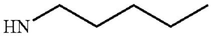 | 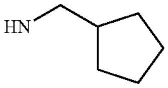 |
| 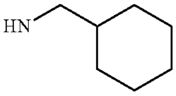 | 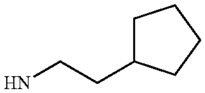 | 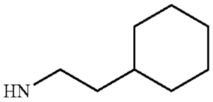 |
| 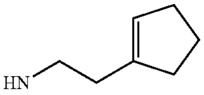 | 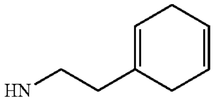 | 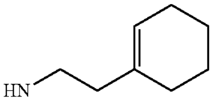 |
| 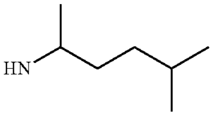 | 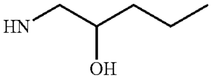 | 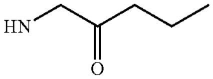 |
| 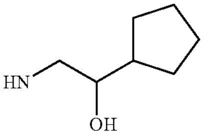 | 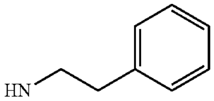 | 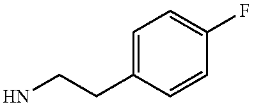 |
| 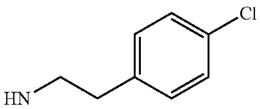 | 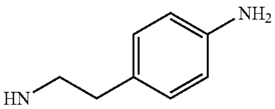 | 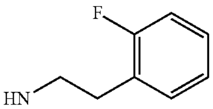 |
| 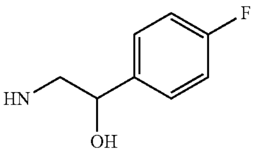 | 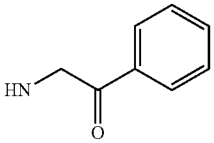 | 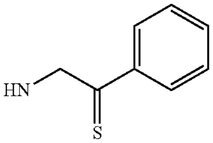 |
| 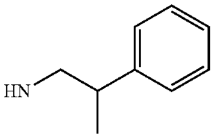 | 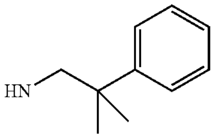 | 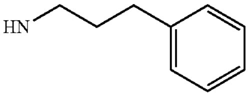 |

-continued
| HN—R | | |
|---|---|---|
| 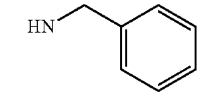 | 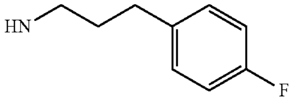 | 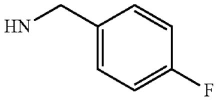 |
| 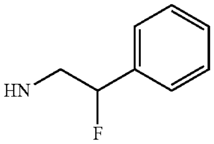 | 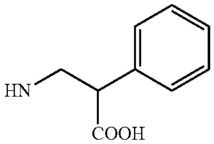 | 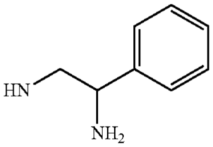 |
| 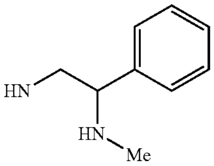 | 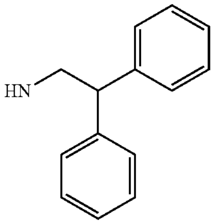 | 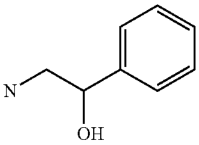 |
| 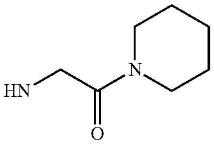 | 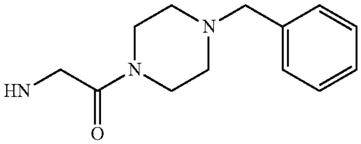 | 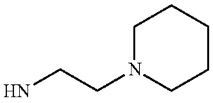 |
| 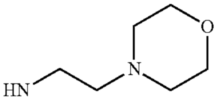 | 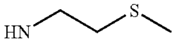 | 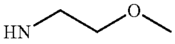 |
| 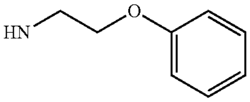 | 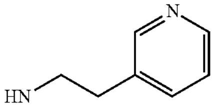 | 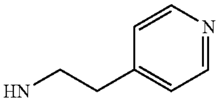 |
| 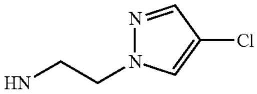 | 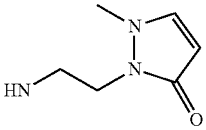 | |
| 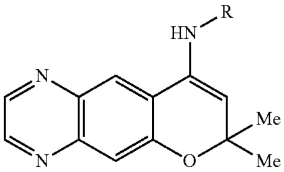 | | |
|---|---|---|
| 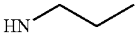 | 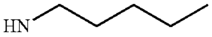 | 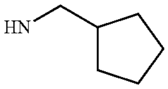 |
| 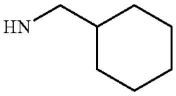 | 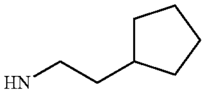 | 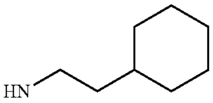 |
| 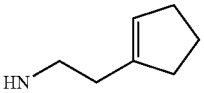 | 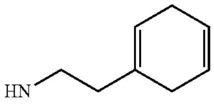 | 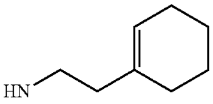 |

-continued
| HN—R | | |
|---|---|---|
| 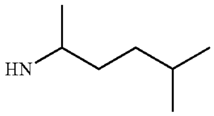 | 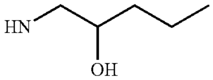 | 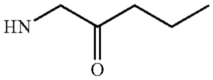 |
| 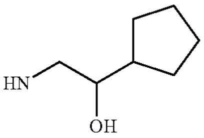 | 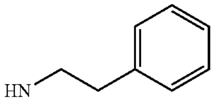 | 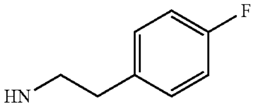 |
| 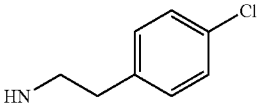 | 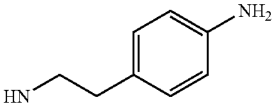 | 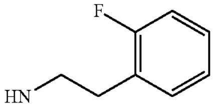 |
| 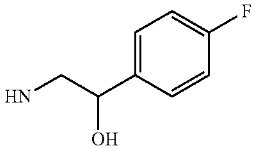 | 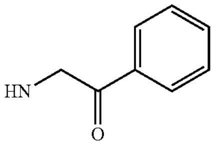 | 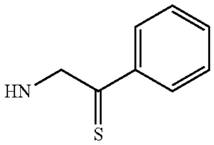 |
| 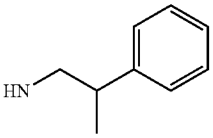 | 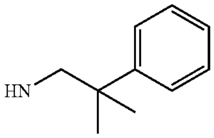 | 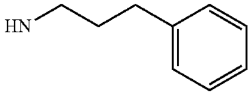 |
| 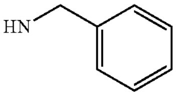 | 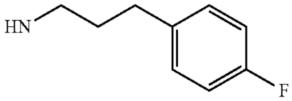 | 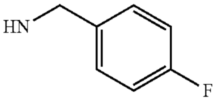 |
| 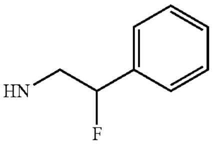 | 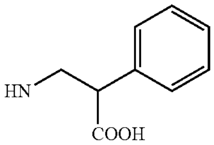 | 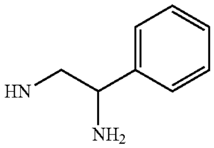 |
| 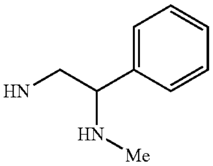 | 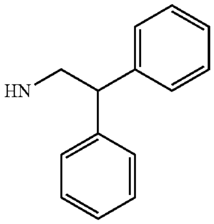 | 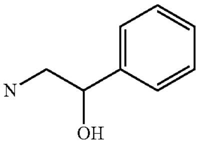 |
| 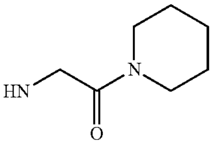 | 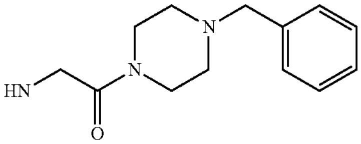 | 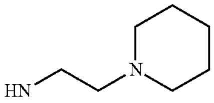 |
| 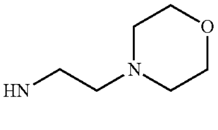 | 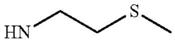 | 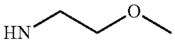 |

-continued
| | HN—R | |
|---|---|---|
| 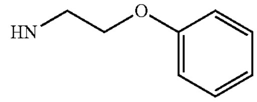 | 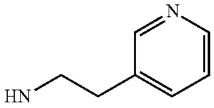 | 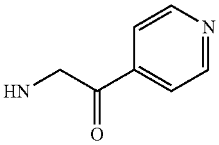 |
| 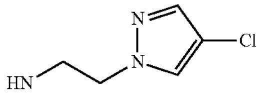 | 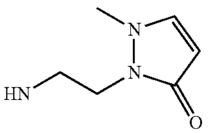 | |
| | 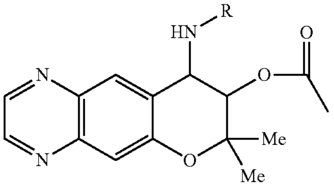 | |
| 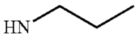 | 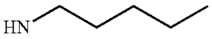 | 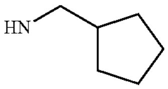 |
| 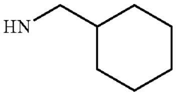 | 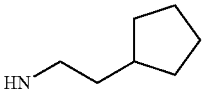 | 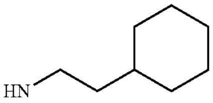 |
| 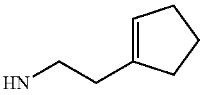 | 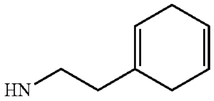 | 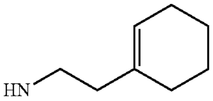 |
| 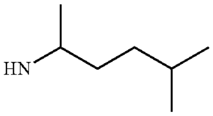 | 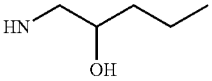 | 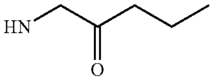 |
| 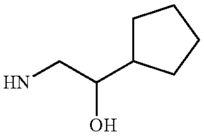 | 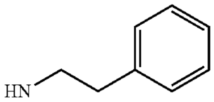 | 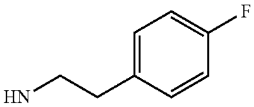 |
| 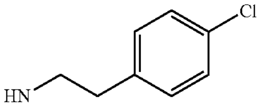 | 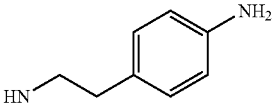 | 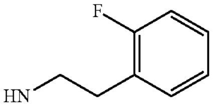 |
| 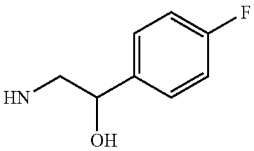 | 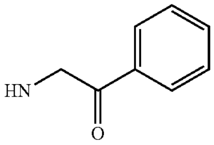 | 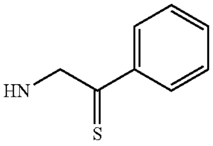 |
| 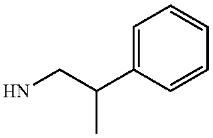 | 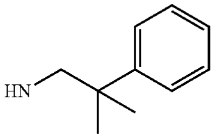 | 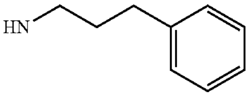 |

-continued
| HN—R | | |
|---|---|---|
| 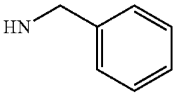 | 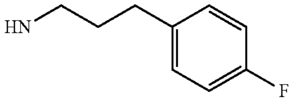 | 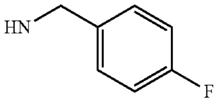 |
| 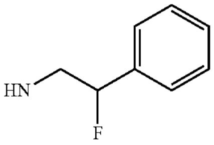 | 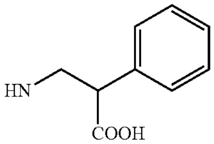 | 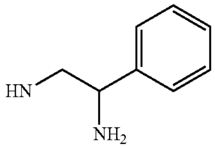 |
| 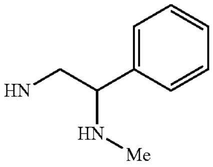 | 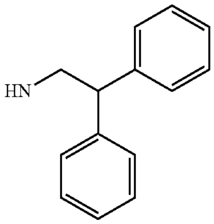 | 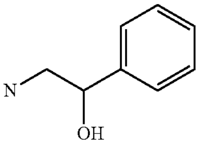 |
| 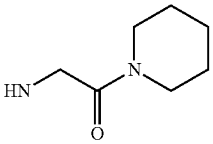 | 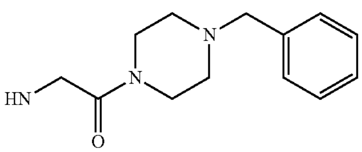 | 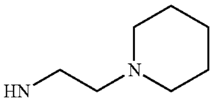 |
| 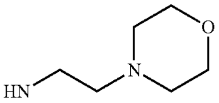 | 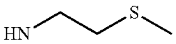 | 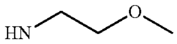 |
| 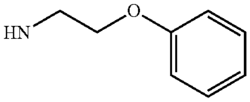 | 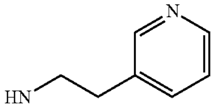 | 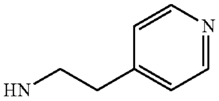 |
| 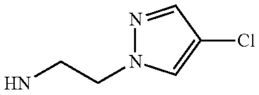 | 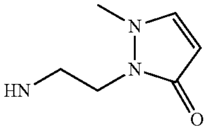 | |
| | 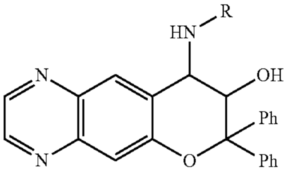 | |
|---|---|---|
| 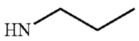 | 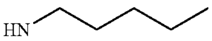 | 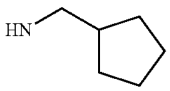 |
| 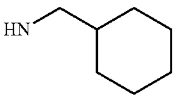 | 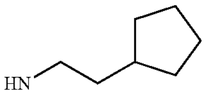 | 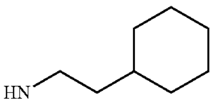 |
| 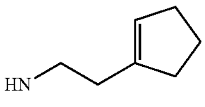 | 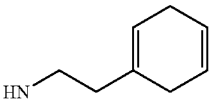 | 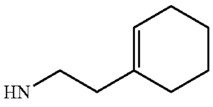 |

-continued
HN—R
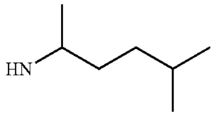 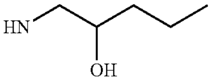 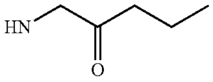
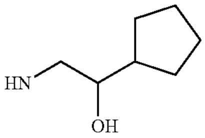 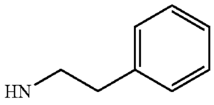 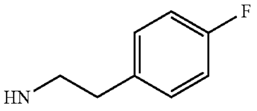
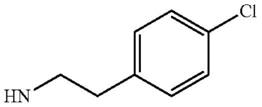 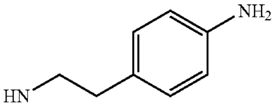 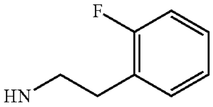
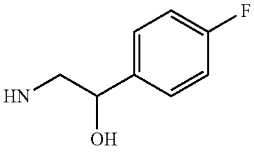 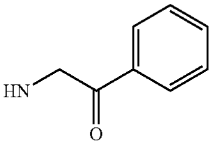 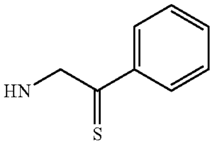
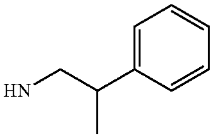 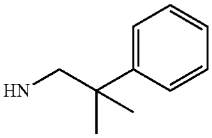 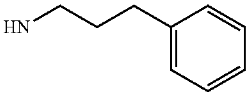
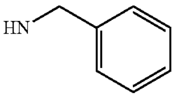 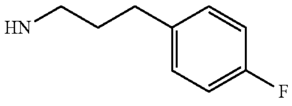 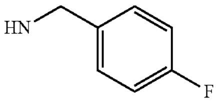
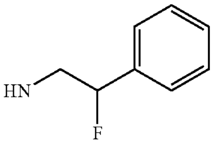 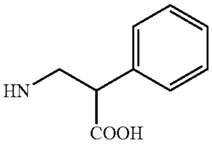 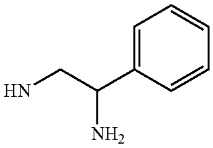
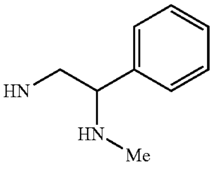 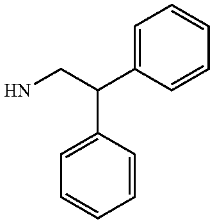 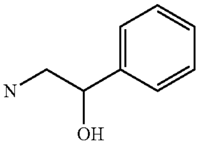
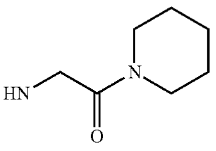 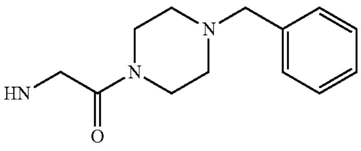 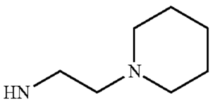
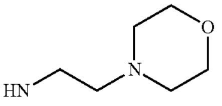 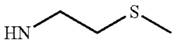 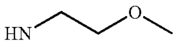

-continued
| | HN—R | |
|---|---|---|
| 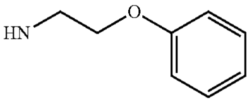 | 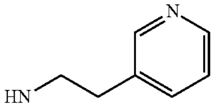 | 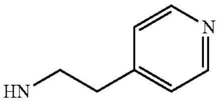 |
| 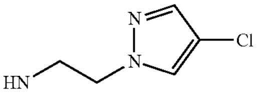 | 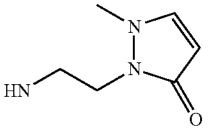 | |
| | 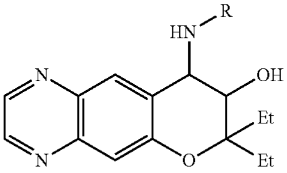 | |
|---|---|---|
| 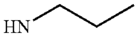 | 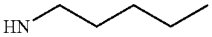 | 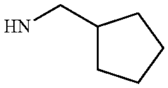 |
| 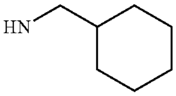 | 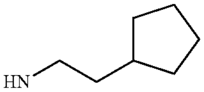 | 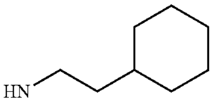 |
| 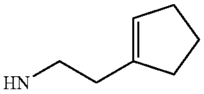 | 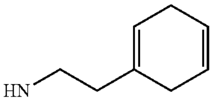 | 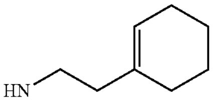 |
| 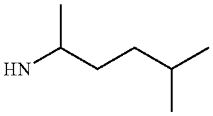 | 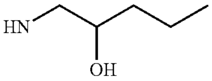 | 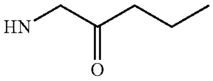 |
| 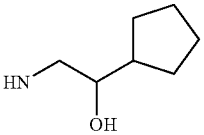 | 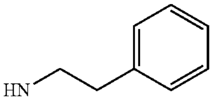 | 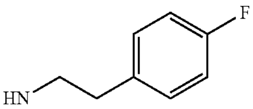 |
| 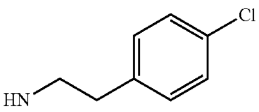 | 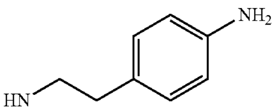 | 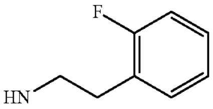 |
| 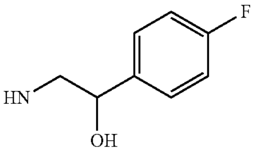 | 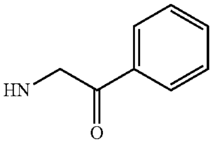 | 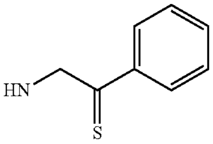 |
| 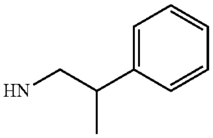 | 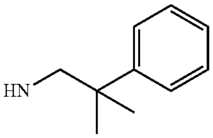 | 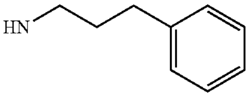 |
| 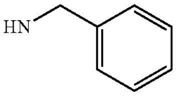 | 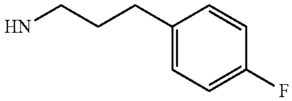 | 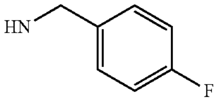 |

-continued
| | HN—R | |
|---|---|---|
| 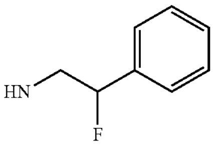 | 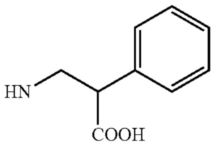 | 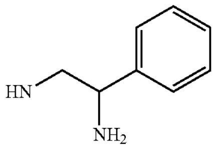 |
| 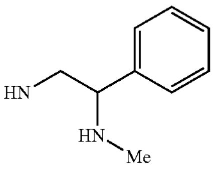 | 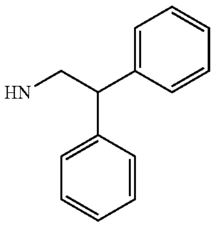 | 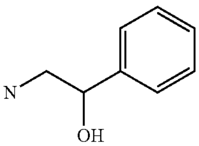 |
| 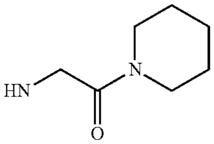 | 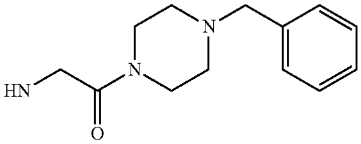 | 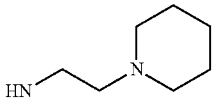 |
| 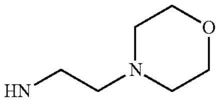 | 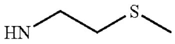 | 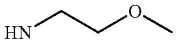 |
| 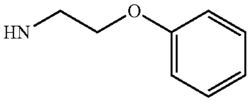 | 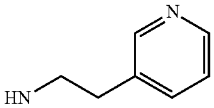 | 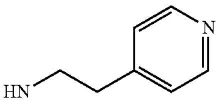 |
| 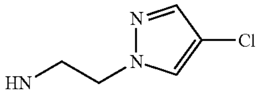 | 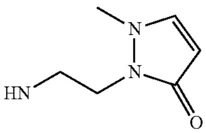 | |
| | 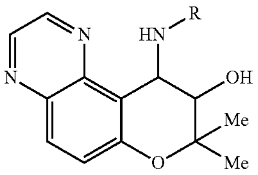 | |
|---|---|---|
| 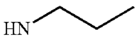 | 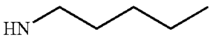 | 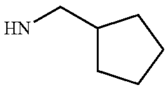 |
| 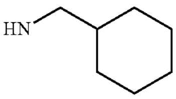 | 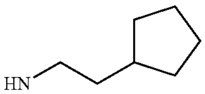 | 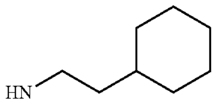 |
| 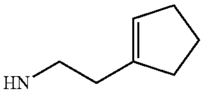 | 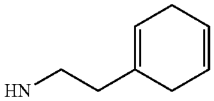 | 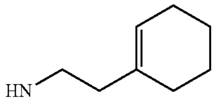 |
| 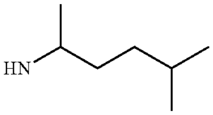 | 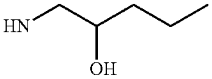 | 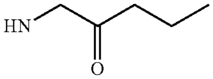 |

-continued
| HN—R | | |
|---|---|---|
| 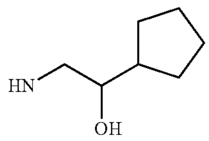 | 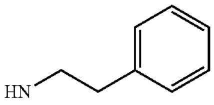 | 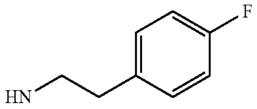 |
| 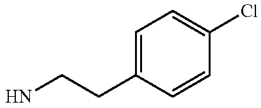 | 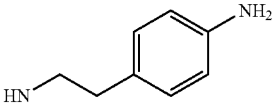 | 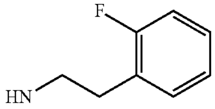 |
| 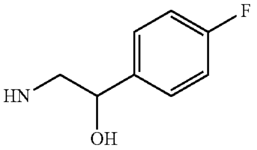 | 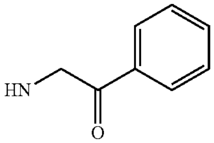 | 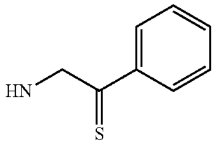 |
| 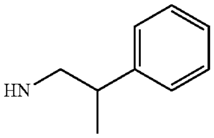 | 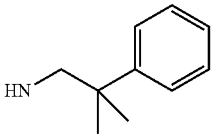 | 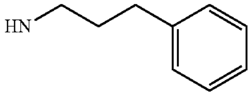 |
| 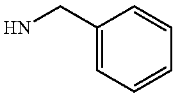 | 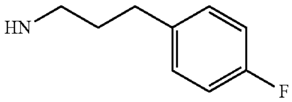 | 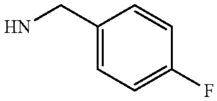 |
| 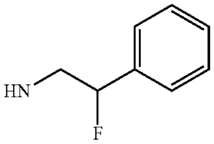 | 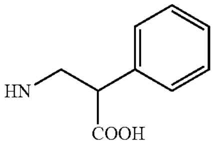 | 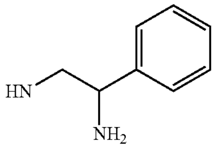 |
| 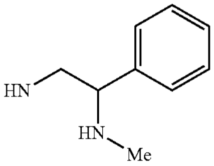 | 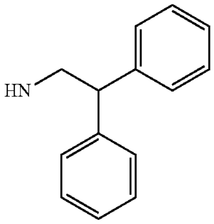 | 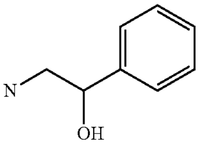 |
| 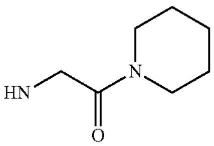 | 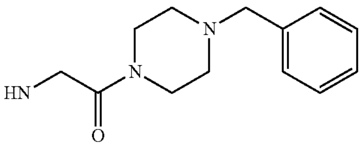 | 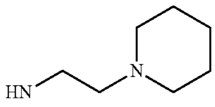 |
| 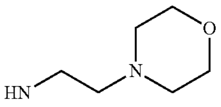 | 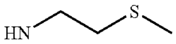 | 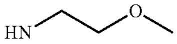 |
| 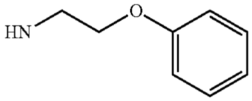 | 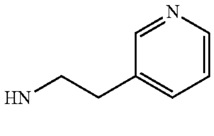 | 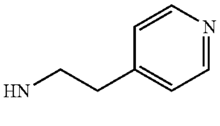 |

-continued
| | | |
|---|---|---|
| | HN—R | |
| 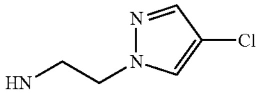 | 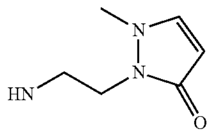 | |
| | 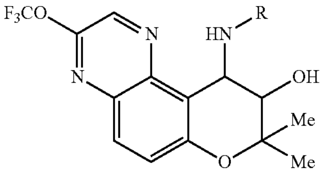 | |
| 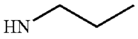 | 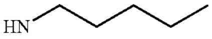 | 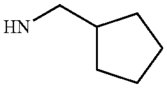 |
| 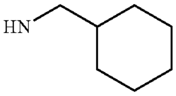 | 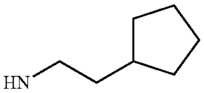 | 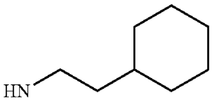 |
| 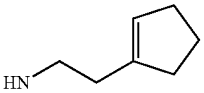 | 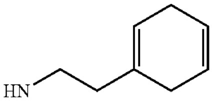 | 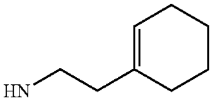 |
| 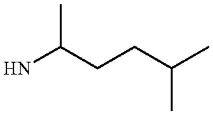 | 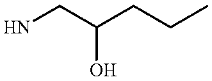 | 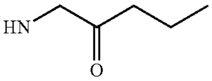 |
| 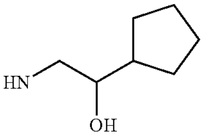 | 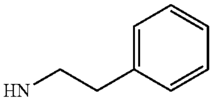 | 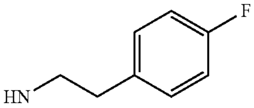 |
| 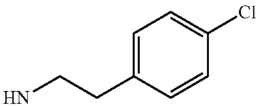 | 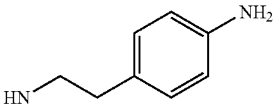 | 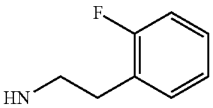 |
| 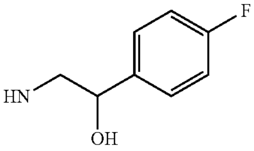 | 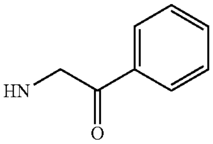 | 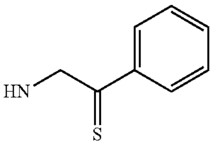 |
| 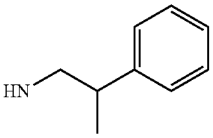 | 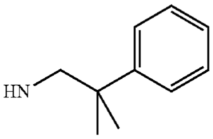 | 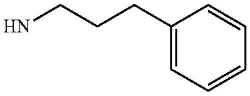 |
| 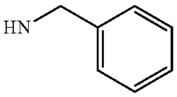 | 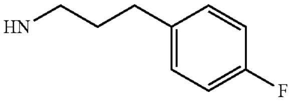 | 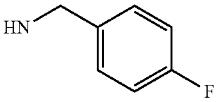 |

-continued
| HN—R | | |
|---|---|---|
| 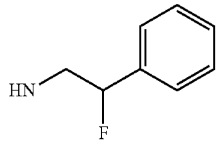 | 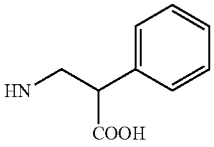 | 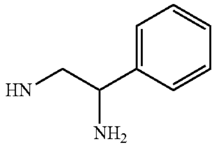 |
| 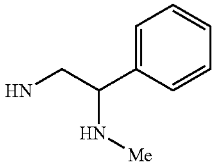 | 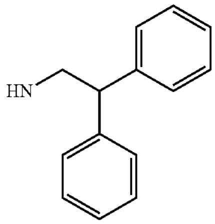 | 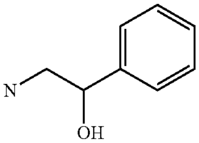 |
| 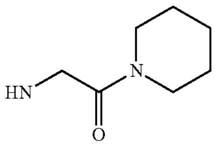 | 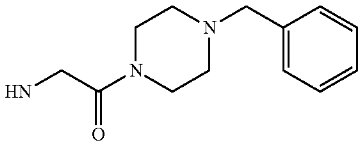 | 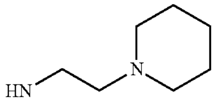 |
| 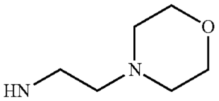 | 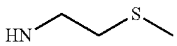 | 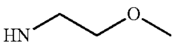 |
| 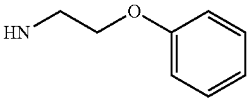 | 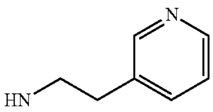 | 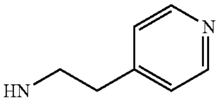 |
| 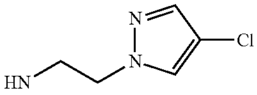 | 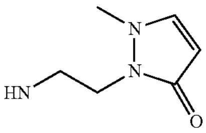 | |
| | 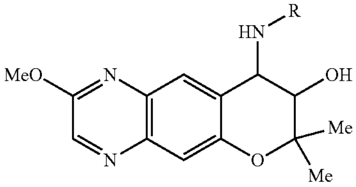 | |
|---|---|---|
| 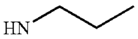 | 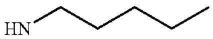 | 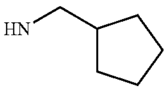 |
| 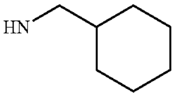 | 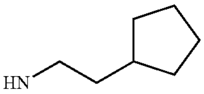 | 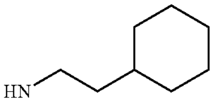 |
| 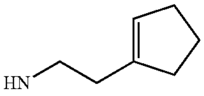 | 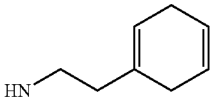 | 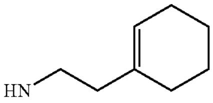 |

-continued
| HN—R | | |
|---|---|---|
| 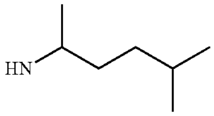 | 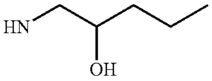 | 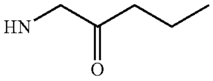 |
| 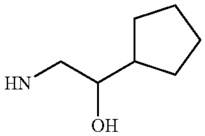 | 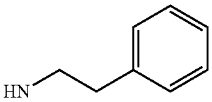 | 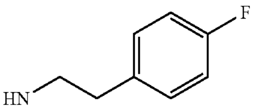 |
| 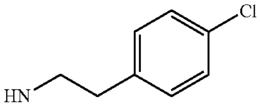 | 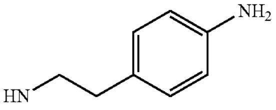 | 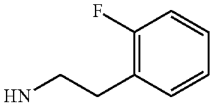 |
| 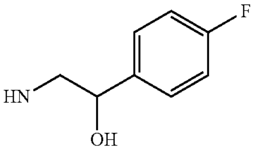 | 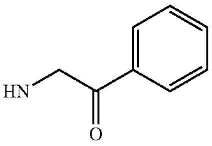 | 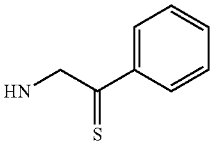 |
| 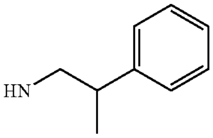 | 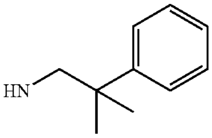 | 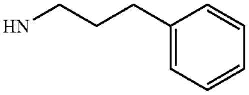 |
| 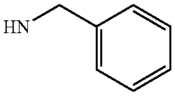 | 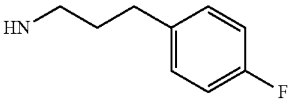 | 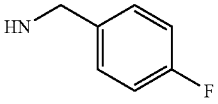 |
| 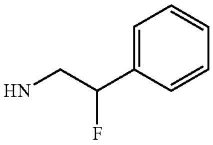 | 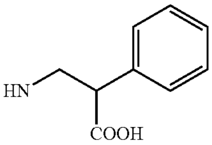 | 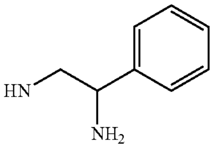 |
| 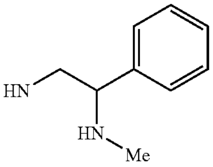 | 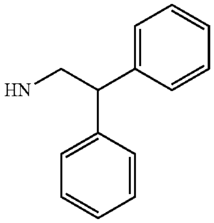 | 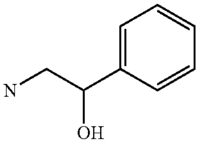 |
| 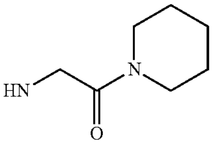 | 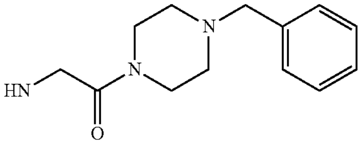 | 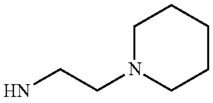 |
| 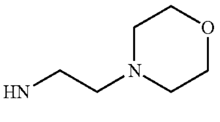 | 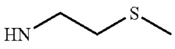 | 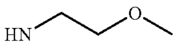 |

-continued
| HN—R | | |
|---|---|---|
| 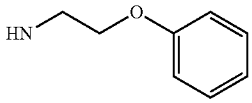 | 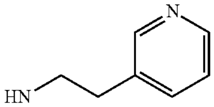 | 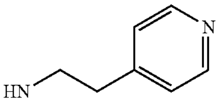 |
| 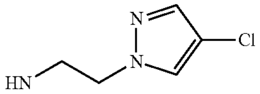 | 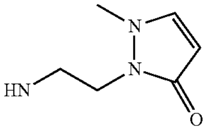 | |
| | 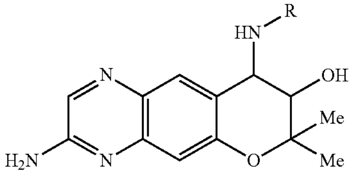 | |
|---|---|---|
| 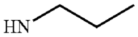 | 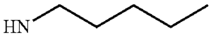 | 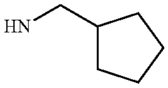 |
| 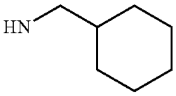 | 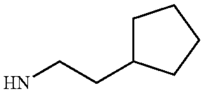 | 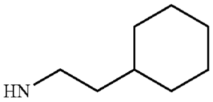 |
| 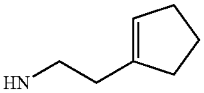 | 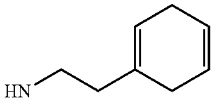 | 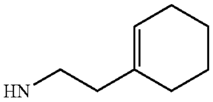 |
| 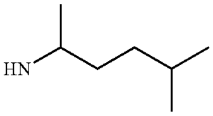 | 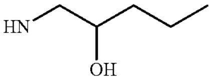 | 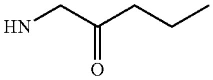 |
| 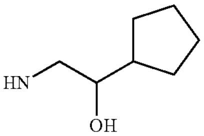 | 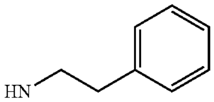 | 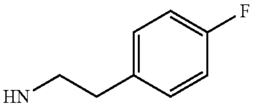 |
| 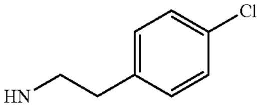 | 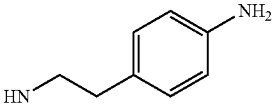 | 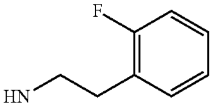 |
| 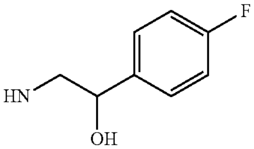 | 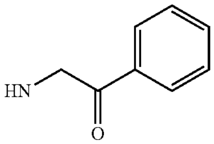 | 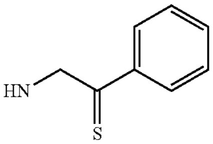 |
| 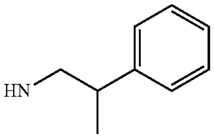 | 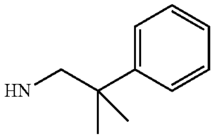 | 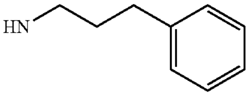 |

-continued
| HN—R | | |
|---|---|---|
| 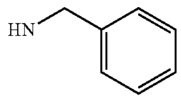 | 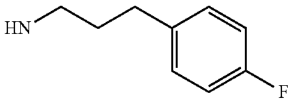 | 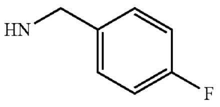 |
| 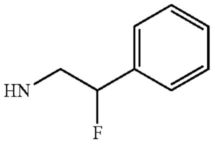 | 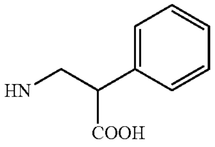 | 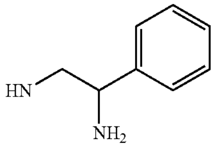 |
| 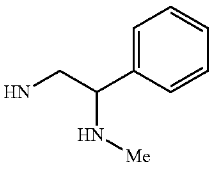 | 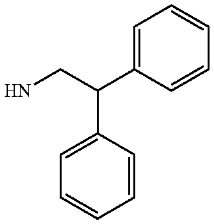 | 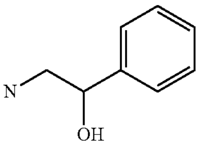 |
| 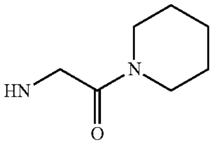 | 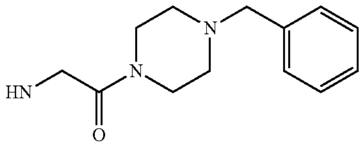 | 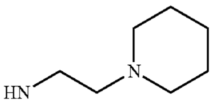 |
| 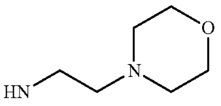 | 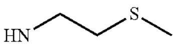 | 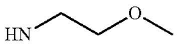 |
| 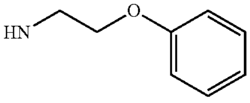 | 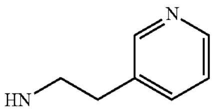 | 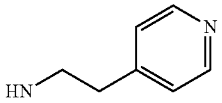 |
| 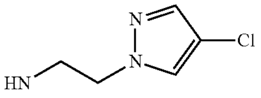 | 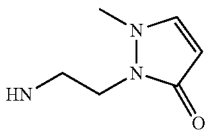 | |
| 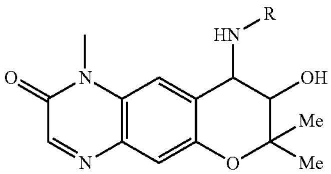 | | |
|---|---|---|
| 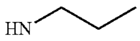 | 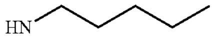 | 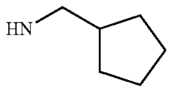 |
| 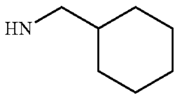 | 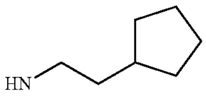 | 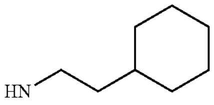 |
| 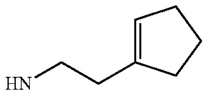 | 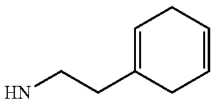 | 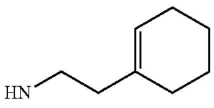 |

-continued
HN—R
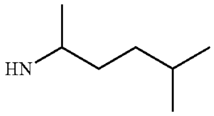
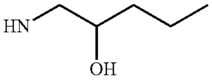
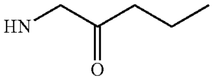
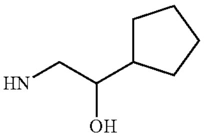
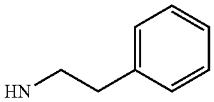
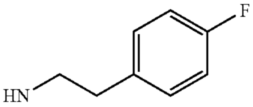
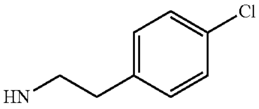
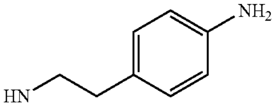
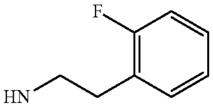
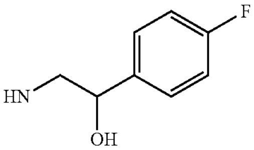
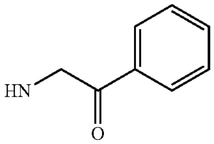
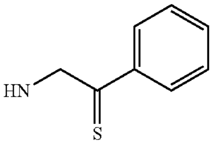
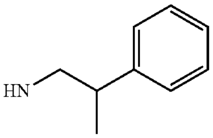
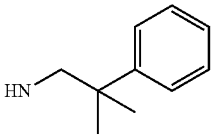
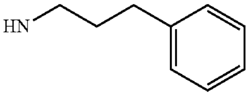
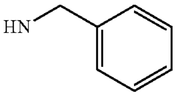
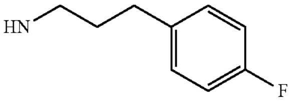
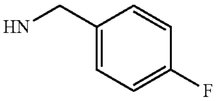
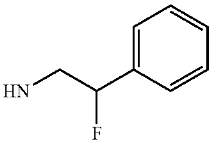
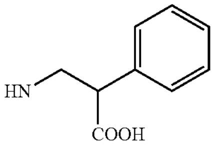
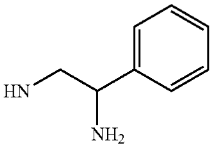
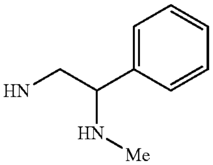
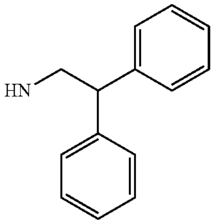
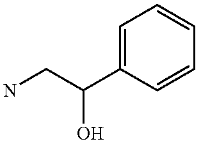
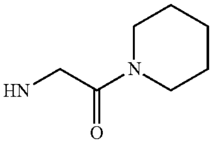
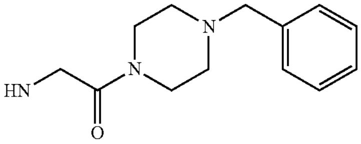
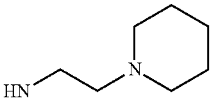
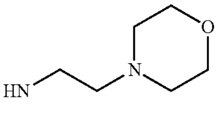
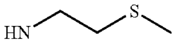
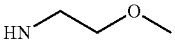

-continued
| | HN—R | |
|---|---|---|
| 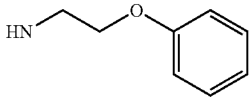 | 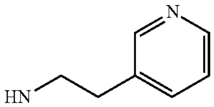 | 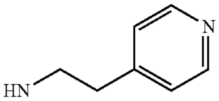 |
| 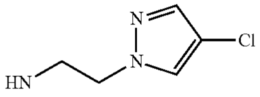 | 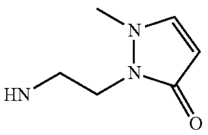 | |
| | 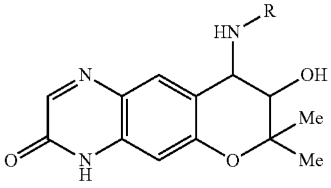 | |
| 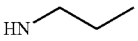 | 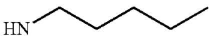 | 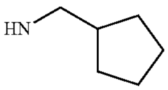 |
| 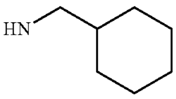 | 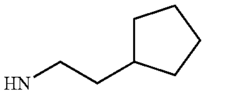 | 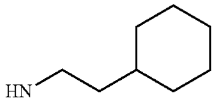 |
| 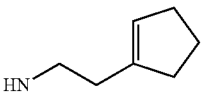 | 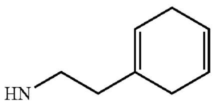 | 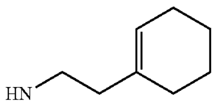 |
| 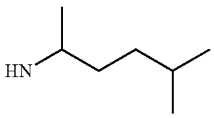 | 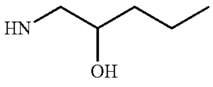 | 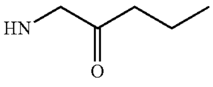 |
| 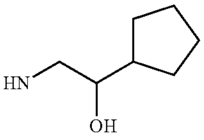 | 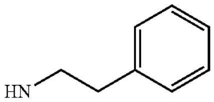 | 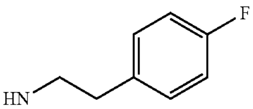 |
| 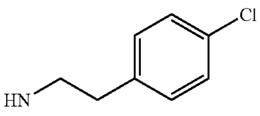 | 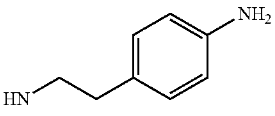 | 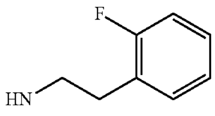 |
| 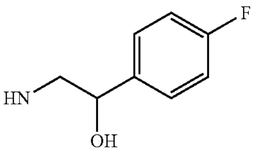 | 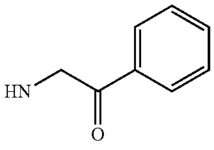 | 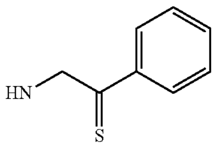 |
| 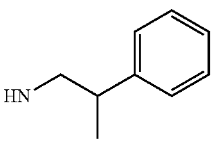 | 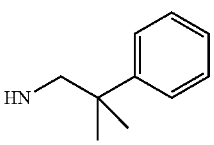 | 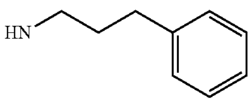 |

-continued
| HN—R | | |
|---|---|---|
| 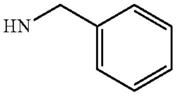 | 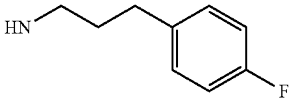 | 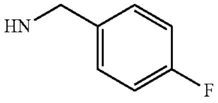 |
| 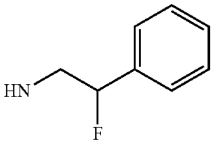 | 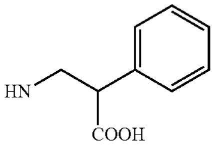 | 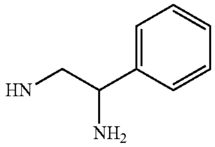 |
| 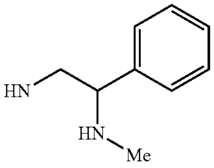 | 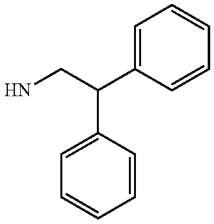 | 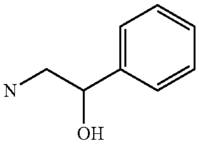 |
| 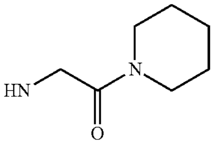 | 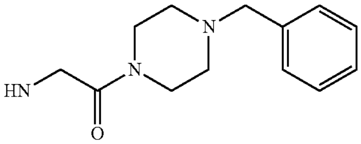 | 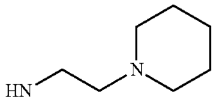 |
| 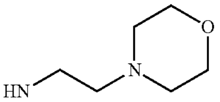 | 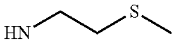 | 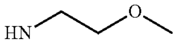 |
| 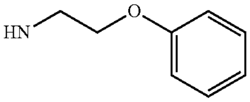 | 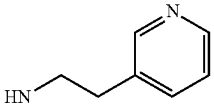 | 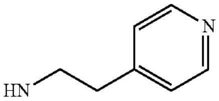 |
| 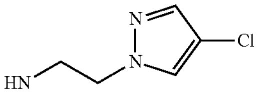 | 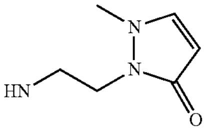 | |
| 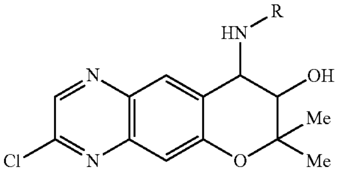 | | |
|---|---|---|
| 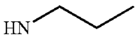 | 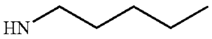 | 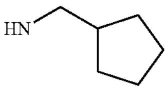 |
| 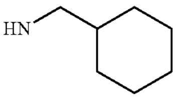 | 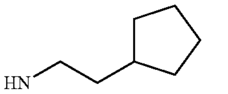 | 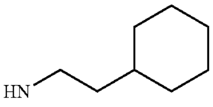 |
| 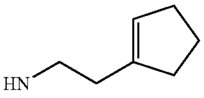 | 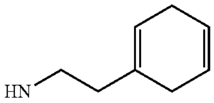 | 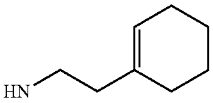 |

-continued
| HN—R | | |
|---|---|---|
| 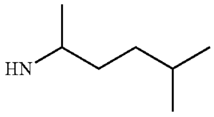 | 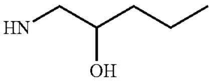 | 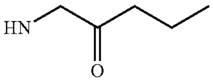 |
| 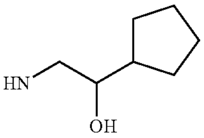 | 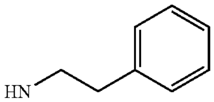 | 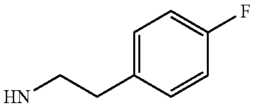 |
| 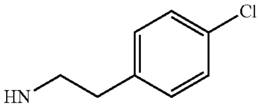 | 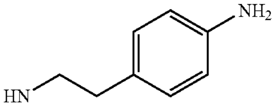 | 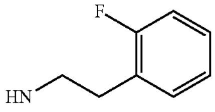 |
| 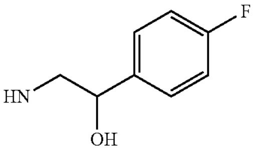 | 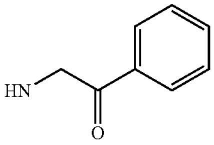 | 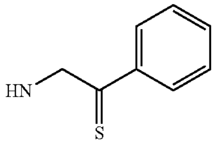 |
| 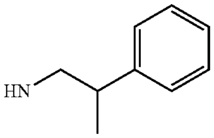 | 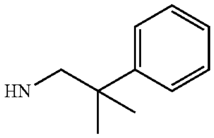 | 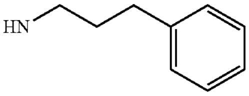 |
| 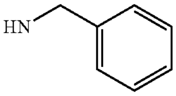 | 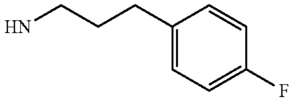 | 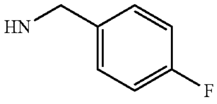 |
| 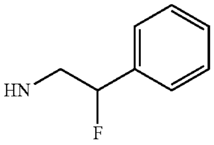 | 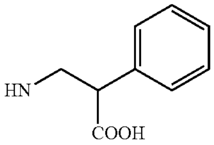 | 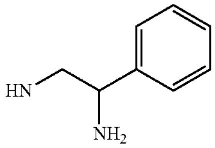 |
| 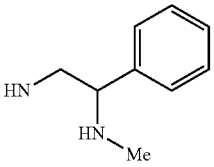 | 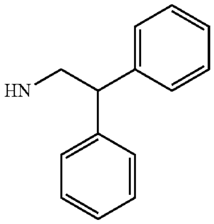 | 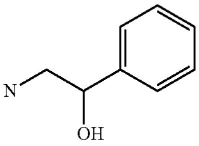 |
| 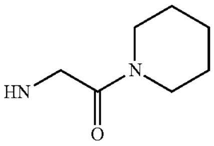 | 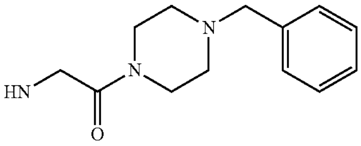 | 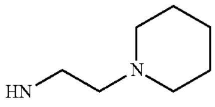 |
| 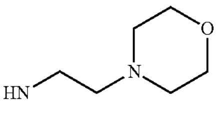 | 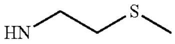 | 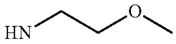 |

-continued
| HN—R | | |
|---|---|---|
| 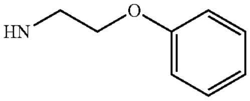 | 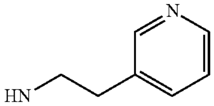 | 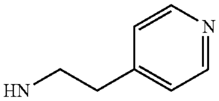 |
| 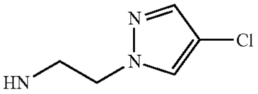 | 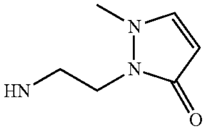 | |
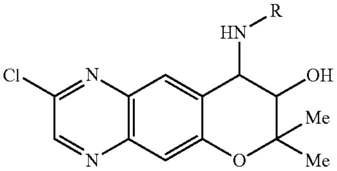
| | | |
|---|---|---|
| 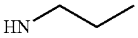 | 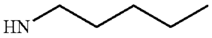 | 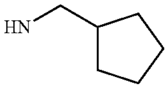 |
| 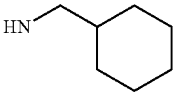 | 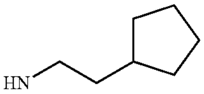 | 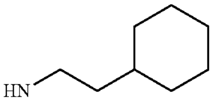 |
| 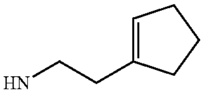 | 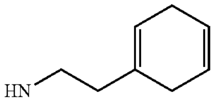 | 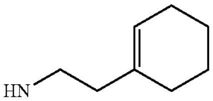 |
| 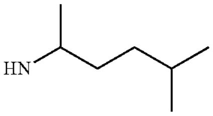 | 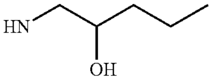 | 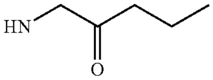 |
| 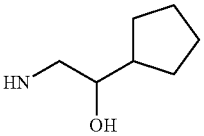 | 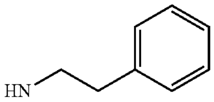 | 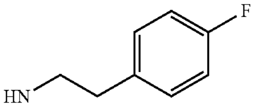 |
| 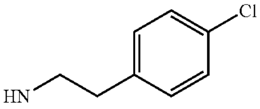 | 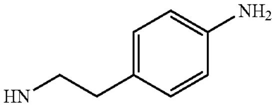 | 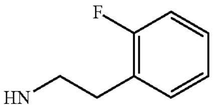 |
| 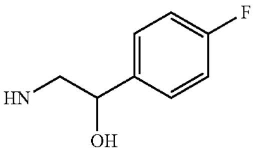 | 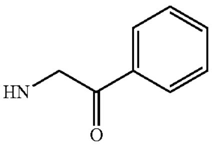 | 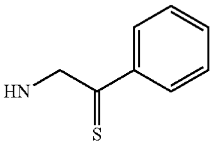 |
| 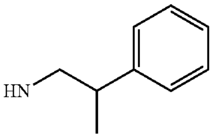 | 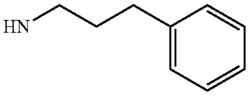 | 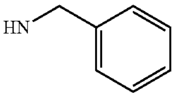 |

-continued
| HN—R | | |
|---|---|---|
| 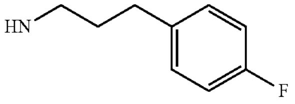 | 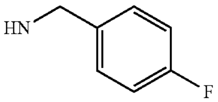 | 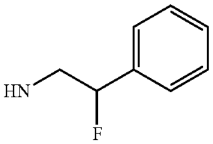 |
| 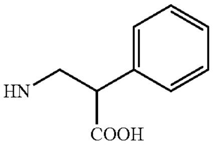 | 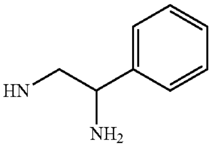 | 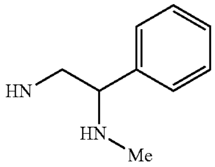 |
| 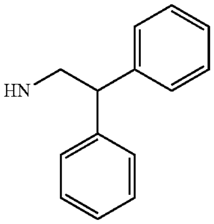 | 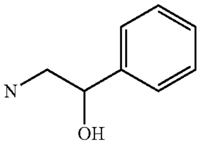 | 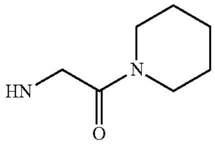 |
| 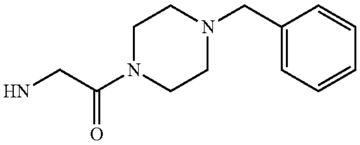 | 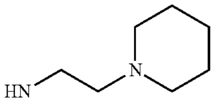 | 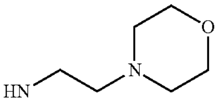 |
| 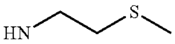 | 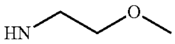 | 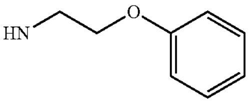 |
| 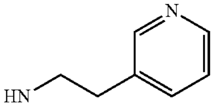 | 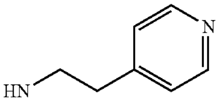 | 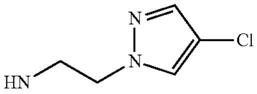 |
| 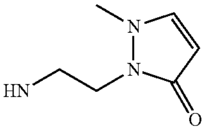 | | |
| | 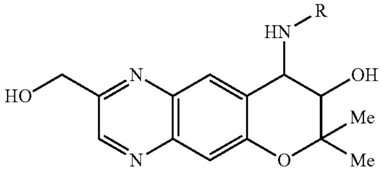 | |
|---|---|---|
| 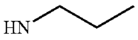 | 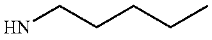 | 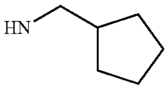 |
| 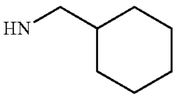 | 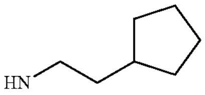 | 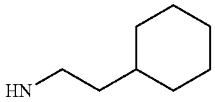 |
| 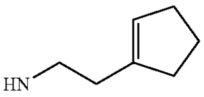 | 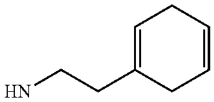 | 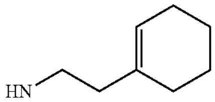 |

-continued
| HN—R | | |
|---|---|---|
| 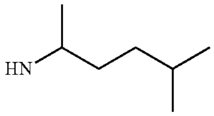 | 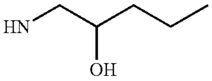 | 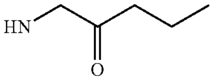 |
| 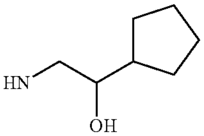 | 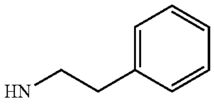 | 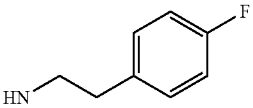 |
| 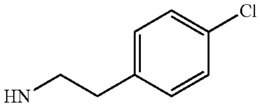 | 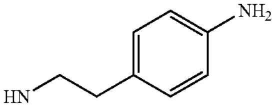 | 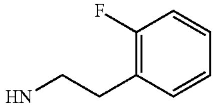 |
| 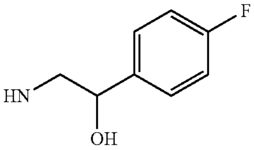 | 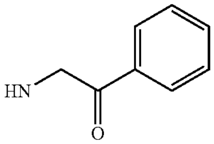 | 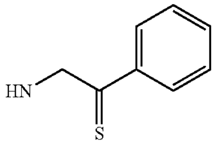 |
| 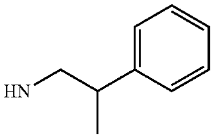 | 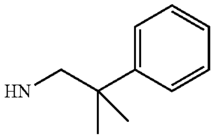 | 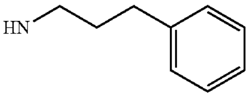 |
| 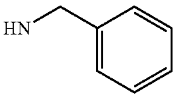 | 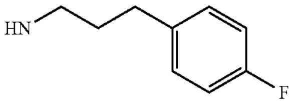 | 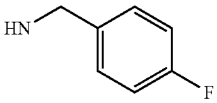 |
| 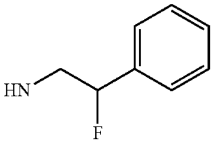 | 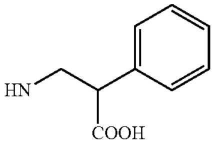 | 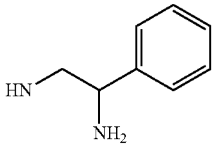 |
| 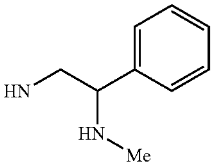 | 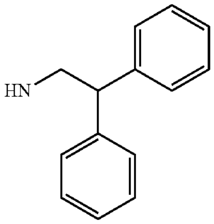 | 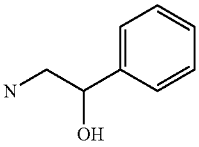 |
| 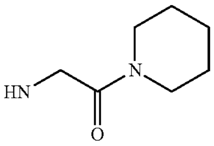 | 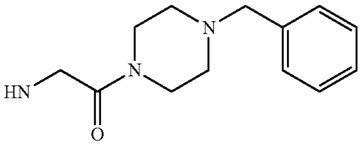 | 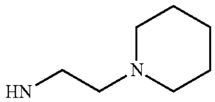 |
| 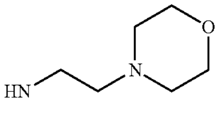 | 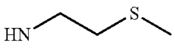 | 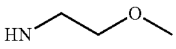 |

-continued
| HN—R | | |
|---|---|---|
| 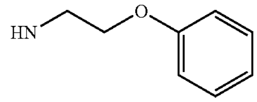 | 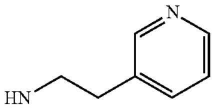 | 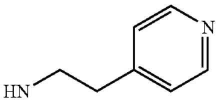 |
| 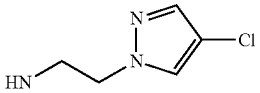 | 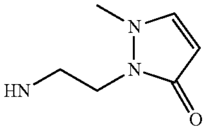 | |
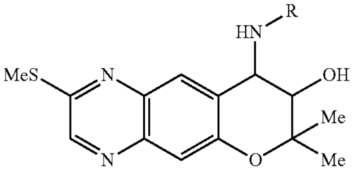
| | | |
|---|---|---|
| 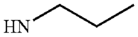 | 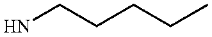 | 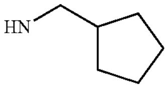 |
| 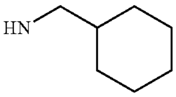 | 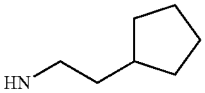 | 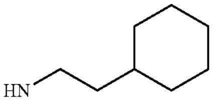 |
| 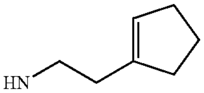 | 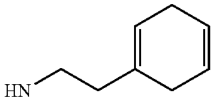 | 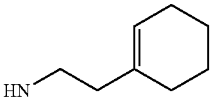 |
| 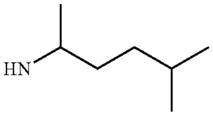 | 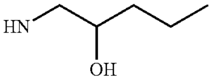 | 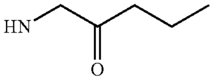 |
| 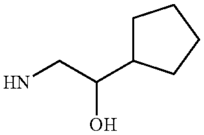 | 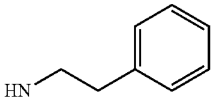 | 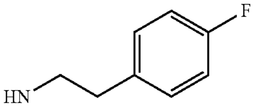 |
| 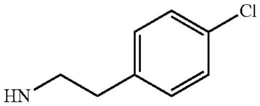 | 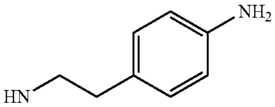 | 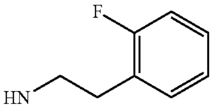 |
| 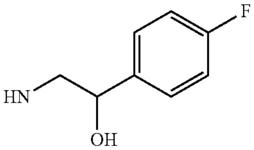 | 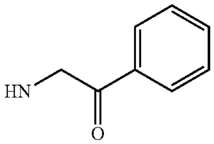 | 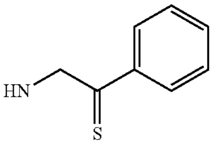 |
| 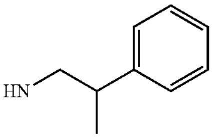 | 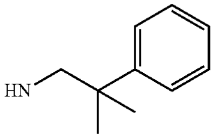 | 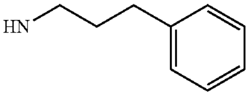 |

-continued

| HN—R | | |
|---|---|---|
| 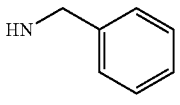 | 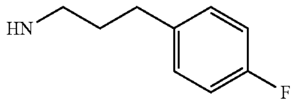 | 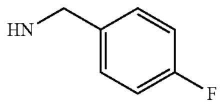 |
| 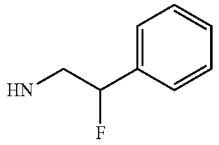 | 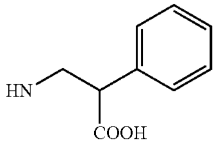 | 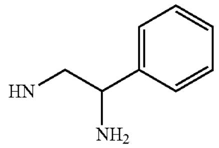 |
| 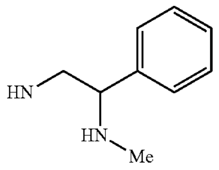 | 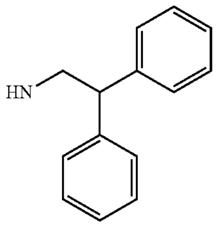 | 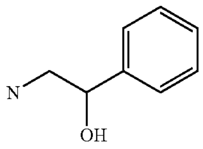 |
| 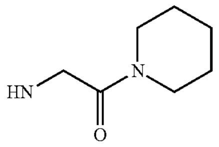 | 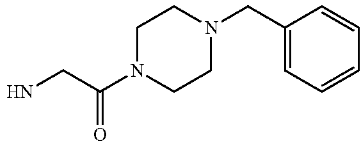 | 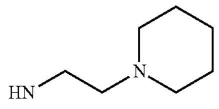 |
| 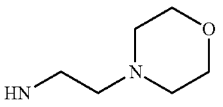 | 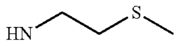 | 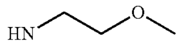 |
| 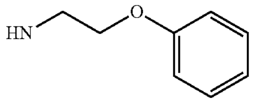 | 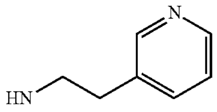 | 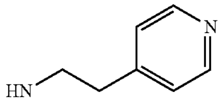 |
| 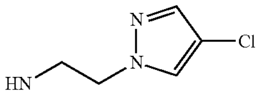 | 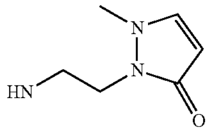 | |

| $R^{13}$ | $R^{14}$ | $R^{13}$ | $R^{14}$ | $R^{13}$ | $R^{14}$ |
|---|---|---|---|---|---|
| 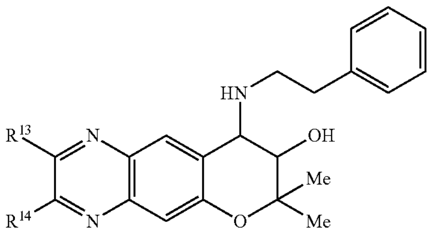 | | | | | |
| Me | Et | H | OH | H | $CH_2OH$ |
| Me | iPr | H | OMe | H | $CH_2NH_2$ |
| Me | nPr | Me | OEt | H | $CH_2NHMe$ |
| Me | nBu | Et | $OCF_3$ | H | $CH_2Ph$ |
| Me | tBu | iPr | OnPr | Me | $CH_2CH_2Ph$ |
| Et | Me | Ph | OiPr | Me | COMe |
| iPr | Et | H | Ph | Me | COOH |
| nPr | iPr | Me | SEt | Me | $CONH_2$ |

-continued

| | | | | | |
|---|---|---|---|---|---|
| nBu | nPr | Et | SiPr | Me | CONHMe |
| tBu | nBu | iPr | $NH_2$ | Et | CONHMs |
| OMe | H | H | NHMe | Et | NHMs |
| OEt | Me | H | NHEt | Et | NHCOMe |
| OiPr | Et | H | NHPh | Et | $NO_2$ |
| OPh | iPr | $CH_2OH$ | Me | iPr | CHO |
| SEt | H | $CH_2NH_2$ | Et | iPr | $SO_3H$ |
| SiPr | Me | $CH_2NHMe$ | iPr | iPr | $SO_2NHMe$ |
| $NH_2$ | H | $CH_2Ph$ | H | iPr | OH |
| NHMe | Me | $CH_2CH_2Ph$ | H | NHMs | Cl |
| NHEt | Ph | COMe | H | NHCOMe | Cl |
| NHPh | H | COOH | H | $NO_2$ | Cl |
| Cl | Me | $CONH_2$ | H | CHO | Br |
| Cl | Et | CONHMe | H | $SO_3H$ | Br |
| Cl | Ph | CONHMs | Me | $SO_2NHMe$ | Br |
| Me | Cl | NHMs | Me | OH | Br |
| Et | Cl | NHCOMe | Me | Cl | NHMs |
| Ph | Cl | $NO_2$ | Me | Cl | NHCOMe |
| Br | Me | CHO | Et | Cl | $NO_2$ |
| Br | Cl | $SO_3H$ | Et | Br | CHO |
| Me | Br | $SO_2NHMe$ | Et | Br | $SO_3H$ |
| Cl | Br | OH | Et | Br | $SO_2NHMe$ |

-continued

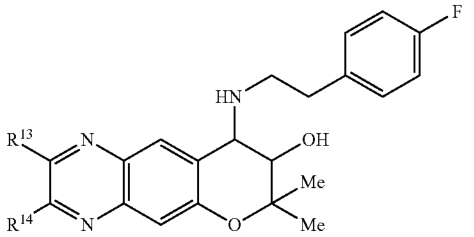

| | | | | | |
|---|---|---|---|---|---|
| Me | Et | H | OH | H | $CH_2OH$ |
| Me | iPr | H | OMe | H | $CH_2NH_2$ |
| Me | nPr | Me | OEt | H | $CH_2NHMe$ |
| Me | nBu | Et | $OCF_3$ | H | $CH_2Ph$ |
| Me | tBu | iPr | OnPr | Me | $CH_2CH_2Ph$ |
| Et | Me | Ph | OiPr | Me | COMe |
| iPr | Et | H | Ph | Me | COOH |
| nPr | iPr | Me | SEt | Me | $CONH_2$ |
| nBu | nPr | Et | SiPr | Me | CONHMe |
| tBu | nBu | iPr | $NH_2$ | Et | CONHMs |
| OMe | H | H | NHMe | Et | NHMs |
| OEt | Me | H | NHEt | Et | NHCOMe |
| OiPr | Et | H | NHPh | Et | $NO_2$ |
| OPh | iPr | $CH_2OH$ | Me | iPr | CHO |
| SEt | H | $CH_2NH_2$ | Et | iPr | $SO_3H$ |
| SiPr | Me | $CH_2NHMe$ | iPr | iPr | $SO_2NHMe$ |
| $NH_2$ | H | $CH_2Ph$ | H | iPr | OH |
| NHMe | Me | $CH_2CH_2Ph$ | H | NHMs | Cl |
| NHEt | Ph | COMe | H | NHCOMe | Cl |
| NHPh | H | COOH | H | $NO_2$ | Cl |
| Cl | Me | $CONH_2$ | H | CHO | Br |
| Cl | Et | CONHMe | H | $SO_3H$ | Br |
| Cl | Ph | CONHMs | Me | $SO_2NHMe$ | Br |
| Me | Cl | NHMs | Me | OH | Br |
| Et | Cl | NHCOMe | Me | Cl | NHMs |
| Ph | Cl | $NO_2$ | Me | Cl | NHCOMe |
| Br | Me | CHO | Et | Cl | $NO_2$ |
| Br | Cl | $SO_3H$ | Et | Br | CHO |
| Me | Br | $SO_2NHMe$ | Et | Br | $SO_3H$ |
| Cl | Br | OH | Et | Br | $SO_2NHMe$ |

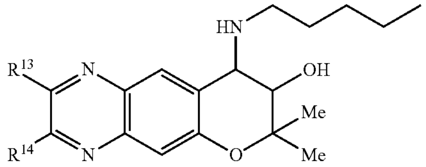

| | | | | | |
|---|---|---|---|---|---|
| Me | Et | H | OH | H | $CH_2OH$ |
| Me | iPr | H | OMe | H | $CH_2NH_2$ |
| Me | nPr | Me | OEt | H | $CH_2NHMe$ |
| Me | nBu | Et | $OCF_3$ | H | $CH_2Ph$ |
| Me | tBu | iPr | OnPr | Me | $CH_2CH_2Ph$ |
| Et | Me | Ph | OiPr | Me | COMe |
| iPr | Et | H | Ph | Me | COOH |
| nPr | iPr | Me | SEt | Me | $CONH_2$ |
| nBu | nPr | Et | SiPr | Me | CONHMe |
| tBu | nBu | iPr | $NH_2$ | Et | CONHMs |
| OMe | H | H | NHMe | Et | NHMs |
| OEt | Me | H | NHEt | Et | NHCOMe |
| OiPr | Et | H | NHPh | Et | $NO_2$ |
| OPh | iPr | $CH_2OH$ | Me | iPr | CHO |
| SEt | H | $CH_2NH_2$ | Et | iPr | $SO_3H$ |
| SiPr | Me | $CH_2NHMe$ | iPr | iPr | $SO_2NHMe$ |
| $NH_2$ | H | $CH_2Ph$ | H | iPr | OH |
| NHMe | Me | $CH_2CH_2Ph$ | H | NHMs | Cl |
| NHEt | Ph | COMe | H | NHCOMe | Cl |
| NHPh | H | COOH | H | $NO_2$ | Cl |
| Cl | Me | $CONH_2$ | H | CHO | Br |
| Cl | Et | CONHMe | H | $SO_3H$ | Br |
| Cl | Ph | CONHMs | Me | $SO_2NHMe$ | Br |
| Me | Cl | NHMs | Me | OH | Br |
| Et | Cl | NHCOMe | Me | Cl | NHMs |
| Ph | Cl | $NO_2$ | Me | Cl | NHCOMe |
| Br | Me | CHO | Et | Cl | $NO_2$ |
| Br | Cl | $SO_3H$ | Et | Br | CHO |
| Me | Br | $SO_2NHMe$ | Et | Br | $SO_3H$ |
| Cl | Br | OH | Et | Br | $SO_2NHMe$ |

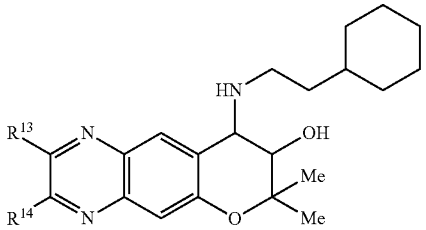

| | | | | | |
|---|---|---|---|---|---|
| Me | Et | H | OH | H | $CH_2OH$ |
| Me | iPr | H | OMe | H | $CH_2NH_2$ |
| Me | nPr | Me | OEt | H | $CH_2NHMe$ |
| Me | nBu | Et | $OCF_3$ | H | $CH_2Ph$ |
| Me | tBu | iPr | OnPr | Me | $CH_2CH_2Ph$ |
| Et | Me | Ph | OiPr | Me | COMe |
| iPr | Et | H | Ph | Me | COOH |
| nPr | iPr | Me | SEt | Me | $CONH_2$ |
| nBu | nPr | Et | SiPr | Me | CONHMe |
| tBu | nBu | iPr | $NH_2$ | Et | CONHMs |
| OMe | H | H | NHMe | Et | NHMs |
| OEt | Me | H | NHEt | Et | NHCOMe |
| OiPr | Et | H | NHPh | Et | $NO_2$ |
| OPh | iPr | $CH_2OH$ | Me | iPr | CHO |
| SEt | H | $CH_2NH_2$ | Et | iPr | $SO_3H$ |
| SiPr | Me | $CH_2NHMe$ | iPr | iPr | $SO_2NHMe$ |
| $NH_2$ | H | $CH_2Ph$ | H | iPr | OH |
| NHMe | Me | $CH_2CH_2Ph$ | H | NHMs | Cl |
| NHEt | Ph | COMe | H | NHCOMe | Cl |
| NHPh | H | COOH | H | $NO_2$ | Cl |
| Cl | Me | $CONH_2$ | H | CHO | Br |
| Cl | Et | CONHMe | H | $SO_3H$ | Br |
| Cl | Ph | CONHMs | Me | $SO_2NHMe$ | Br |
| Me | Cl | NHMs | Me | OH | Br |
| Et | Cl | NHCOMe | Me | Cl | NHMs |
| Ph | Cl | $NO_2$ | Me | Cl | NHCOMe |
| Br | Me | CHO | Et | Cl | $NO_2$ |
| Br | Cl | $SO_3H$ | Et | Br | CHO |
| Me | Br | $SO_2NHMe$ | Et | Br | $SO_3H$ |
| Cl | Br | OH | Et | Br | $SO_2NHMe$ |

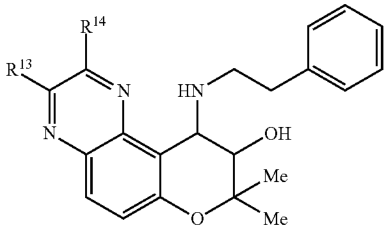

| | | | | | |
|---|---|---|---|---|---|
| Me | Et | H | OH | H | $CH_2OH$ |
| Me | iPr | H | OMe | H | $CH_2NH_2$ |
| Me | nPr | Me | OEt | H | $CH_2NHMe$ |
| Me | nBu | Et | $OCF_3$ | H | $CH_2Ph$ |
| Me | tBu | iPr | OnPr | Me | $CH_2CH_2Ph$ |
| Et | Me | Ph | OiPr | Me | COMe |
| iPr | Et | H | Ph | Me | COOH |
| nPr | iPr | Me | SEt | Me | $CONH_2$ |
| nBu | nPr | Et | SiPr | Me | CONHMe |
| tBu | nBu | iPr | $NH_2$ | Et | CONHMs |
| OMe | H | H | NHMe | Et | NHMs |
| OEt | Me | H | NHEt | Et | NHCOMe |
| OiPr | Et | H | NHPh | Et | $NO_2$ |
| OPh | iPr | $CH_2OH$ | Me | iPr | CHO |
| SEt | H | $CH_2NH_2$ | Et | iPr | $SO_3H$ |
| SiPr | Me | $CH_2NHMe$ | iPr | iPr | $SO_2NHMe$ |
| $NH_2$ | H | $CH_2Ph$ | H | iPr | OH |
| NHMe | Me | $CH_2CH_2Ph$ | H | NHMs | Cl |
| NHEt | Ph | COMe | H | NHCOMe | Cl |
| NHPh | H | COON | H | $NO_2$ | Cl |
| Cl | Me | $CONH_2$ | H | CHO | Br |

-continued

| | | | | | |
|---|---|---|---|---|---|
| Cl | Et | CONHMe | H | $SO_3H$ | Br |
| Cl | Ph | CONHMs | Me | $SO_2NHMe$ | Br |
| Me | Cl | NHMs | Me | OH | Br |
| Et | Cl | NHCOMe | Me | Cl | NHMs |
| Ph | Cl | $NO_2$ | Me | Cl | NHCOMe |
| Br | Me | CHO | Et | Cl | $NO_2$ |
| Br | Cl | $SO_3H$ | Et | Br | CHO |
| Me | Br | $SO_2NHMe$ | Et | Br | $SO_3H$ |
| Cl | Br | OH | Et | Br | $SO_2NHMe$ |

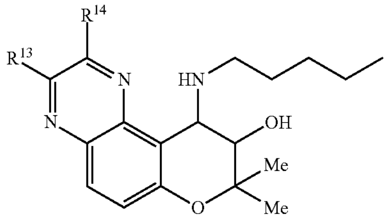

| | | | | | |
|---|---|---|---|---|---|
| Me | Et | H | OH | H | $CH_2OH$ |
| Me | iPr | H | OMe | H | $CH_2NH_2$ |
| Me | nPr | Me | OEt | H | $CH_2NHMe$ |
| Me | nBu | Et | $OCF_3$ | H | $CH_2Ph$ |
| Me | tBu | iPr | OnPr | Me | $CH_2CH_2Ph$ |
| Et | Me | Ph | OiPr | Me | COMe |
| iPr | Et | H | Ph | Me | COOH |
| nPr | iPr | Me | SEt | Me | $CONH_2$ |
| nBu | nPr | Et | SiPr | Me | CONHMe |
| tBu | nBu | iPr | $NH_2$ | Et | CONHMs |
| OMe | H | H | NHMe | Et | NHMs |
| OEt | Me | H | NHEt | Et | NHCOMe |
| OiPr | Et | H | NHPh | Et | $NO_2$ |
| OPh | iPr | $CH_2OH$ | Me | iPr | CHO |
| SEt | H | $CH_2NH_2$ | Et | iPr | $SO_3H$ |
| SiPr | Me | $CH_2NHMe$ | iPr | iPr | $SO_2NHMe$ |
| $NH_2$ | H | $CH_2Ph$ | H | iPr | OH |
| NHMe | Me | $CH_2CH_2Ph$ | H | NHMs | Cl |
| NHEt | Ph | COMe | H | NHCOMe | Cl |
| NHPh | H | COOH | H | $NO_2$ | Cl |
| Cl | Me | $CONH_2$ | H | CHO | Br |
| Cl | Et | CONHMe | H | $SO_3H$ | Br |
| Cl | Ph | CONHMs | Me | $SO_2NHMe$ | Br |
| Me | Cl | NHMs | Me | OH | Br |
| Et | Cl | NHCOMe | Me | Cl | NHMs |
| Ph | Cl | $NO_2$ | Me | Cl | NHCOMe |
| Br | Me | CHO | Et | Cl | $NO_2$ |
| Br | Cl | $SO_3H$ | Et | Br | CHO |
| Me | Br | $SO_2NHMe$ | Et | Br | $SO_3H$ |
| Cl | Br | OH | Et | Br | $SO_2NHMe$ |

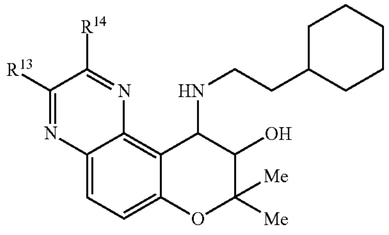

| | | | | | |
|---|---|---|---|---|---|
| Me | Et | H | OH | H | $CH_2OH$ |
| Me | iPr | H | OMe | H | $CH_2NH_2$ |
| Me | nPr | Me | OEt | H | $CH_2NHMe$ |
| Me | nBu | Et | $OCF_3$ | H | $CH_2Ph$ |
| Me | tBu | iPr | OnPr | Me | $CH_2CH_2Ph$ |
| Et | Me | Ph | OiPr | Me | COMe |
| iPr | Et | H | Ph | Me | COOH |
| nPr | iPr | Me | SEt | Me | $CONH_2$ |
| nBu | nPr | Et | SiPr | Me | CONHMe |
| tBu | nBu | iPr | $NH_2$ | Et | CONHMs |
| OMe | H | H | NHMe | Et | NHMs |
| OEt | Me | H | NHEt | Et | NHCOMe |
| OiPr | Et | H | NHPh | Et | $NO_2$ |
| OPh | iPr | $CH_2OH$ | Me | iPr | CHO |
| SEt | H | $CH_2NH_2$ | Et | iPr | $SO_3H$ |
| SiPr | Me | $CH_2NHMe$ | iPr | iPr | $SO_2NHMe$ |

-continued

| | | | | | |
|---|---|---|---|---|---|
| $NH_2$ | H | $CH_2Ph$ | H | iPr | OH |
| NHMe | Me | $CH_2CH_2Ph$ | H | NHMs | Cl |
| NHEt | Ph | COMe | H | NHCOMe | Cl |
| NHPh | H | COOH | H | $NO_2$ | Cl |
| Cl | Me | $CONH_2$ | H | CHO | Br |
| Cl | Et | CONHMe | H | $SO_3H$ | Br |
| Cl | Ph | CONHMs | Me | $SO_2NHMe$ | Br |
| Me | Cl | NHMs | Me | OH | Br |
| Et | Cl | NHCOMe | Me | Cl | NHMs |
| Ph | Cl | $NO_2$ | Me | Cl | NHCOMe |
| Br | Me | CHO | Et | Cl | $NO_2$ |
| Br | Cl | $SO_3H$ | Et | Br | CHO |
| Me | Br | $SO_2NHMe$ | Et | Br | $SO_3H$ |
| Cl | Br | OH | Et | Br | $SO_2NHMe$ |

| $R^{11}$ | $R^{13}$ | $R^{11}$ | $R^{13}$ | $R^{11}$ | $R^{13}$ |
|---|---|---|---|---|---|

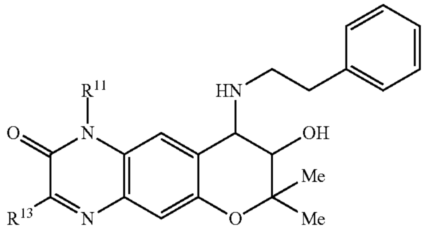

| | | | | | |
|---|---|---|---|---|---|
| H | Et | H | Cl | H | OMe |
| H | iPr | H | Br | H | $OCF_3$ |
| H | nPr | H | $NO_2$ | H | OEt |
| H | nBu | H | CHO | H | OiPr |
| H | tBu | H | $SO_3H$ | H | SMe |
| Me | H | Me | Cl | Me | OMe |
| Me | Me | Me | Br | Me | $OCF_3$ |
| Me | Et | Me | $CH_2OH$ | Me | OEt |
| Me | iPr | Me | $CH_2NH_2$ | Me | SMe |
| Me | nPr | Me | $CH_2NHMe$ | Me | OiPr |
| Me | nBu | Me | $CH_2Ph$ | Me | OnPr |
| Et | H | Et | COMe | Et | NHMe |
| Et | Me | Et | COOH | Et | NHEt |
| Et | Et | Et | $CONH_2$ | Et | $NMe_2$ |
| iPr | H | iPr | CONHMe | iPr | NMeEt |
| nPr | Me | nPr | CONHMs | nPr | OMe |
| nBu | Et | nBu | NHMs | nBu | $OCF_3$ |
| tBu | Me | tBu | NHCOMe | tBu | OEt |
| Ph | Ph | Ph | $NO_2$ | Ph | OiPr |
| $CH_2OH$ | H | $CH_2OH$ | CHO | $CH_2OH$ | SMe |
| $CH_2OH$ | Me | $CH_2OH$ | $SO_3H$ | $CH_2OH$ | OPh |
| $CH_2OMe$ | Et | $CH_2OMe$ | $SO_2NHMe$ | $CH_2OMe$ | SPh |
| $CH_2OMe$ | Ph | $CH_2OMe$ | OH | $CH_2OMe$ | NHPh |
| $CH_2NH_2$ | H | $CH_2NH_2$ | COMe | $CH_2NH_2$ | OMe |
| $CH_2NH_2$ | Me | $CH_2NH_2$ | COOH | $CH_2NH_2$ | $OCF_3$ |
| $CH_2NH_2$ | Et | $CH_2NH_2$ | $CONH_2$ | $CH_2NH_2$ | OEt |
| $CH_2NHMe$ | Me | $CH_2NHMe$ | CONHMe | $CH_2NHMe$ | OiPr |
| $CH_2Ph$ | Me | $CH_2Ph$ | CONHMs | $CH_2Ph$ | SMe |
| $CH_2Ph$ | Et | $CH_2Ph$ | NHMs | $CH_2Ph$ | OPh |
| $CH_2CH_2Ph$ | iPr | $CH_2CH_2Ph$ | $NO_2$ | $CH_2CH_2Ph$ | SPh |

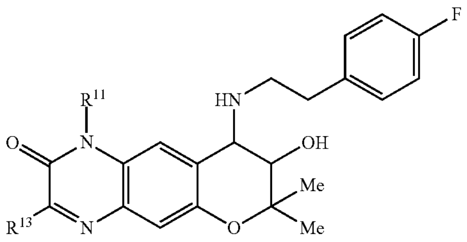

| | | | | | |
|---|---|---|---|---|---|
| H | Et | H | Cl | H | OMe |
| H | iPr | H | Br | H | $OCF_3$ |
| H | nPr | H | $NO_2$ | H | OEt |
| H | nBu | H | CHO | H | OiPr |
| H | tBu | H | $SO_3H$ | H | SMe |
| Me | H | Me | Cl | Me | OMe |
| Me | Me | Me | Br | Me | $OCF_3$ |
| Me | Et | Me | $CH_2OH$ | Me | OEt |

-continued

| | | | | | |
|---|---|---|---|---|---|
| Me | iPr | Me | $CH_2NH_2$ | Me | SMe |
| Me | nPr | Me | $CH_2NHMe$ | Me | OiPr |
| Me | nBu | Me | $CH_2Ph$ | Me | OnPr |
| Et | H | Et | COMe | Et | NHMe |
| Et | Me | Et | COOH | Et | NHEt |
| Et | Et | Et | $CONH_2$ | Et | $NMe_2$ |
| iPr | H | iPr | CONHMe | iPr | NMeEt |
| nPr | Me | nPr | CONHMs | nPr | OMe |
| nBu | Et | nBu | NHMs | nBu | $OCF_3$ |
| tBu | Me | tBu | NHCOMe | tBu | OEt |
| Ph | Ph | Ph | $NO_2$ | Ph | OiPr |
| $CH_2OH$ | H | $CH_2OH$ | CHO | $CH_2OH$ | SMe |
| $CH_2OH$ | Me | $CH_2OH$ | $SO_3H$ | $CH_2OH$ | OPh |
| $CH_2OMe$ | Et | $CH_2OMe$ | $SO_2NHMe$ | $CH_2OMe$ | SPh |
| $CH_2OMe$ | Ph | $CH_2OMe$ | OH | $CH_2OMe$ | NHPh |
| $CH_2NH_2$ | H | $CH_2NH_2$ | COMe | $CH_2NH_2$ | OMe |
| $CH_2NH_2$ | Me | $CH_2NH_2$ | COOH | $CH_2NH_2$ | $OCF_3$ |
| $CH_2NH_2$ | Et | $CH_2NH_2$ | $CONH_2$ | $CH_2NH_2$ | OEt |
| $CH_2NHMe$ | Me | $CH_2NHMe$ | CONHMe | $CH_2NHMe$ | OiPr |
| $CH_2Ph$ | Me | $CH_2Ph$ | CONHMs | $CH_2Ph$ | SMe |
| $CH_2Ph$ | Et | $CH_2Ph$ | NHMs | $CH_2Ph$ | OPh |
| $CH_2CH_2Ph$ | iPr | $CH_2CH_2Ph$ | $NO_2$ | $CH_2CH_2Ph$ | SPh |

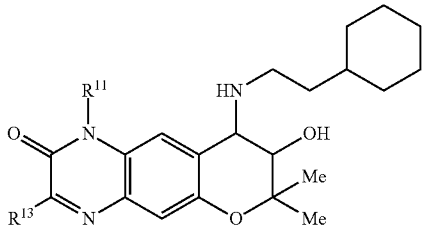

| | | | | | |
|---|---|---|---|---|---|
| H | Et | H | Cl | H | OMe |
| H | iPr | H | Br | H | $OCF_3$ |
| H | nPr | H | $NO_2$ | H | OEt |
| H | nBu | H | CHO | H | OiPr |
| H | tBu | H | $SO_3H$ | H | SMe |
| Me | H | Me | Cl | Me | OMe |
| Me | Me | Me | Br | Me | $OCF_3$ |
| Me | Et | Me | $CH_2OH$ | Me | OEt |
| Me | iPr | Me | $CH_2NH_2$ | Me | SMe |
| Me | nPr | Me | $CH_2NHMe$ | Me | OiPr |
| Me | nBu | Me | $CH_2Ph$ | Me | OnPr |
| Et | H | Et | COMe | Et | NHMe |
| Et | Me | Et | COOH | Et | NHEt |
| Et | Et | Et | $CONH_2$ | Et | $NMe_2$ |
| iPr | H | iPr | CONHMe | iPr | NMeEt |
| nPr | Me | nPr | CONHMs | nPr | OMe |
| nBu | Et | nBu | NHMs | nBu | $OCF_3$ |
| tBu | Me | tBu | NHCOMe | tBu | OEt |
| Ph | Ph | Ph | $NO_2$ | Ph | OiPr |
| $CH_2OH$ | H | $CH_2OH$ | CHO | $CH_2OH$ | SMe |
| $CH_2OH$ | Me | $CH_2OH$ | $SO_3H$ | $CH_2OH$ | OPh |
| $CH_2OMe$ | Et | $CH_2OMe$ | $SO_2NHMe$ | $CH_2OMe$ | SPh |
| $CH_2OMe$ | Ph | $CH_2OMe$ | OH | $CH_2OMe$ | NHPh |
| $CH_2NH_2$ | H | $CH_2NH_2$ | COMe | $CH_2NH_2$ | OMe |
| $CH_2NH_2$ | Me | $CH_2NH_2$ | COOH | $CH_2NH_2$ | $OCF_3$ |
| $CH_2NH_2$ | Et | $CH_2NH_2$ | $CONH_2$ | $CH_2NH_2$ | OEt |
| $CH_2NHMe$ | Me | $CH_2NHMe$ | CONHMe | $CH_2NHMe$ | OiPr |
| $CH_2Ph$ | Me | $CH_2Ph$ | CONHMs | $CH_2Ph$ | SMe |
| $CH_2Ph$ | Et | $CH_2Ph$ | NHMs | $CH_2Ph$ | OPh |
| $CH_2CH_2Ph$ | iPr | $CH_2CH_2Ph$ | $NO_2$ | $CH_2CH_2Ph$ | SPh |

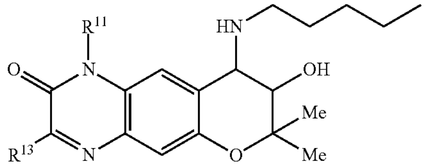

| | | | | | |
|---|---|---|---|---|---|
| H | Et | H | Cl | H | OMe |
| H | iPr | H | Br | H | $OCF_3$ |
| H | nPr | H | $NO_2$ | H | OEt |
| H | nBu | H | CHO | H | OiPr |
| H | tBu | H | $SO_3H$ | H | SMe |

-continued

| | | | | | |
|---|---|---|---|---|---|
| Me | H | Me | Cl | Me | OMe |
| Me | Me | Me | Br | Me | $OCF_3$ |
| Me | Et | Me | $CH_2OH$ | Me | OEt |
| Me | iPr | Me | $CH_2NH_2$ | Me | SMe |
| Me | nPr | Me | $CH_2NHMe$ | Me | OiPr |
| Me | nBu | Me | $CH_2Ph$ | Me | OnPr |
| Et | H | Et | COMe | Et | NHMe |
| Et | Me | Et | COOH | Et | NHEt |
| Et | Et | Et | $CONH_2$ | Et | $NMe_2$ |
| iPr | H | iPr | CONHMe | iPr | NMeEt |
| nPr | Me | nPr | CONHMs | nPr | OMe |
| nBu | Et | nBu | NHMs | nBu | $OCF_3$ |
| tBu | Me | tBu | NHCOMe | tBu | OEt |
| Ph | Ph | Ph | $NO_2$ | Ph | OiPr |
| $CH_2OH$ | H | $CH_2OH$ | CHO | $CH_2OH$ | SMe |
| $CH_2OH$ | Me | $CH_2OH$ | $SO_3H$ | $CH_2OH$ | OPh |
| $CH_2OMe$ | Et | $CH_2OMe$ | $SO_2NHMe$ | $CH_2OMe$ | SPh |
| $CH_2OMe$ | Ph | $CH_2OMe$ | OH | $CH_2OMe$ | NHPh |
| $CH_2NH_2$ | H | $CH_2NH_2$ | COMe | $CH_2NH_2$ | OMe |
| $CH_2NH_2$ | Me | $CH_2NH_2$ | COOH | $CH_2NH_2$ | $OCF_3$ |
| $CH_2NH_2$ | Et | $CH_2NH_2$ | $CONH_2$ | $CH_2NH_2$ | OEt |
| $CH_2NHMe$ | Me | $CH_2NHMe$ | CONHMe | $CH_2NHMe$ | OiPr |
| $CH_2Ph$ | Me | $CH_2Ph$ | CONHMs | $CH_2Ph$ | SMe |
| $CH_2Ph$ | Et | $CH_2Ph$ | NHMs | $CH_2Ph$ | OPh |
| $CH_2CH_2Ph$ | iPr | $CH_2CH_2Ph$ | $NO_2$ | $CH_2CH_2Ph$ | SPh |

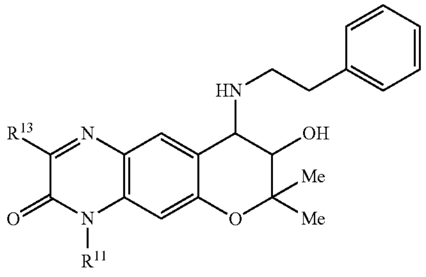

| | | | | | |
|---|---|---|---|---|---|
| H | Et | H | Cl | H | OMe |
| H | iPr | H | Br | H | $OCF_3$ |
| H | nPr | H | $NO_2$ | H | OEt |
| H | nBu | H | CHO | H | OiPr |
| H | tBu | H | $SO_3H$ | H | SMe |
| Me | H | Me | Cl | Me | OMe |
| Me | Me | Me | Br | Me | $OCF_3$ |
| Me | Et | Me | $CH_2OH$ | Me | OEt |
| Me | iPr | Me | $CH_2NH_2$ | Me | SMe |
| Me | nPr | Me | $CH_2NHMe$ | Me | OiPr |
| Me | nBu | Me | $CH_2Ph$ | Me | OnPr |
| Et | H | Et | COMe | Et | NHMe |
| Et | Me | Et | COOH | Et | NHEt |
| Et | Et | Et | $CONH_2$ | Et | $NMe_2$ |
| iPr | H | iPr | CONHMe | iPr | NMeEt |
| nPr | Me | nPr | CONHMs | nPr | OMe |
| nBu | Et | nBu | NHMs | nBu | $OCF_3$ |
| tBu | Me | tBu | NHCOMe | tBu | OEt |
| Ph | Ph | Ph | $NO_2$ | Ph | OiPr |
| $CH_2OH$ | H | $CH_2OH$ | CHO | $CH_2OH$ | SMe |
| $CH_2OH$ | Me | $CH_2OH$ | $SO_3H$ | $CH_2OH$ | OPh |
| $CH_2OMe$ | Et | $CH_2OMe$ | $SO_2NHMe$ | $CH_2OMe$ | SPh |
| $CH_2OMe$ | Ph | $CH_2OMe$ | OH | $CH_2OMe$ | NHPh |
| $CH_2NH_2$ | H | $CH_2NH_2$ | COMe | $CH_2NH_2$ | OMe |
| $CH_2NH_2$ | Me | $CH_2NH_2$ | COOH | $CH_2NH_2$ | $OCF_3$ |
| $CH_2NH_2$ | Et | $CH_2NH_2$ | $CONH_2$ | $CH_2NH_2$ | OEt |
| $CH_2NHMe$ | Me | $CH_2NHMe$ | CONHMe | $CH_2NHMe$ | OiPr |
| $CH_2Ph$ | Me | $CH_2Ph$ | CONHMs | $CH_2Ph$ | SMe |
| $CH_2Ph$ | Et | $CH_2Ph$ | NHMs | $CH_2Ph$ | OPh |
| $CH_2CH_2Ph$ | iPr | $CH_2CH_2Ph$ | $NO_2$ | $CH_2CH_2Ph$ | SPh |

-continued

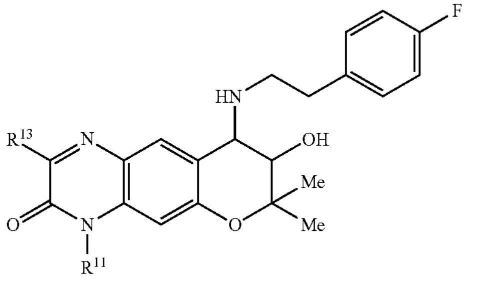

| | | | | | |
|---|---|---|---|---|---|
| H | Et | H | Cl | H | OMe |
| H | iPr | H | Br | H | $OCF_3$ |
| H | nPr | H | $NO_2$ | H | OEt |
| H | nBu | H | CHO | H | OiPr |
| H | tBu | H | $SO_3H$ | H | SMe |
| Me | H | Me | Cl | Me | OMe |
| Me | Me | Me | Br | Me | $OCF_3$ |
| Me | Et | Me | $CH_2OH$ | Me | OEt |
| Me | iPr | Me | $CH_2NH_2$ | Me | SMe |
| Me | nPr | Me | $CH_2NHMe$ | Me | OiPr |
| Me | nBu | Me | $CH_2Ph$ | Me | OnPr |
| Et | H | Et | COMe | Et | NHMe |
| Et | Me | Et | COOH | Et | NHEt |
| Et | Et | Et | $CONH_2$ | Et | $NMe_2$ |
| iPr | H | iPr | CONHMe | iPr | NMeEt |
| nPr | Me | nPr | CONHMs | nPr | OMe |
| nBu | Et | nBu | NHMs | nBu | $OCF_3$ |
| tBu | Me | tBu | NHCOMe | tBu | OEt |
| Ph | Ph | Ph | $NO_2$ | Ph | OiPr |
| $CH_2OH$ | H | $CH_2OH$ | CHO | $CH_2OH$ | SMe |
| $CH_2OH$ | Me | $CH_2OH$ | $SO_3H$ | $CH_2OH$ | OPh |
| $CH_2OMe$ | Et | $CH_2OMe$ | $SO_2NHMe$ | $CH_2OMe$ | SPh |
| $CH_2OMe$ | Ph | $CH_2OMe$ | OH | $CH_2OMe$ | NHPh |
| $CH_2NH_2$ | H | $CH_2NH_2$ | COMe | $CH_2NH_2$ | OMe |
| $CH_2NH_2$ | Me | $CH_2NH_2$ | COOH | $CH_2NH_2$ | $OCF_3$ |
| $CH_2NH_2$ | Et | $CH_2NH_2$ | $CONH_2$ | $CH_2NH_2$ | OEt |
| $CH_2NHMe$ | Me | $CH_2NHMe$ | CONHMe | $CH_2NHMe$ | OiPr |
| $CH_2Ph$ | Me | $CH_2Ph$ | CONHMs | $CH_2Ph$ | SMe |
| $CH_2Ph$ | Et | $CH_2Ph$ | NHMs | $CH_2Ph$ | OPh |
| $CH_2CH_2Ph$ | iPr | $CH_2CH_2Ph$ | $NO_2$ | $CH_2CH_2Ph$ | SPh |

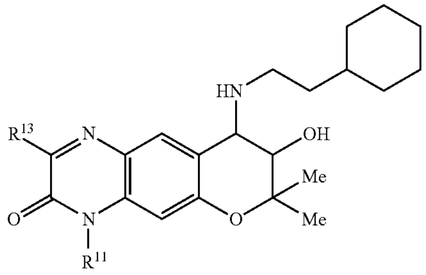

| | | | | | |
|---|---|---|---|---|---|
| H | Et | H | Cl | H | OMe |
| H | iPr | H | Br | H | $OCF_3$ |
| H | nPr | H | $NO_2$ | H | OEt |
| H | nBu | H | CHO | H | OiPr |
| H | tBu | H | $SO_3H$ | H | SMe |
| Me | H | Me | Cl | Me | OMe |
| Me | Me | Me | Br | Me | $OCF_3$ |
| Me | Et | Me | $CH_2OH$ | Me | OEt |
| Me | iPr | Me | $CH_2NH_2$ | Me | SMe |
| Me | nPr | Me | $CH_2NHMe$ | Me | OiPr |
| Me | nBu | Me | $CH_2Ph$ | Me | OnPr |
| Et | H | Et | COMe | Et | NHMe |
| Et | Me | Et | COOH | Et | NHEt |
| Et | Et | Et | $CONH_2$ | Et | NMe2 |
| iPr | H | iPr | CONHMe | iPr | NMeEt |
| nPr | Me | nPr | CONHMs | nPr | OMe |
| nBu | Et | nBu | NHMs | nBu | $OCF_3$ |
| tBu | Me | tBu | NHCOMe | tBu | OEt |

-continued

| | | | | | |
|---|---|---|---|---|---|
| Ph | Ph | Ph | $NO_2$ | Ph | OiPr |
| $CH_2OH$ | H | $CH_2OH$ | CHO | $CH_2OH$ | SMe |
| $CH_2OH$ | Me | $CH_2OH$ | $SO_3H$ | $CH_2OH$ | OPh |
| $CH_2OMe$ | Et | $CH_2OMe$ | $SO_2NHMe$ | $CH_2OMe$ | SPh |
| $CH_2OMe$ | Ph | $CH_2OMe$ | OH | $CH_2OMe$ | NHPh |
| $CH_2NH_2$ | H | $CH_2NH_2$ | COMe | $CH_2NH_2$ | OMe |
| $CH_2NH_2$ | Me | $CH_2NH_2$ | COOH | $CH_2NH_2$ | $OCF_3$ |
| $CH_2NH_2$ | Et | $CH_2NH_2$ | $CONH_2$ | $CH_2NH_2$ | OEt |
| $CH_2NHMe$ | Me | $CH_2NHMe$ | CONHMe | $CH_2NHMe$ | OiPr |
| $CH_2Ph$ | Me | $CH_2Ph$ | CONHMs | $CH_2Ph$ | SMe |
| $CH_2Ph$ | Et | $CH_2Ph$ | NHMs | $CH_2Ph$ | OPh |
| $CH_2CH_2Ph$ | iPr | $CH_2CH_2Ph$ | $NO_2$ | $CH_2CH_2Ph$ | SPh |

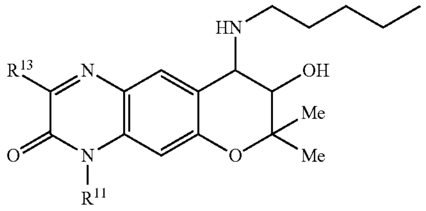

| | | | | | |
|---|---|---|---|---|---|
| H | Et | H | Cl | H | OMe |
| H | iPr | H | Br | H | $OCF_3$ |
| H | nPr | H | $NO_2$ | H | OEt |
| H | nBu | H | CHO | H | OiPr |
| H | tBu | H | $SO_3H$ | H | SMe |
| Me | H | Me | Cl | Me | OMe |
| Me | Me | Me | Br | Me | $OCF_3$ |
| Me | Et | Me | $CH_2OH$ | Me | OEt |
| Me | iPr | Me | $CH_2NH_2$ | Me | SMe |
| Me | nPr | Me | $CH_2NHMe$ | Me | OiPr |
| Me | nBu | Me | $CH_2Ph$ | Me | OnPr |
| Et | H | Et | COMe | Et | NHMe |
| Et | Me | Et | COOH | Et | NHEt |
| Et | Et | Et | $CONH_2$ | Et | $NMe_2$ |
| iPr | H | iPr | CONHMe | iPr | NMeEt |
| nPr | Me | nPr | CONHMs | nPr | OMe |
| nBu | Et | nBu | NHMs | nBu | $OCF_3$ |
| tBu | Me | tBu | NHCOMe | tBu | OEt |
| Ph | Ph | Ph | $NO_2$ | Ph | OiPr |
| $CH_2OH$ | H | $CH_2OH$ | CHO | $CH_2OH$ | SMe |
| $CH_2OH$ | Me | $CH_2OH$ | $SO_3H$ | $CH_2OH$ | OPh |
| $CH_2OMe$ | Et | $CH_2OMe$ | $SO_2NHMe$ | $CH_2OMe$ | SPh |
| $CH_2OMe$ | Ph | $CH_2OMe$ | OH | $CH_2OMe$ | NHPh |
| $CH_2NH_2$ | H | $CH_2NH_2$ | COMe | $CH_2NH_2$ | OMe |
| $CH_2NH_2$ | Me | $CH_2NH_2$ | COOH | $CH_2NH_2$ | $OCF_3$ |
| $CH_2NH_2$ | Et | $CH_2NH_2$ | $CONH_2$ | $CH_2NH_2$ | OEt |
| $CH_2NHMe$ | Me | $CH_2NHMe$ | CONHMe | $CH_2NHMe$ | OiPr |
| $CH_2Ph$ | Me | $CH_2Ph$ | CONHMs | $CH_2Ph$ | SMe |
| $CH_2Ph$ | Et | $CH_2Ph$ | NHMs | $CH_2Ph$ | OPh |
| $CH_2CH_2Ph$ | iPr | $CH_2CH_2Ph$ | $NO_2$ | $CH_2$CH2Ph | SPh |

| | HN—R | |
|---|---|---|
| | 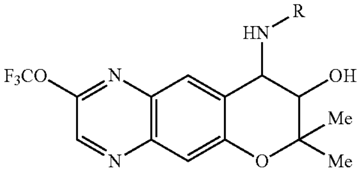 | |
| 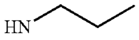 | 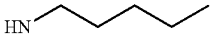 | 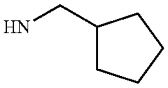 |
| 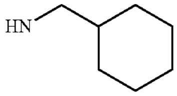 | 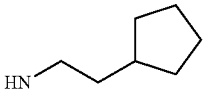 | 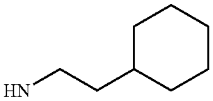 |
| 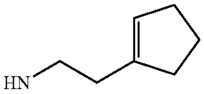 | 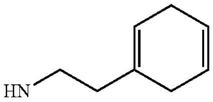 | 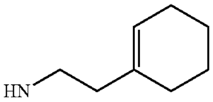 |
| 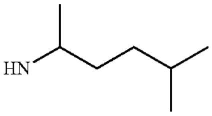 | 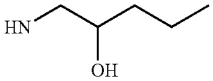 | 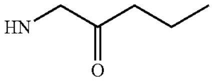 |
| 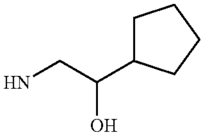 | 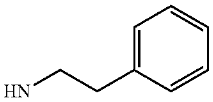 | 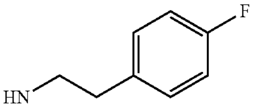 |
| 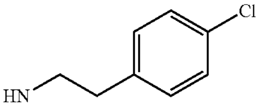 | 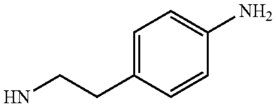 | 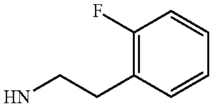 |
| 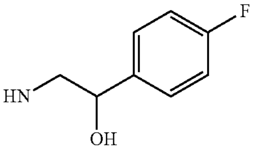 | 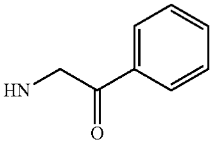 | 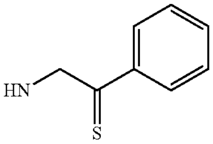 |
| 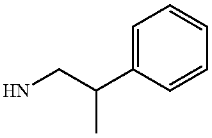 | 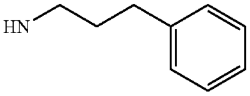 | 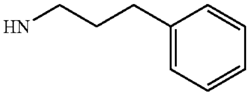 |
| 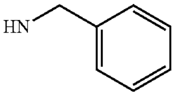 | 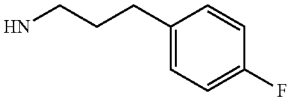 | 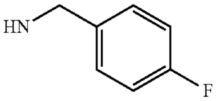 |
| 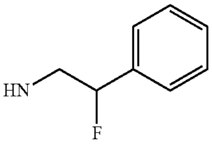 | 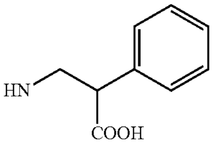 | 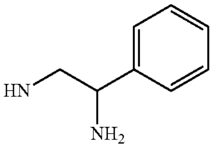 |

-continued
| HN—R | | |
|---|---|---|
| 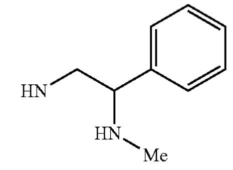 | 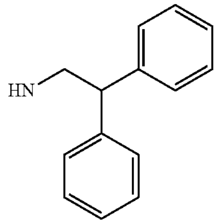 | 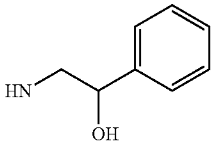 |
| 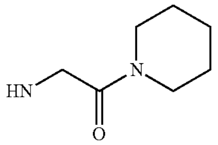 | 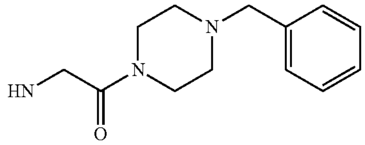 | 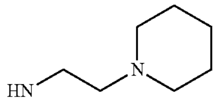 |
| 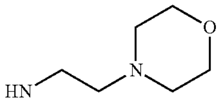 | 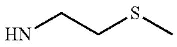 | 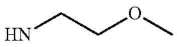 |
| 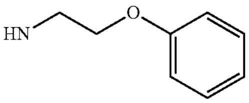 | 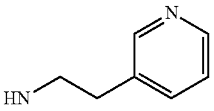 | 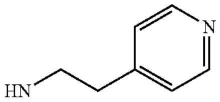 |
| 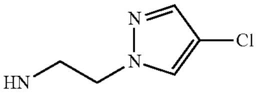 | 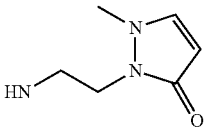 | |
| 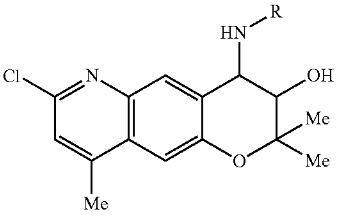 | | |
|---|---|---|
| HN—Me | HN—Et | 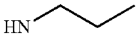 |
| 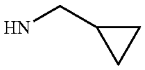 | 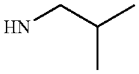 | 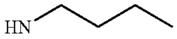 |
| 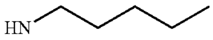 | 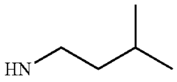 | 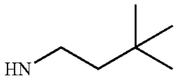 |
| 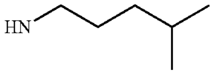 | 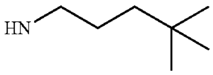 | 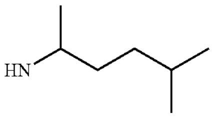 |
| 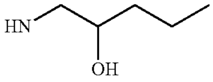 | 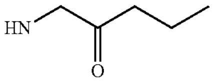 | 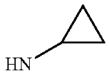 |
| 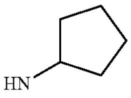 | 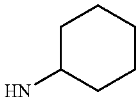 | 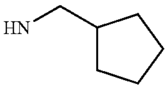 |

-continued
| HN—R | | |
|---|---|---|
| 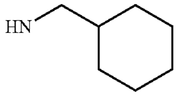 | 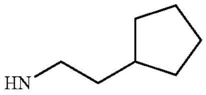 | 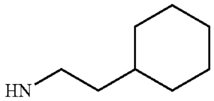 |
| 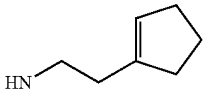 | 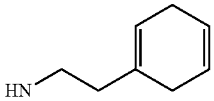 | 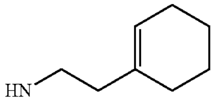 |
| 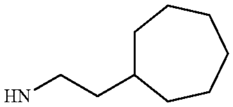 | 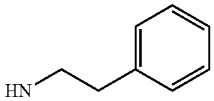 | 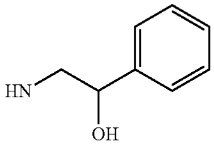 |
| 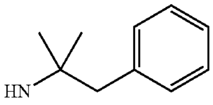 | 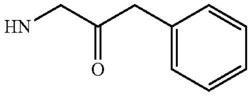 | 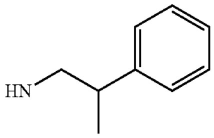 |
| 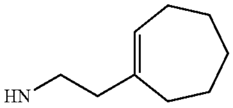 | 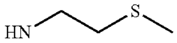 | 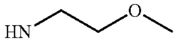 |
| 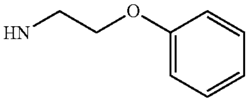 | 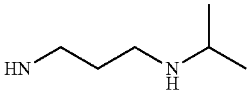 | 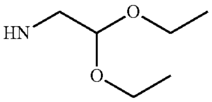 |
| 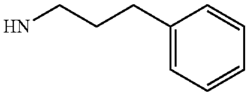 | 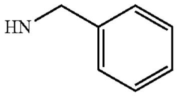 | 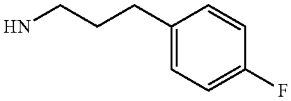 |
| 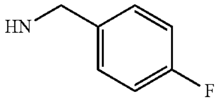 | 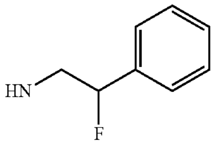 | 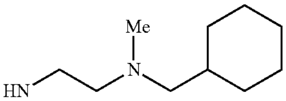 |
| 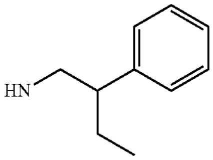 | 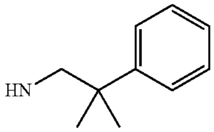 | 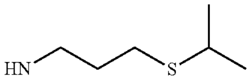 |
| 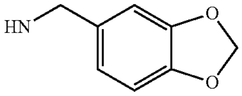 | 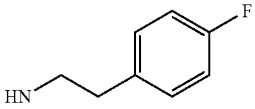 | 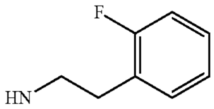 |
| 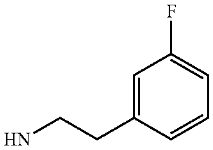 | 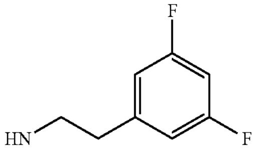 | 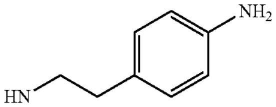 |

-continued
| HN—R | | |
|---|---|---|
| 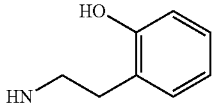 | 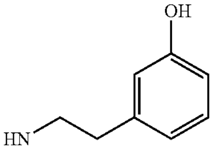 | 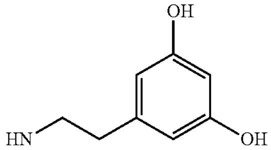 |
| 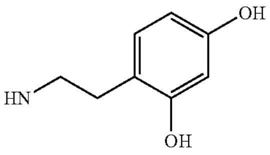 | 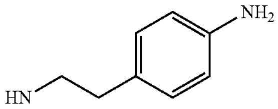 | 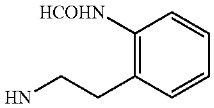 |
| 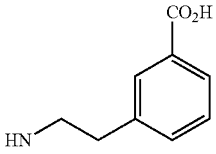 | 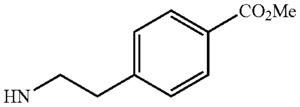 | 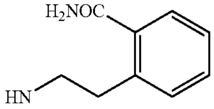 |
| 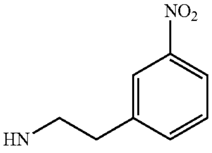 | 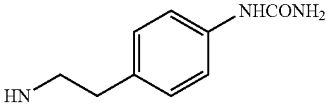 | 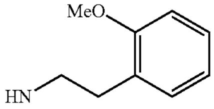 |
| 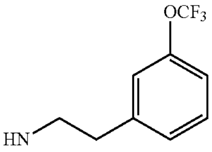 | 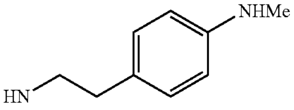 | 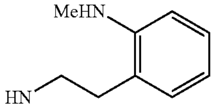 |
| 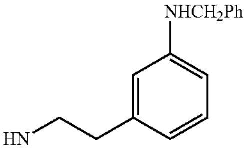 | 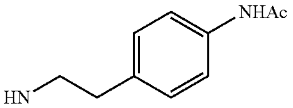 | 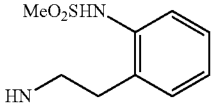 |
| 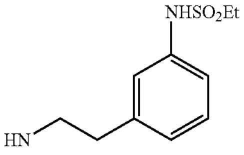 | 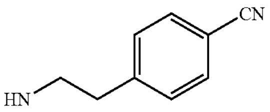 | 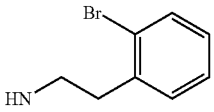 |
| 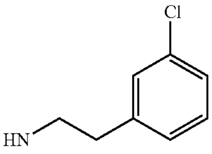 | 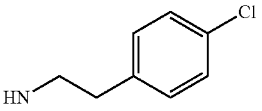 | 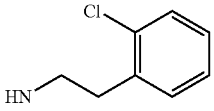 |
| 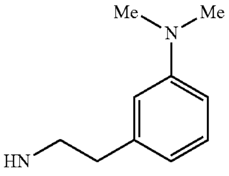 | 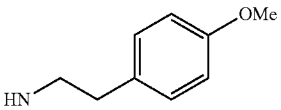 | 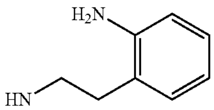 |

-continued
| HN—R | | |
|---|---|---|
| 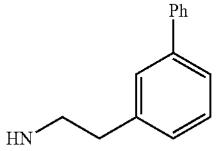 | 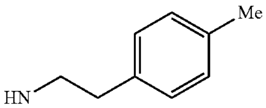 | 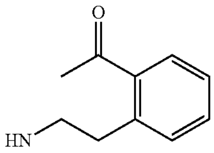 |
| 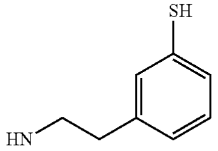 | | |
| 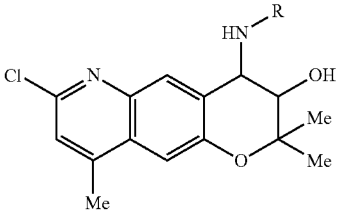 HN—R | | |
|---|---|---|
| 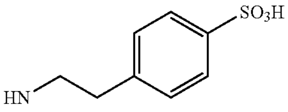 | 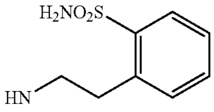 | 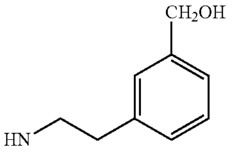 |
| 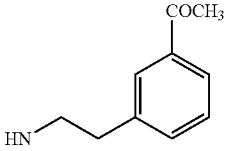 | 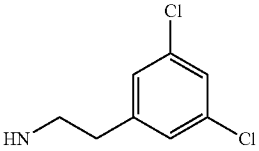 | 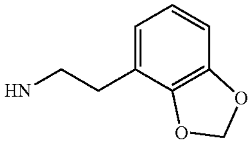 |
| 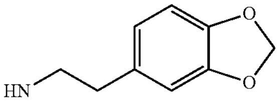 | 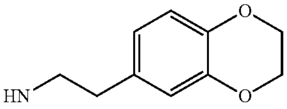 | 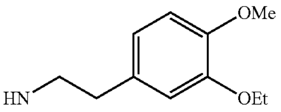 |
| 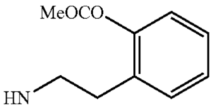 | 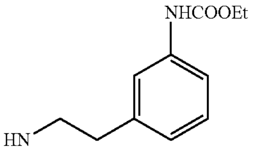 | 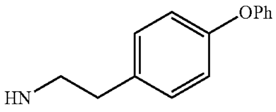 |
| 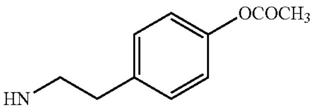 | 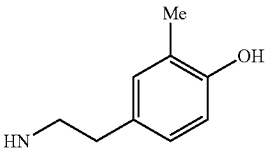 | 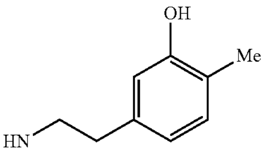 |

-continued
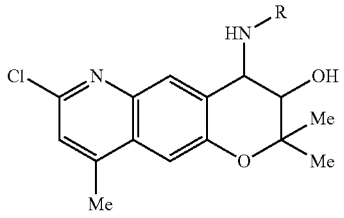
HN—R
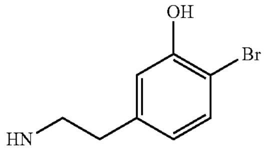
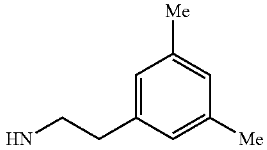
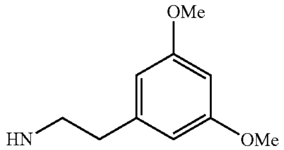
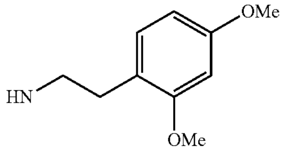
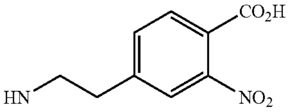
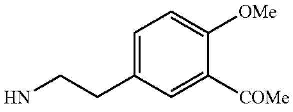
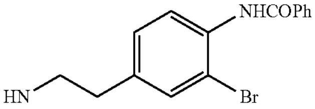
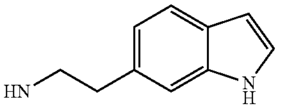
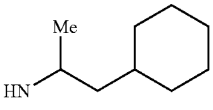
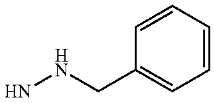
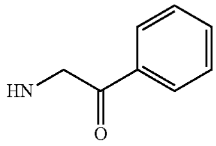
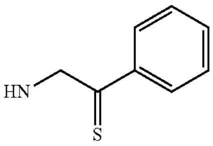
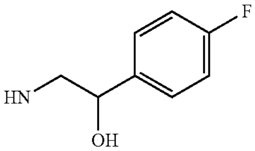
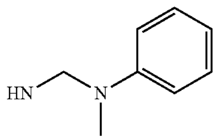
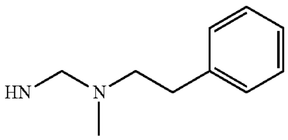
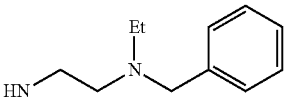
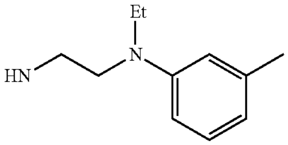
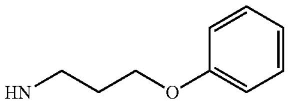
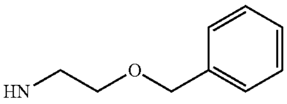
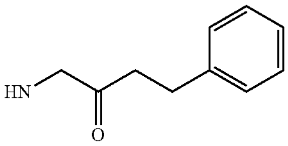
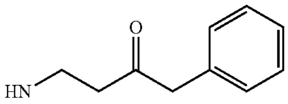
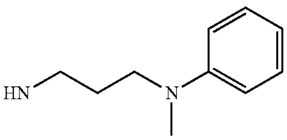
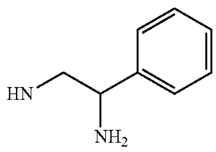
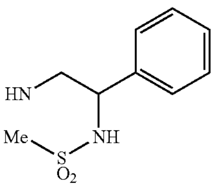

-continued
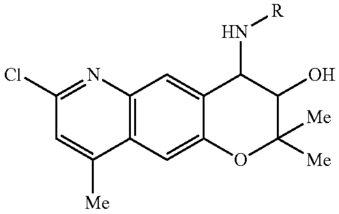
HN—R
| | | |
|---|---|---|
| 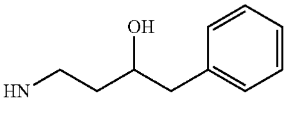 | 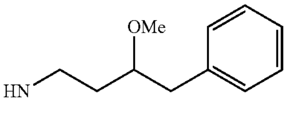 | 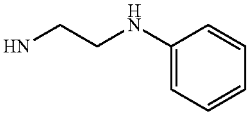 |
| 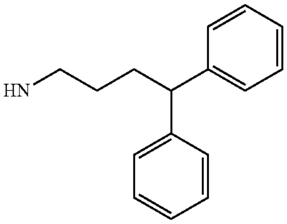 | 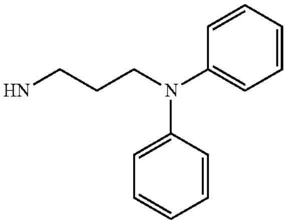 | 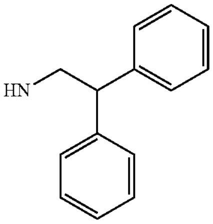 |
| 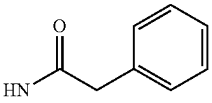 | 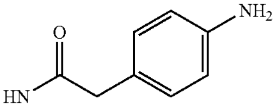 | 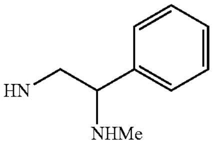 |
| 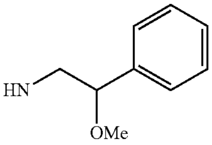 | 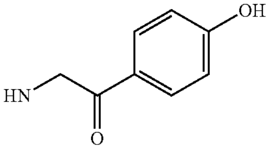 | 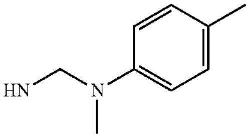 |
| 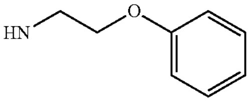 | 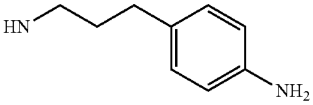 | 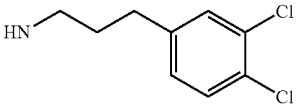 |
HN—R
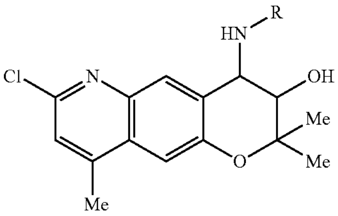
| | | |
|---|---|---|
| 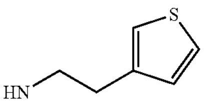 | 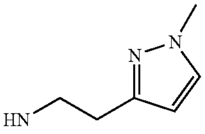 | 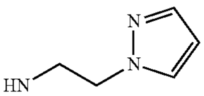 |

-continued
| HN—R | | |
|---|---|---|
| 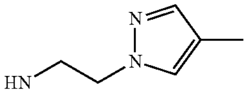 | 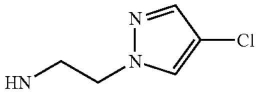 | 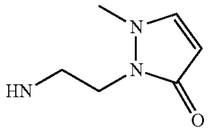 |
| 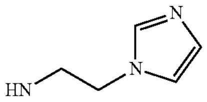 | 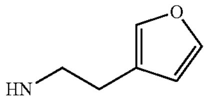 | 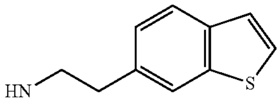 |
| 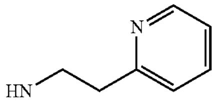 | 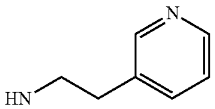 | 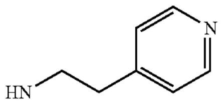 |
| 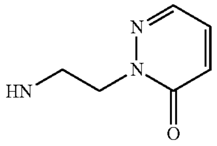 | 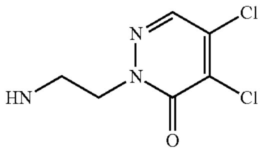 | 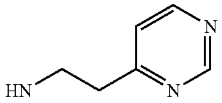 |
| 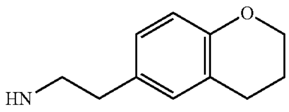 | 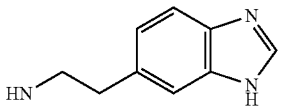 | 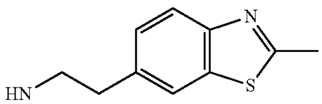 |
| 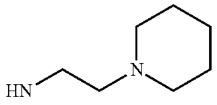 | 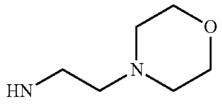 | 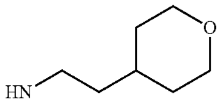 |
| 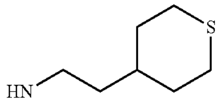 | 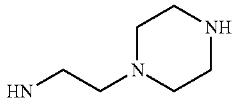 | 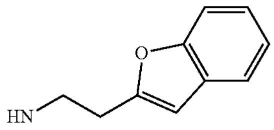 |
| 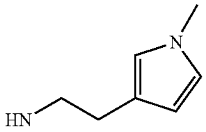 | 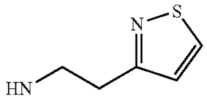 | 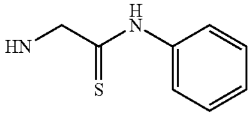 |
| 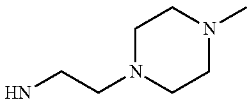 | 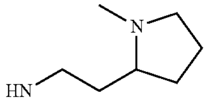 | 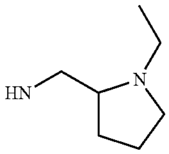 |
| 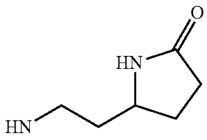 | 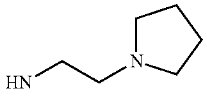 | 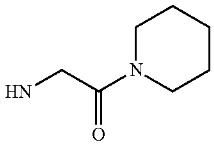 |
| 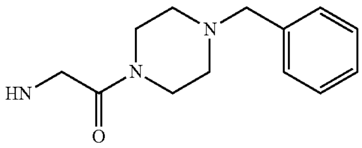 | 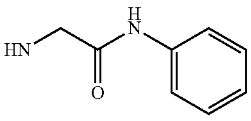 | |

-continued
| HN—R | | |
|---|---|---|
| | 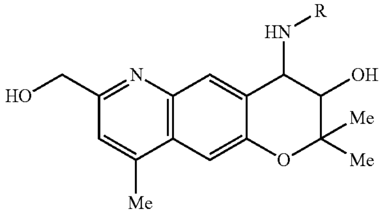 | |
| HN—Me | HN—Et | 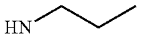 |
| 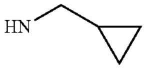 | 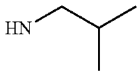 | 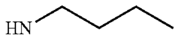 |
| 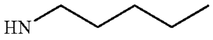 | 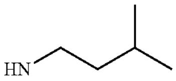 | 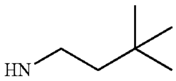 |
| 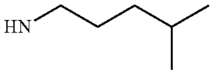 | 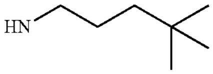 | 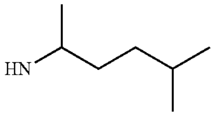 |
| 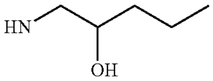 | 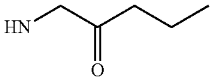 | 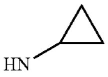 |
| 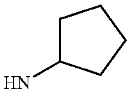 | 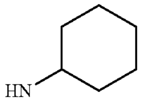 | 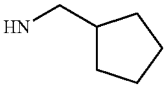 |
| 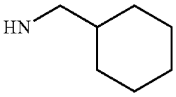 | 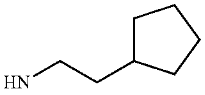 | 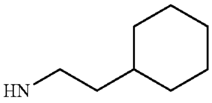 |
| 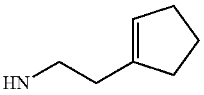 | 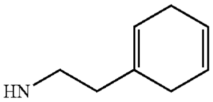 | 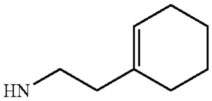 |
| 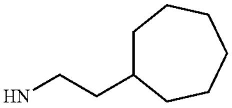 | 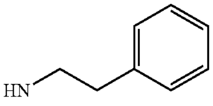 | 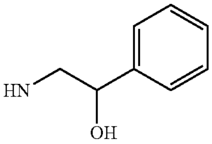 |
| 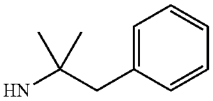 | 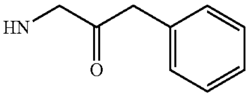 | 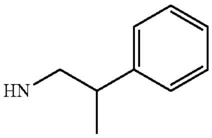 |
| 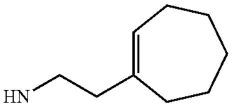 | 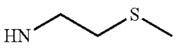 | 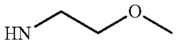 |
| 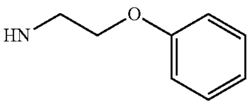 | 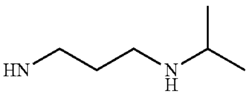 | 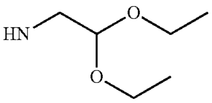 |

-continued
| HN—R | | |
|---|---|---|
| 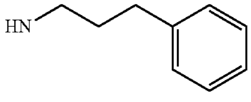 | 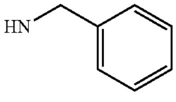 | 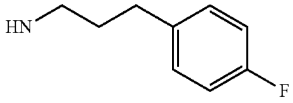 |
| 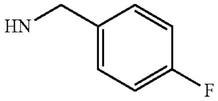 | 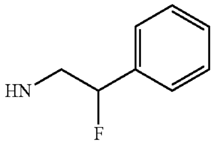 | 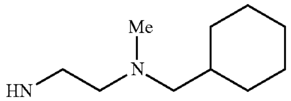 |
| 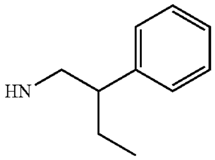 | 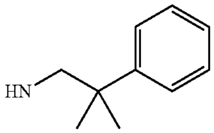 | 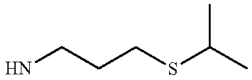 |
| 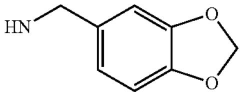 | 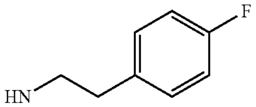 | 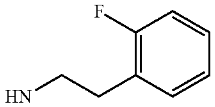 |
| 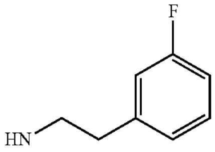 | 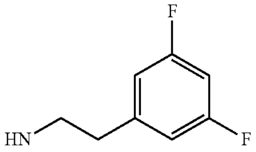 | 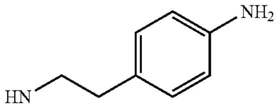 |
| 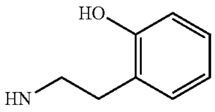 | 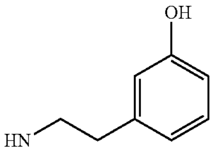 | 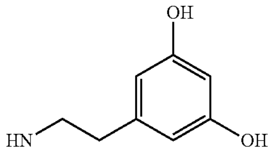 |
| 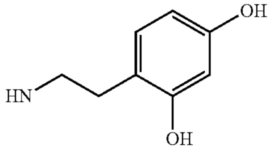 | 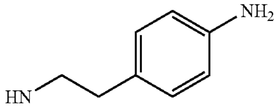 | 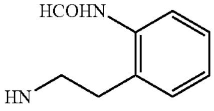 |
| 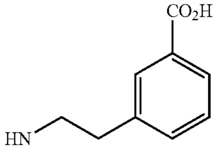 | 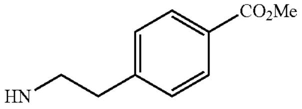 | 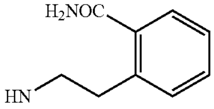 |
| 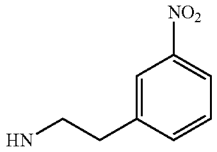 | 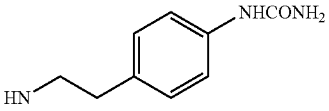 | 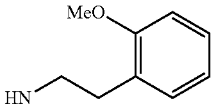 |
| 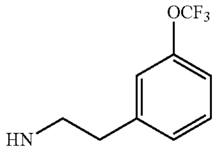 | 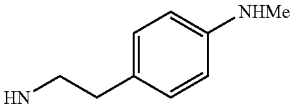 | 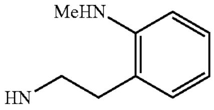 |

-continued
| | HN—R | |
|---|---|---|
| 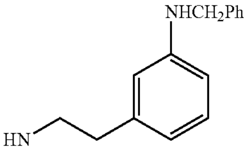 | 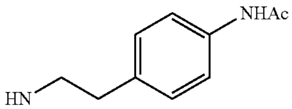 | 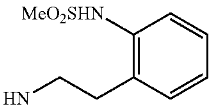 |
| 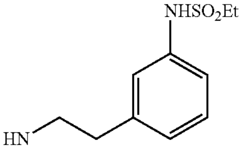 | 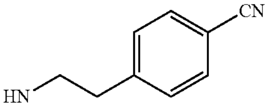 | 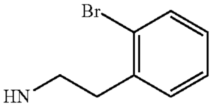 |
| 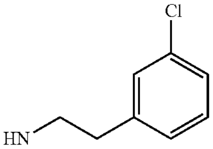 | 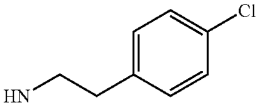 | 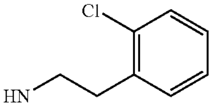 |
| 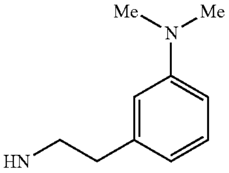 | 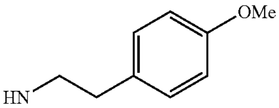 | 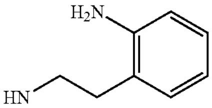 |
| 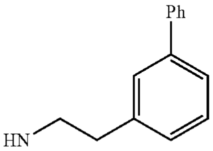 | 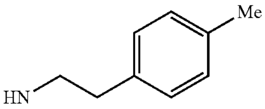 | 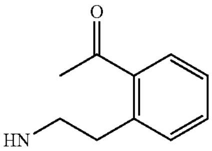 |
| 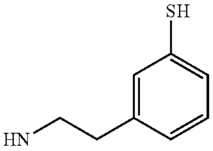 | | |
| | 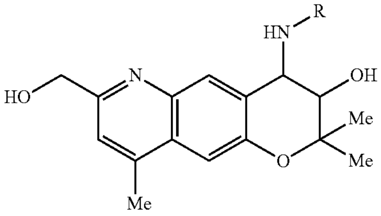 HN—R | |
|---|---|---|
| 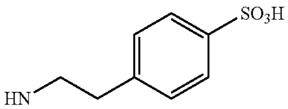 | 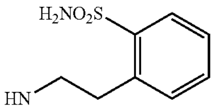 | 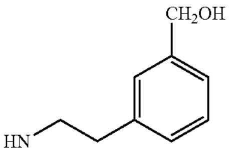 |

-continued
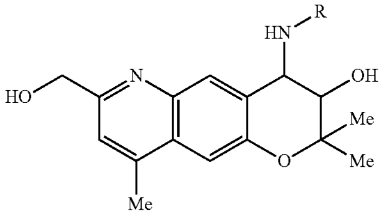
HN—R
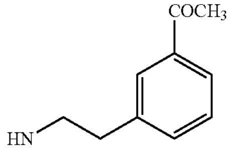 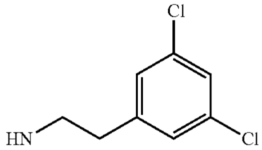 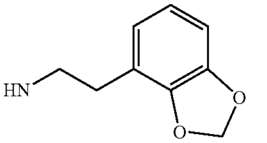
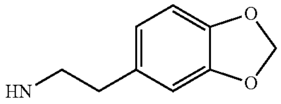 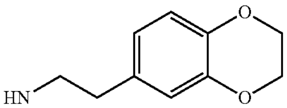 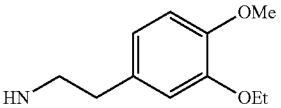
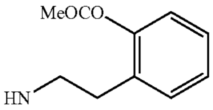 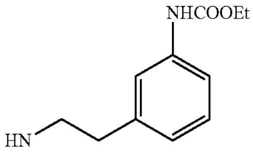 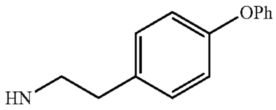
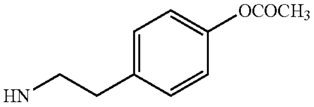 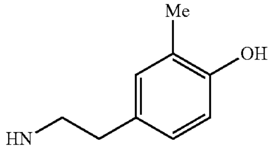 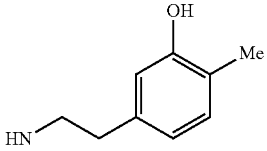
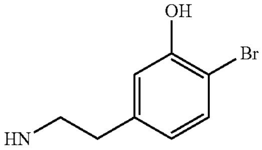 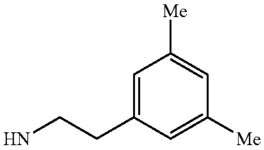 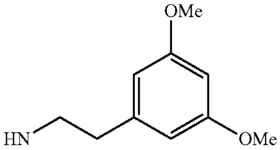
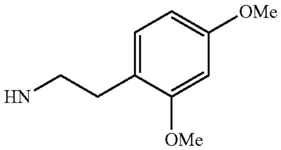 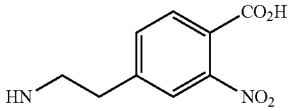 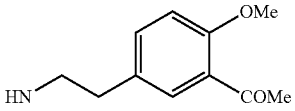
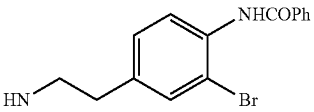 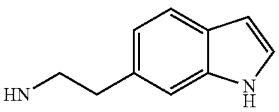 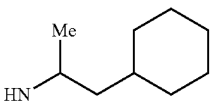
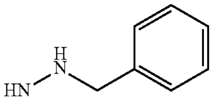 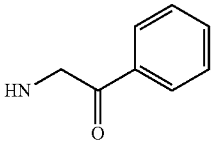 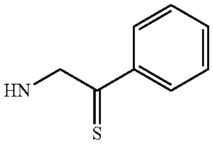
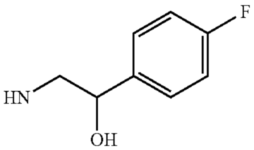 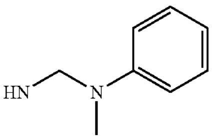 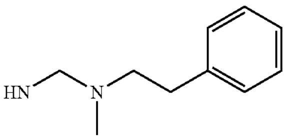

-continued
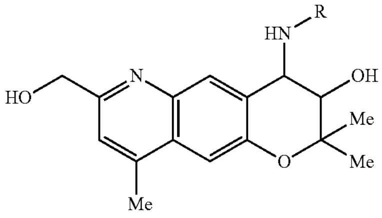
HN—R
| | | |
|---|---|---|
| 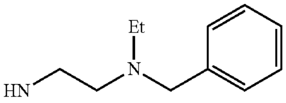 | 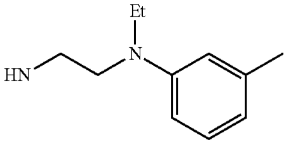 | 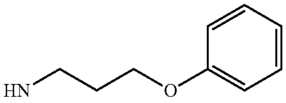 |
| 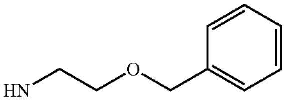 | 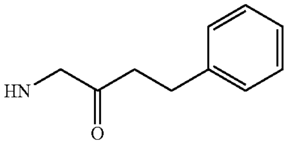 | 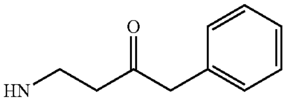 |
| 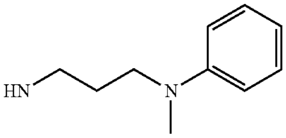 | 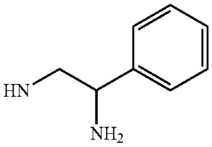 | 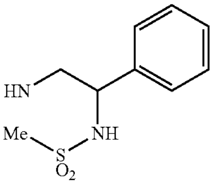 |
| 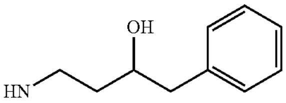 | 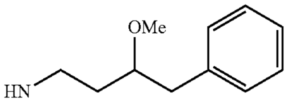 | 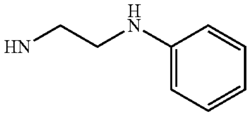 |
| 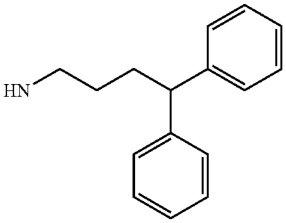 | 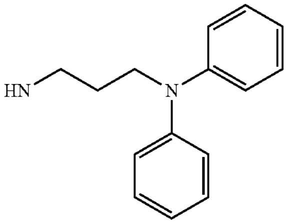 | 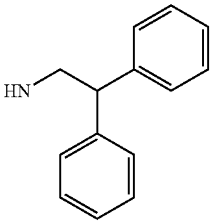 |
| 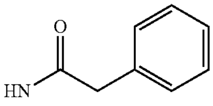 | 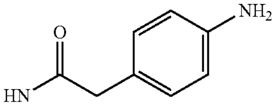 | 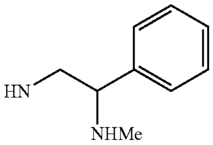 |
| 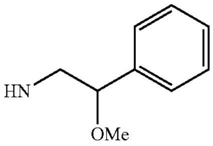 | 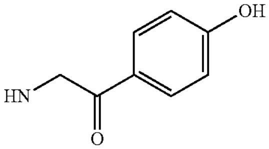 | 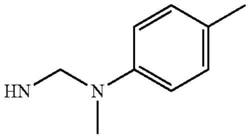 |
| 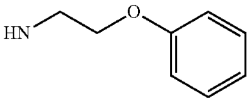 | 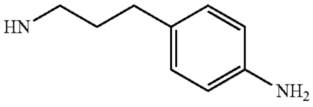 | 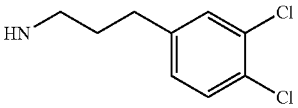 |

| | HN—R | |
|---|---|---|
| | 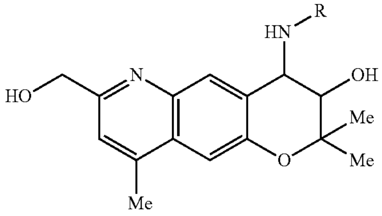 | |
| 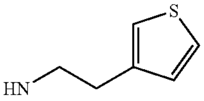 | 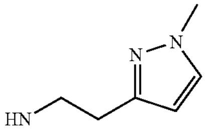 | 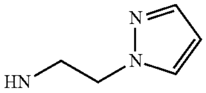 |
| 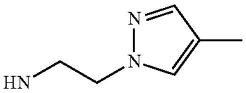 | 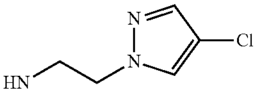 | 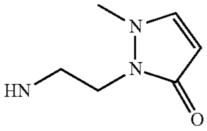 |
| 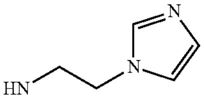 | 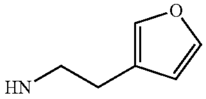 | 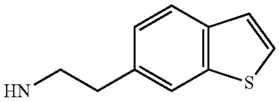 |
| 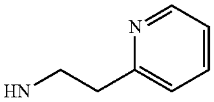 | 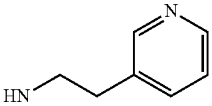 | 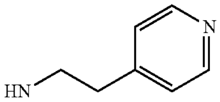 |
| 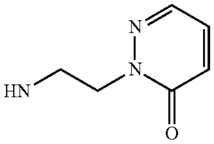 | 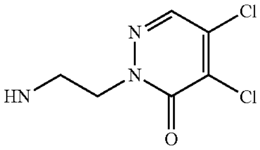 | 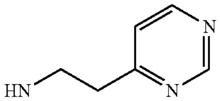 |
| 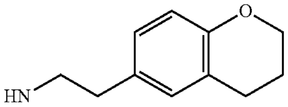 | 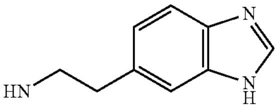 | 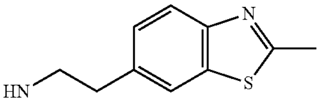 |
| 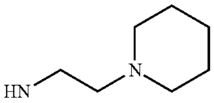 | 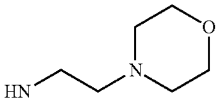 | 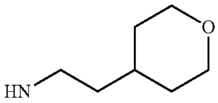 |
| 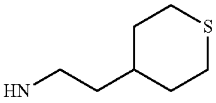 | 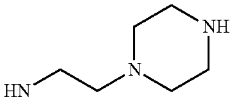 | 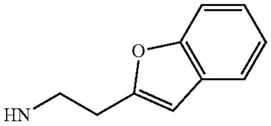 |
| 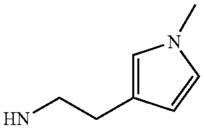 | 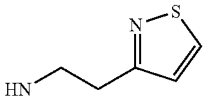 | 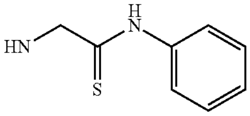 |
| 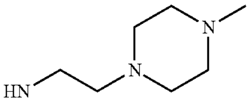 | 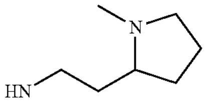 | 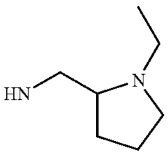 |

-continued
| HN—R | | |
|---|---|---|
| 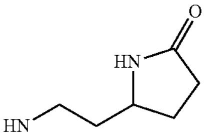 | 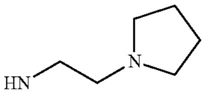 | 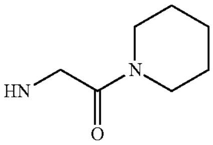 |
| 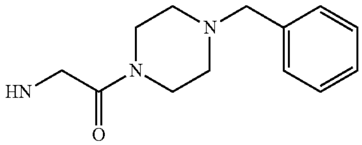 | 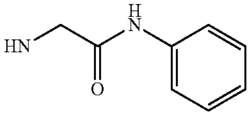 | |
| | 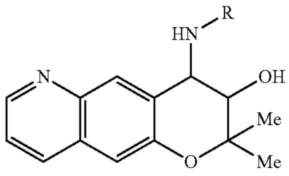 | |
|---|---|---|
| HN—Me | HN—Et | 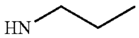 |
| 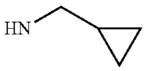 | 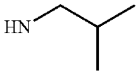 | 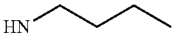 |
| 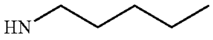 | 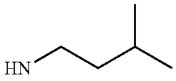 | 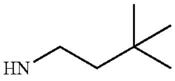 |
| 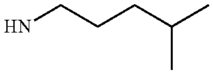 | 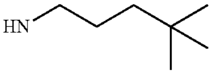 | 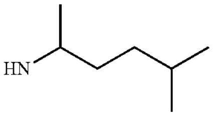 |
| 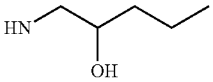 | 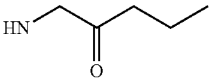 | 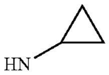 |
| 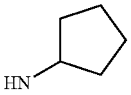 | 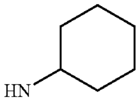 | 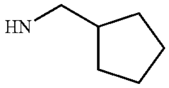 |
| 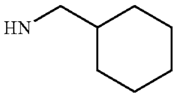 | 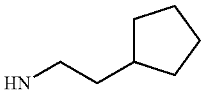 | 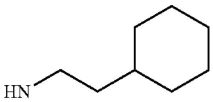 |
| 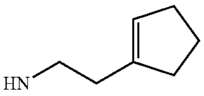 | 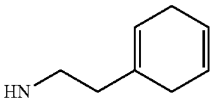 | 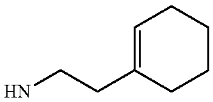 |
| 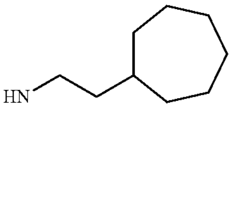 | 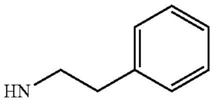 | 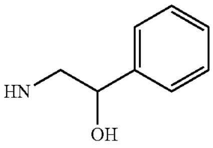 |

-continued
| HN—R | | |
| --- | --- | --- |
| 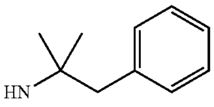 | 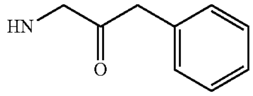 | 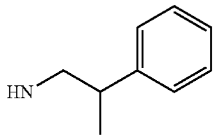 |
| 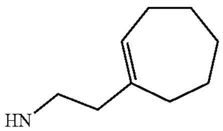 | 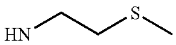 | 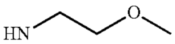 |
| 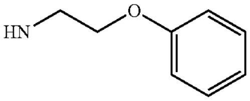 | 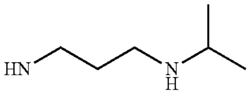 | 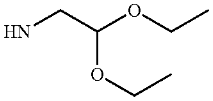 |
| 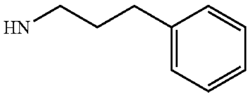 | 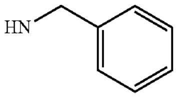 | 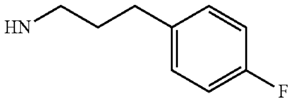 |
| 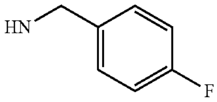 | 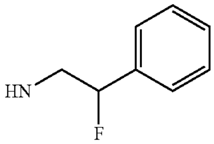 | 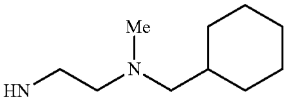 |
| 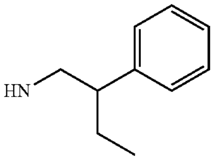 | 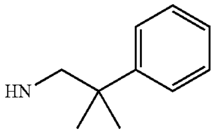 | 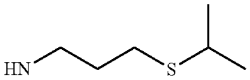 |
| 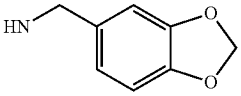 | 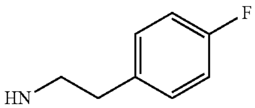 | 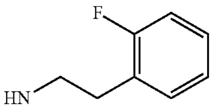 |
| 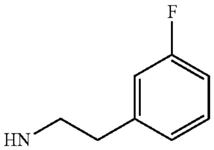 | 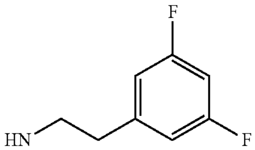 | 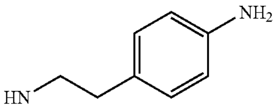 |
| 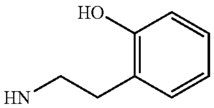 | 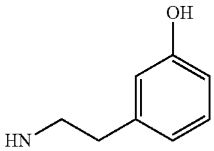 | 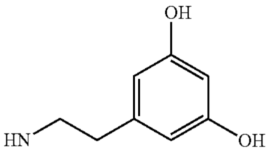 |
| 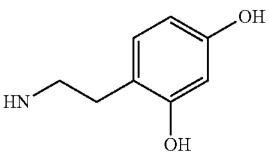 | 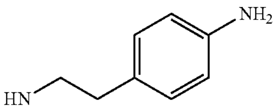 | 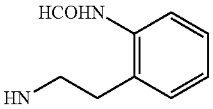 |

-continued
| | HN—R | |
|---|---|---|
| 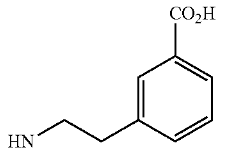 | 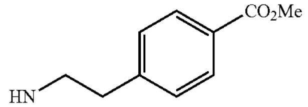 | 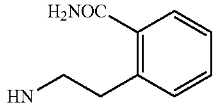 |
| 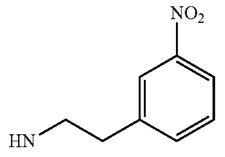 | 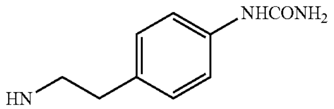 | 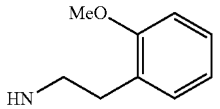 |
| 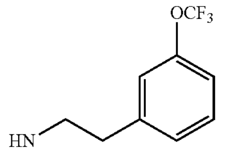 | 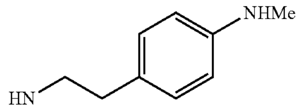 | 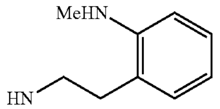 |
| 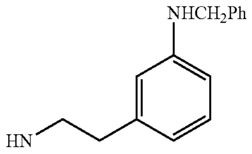 | 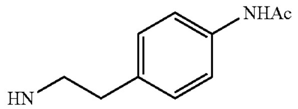 | 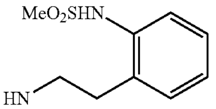 |
| 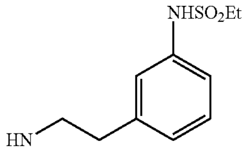 | 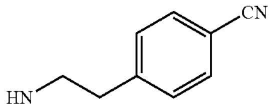 | 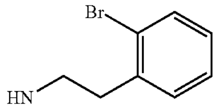 |
| 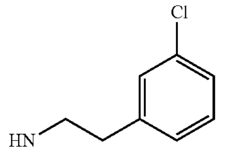 | 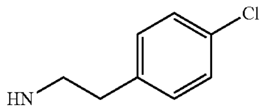 | 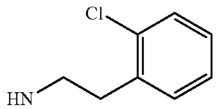 |
| 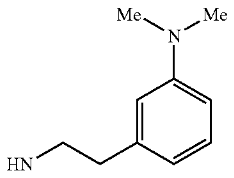 | 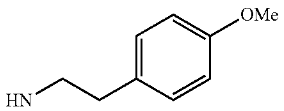 | 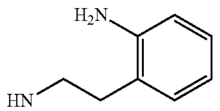 |
| 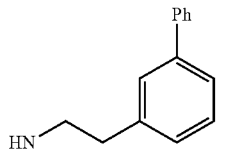 | 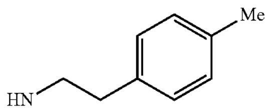 | 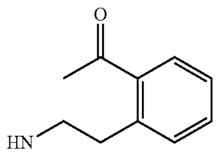 |
| 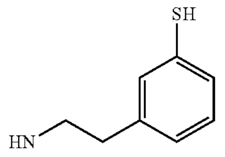 | | |

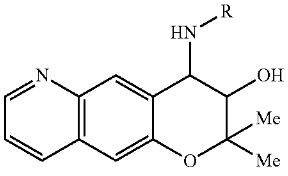
HN—R
| | | |
|---|---|---|
| 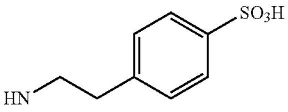 | 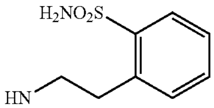 | 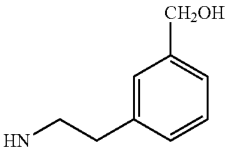 |
| 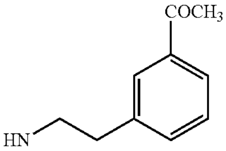 | 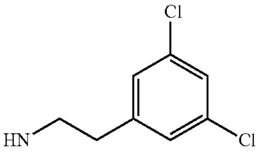 | 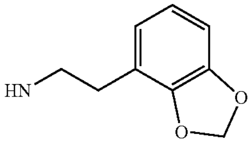 |
| 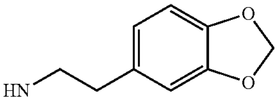 | 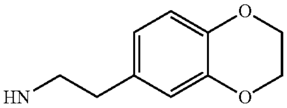 | 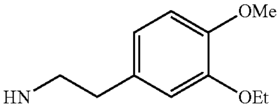 |
| 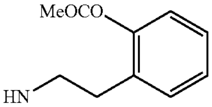 | 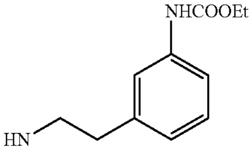 | 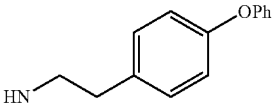 |
| 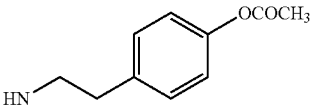 | 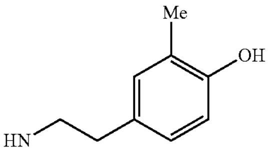 | 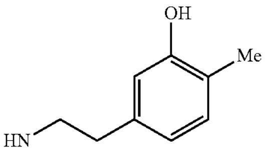 |
| 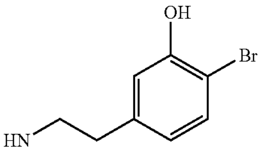 | 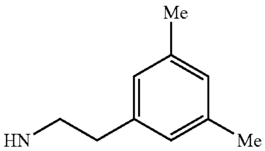 | 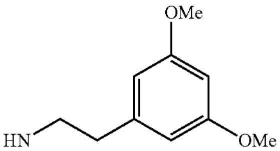 |
| 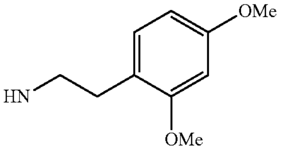 | 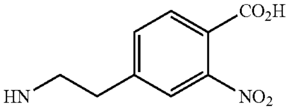 | 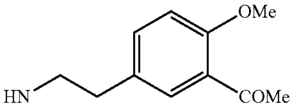 |
| 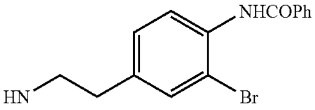 | 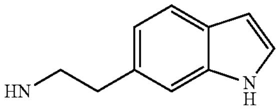 | 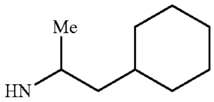 |
| 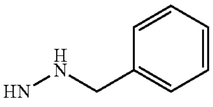 | 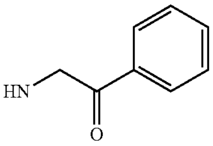 | 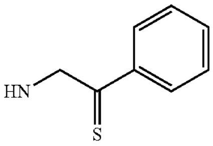 |

-continued
| | 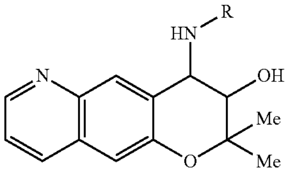<br>HN—R | |
|---|---|---|
| 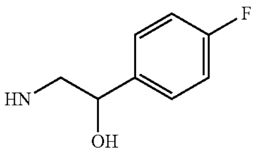 | 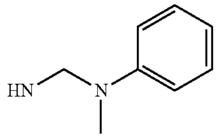 | 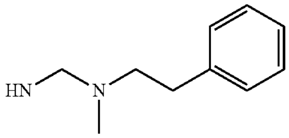 |
| 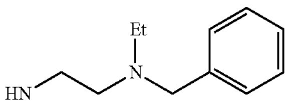 | 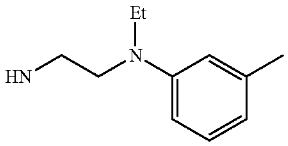 | 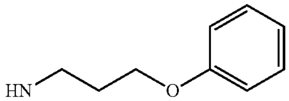 |
| 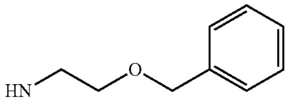 | 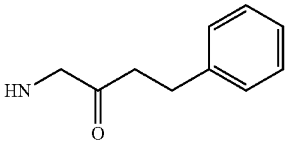 | 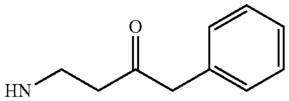 |
| 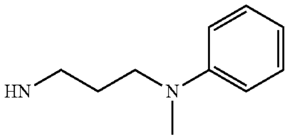 | 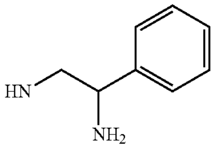 | 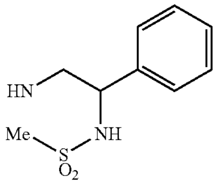 |
| 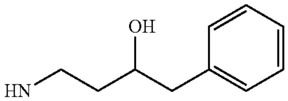 | 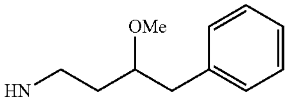 | 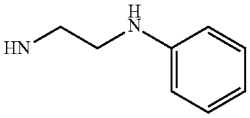 |
| 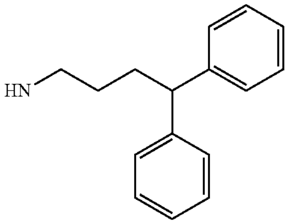 | 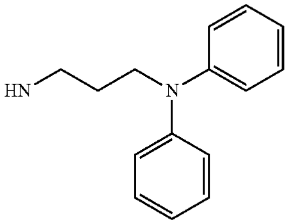 | 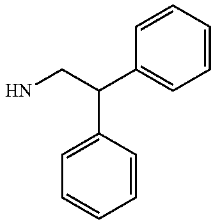 |
| 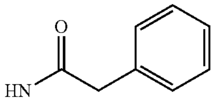 | 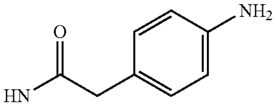 | 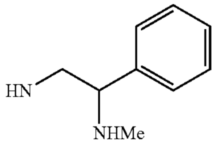 |
| 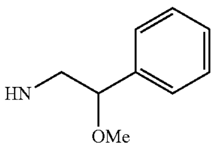 | 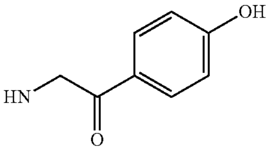 | 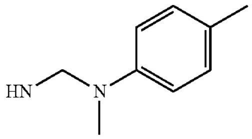 |

-continued
| 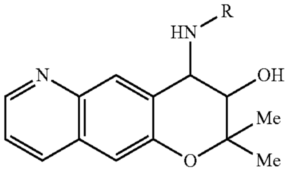<br>HN—R | | |
|---|---|---|
| 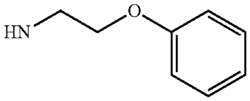 | 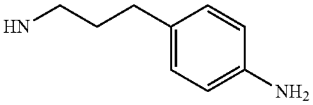 | 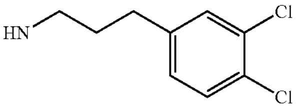 |
| HN—R | | |
|---|---|---|
| 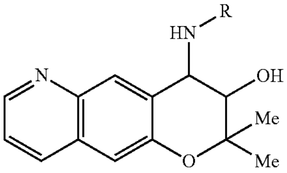 | | |
| 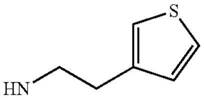 | 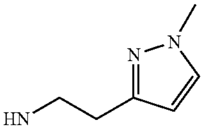 | 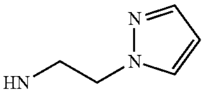 |
| 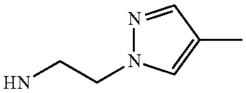 | 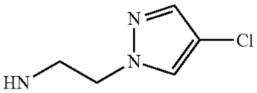 | 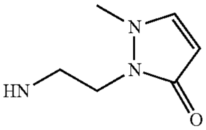 |
| 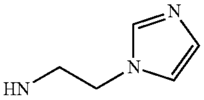 | 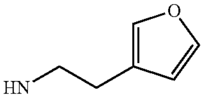 | 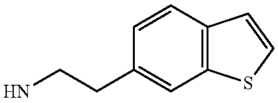 |
| 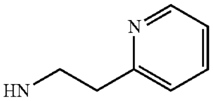 | 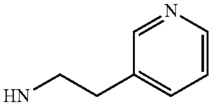 | 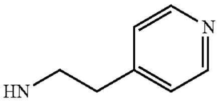 |
| 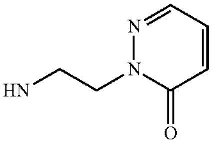 | 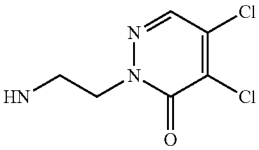 | 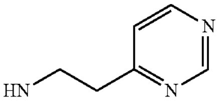 |
| 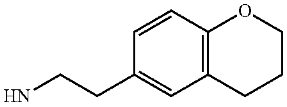 | 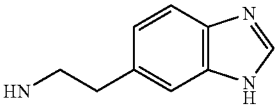 | 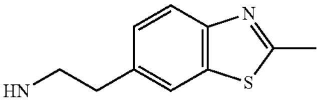 |
| 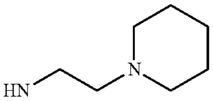 | 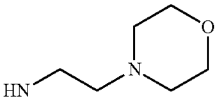 | 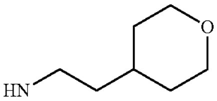 |

-continued
| HN—R | | |
|---|---|---|
| 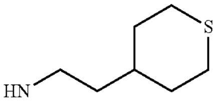 | 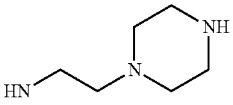 | 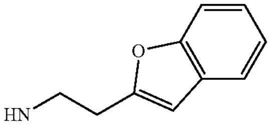 |
| 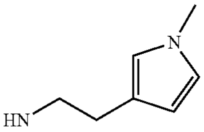 | 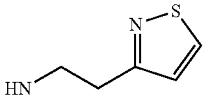 | 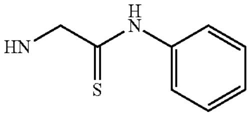 |
| 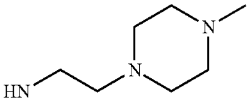 | 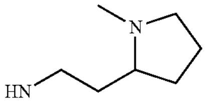 | 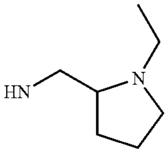 |
| 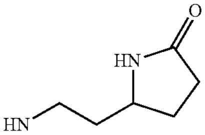 | 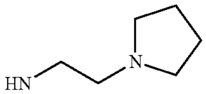 | 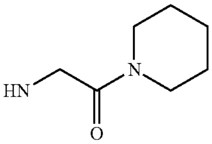 |
| 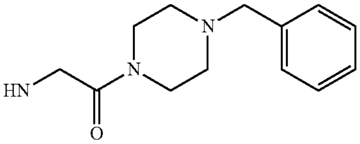 | 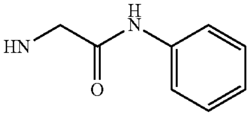 | |
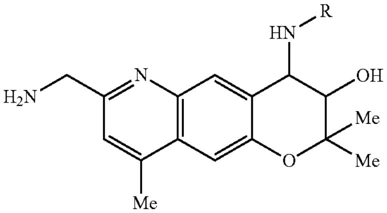
| | | |
|---|---|---|
| HN—Me | HN—Et | 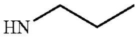 |
| 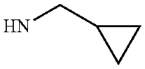 | 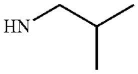 | 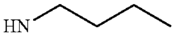 |
| 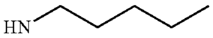 | 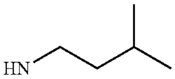 | 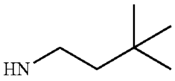 |
| 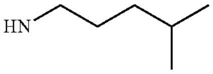 | 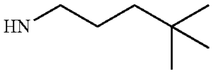 | 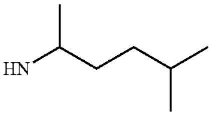 |
| 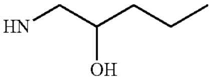 | 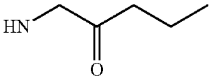 | 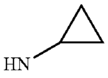 |
| 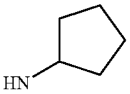 | 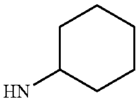 | 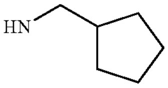 |

-continued
| HN—R | | |
|---|---|---|
| 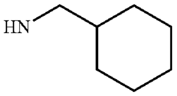 | 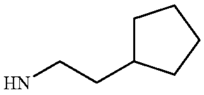 | 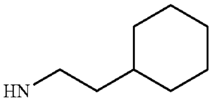 |
| 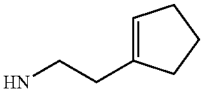 | 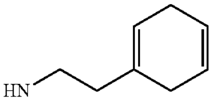 | 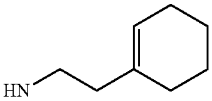 |
| 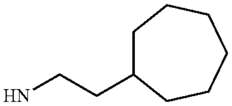 | 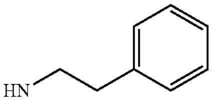 | 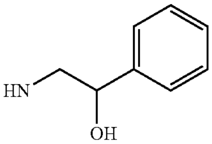 |
| 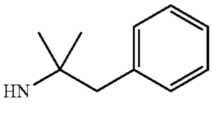 | 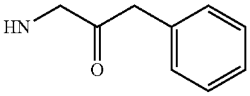 | 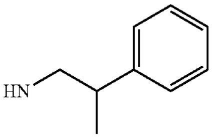 |
| 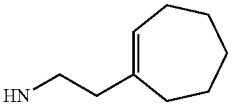 | 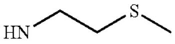 | 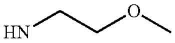 |
| 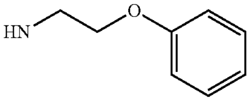 | 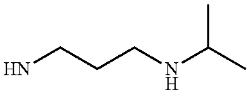 | 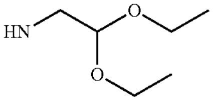 |
| 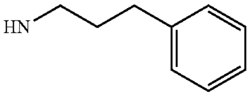 | 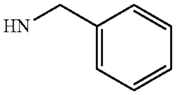 | 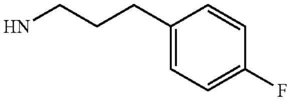 |
| 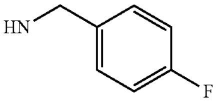 | 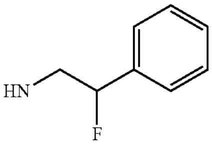 | 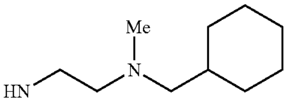 |
| 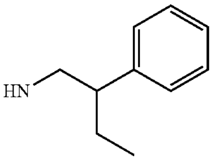 | 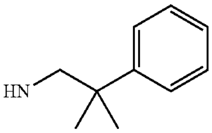 | 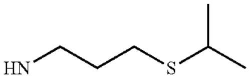 |
| 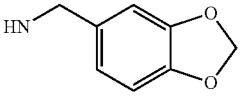 | 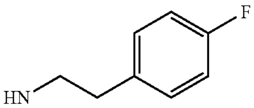 | 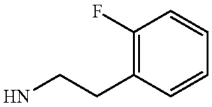 |
| 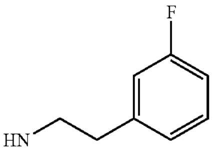 | 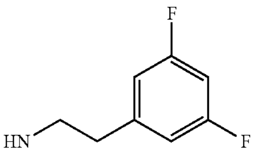 | 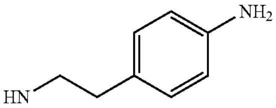 |

-continued
| HN—R | | |
|---|---|---|
| 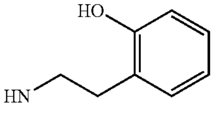 | 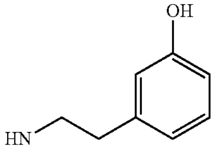 | 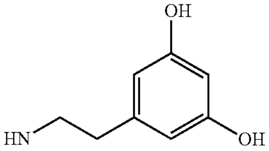 |
| 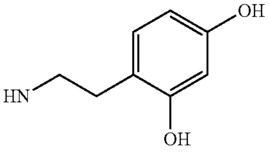 | 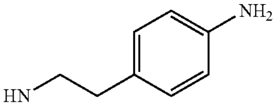 | 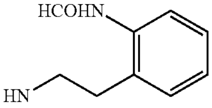 |
| 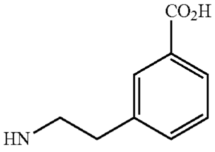 | 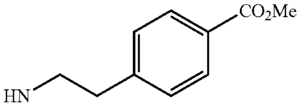 | 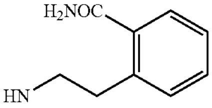 |
| 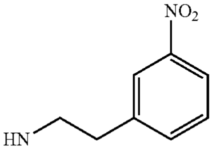 | 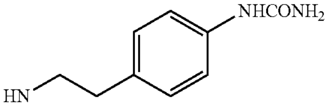 | 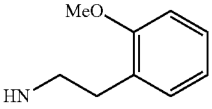 |
| 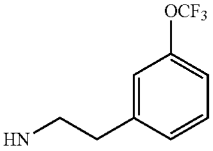 | 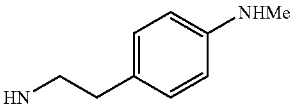 | 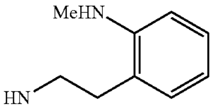 |
| 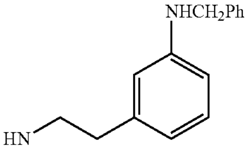 | 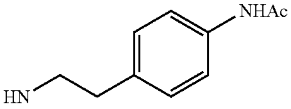 | 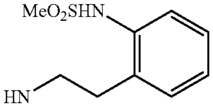 |
| 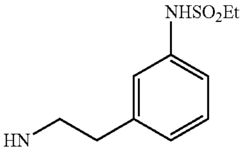 | 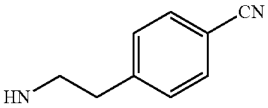 | 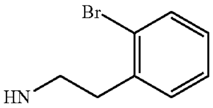 |
| 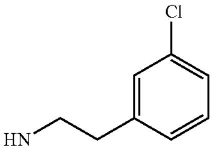 | 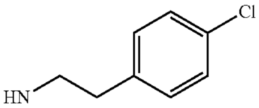 | 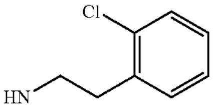 |
| 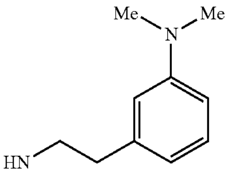 | 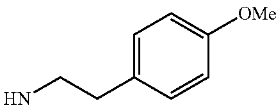 | 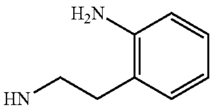 |

-continued
| HN—R | | |
|---|---|---|
| 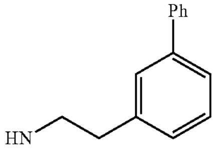 | 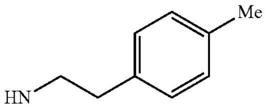 | 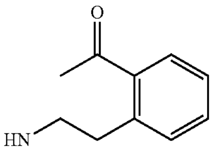 |
| 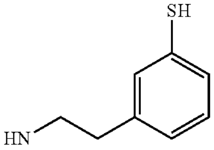 | | |
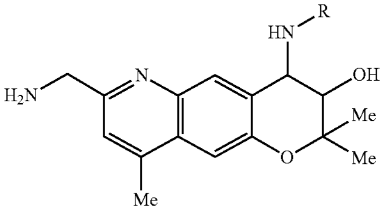
| HN—R | | |
|---|---|---|
| 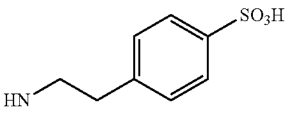 | 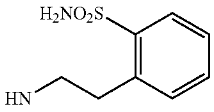 | 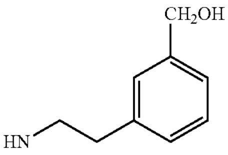 |
| 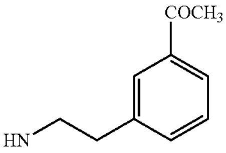 | 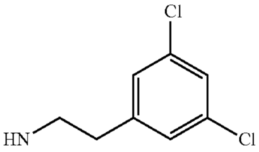 | 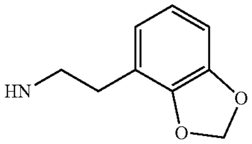 |
| 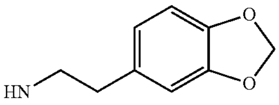 | 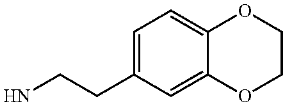 | 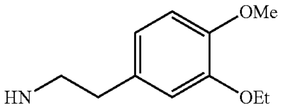 |
| 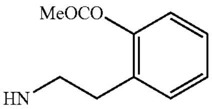 | 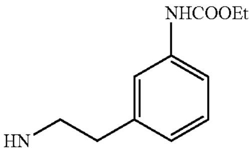 | 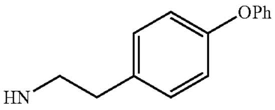 |
| 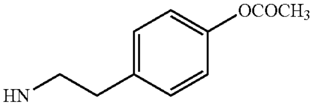 | 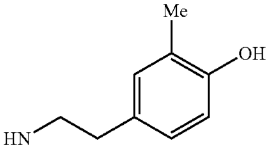 | 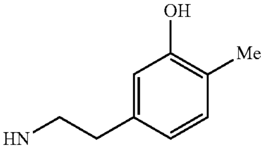 |
| 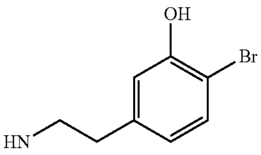 | 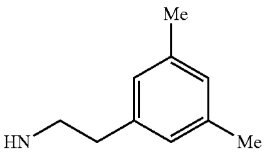 | 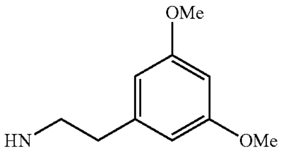 |

-continued
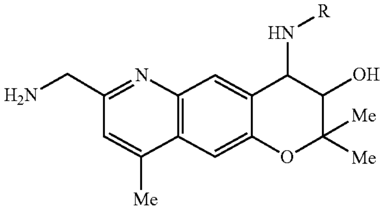
HN—R
| | | |
|---|---|---|
| 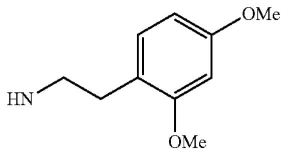 | 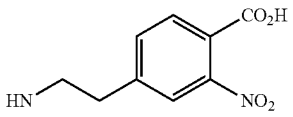 | 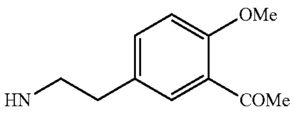 |
| 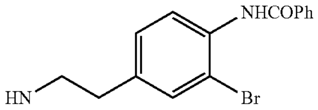 | 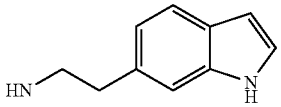 | 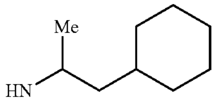 |
| 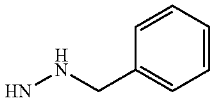 | 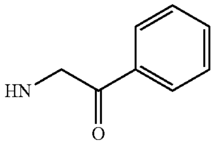 | 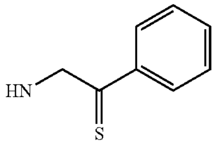 |
| 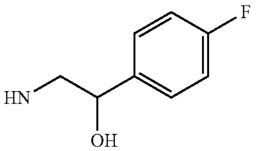 | 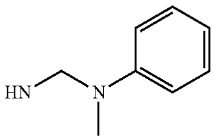 | 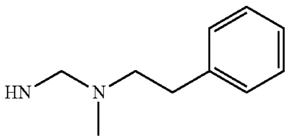 |
| 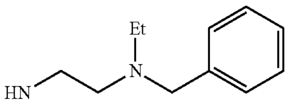 | 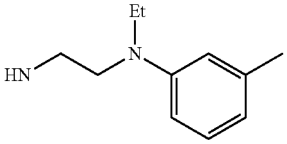 | 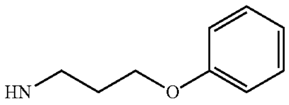 |
| 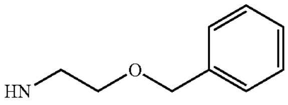 | 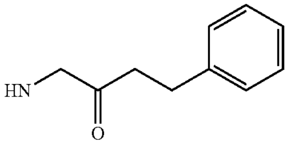 | 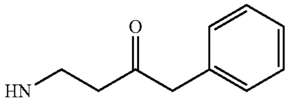 |
| 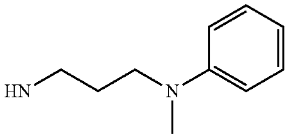 | 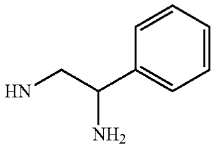 | 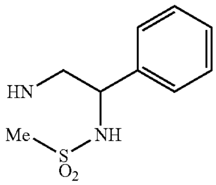 |
| 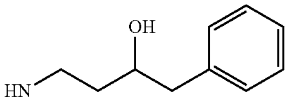 | 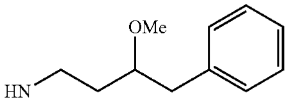 | 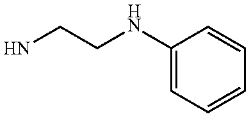 |

-continued
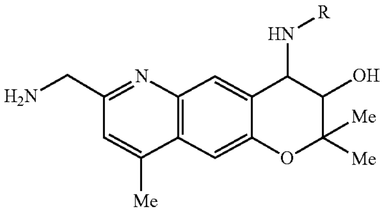
HN—R
| | | |
|---|---|---|
| 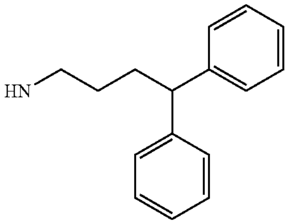 | 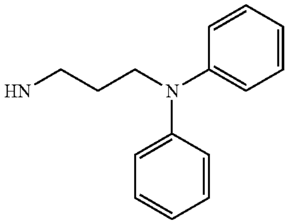 | 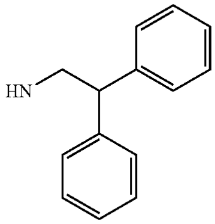 |
| 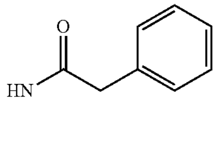 | 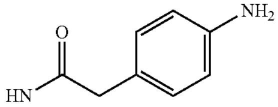 | 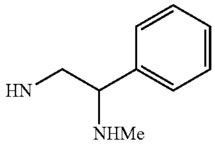 |
| 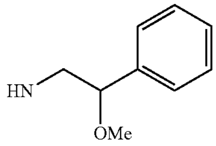 | 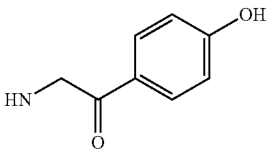 | 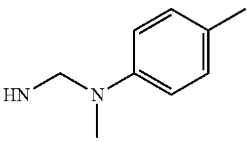 |
| 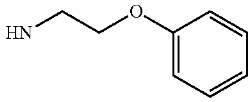 | 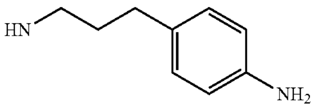 | 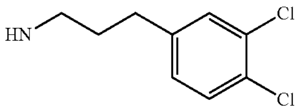 |
HN—R
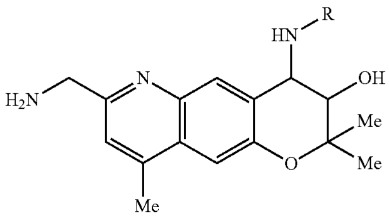
| | | |
|---|---|---|
| 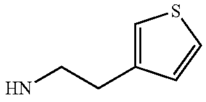 | 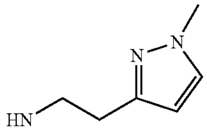 | 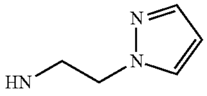 |
| 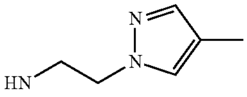 | 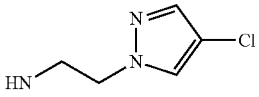 | 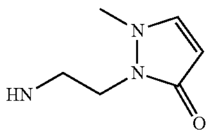 |

-continued
| HN—R | | |
|---|---|---|
| 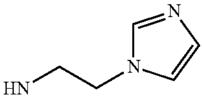 | 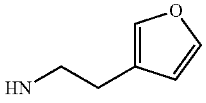 | 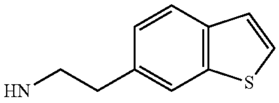 |
| 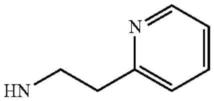 | 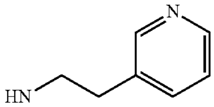 | 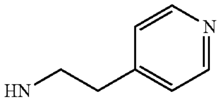 |
| 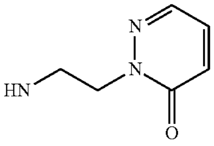 | 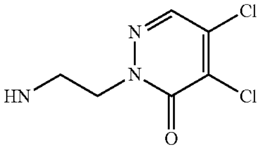 | 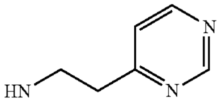 |
| 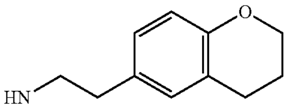 | 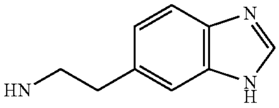 | 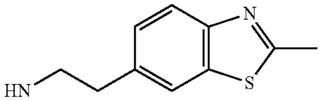 |
| 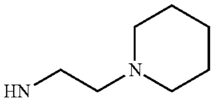 | 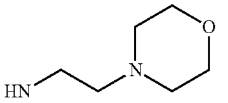 | 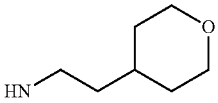 |
| 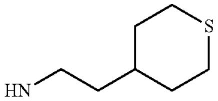 | 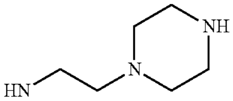 | 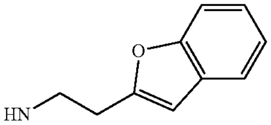 |
| 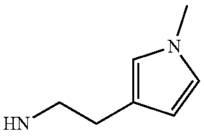 | 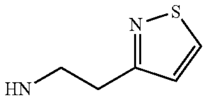 | 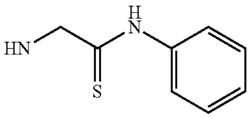 |
| 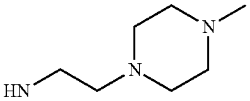 | 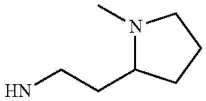 | 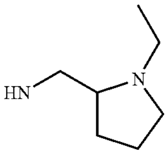 |
| 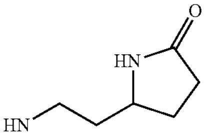 | 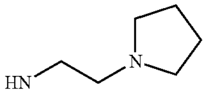 | 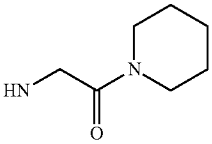 |
| 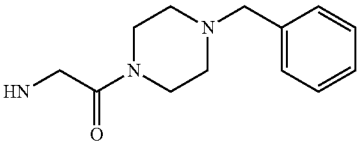 | 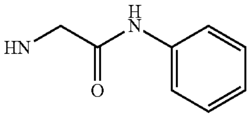 | |

-continued
| | HN—R | |
|---|---|---|
| | 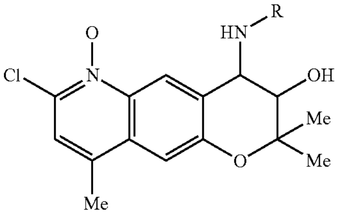 | |
| HN—Me | HN—Et | 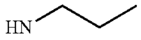 |
| 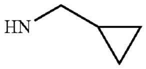 | 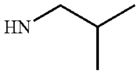 | 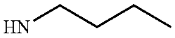 |
| 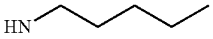 | 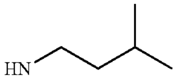 | 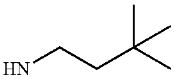 |
| 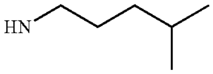 | 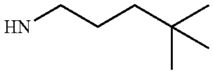 | 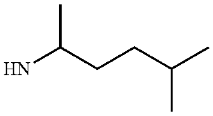 |
| 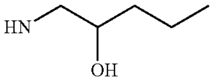 | 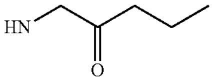 | 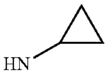 |
| 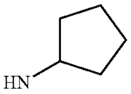 | 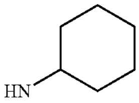 | 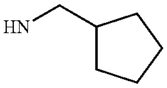 |
| 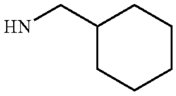 | 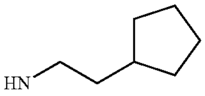 | 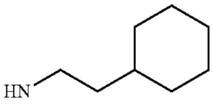 |
| 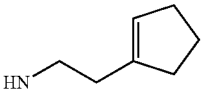 | 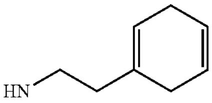 | 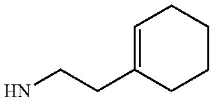 |
| 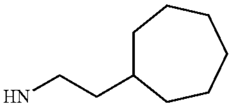 | 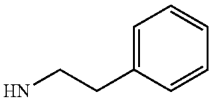 | 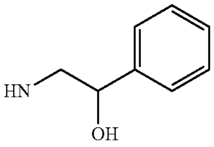 |
| 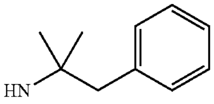 | 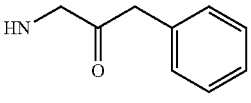 | 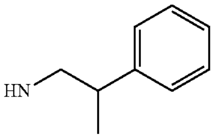 |
| 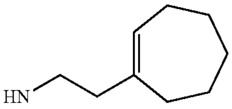 | 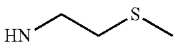 | 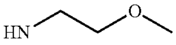 |
| 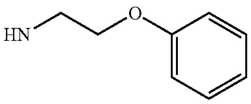 | 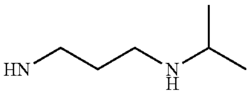 | 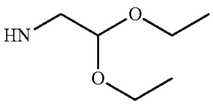 |

-continued
| HN—R | | |
|---|---|---|
| 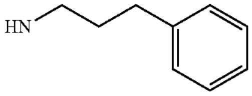 | 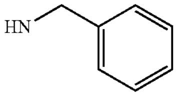 | 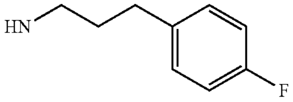 |
| 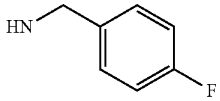 | 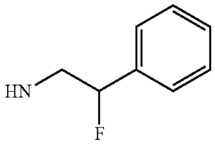 | 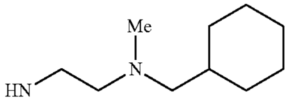 |
| 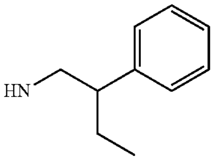 | 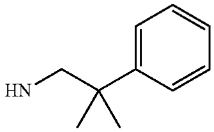 | 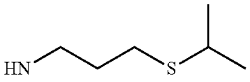 |
| 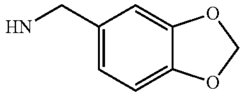 | 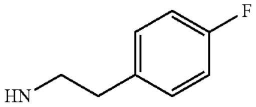 | 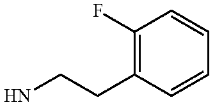 |
| 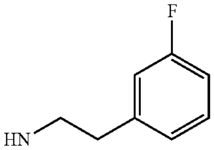 | 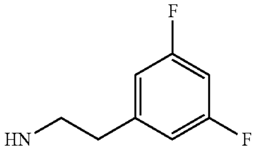 | 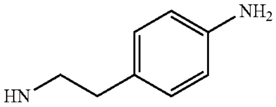 |
| 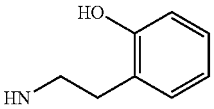 | 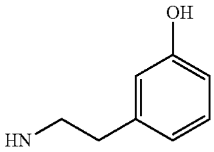 | 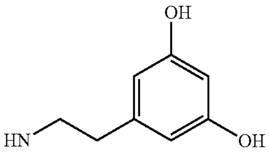 |
| 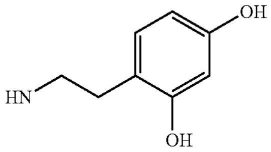 | 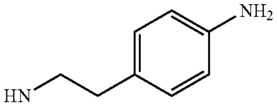 | 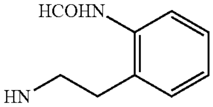 |
| 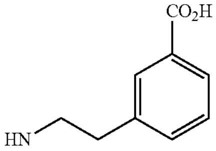 | 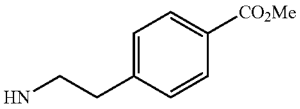 | 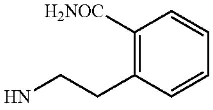 |
| 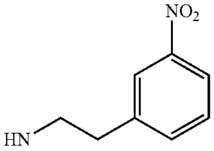 | 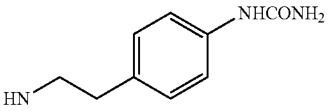 | 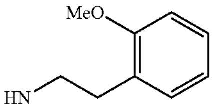 |
| 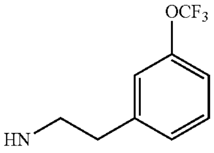 | 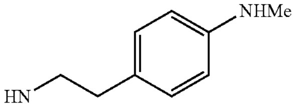 | 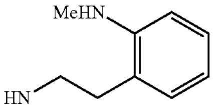 |

-continued
| HN—R | | |
|---|---|---|
| 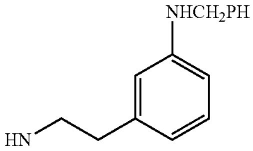 | 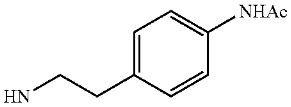 | 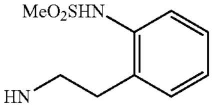 |
| 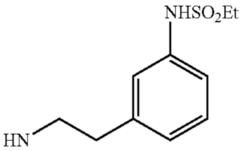 | 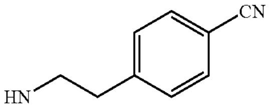 | 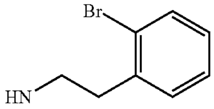 |
| 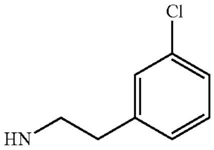 | 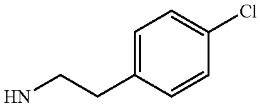 | 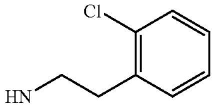 |
| 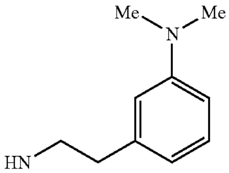 | 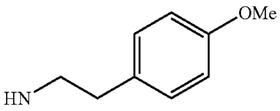 | 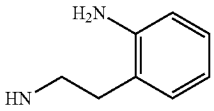 |
| 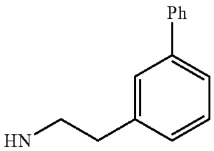 | 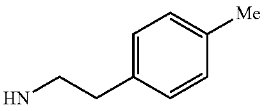 | 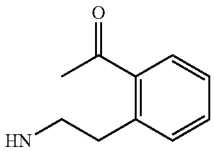 |
| 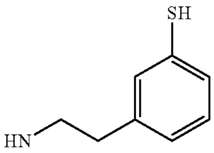 | | |
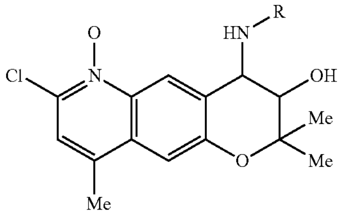
| HN—R | | |
|---|---|---|
| 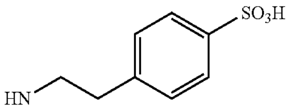 | 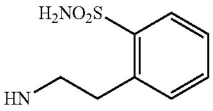 | 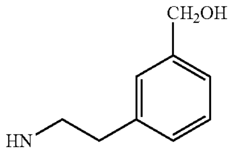 |

-continued
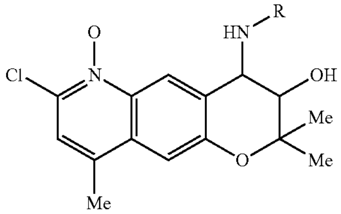
HN—R
| | | |
|---|---|---|
| 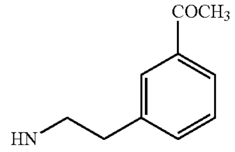 | 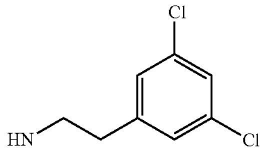 | 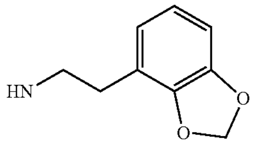 |
| 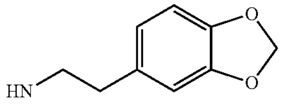 | 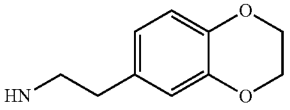 | 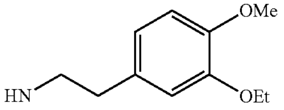 |
| 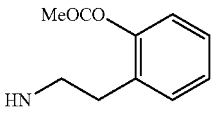 | 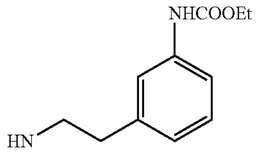 | 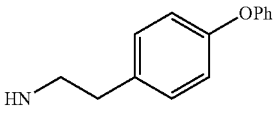 |
| 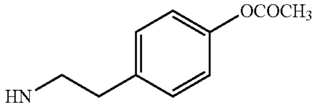 | 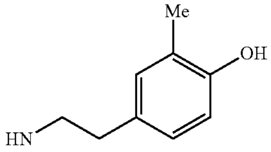 | 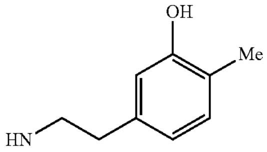 |
| 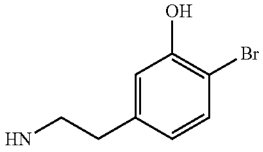 | 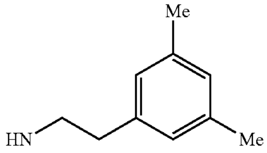 | 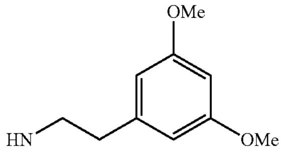 |
| 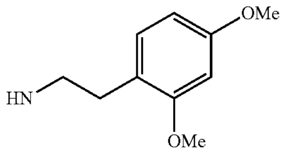 | 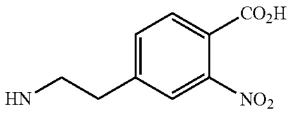 | 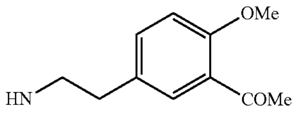 |
| 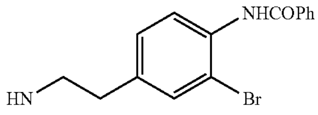 | 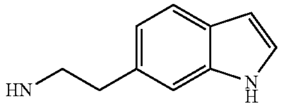 | 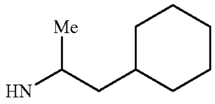 |
| 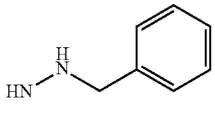 | 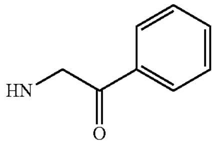 | 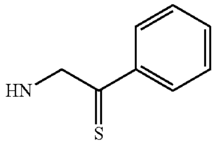 |
| 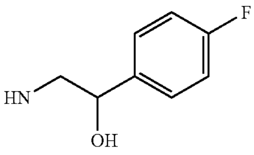 | 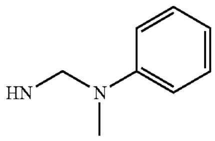 | 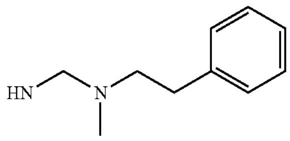 |

-continued
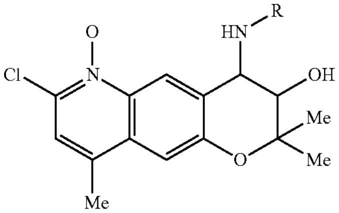
HN—R
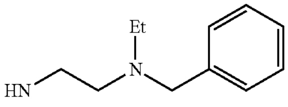
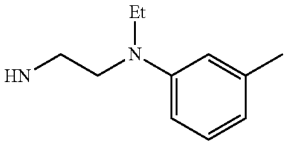
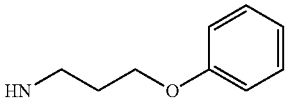
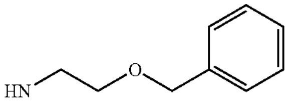
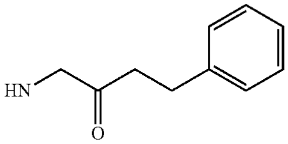
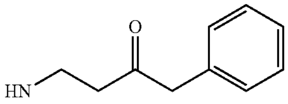
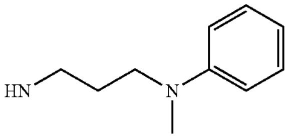
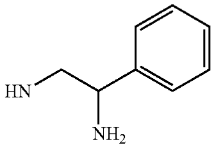
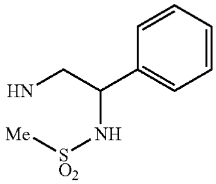
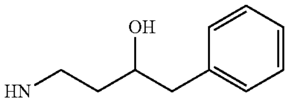
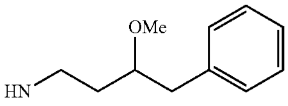
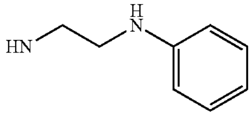
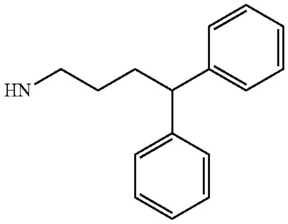
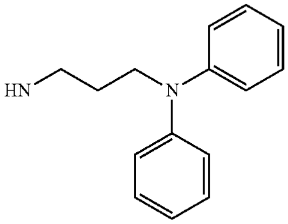
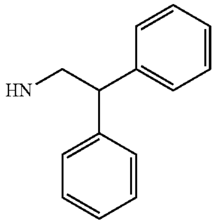
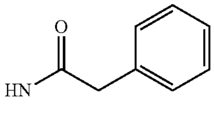
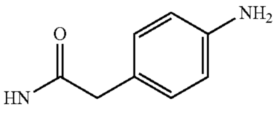
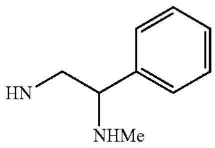
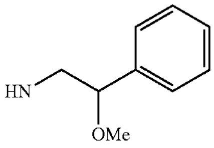
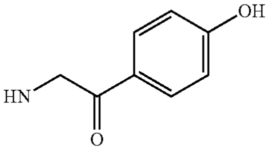
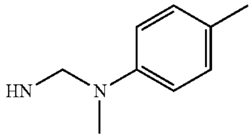
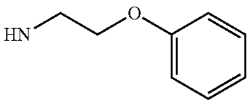
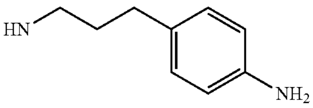
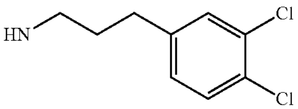

| HN—R | | |
|---|---|---|
| | 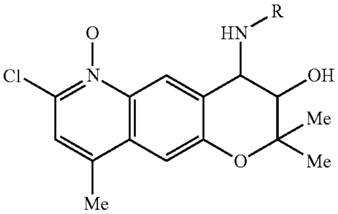 | |
| 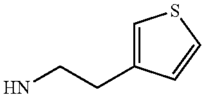 | 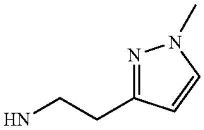 | 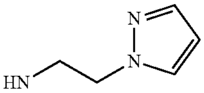 |
| 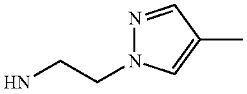 | 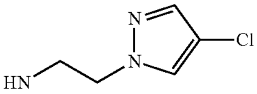 | 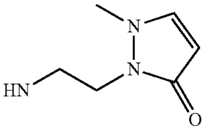 |
| 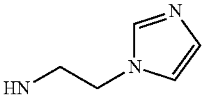 | 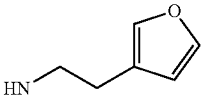 | 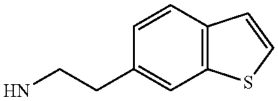 |
| 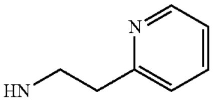 | 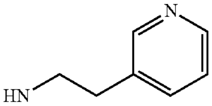 | 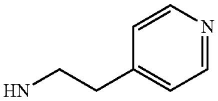 |
| 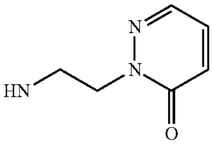 | 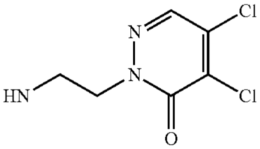 | 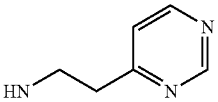 |
| 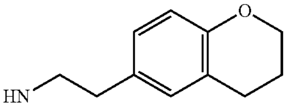 | 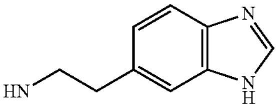 | 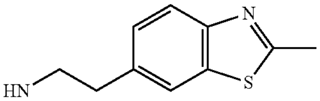 |
| 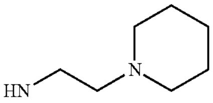 | 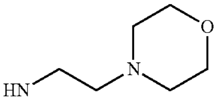 | 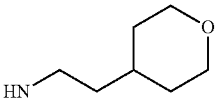 |
| 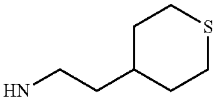 | 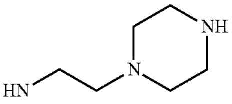 | 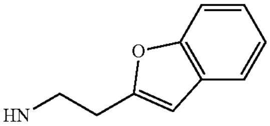 |
| 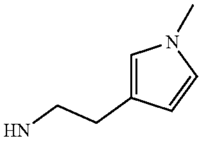 | 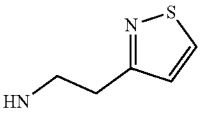 | 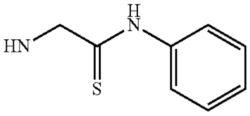 |
| 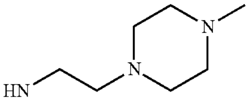 | 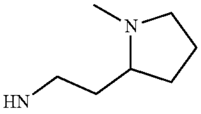 | 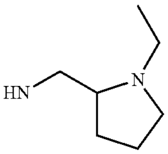 |

-continued
| HN—R | | |
| --- | --- | --- |
| 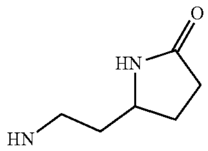 | 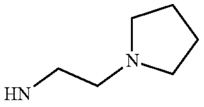 | 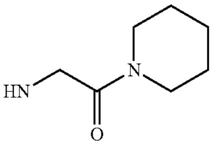 |
| 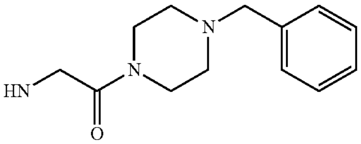 | 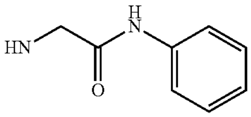 | |
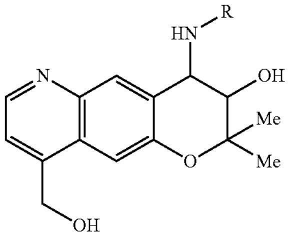
| | | |
| --- | --- | --- |
| 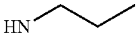 | 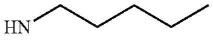 | 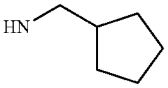 |
| 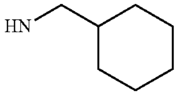 | 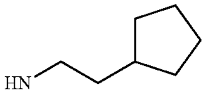 | 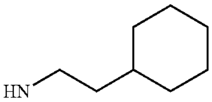 |
| 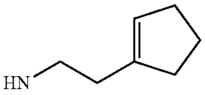 | 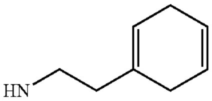 | 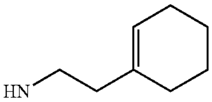 |
| 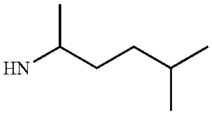 | 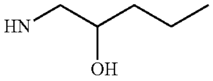 | 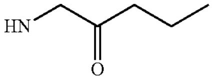 |
| 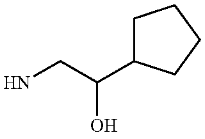 | 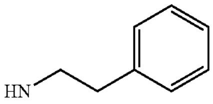 | 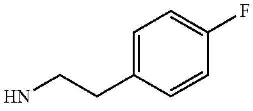 |
| 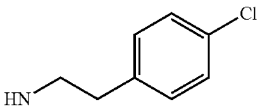 | 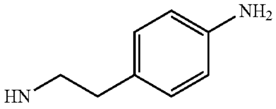 | 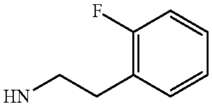 |
| 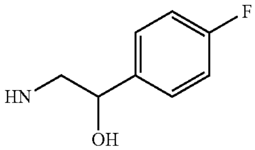 | 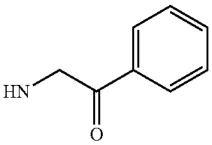 | 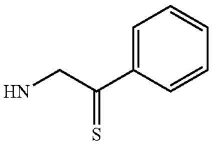 |

-continued
| HN—R | | |
|---|---|---|
| 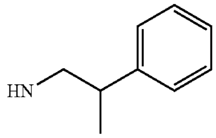 | 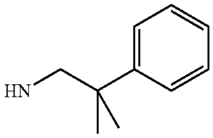 | 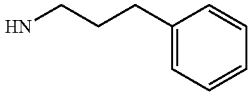 |
| 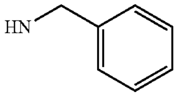 | 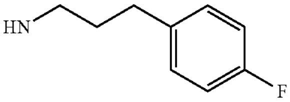 | 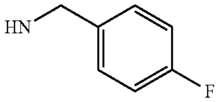 |
| 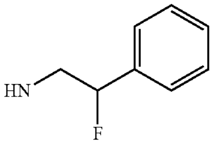 | 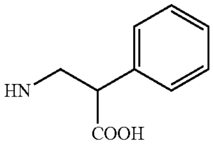 | 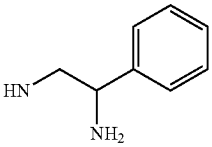 |
| 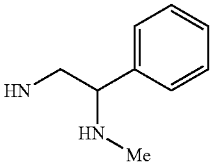 | 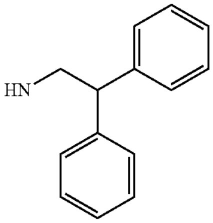 | 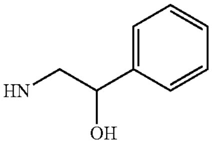 |
| 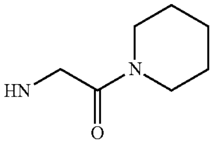 | 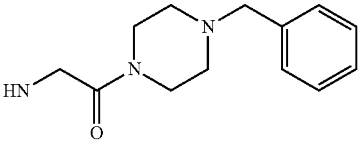 | 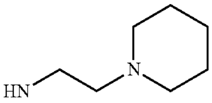 |
| 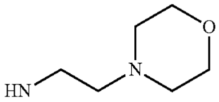 | 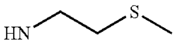 | 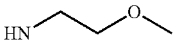 |
| 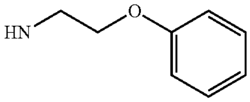 | 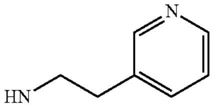 | 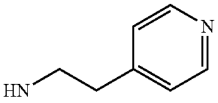 |
| 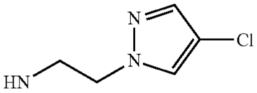 | 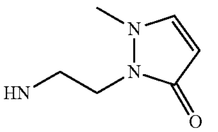 | |
| | 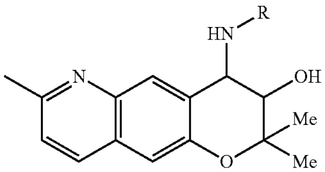 | |
|---|---|---|
| 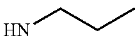 | 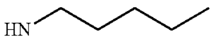 | 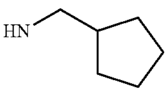 |
| 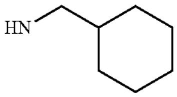 | 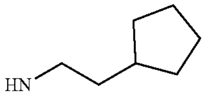 | 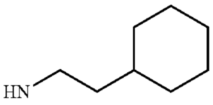 |

-continued
| HN—R | | |
|---|---|---|
| 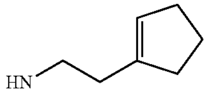 | 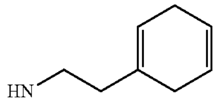 | 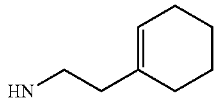 |
| 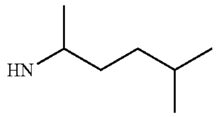 | 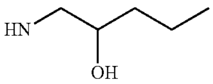 | 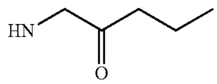 |
| 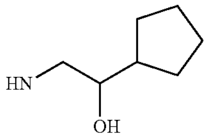 | 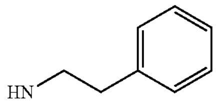 | 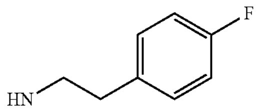 |
| 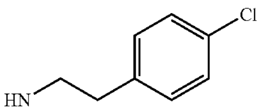 | 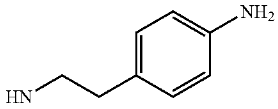 | 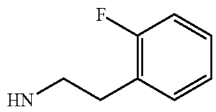 |
| 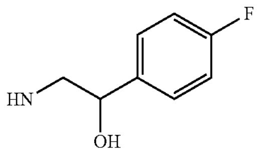 | 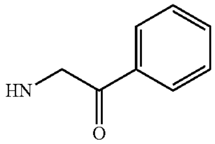 | 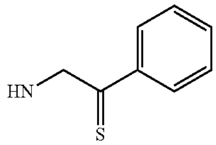 |
| 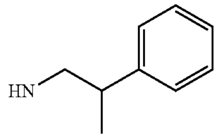 | 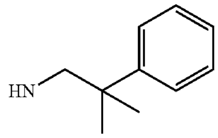 | 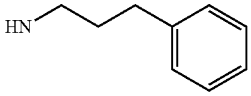 |
| 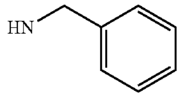 | 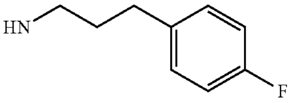 | 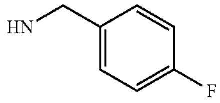 |
| 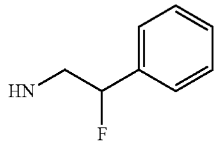 | 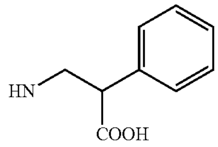 | 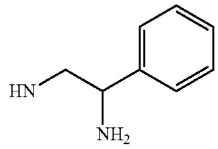 |
| 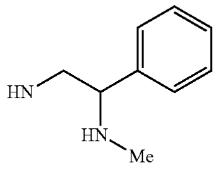 | 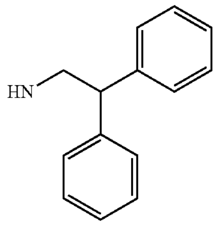 | 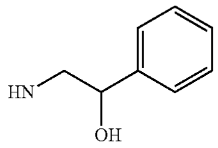 |
| 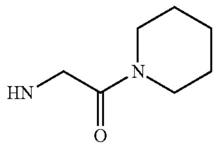 | 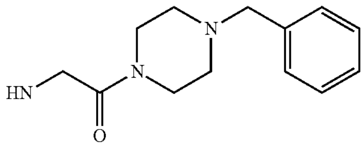 | 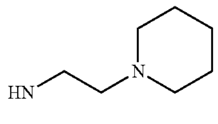 |

-continued
| HN—R | | |
|---|---|---|
| 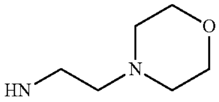 | 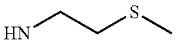 | 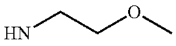 |
| 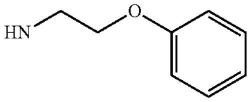 | 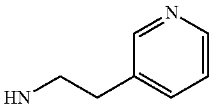 | 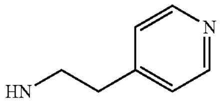 |
| 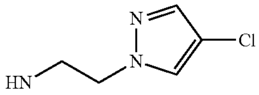 | 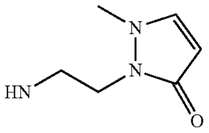 | |
| 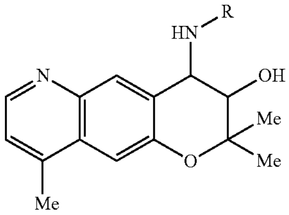 | | |
|---|---|---|
| 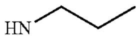 | 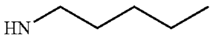 | 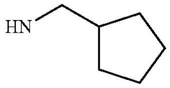 |
| 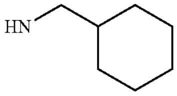 | 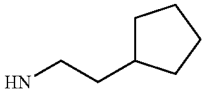 | 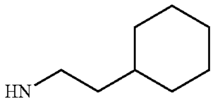 |
| 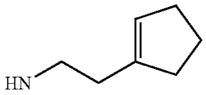 | 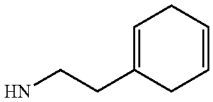 | 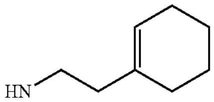 |
| 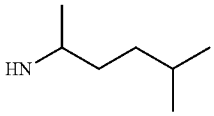 | 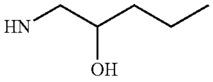 | 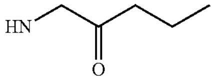 |
| 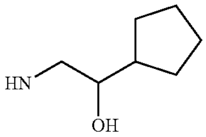 | 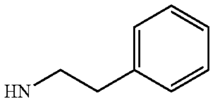 | 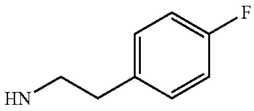 |
| 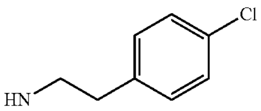 | 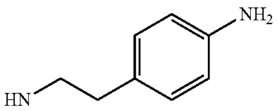 | 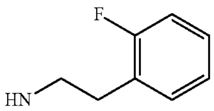 |
| 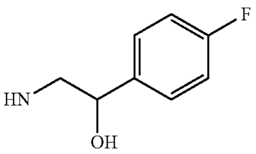 | 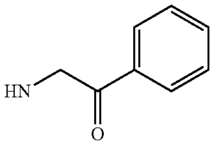 | 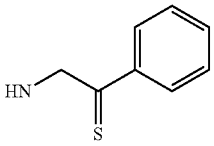 |

-continued
| HN—R | | |
|---|---|---|
| 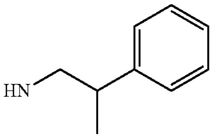 | 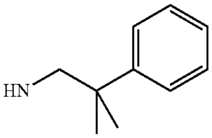 | 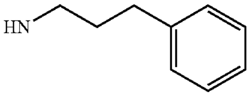 |
| 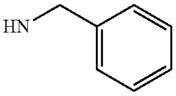 | 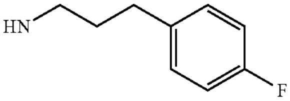 | 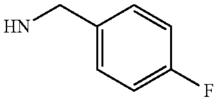 |
| 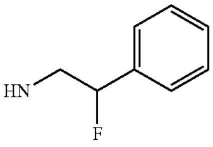 | 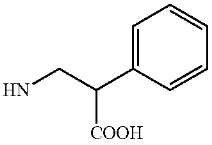 | 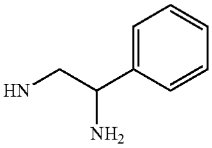 |
| 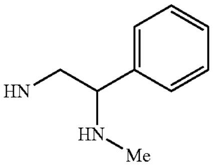 | 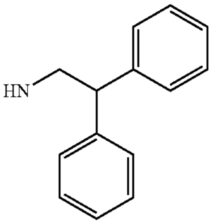 | 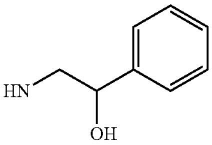 |
| 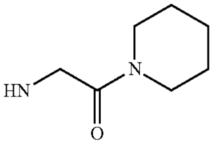 | 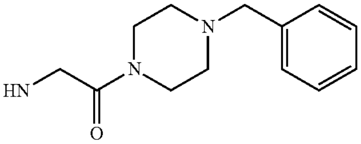 | 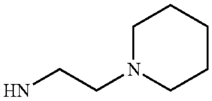 |
| 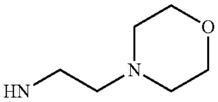 | 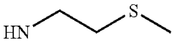 | 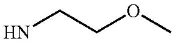 |
| 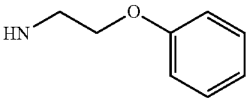 | 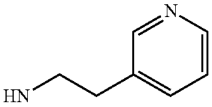 | 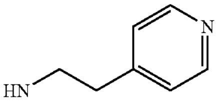 |
| 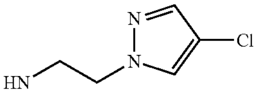 | 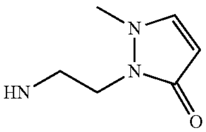 | |
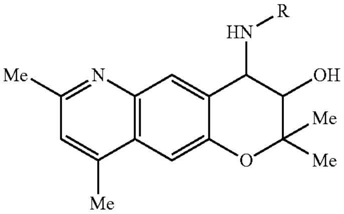
| | | |
|---|---|---|
| 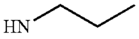 | 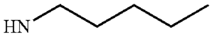 | 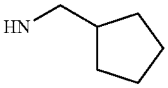 |

-continued
| HN—R | | |
|---|---|---|
| 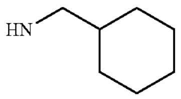 | 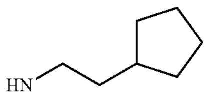 | 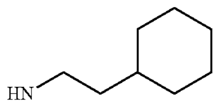 |
| 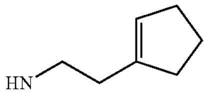 | 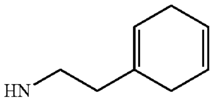 | 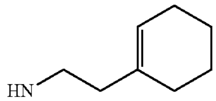 |
| 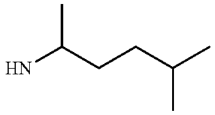 | 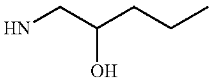 | 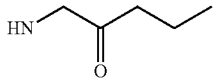 |
| 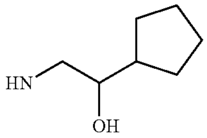 | 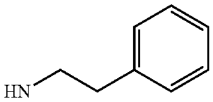 | 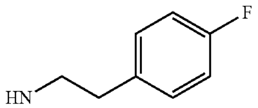 |
| 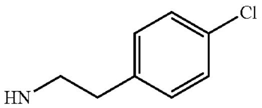 | 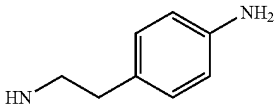 | 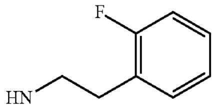 |
| 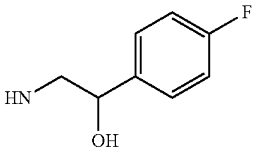 | 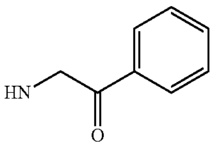 | 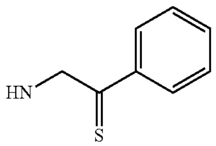 |
| 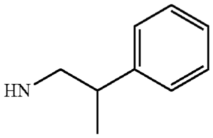 | 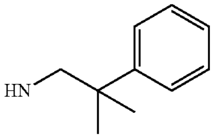 | 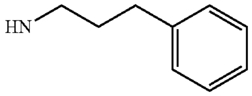 |
| 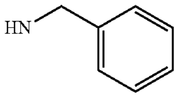 | 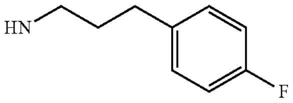 | 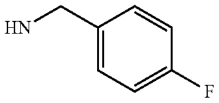 |
| 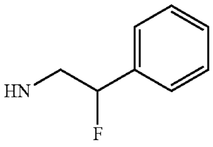 | 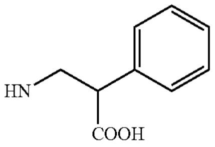 | 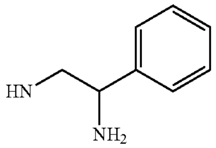 |
| 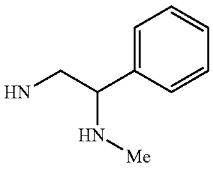 | 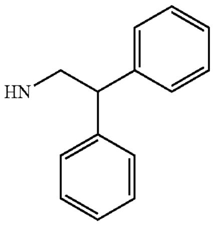 | 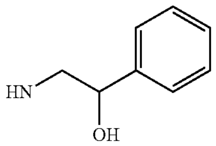 |

-continued
| | HN—R | |
|---|---|---|
| 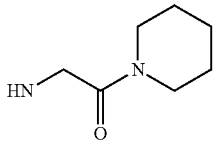 | 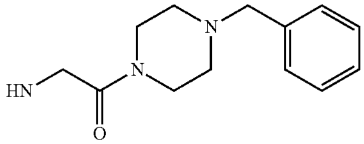 | 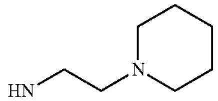 |
| 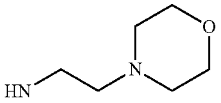 | 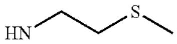 | 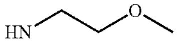 |
| 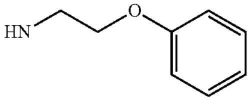 | 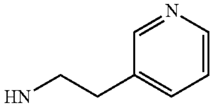 | 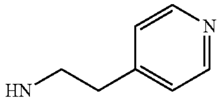 |
| 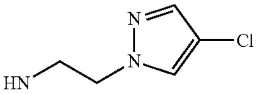 | 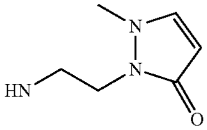 | |
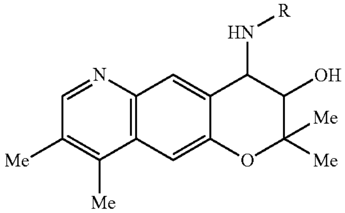
| | | |
|---|---|---|
| 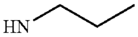 | 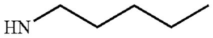 | 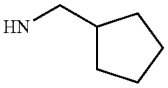 |
| 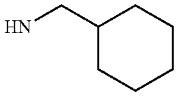 | 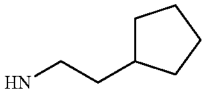 | 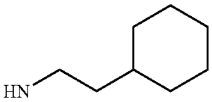 |
| 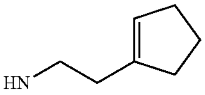 | 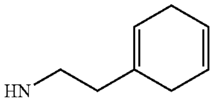 | 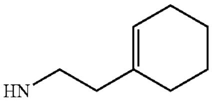 |
| 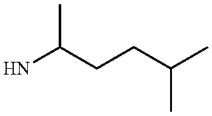 | 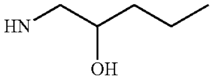 | 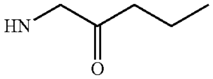 |
| 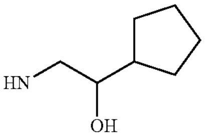 | 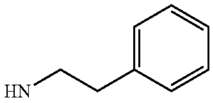 | 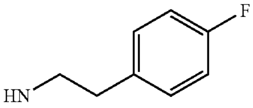 |
| 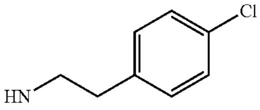 | 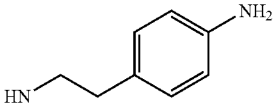 | 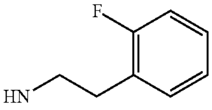 |

-continued
| HN—R | | |
|---|---|---|
| 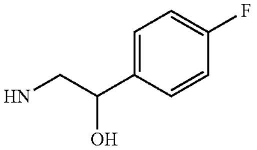 | 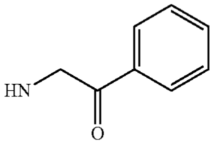 | 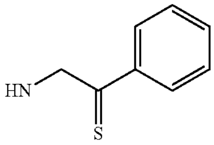 |
| 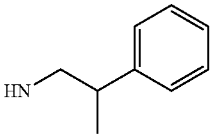 | 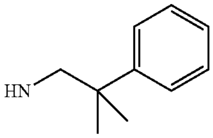 | 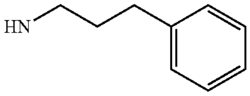 |
| 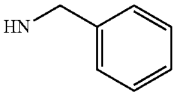 | 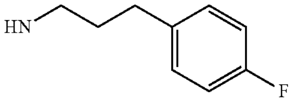 | 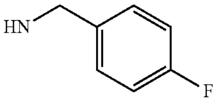 |
| 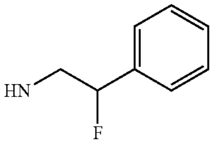 | 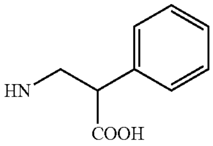 | 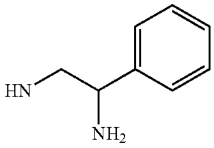 |
| 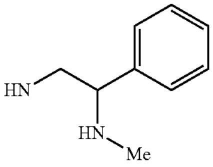 | 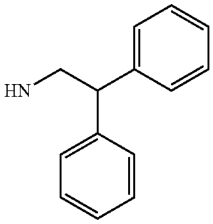 | 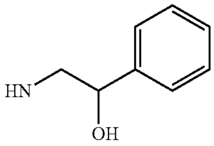 |
| 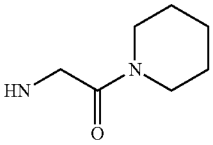 | 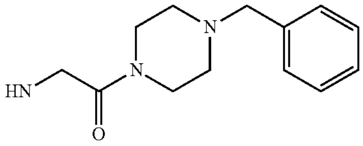 | 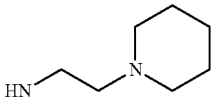 |
| 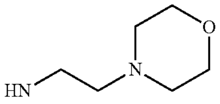 | 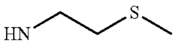 | 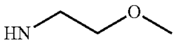 |
| 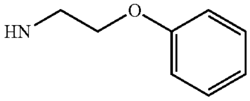 | 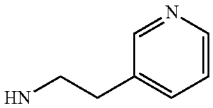 | 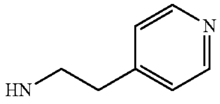 |
| 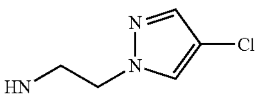 | 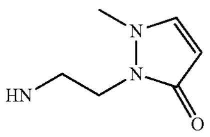 | |

-continued
| HN—R | | |
|---|---|---|
| | 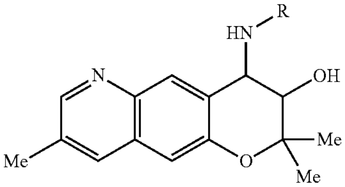 | |
| 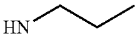 | 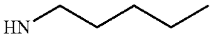 | 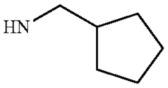 |
| 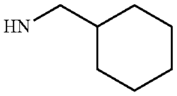 | 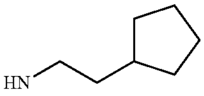 | 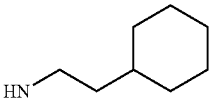 |
| 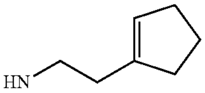 | 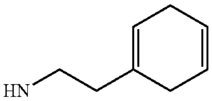 | 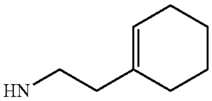 |
| 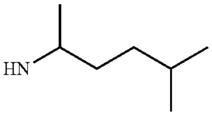 | 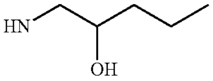 | 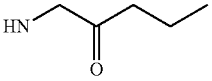 |
| 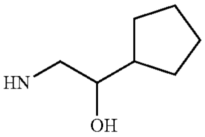 | 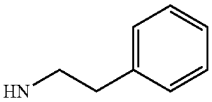 | 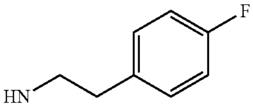 |
| 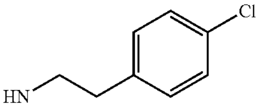 | 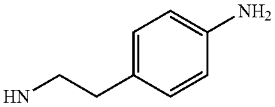 | 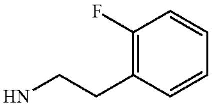 |
| 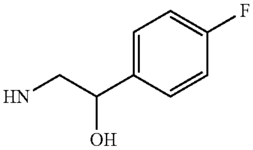 | 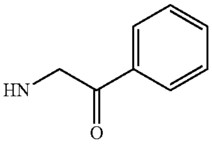 | 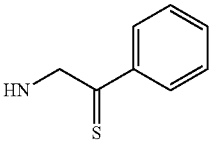 |
| 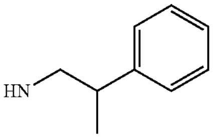 | 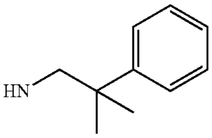 | 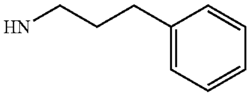 |
| 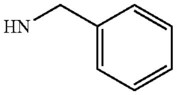 | 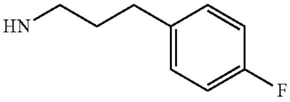 | 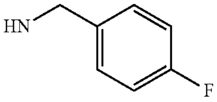 |
| 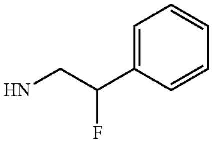 | 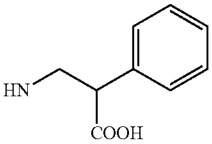 | 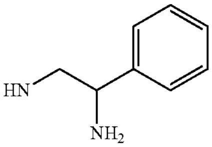 |

-continued
| HN—R | | |
|---|---|---|
| 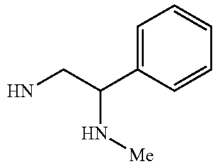 | 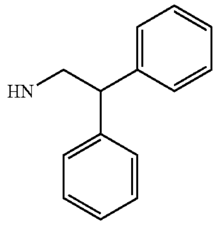 | 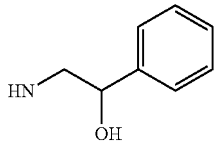 |
| 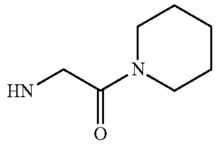 | 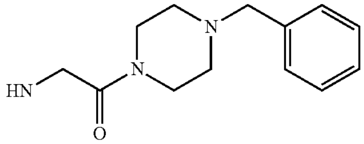 | 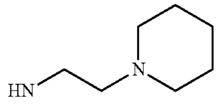 |
| 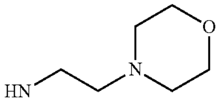 | 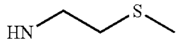 | 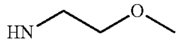 |
| 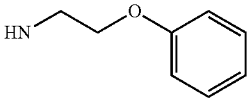 | 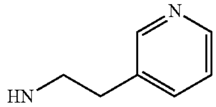 | 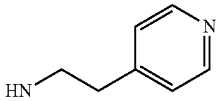 |
| 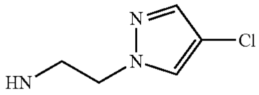 | 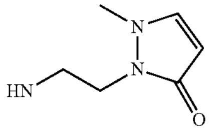 | |
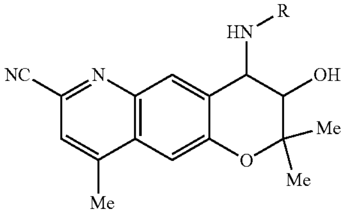
| | | |
|---|---|---|
| 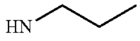 | 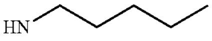 | 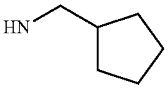 |
| 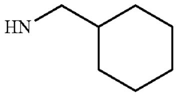 | 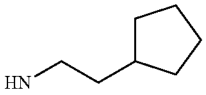 | 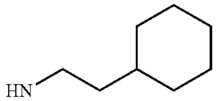 |
| 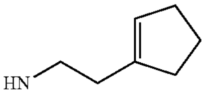 | 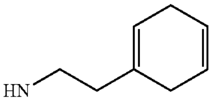 | 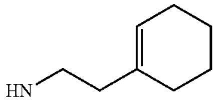 |
| 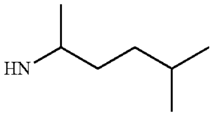 | 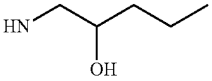 | 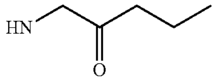 |
| 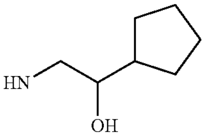 | 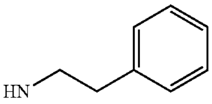 | 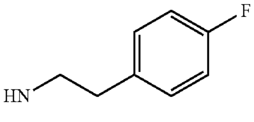 |

-continued
HN—R
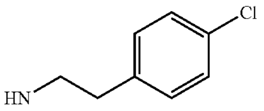
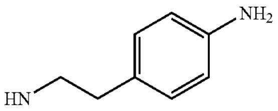
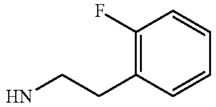
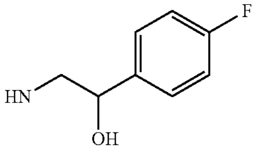
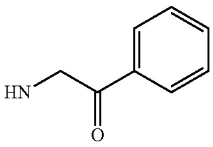
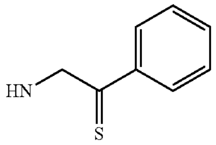
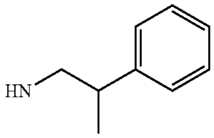
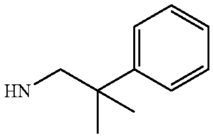
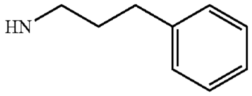
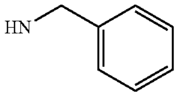
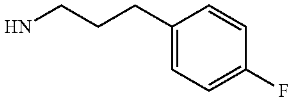
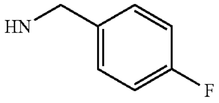
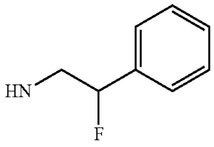
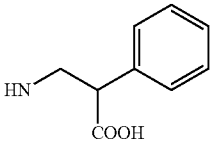
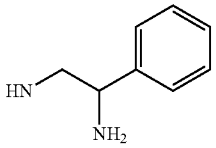
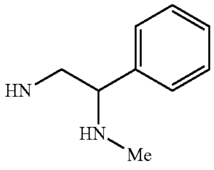
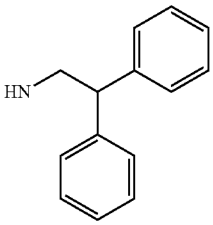
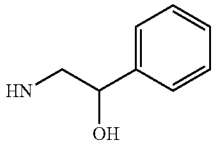
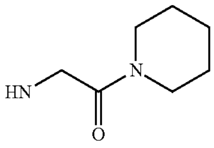
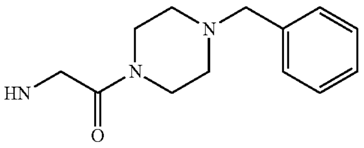
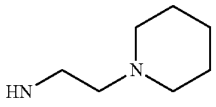
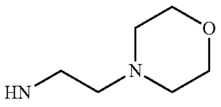
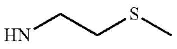
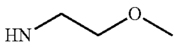
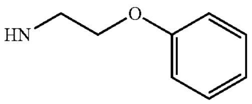
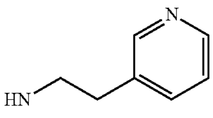
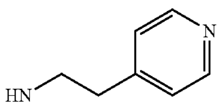
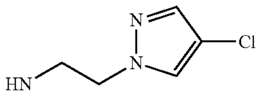
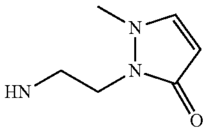

-continued
| HN—R | | |
|---|---|---|
| | 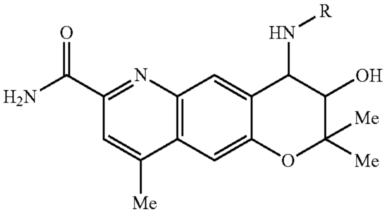 | |
| 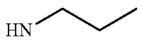 | 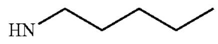 | 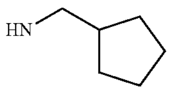 |
| 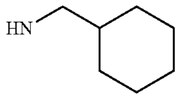 | 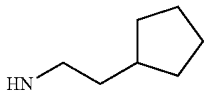 | 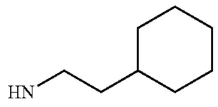 |
| 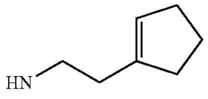 | 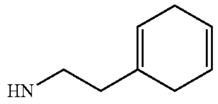 | 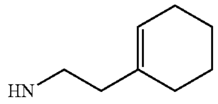 |
| 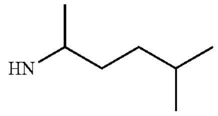 | 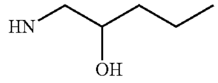 | 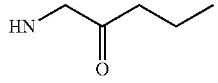 |
| 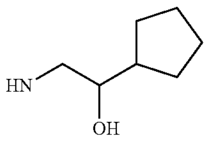 | 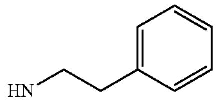 | 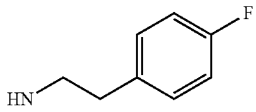 |
| 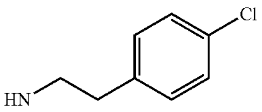 | 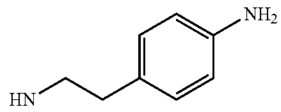 | 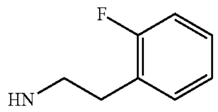 |
| 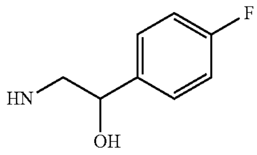 | 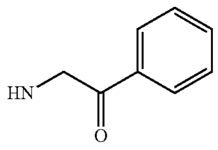 | 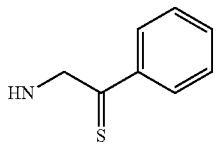 |
| 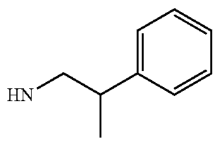 | 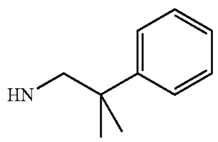 | 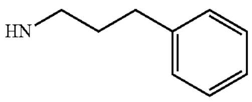 |
| 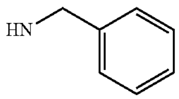 | 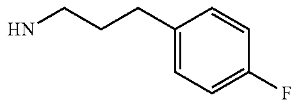 | 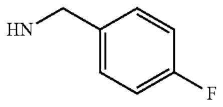 |
| 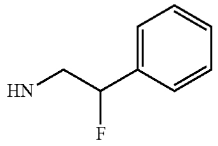 | 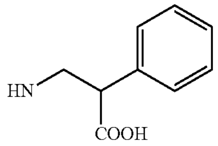 | 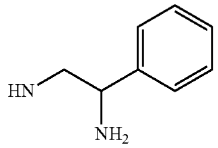 |

-continued
| | HN—R | |
|---|---|---|
| 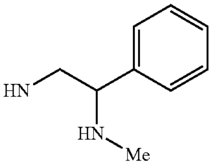 | 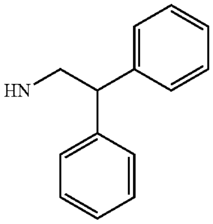 | 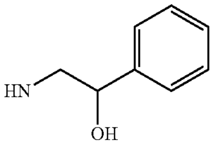 |
| 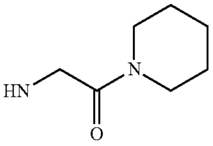 | 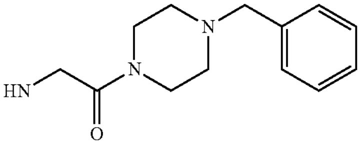 | 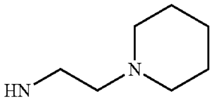 |
| 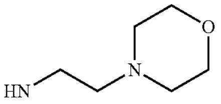 | 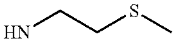 | 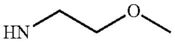 |
| 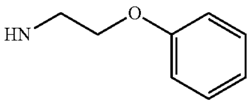 | 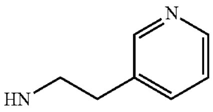 | 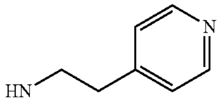 |
| 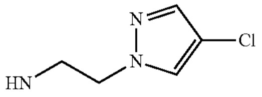 | 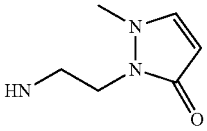 | |
| | 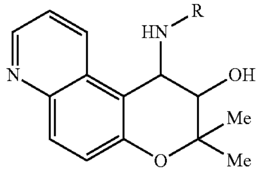 | |
| 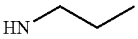 | 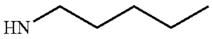 | 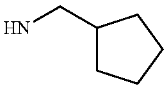 |
| 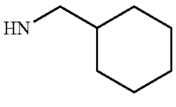 | 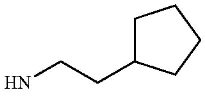 | 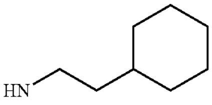 |
| 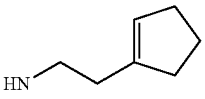 | 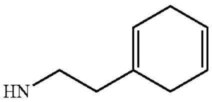 | 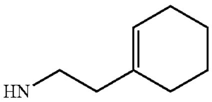 |
| 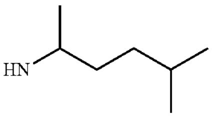 | 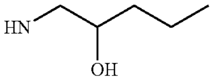 | 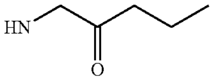 |
| 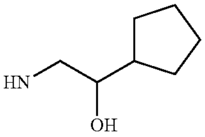 | 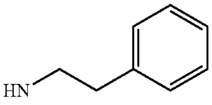 | 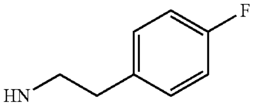 |

-continued
| HN—R | | |
|---|---|---|
| 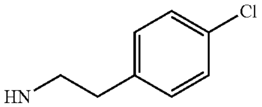 | 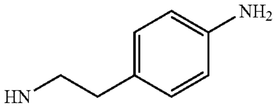 | 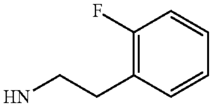 |
| 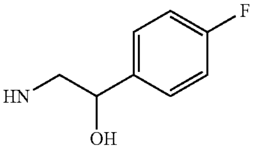 | 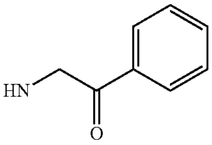 | 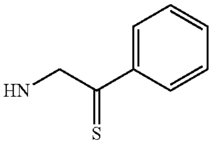 |
| 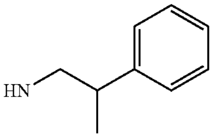 | 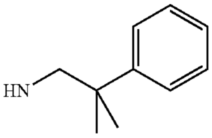 | 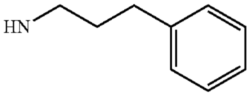 |
| 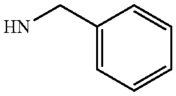 | 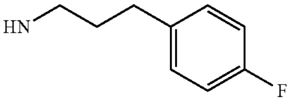 | 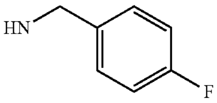 |
| 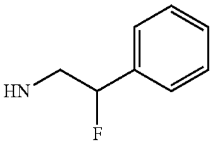 | 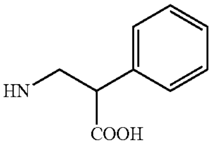 | 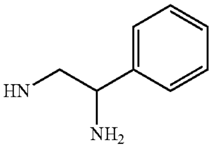 |
| 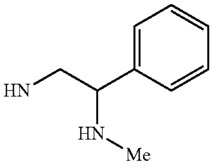 | 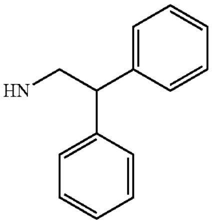 | 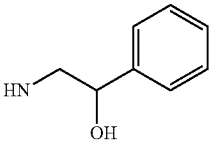 |
| 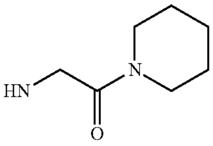 | 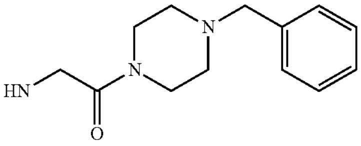 | 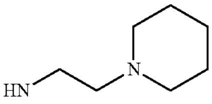 |
| 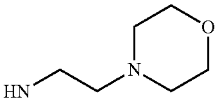 | 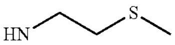 | 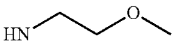 |
| 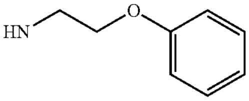 | 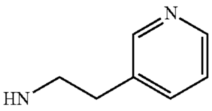 | 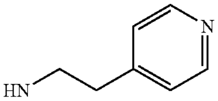 |
| 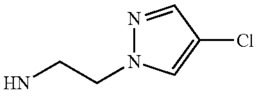 | 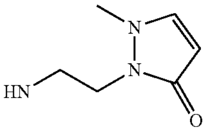 | |

-continued
| | HN—R | |
|---|---|---|
| | 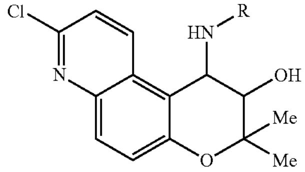 | |
| 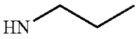 | 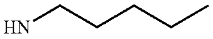 | 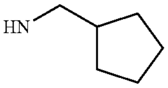 |
| 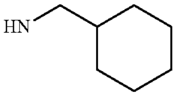 | 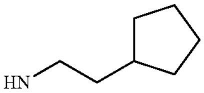 | 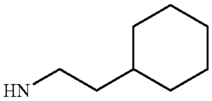 |
| 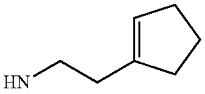 | 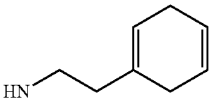 | 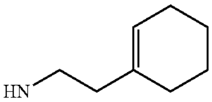 |
| 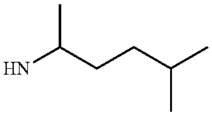 | 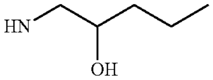 | 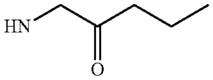 |
| 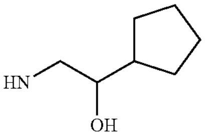 | 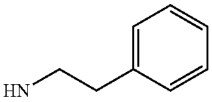 | 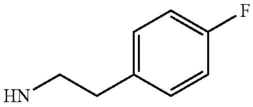 |
| 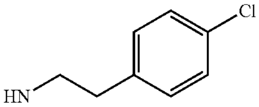 | 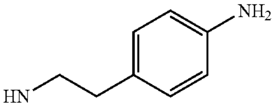 | 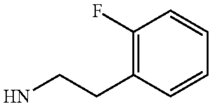 |
| 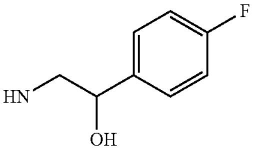 | 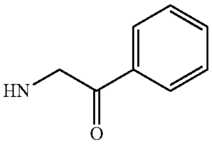 | 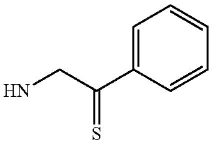 |
| 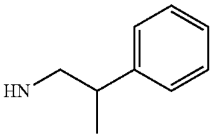 | 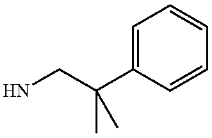 | 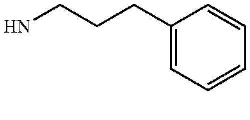 |
| 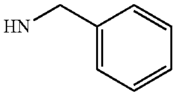 | 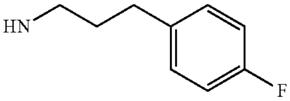 | 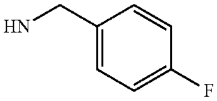 |
| 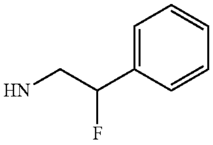 | 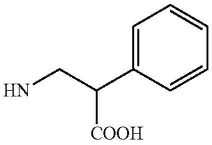 | 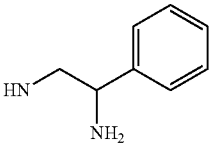 |

-continued
| HN—R | | |
|---|---|---|
| 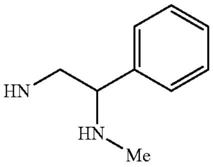 | 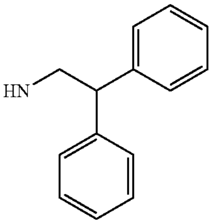 | 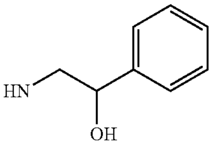 |
| 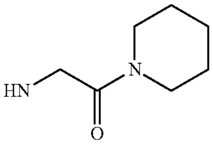 | 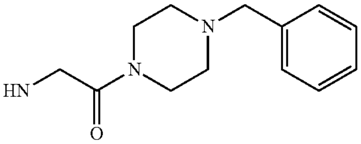 | 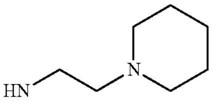 |
| 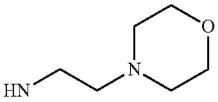 | 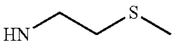 | 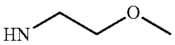 |
| 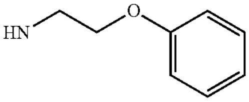 | 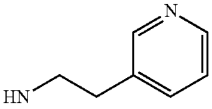 | 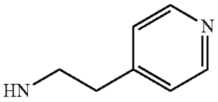 |
| 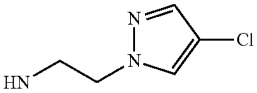 | 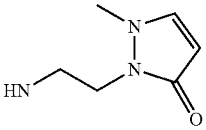 | |
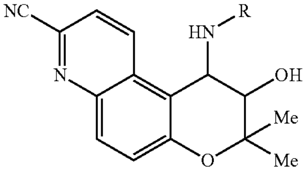
| | | |
|---|---|---|
| 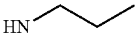 | 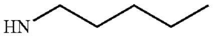 | 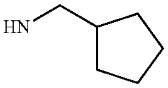 |
| 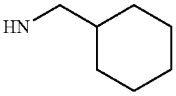 | 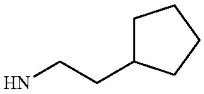 | 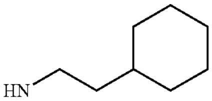 |
| 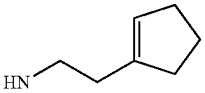 | 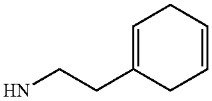 | 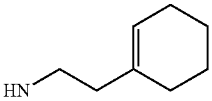 |
| 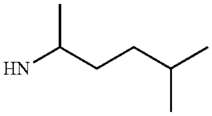 | 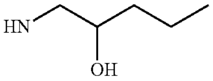 | 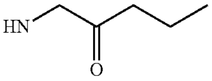 |
| 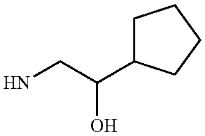 | 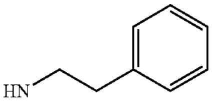 | 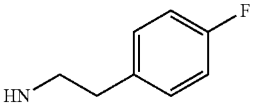 |

-continued
| HN—R | | |
|---|---|---|
| 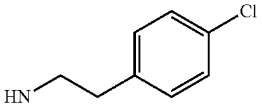 | 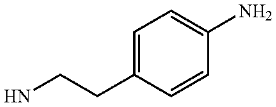 | 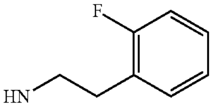 |
| 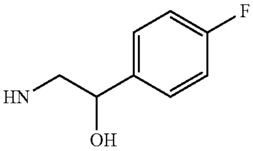 | 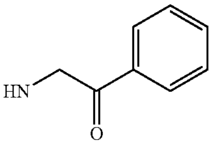 | 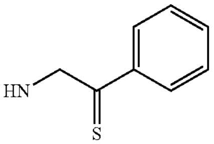 |
| 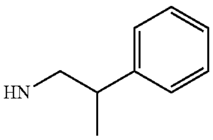 | 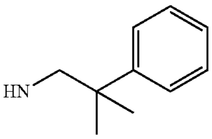 | 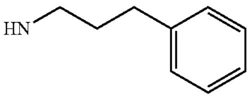 |
| 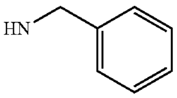 | 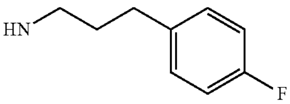 | 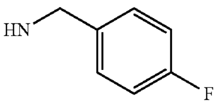 |
| 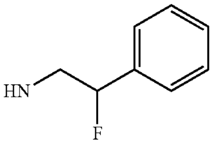 | 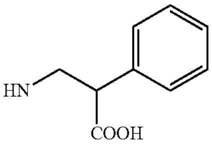 | 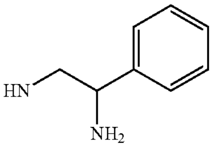 |
| 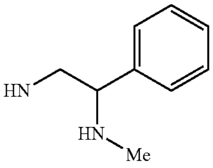 | 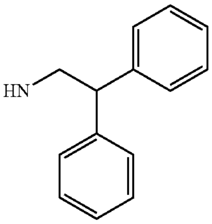 | 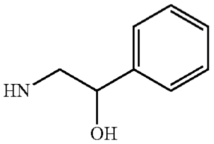 |
| 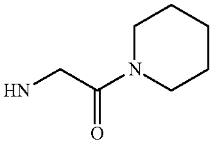 | 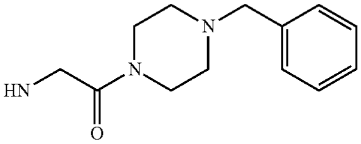 | 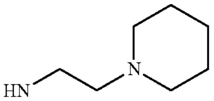 |
| 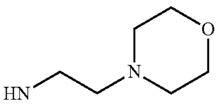 | 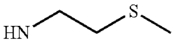 | 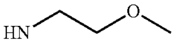 |
| 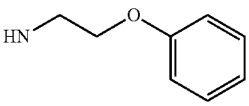 | 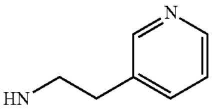 | 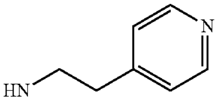 |
| 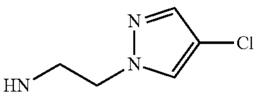 | 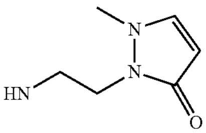 | |

-continued
| HN—R | | |
| --- | --- | --- |
| | 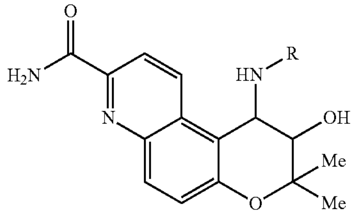 | |
| 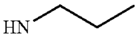 | 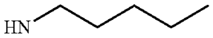 | 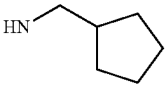 |
| 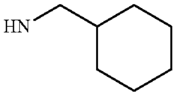 | 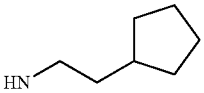 | 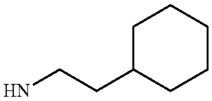 |
| 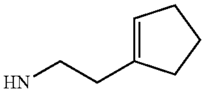 | 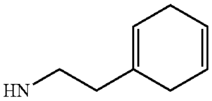 | 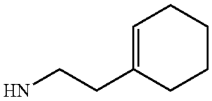 |
| 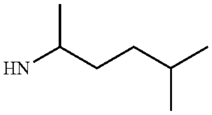 | 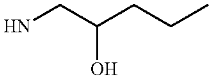 | 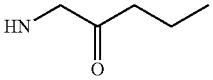 |
| 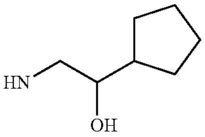 | 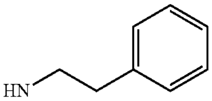 | 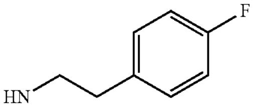 |
| 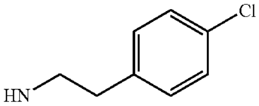 | 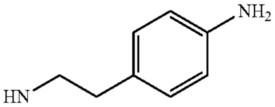 | 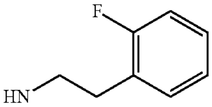 |
| 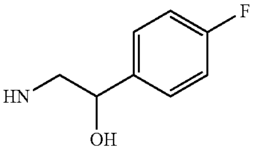 | 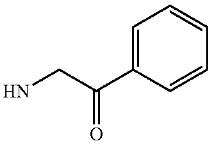 | 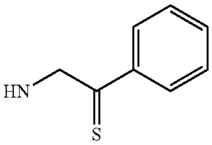 |
| 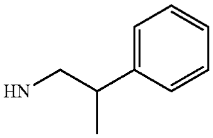 | 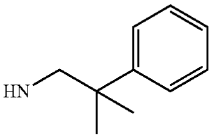 | 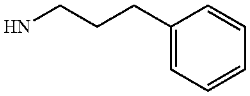 |
| 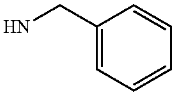 | 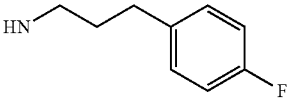 | 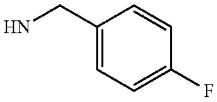 |
| 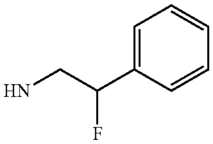 | 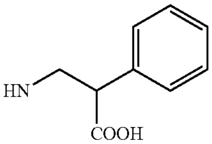 | 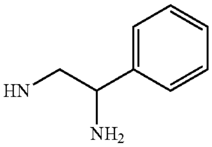 |

-continued
| HN—R | | |
|---|---|---|
| 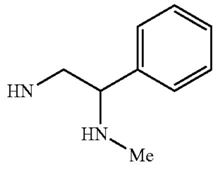 | 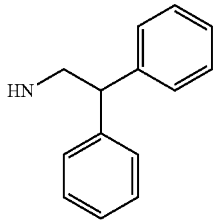 | 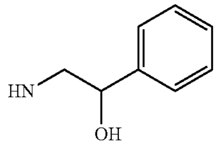 |
| 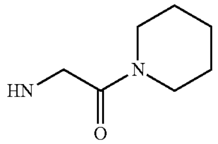 | 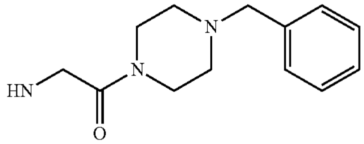 | 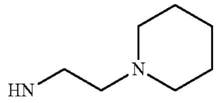 |
| 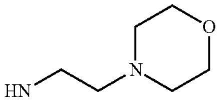 | 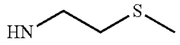 | 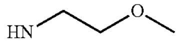 |
| 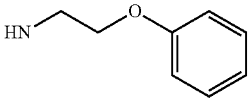 | 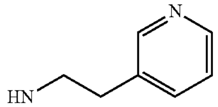 | 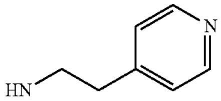 |
| 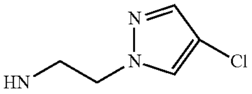 | 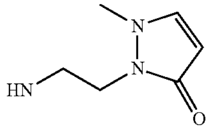 | |
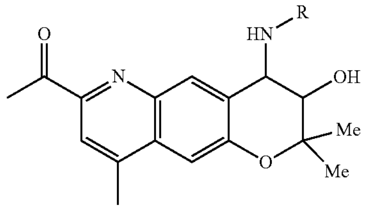
| | | |
|---|---|---|
| 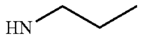 | 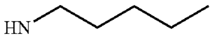 | 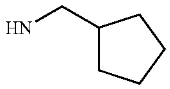 |
| 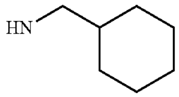 | 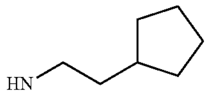 | 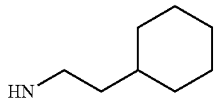 |
| 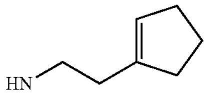 | 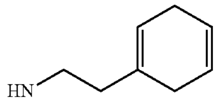 | 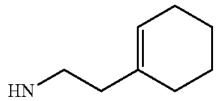 |
| 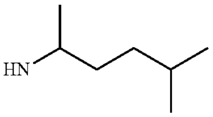 | 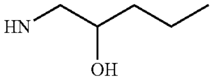 | 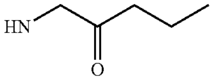 |
| 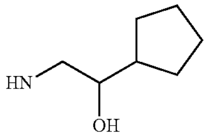 | 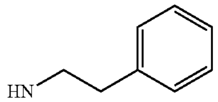 | 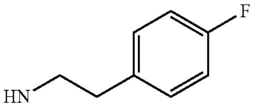 |

-continued
| HN—R | | |
|---|---|---|
| 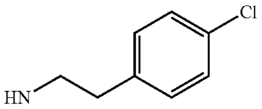 | 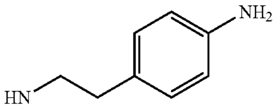 | 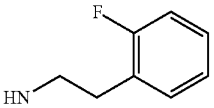 |
| 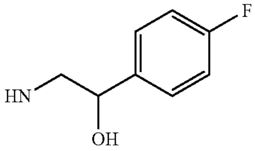 | 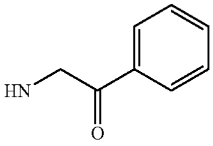 | 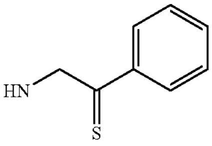 |
| 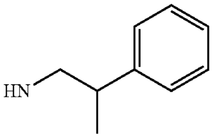 | 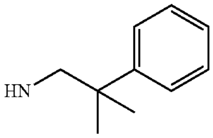 | 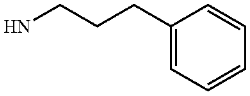 |
| 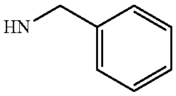 | 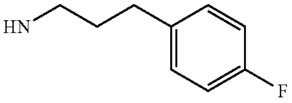 | 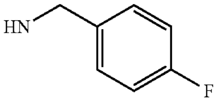 |
| 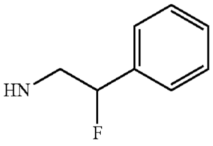 | 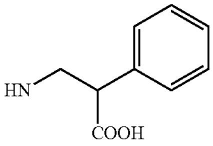 | 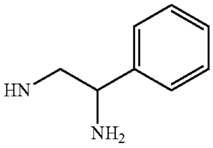 |
| 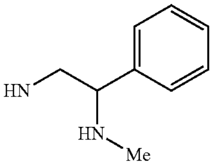 | 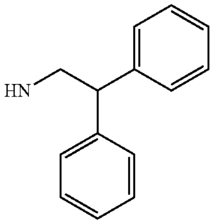 | 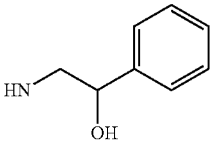 |
| 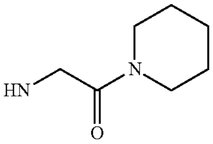 | 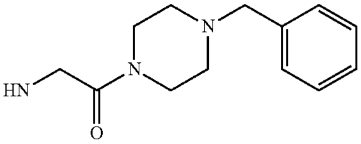 | 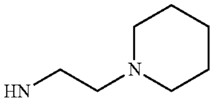 |
| 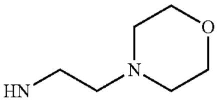 | 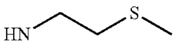 | 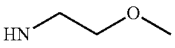 |
| 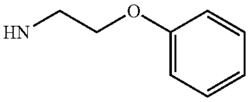 | 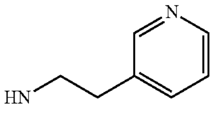 | 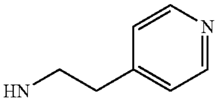 |
| 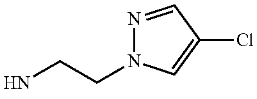 | 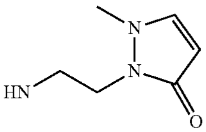 | |

-continued
HN—R
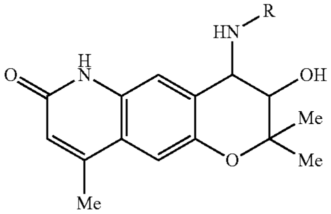
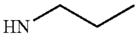 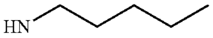 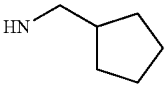
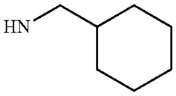 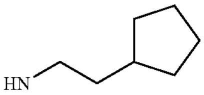 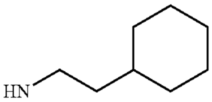
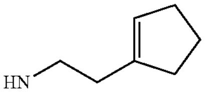 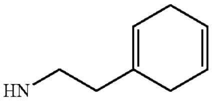 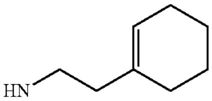
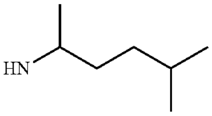 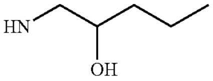 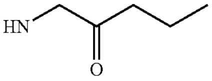
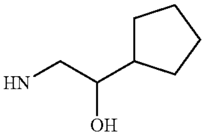 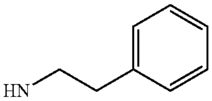 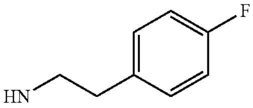
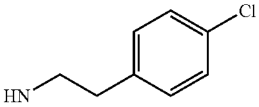 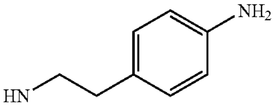 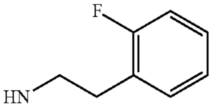
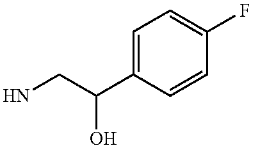 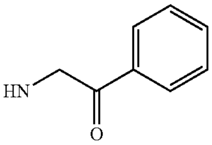 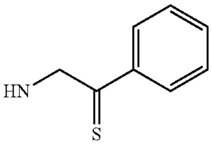
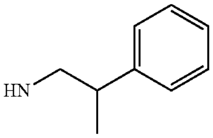 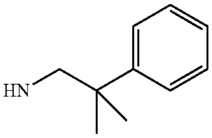 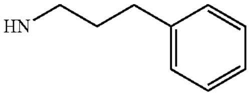
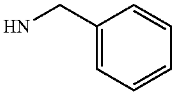 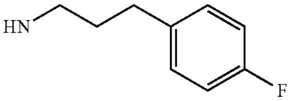 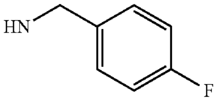
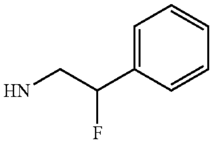 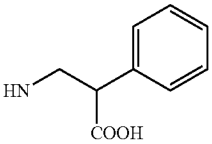 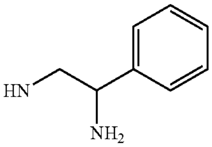

-continued
| | HN—R | |
|---|---|---|
| 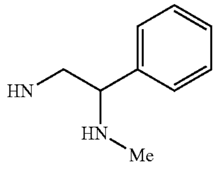 | 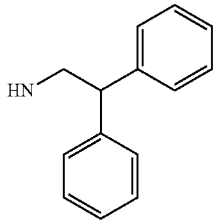 | 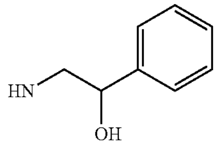 |
| 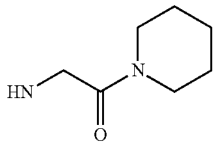 | 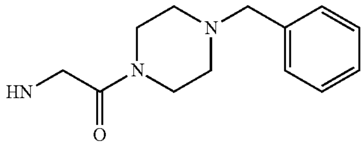 | 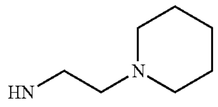 |
| 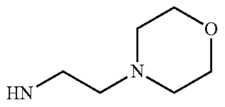 | 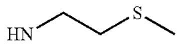 | 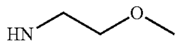 |
| 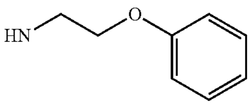 | 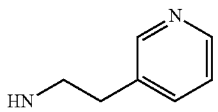 | 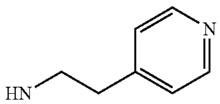 |
| 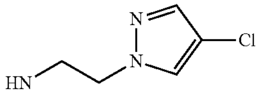 | 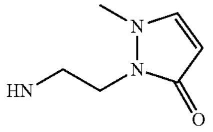 | |
| | 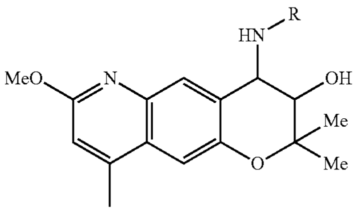 | |
|---|---|---|
| 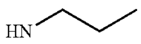 | 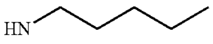 | 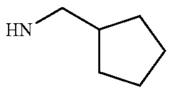 |
| 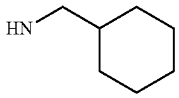 | 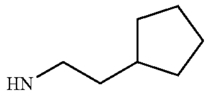 | 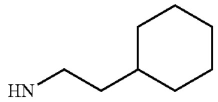 |
| 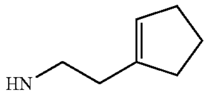 | 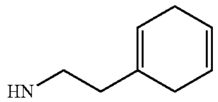 | 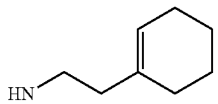 |
| 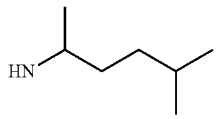 | 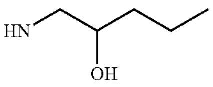 | 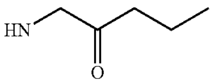 |
| 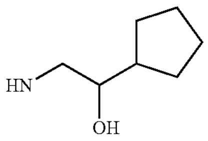 | 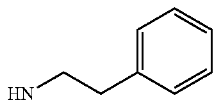 | 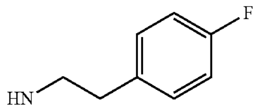 |

-continued
| HN—R | | |
|---|---|---|
| 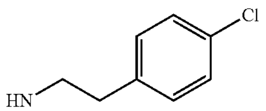 | 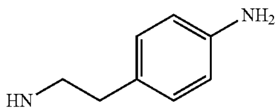 | 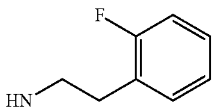 |
| 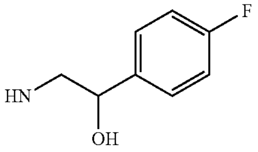 | 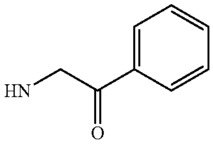 | 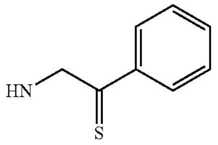 |
| 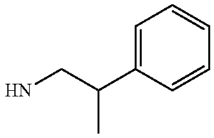 | 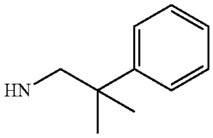 | 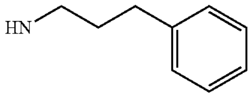 |
| 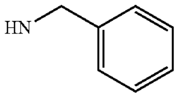 | 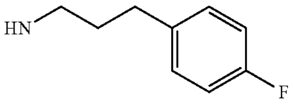 | 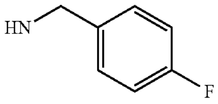 |
| 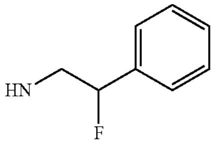 | 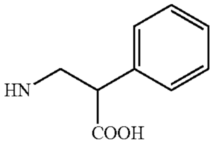 | 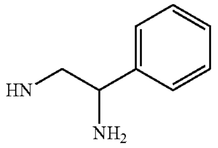 |
| 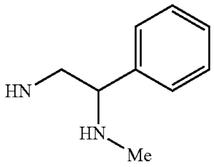 | 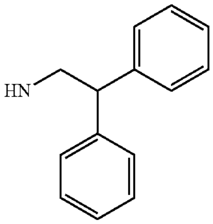 | 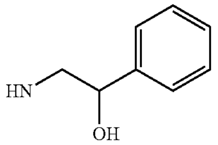 |
| 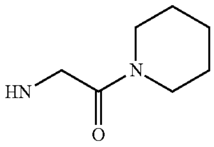 | 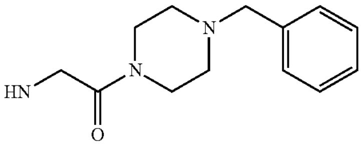 | 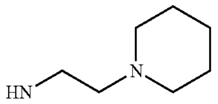 |
| 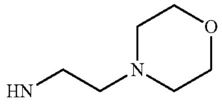 | 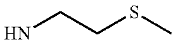 | 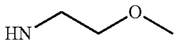 |
| 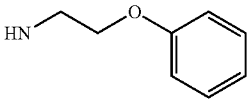 | 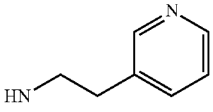 | 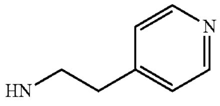 |
| 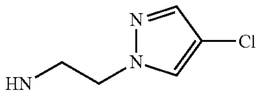 | 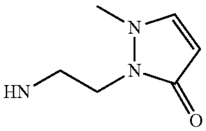 | |

-continued
| | HN—R | |
|---|---|---|
| | 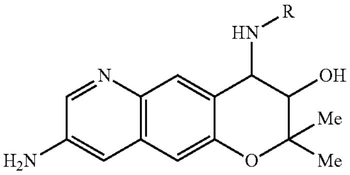 | |
| 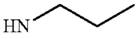 | 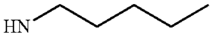 | 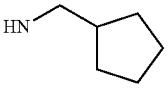 |
| 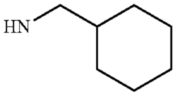 | 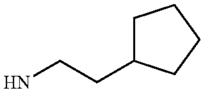 | 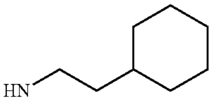 |
| 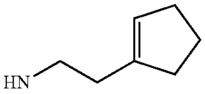 | 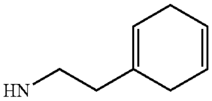 | 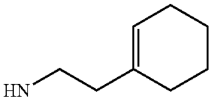 |
| 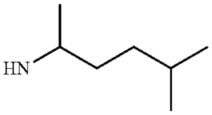 | 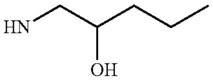 | 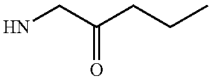 |
| 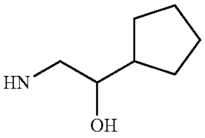 | 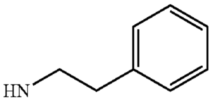 | 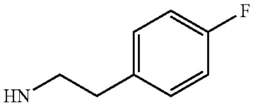 |
| 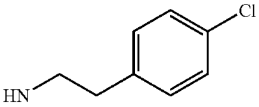 | 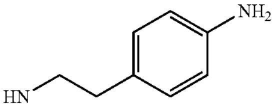 | 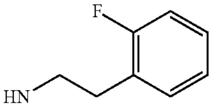 |
| 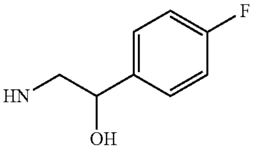 | 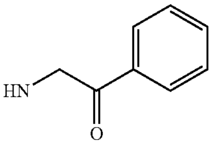 | 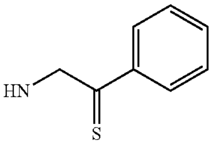 |
| 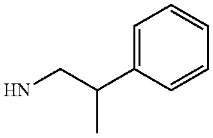 | 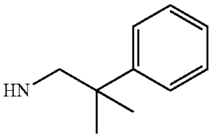 | 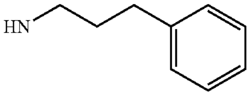 |
| 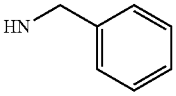 | 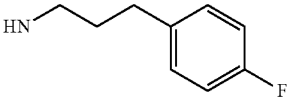 | 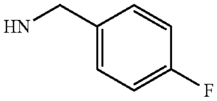 |
| 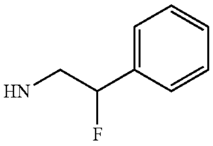 | 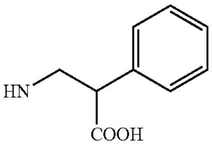 | 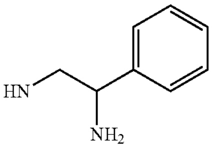 |

-continued
| HN—R | | |
|---|---|---|
| 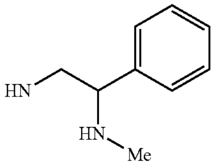 | 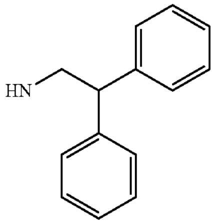 | 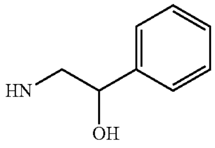 |
| 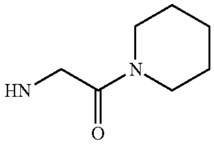 | 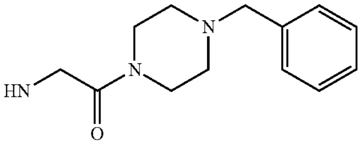 | 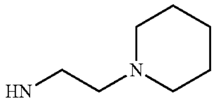 |
| 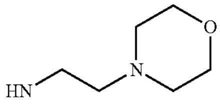 | 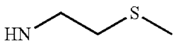 | 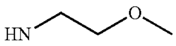 |
| 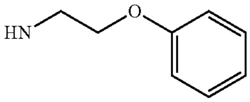 | 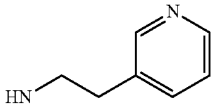 | 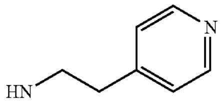 |
| 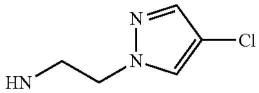 | 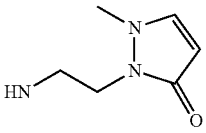 | |
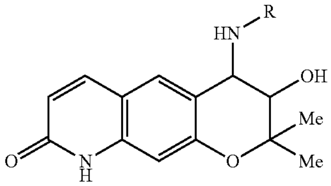
| | | |
|---|---|---|
| 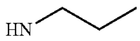 | 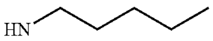 | 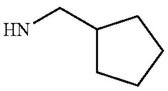 |
| 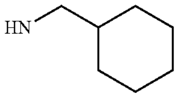 | 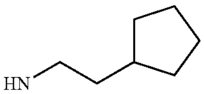 | 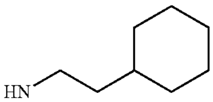 |
| 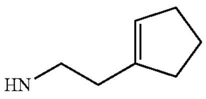 | 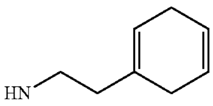 | 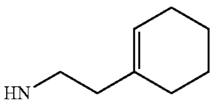 |
| 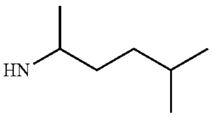 | 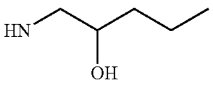 | 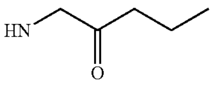 |
| 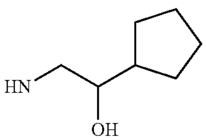 | 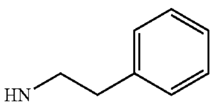 | 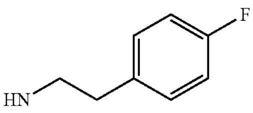 |

-continued
| HN—R | | |
|---|---|---|
| 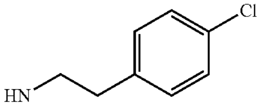 | 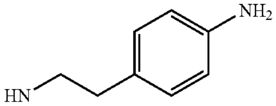 | 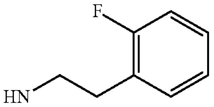 |
| 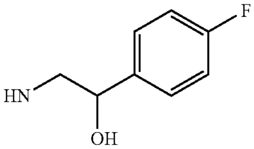 | 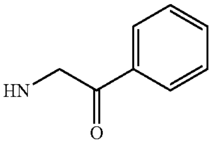 | 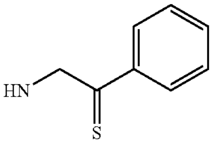 |
| 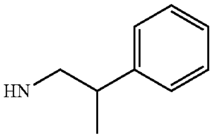 | 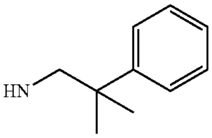 | 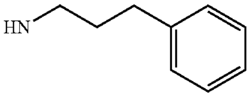 |
| 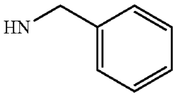 | 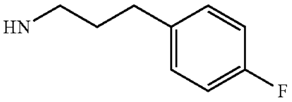 | 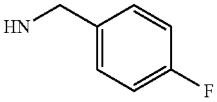 |
| 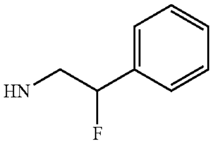 | 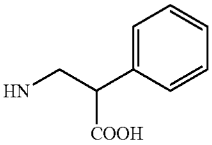 | 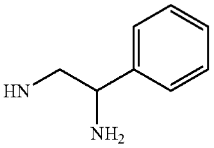 |
| 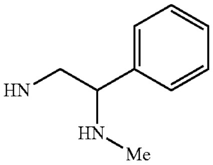 | 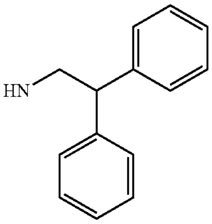 | 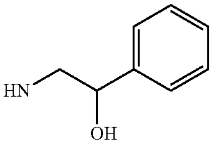 |
| 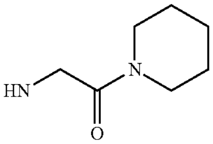 | 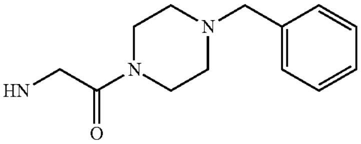 | 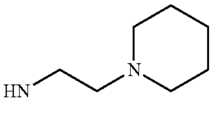 |
| 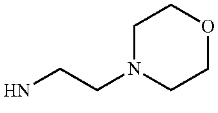 | 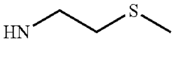 | 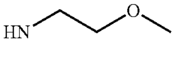 |
| 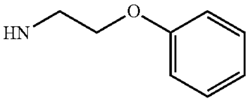 | 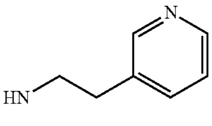 | 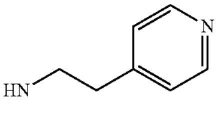 |
| 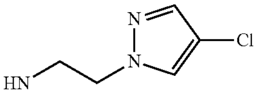 | 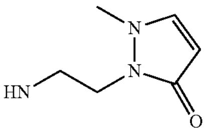 | |

-continued
HN—R
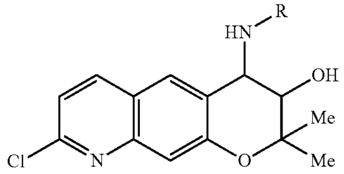
| | | |
|---|---|---|
| 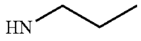 | 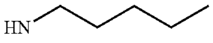 | 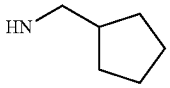 |
| 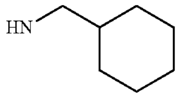 | 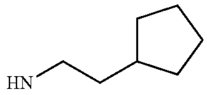 | 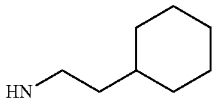 |
| 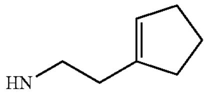 | 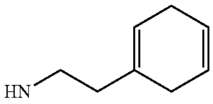 | 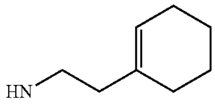 |
| 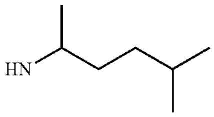 | 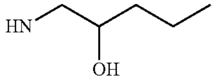 | 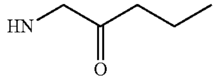 |
| 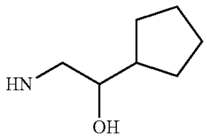 | 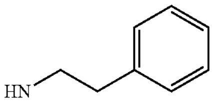 | 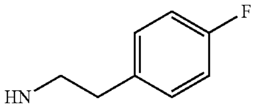 |
| 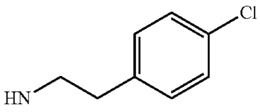 | 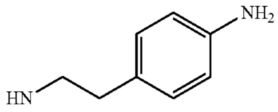 | 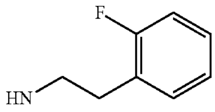 |
| 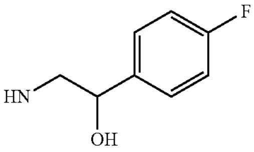 | 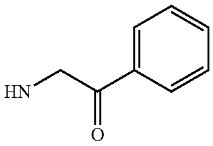 | 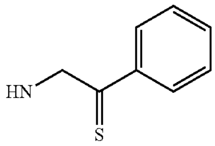 |
| 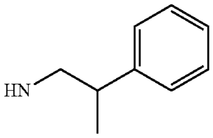 | 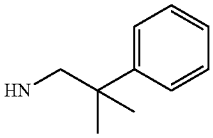 | 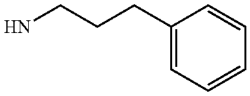 |
| 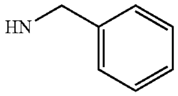 | 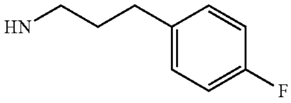 | 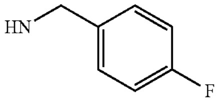 |
| 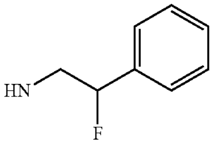 | 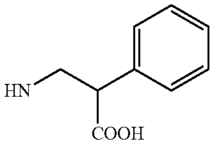 | 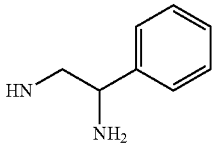 |

-continued
| | HN—R | |
|---|---|---|
| 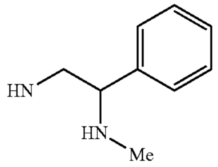 | 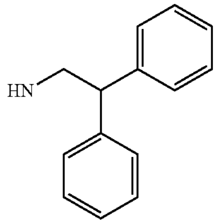 | 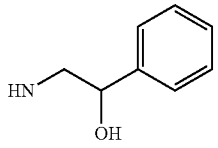 |
| 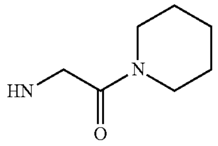 | 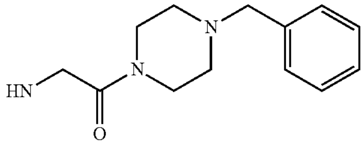 | 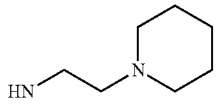 |
| 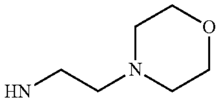 | 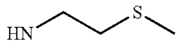 | 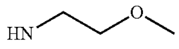 |
| 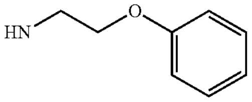 | 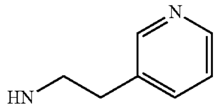 | 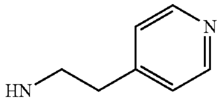 |
| 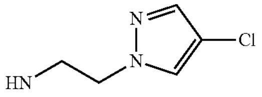 | 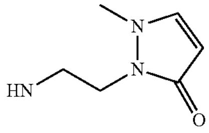 | |
| | 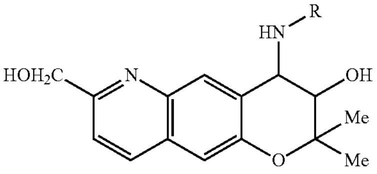 | |
|---|---|---|
| 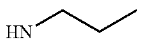 | 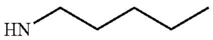 | 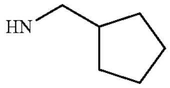 |
| 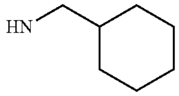 | 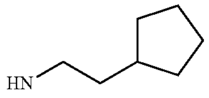 | 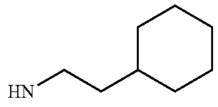 |
| 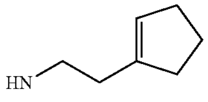 | 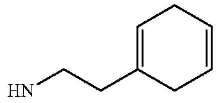 | 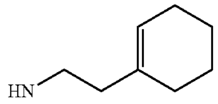 |
| 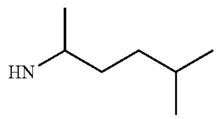 | 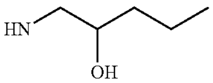 | 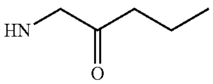 |
| 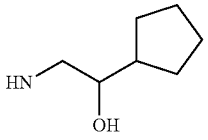 | 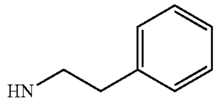 | 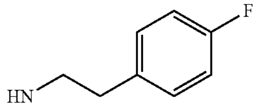 |

-continued
| HN—R | | |
|---|---|---|
| 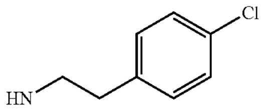 | 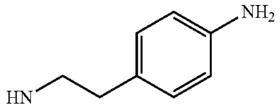 | 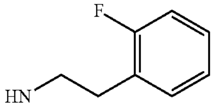 |
| 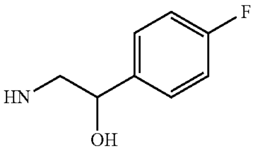 | 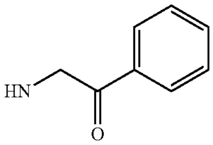 | 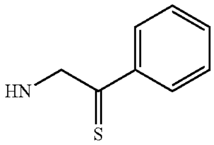 |
| 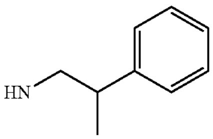 | 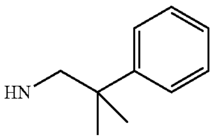 | 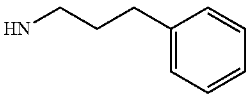 |
| 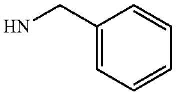 | 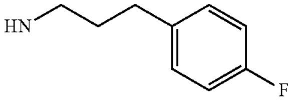 | 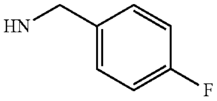 |
| 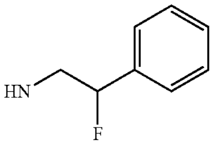 | 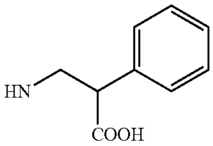 | 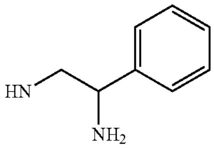 |
| 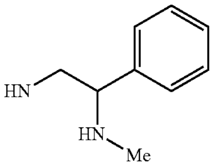 | 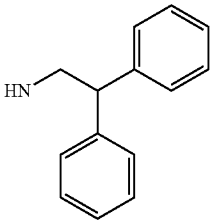 | 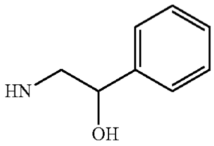 |
| 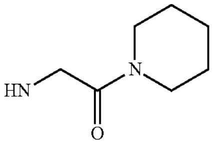 | 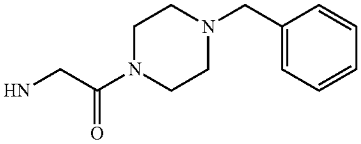 | 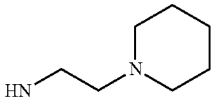 |
| 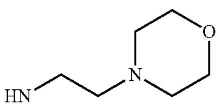 | 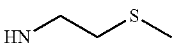 | 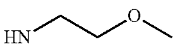 |
| 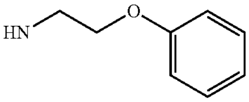 | 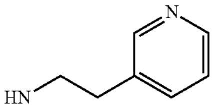 | 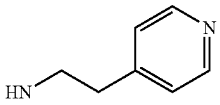 |
| 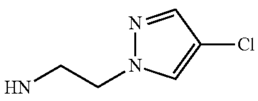 | 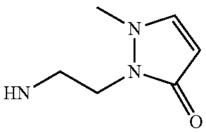 | |

-continued
| HN—R | | |
|---|---|---|
| | 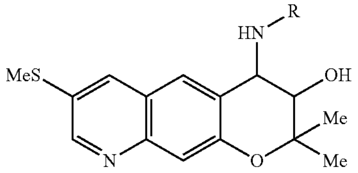 | |
| 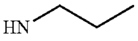 | 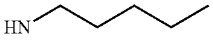 | 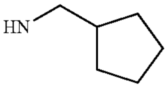 |
| 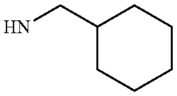 | 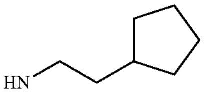 | 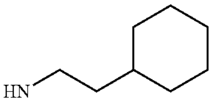 |
| 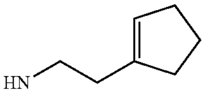 | 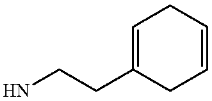 | 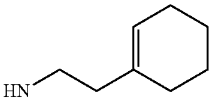 |
| 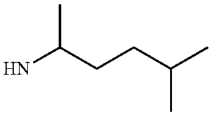 | 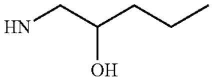 | 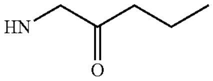 |
| 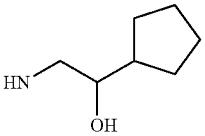 | 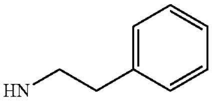 | 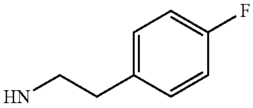 |
| 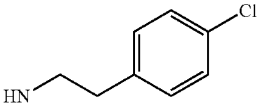 | 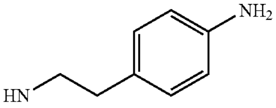 | 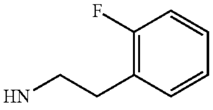 |
| 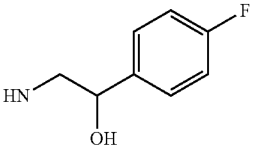 | 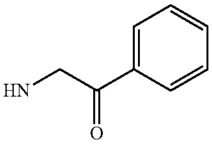 | 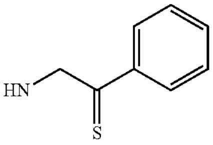 |
| 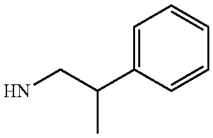 | 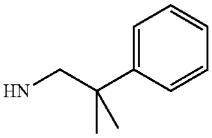 | 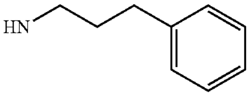 |
| 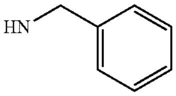 | 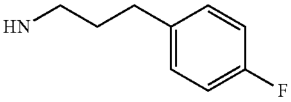 | 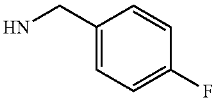 |
| 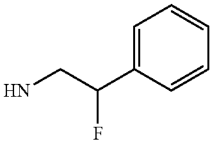 | 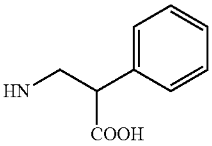 | 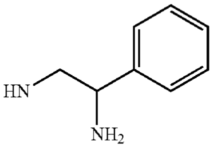 |

-continued
| HN—R | | |
|---|---|---|
| 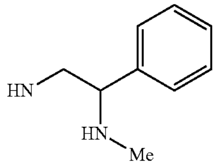 | 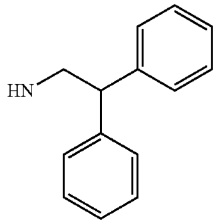 | 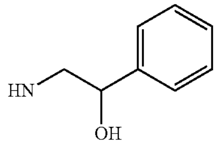 |
| 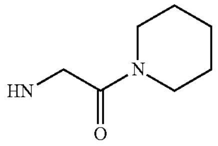 | 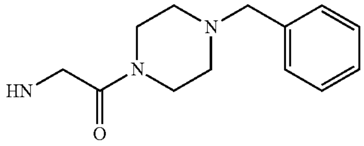 | 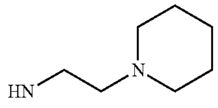 |
| 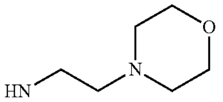 | 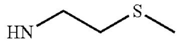 | 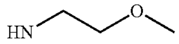 |
| 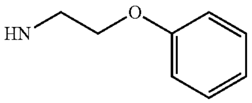 | 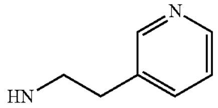 | 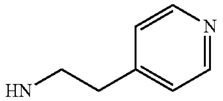 |
| 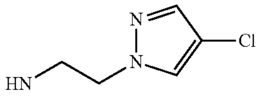 | 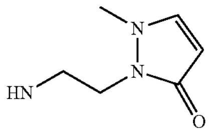 | |
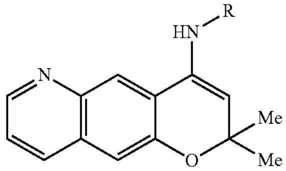
| | | |
|---|---|---|
| 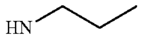 | 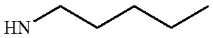 | 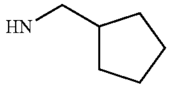 |
| 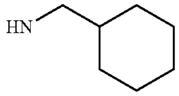 | 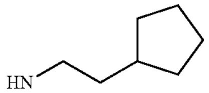 | 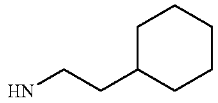 |
| 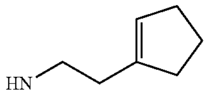 | 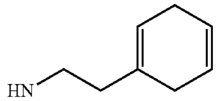 | 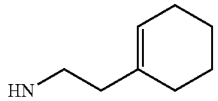 |
| 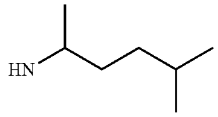 | 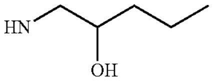 | 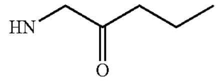 |
| 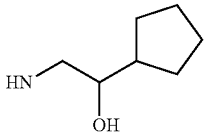 | 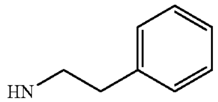 | 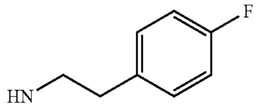 |

-continued
| HN—R | | |
|---|---|---|
| 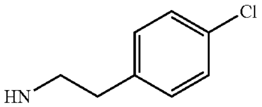 | 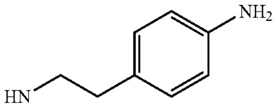 | 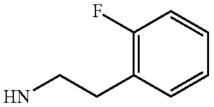 |
| 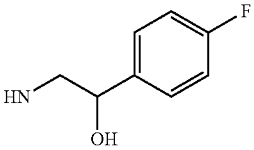 | 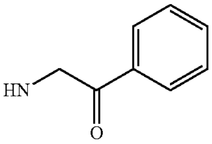 | 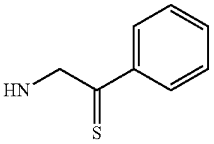 |
| 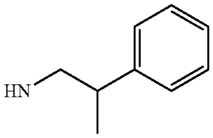 | 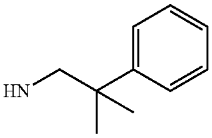 | 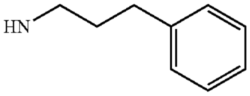 |
| 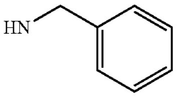 | 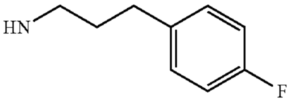 | 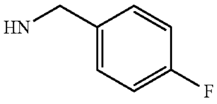 |
| 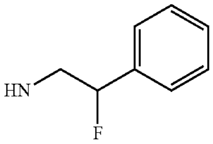 | 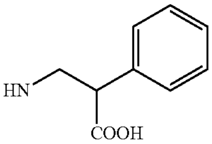 | 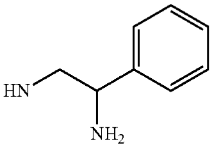 |
| 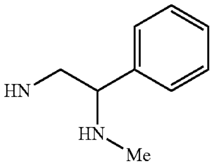 | 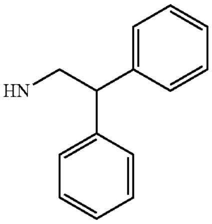 | 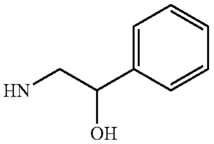 |
| 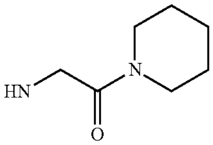 | 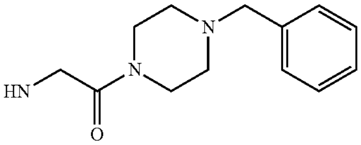 | 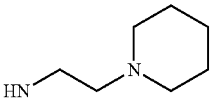 |
| 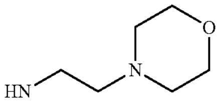 | 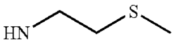 | 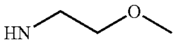 |
| 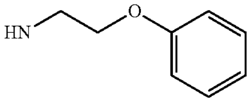 | 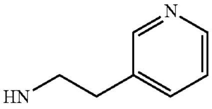 | 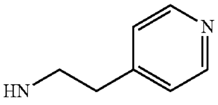 |
| 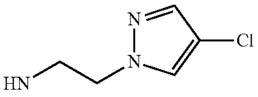 | 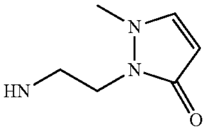 | |

-continued
HN—R
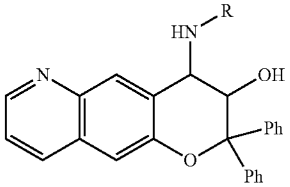
| | | |
|---|---|---|
| 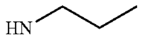 | 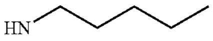 | 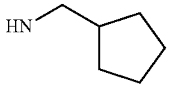 |
| 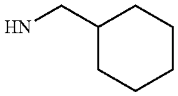 | 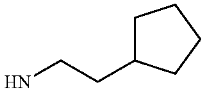 | 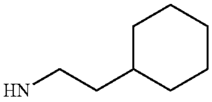 |
| 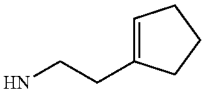 | 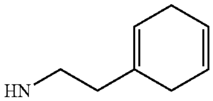 | 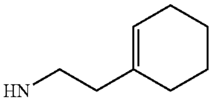 |
| 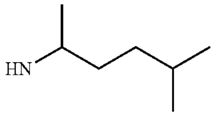 | 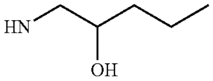 | 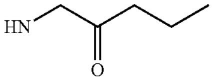 |
| 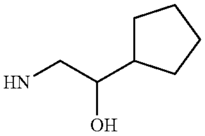 | 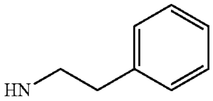 | 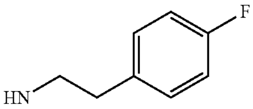 |
| 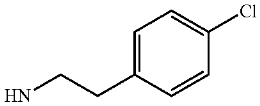 | 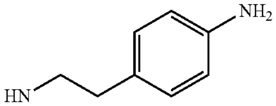 | 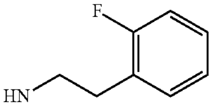 |
| 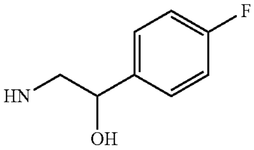 | 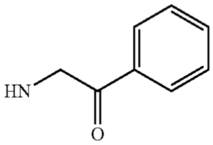 | 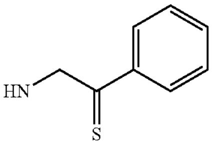 |
| 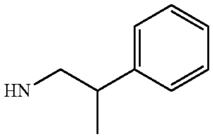 | 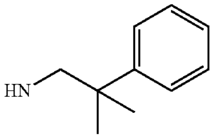 | 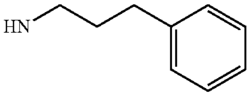 |
| 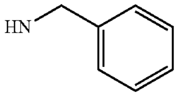 | 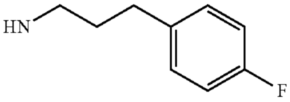 | 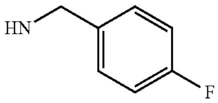 |
| 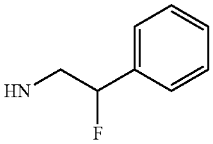 | 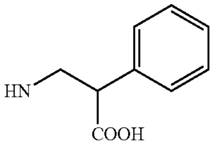 | 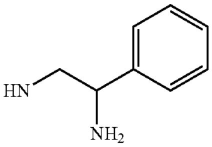 |

-continued
| HN—R | | |
|---|---|---|
| 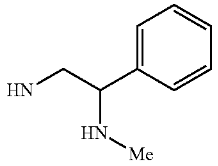 | 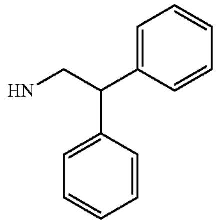 | 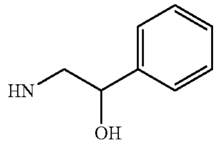 |
| 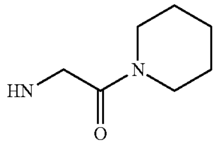 | 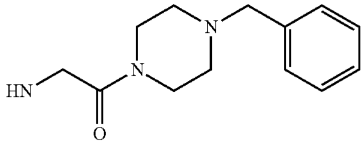 | 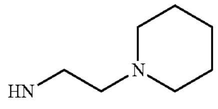 |
| 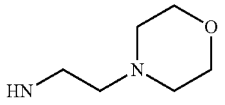 | 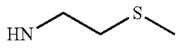 | 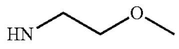 |
| 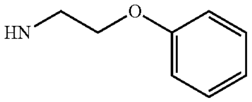 | 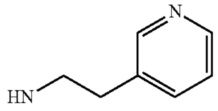 | 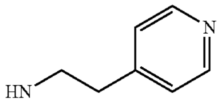 |
| 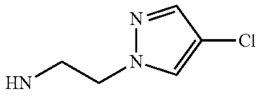 | 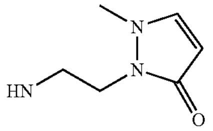 | |
| | 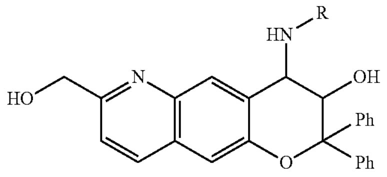 | |
|---|---|---|
| 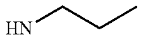 | 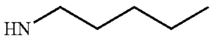 | 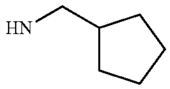 |
| 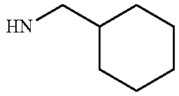 | 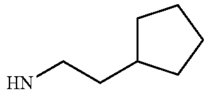 | 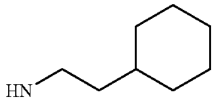 |
| 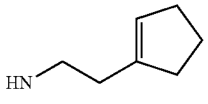 | 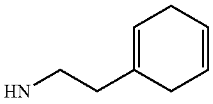 | 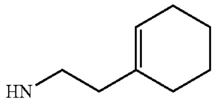 |
| 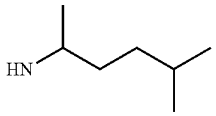 | 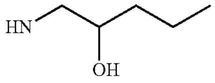 | 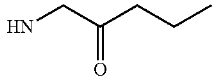 |
| 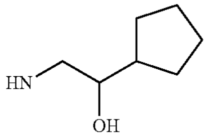 | 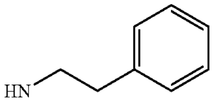 | 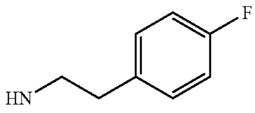 |

-continued
| HN—R | | |
|---|---|---|
| 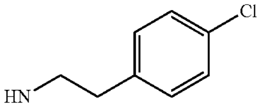 | 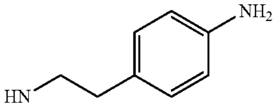 | 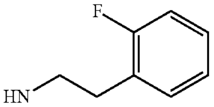 |
| 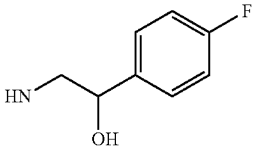 | 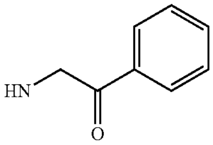 | 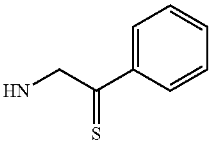 |
| 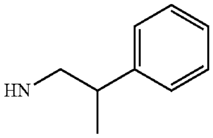 | 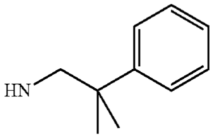 | 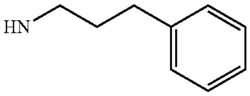 |
| 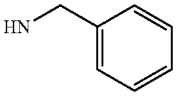 | 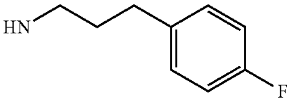 | 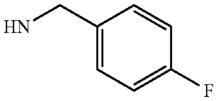 |
| 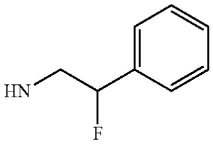 | 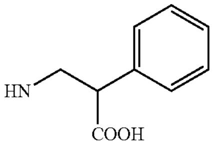 | 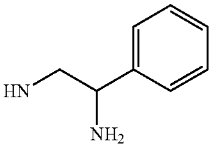 |
| 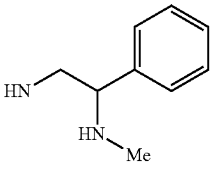 | 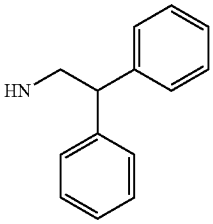 | 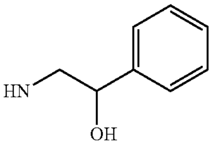 |
| 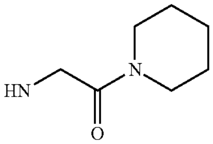 | 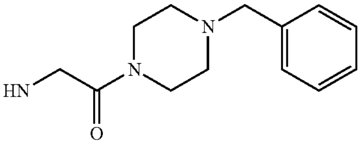 | 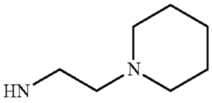 |
| 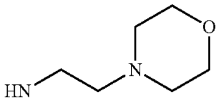 | 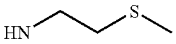 | 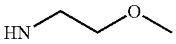 |
| 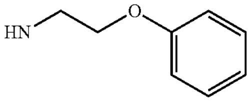 | 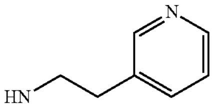 | 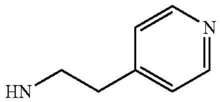 |
| 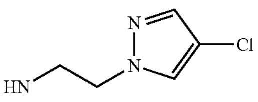 | 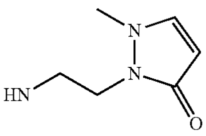 | |

-continued
| | HN—R | |
|---|---|---|
| | 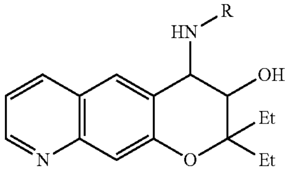 | |
| 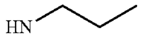 | 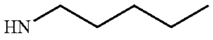 | 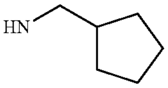 |
| 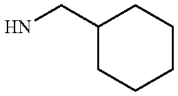 | 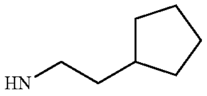 | 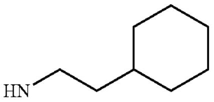 |
| 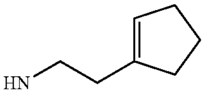 | 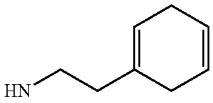 | 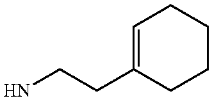 |
| 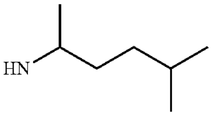 | 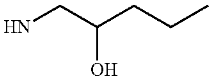 | 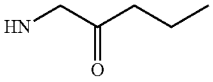 |
| 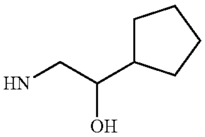 | 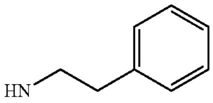 | 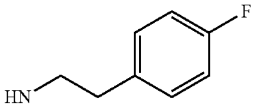 |
| 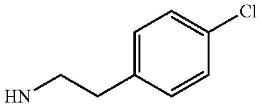 | 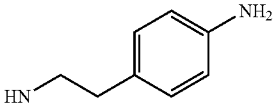 | 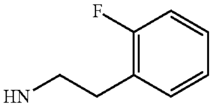 |
| 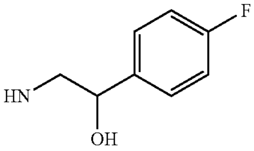 | 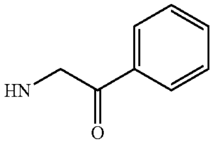 | 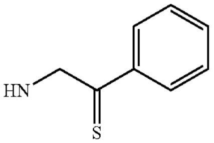 |
| 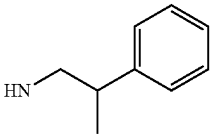 | 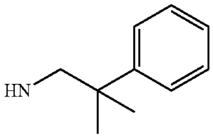 | 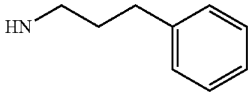 |
| 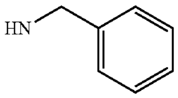 | 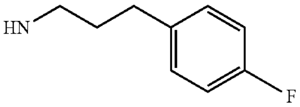 | 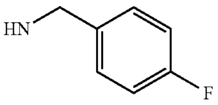 |
| 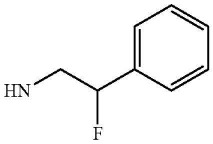 | 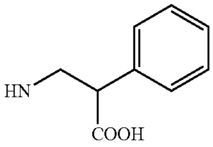 | 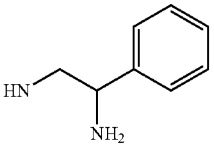 |

-continued

| HN—R | | |
|---|---|---|
| 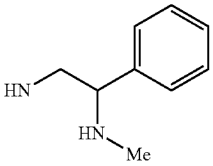 | 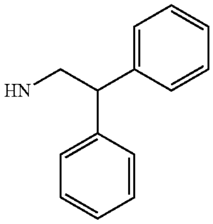 | 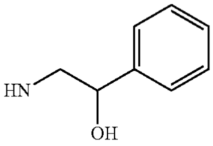 |
| 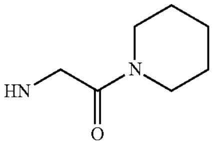 | 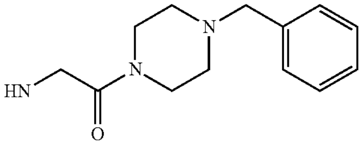 | 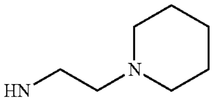 |
| 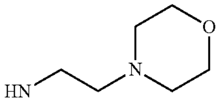 | 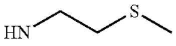 | 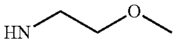 |
| 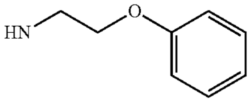 | 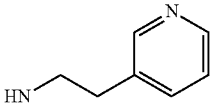 | 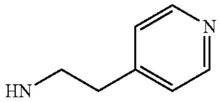 |
| 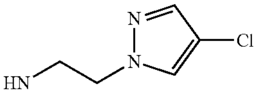 | 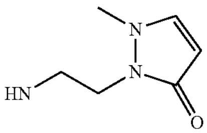 | |

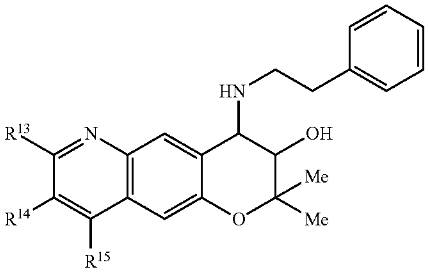

| $R^{13}$ | $R^{14}$ | $R^{15}$ | $R^{13}$ | $R^{14}$ | $R^{15}$ | $R^{13}$ | $R^{14}$ | $R^{15}$ |
|---|---|---|---|---|---|---|---|---|
| H | H | Et | $NO_2$ | H | Et | H | $NO_2$ | Et |
| H | H | iPr | CHO | H | iPr | H | CHO | iPr |
| H | H | nPr | $SO_3H$ | H | nPr | H | $SO_3H$ | nPr |
| H | H | nBu | Cl | H | nBu | H | Cl | nBu |
| H | H | tBu | Br | H | tBu | H | Br | tBu |
| H | H | Ph | $CH_2OH$ | H | Ph | H | $CH_2OH$ | Ph |
| Et | H | H | $CH_2NH_2$ | H | H | H | $CH_2NH_2$ | H |
| iPr | H | H | $CH_2NHMe$ | H | H | H | $CH_2NHMe$ | H |
| nPr | H | H | $CH_2Ph$ | H | H | H | $CH_2Ph$ | H |
| nBu | H | H | COMe | H | H | H | COMe | H |
| tBu | H | H | COOH | H | H | H | COOH | H |
| Ph | H | H | $CONH_2$ | H | H | H | $CONH_2$ | H |
| H | Et | H | CONHMe | Et | H | Et | CONHMe | H |
| H | iPr | H | CONHMs | iPr | H | iPr | CONHMs | H |
| H | nPr | H | NHMs | nPr | H | nPr | NHMs | H |
| H | nBu | H | NHCOMe | nBu | H | nBu | NHCOMe | H |
| H | tBu | H | $NO_2$ | tBu | H | tBu | $NO_2$ | H |
| H | Ph | H | CHO | Ph | H | Ph | H | $SO_3H$ |
| Cl | Et | H | $SO_3H$ | Et | H | Et | H | $SO_2NHMe$ |
| Cl | nPr | H | $SO_2NHMe$ | nPr | H | nPr | H | OH |

-continued

| $R^{13}$ | $R^{14}$ | $R^{15}$ | $R^{13}$ | $R^{14}$ | $R^{15}$ | $R^{13}$ | $R^{14}$ | $R^{15}$ |
|---|---|---|---|---|---|---|---|---|
| Cl | Ph | H | OH | Ph | H | Ph | H | COMe |
| Et | Cl | H | COMe | Cl | H | Cl | Cl | COOH |
| nPr | Cl | H | COOH | Cl | H | Cl | Cl | $CONH_2$ |
| Ph | Cl | H | $CONH_2$ | Cl | H | Cl | Cl | CONHMe |
| H | Et | Cl | CONHMe | Et | Cl | Et | H | CONHMs |
| H | nPr | Cl | CONHMs | nPr | Cl | nPr | H | NHMs |
| H | Ph | Cl | NHMs | Ph | Cl | Ph | H | $NO_2$ |
| Me | Me | H | $NO_2$ | Me | H | Me | H | OH |
| Et | Et | H | OH | Et | H | Et | H | COMe |
| nPr | nPr | H | COMe | nPr | H | nPr | H | COOH |
| Ph | Ph | H | COOH | Ph | H | Ph | H | $NO_2$ |

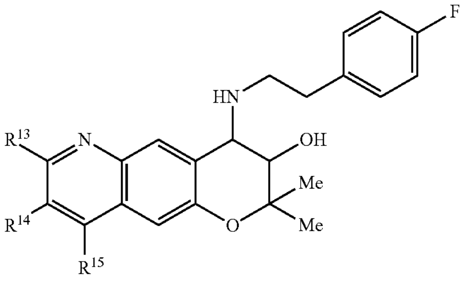

| | | | | | | | | |
|---|---|---|---|---|---|---|---|---|
| H | H | Et | $NO_2$ | H | Et | H | $NO_2$ | Et |
| H | H | iPr | CHO | H | iPr | H | CHO | iPr |
| H | H | nPr | $SO_3H$ | H | nPr | H | $SO_3H$ | nPr |
| H | H | nBu | Cl | H | nBu | H | Cl | nBu |
| H | H | tBu | Br | H | tBu | H | Br | tBu |
| H | H | Ph | $CH_2OH$ | H | Ph | H | $CH_2OH$ | Ph |
| Et | H | H | $CH_2NH_2$ | H | H | H | $CH_2NH_2$ | H |
| iPr | H | H | $CH_2NHMe$ | H | H | H | $CH_2NHMe$ | H |
| nPr | H | H | $CH_2Ph$ | H | H | H | $CH_2Ph$ | H |
| nBu | H | H | COMe | H | H | H | COMe | H |
| tBu | H | H | COOH | H | H | H | COOH | H |
| Ph | H | H | $CONH_2$ | H | H | H | $CONH_2$ | H |
| H | Et | H | CONHMe | Et | H | Et | CONHMe | H |
| H | iPr | H | CONHMs | iPr | H | iPr | CONHMs | H |
| H | nPr | H | NHMs | nPr | H | nPr | NHMs | H |
| H | nBu | H | NHCOMe | nBu | H | nBu | NHCOMe | H |
| H | tBu | H | $NO_2$ | tBu | H | tBu | $NO_2$ | H |
| H | Ph | H | CHO | Ph | H | Ph | H | $SO_3H$ |
| Cl | Et | H | $SO_3H$ | Et | H | Et | H | $SO_2NHMe$ |
| Cl | nPr | H | $SO_2NHMe$ | nPr | H | nPr | H | OH |
| Cl | Ph | H | OH | Ph | H | Ph | H | COMe |
| Et | Cl | H | COMe | Cl | H | Cl | Cl | COOH |
| nPr | Cl | H | COOH | Cl | H | Cl | Cl | $CONH_2$ |
| Ph | Cl | H | $CONH_2$ | Cl | H | Cl | Cl | CONHMe |
| H | Et | Cl | CONHMe | Et | Cl | Et | H | CONHMs |
| H | nPr | Cl | CONHMs | nPr | Cl | nPr | H | NHMs |
| H | Ph | Cl | NHMs | Ph | Cl | Ph | H | $NO_2$ |
| Me | Me | H | $NO_2$ | Me | H | Me | H | OH |
| Et | Et | H | OH | Et | H | Et | H | COMe |
| nPr | nPr | H | COMe | nPr | H | nPr | H | COOH |
| Ph | Ph | H | COOH | Ph | H | Ph | H | $NO_2$ |

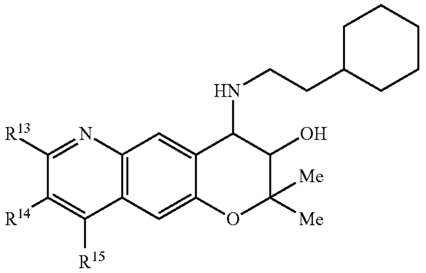

| | | | | | | | | |
|---|---|---|---|---|---|---|---|---|
| H | H | Et | $NO_2$ | H | Et | H | $NO_2$ | Et |
| H | H | iPr | CHO | H | iPr | H | CHO | iPr |
| H | H | nPr | $SO_3H$ | H | nPr | H | $SO_3H$ | nPr |
| H | H | nBu | Cl | H | nBu | H | Cl | nBu |
| H | H | tBu | Br | H | tBu | H | Br | tBu |
| H | H | Ph | $CH_2OH$ | H | Ph | H | $CH_2OH$ | Ph |

-continued

| $R^{13}$ | $R^{14}$ | $R^{15}$ | $R^{13}$ | $R^{14}$ | $R^{15}$ | $R^{13}$ | $R^{14}$ | $R^{15}$ |
|---|---|---|---|---|---|---|---|---|
| Et | H | H | $CH_2NH_2$ | H | H | H | $CH_2NH_2$ | H |
| iPr | H | H | $CH_2NHMe$ | H | H | H | $CH_2NHMe$ | H |
| nPr | H | H | $CH_2Ph$ | H | H | H | $CH_2Ph$ | H |
| nBu | H | H | COMe | H | H | H | COMe | H |
| tBu | H | H | COOH | H | H | H | COOH | H |
| Ph | H | H | $CONH_2$ | H | H | H | $CONH_2$ | H |
| H | Et | H | CONHMe | Et | H | Et | CONHMe | H |
| H | iPr | H | CONHMs | iPr | H | iPr | CONHMs | H |
| H | nPr | H | NHMs | nPr | H | nPr | NHMs | H |
| H | nBu | H | NHCOMe | nBu | H | nBu | NHCOMe | H |
| H | tBu | H | $NO_2$ | tBu | H | tBu | $NO_2$ | H |
| H | Ph | H | CHO | Ph | H | Ph | H | $SO_3H$ |
| Cl | Et | H | $SO_3H$ | Et | H | Et | H | $SO_2NHMe$ |
| Cl | nPr | H | $SO_2NHMe$ | nPr | H | nPr | H | OH |
| Cl | Ph | H | OH | Ph | H | Ph | H | COMe |
| Et | Cl | H | COMe | Cl | H | Cl | Cl | COOH |
| nPr | Cl | H | COOH | Cl | H | Cl | Cl | $CONH_2$ |
| Ph | Cl | H | $CONH_2$ | Cl | H | Cl | Cl | CONHMe |
| H | Et | Cl | CONHMe | Et | Cl | Et | H | CONHMs |
| H | nPr | Cl | CONHMs | nPr | Cl | nPr | H | NHMs |
| H | Ph | Cl | NHMs | Ph | Cl | Ph | H | $NO_2$ |
| Me | Me | H | $NO_2$ | Me | H | Me | H | OH |
| Et | Et | H | OH | Et | H | Et | H | COMe |
| nPr | nPr | H | COMe | nPr | H | nPr | H | COOH |
| Ph | Ph | H | COOH | Ph | H | Ph | H | $NO_2$ |

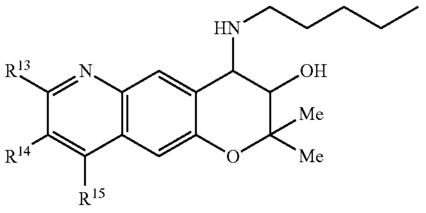

| | | | | | | | | |
|---|---|---|---|---|---|---|---|---|
| H | H | Et | $NO_2$ | H | Et | H | $NO_2$ | Et |
| H | H | iPr | CHO | H | iPr | H | CHO | iPr |
| H | H | nPr | $SO_3H$ | H | nPr | H | $SO_3H$ | nPr |
| H | H | nBu | Cl | H | nBu | H | Cl | nBu |
| H | H | tBu | Br | H | tBu | H | Br | tBu |
| H | H | Ph | $CH_2OH$ | H | Ph | H | $CH_2OH$ | Ph |
| Et | H | H | $CH_2NH_2$ | H | H | H | $CH_2NH_2$ | H |
| iPr | H | H | $CH_2NHMe$ | H | H | H | $CH_2NHMe$ | H |
| nPr | H | H | $CH_2Ph$ | H | H | H | $CH_2Ph$ | H |
| nBu | H | H | COMe | H | H | H | COMe | H |
| tBu | H | H | COOH | H | H | H | COOH | H |
| Ph | H | H | $CONH_2$ | H | H | H | $CONH_2$ | H |
| H | Et | H | CONHMe | Et | H | Et | CONHMe | H |
| H | iPr | H | CONHMs | iPr | H | iPr | CONHMs | H |
| H | nPr | H | NHMs | nPr | H | nPr | NHMs | H |
| H | nBu | H | NHCOMe | nBu | H | nBu | NHCOMe | H |
| H | tBu | H | $NO_2$ | tBu | H | tBu | $NO_2$ | H |
| H | Ph | H | CHO | Ph | H | Ph | H | $SO_3H$ |
| Cl | Et | H | $SO_3H$ | Et | H | Et | H | $SO_2NHMe$ |
| Cl | nPr | H | $SO_2NHMe$ | nPr | H | nPr | H | OH |
| Cl | Ph | H | OH | Ph | H | Ph | H | COMe |
| Et | Cl | H | COMe | Cl | H | Cl | Cl | COOH |
| nPr | Cl | H | COOH | Cl | H | Cl | Cl | $CONH_2$ |
| Ph | Cl | H | $CONH_2$ | Cl | H | Cl | Cl | CONHMe |
| H | Et | Cl | CONHMe | Et | Cl | Et | H | CONHMs |
| H | nPr | Cl | CONHMs | nPr | Cl | nPr | H | NHMs |
| H | Ph | Cl | NHMs | Ph | Cl | Ph | H | $NO_2$ |
| Me | Me | H | $NO_2$ | Me | H | Me | H | OH |
| Et | Et | H | OH | Et | H | Et | H | COMe |
| nPr | nPr | H | COMe | nPr | H | nPr | H | COOH |
| Ph | Ph | H | COOH | Ph | H | Ph | H | $NO_2$ |

-continued

| $R^{13}$ | $R^{14}$ | $R^{15}$ | $R^{13}$ | $R^{14}$ | $R^{15}$ | $R^{13}$ | $R^{14}$ | $R^{15}$ |
|---|---|---|---|---|---|---|---|---|
| 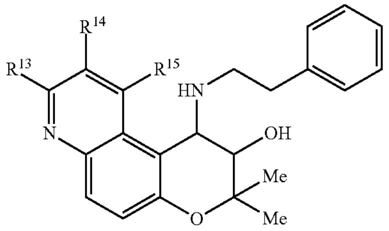 | | | | | | | | |
| H | H | Et | $NO_2$ | H | Et | H | $NO_2$ | Et |
| H | H | iPr | CHO | H | iPr | H | CHO | iPr |
| H | H | nPr | $SO_3H$ | H | nPr | H | $SO_3H$ | nPr |
| H | H | nBu | Cl | H | nBu | H | Cl | nBu |
| H | H | tBu | Br | H | tBu | H | Br | tBu |
| H | H | Ph | $CH_2OH$ | H | Ph | H | $CH_2OH$ | Ph |
| Et | H | H | $CH_2NH_2$ | H | H | H | $CH_2NH_2$ | H |
| iPr | H | H | $CH_2NHMe$ | H | H | H | $CH_2NHMe$ | H |
| nPr | H | H | $CH_2Ph$ | H | H | H | $CH_2Ph$ | H |
| nBu | H | H | COMe | H | H | H | COMe | H |
| tBu | H | H | COOH | H | H | H | COOH | H |
| Ph | H | H | $CONH_2$ | H | H | H | $CONH_2$ | H |
| H | Et | H | CONHMe | Et | H | Et | CONHMe | H |
| H | iPr | H | CONHMs | iPr | H | iPr | CONHMs | H |
| H | nPr | H | NHMs | nPr | H | nPr | NHMs | H |
| H | nBu | H | NHCOMe | nBu | H | nBu | NHCOMe | H |
| H | tBu | H | $NO_2$ | tBu | H | tBu | $NO_2$ | H |
| H | Ph | H | CHO | Ph | H | Ph | H | $SO_3H$ |
| Cl | Et | H | $SO_3H$ | Et | H | Et | H | $SO_2NHMe$ |
| Cl | nPr | H | $SO_2NHMe$ | nPr | H | nPr | H | OH |
| Cl | Ph | H | OH | Ph | H | Ph | H | COMe |
| Et | Cl | H | COMe | Cl | H | Cl | Cl | COOH |
| nPr | Cl | H | COOH | Cl | H | Cl | Cl | $CONH_2$ |
| Ph | Cl | H | $CONH_2$ | Cl | H | Cl | Cl | CONHMe |
| H | Et | Cl | CONHMe | Et | Cl | Et | H | CONHMs |
| H | nPr | Cl | CONHMs | nPr | Cl | nPr | H | NHMs |
| H | Ph | Cl | NHMs | Ph | Cl | Ph | H | $NO_2$ |
| Me | Me | H | $NO_2$ | Me | H | Me | H | OH |
| Et | Et | H | OH | Et | H | Et | H | COMe |
| nPr | nPr | H | COMe | nPr | H | nPr | H | COOH |
| Ph | Ph | H | COOH | Ph | H | Ph | H | $NO_2$ |
| 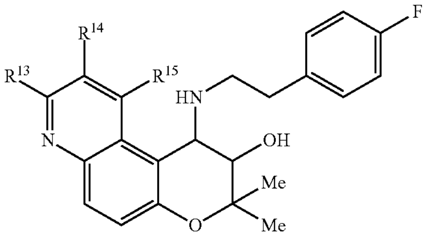 | | | | | | | | |
| H | H | Et | $NO_2$ | H | Et | H | $NO_2$ | Et |
| H | H | iPr | CHO | H | iPr | H | CHO | iPr |
| H | H | nPr | $SO_3H$ | H | nPr | H | $SO_3H$ | nPr |
| H | H | nBu | Cl | H | nBu | H | Cl | nBu |
| H | H | tBu | Br | H | tBu | H | Br | tBu |
| H | H | Ph | $CH_2OH$ | H | Ph | H | $CH_2OH$ | Ph |
| Et | H | H | $CH_2NH_2$ | H | H | H | $CH_2NH_2$ | H |
| iPr | H | H | $CH_2NHMe$ | H | H | H | $CH_2NHMe$ | H |
| nPr | H | H | $CH_2Ph$ | H | H | H | $CH_2Ph$ | H |
| nBu | H | H | COMe | H | H | H | COMe | H |
| tBu | H | H | COOH | H | H | H | COOH | H |
| Ph | H | H | $CONH_2$ | H | H | H | $CONH_2$ | H |
| H | Et | H | CONHMe | Et | H | Et | CONHMe | H |
| H | iPr | H | CONHMs | iPr | H | iPr | CONHMs | H |
| H | nPr | H | NHMs | nPr | H | nPr | NHMs | H |
| H | nBu | H | NHCOMe | nBu | H | nBu | NHCOMe | H |
| H | tBu | H | $NO_2$ | tBu | H | tBu | $NO_2$ | H |
| H | Ph | H | CHO | Ph | H | Ph | H | $SO_3H$ |
| Cl | Et | H | $SO_3H$ | Et | H | Et | H | $SO_2NHMe$ |
| Cl | nPr | H | $SO_2NHMe$ | nPr | H | nPr | H | OH |
| Cl | Ph | H | OH | Ph | H | Ph | H | COMe |
| Et | Cl | H | COMe | Cl | H | Cl | Cl | COOH |

-continued

| $R^{13}$ | $R^{14}$ | $R^{15}$ | $R^{13}$ | $R^{14}$ | $R^{15}$ | $R^{13}$ | $R^{14}$ | $R^{15}$ |
|---|---|---|---|---|---|---|---|---|
| nPr | Cl | H | COOH | Cl | H | Cl | Cl | $CONH_2$ |
| Ph | Cl | H | $CONH_2$ | Cl | H | Cl | Cl | CONHMe |
| H | Et | Cl | CONHMe | Et | Cl | Et | H | CONHMs |
| H | nPr | Cl | CONHMs | nPr | Cl | nPr | H | NHMs |
| H | Ph | Cl | NHMs | Ph | Cl | Ph | H | $NO_2$ |
| Me | Me | H | $NO_2$ | Me | H | Me | H | OH |
| Et | Et | H | OH | Et | H | Et | H | COMe |
| nPr | nPr | H | COMe | nPr | H | nPr | H | COOH |
| Ph | Ph | H | COOH | Ph | H | Ph | H | $NO_2$ |

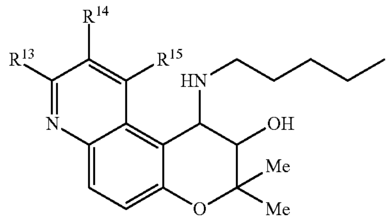

| | | | | | | | | |
|---|---|---|---|---|---|---|---|---|
| H | H | Et | $NO_2$ | H | Et | H | $NO_2$ | Et |
| H | H | iPr | CHO | H | iPr | H | CHO | iPr |
| H | H | nPr | $SO_3H$ | H | nPr | H | $SO_3H$ | nPr |
| H | H | nBu | Cl | H | nBu | H | Cl | nBu |
| H | H | tBu | Br | H | tBu | H | Br | tBu |
| H | H | Ph | $CH_2OH$ | H | Ph | H | $CH_2OH$ | Ph |
| Et | H | H | $CH_2NH_2$ | H | H | H | $CH_2NH_2$ | H |
| iPr | H | H | $CH_2NHMe$ | H | H | H | $CH_2NHMe$ | H |
| nPr | H | H | $CH_2Ph$ | H | H | H | $CH_2Ph$ | H |
| nBu | H | H | COMe | H | H | H | COMe | H |
| tBu | H | H | COOH | H | H | H | COOH | H |
| Ph | H | H | $CONH_2$ | H | H | H | $CONH_2$ | H |
| H | Et | H | CONHMe | Et | H | Et | CONHMe | H |
| H | iPr | H | CONHMs | iPr | H | iPr | CONHMs | H |
| H | nPr | H | NHMs | nPr | H | nPr | NHMs | H |
| H | nBu | H | NHCOMe | nBu | H | nBu | NHCOMe | H |
| H | tBu | H | $NO_2$ | tBu | H | tBu | $NO_2$ | H |
| H | Ph | H | CHO | Ph | H | Ph | H | $SO_3H$ |
| Cl | Et | H | $SO_3H$ | Et | H | Et | H | $SO_2NHMe$ |
| Cl | nPr | H | $SO_2NHMe$ | nPr | H | nPr | H | OH |
| Cl | Ph | H | OH | Ph | H | Ph | H | COMe |
| Et | Cl | H | COMe | Cl | H | Cl | Cl | COOH |
| nPr | Cl | H | COOH | Cl | H | Cl | Cl | $CONH_2$ |
| Ph | Cl | H | $CONH_2$ | Cl | H | Cl | Cl | CONHMe |
| H | Et | Cl | CONHMe | Et | Cl | Et | H | CONHMs |
| H | nPr | Cl | CONHMs | nPr | Cl | nPr | H | NHMs |
| H | Ph | Cl | NHMs | Ph | Cl | Ph | H | $NO_2$ |
| Me | Me | H | $NO_2$ | Me | H | Me | H | OH |
| Et | Et | H | OH | Et | H | Et | H | COMe |
| nPr | nPr | H | COMe | nPr | H | nPr | H | COOH |
| Ph | Ph | H | COOH | Ph | H | Ph | H | $NO_2$ |

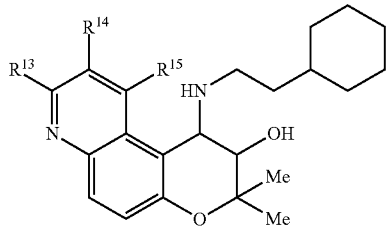

| | | | | | | | | |
|---|---|---|---|---|---|---|---|---|
| H | H | Et | $NO_2$ | H | Et | H | $NO_2$ | Et |
| H | H | iPr | CHO | H | iPr | H | CHO | iPr |
| H | H | nPr | $SO_3H$ | H | nPr | H | $SO_3H$ | nPr |
| H | H | nBu | Cl | H | nBu | H | Cl | nBu |
| H | H | tBu | Br | H | tBu | H | Br | tBu |
| H | H | Ph | $CH_2OH$ | H | Ph | H | $CH_2OH$ | Ph |
| Et | H | H | $CH_2NH_2$ | H | H | H | $CH_2NH_2$ | H |
| iPr | H | H | $CH_2NHMe$ | H | H | H | $CH_2NHMe$ | H |
| nPr | H | H | $CH_2Ph$ | H | H | H | $CH_2Ph$ | H |
| nBu | H | H | COMe | H | H | H | COMe | H |
| tBu | H | H | COOH | H | H | H | COOH | H |
| Ph | H | H | $CONH_2$ | H | H | H | $CONH_2$ | H |
| H | Et | H | CONHMe | Et | H | Et | CONHMe | H |

-continued

| $R^{13}$ | $R^{14}$ | $R^{15}$ | $R^{13}$ | $R^{14}$ | $R^{15}$ | $R^{13}$ | $R^{14}$ | $R^{15}$ |
|---|---|---|---|---|---|---|---|---|
| H | iPr | H | CONHMs | iPr | H | iPr | CONHMs | H |
| H | nPr | H | NHMs | nPr | H | nPr | NHMs | H |
| H | nBu | H | NHCOMe | nBu | H | nBu | NHCOMe | H |
| H | tBu | H | $NO_2$ | tBu | H | tBu | $NO_2$ | H |
| H | Ph | H | CHO | Ph | H | Ph | H | $SO_3H$ |
| Cl | Et | H | $SO_3H$ | Et | H | Et | H | $SO_2NHMe$ |
| Cl | nPr | H | $SO_2NHMe$ | nPr | H | nPr | H | OH |
| Cl | Ph | H | OH | Ph | H | Ph | H | COMe |
| Et | Cl | H | COMe | Cl | H | Cl | Cl | COOH |
| nPr | Cl | H | COOH | Cl | H | Cl | Cl | $CONH_2$ |
| Ph | Cl | H | $CONH_2$ | Cl | H | Cl | Cl | CONHMe |
| H | Et | Cl | CONHMe | Et | Cl | Et | H | CONHMs |
| H | nPr | Cl | CONHMs | nPr | Cl | nPr | H | NHMs |
| H | Ph | Cl | NHMs | Ph | Cl | Ph | H | $NO_2$ |
| Me | Me | H | $NO_2$ | Me | H | Me | H | OH |
| Et | Et | H | OH | Et | H | Et | H | COMe |
| nPr | nPr | H | COMe | nPr | H | nPr | H | COOH |
| Ph | Ph | H | COOH | Ph | H | Ph | H | $NO_2$ |

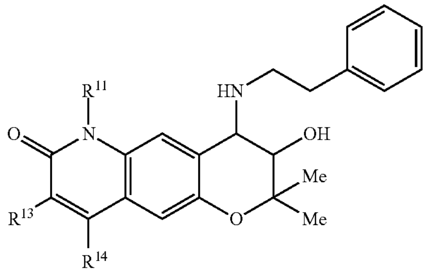

| $R^{11}$ | $R^{13}$ | $R^{14}$ | $R^{11}$ | $R^{13}$ | $R^{14}$ | $R^{11}$ | $R^{13}$ | $R^{14}$ |
|---|---|---|---|---|---|---|---|---|
| H | H | Et | H | $NO_2$ | H | H | H | $NO_2$ |
| H | H | iPr | H | CHO | H | H | H | CHO |
| H | H | nPr | H | $SO_3H$ | H | H | H | $SO_3H$ |
| H | H | nBu | H | Cl | H | H | H | Cl |
| H | H | tBu | H | Br | H | H | H | Br |
| Me | H | H | Me | $CH_2OH$ | H | Me | H | $CH_2OH$ |
| Me | Et | Ph | Me | $CH_2NH_2$ | H | Me | H | $CH_2NH_2$ |
| Me | iPr | H | Me | $CH_2NHMe$ | H | Me | H | $CH_2NHMe$ |
| Me | nPr | H | Me | $CH_2Ph$ | H | Me | H | $CH_2Ph$ |
| Me | nBu | H | Me | COMe | H | Me | H | COMe |
| Me | tBu | H | Me | COOH | H | Me | H | COOH |
| Et | Ph | H | Et | $CONH_2$ | H | Et | H | $CONH_2$ |
| Et | H | Et | Et | CONHMe | Et | Et | Et | CONHMe |
| Et | H | iPr | Et | CONHMs | iPr | Et | iPr | CONHMs |
| iPr | H | nPr | iPr | NHMs | nPr | iPr | nPr | NHMs |
| nPr | H | nBu | nPr | NHCOMe | nBu | nPr | nBu | NHCOMe |
| nBu | H | tBu | nBu | $NO_2$ | tBu | nBu | tBu | $NO_2$ |
| tBu | H | Ph | tBu | CHO | Ph | tBu | Ph | H |
| Ph | Cl | Et | Ph | $SO_3H$ | Et | Ph | Et | H |
| $CH_2OH$ | Cl | nPr | $CH_2OH$ | $SO_2NHMe$ | nPr | $CH_2OH$ | nPr | H |
| $CH_2OH$ | Cl | Ph | $CH_2OH$ | OH | Ph | $CH_2OH$ | Ph | H |
| $CH_2OMe$ | Et | Cl | $CH_2OMe$ | COMe | Cl | $CH_2OMe$ | Cl | Cl |
| $CH_2OMe$ | nPr | Cl | $CH_2OMe$ | COOH | Cl | $CH_2OMe$ | Cl | Cl |
| $CH_2NH_2$ | Ph | Cl | $CH_2NH_2$ | $CONH_2$ | Cl | $CH_2NH_2$ | Cl | Cl |
| $CH_2NH_2$ | H | Et | $CH_2NH_2$ | CONHMe | Et | $CH_2NH_2$ | Et | H |
| $CH_2NH_2$ | H | nPr | $CH_2NH_2$ | CONHMs | nPr | $CH_2NH_2$ | nPr | H |
| $CH_2NH_2$ | H | Ph | $CH_2NH_2$ | NHMs | Ph | $CH_2NH_2$ | Ph | H |
| $CH_2NHMe$ | Me | Me | $CH_2NHMe$ | $NO_2$ | Me | $CH_2NHMe$ | Me | H |
| $CH_2Ph$ | Et | Et | $CH_2Ph$ | OH | Et | $CH_2Ph$ | Et | H |
| $CH_2Ph$ | nPr | nPr | $CH_2Ph$ | COMe | nPr | $CH_2Ph$ | nPr | H |
| $CH_2CH_2Ph$ | Ph | Ph | $CH_2CH_2Ph$ | COOH | Ph | $CH_2CH_2Ph$ | Ph | H |

-continued

| $R^{11}$ | $R^{13}$ | $R^{14}$ | $R^{11}$ | $R^{13}$ | $R^{14}$ | $R^{11}$ | $R^{13}$ | $R^{14}$ |
|---|---|---|---|---|---|---|---|---|
| 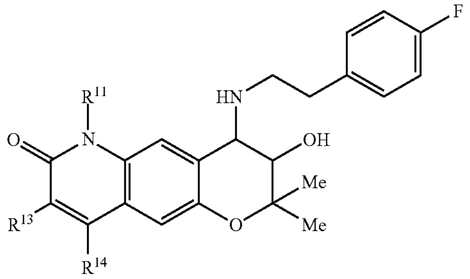 | | | | | | | | |
| H | H | Et | H | $NO_2$ | H | H | H | $NO_2$ |
| H | H | iPr | H | CHO | H | H | H | CHO |
| H | H | nPr | H | $SO_3H$ | H | H | H | $SO_3H$ |
| H | H | nBu | H | Cl | H | H | H | Cl |
| H | H | tBu | H | Br | H | H | H | Br |
| Me | H | H | Me | $CH_2OH$ | H | Me | H | $CH_2OH$ |
| Me | Et | Ph | Me | $CH_2NH_2$ | H | Me | H | $CH_2NH_2$ |
| Me | iPr | H | Me | $CH_2NHMe$ | H | Me | H | $CH_2NHMe$ |
| Me | nPr | H | Me | $CH_2Ph$ | H | Me | H | $CH_2Ph$ |
| Me | nBu | H | Me | COMe | H | Me | H | COMe |
| Me | tBu | H | Me | COOH | H | Me | H | COOH |
| Et | Ph | H | Et | $CONH_2$ | H | Et | H | $CONH_2$ |
| Et | H | Et | Et | CONHMe | Et | Et | Et | CONHMe |
| Et | H | iPr | Et | CONHMs | iPr | Et | iPr | CONHMs |
| iPr | H | nPr | iPr | NHMs | nPr | iPr | nPr | NHMs |
| nPr | H | nBu | nPr | NHCOMe | nBu | nPr | nBu | NHCOMe |
| nBu | H | tBu | nBu | $NO_2$ | tBu | nBu | tBu | $NO_2$ |
| tBu | H | Ph | tBu | CHO | Ph | tBu | Ph | H |
| Ph | Cl | Et | Ph | $SO_3H$ | Et | Ph | Et | H |
| $CH_2OH$ | Cl | nPr | $CH_2OH$ | $SO_2NHMe$ | nPr | $CH_2OH$ | nPr | H |
| $CH_2OH$ | Cl | Ph | $CH_2OH$ | OH | Ph | $CH_2OH$ | Ph | H |
| $CH_2OMe$ | Et | Cl | $CH_2OMe$ | COMe | Cl | $CH_2OMe$ | Cl | Cl |
| $CH_2OMe$ | nPr | Cl | $CH_2OMe$ | COOH | Cl | $CH_2OMe$ | Cl | Cl |
| $CH_2NH_2$ | Ph | Cl | $CH_2NH_2$ | $CONH_2$ | Cl | $CH_2NH_2$ | Cl | Cl |
| $CH_2NH_2$ | H | Et | $CH_2NH_2$ | CONHMe | Et | $CH_2NH_2$ | Et | H |
| $CH_2NH_2$ | H | nPr | $CH_2NH_2$ | CONHMs | nPr | $CH_2NH_2$ | nPr | H |
| $CH_2NH_2$ | H | Ph | $CH_2NH_2$ | NHMs | Ph | $CH_2NH_2$ | Ph | H |
| $CH_2NHMe$ | Me | Me | $CH_2NHMe$ | $NO_2$ | Me | $CH_2NHMe$ | Me | H |
| $CH_2Ph$ | Et | Et | $CH_2Ph$ | OH | Et | $CH_2Ph$ | Et | H |
| $CH_2Ph$ | nPr | nPr | $CH_2Ph$ | COMe | nPr | $CH_2Ph$ | nPr | H |
| $CH_2CH_2Ph$ | Ph | Ph | $CH_2CH_2Ph$ | COOH | Ph | $CH_2CH_2Ph$ | Ph | H |
| 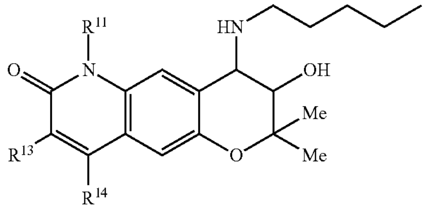 | | | | | | | | |
| H | H | Et | H | $NO_2$ | H | H | H | $NO_2$ |
| H | H | iPr | H | CHO | H | H | H | CHO |
| H | H | nPr | H | $SO_3H$ | H | H | H | $SO_3H$ |
| H | H | nBu | H | Cl | H | H | H | Cl |
| H | H | tBu | H | Br | H | H | H | Br |
| Me | H | H | Me | $CH_2OH$ | H | Me | H | $CH_2OH$ |
| Me | Et | Ph | Me | $CH_2NH_2$ | H | Me | H | $CH_2NH_2$ |
| Me | iPr | H | Me | $CH_2NHMe$ | H | Me | H | $CH_2NHMe$ |
| Me | nPr | H | Me | $CH_2Ph$ | H | Me | H | $CH_2Ph$ |
| Me | nBu | H | Me | COMe | H | Me | H | COMe |
| Me | tBu | H | Me | COOH | H | Me | H | COOH |
| Et | Ph | H | Et | $CONH_2$ | H | Et | H | $CONH_2$ |
| Et | H | Et | Et | CONHMe | Et | Et | Et | CONHMe |
| Et | H | iPr | Et | CONHMs | iPr | Et | iPr | CONHMs |
| iPr | H | nPr | iPr | NHMs | nPr | iPr | nPr | NHMs |
| nPr | H | nBu | nPr | NHCOMe | nBu | nPr | nBu | NHCOMe |
| nBu | H | tBu | nBu | $NO_2$ | tBu | nBu | tBu | $NO_2$ |
| tBu | H | Ph | tBu | CHO | Ph | tBu | Ph | H |
| Ph | Cl | Et | Ph | $SO_3H$ | Et | Ph | Et | H |
| $CH_2OH$ | Cl | nPr | $CH_2OH$ | $SO_2NHMe$ | nPr | $CH_2OH$ | nPr | H |
| $CH_2OH$ | Cl | Ph | $CH_2OH$ | OH | Ph | $CH_2OH$ | Ph | H |

-continued

| $R^{11}$ | $R^{13}$ | $R^{14}$ | $R^{11}$ | $R^{13}$ | $R^{14}$ | $R^{11}$ | $R^{13}$ | $R^{14}$ |
|---|---|---|---|---|---|---|---|---|
| $CH_2OMe$ | Et | Cl | $CH_2OMe$ | COMe | Cl | $CH_2OMe$ | Cl | Cl |
| $CH_2OMe$ | nPr | Cl | $CH_2OMe$ | COOH | Cl | $CH_2OMe$ | Cl | Cl |
| $CH_2NH_2$ | Ph | Cl | $CH_2NH_2$ | $CONH_2$ | Cl | $CH_2NH_2$ | Cl | Cl |
| $CH_2NH_2$ | H | Et | $CH_2NH_2$ | CONHMe | Et | $CH_2NH_2$ | Et | H |
| $CH_2NH_2$ | H | nPr | $CH_2NH_2$ | CONHMs | nPr | $CH_2NH_2$ | nPr | H |
| $CH_2NH_2$ | H | Ph | $CH_2NH_2$ | NHMs | Ph | $CH_2NH_2$ | Ph | H |
| $CH_2NHMe$ | Me | Me | $CH_2NHMe$ | $NO_2$ | Me | $CH_2NHMe$ | Me | H |
| $CH_2Ph$ | Et | Et | $CH_2Ph$ | OH | Et | $CH_2Ph$ | Et | H |
| $CH_2Ph$ | nPr | nPr | $CH_2Ph$ | COMe | nPr | $CH_2Ph$ | nPr | H |
| $CH_2CH_2Ph$ | Ph | Ph | $CH_2CH_2Ph$ | COOH | Ph | $CH_2CH_2Ph$ | Ph | H |

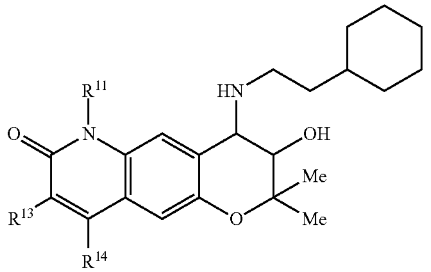

| | | | | | | | | |
|---|---|---|---|---|---|---|---|---|
| H | H | Et | H | $NO_2$ | H | H | H | $NO_2$ |
| H | H | iPr | H | CHO | H | H | H | CHO |
| H | H | nPr | H | $SO_3H$ | H | H | H | $SO_3H$ |
| H | H | nBu | H | Cl | H | H | H | Cl |
| H | H | tBu | H | Br | H | H | H | Br |
| Me | H | H | Me | $CH_2OH$ | H | Me | H | $CH_2OH$ |
| Me | Et | Ph | Me | $CH_2NH_2$ | H | Me | H | $CH_2NH_2$ |
| Me | iPr | H | Me | $CH_2NHMe$ | H | Me | H | $CH_2NHMe$ |
| Me | nPr | H | Me | $CH_2Ph$ | H | Me | H | $CH_2Ph$ |
| Me | nBu | H | Me | COMe | H | Me | H | COMe |
| Me | tBu | H | Me | COOH | H | Me | H | COOH |
| Et | Ph | H | Et | $CONH_2$ | H | Et | H | $CONH_2$ |
| Et | H | Et | Et | CONHMe | Et | Et | Et | CONHMe |
| Et | H | iPr | Et | CONHMs | iPr | Et | iPr | CONHMs |
| iPr | H | nPr | iPr | NHMs | nPr | iPr | nPr | NHMs |
| nPr | H | nBu | nPr | NHCOMe | nBu | nPr | nBu | NHCOMe |
| nBu | H | tBu | nBu | $NO_2$ | tBu | nBu | tBu | $NO_2$ |
| tBu | H | Ph | tBu | CHO | Ph | tBu | Ph | H |
| Ph | Cl | Et | Ph | $SO_3H$ | Et | Ph | Et | H |
| $CH_2OH$ | Cl | nPr | $CH_2OH$ | $SO_2NHMe$ | nPr | $CH_2OH$ | nPr | H |
| $CH_2OH$ | Cl | Ph | $CH_2OH$ | OH | Ph | $CH_2OH$ | Ph | H |
| $CH_2OMe$ | Et | Cl | $CH_2OMe$ | COMe | Cl | $CH_2OMe$ | Cl | Cl |
| $CH_2OMe$ | nPr | Cl | $CH_2OMe$ | COOH | Cl | $CH_2OMe$ | Cl | Cl |
| $CH_2NH_2$ | Ph | Cl | $CH_2NH_2$ | $CONH_2$ | Cl | $CH_2NH_2$ | Cl | Cl |
| $CH_2NH_2$ | H | Et | $CH_2NH_2$ | CONHMe | Et | $CH_2NH_2$ | Et | H |
| $CH_2NH_2$ | H | nPr | $CH_2NH_2$ | CONHMs | nPr | $CH_2NH_2$ | nPr | H |
| $CH_2NH_2$ | H | Ph | $CH_2NH_2$ | NHMs | Ph | $CH_2NH_2$ | Ph | H |
| $CH_2NHMe$ | Me | Me | $CH_2NHMe$ | $NO_2$ | Me | $CH_2NHMe$ | Me | H |
| $CH_2Ph$ | Et | Et | $CH_2Ph$ | OH | Et | $CH_2Ph$ | Et | H |
| $CH_2Ph$ | nPr | nPr | $CH_2Ph$ | COMe | nPr | $CH_2Ph$ | nPr | H |
| $CH_2CH_2Ph$ | Ph | Ph | $CH_2CH_2Ph$ | COOH | Ph | $CH_2CH_2Ph$ | Ph | H |

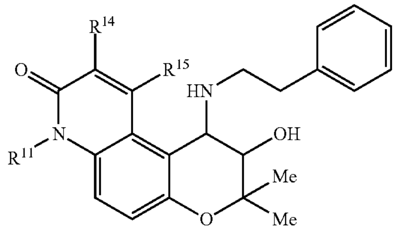

| | | | | | | | | |
|---|---|---|---|---|---|---|---|---|
| H | H | Et | H | $NO_2$ | H | H | H | $NO_2$ |
| H | H | iPr | H | CHO | H | H | H | CHO |
| H | H | nPr | H | $SO_3H$ | H | H | H | $SO_3H$ |
| H | H | nBu | H | Cl | H | H | H | Cl |
| H | H | tBu | H | Br | H | H | H | Br |
| Me | H | H | Me | $CH_2OH$ | H | Me | H | $CH_2OH$ |
| Me | Et | Ph | Me | $CH_2NH_2$ | H | Me | H | $CH_2NH_2$ |
| Me | iPr | H | Me | $CH_2NHMe$ | H | Me | H | $CH_2NHMe$ |
| Me | nPr | H | Me | $CH_2Ph$ | H | Me | H | $CH_2Ph$ |

-continued

| $R^{11}$ | $R^{13}$ | $R^{14}$ | $R^{11}$ | $R^{13}$ | $R^{14}$ | $R^{11}$ | $R^{13}$ | $R^{14}$ |
|---|---|---|---|---|---|---|---|---|
| Me | nBu | H | Me | COMe | H | Me | H | COMe |
| Me | tBu | H | Me | COOH | H | Me | H | COOH |
| Et | Ph | H | Et | $CONH_2$ | H | Et | H | $CONH_2$ |
| Et | H | Et | Et | CONHMe | Et | Et | Et | CONHMe |
| Et | H | iPr | Et | CONHMs | iPr | Et | iPr | CONHMs |
| iPr | H | nPr | iPr | NHMs | nPr | iPr | nPr | NHMs |
| nPr | H | nBu | nPr | NHCOMe | nBu | nPr | nBu | NHCOMe |
| nBu | H | tBu | nBu | $NO_2$ | tBu | nBu | tBu | $NO_2$ |
| tBu | H | Ph | tBu | CHO | Ph | tBu | Ph | H |
| Ph | Cl | Et | Ph | $SO_3H$ | Et | Ph | Et | H |
| $CH_2OH$ | Cl | nPr | $CH_2OH$ | $SO_2NHMe$ | nPr | $CH_2OH$ | nPr | H |
| $CH_2OH$ | Cl | Ph | $CH_2OH$ | OH | Ph | $CH_2OH$ | Ph | H |
| $CH_2OMe$ | Et | Cl | $CH_2OMe$ | COMe | Cl | $CH_2OMe$ | Cl | Cl |
| $CH_2OMe$ | nPr | Cl | $CH_2OMe$ | COOH | Cl | $CH_2OMe$ | Cl | Cl |
| $CH_2NH_2$ | Ph | Cl | $CH_2NH_2$ | $CONH_2$ | Cl | $CH_2NH_2$ | Cl | Cl |
| $CH_2NH_2$ | H | Et | $CH_2NH_2$ | CONHMe | Et | $CH_2NH_2$ | Et | H |
| $CH_2NH_2$ | H | nPr | $CH_2NH_2$ | CONHMs | nPr | $CH_2NH_2$ | nPr | H |
| $CH_2NH_2$ | H | Ph | $CH_2NH_2$ | NHMs | Ph | $CH_2NH_2$ | Ph | H |
| $CH_2NHMe$ | Me | Me | $CH_2NHMe$ | $NO_2$ | Me | $CH_2NHMe$ | Me | H |
| $CH_2Ph$ | Et | Et | $CH_2Ph$ | OH | Et | $CH_2Ph$ | Et | H |
| $CH_2Ph$ | nPr | nPr | $CH_2Ph$ | COMe | nPr | $CH_2Ph$ | nPr | H |
| $CH_2CH_2Ph$ | Ph | Ph | $CH_2CH_2Ph$ | COOH | Ph | $CH_2CH_2Ph$ | Ph | H |

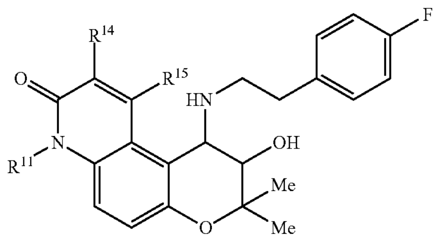

| | | | | | | | | |
|---|---|---|---|---|---|---|---|---|
| H | H | Et | H | $NO_2$ | H | H | H | $NO_2$ |
| H | H | iPr | H | CHO | H | H | H | CHO |
| H | H | nPr | H | $SO_3H$ | H | H | H | $SO_3H$ |
| H | H | nBu | H | Cl | H | H | H | Cl |
| H | H | tBu | H | Br | H | H | H | Br |
| Me | H | H | Me | $CH_2OH$ | H | Me | H | $CH_2OH$ |
| Me | Et | Ph | Me | $CH_2NH_2$ | H | Me | H | $CH_2NH_2$ |
| Me | iPr | H | Me | $CH_2NHMe$ | H | Me | H | $CH_2NHMe$ |
| Me | nPr | H | Me | $CH_2Ph$ | H | Me | H | $CH_2Ph$ |
| Me | nBu | H | Me | COMe | H | Me | H | COMe |
| Me | tBu | H | Me | COOH | H | Me | H | COOH |
| Et | Ph | H | Et | $CONH_2$ | H | Et | H | $CONH_2$ |
| Et | H | Et | Et | CONHMe | Et | Et | Et | CONHMe |
| Et | H | iPr | Et | CONHMs | iPr | Et | iPr | CONHMs |
| iPr | H | nPr | iPr | NHMs | nPr | iPr | nPr | NHMs |
| nPr | H | nBu | nPr | NHCOMe | nBu | nPr | nBu | NHCOMe |
| nBu | H | tBu | nBu | $NO_2$ | tBu | nBu | tBu | $NO_2$ |
| tBu | H | Ph | tBu | CHO | Ph | tBu | Ph | H |
| Ph | Cl | Et | Ph | $SO_3H$ | Et | Ph | Et | H |
| $CH_2OH$ | Cl | nPr | $CH_2OH$ | $SO_2NHMe$ | nPr | $CH_2OH$ | nPr | H |
| $CH_2OH$ | Cl | Ph | $CH_2OH$ | OH | Ph | $CH_2OH$ | Ph | H |
| $CH_2OMe$ | Et | Cl | $CH_2OMe$ | COMe | Cl | $CH_2OMe$ | Cl | Cl |
| $CH_2OMe$ | nPr | Cl | $CH_2OMe$ | COOH | Cl | $CH_2OMe$ | Cl | Cl |
| $CH_2NH_2$ | Ph | Cl | $CH_2NH_2$ | $CONH_2$ | Cl | $CH_2NH_2$ | Cl | Cl |
| $CH_2NH_2$ | H | Et | $CH_2NH_2$ | CONHMe | Et | $CH_2NH_2$ | Et | H |
| $CH_2NH_2$ | H | nPr | $CH_2NH_2$ | CONHMs | nPr | $CH_2NH_2$ | nPr | H |
| $CH_2NH_2$ | H | Ph | $CH_2NH_2$ | NHMs | Ph | $CH_2NH_2$ | Ph | H |
| $CH_2NHMe$ | Me | Me | $CH_2NHMe$ | $NO_2$ | Me | $CH_2NHMe$ | Me | H |
| $CH_2Ph$ | Et | Et | $CH_2Ph$ | OH | Et | $CH_2Ph$ | Et | H |
| $CH_2Ph$ | nPr | nPr | $CH_2Ph$ | COMe | nPr | $CH_2Ph$ | nPr | H |
| $CH_2CH_2Ph$ | Ph | Ph | $CH_2CH_2Ph$ | COOH | Ph | $CH_2CH_2Ph$ | Ph | H |

-continued

| $R^{11}$ | $R^{13}$ | $R^{14}$ | $R^{11}$ | $R^{13}$ | $R^{14}$ | $R^{11}$ | $R^{13}$ | $R^{14}$ |
|---|---|---|---|---|---|---|---|---|
| 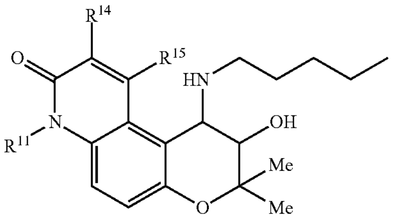 | | | | | | | | |
| H | H | Et | H | $NO_2$ | H | H | H | $NO_2$ |
| H | H | iPr | H | CHO | H | H | H | CHO |
| H | H | nPr | H | $SO_3H$ | H | H | H | $SO_3H$ |
| H | H | nBu | H | Cl | H | H | H | Cl |
| H | H | tBu | H | Br | H | H | H | Br |
| Me | H | H | Me | $CH_2OH$ | H | Me | H | $CH_2OH$ |
| Me | Et | Ph | Me | $CH_2NH_2$ | H | Me | H | $CH_2NH_2$ |
| Me | iPr | H | Me | $CH_2NHMe$ | H | Me | H | $CH_2NHMe$ |
| Me | nPr | H | Me | $CH_2Ph$ | H | Me | H | $CH_2Ph$ |
| Me | nBu | H | Me | COMe | H | Me | H | COMe |
| Me | tBu | H | Me | COOH | H | Me | H | COOH |
| Et | Ph | H | Et | $CONH_2$ | H | Et | H | $CONH_2$ |
| Et | H | Et | Et | CONHMe | Et | Et | Et | CONHMe |
| Et | H | iPr | Et | CONHMs | iPr | Et | iPr | CONHMs |
| iPr | H | nPr | iPr | NHMs | nPr | iPr | nPr | NHMs |
| nPr | H | nBu | nPr | NHCOMe | nBu | nPr | nBu | NHCOMe |
| nBu | H | tBu | nBu | $NO_2$ | tBu | nBu | tBu | $NO_2$ |
| tBu | H | Ph | tBu | CHO | Ph | tBu | Ph | H |
| Ph | Cl | Et | Ph | $SO_3H$ | Et | Ph | Et | H |
| $CH_2OH$ | Cl | nPr | $CH_2OH$ | $SO_2NHMe$ | nPr | $CH_2OH$ | nPr | H |
| $CH_2OH$ | Cl | Ph | $CH_2OH$ | OH | Ph | $CH_2OH$ | Ph | H |
| $CH_2OMe$ | Et | Cl | $CH_2OMe$ | COMe | Cl | $CH_2OMe$ | Cl | Cl |
| $CH_2OMe$ | nPr | Cl | $CH_2OMe$ | COOH | Cl | $CH_2OMe$ | Cl | Cl |
| $CH_2NH_2$ | Ph | Cl | $CH_2NH_2$ | $CONH_2$ | Cl | $CH_2NH_2$ | Cl | Cl |
| $CH_2NH_2$ | H | Et | $CH_2NH_2$ | CONHMe | Et | $CH_2NH_2$ | Et | H |
| $CH_2NH_2$ | H | nPr | $CH_2NH_2$ | CONHMs | nPr | $CH_2NH_2$ | nPr | H |
| $CH_2NH_2$ | H | Ph | $CH_2NH_2$ | NHMs | Ph | $CH_2NH_2$ | Ph | H |
| $CH_2NHMe$ | Me | Me | $CH_2NHMe$ | $NO_2$ | Me | $CH_2NHMe$ | Me | H |
| $CH_2Ph$ | Et | Et | $CH_2Ph$ | OH | Et | $CH_2Ph$ | Et | H |
| $CH_2Ph$ | nPr | nPr | $CH_2Ph$ | COMe | nPr | $CH_2Ph$ | nPr | H |
| $CH_2CH_2Ph$ | Ph | Ph | $CH_2CH_2Ph$ | COOH | Ph | $CH_2CH_2Ph$ | Ph | H |
| 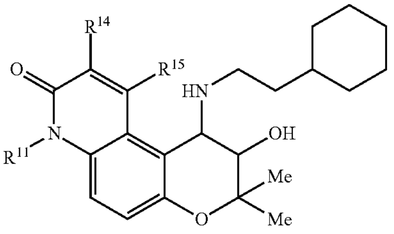 | | | | | | | | |
| H | H | Et | H | $NO_2$ | H | H | H | $NO_2$ |
| H | H | iPr | H | CHO | H | H | H | CHO |
| H | H | nPr | H | $SO_3H$ | H | H | H | $SO_3H$ |
| H | H | nBu | H | Cl | H | H | H | Cl |
| H | H | tBu | H | Br | H | H | H | Br |
| Me | H | H | Me | $CH_2OH$ | H | Me | H | $CH_2OH$ |
| Me | Et | Ph | Me | $CH_2NH_2$ | H | Me | H | $CH_2NH_2$ |
| Me | iPr | H | Me | $CH_2NHMe$ | H | Me | H | $CH_2NHMe$ |
| Me | nPr | H | Me | $CH_2Ph$ | H | Me | H | $CH_2Ph$ |
| Me | nBu | H | Me | COMe | H | Me | H | COMe |
| Me | tBu | H | Me | COOH | H | Me | H | COOH |
| Et | Ph | H | Et | $CONH_2$ | H | Et | H | $CONH_2$ |
| Et | H | Et | Et | CONHMe | Et | Et | Et | CONHMe |
| Et | H | iPr | Et | CONHMs | iPr | Et | iPr | CONHMs |
| iPr | H | nPr | iPr | NHMs | nPr | iPr | nPr | NHMs |
| nPr | H | nBu | nPr | NHCOMe | nBu | nPr | nBu | NHCOMe |
| nBu | H | tBu | nBu | $NO_2$ | tBu | nBu | tBu | $NO_2$ |
| tBu | H | Ph | tBu | CHO | Ph | tBu | Ph | H |
| Ph | Cl | Et | Ph | $SO_3H$ | Et | Ph | Et | H |
| $CH_2OH$ | Cl | nPr | $CH_2OH$ | $SO_2NHMe$ | nPr | $CH_2OH$ | nPr | H |
| $CH_2OH$ | Cl | Ph | $CH_2OH$ | OH | Ph | $CH_2OH$ | Ph | H |
| $CH_2OMe$ | Et | Cl | $CH_2OMe$ | COMe | Cl | $CH_2OMe$ | Cl | Cl |
| $CH_2OMe$ | nPr | Cl | $CH_2OMe$ | COOH | Cl | $CH_2OMe$ | Cl | Cl |

-continued

| $R^{11}$ | $R^{13}$ | $R^{14}$ | $R^{11}$ | $R^{13}$ | $R^{14}$ | $R^{11}$ | $R^{13}$ | $R^{14}$ |
|---|---|---|---|---|---|---|---|---|
| $CH_2NH_2$ | Ph | Cl | $CH_2NH_2$ | $CONH_2$ | Cl | $CH_2NH_2$ | Cl | Cl |
| $CH_2NH_2$ | H | Et | $CH_2NH_2$ | CONHMe | Et | $CH_2NH_2$ | Et | H |
| $CH_2NH_2$ | H | nPr | $CH_2NH_2$ | CONHMs | nPr | $CH_2NH_2$ | nPr | H |
| $CH_2NH_2$ | H | Ph | $CH_2NH_2$ | NHMs | Ph | $CH_2NH_2$ | Ph | H |
| $CH_2NHMe$ | Me | Me | $CH_2NHMe$ | $NO_2$ | Me | $CH_2NHMe$ | Me | H |
| $CH_2Ph$ | Et | Et | $CH_2Ph$ | OH | Et | $CH_2Ph$ | Et | H |
| $CH_2Ph$ | nPr | nPr | $CH_2Ph$ | COMe | nPr | $CH_2Ph$ | nPr | H |
| $CH_2CH_2Ph$ | Ph | Ph | $CH_2CH_2Ph$ | COOH | Ph | $CH_2CH_2Ph$ | Ph | H |

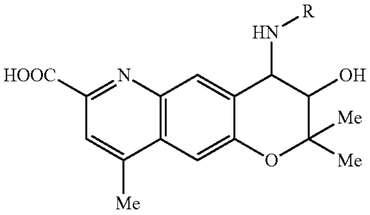

| HN—R | | |
|---|---|---|
| NH—Me | HN—Et | 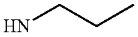 |
| 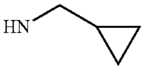 | 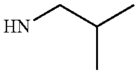 | 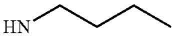 |
| 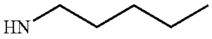 | 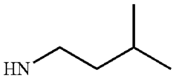 | 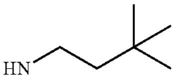 |
| 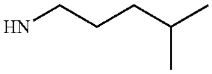 | 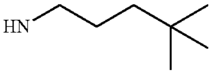 | 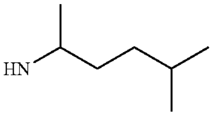 |
| 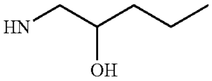 | 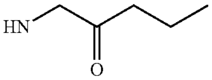 | 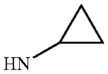 |
| 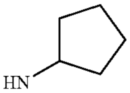 | 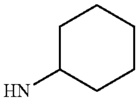 | 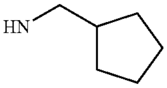 |
| 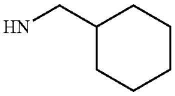 | 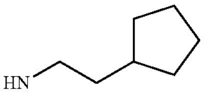 | 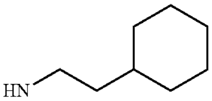 |
| 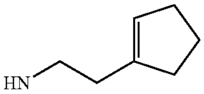 | 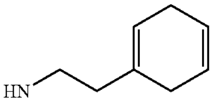 | 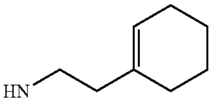 |
| 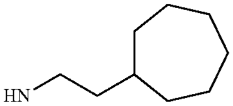 | 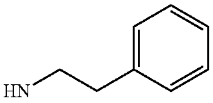 | 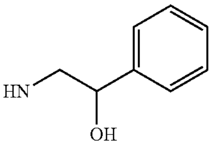 |

-continued
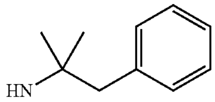 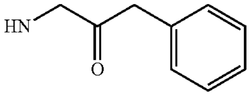 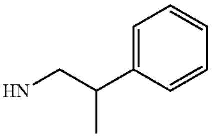
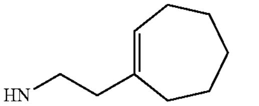 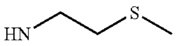 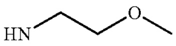
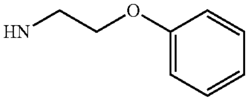 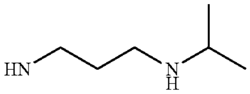 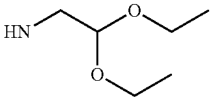
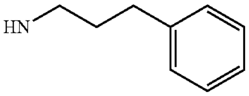 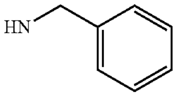 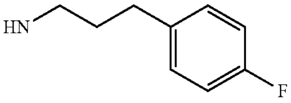
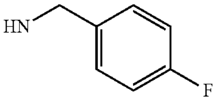 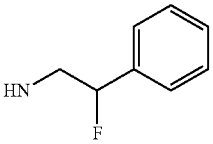 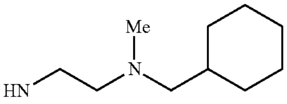
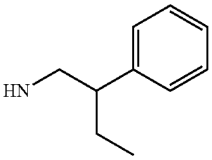 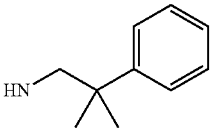 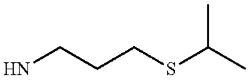
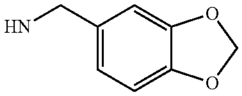 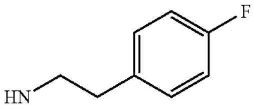 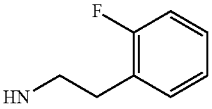
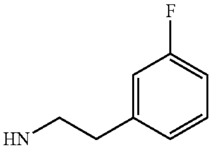 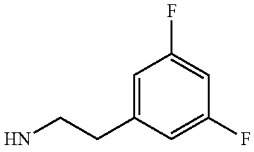 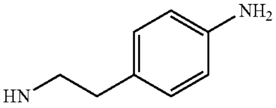
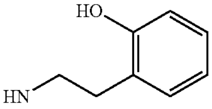 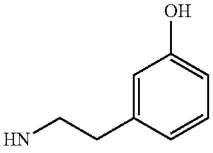 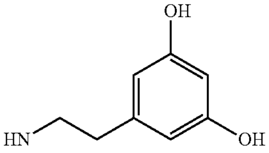
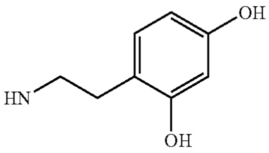 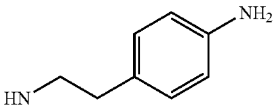 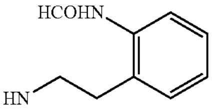
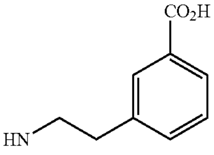 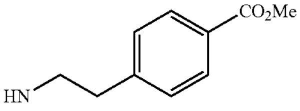 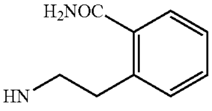

-continued
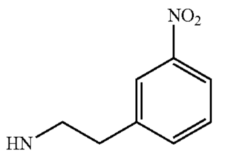
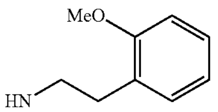
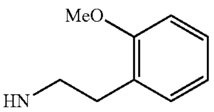
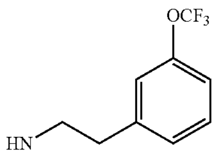
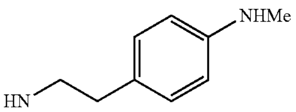
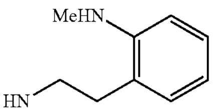
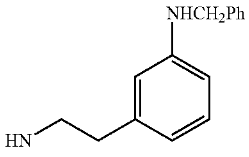
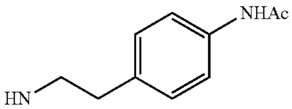
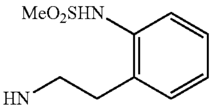
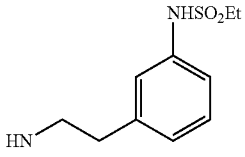
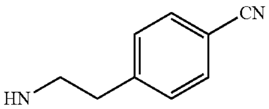
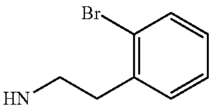
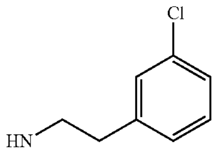
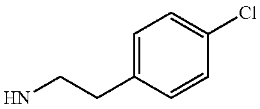
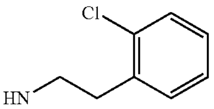
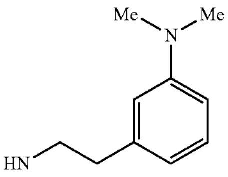
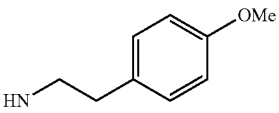
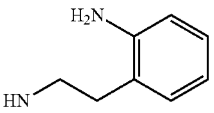
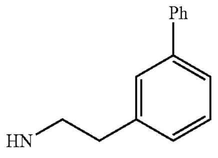
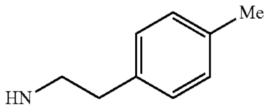
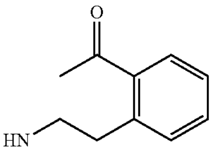
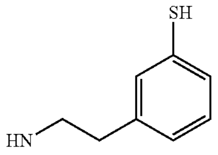

| HN—R | | |
|---|---|---|
| 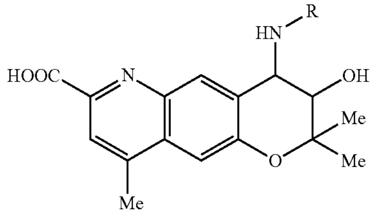 | | |
| 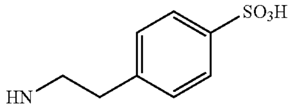 | 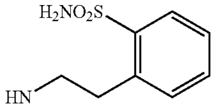 | 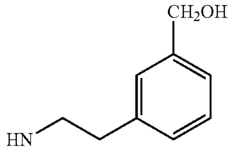 |
| 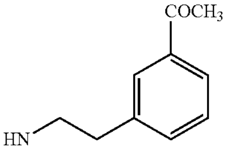 | 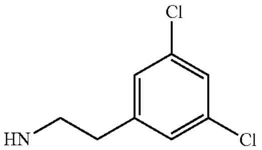 | 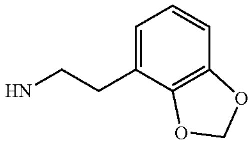 |
| 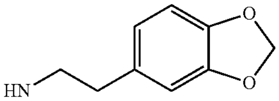 | 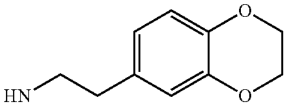 | 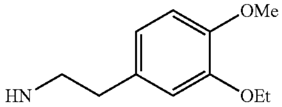 |
| 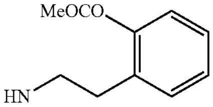 | 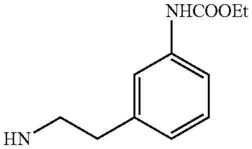 | 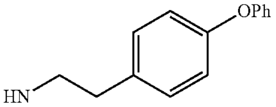 |
| 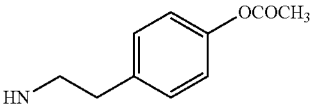 | 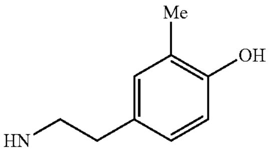 | 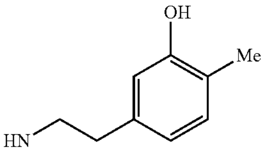 |
| 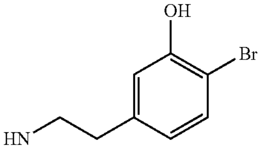 | 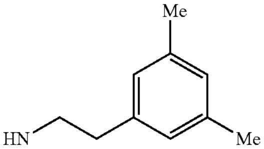 | 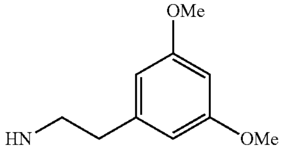 |
| 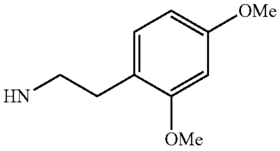 | 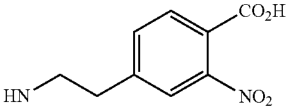 | 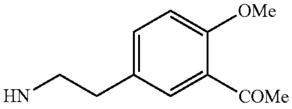 |
| 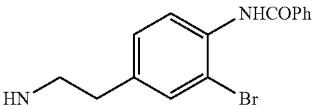 | 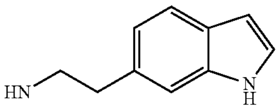 | 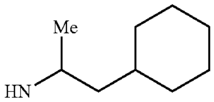 |
| 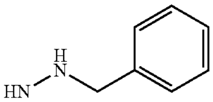 | 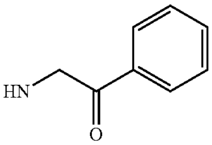 | 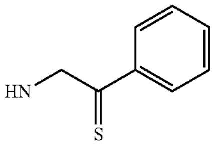 |

-continued
| HN—R | | |
|---|---|---|
| 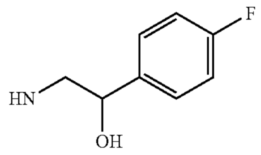 | 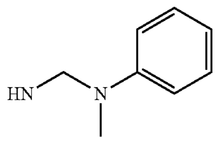 | 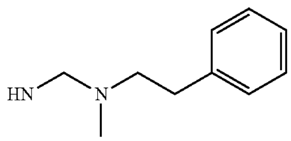 |
| 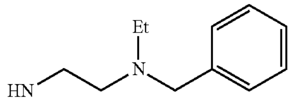 | 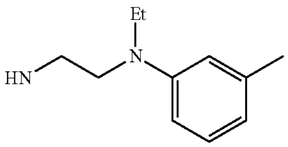 | 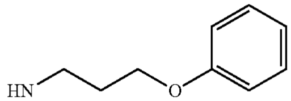 |
| 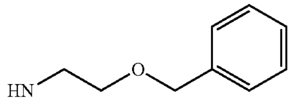 | 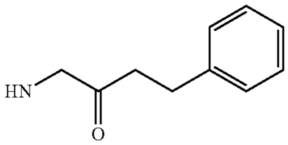 | 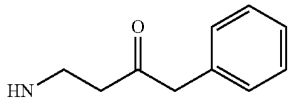 |
| 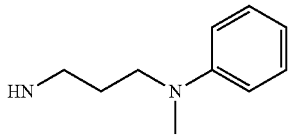 | 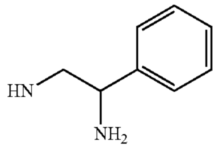 | 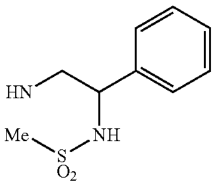 |
| 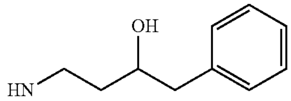 | 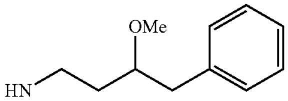 | 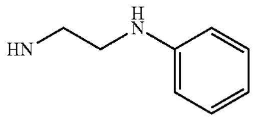 |
| 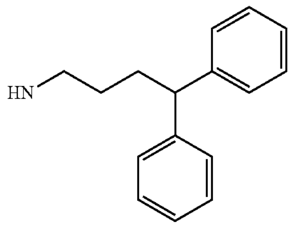 | 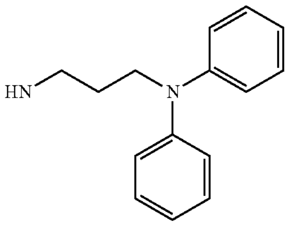 | 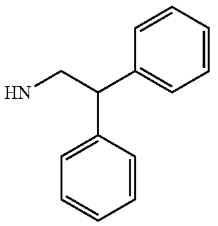 |
| 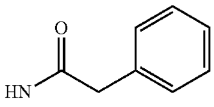 | 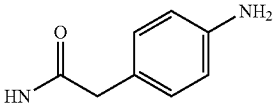 | 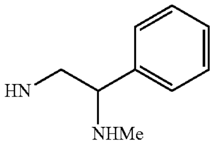 |
| 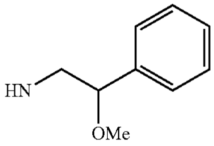 | 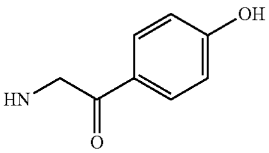 | 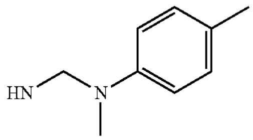 |
| 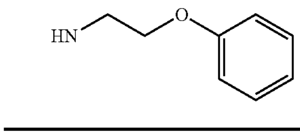 | 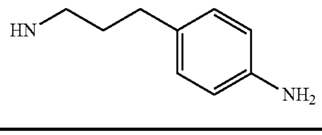 | 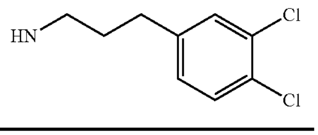 |

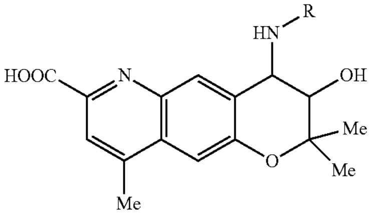
HN—R
| | | |
|---|---|---|
| 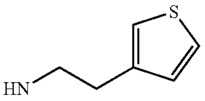 | 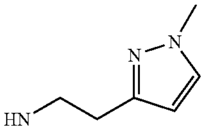 | 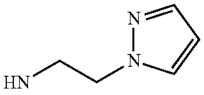 |
| 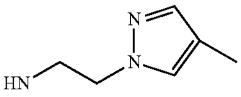 | 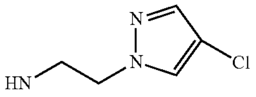 | 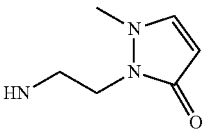 |
| 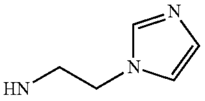 | 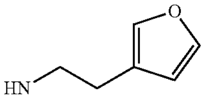 | 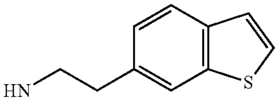 |
| 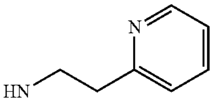 | 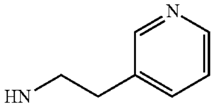 | 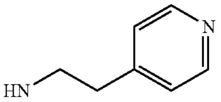 |
| 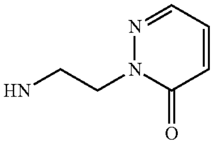 | 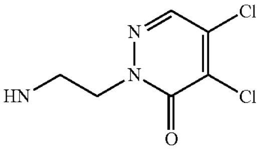 | 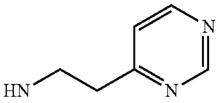 |
| 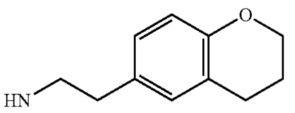 | 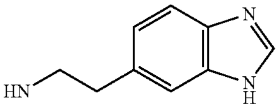 | 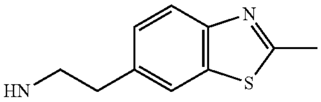 |
| 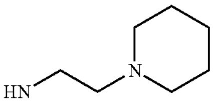 | 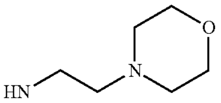 | 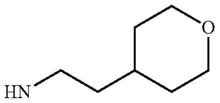 |
| 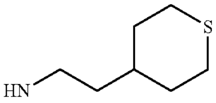 | 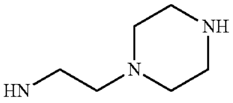 | 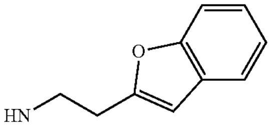 |
| 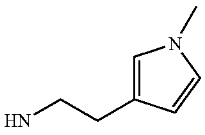 | 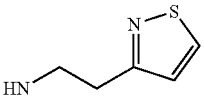 | 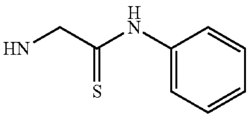 |
| 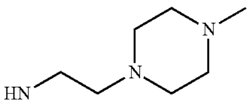 | 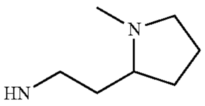 | 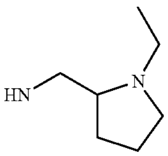 |

-continued
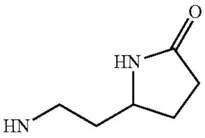
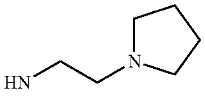
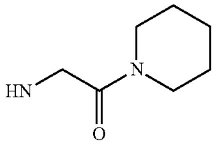
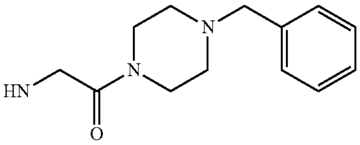
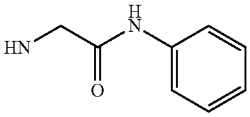
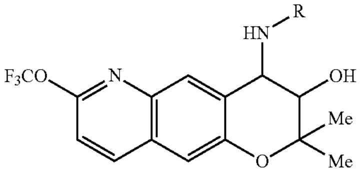
HN—R
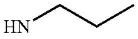
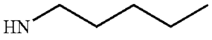
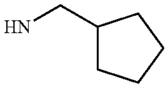
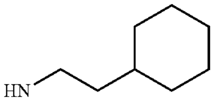
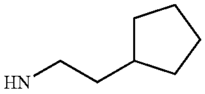
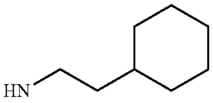
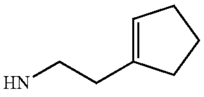
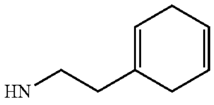
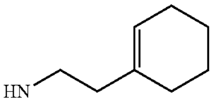
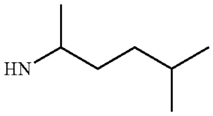
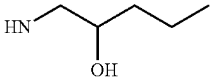
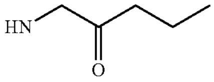
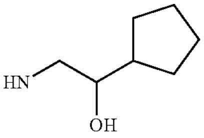
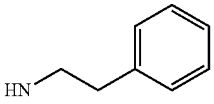
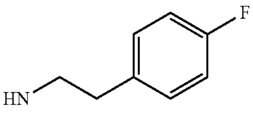
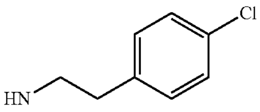
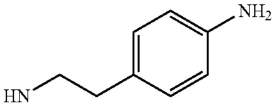
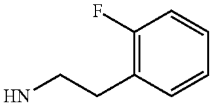
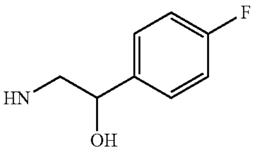
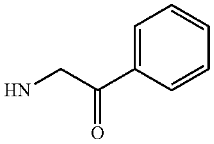
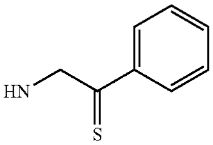
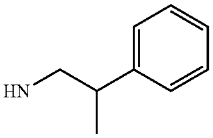
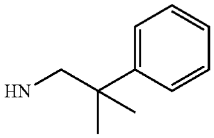
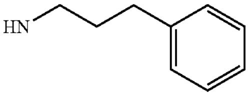

-continued
| | | |
|---|---|---|
| 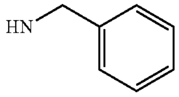 | 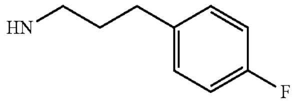 | 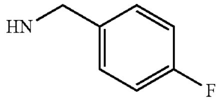 |
| 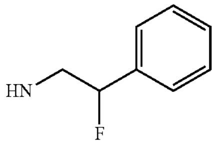 | 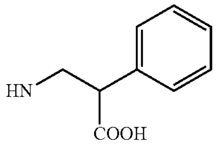 | 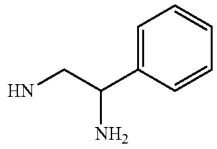 |
| 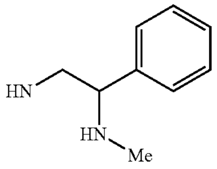 | 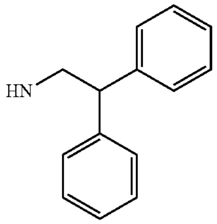 | 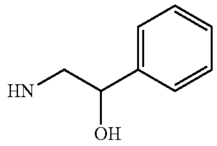 |
| 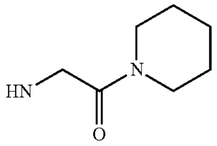 | 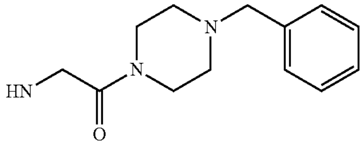 | 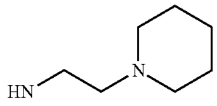 |
| 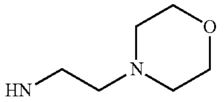 | 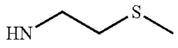 | 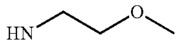 |
| 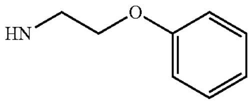 | 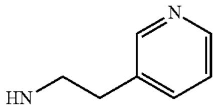 | 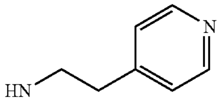 |
| 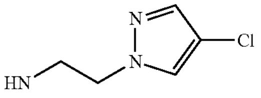 | 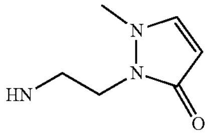 | |
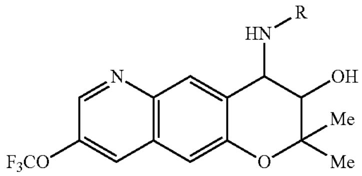
HN—R
| | | |
|---|---|---|
| 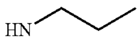 | 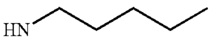 | 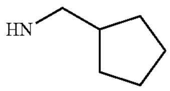 |
| 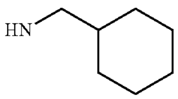 | 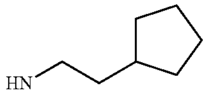 | 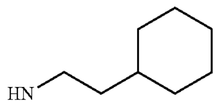 |
| 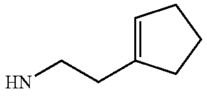 | 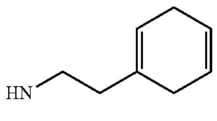 | 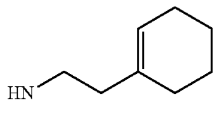 |

-continued
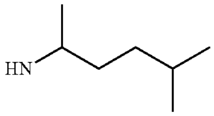
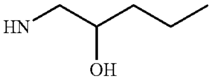
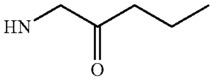
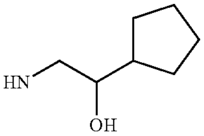
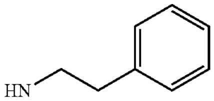
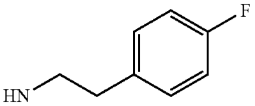
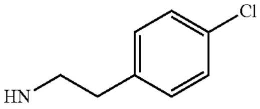
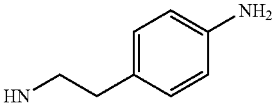
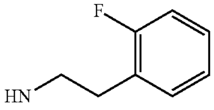
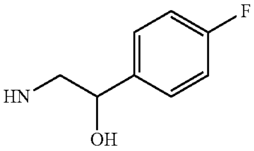
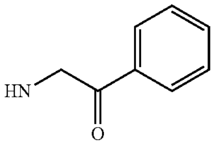
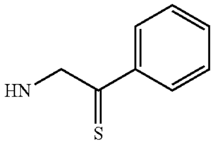
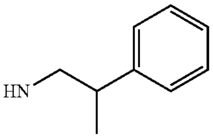
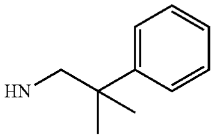
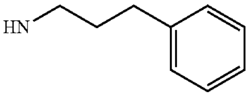
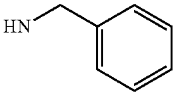
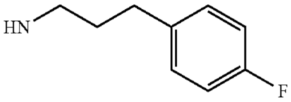
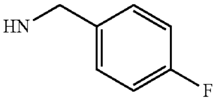
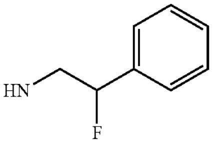
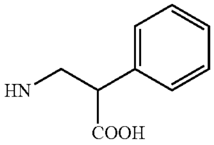
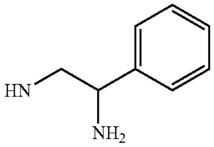
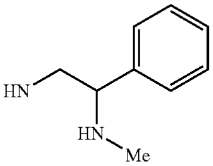
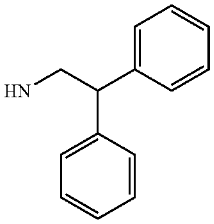
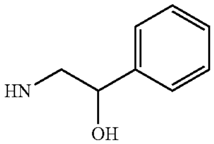
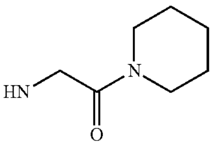
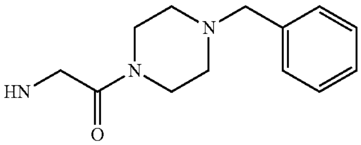
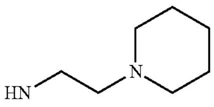
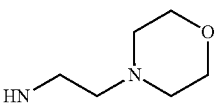
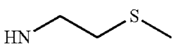
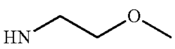
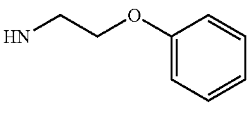
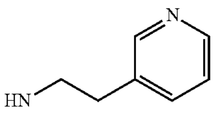
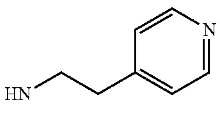

-continued
| | | |
|---|---|---|
| 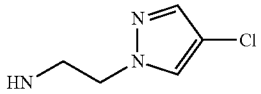 | 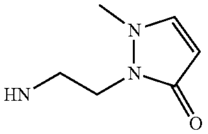 | |
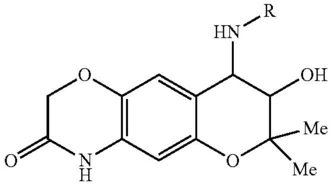
| | HN—R | |
|---|---|---|
| HN—Me | HN—Et | 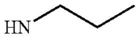 |
| 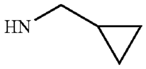 | 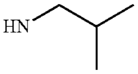 | 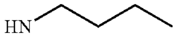 |
| 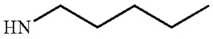 | 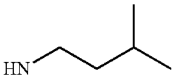 | 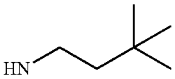 |
| 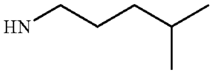 | 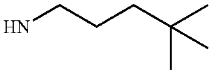 | 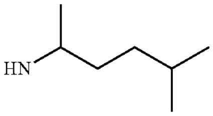 |
| 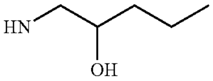 | 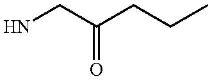 | 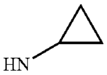 |
| 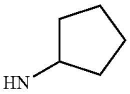 | 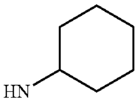 | 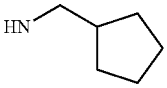 |
| 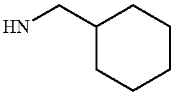 | 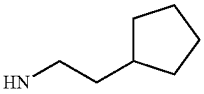 | 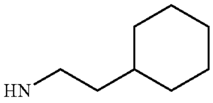 |
| 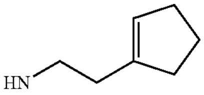 | 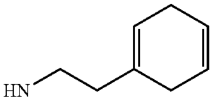 | 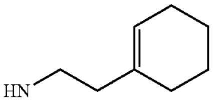 |
| 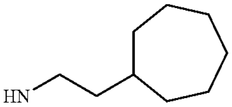 | 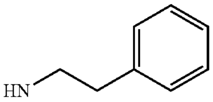 | 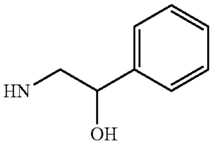 |
| 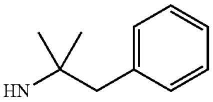 | 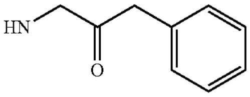 | 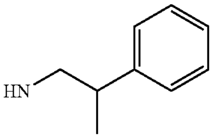 |
| 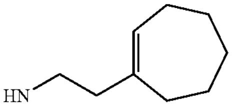 | 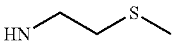 | 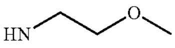 |

-continued
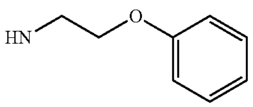
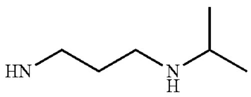
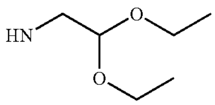
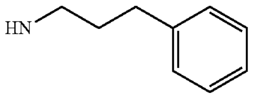
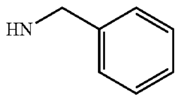
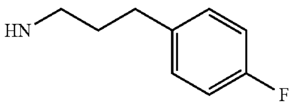
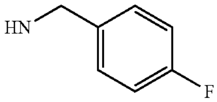
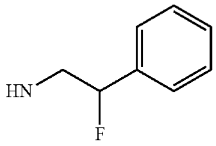
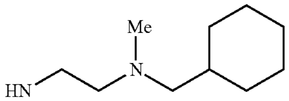
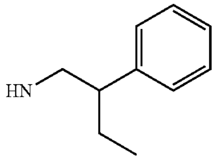
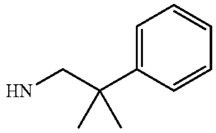
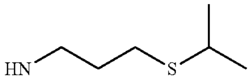
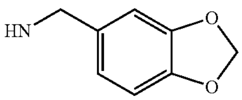
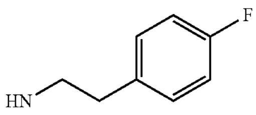
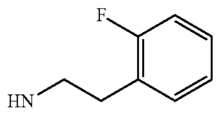
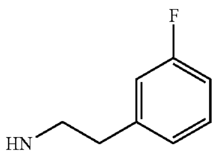
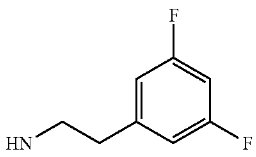
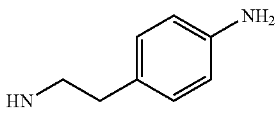
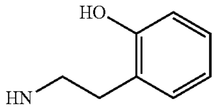
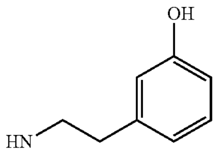
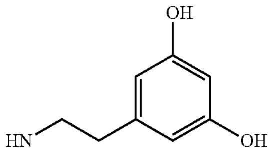
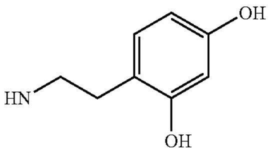
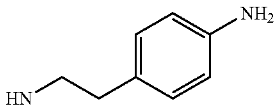
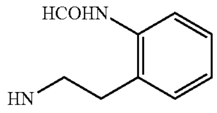
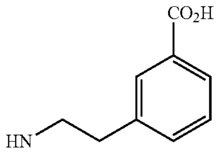
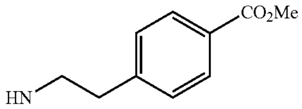
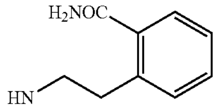
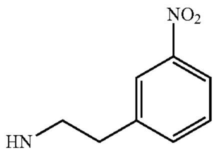
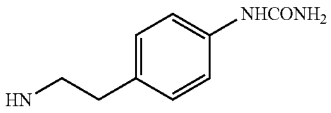
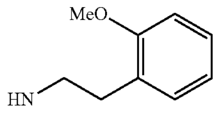

-continued
| | | |
|---|---|---|
| 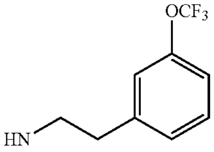 | 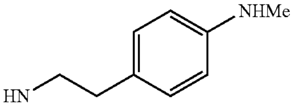 | 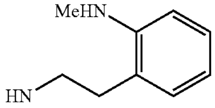 |
| 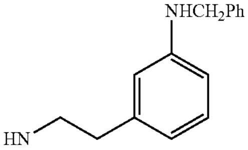 | 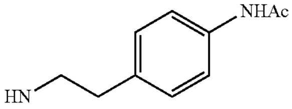 | 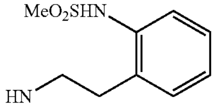 |
| 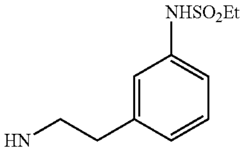 | 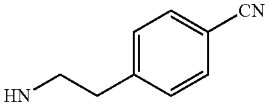 | 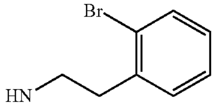 |
| 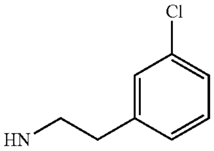 | 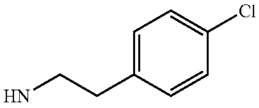 | 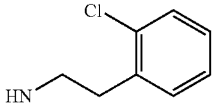 |
| 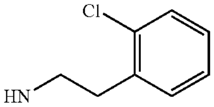 | 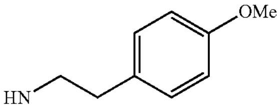 | 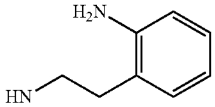 |
| 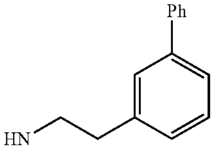 | 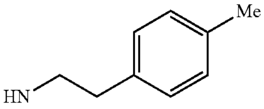 | 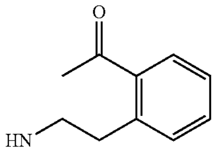 |
| 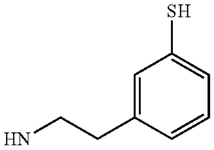 | | |
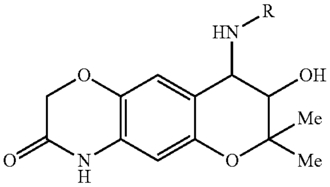
HN—R
| | | |
|---|---|---|
| 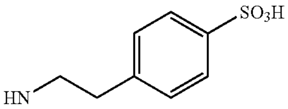 | 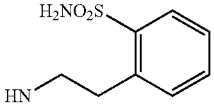 | 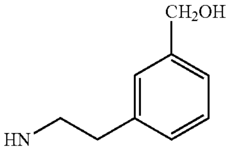 |

-continued
| 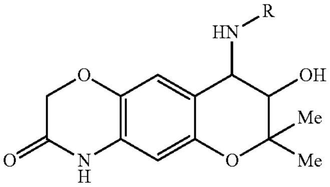<br>HN—R | | |
|---|---|---|
| 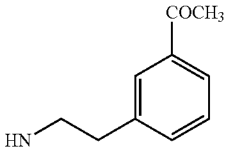 | 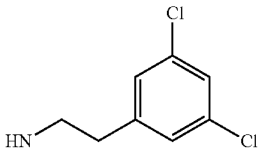 | 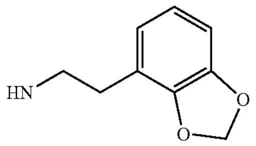 |
| 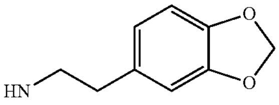 | 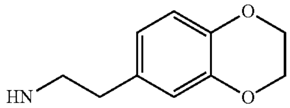 | 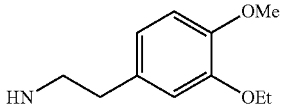 |
| 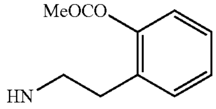 | 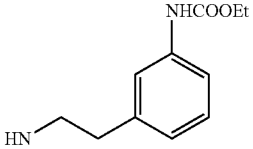 | 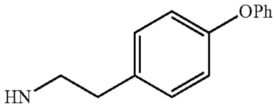 |
| 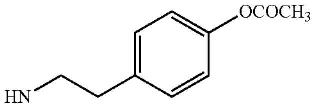 | 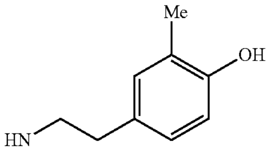 | 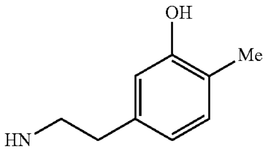 |
| 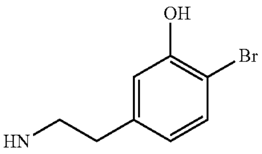 | 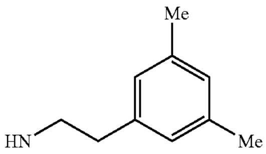 | 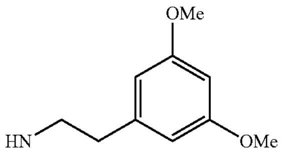 |
| 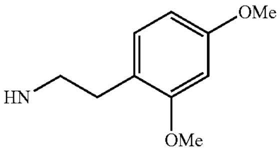 | 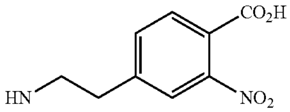 | 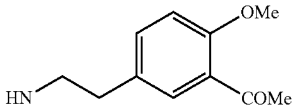 |
| 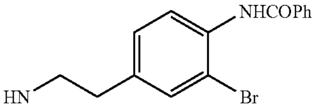 | 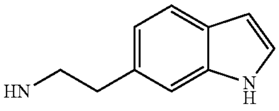 | 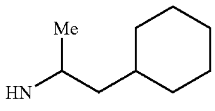 |
| 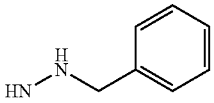 | 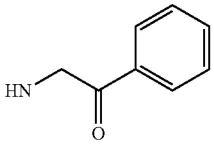 | 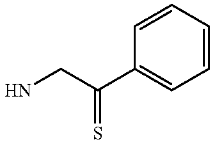 |
| 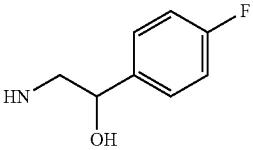 | 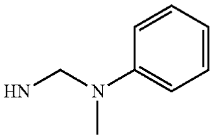 | 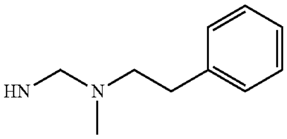 |

-continued
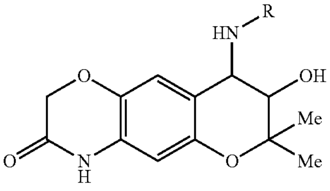
HN—R
| | | |
|---|---|---|
| 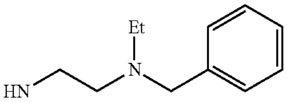 | 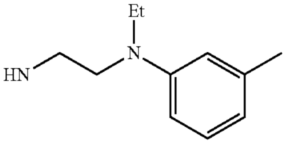 | 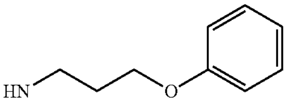 |
| 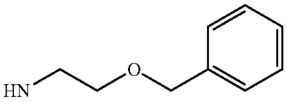 | 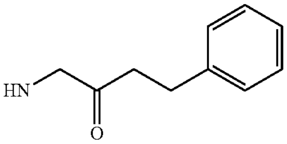 | 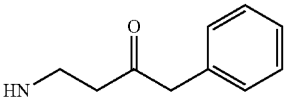 |
| 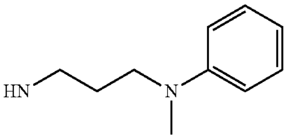 | 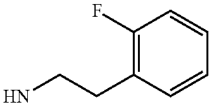 | 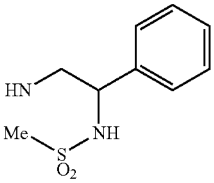 |
| 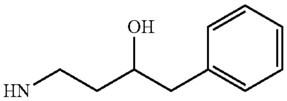 | 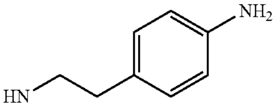 | 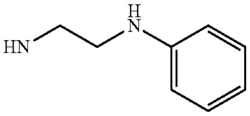 |
| 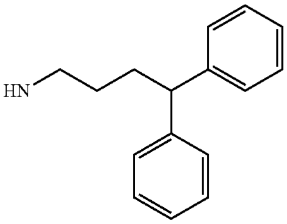 | 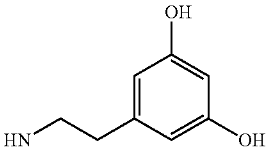 | 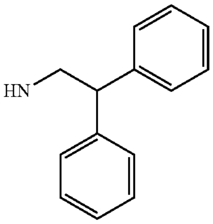 |
| 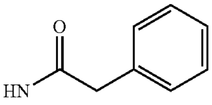 | 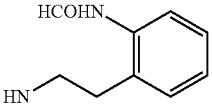 | 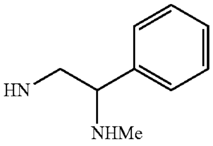 |
| 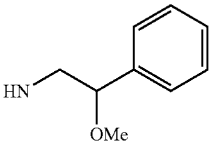 | 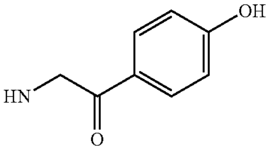 | 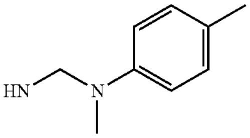 |
| 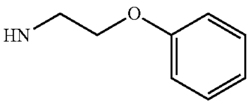 | 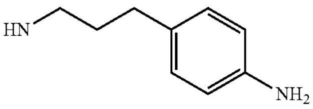 | 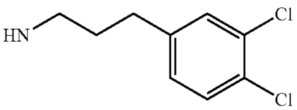 |

HN—R
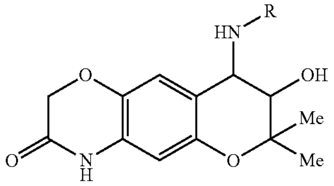
| | | |
|---|---|---|
| 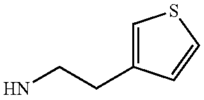 | 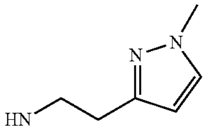 | 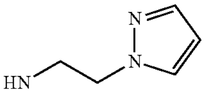 |
| 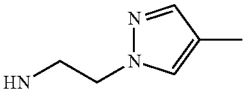 | 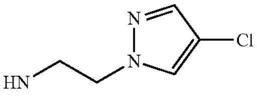 | 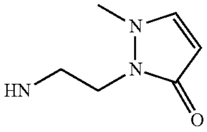 |
| 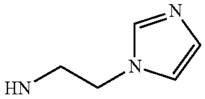 | 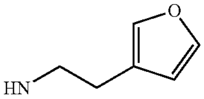 | 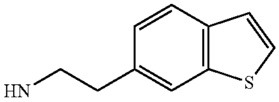 |
| 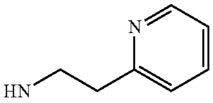 | 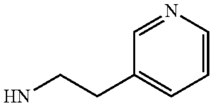 | 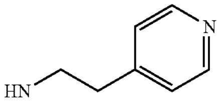 |
| 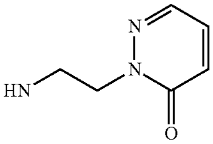 | 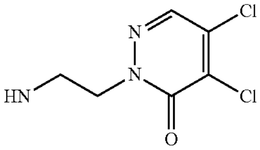 | 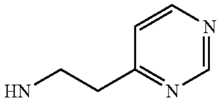 |
| 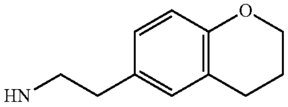 | 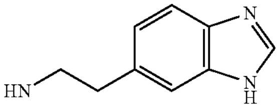 | 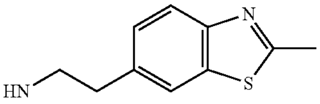 |
| 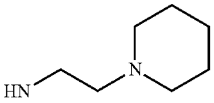 | 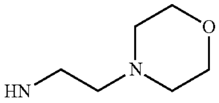 | 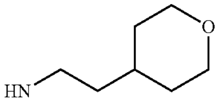 |
| 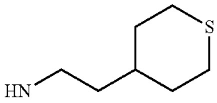 | 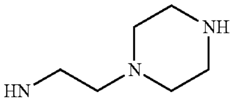 | 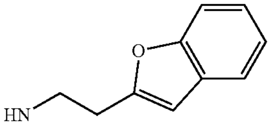 |
| 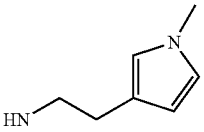 | 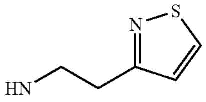 | 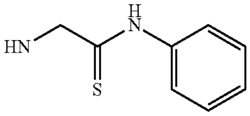 |
| 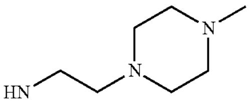 | 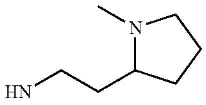 | 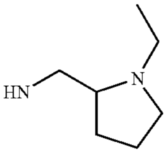 |
| 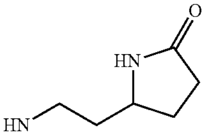 | 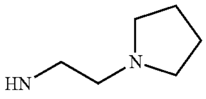 | 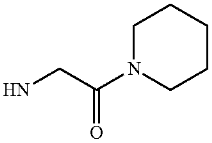 |

-continued
| HN—R | | |
|---|---|---|
| 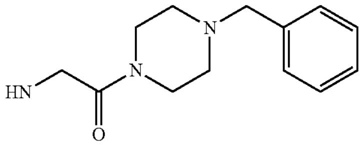 | 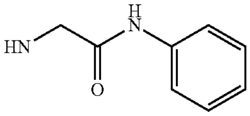 | |
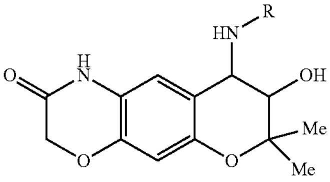
| | | |
|---|---|---|
| HN—Me | HN—Et | 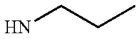 |
| 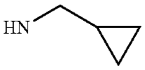 | 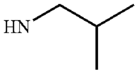 | 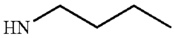 |
| 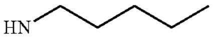 | 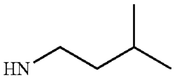 | 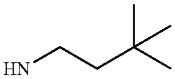 |
| 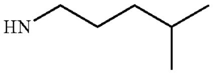 | 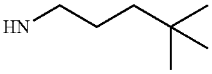 | 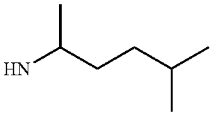 |
| 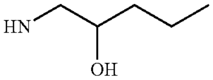 | 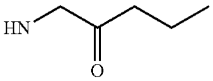 | 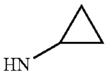 |
| 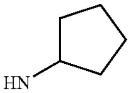 | 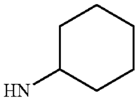 | 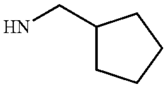 |
| 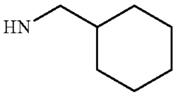 | 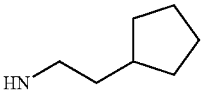 | 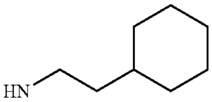 |
| 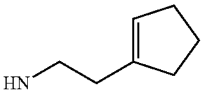 | 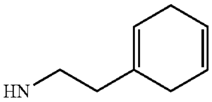 | 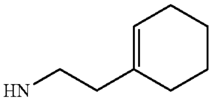 |
| 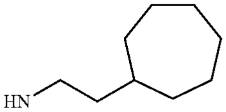 | 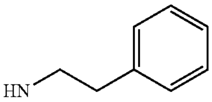 | 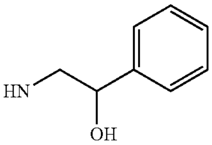 |
| 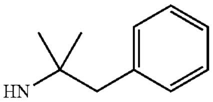 | 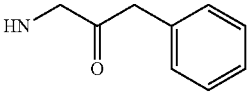 | 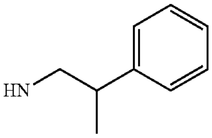 |
| 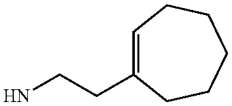 | 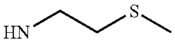 | 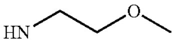 |

-continued
| | HN—R | |
|---|---|---|
| 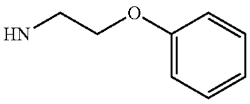 | 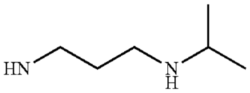 | 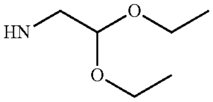 |
| 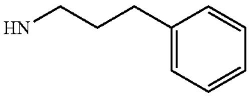 | 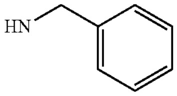 | 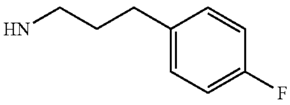 |
| 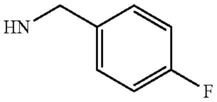 | 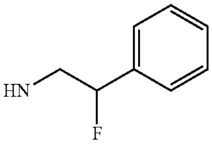 | 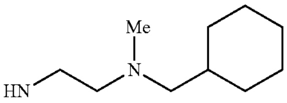 |
| 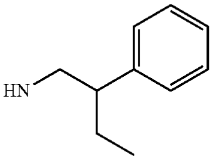 | 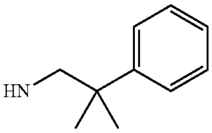 | 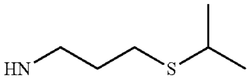 |
| 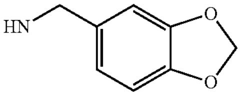 | 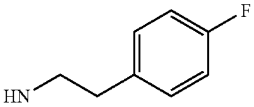 | 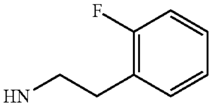 |
| 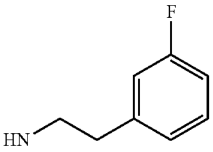 | 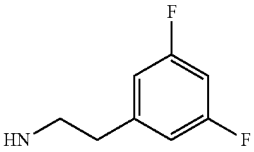 | 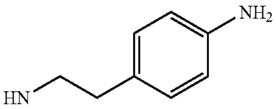 |
| 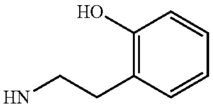 | 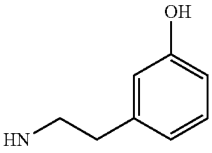 | 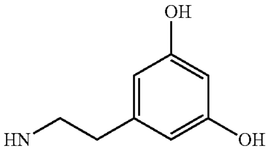 |
| 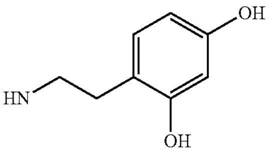 | 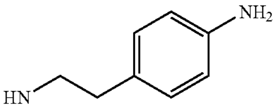 | 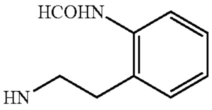 |
| 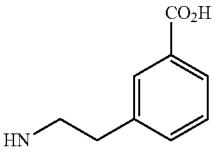 | 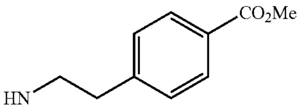 | 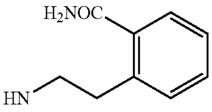 |
| 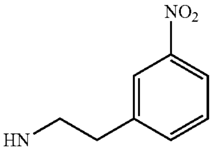 | 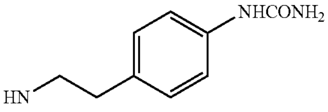 | 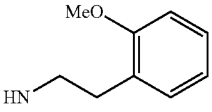 |

-continued
| | HN—R | |
|---|---|---|
| 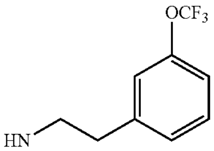 | 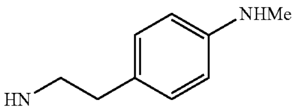 | 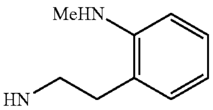 |
| 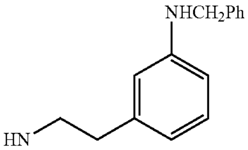 | 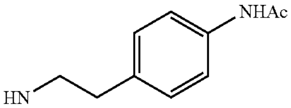 | 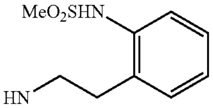 |
| 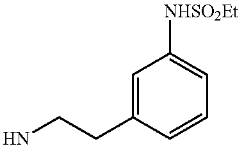 | 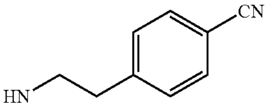 | 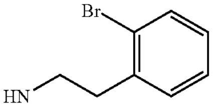 |
| 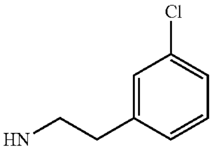 | 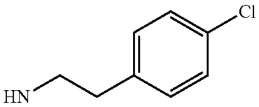 | 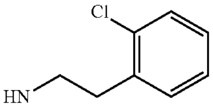 |
| 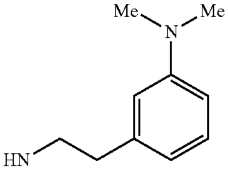 | 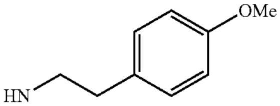 | 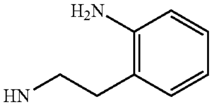 |
| 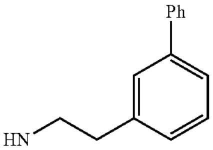 | 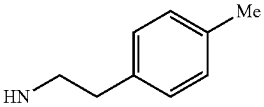 | 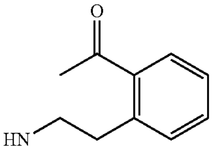 |
| 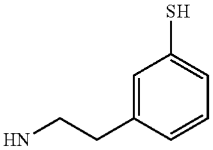 | | |
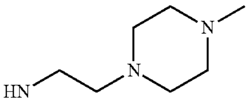
| | HN—R | |
|---|---|---|
| 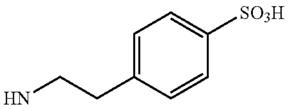 | 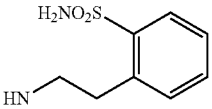 | 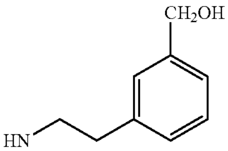 |

-continued
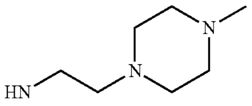
HN—R
| | | |
|---|---|---|
| 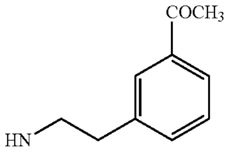 | 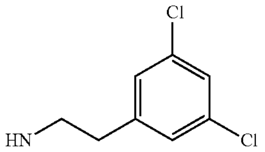 | 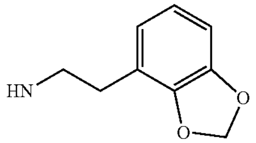 |
| 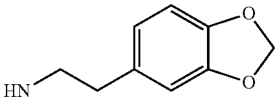 | 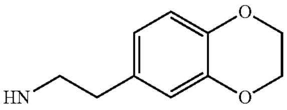 | 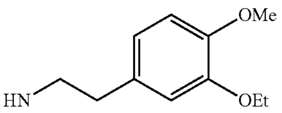 |
| 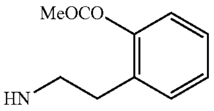 | 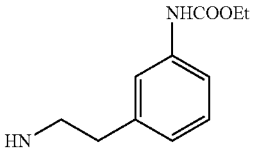 | 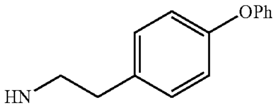 |
| 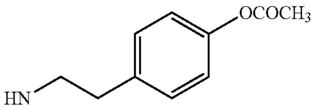 | 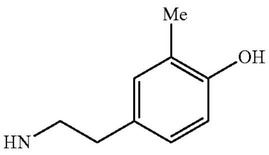 | 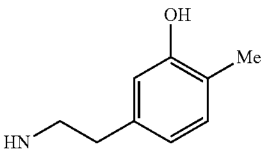 |
| 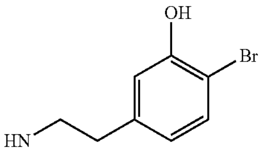 | 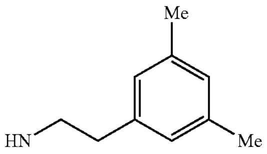 | 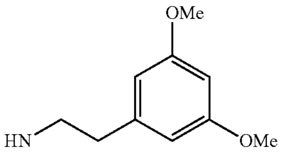 |
| 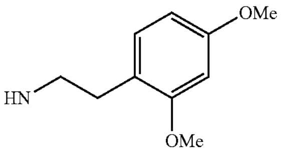 | 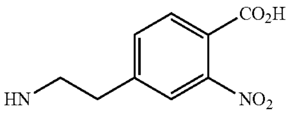 | 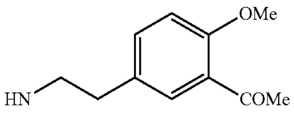 |
| 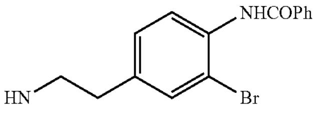 | 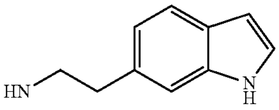 | 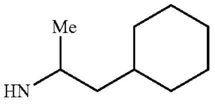 |
| 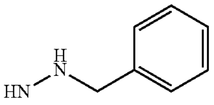 | 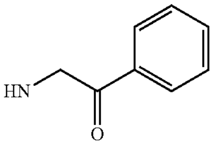 | 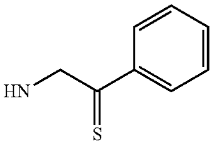 |
| 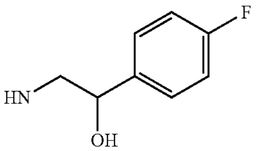 | 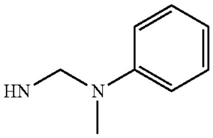 | 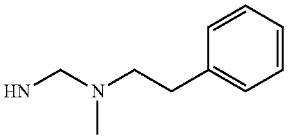 |

-continued
| | 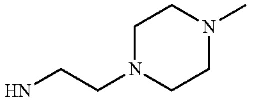<br>HN—R | |
|---|---|---|
| 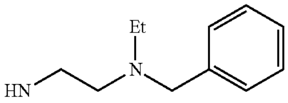 | 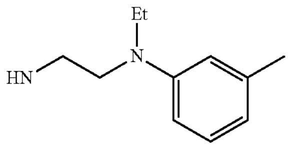 | 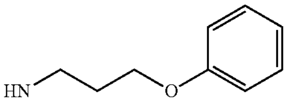 |
| 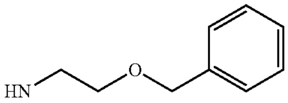 | 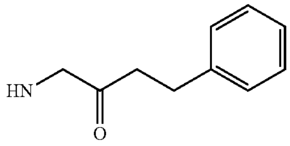 | 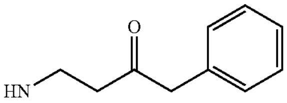 |
| 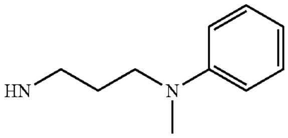 | 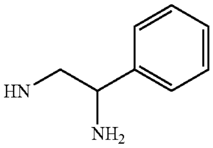 | 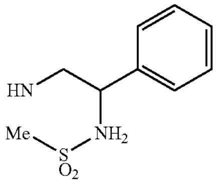 |
| 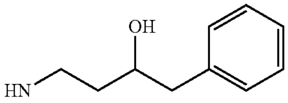 | 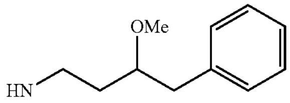 | 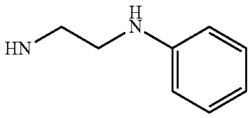 |
| 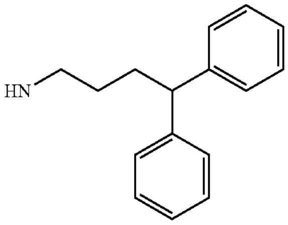 | 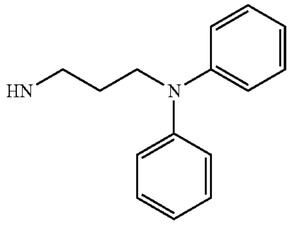 | 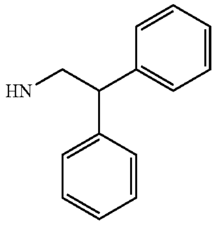 |
| 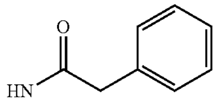 | 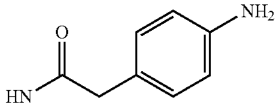 | 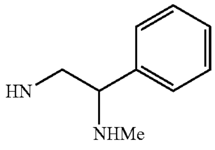 |
| 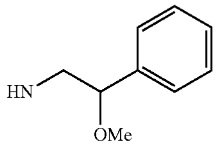 | 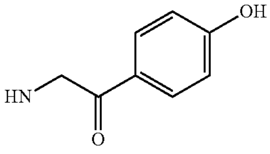 | 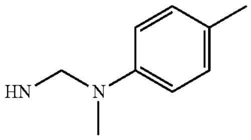 |
| 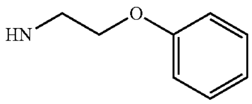 | 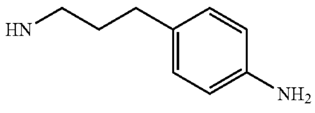 | 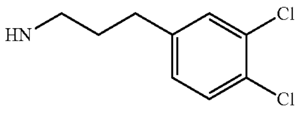 |

| HN—R | | |
|---|---|---|
| | 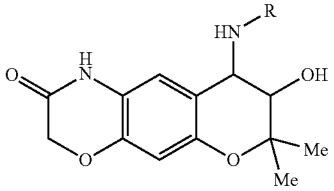 | |
| 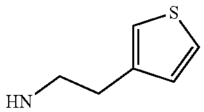 | 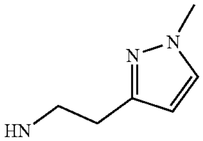 | 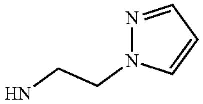 |
| 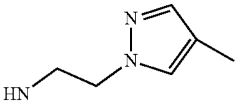 | 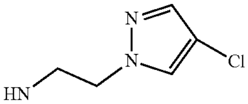 | 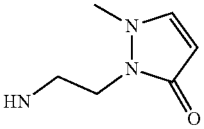 |
| 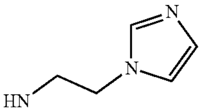 | 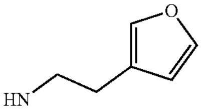 | 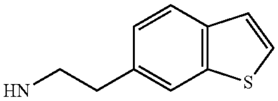 |
| 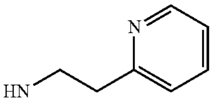 | 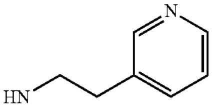 | 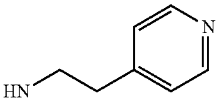 |
| 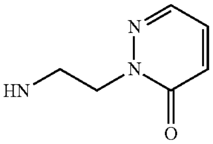 | 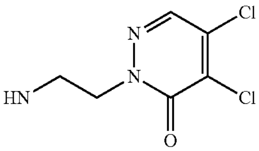 | 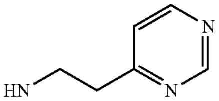 |
| 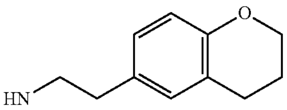 | 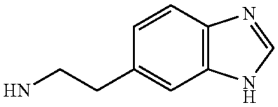 | 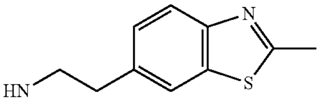 |
| 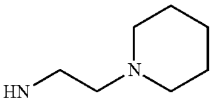 | 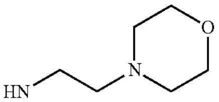 | 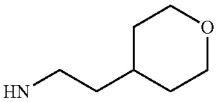 |
| 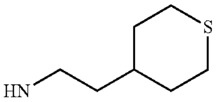 | 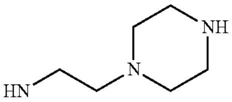 | 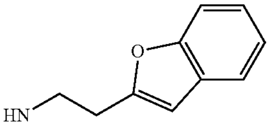 |
| 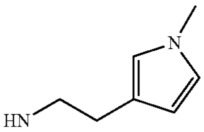 | 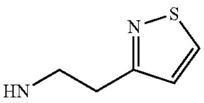 | 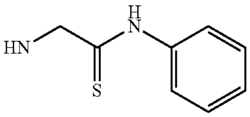 |
| 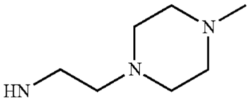 | 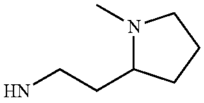 | 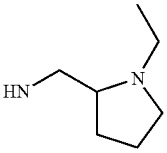 |

-continued
| HN—R | | |
|---|---|---|
| 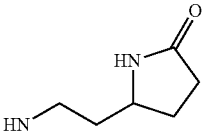 | 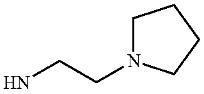 | 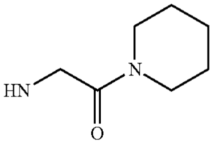 |
| 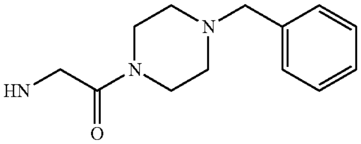 | 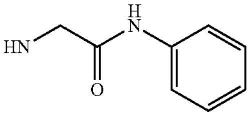 | |
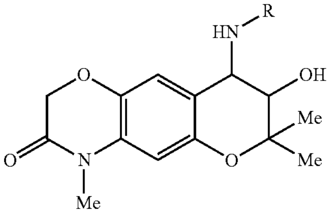
| | | |
|---|---|---|
| HN—Me | HN—Et | 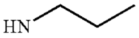 |
| 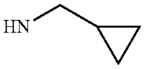 | 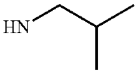 | 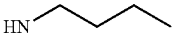 |
| 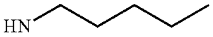 | 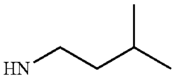 | 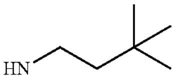 |
| 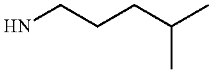 | 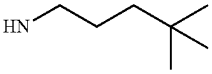 | 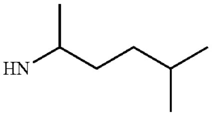 |
| 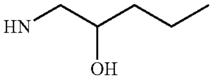 | 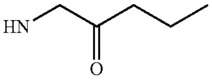 | 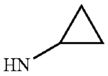 |
| 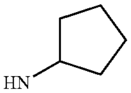 | 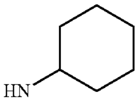 | 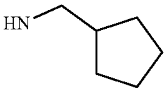 |
| 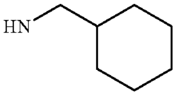 | 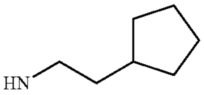 | 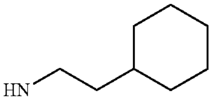 |
| 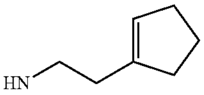 | 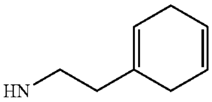 | 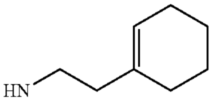 |
| 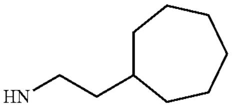 | 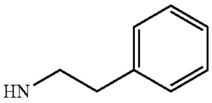 | 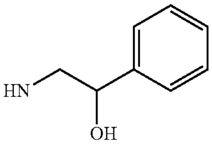 |

-continued
| HN—R | | |
|---|---|---|
| 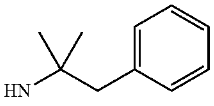 | 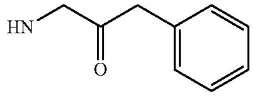 | 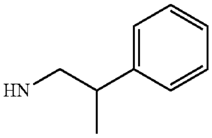 |
| 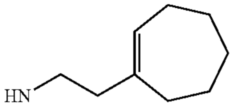 | 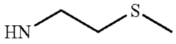 | 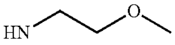 |
| 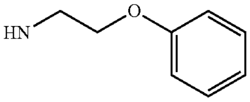 | 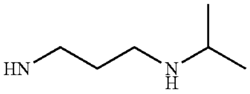 | 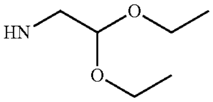 |
| 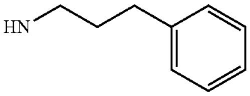 | 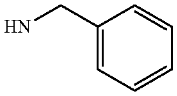 | 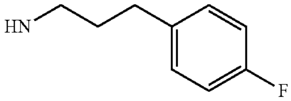 |
| 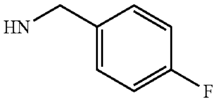 | 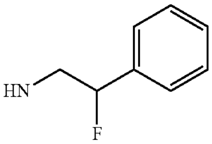 | 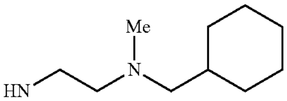 |
| 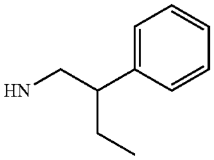 | 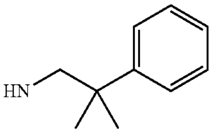 | 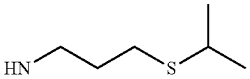 |
| 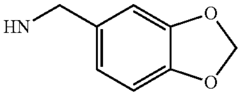 | 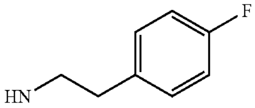 | 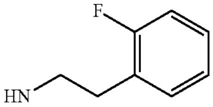 |
| 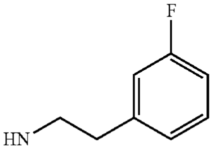 | 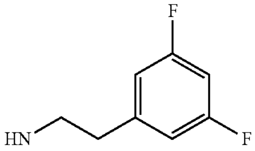 | 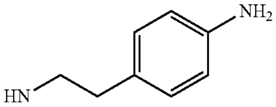 |
| 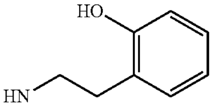 | 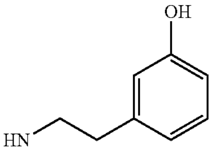 | 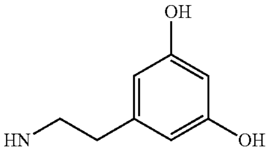 |
| 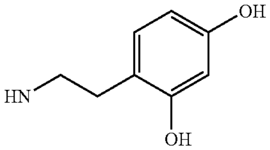 | 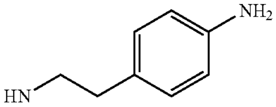 | 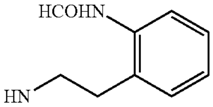 |
| 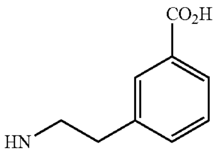 | 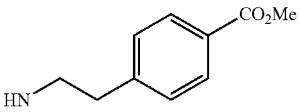 | 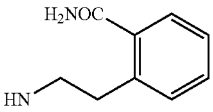 |

-continued
| | HN—R | |
|---|---|---|
| 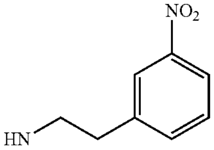 | 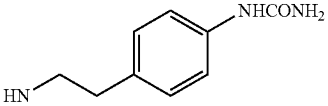 | 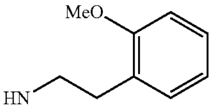 |
| 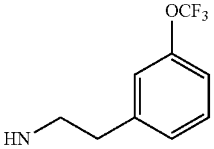 | 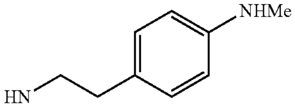 | 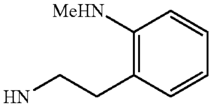 |
| 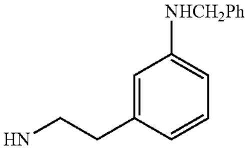 | 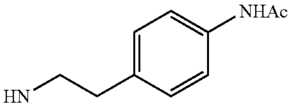 | 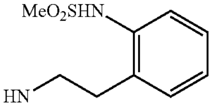 |
| 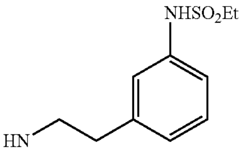 | 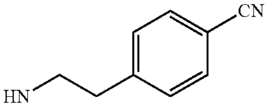 | 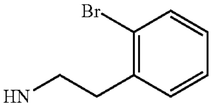 |
| 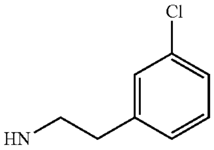 | 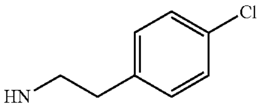 | 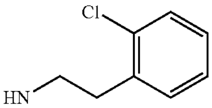 |
| 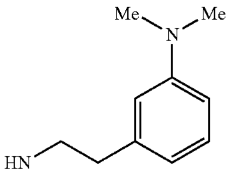 | 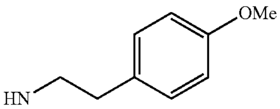 | 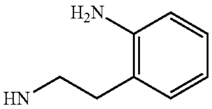 |
| 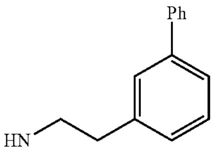 | 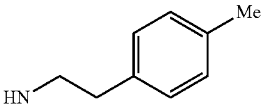 | 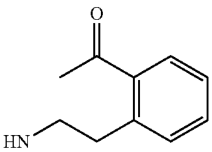 |
| 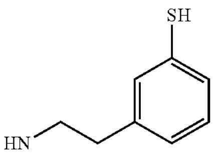 | | |

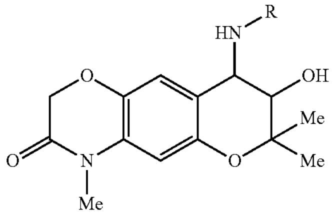
HN—R
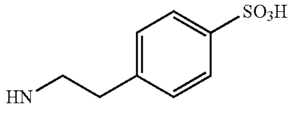
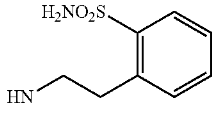
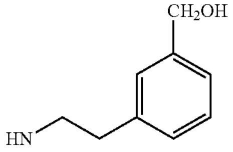
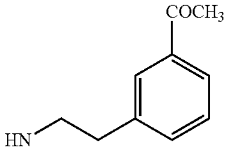
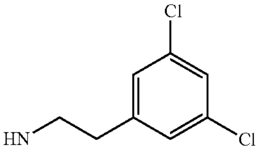
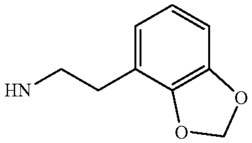
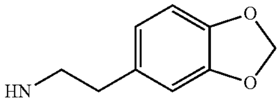
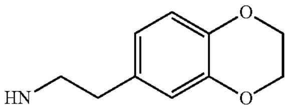
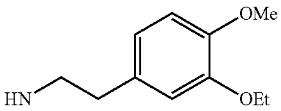
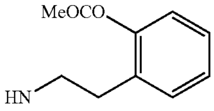
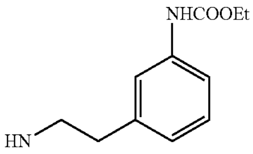
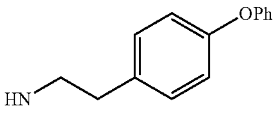
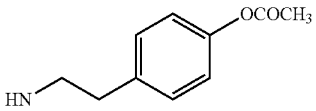
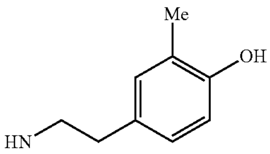
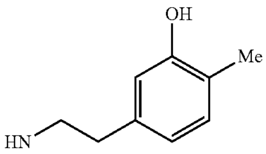
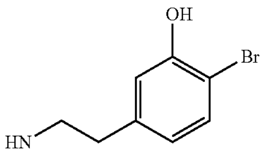
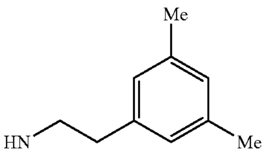
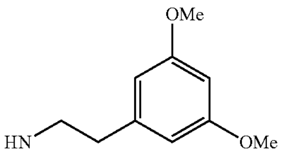
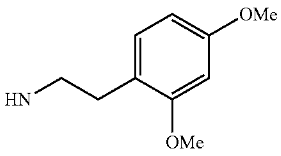
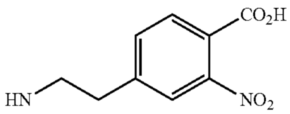
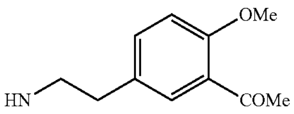
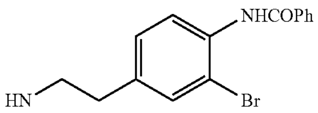
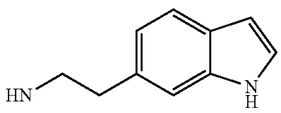
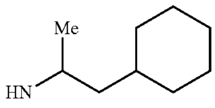

-continued
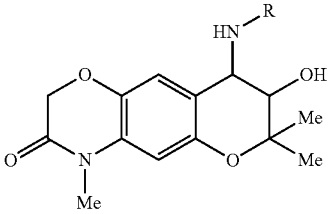
HN—R
| | | |
|---|---|---|
| 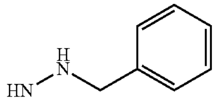 | 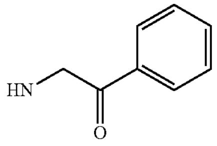 | 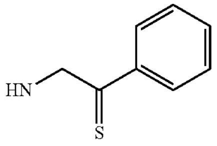 |
| 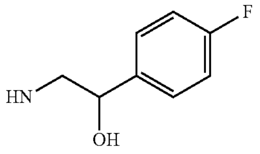 | 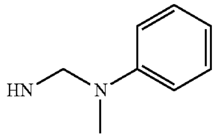 | 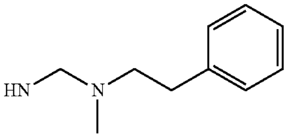 |
| 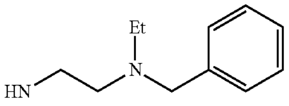 | 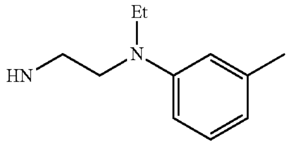 | 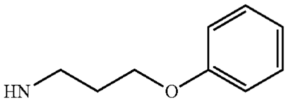 |
| 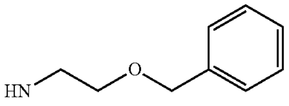 | 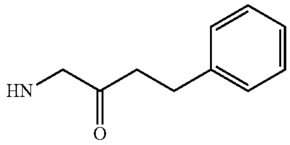 | 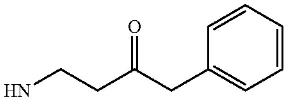 |
| 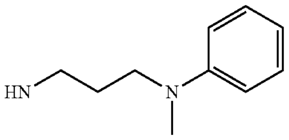 | 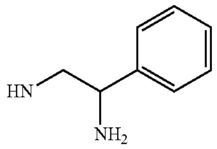 | 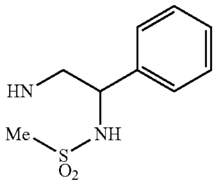 |
| 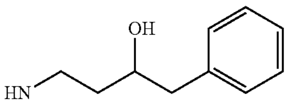 | 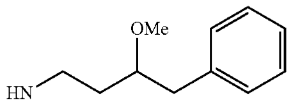 | 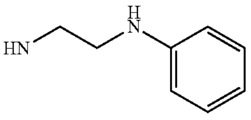 |
| 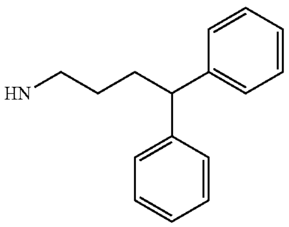 | 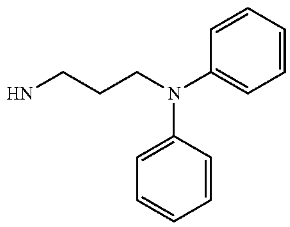 | 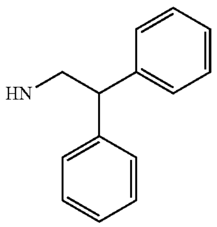 |
| 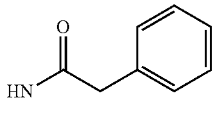 | 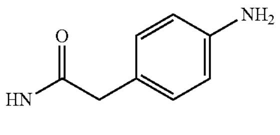 | 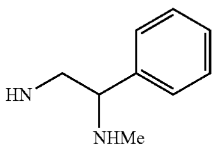 |

-continued
| | 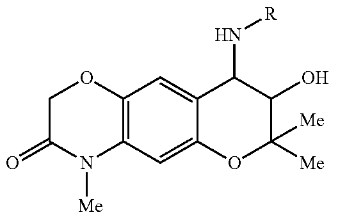<br>HN—R | |
|---|---|---|
| 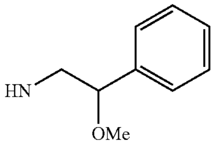 | 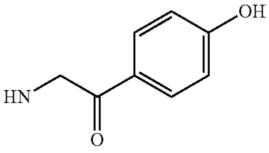 | 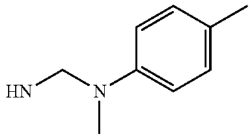 |
| 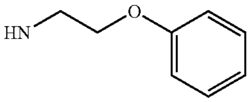 | 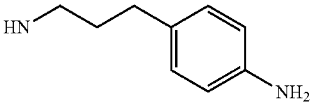 | 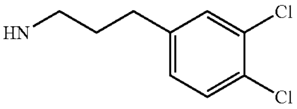 |
| | HN—R<br>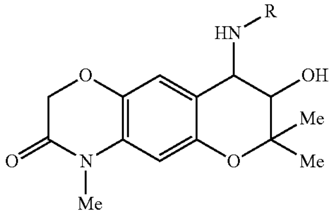 | |
|---|---|---|
| 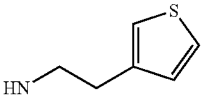 | 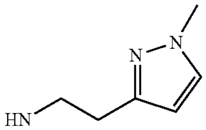 | 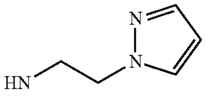 |
| 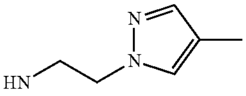 | 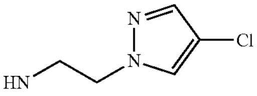 | 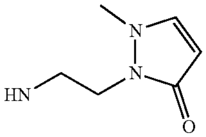 |
| 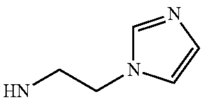 | 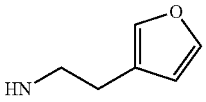 | 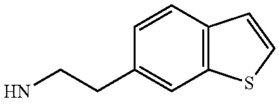 |
| 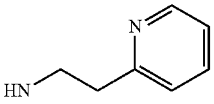 | 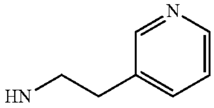 | 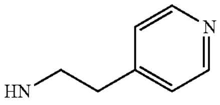 |
| 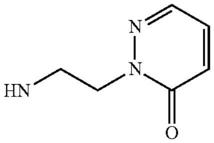 | 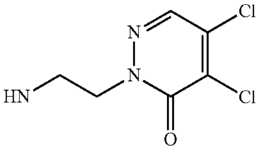 | 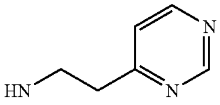 |

-continued
| HN—R | | |
|---|---|---|
| 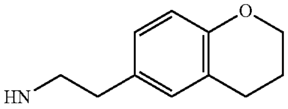 | 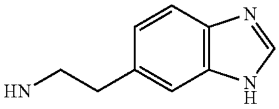 | 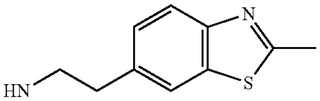 |
| 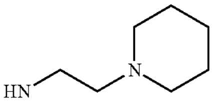 | 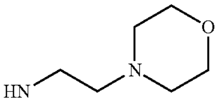 | 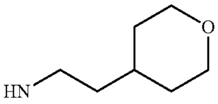 |
| 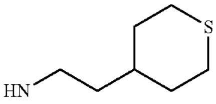 | 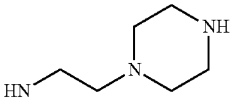 | 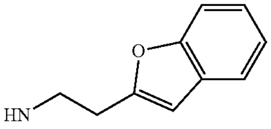 |
| 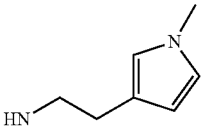 | 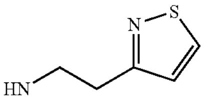 | 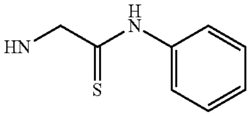 |
| 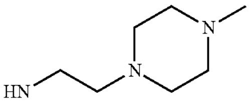 | 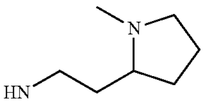 | 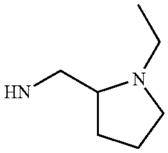 |
| 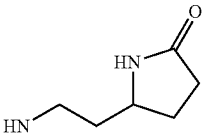 | 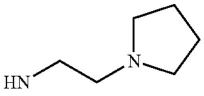 | 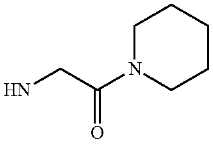 |
| 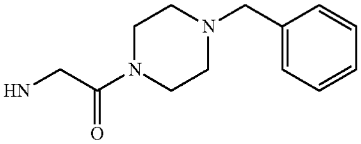 | 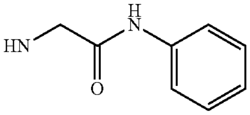 | |
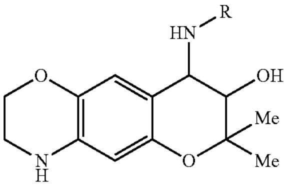
| | | |
|---|---|---|
| HN—Me | HN—Et | 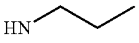 |
| 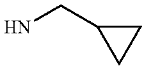 | 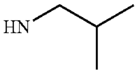 | 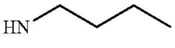 |
| 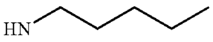 | 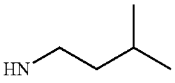 | 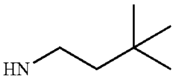 |
| 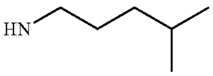 | 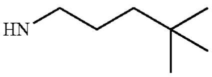 | 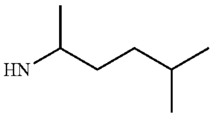 |

-continued
HN—R
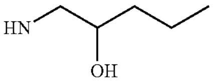 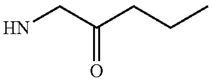 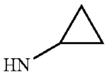
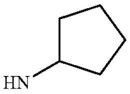 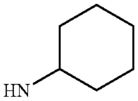 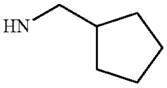
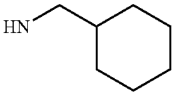 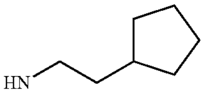 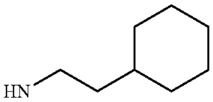
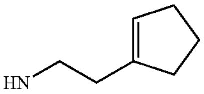 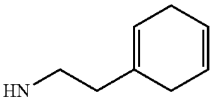 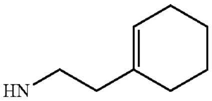
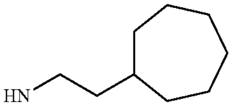 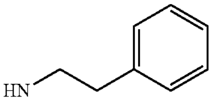 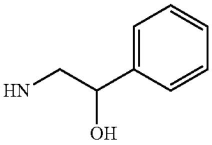
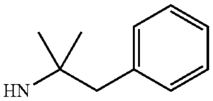 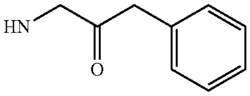 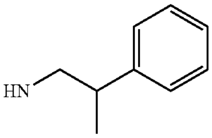
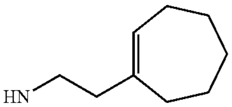 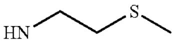 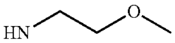
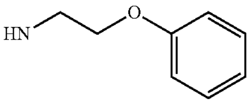 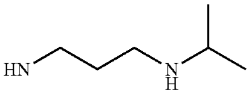 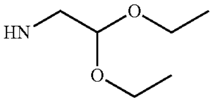
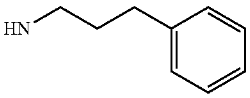 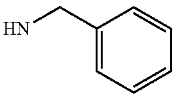 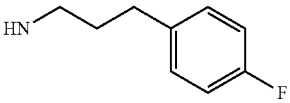
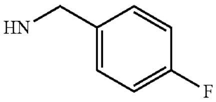 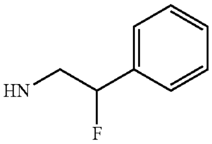 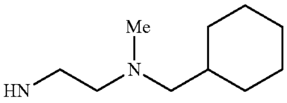
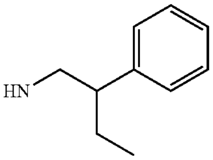 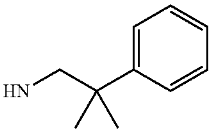 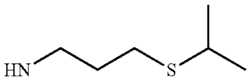
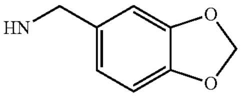 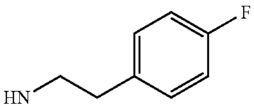 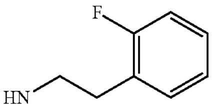

-continued
| HN—R | | |
|---|---|---|
| 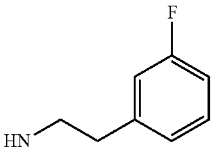 | 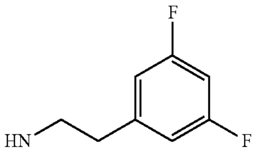 | 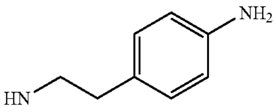 |
| 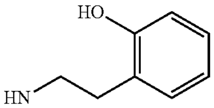 | 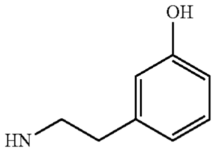 | 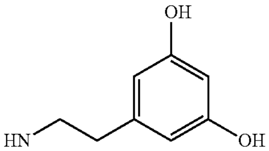 |
| 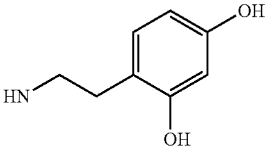 | 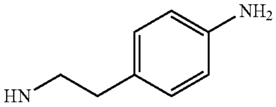 | 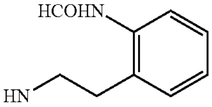 |
| 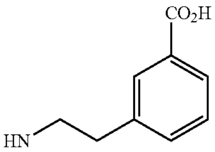 | 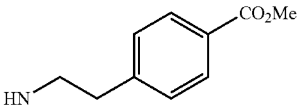 | 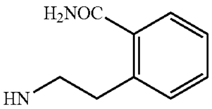 |
| 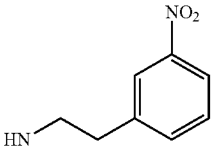 | 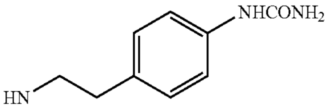 | 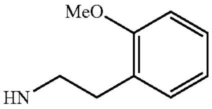 |
| 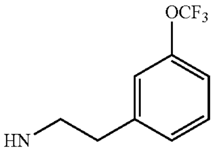 | 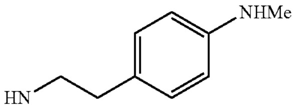 | 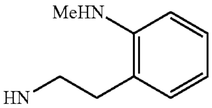 |
| 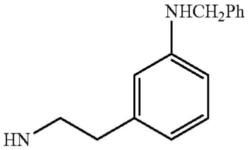 | 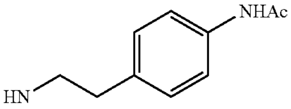 | 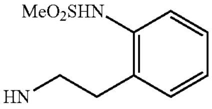 |
| 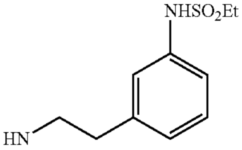 | 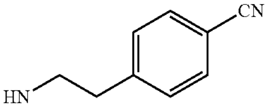 | 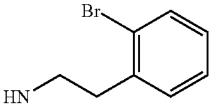 |
| 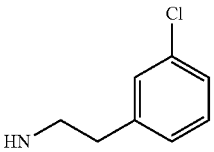 | 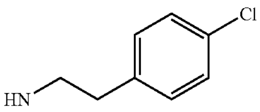 | 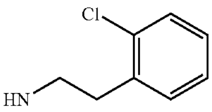 |

-continued
| HN—R | | |
|---|---|---|
| 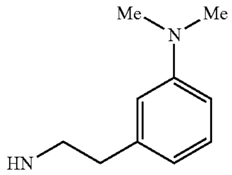 | 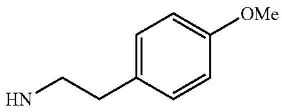 | 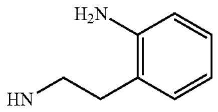 |
| 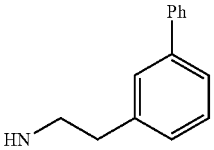 | 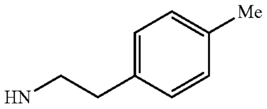 | 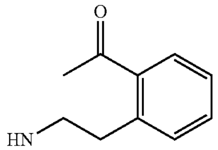 |
| 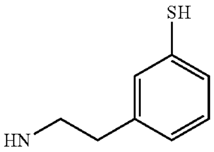 | | |
| 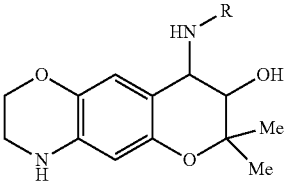<br>HN—R | | |
|---|---|---|
| 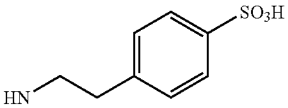 | 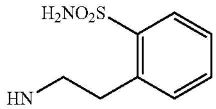 | 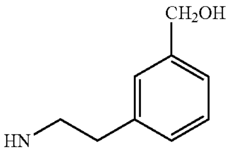 |
| 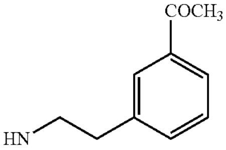 | 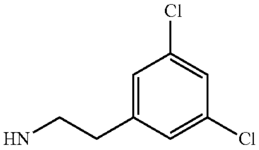 | 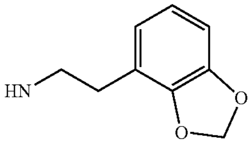 |
| 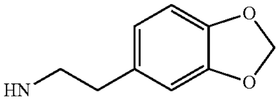 | 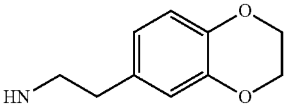 | 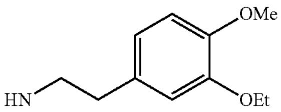 |
| 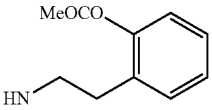 | 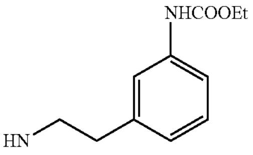 | 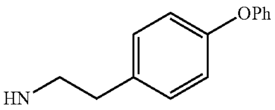 |

-continued
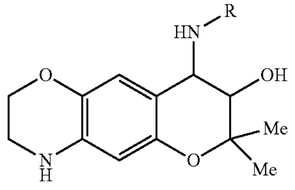
HN—R
| | | |
|---|---|---|
| 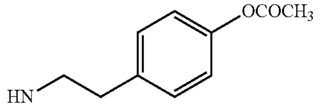 | 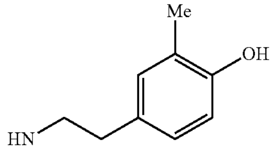 | 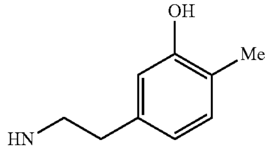 |
| 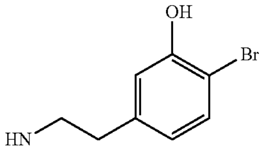 | 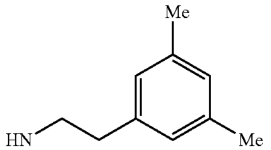 | 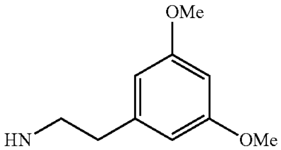 |
| 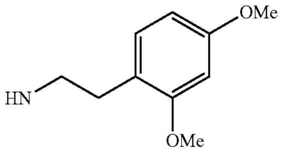 | 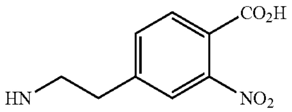 | 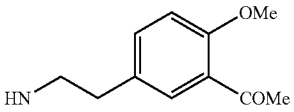 |
| 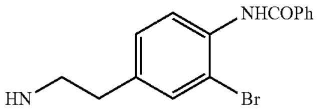 | 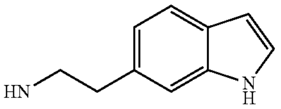 | 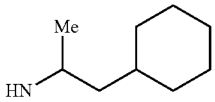 |
| 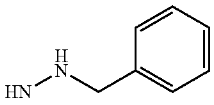 | 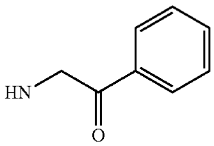 | 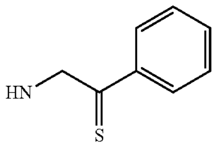 |
| 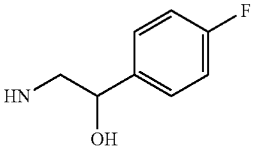 | 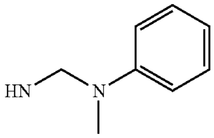 | 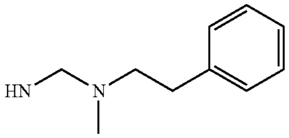 |
| 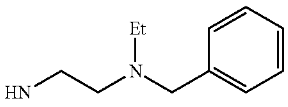 | 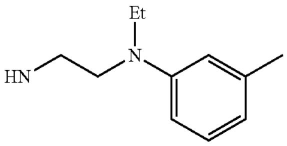 | 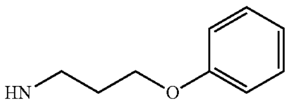 |
| 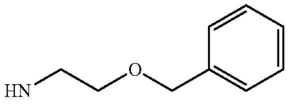 | 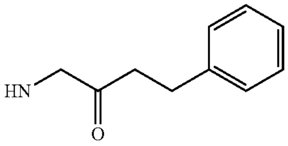 | 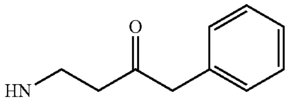 |

-continued
| | 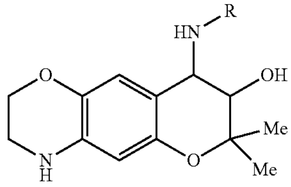 HN—R | |
|---|---|---|
| 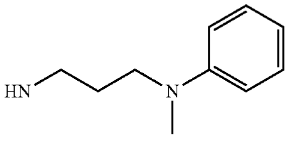 | 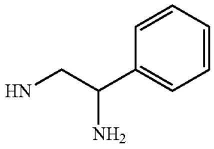 | 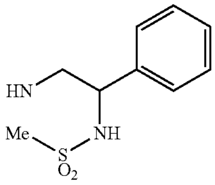 |
| 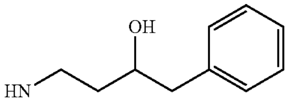 | 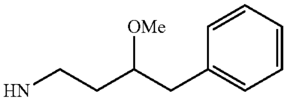 | 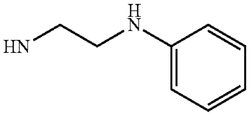 |
| 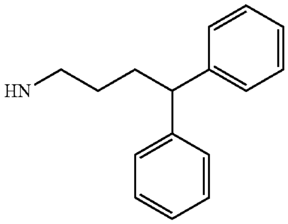 | 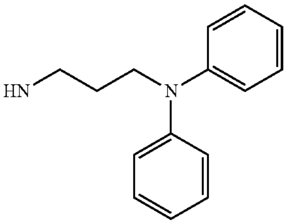 | 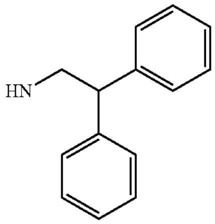 |
| 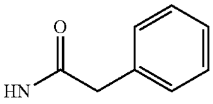 | 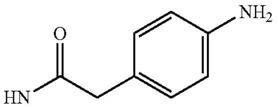 | 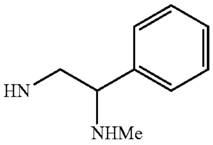 |
| 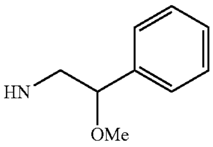 | 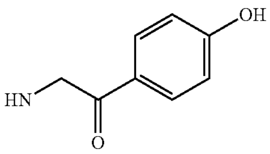 | 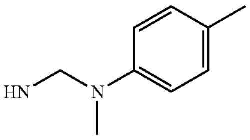 |
| 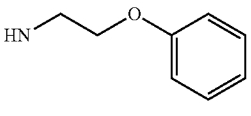 | 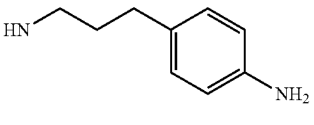 | 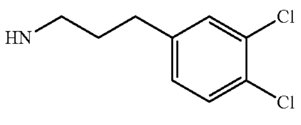 |

HN—R
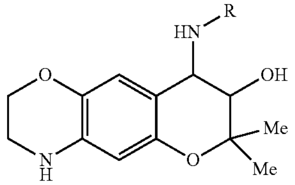
| | | |
|---|---|---|
| 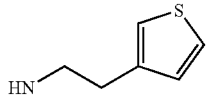 | 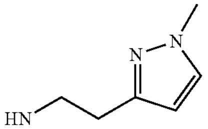 | 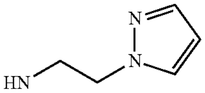 |
| 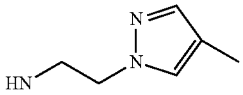 | 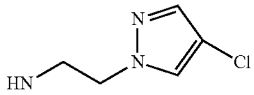 | 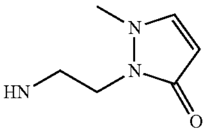 |
| 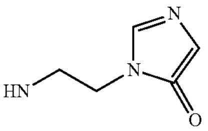 | 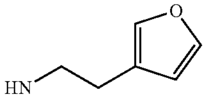 | 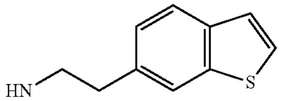 |
| 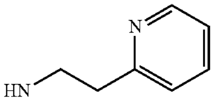 | 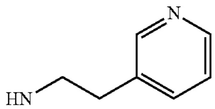 | 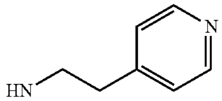 |
| 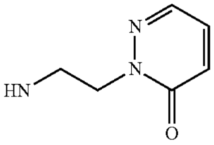 | 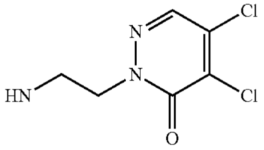 | 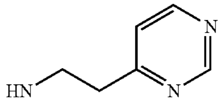 |
| 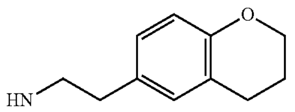 | 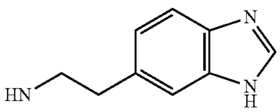 | 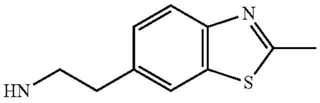 |
| 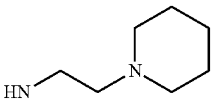 | 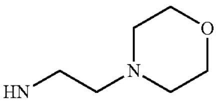 | 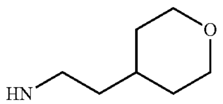 |
| 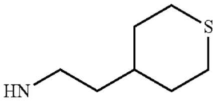 | 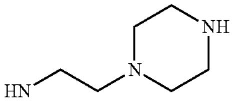 | 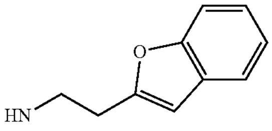 |
| 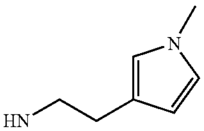 | 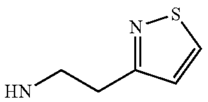 | 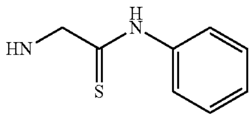 |
| 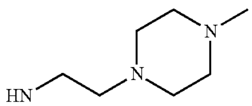 | 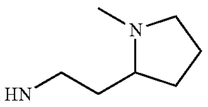 | 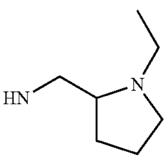 |

-continued
| HN—R | | |
|---|---|---|
| 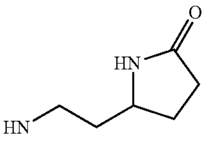 | 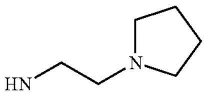 | 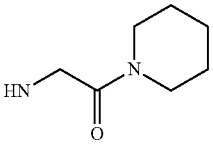 |
| 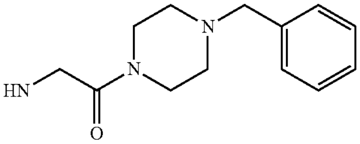 | 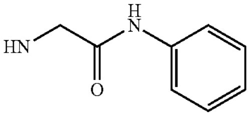 | |
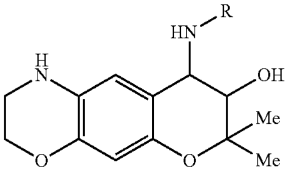
| | | |
|---|---|---|
| HN—Me | HN—Et | 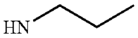 |
| 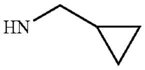 | 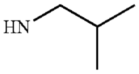 | 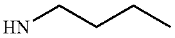 |
| 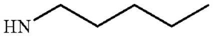 | 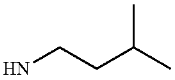 | 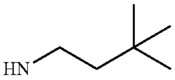 |
| 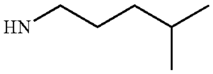 | 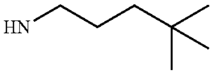 | 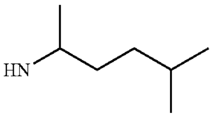 |
| 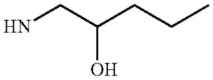 | 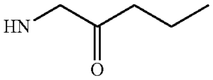 | 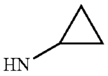 |
| 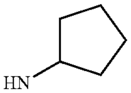 | 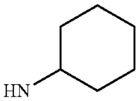 | 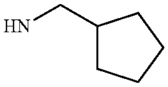 |
| 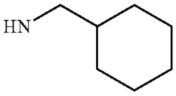 | 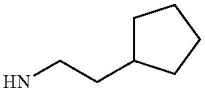 | 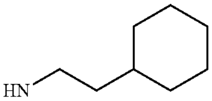 |
| 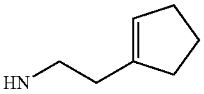 | 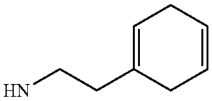 | 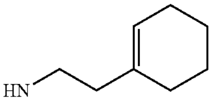 |
| 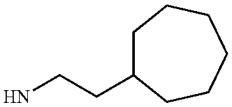 | 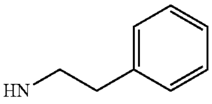 | 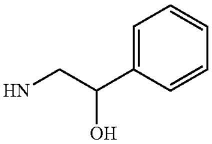 |

-continued
| HN—R | | |
|---|---|---|
| 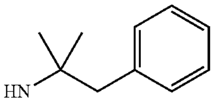 | 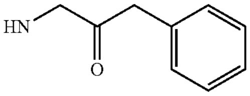 | 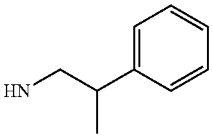 |
| 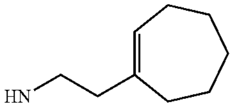 | 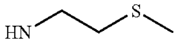 | 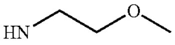 |
| 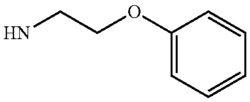 | 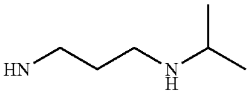 | 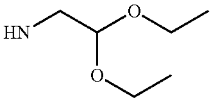 |
| 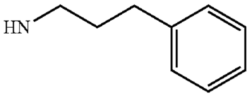 | 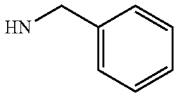 | 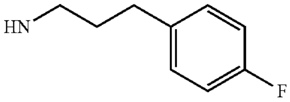 |
| 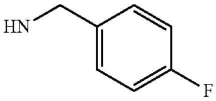 | 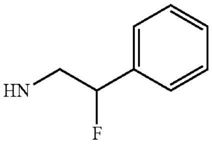 | 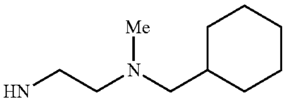 |
| 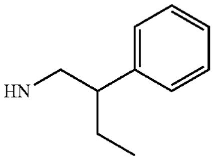 | 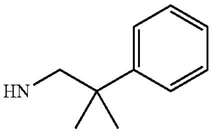 | 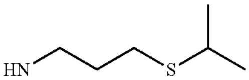 |
| 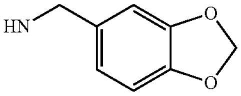 | | |
| 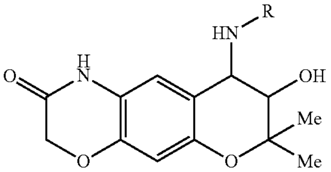 | | |
|---|---|---|
| 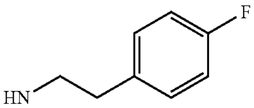 | 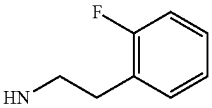 | 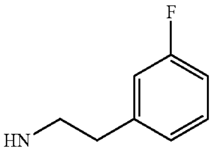 |
| 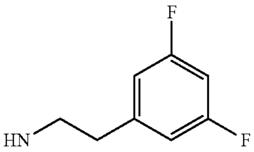 | 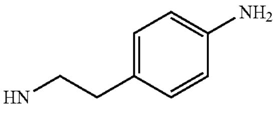 | 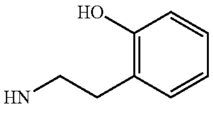 |
| 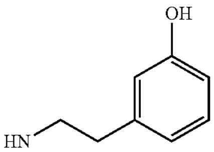 | 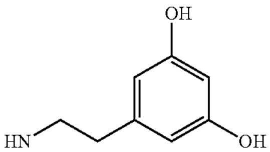 | 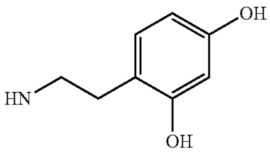 |

-continued
| HN—R | | |
|---|---|---|
| 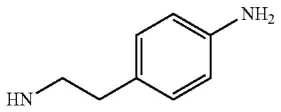 | 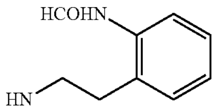 | 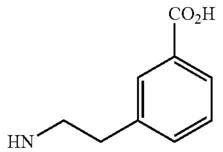 |
| 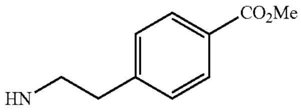 | 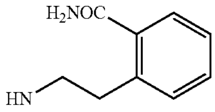 | 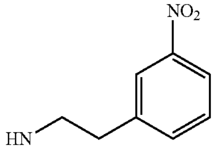 |
| 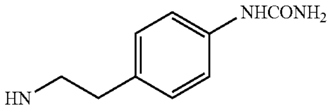 | 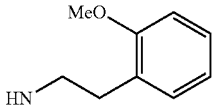 | 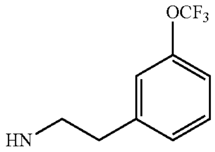 |
| 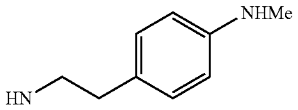 | 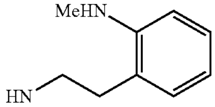 | 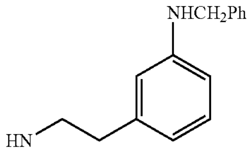 |
| 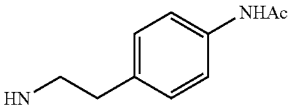 | 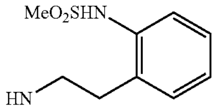 | 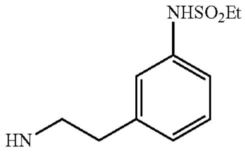 |
| 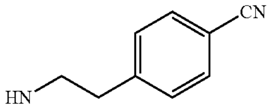 | 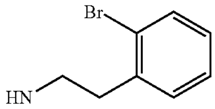 | 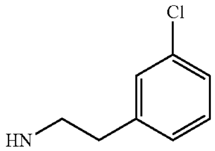 |
| 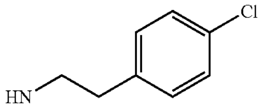 | 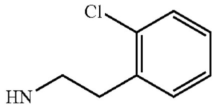 | 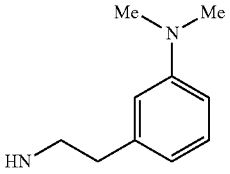 |
| 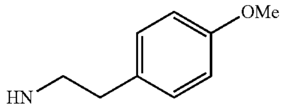 | 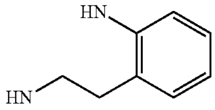 | 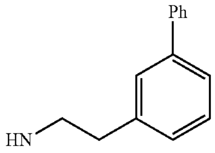 |
| 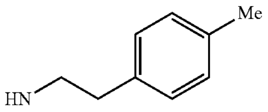 | 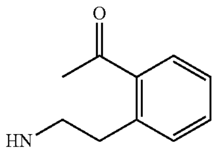 | 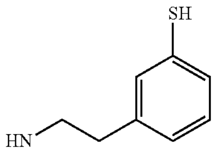 |

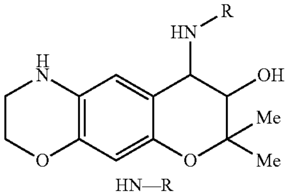
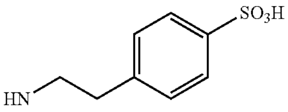 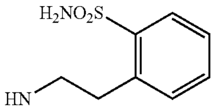 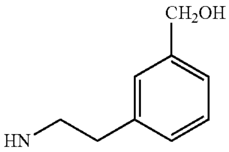
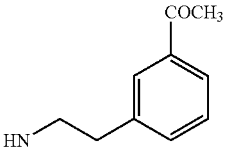 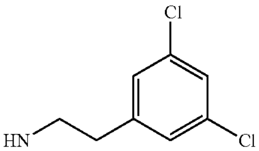 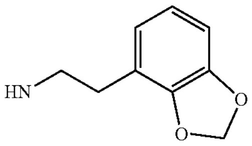
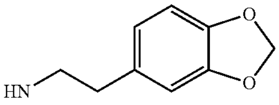 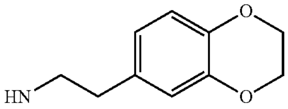 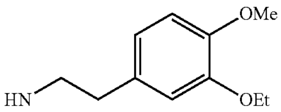
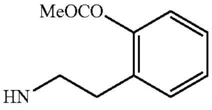 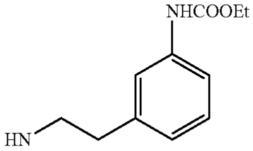 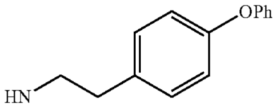
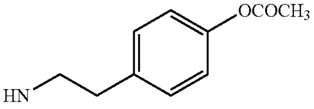 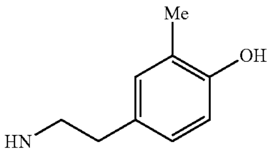 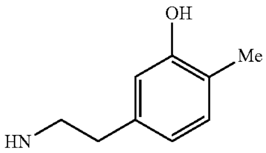
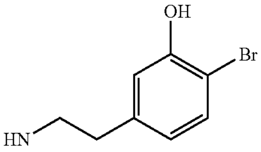 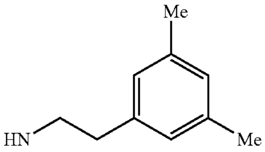 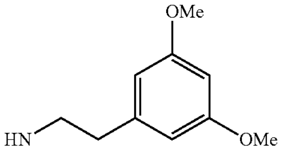
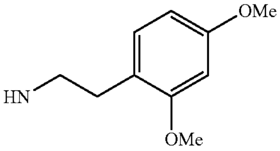 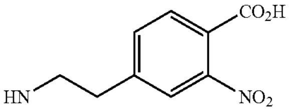 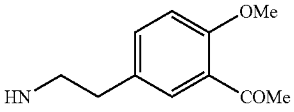
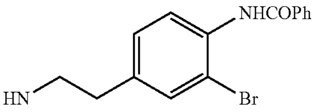 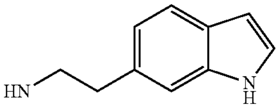 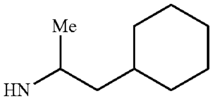
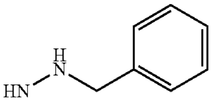 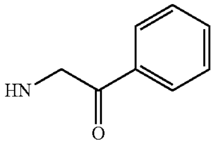 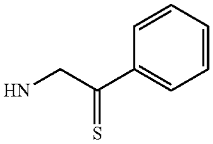

-continued
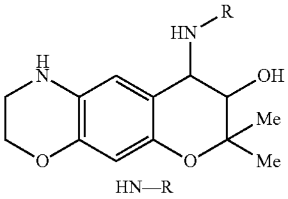
| | | |
|---|---|---|
| 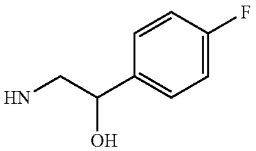 | 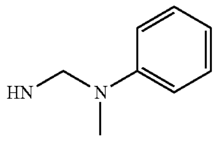 | 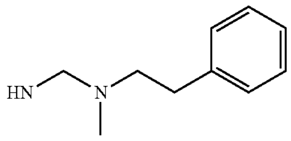 |
| 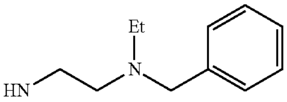 | 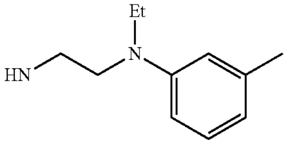 | 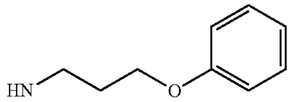 |
| 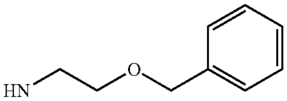 | 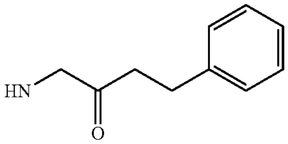 | 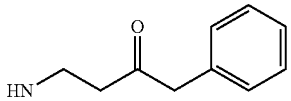 |
| 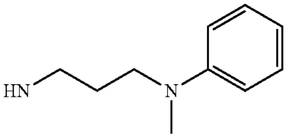 | 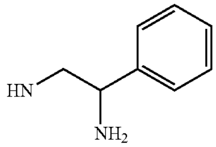 | 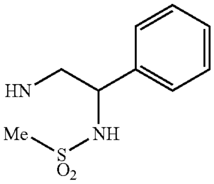 |
| 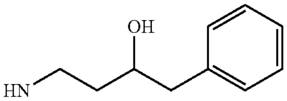 | 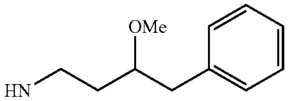 | 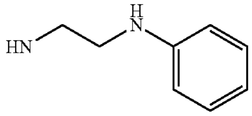 |
| 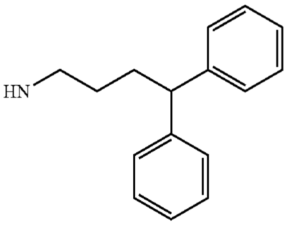 | 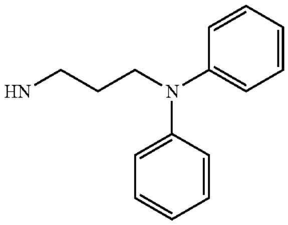 | 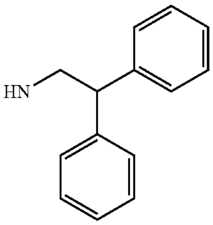 |
| 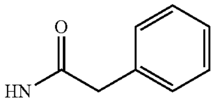 | 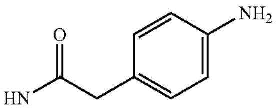 | 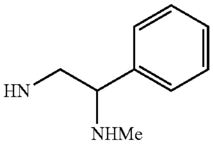 |
| 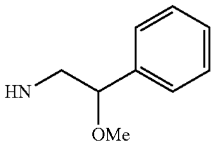 | 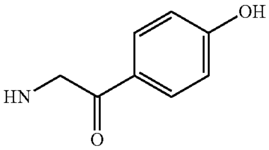 | 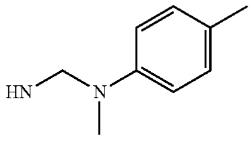 |

-continued
| | 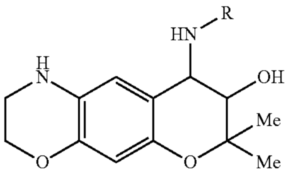 | |
|---|---|---|
| | HN—R | |
| 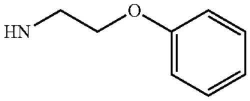 | 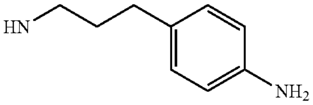 | 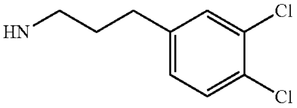 |
| | HN—R | |
|---|---|---|
| | 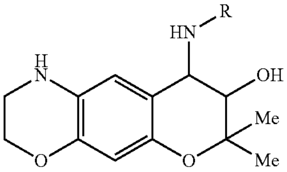 | |
| 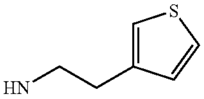 | 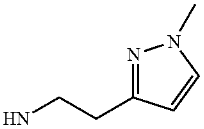 | 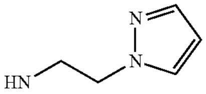 |
| 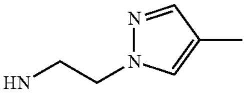 | 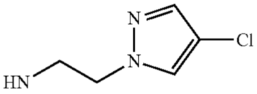 | 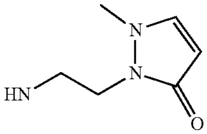 |
| 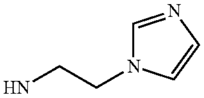 | 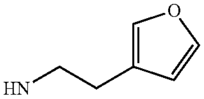 | 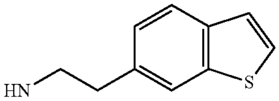 |
| 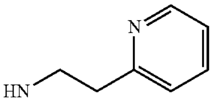 | 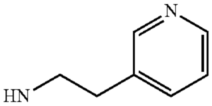 | 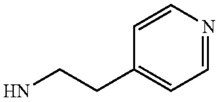 |
| 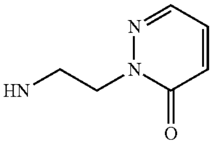 | 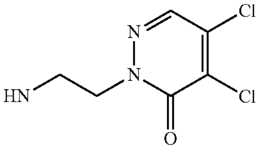 | 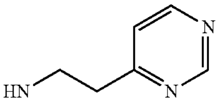 |
| 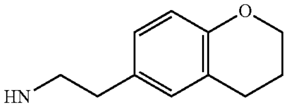 | 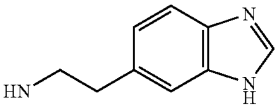 | 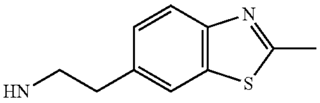 |
| 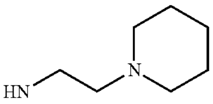 | 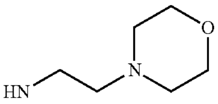 | 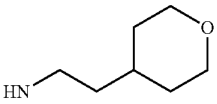 |

-continued
| | HN—R | |
|---|---|---|
| 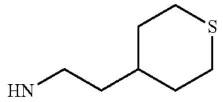 | 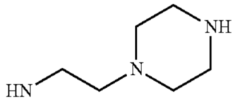 | 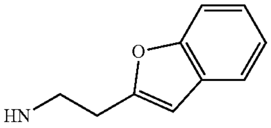 |
| 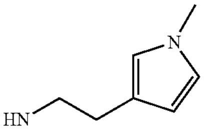 | 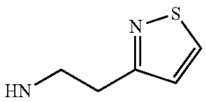 | 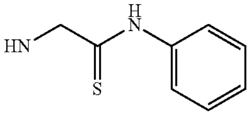 |
| 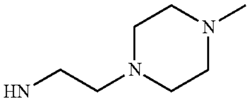 | 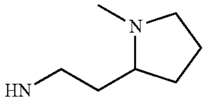 | 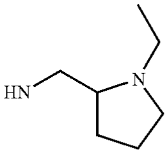 |
| 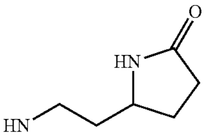 | 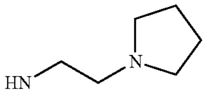 | 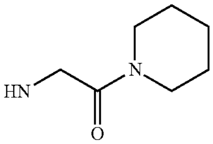 |
| 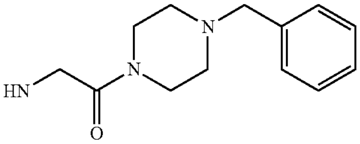 | 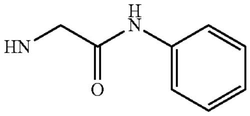 | |
| | 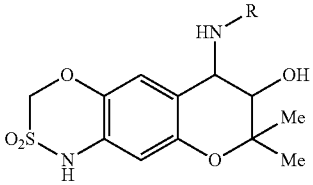 | |
|---|---|---|
| HN—Me | HN—Et | 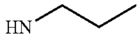 |
| 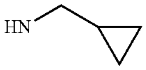 | 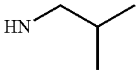 | 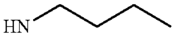 |
| 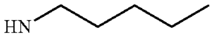 | 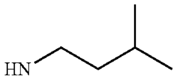 | 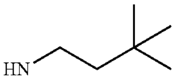 |
| 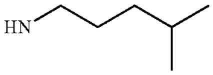 | 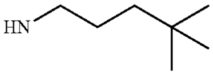 | 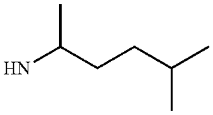 |
| 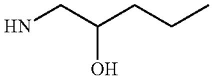 | 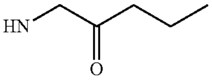 | 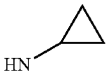 |
| 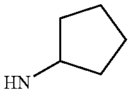 | 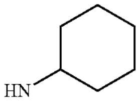 | 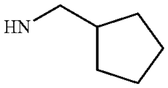 |

-continued
HN—R
| | | |
|---|---|---|
| 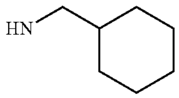 | 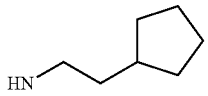 | 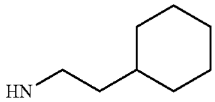 |
| 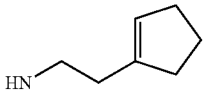 | 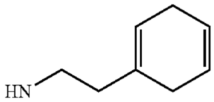 | 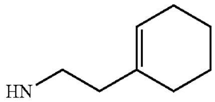 |
| 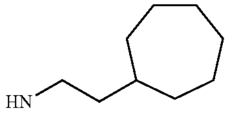 | 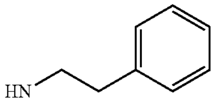 | 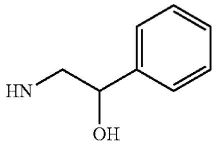 |
| 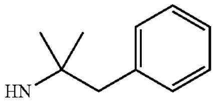 | 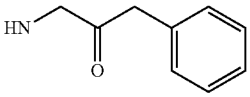 | 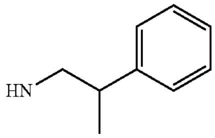 |
| 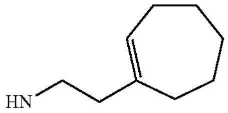 | 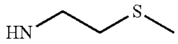 | 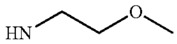 |
| 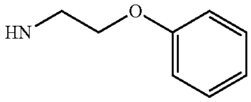 | 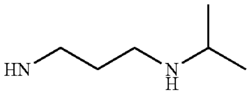 | 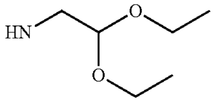 |
| 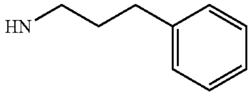 | 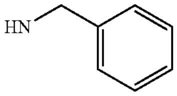 | 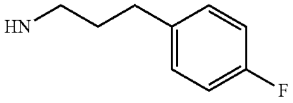 |
| 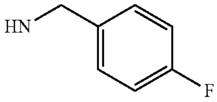 | 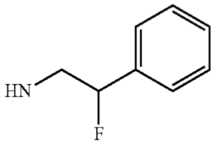 | 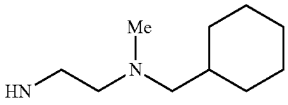 |
| 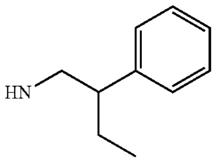 | 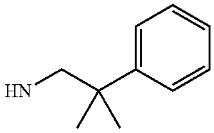 | 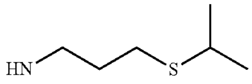 |
| 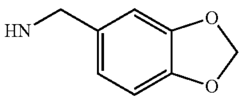 | 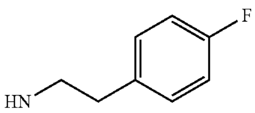 | 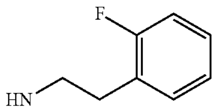 |
| 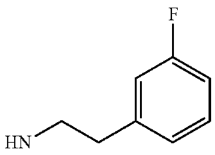 | 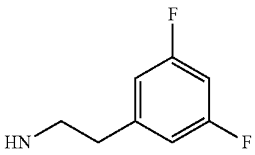 | 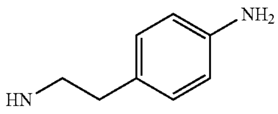 |

-continued
| | HN—R | |
|---|---|---|
| 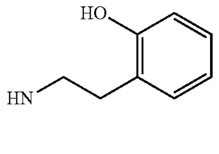 | 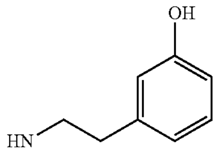 | 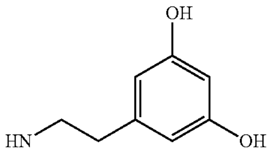 |
| 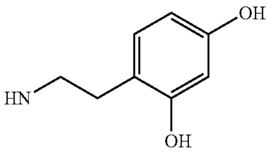 | 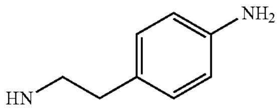 | 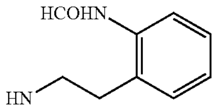 |
| 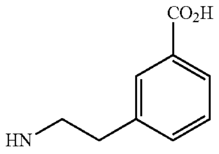 | 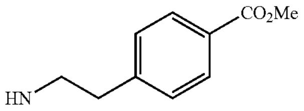 | 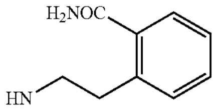 |
| 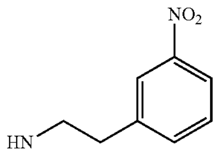 | 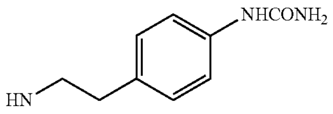 | 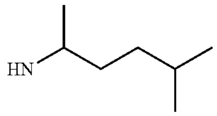 |
| 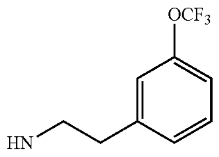 | 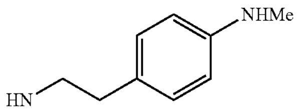 | 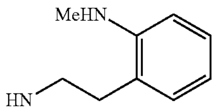 |
| 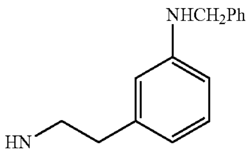 | 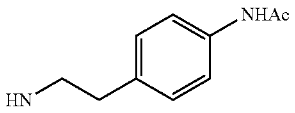 | 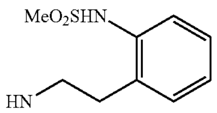 |
| 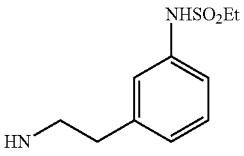 | 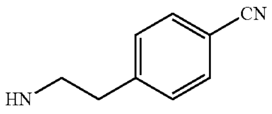 | 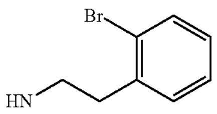 |
| 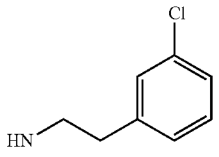 | 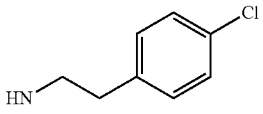 | 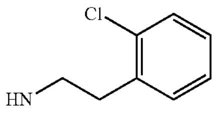 |
| 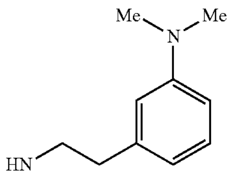 | 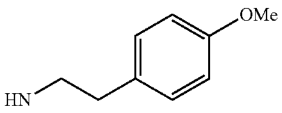 | 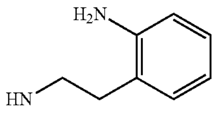 |

-continued
| HN—R | | |
|---|---|---|
| 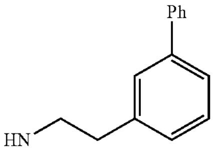 | 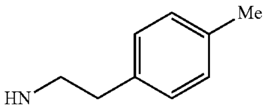 | 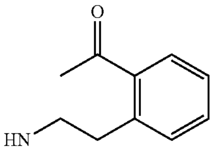 |
| 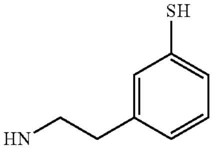 | | |
| HN—R | | |
|---|---|---|
| | 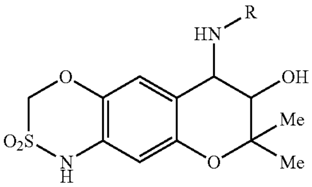 | |
| 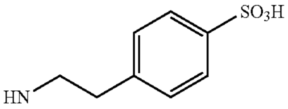 | 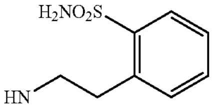 | 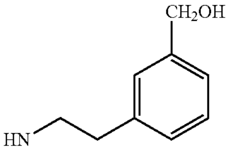 |
| 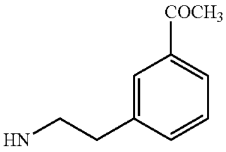 | 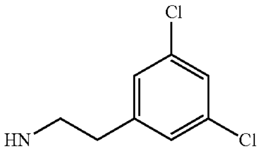 | 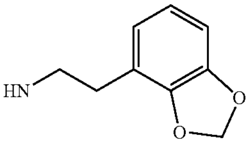 |
| 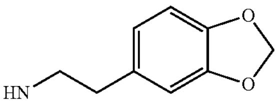 | 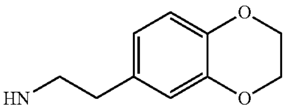 | 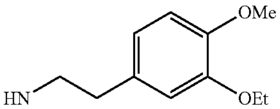 |
| 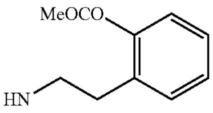 | 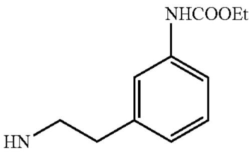 | 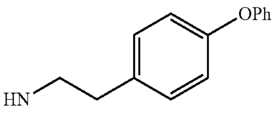 |
| 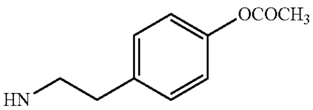 | 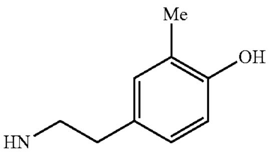 | 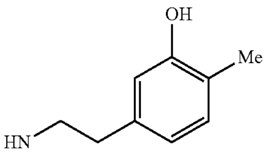 |

-continued
| HN—R | | |
|---|---|---|
| 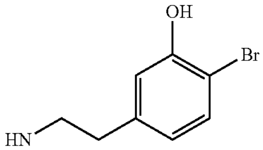 | 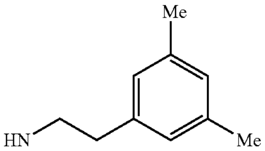 | 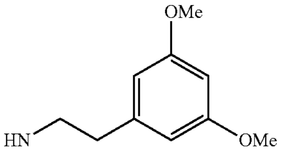 |
| 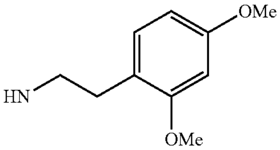 | 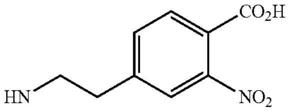 | 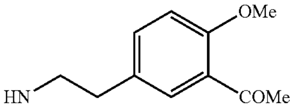 |
| 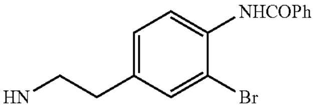 | 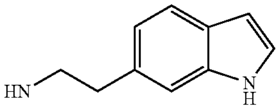 | |
| | 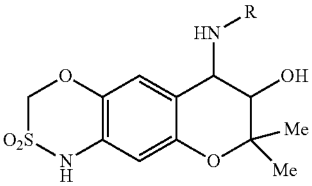 | |
| 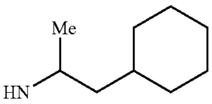 | 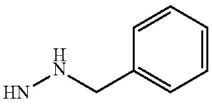 | 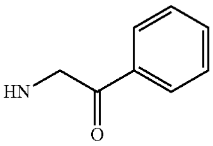 |
| 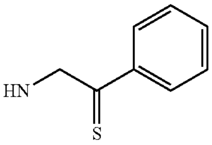 | 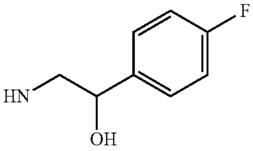 | 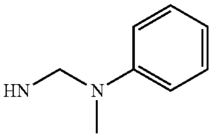 |
| 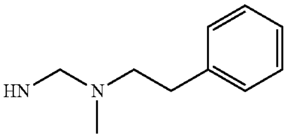 | 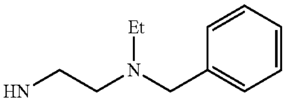 | 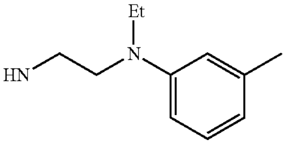 |
| 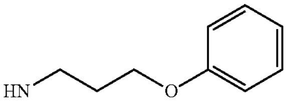 | 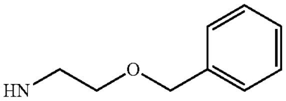 | 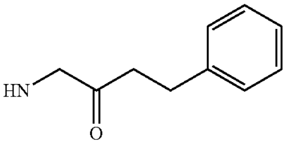 |
| 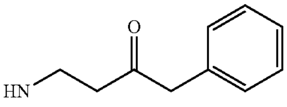 | 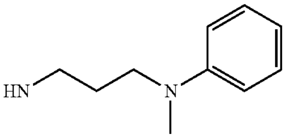 | 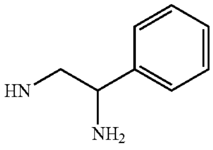 |

-continued
| HN—R | | |
|---|---|---|
| 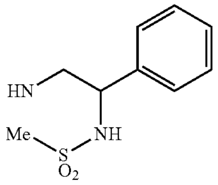 | 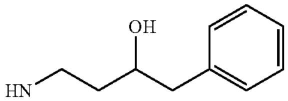 | 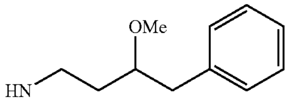 |
| 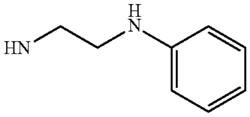 | 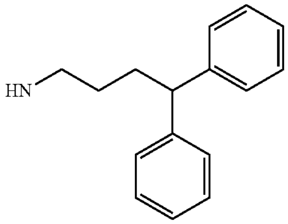 | 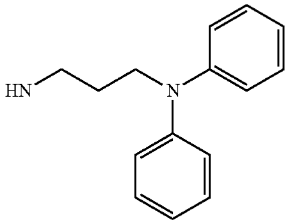 |
| 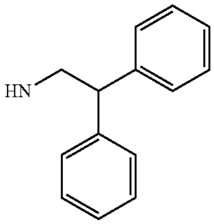 | 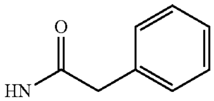 | 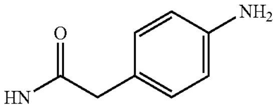 |
| 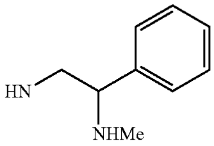 | 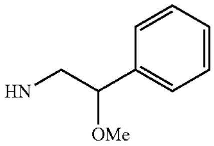 | 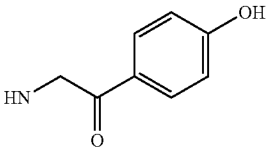 |
| 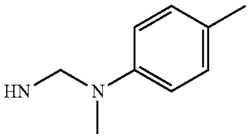 | 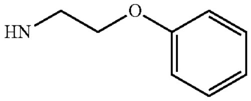 | 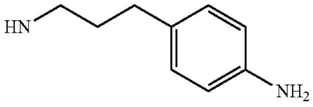 |
| 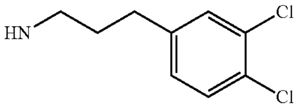 | | |
| HN—R | | |
|---|---|---|
| | 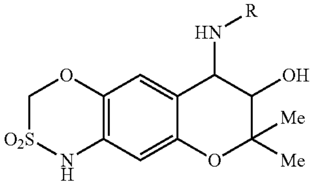 | |
| 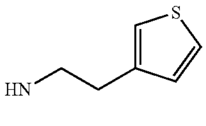 | 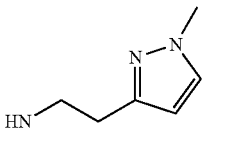 | 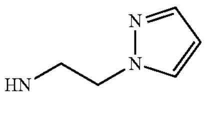 |

-continued
| HN—R | | |
|---|---|---|
| 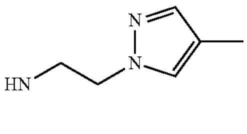 | 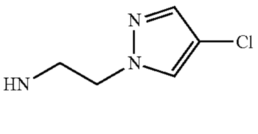 | 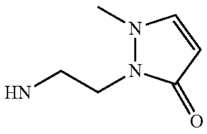 |
| 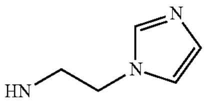 | 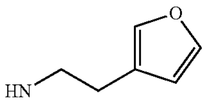 | 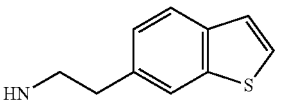 |
| 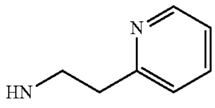 | 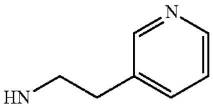 | 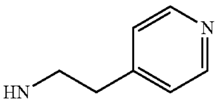 |
| 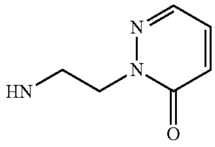 | 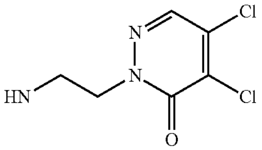 | 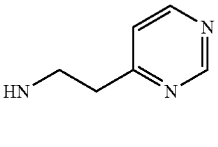 |
| 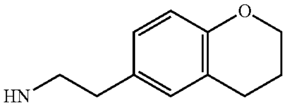 | 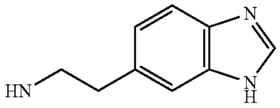 | 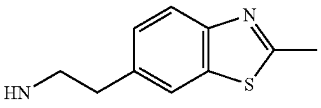 |
| 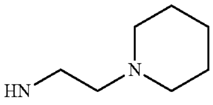 | 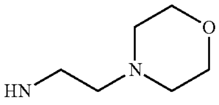 | 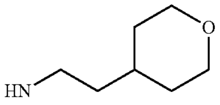 |
| 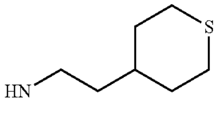 | 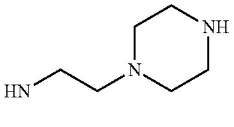 | 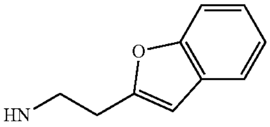 |
| 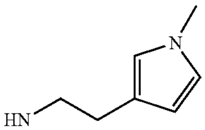 | 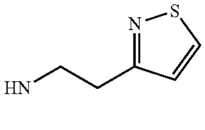 | 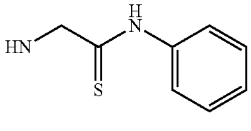 |
| 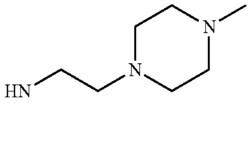 | 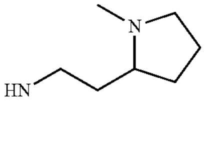 | 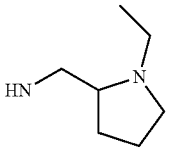 |
| 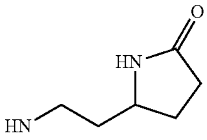 | 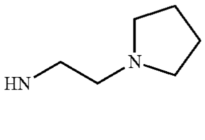 | 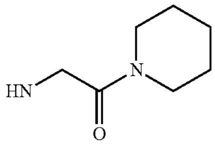 |
| 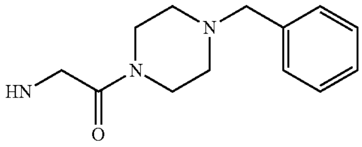 | 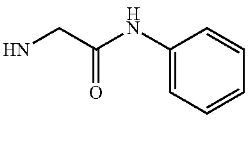 | |

-continued
| HN—R | | |
|---|---|---|
| | 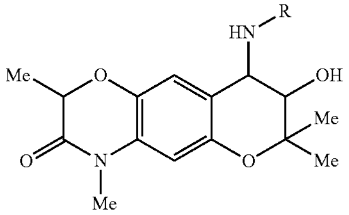 | |
| 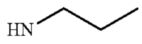 | 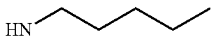 | 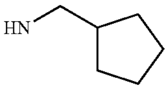 |
| 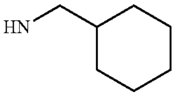 | 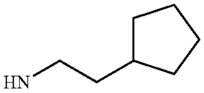 | 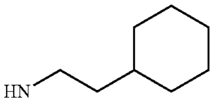 |
| 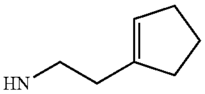 | 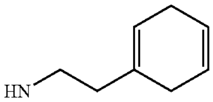 | 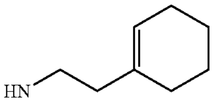 |
| 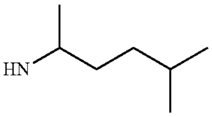 | 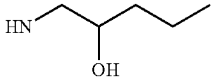 | 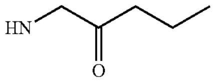 |
| 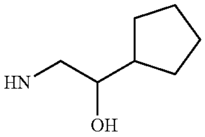 | 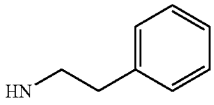 | 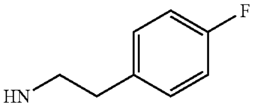 |
| 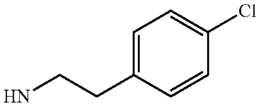 | 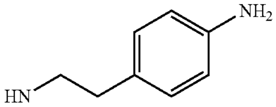 | 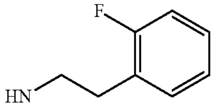 |
| 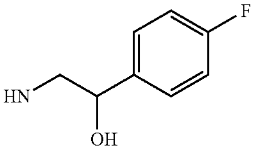 | 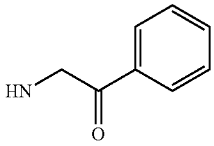 | 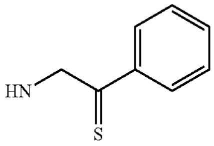 |
| 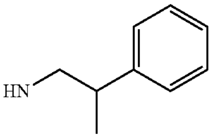 | 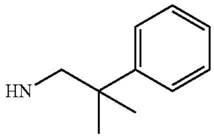 | 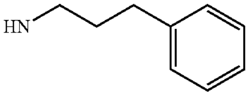 |
| 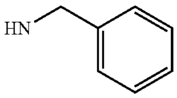 | 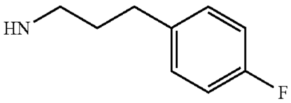 | 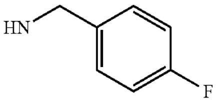 |
| 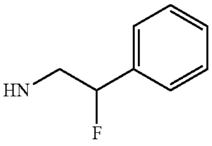 | 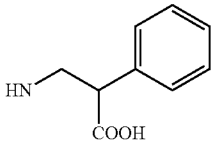 | 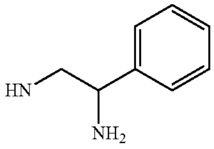 |

-continued
| HN—R | | |
|---|---|---|
| 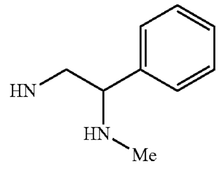 | 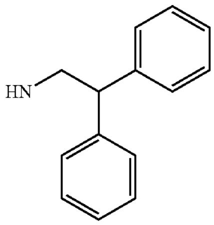 | 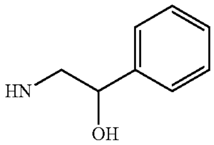 |
| 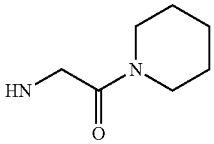 | 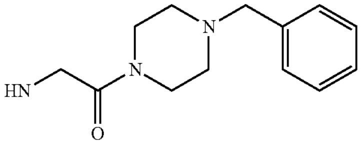 | 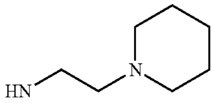 |
| 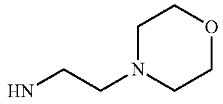 | 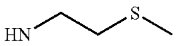 | 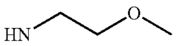 |
| 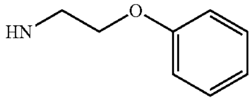 | 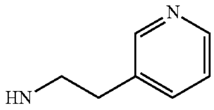 | 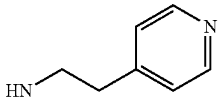 |
| 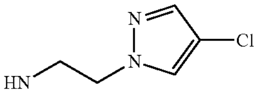 | 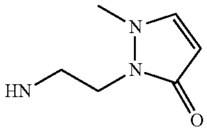 | |
| 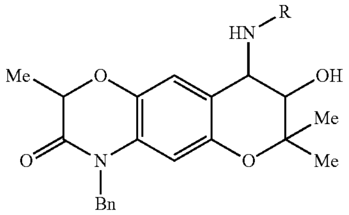 | | |
|---|---|---|
| 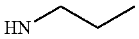 | 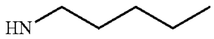 | 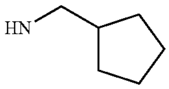 |
| 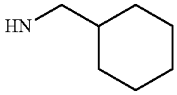 | 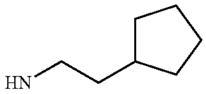 | 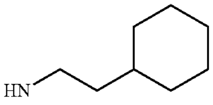 |
| 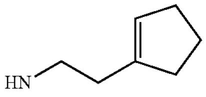 | 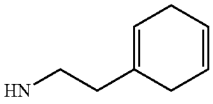 | 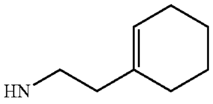 |
| 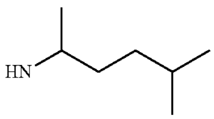 | 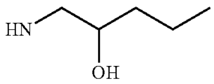 | 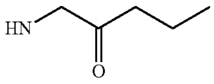 |

-continued
| HN—R | | |
|---|---|---|
| 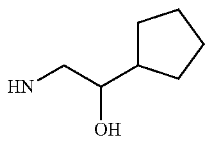 | 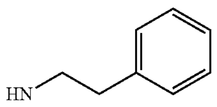 | 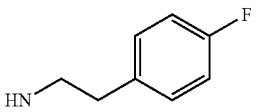 |
| 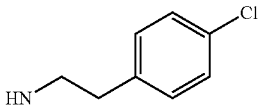 | 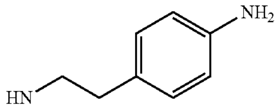 | 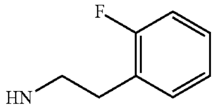 |
| 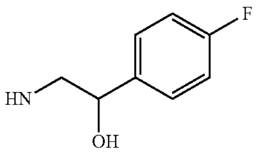 | 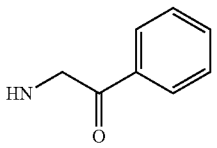 | 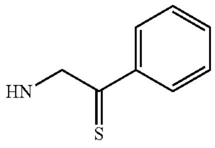 |
| 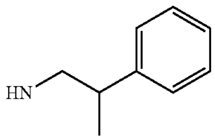 | 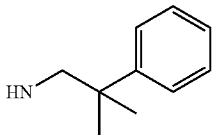 | 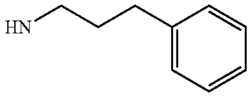 |
| 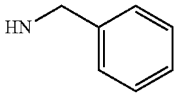 | 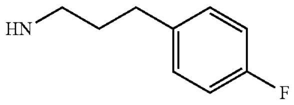 | 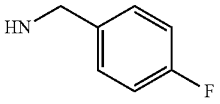 |
| 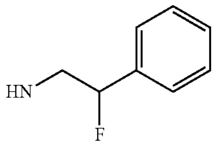 | 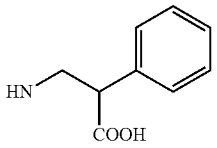 | 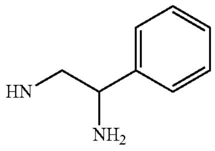 |
| 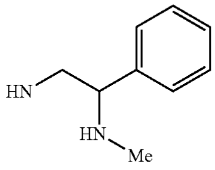 | 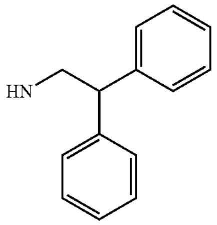 | 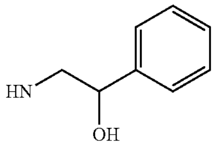 |
| 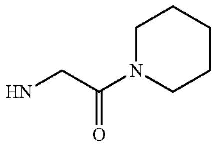 | 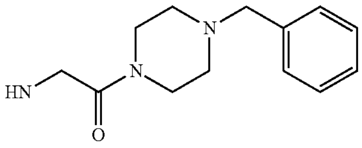 | 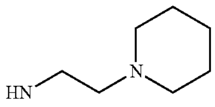 |
| 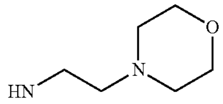 | 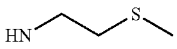 | 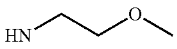 |
| 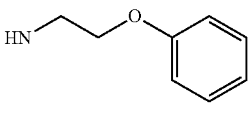 | 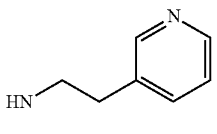 | 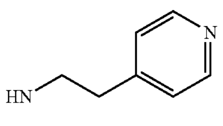 |

-continued
| HN—R | | |
|---|---|---|
| 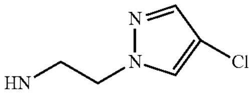 | 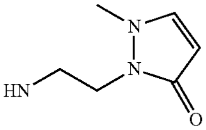 | |
| | 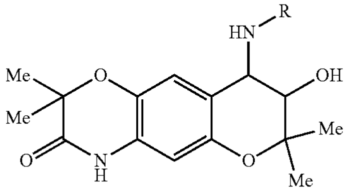 | |
| 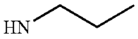 | 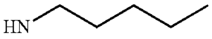 | 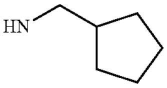 |
| 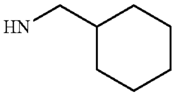 | 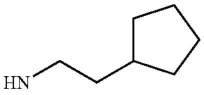 | 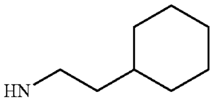 |
| 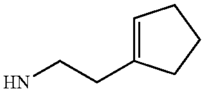 | 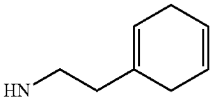 | 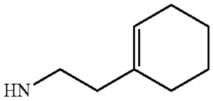 |
| 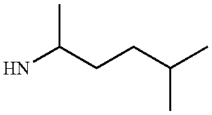 | 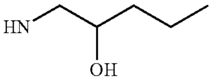 | 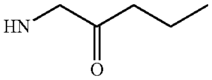 |
| 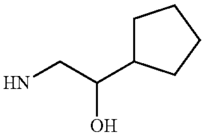 | 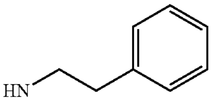 | 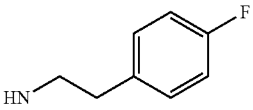 |
| 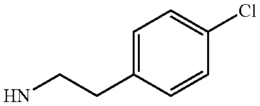 | 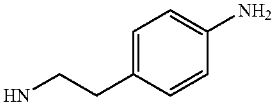 | 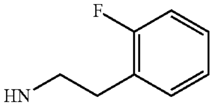 |
| 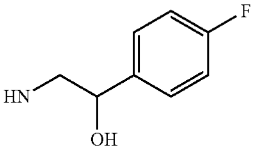 | 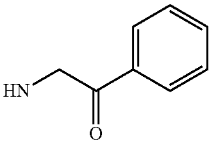 | 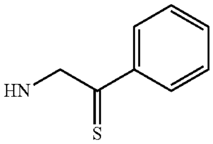 |
| 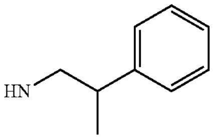 | 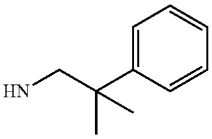 | 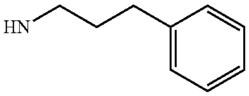 |
| 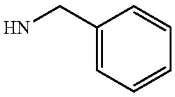 | 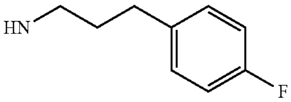 | 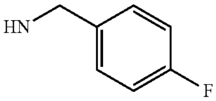 |

-continued
| HN—R | | |
|---|---|---|
| 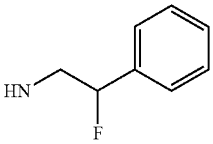 | 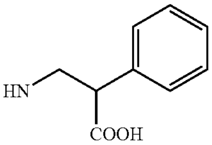 | 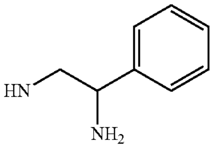 |
| 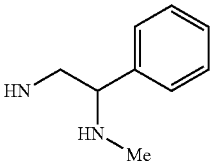 | 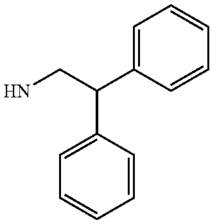 | 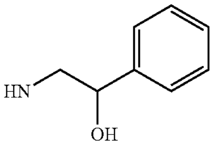 |
| 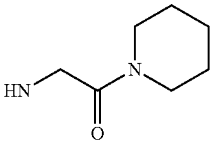 | 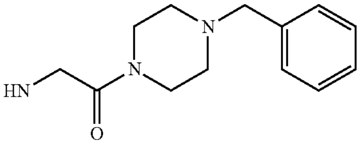 | 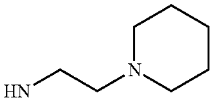 |
| 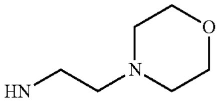 | 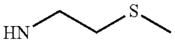 | 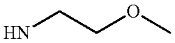 |
| 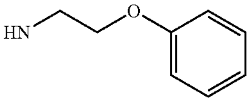 | 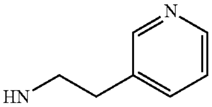 | 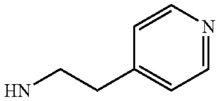 |
| 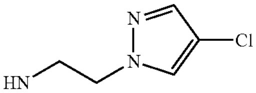 | 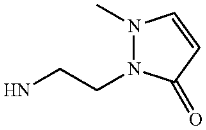 | |
| | 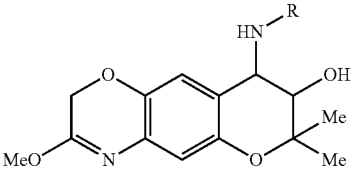 | |
|---|---|---|
| 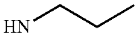 | 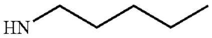 | 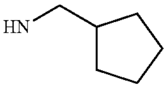 |
| 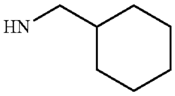 | 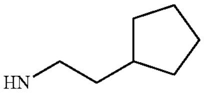 | 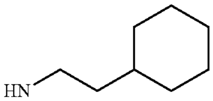 |
| 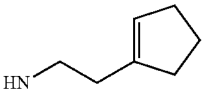 | 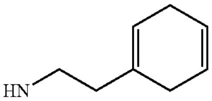 | 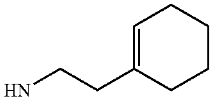 |
| 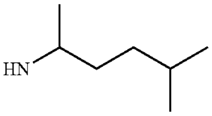 | 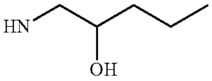 | 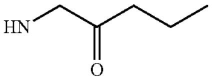 |

-continued
| HN—R | | |
|---|---|---|
| 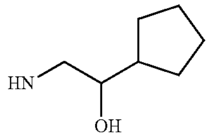 | 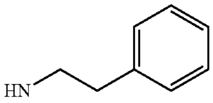 | 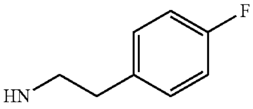 |
| 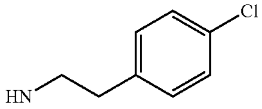 | 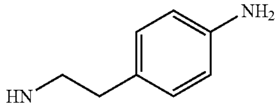 | 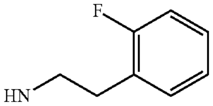 |
| 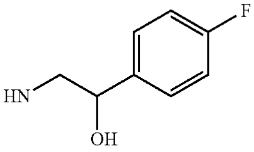 | 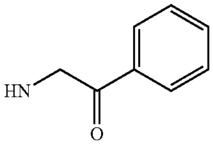 | 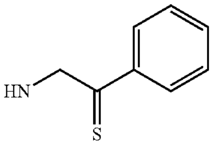 |
| 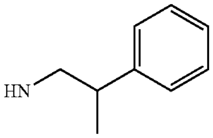 | 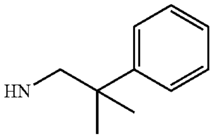 | 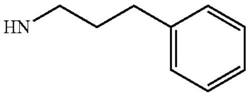 |
| 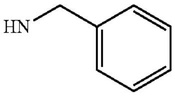 | 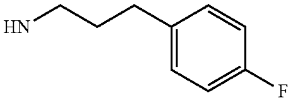 | 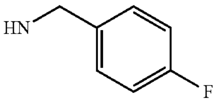 |
| 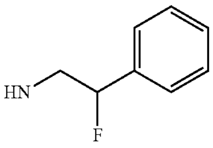 | 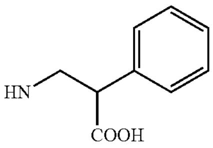 | 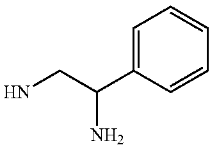 |
| 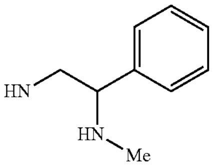 | 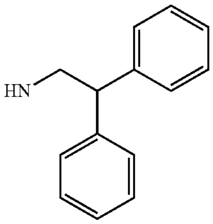 | 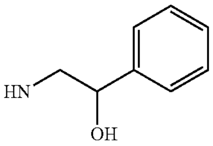 |
| 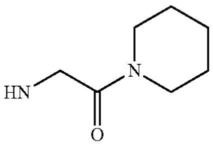 | 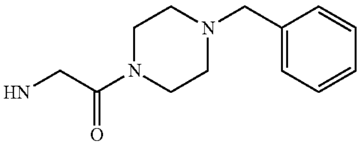 | 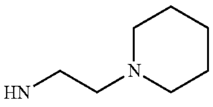 |
| 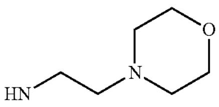 | 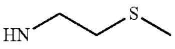 | 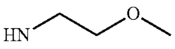 |
| 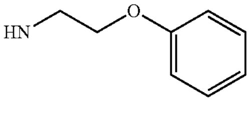 | 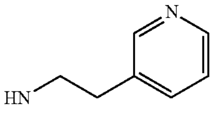 | 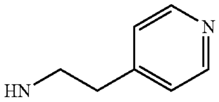 |

-continued
| HN—R | | |
|---|---|---|
| 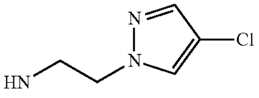 | 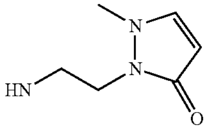 | |
| | 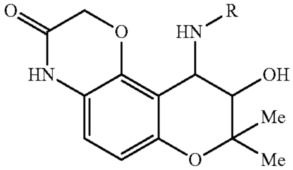 | |
| 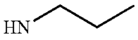 | 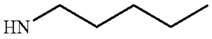 | 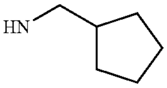 |
| 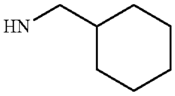 | 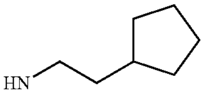 | 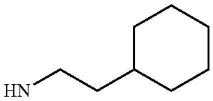 |
| 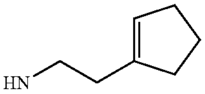 | 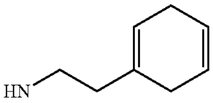 | 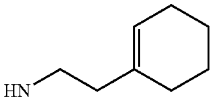 |
| 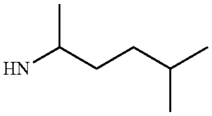 | 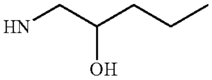 | 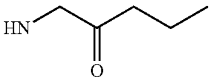 |
| 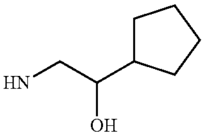 | 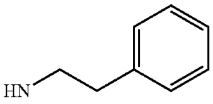 | 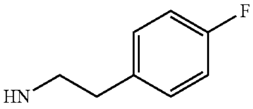 |
| 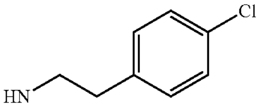 | 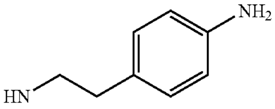 | 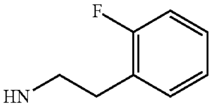 |
| 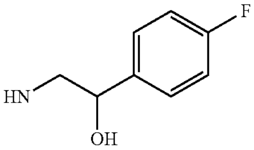 | 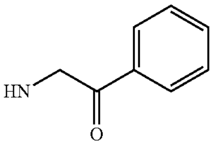 | 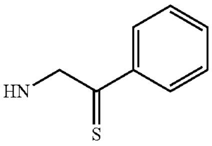 |
| 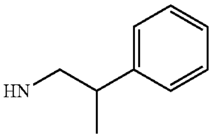 | 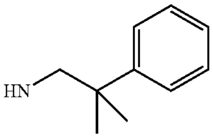 | 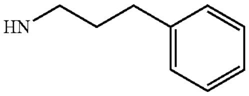 |
| 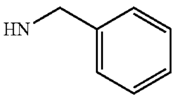 | 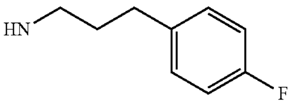 | 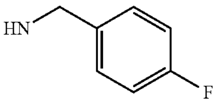 |

-continued
| HN—R | | |
|---|---|---|
| 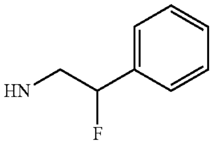 | 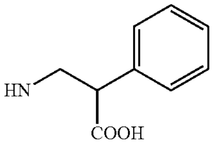 | 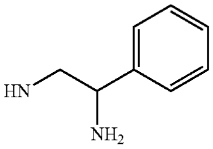 |
| 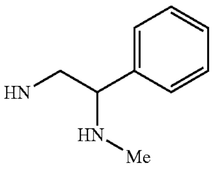 | 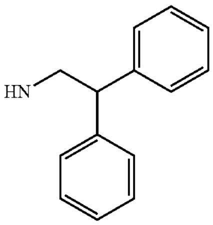 | 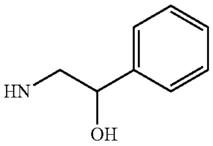 |
| 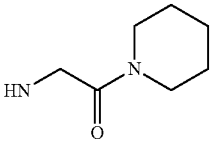 | 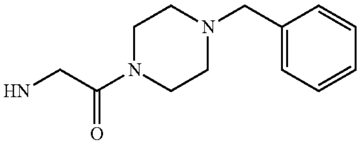 | 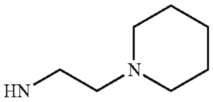 |
| 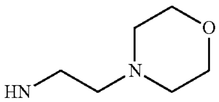 | 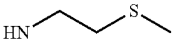 | 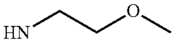 |
| 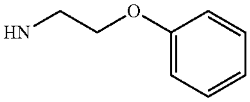 | 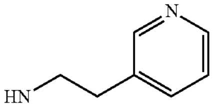 | 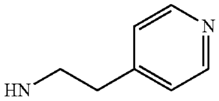 |
| 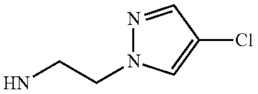 | 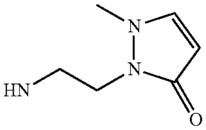 | |
| | 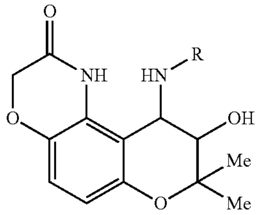 | |
|---|---|---|
| 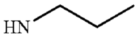 | 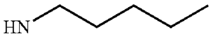 | 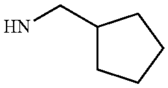 |
| 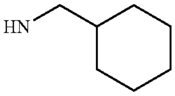 | 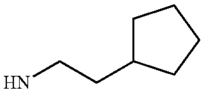 | 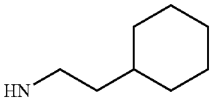 |
| 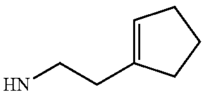 | 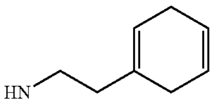 | 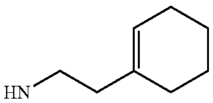 |

-continued
| HN—R | | |
|---|---|---|
| 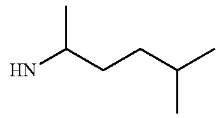 | 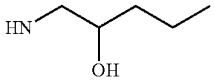 | 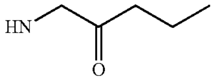 |
| 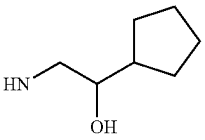 | 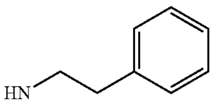 | 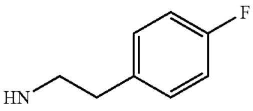 |
| 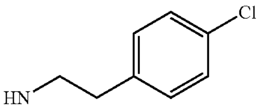 | 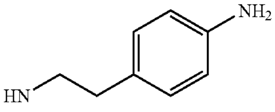 | 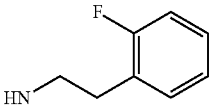 |
| 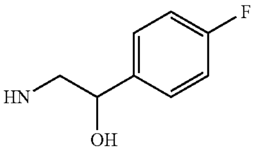 | 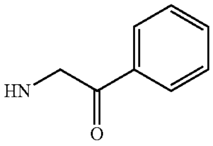 | 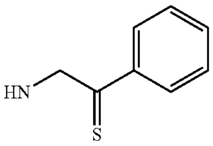 |
| 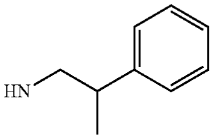 | 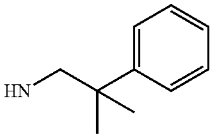 | 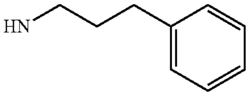 |
| 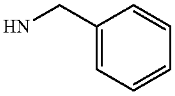 | 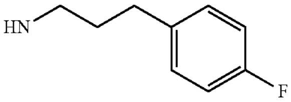 | 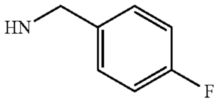 |
| 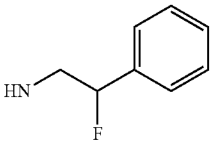 | 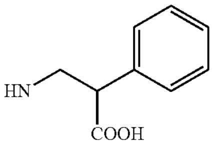 | 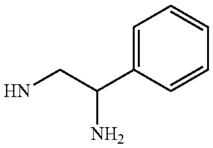 |
| 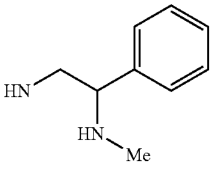 | 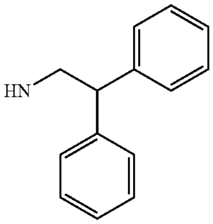 | 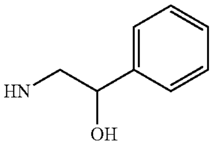 |
| 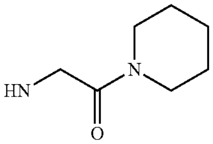 | 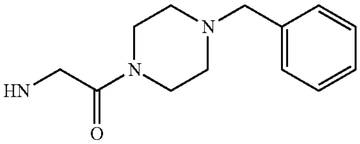 | 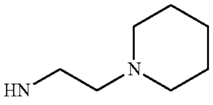 |
| 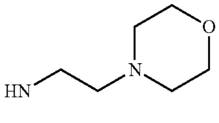 | 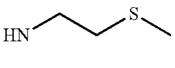 | 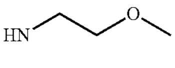 |

-continued
| HN—R | | |
|---|---|---|
| 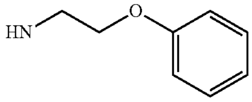 | 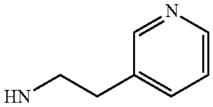 | 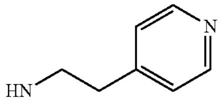 |
| 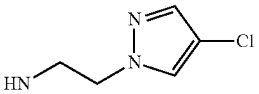 | 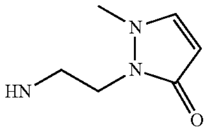 | |
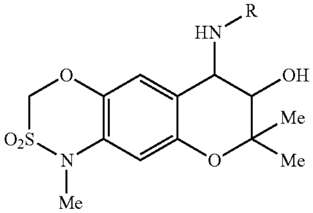
| | | |
|---|---|---|
| 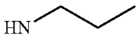 | 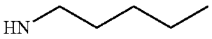 | 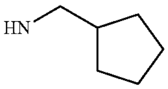 |
| 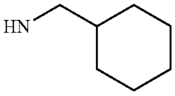 | 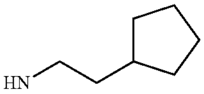 | 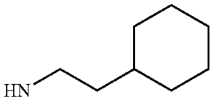 |
| 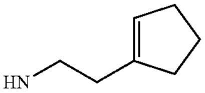 | 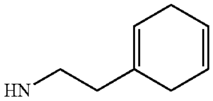 | 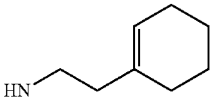 |
| 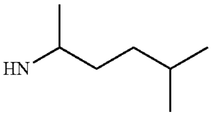 | 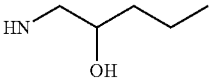 | 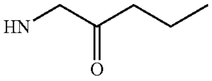 |
| 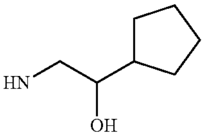 | 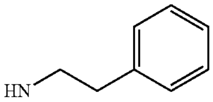 | 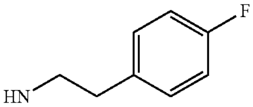 |
| 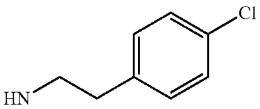 | 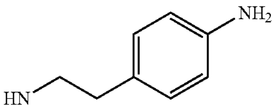 | 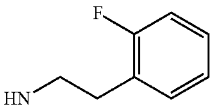 |
| 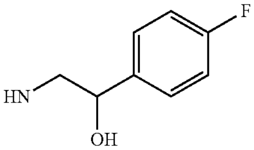 | 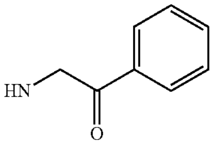 | 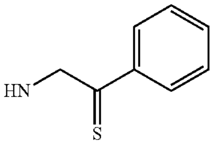 |
| 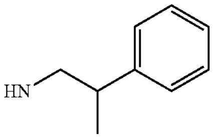 | 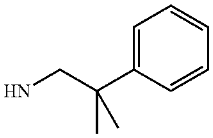 | 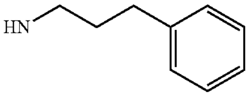 |

-continued
| HN—R | | |
|---|---|---|
| 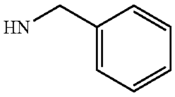 | 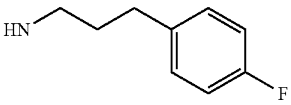 | 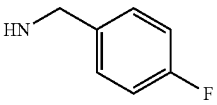 |
| 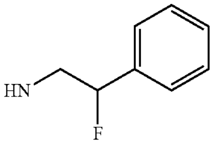 | 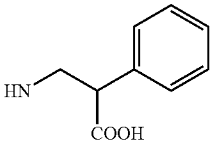 | 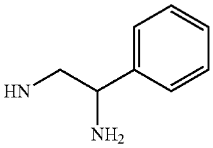 |
| 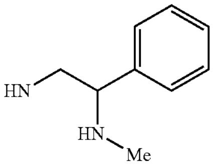 | 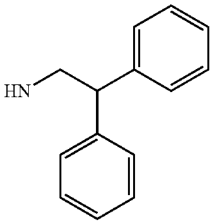 | 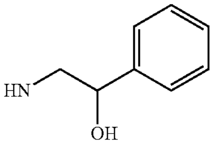 |
| 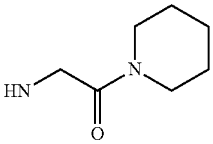 | 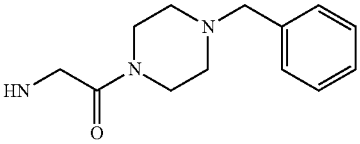 | 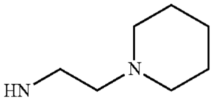 |
| 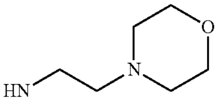 | 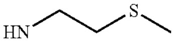 | 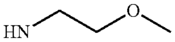 |
| 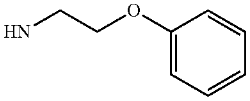 | 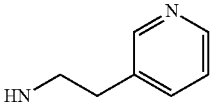 | 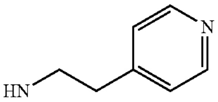 |
| 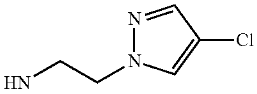 | 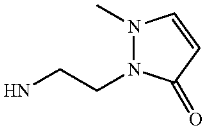 | |
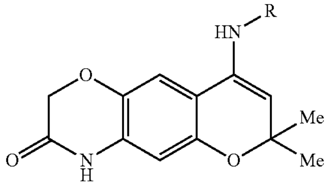
| | | |
|---|---|---|
| 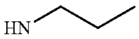 | 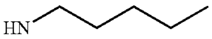 | 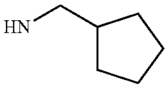 |
| 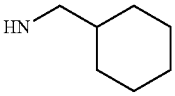 | 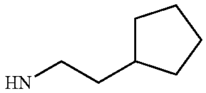 | 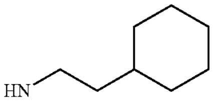 |
| 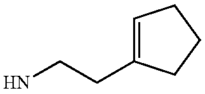 | 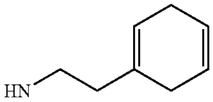 | 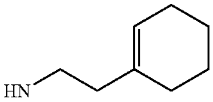 |

-continued
| HN—R | | |
|---|---|---|
| 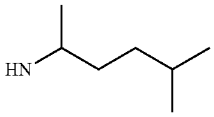 | 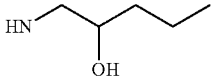 | 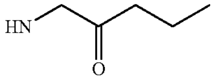 |
| 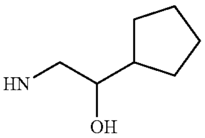 | 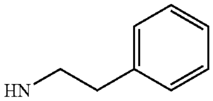 | 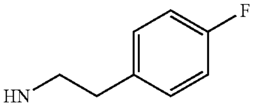 |
| 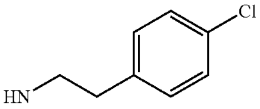 | 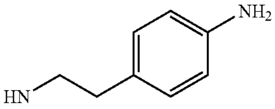 | 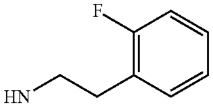 |
| 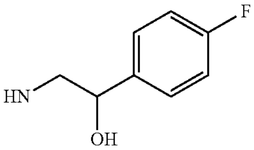 | 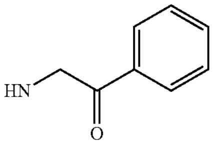 | 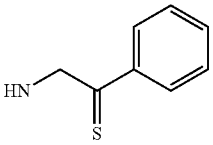 |
| 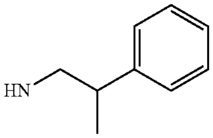 | 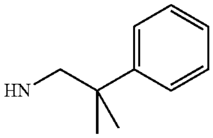 | 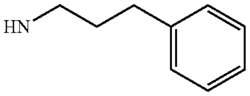 |
| 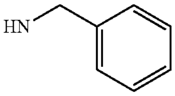 | 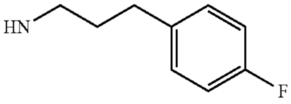 | 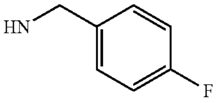 |
| 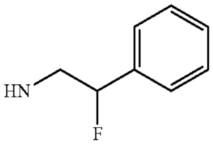 | 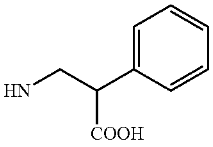 | 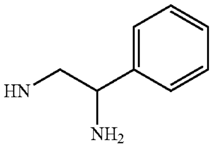 |
| 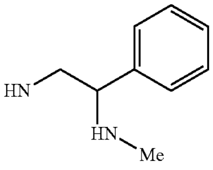 | 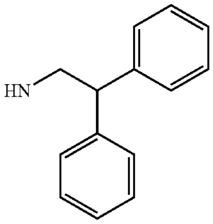 | 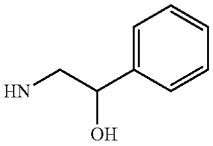 |
| 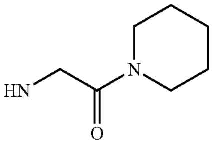 | 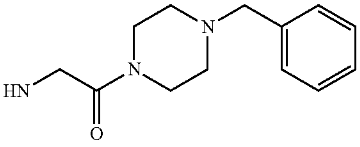 | 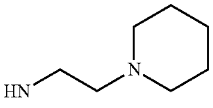 |
| 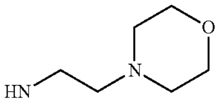 | 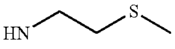 | 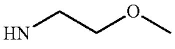 |

-continued

| HN—R | | |
|---|---|---|
| 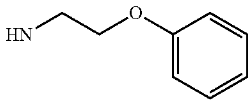 | 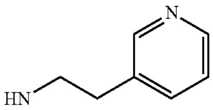 | 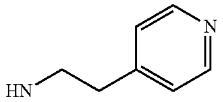 |
| 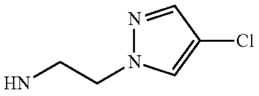 | 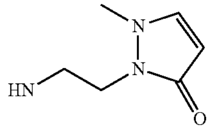 | |

| $R^{11}$ | $R^{13}$ | $R^{14}$ | $R^{11}$ | $R^{13}$ | $R^{14}$ | $R^{11}$ | $R^{13}$ | $R^{14}$ |
|---|---|---|---|---|---|---|---|---|
| 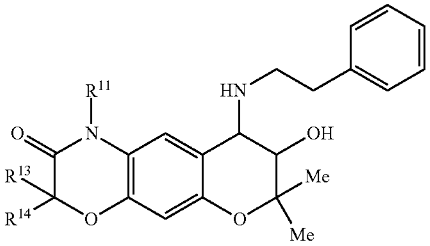 | | | | | | | | |
| H | H | Et | H | $NO_2$ | H | H | H | $NO_2$ |
| H | H | iPr | H | CHO | H | H | H | CHO |
| H | H | nPr | H | $SO_3H$ | H | H | H | $SO_3H$ |
| H | H | nBu | H | Cl | H | H | H | Cl |
| H | H | tBu | H | Br | H | H | H | Br |
| Me | H | Ph | Me | $CH_2OH$ | H | Me | H | $CH_2OH$ |
| Me | Et | Ph | Me | $CH_2NH_2$ | H | Me | H | $CH_2NH_2$ |
| Me | iPr | H | Me | $CH_2NHMe$ | H | Me | H | $CH_2NHMe$ |
| Me | nPr | H | Me | $CH_2Ph$ | H | Me | H | $CH_2Ph$ |
| Me | nBu | H | Me | COMe | H | Me | H | COMe |
| Me | tBu | H | Me | COOH | H | Me | H | COOH |
| Et | Ph | H | Et | $CONH_2$ | H | Et | H | $CONH_2$ |
| Et | H | Et | Et | CONHMe | Et | Et | Et | CONHMe |
| Et | H | iPr | Et | CONHMs | iPr | Et | iPr | CONHMs |
| iPr | H | nPr | iPr | NHMs | nPr | iPr | nPr | NHMs |
| nPr | H | nBu | nPr | NHCOMe | nBu | nPr | nBu | NHCOMe |
| nBu | H | tBu | nBu | $NO_2$ | tBu | nBu | tBu | $NO_2$ |
| tBu | H | Ph | tBu | CHO | Ph | tBu | Ph | H |
| Ph | Cl | Et | Ph | $SO_3H$ | Et | Ph | Et | H |
| $CH_2OH$ | Cl | nPr | $CH_2OH$ | $SO_2NHMe$ | nPr | $CH_2OH$ | nPr | H |
| $CH_2OH$ | Cl | Ph | $CH_2OH$ | OH | Ph | $CH_2OH$ | Ph | H |
| $CH_2OMe$ | Et | Cl | $CH_2OMe$ | COMe | Cl | $CH_2OMe$ | Cl | Cl |
| $CH_2OMe$ | nPr | Cl | $CH_2OMe$ | COON | Cl | $CH_2OMe$ | Cl | Cl |
| $CH_2NH_2$ | Ph | Cl | $CH_2NH_2$ | $CONH_2$ | Cl | $CH_2NH_2$ | Cl | Cl |
| $CH_2NH_2$ | H | Et | $CH_2NH_2$ | CONHMe | Et | $CH_2NH_2$ | Et | H |
| $CH_2NH_2$ | H | nPr | $CH_2NH_2$ | CONHMs | nPr | $CH_2NH_2$ | nPr | H |
| $CH_2NH_2$ | H | Ph | $CH_2NH_2$ | NHMs | Ph | $CH_2NH_2$ | Ph | H |
| $CH_2NHMe$ | Me | Me | $CH_2NHMe$ | $NO_2$ | Me | $CH_2NHMe$ | Me | H |
| $CH_2Ph$ | Et | Et | $CH_2Ph$ | OH | Et | $CH_2Ph$ | Et | H |
| $CH_2Ph$ | nPr | nPr | $CH_2Ph$ | COMe | nPr | $CH_2Ph$ | nPr | H |
| $CH_2CH_2Ph$ | Ph | Ph | $CH_2CH_2Ph$ | COOH | Ph | $CH_2CH_2Ph$ | Ph | H |
| 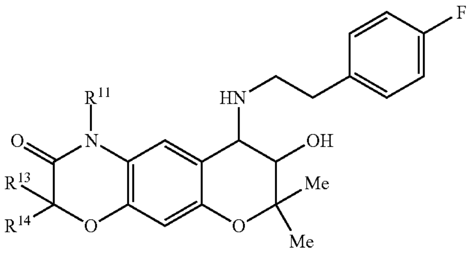 | | | | | | | | |
| H | H | Et | H | $NO_2$ | H | H | H | $NO_2$ |
| H | H | iPr | H | CHO | H | H | H | CHO |
| H | H | nPr | H | $SO_3H$ | H | H | H | $SO_3H$ |
| H | H | nBu | H | Cl | H | H | H | Cl |

-continued

| $R^{11}$ | $R^{13}$ | $R^{14}$ | $R^{11}$ | $R^{13}$ | $R^{14}$ | $R^{11}$ | $R^{13}$ | $R^{14}$ |
|---|---|---|---|---|---|---|---|---|
| H | H | tBu | H | Br | H | H | H | Br |
| Me | H | Ph | Me | $CH_2OH$ | H | Me | H | $CH_2OH$ |
| Me | Et | Ph | Me | $CH_2NH_2$ | H | Me | H | $CH_2NH_2$ |
| Me | iPr | H | Me | $CH_2NHMe$ | H | Me | H | $CH_2NHMe$ |
| Me | nPr | H | Me | $CH_2Ph$ | H | Me | H | $CH_2Ph$ |
| Me | nBu | H | Me | COMe | H | Me | H | COMe |
| Me | tBu | H | Me | COOH | H | Me | H | COOH |
| Et | Ph | H | Et | $CONH_2$ | H | Et | H | $CONH_2$ |
| Et | H | Et | Et | CONHMe | Et | Et | Et | CONHMe |
| Et | H | iPr | Et | CONHMs | iPr | Et | iPr | CONHMs |
| iPr | H | nPr | iPr | NHMs | nPr | iPr | nPr | NHMs |
| nPr | H | nBu | nPr | NHCOMe | nBu | nPr | nBu | NHCOMe |
| nBu | H | tBu | nBu | $NO_2$ | tBu | nBu | tBu | $NO_2$ |
| tBu | H | Ph | tBu | CHO | Ph | tBu | Ph | H |
| Ph | Cl | Et | Ph | $SO_3H$ | Et | Ph | Et | H |
| $CH_2OH$ | Cl | nPr | $CH_2OH$ | $SO_2NHMe$ | nPr | $CH_2OH$ | nPr | H |
| $CH_2OH$ | Cl | Ph | $CH_2OH$ | OH | Ph | $CH_2OH$ | Ph | H |
| $CH_2OMe$ | Et | Cl | $CH_2OMe$ | COMe | Cl | $CH_2OMe$ | Cl | Cl |
| $CH_2OMe$ | nPr | Cl | $CH_2OMe$ | COOH | Cl | $CH_2OMe$ | Cl | Cl |
| $CH_2NH_2$ | Ph | Cl | $CH_2NH_2$ | $CONH_2$ | Cl | $CH_2NH_2$ | Cl | Cl |
| $CH_2NH_2$ | H | Et | $CH_2NH_2$ | CONHMe | Et | $CH_2NH_2$ | Et | H |
| $CH_2NH_2$ | H | nPr | $CH_2NH_2$ | CONHMs | nPr | $CH_2NH_2$ | nPr | H |
| $CH_2NH_2$ | H | Ph | $CH_2NH_2$ | NHMs | Ph | $CH_2NH_2$ | Ph | H |
| $CH_2NHMe$ | Me | Me | $CH_2NHMe$ | $NO_2$ | Me | $CH_2NHMe$ | Me | H |
| $CH_2Ph$ | Et | Et | $CH_2Ph$ | OH | Et | $CH_2Ph$ | Et | H |
| $CH_2Ph$ | nPr | nPr | $CH_2Ph$ | COMe | nPr | $CH_2Ph$ | nPr | H |
| $CH_2CH_2Ph$ | Ph | Ph | $CH_2CH_2Ph$ | COOH | Ph | $CH_2CH_2Ph$ | Ph | H |

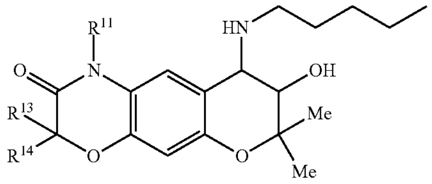

| | | | | | | | | |
|---|---|---|---|---|---|---|---|---|
| H | H | Et | H | $NO_2$ | H | H | H | $NO_2$ |
| H | H | iPr | H | CHO | H | H | H | CHO |
| H | H | nPr | H | $SO_3H$ | H | H | H | $SO_3H$ |
| H | H | nBu | H | Cl | H | H | H | Cl |
| H | H | tBu | H | Br | H | H | H | Br |
| Me | H | Ph | Me | $CH_2OH$ | H | Me | H | $CH_2OH$ |
| Me | Et | Ph | Me | $CH_2NH_2$ | H | Me | H | $CH_2NH_2$ |
| Me | iPr | H | Me | $CH_2NHMe$ | H | Me | H | $CH_2NHMe$ |
| Me | nPr | H | Me | $CH_2Ph$ | H | Me | H | $CH_2Ph$ |
| Me | nBu | H | Me | COMe | H | Me | H | COMe |
| Me | tBu | H | Me | COOH | H | Me | H | COOH |
| Et | Ph | H | Et | $CONH_2$ | H | Et | H | $CONH_2$ |
| Et | H | Et | Et | CONHMe | Et | Et | Et | CONHMe |
| Et | H | iPr | Et | CONHMs | iPr | Et | iPr | CONHMs |
| iPr | H | nPr | iPr | NHMs | nPr | iPr | nPr | NHMs |
| nPr | H | nBu | nPr | NHCOMe | nBu | nPr | nBu | NHCOMe |
| nBu | H | tBu | nBu | $NO_2$ | tBu | nBu | tBu | $NO_2$ |
| tBu | H | Ph | tBu | CHO | Ph | tBu | Ph | H |
| Ph | Cl | Et | Ph | $SO_3H$ | Et | Ph | Et | H |
| $CH_2OH$ | Cl | nPr | $CH_2OH$ | $SO_2NHMe$ | nPr | $CH_2OH$ | nPr | H |
| $CH_2OH$ | Cl | Ph | $CH_2OH$ | OH | Ph | $CH_2OH$ | Ph | H |
| $CH_2OMe$ | Et | Cl | $CH_2OMe$ | COMe | Cl | $CH_2OMe$ | Cl | Cl |
| $CH_2OMe$ | nPr | Cl | $CH_2OMe$ | COOH | Cl | $CH_2OMe$ | Cl | Cl |
| $CH_2NH_2$ | Ph | Cl | $CH_2NH_2$ | $CONH_2$ | Cl | $CH_2NH_2$ | Cl | Cl |
| $CH_2NH_2$ | H | Et | $CH_2NH_2$ | CONHMe | Et | $CH_2NH_2$ | Et | H |
| $CH_2NH_2$ | H | nPr | $CH_2NH_2$ | CONHMs | nPr | $CH_2NH_2$ | nPr | H |
| $CH_2NH_2$ | H | Ph | $CH_2NH_2$ | NHMs | Ph | $CH_2NH_2$ | Ph | H |
| $CH_2NHMe$ | Me | Me | $CH_2NHMe$ | $NO_2$ | Me | $CH_2NHMe$ | Me | H |
| $CH_2Ph$ | Et | Et | $CH_2Ph$ | OH | Et | $CH_2Ph$ | Et | H |
| $CH_2Ph$ | nPr | nPr | $CH_2Ph$ | COMe | nPr | $CH_2Ph$ | nPr | H |
| $CH_2CH_2Ph$ | Ph | Ph | $CH_2CH_2Ph$ | COOH | Ph | $CH_2CH_2Ph$ | Ph | H |

-continued

| $R^{11}$ | $R^{13}$ | $R^{14}$ | $R^{11}$ | $R^{13}$ | $R^{14}$ | $R^{11}$ | $R^{13}$ | $R^{14}$ |
|---|---|---|---|---|---|---|---|---|
| 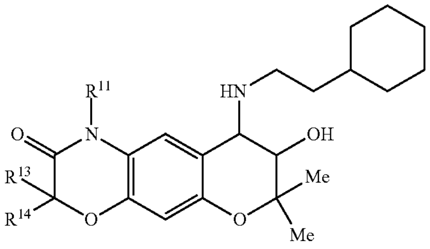 | | | | | | | | |
| H | H | Et | H | $NO_2$ | H | H | H | $NO_2$ |
| H | H | iPr | H | CHO | H | H | H | CHO |
| H | H | nPr | H | $SO_3H$ | H | H | H | $SO_3H$ |
| H | H | nBu | H | Cl | H | H | H | Cl |
| H | H | tBu | H | Br | H | H | H | Br |
| Me | H | Ph | Me | $CH_2OH$ | H | Me | H | $CH_2OH$ |
| Me | Et | Ph | Me | $CH_2NH_2$ | H | Me | H | $CH_2NH_2$ |
| Me | iPr | H | Me | $CH_2NHMe$ | H | Me | H | $CH_2NHMe$ |
| Me | nPr | H | Me | $CH_2Ph$ | H | Me | H | $CH_2Ph$ |
| Me | nBu | H | Me | COMe | H | Me | H | COMe |
| Me | tBu | H | Me | COOH | H | Me | H | COOH |
| Et | Ph | H | Et | $CONH_2$ | H | Et | H | $CONH_2$ |
| Et | H | Et | Et | CONHMe | Et | Et | Et | CONHMe |
| Et | H | iPr | Et | CONHMs | iPr | Et | iPr | CONHMs |
| iPr | H | nPr | iPr | NHMs | nPr | iPr | nPr | NHMs |
| nPr | H | nBu | nPr | NHCOMe | nBu | nPr | nBu | NHCOMe |
| nBu | H | tBu | nBu | $NO_2$ | tBu | nBu | tBu | $NO_2$ |
| tBu | H | Ph | tBu | CHO | Ph | tBu | Ph | H |
| Ph | Cl | Et | Ph | $SO_3H$ | Et | Ph | Et | H |
| $CH_2OH$ | Cl | nPr | $CH_2OH$ | $SO_2NHMe$ | nPr | $CH_2OH$ | nPr | H |
| $CH_2OH$ | Cl | Ph | $CH_2OH$ | OH | Ph | $CH_2OH$ | Ph | H |
| $CH_2OMe$ | Et | Cl | $CH_2OMe$ | COMe | Cl | $CH_2OMe$ | Cl | Cl |
| $CH_2OMe$ | nPr | Cl | $CH_2OMe$ | COOH | Cl | $CH_2OMe$ | Cl | Cl |
| $CH_2NH_2$ | Ph | Cl | $CH_2NH_2$ | $CONH_2$ | Cl | $CH_2NH_2$ | Cl | Cl |
| $CH_2NH_2$ | H | Et | $CH_2NH_2$ | CONHMe | Et | $CH_2NH_2$ | Et | H |
| $CH_2NH_2$ | H | nPr | $CH_2NH_2$ | CONHMs | nPr | $CH_2NH_2$ | nPr | H |
| $CH_2NH_2$ | H | Ph | $CH_2NH_2$ | NHMs | Ph | $CH_2NH_2$ | Ph | H |
| $CH_2NHMe$ | Me | Me | $CH_2NHMe$ | $NO_2$ | Me | $CH_2NHMe$ | Me | H |
| $CH_2Ph$ | Et | Et | $CH_2Ph$ | OH | Et | $CH_2Ph$ | Et | H |
| $CH_2Ph$ | nPr | nPr | $CH_2Ph$ | COMe | nPr | $CH_2Ph$ | nPr | H |
| $CH_2CH_2Ph$ | Ph | Ph | $CH_2CH_2Ph$ | COOH | Ph | $CH_2CH_2Ph$ | Ph | H |
| 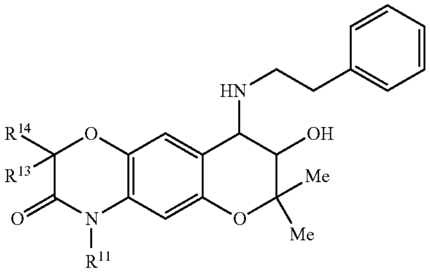 | | | | | | | | |
| H | H | Et | H | $NO_2$ | H | H | H | $NO_2$ |
| H | H | iPr | H | CHO | H | H | H | CHO |
| H | H | nPr | H | $SO_3H$ | H | H | H | $SO_3H$ |
| H | H | nBu | H | Cl | H | H | H | Cl |
| H | H | tBu | H | Br | H | H | H | Br |
| Me | H | Ph | Me | $CH_2OH$ | H | Me | H | $CH_2OH$ |
| Me | Et | Ph | Me | $CH_2NH_2$ | H | Me | H | $CH_2NH_2$ |
| Me | iPr | H | Me | $CH_2NHMe$ | H | Me | H | $CH_2NHMe$ |
| Me | nPr | H | Me | $CH_2Ph$ | H | Me | H | $CH_2Ph$ |
| Me | nBu | H | Me | COMe | H | Me | H | COMe |
| Me | tBu | H | Me | COOH | H | Me | H | COOH |
| Et | Ph | H | Et | $CONH_2$ | H | Et | H | $CONH_2$ |
| Et | H | Et | Et | CONHMe | Et | Et | Et | CONHMe |
| Et | H | iPr | Et | CONHMs | iPr | Et | iPr | CONHMs |
| iPr | H | nPr | iPr | NHMs | nPr | iPr | nPr | NHMs |
| nPr | H | nBu | nPr | NHCOMe | nBu | nPr | nBu | NHCOMe |
| nBu | H | tBu | nBu | $NO_2$ | tBu | nBu | tBu | $NO_2$ |
| tBu | H | Ph | tBu | CHO | Ph | tBu | Ph | H |
| Ph | Cl | Et | Ph | $SO_3H$ | Et | Ph | Et | H |
| $CH_2OH$ | Cl | nPr | $CH_2OH$ | $SO_2NHMe$ | nPr | $CH_2OH$ | nPr | H |

-continued

| $R^{11}$ | $R^{13}$ | $R^{14}$ | $R^{11}$ | $R^{13}$ | $R^{14}$ | $R^{11}$ | $R^{13}$ | $R^{14}$ |
|---|---|---|---|---|---|---|---|---|
| $CH_2OH$ | Cl | Ph | $CH_2OH$ | OH | Ph | $CH_2OH$ | Ph | H |
| $CH_2OMe$ | Et | Cl | $CH_2OMe$ | COMe | Cl | $CH_2OMe$ | Cl | Cl |
| $CH_2OMe$ | nPr | Cl | $CH_2OMe$ | COOH | Cl | $CH_2OMe$ | Cl | Cl |
| $CH_2NH_2$ | Ph | Cl | $CH_2NH_2$ | $CONH_2$ | Cl | $CH_2NH_2$ | Cl | Cl |
| $CH_2NH_2$ | H | Et | $CH_2NH_2$ | CONHMe | Et | $CH_2NH_2$ | Et | H |
| $CH_2NH_2$ | H | nPr | $CH_2NH_2$ | CONHMs | nPr | $CH_2NH_2$ | nPr | H |
| $CH_2NH_2$ | H | Ph | $CH_2NH_2$ | NHMs | Ph | $CH_2NH_2$ | Ph | H |
| $CH_2NHMe$ | Me | Me | $CH_2NHMe$ | $NO_2$ | Me | $CH_2NHMe$ | Me | H |
| $CH_2Ph$ | Et | Et | $CH_2Ph$ | OH | Et | $CH_2Ph$ | Et | H |
| $CH_2Ph$ | nPr | nPr | $CH_2Ph$ | COMe | nPr | $CH_2Ph$ | nPr | H |
| $CH_2CH_2Ph$ | Ph | Ph | $CH_2CH_2Ph$ | COOH | Ph | $CH_2CH_2Ph$ | Ph | H |

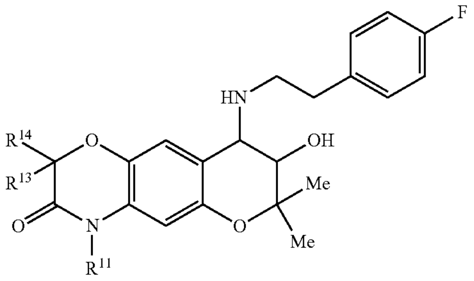

| | | | | | | | | |
|---|---|---|---|---|---|---|---|---|
| H | H | Et | H | $NO_2$ | H | H | H | $NO_2$ |
| H | H | iPr | H | CHO | H | H | H | CHO |
| H | H | nPr | H | $SO_3H$ | H | H | H | $SO_3H$ |
| H | H | nBu | H | Cl | H | H | H | Cl |
| H | H | tBu | H | Br | H | H | H | Br |
| Me | H | Ph | Me | $CH_2OH$ | H | Me | H | $CH_2OH$ |
| Me | Et | Ph | Me | $CH_2NH_2$ | H | Me | H | $CH_2NH_2$ |
| Me | iPr | H | Me | $CH_2NHMe$ | H | Me | H | $CH_2NHMe$ |
| Me | nPr | H | Me | $CH_2Ph$ | H | Me | H | $CH_2Ph$ |
| Me | nBu | H | Me | COMe | H | Me | H | COMe |
| Me | tBu | H | Me | COOH | H | Me | H | COOH |
| Et | Ph | H | Et | $CONH_2$ | H | Et | H | $CONH_2$ |
| Et | H | Et | Et | CONHMe | Et | Et | Et | CONHMe |
| Et | H | iPr | Et | CONHMs | iPr | Et | iPr | CONHMs |
| iPr | H | nPr | iPr | NHMs | nPr | iPr | nPr | NHMs |
| nPr | H | nBu | nPr | NHCOMe | nBu | nPr | nBu | NHCOMe |
| nBu | H | tBu | nBu | $NO_2$ | tBu | nBu | tBu | $NO_2$ |
| tBu | H | Ph | tBu | CHO | Ph | tBu | Ph | H |
| Ph | Cl | Et | Ph | $SO_3H$ | Et | Ph | Et | H |
| $CH_2OH$ | Cl | nPr | $CH_2OH$ | $SO_2NHMe$ | nPr | $CH_2OH$ | nPr | H |
| $CH_2OH$ | Cl | Ph | $CH_2OH$ | OH | Ph | $CH_2OH$ | Ph | H |
| $CH_2OMe$ | Et | Cl | $CH_2OMe$ | COMe | Cl | $CH_2OMe$ | Cl | Cl |
| $CH_2OMe$ | nPr | Cl | $CH_2OMe$ | COOH | Cl | $CH_2OMe$ | Cl | Cl |
| $CH_2NH_2$ | Ph | Cl | $CH_2NH_2$ | $CONH_2$ | Cl | $CH_2NH_2$ | Cl | Cl |
| $CH_2NH_2$ | H | Et | $CH_2NH_2$ | CONHMe | Et | $CH_2NH_2$ | Et | H |
| $CH_2NH_2$ | H | nPr | $CH_2NH_2$ | CONHMs | nPr | $CH_2NH_2$ | nPr | H |
| $CH_2NH_2$ | H | Ph | $CH_2NH_2$ | NHMs | Ph | $CH_2NH_2$ | Ph | H |
| $CH_2NHMe$ | Me | Me | $CH_2NHMe$ | $NO_2$ | Me | $CH_2NHMe$ | Me | H |
| $CH_2Ph$ | Et | Et | $CH_2Ph$ | OH | Et | $CH_2Ph$ | Et | H |
| $CH_2Ph$ | nPr | nPr | $CH_2Ph$ | COMe | nPr | $CH_2Ph$ | nPr | H |
| $CH_2CH_2Ph$ | Ph | Ph | $CH_2CH_2Ph$ | COOH | Ph | $CH_2CH_2Ph$ | Ph | H |

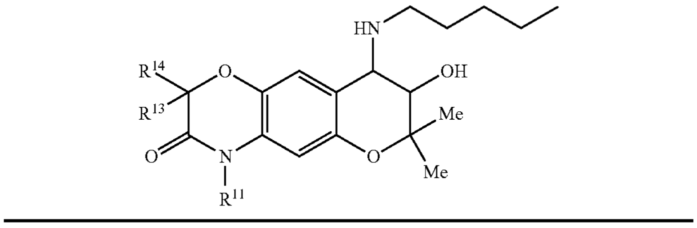

| | | | | | | | | |
|---|---|---|---|---|---|---|---|---|
| H | H | Et | H | $NO_2$ | H | H | H | $NO_2$ |
| H | H | iPr | H | CHO | H | H | H | CHO |
| H | H | nPr | H | $SO_3H$ | H | H | H | $SO_3H$ |
| H | H | nBu | H | Cl | H | H | H | Cl |
| H | H | tBu | H | Br | H | H | H | Br |
| Me | H | Ph | Me | $CH_2OH$ | H | Me | H | $CH_2OH$ |
| Me | Et | Ph | Me | $CH_2NH_2$ | H | Me | H | $CH_2NH_2$ |
| Me | iPr | H | Me | $CH_2NHMe$ | H | Me | H | $CH_2NHMe$ |
| Me | nPr | H | Me | $CH_2Ph$ | H | Me | H | $CH_2Ph$ |

-continued

| $R^{11}$ | $R^{13}$ | $R^{14}$ | $R^{11}$ | $R^{13}$ | $R^{14}$ | $R^{11}$ | $R^{13}$ | $R^{14}$ |
|---|---|---|---|---|---|---|---|---|
| Me | nBu | H | Me | COMe | H | Me | H | COMe |
| Me | tBu | H | Me | COOH | H | Me | H | COOH |
| Et | Ph | H | Et | $CONH_2$ | H | Et | H | $CONH_2$ |
| Et | H | Et | Et | CONHMe | Et | Et | Et | CONHMe |
| Et | H | iPr | Et | CONHMs | iPr | Et | iPr | CONHMs |
| iPr | H | nPr | iPr | NHMs | nPr | iPr | nPr | NHMs |
| nPr | H | nBu | nPr | NHCOMe | nBu | nPr | nBu | NHCOMe |
| nBu | H | tBu | nBu | $NO_2$ | tBu | nBu | tBu | $NO_2$ |
| tBu | H | Ph | tBu | CHO | Ph | tBu | Ph | H |
| Ph | Cl | Et | Ph | $SO_3H$ | Et | Ph | Et | H |
| $CH_2OH$ | Cl | nPr | $CH_2OH$ | $SO_2NHMe$ | nPr | $CH_2OH$ | nPr | H |
| $CH_2OH$ | Cl | Ph | $CH_2OH$ | OH | Ph | $CH_2OH$ | Ph | H |
| $CH_2OMe$ | Et | Cl | $CH_2OMe$ | COMe | Cl | $CH_2OMe$ | Cl | Cl |
| $CH_2OMe$ | nPr | Cl | $CH_2OMe$ | COOH | Cl | $CH_2OMe$ | Cl | Cl |
| $CH_2NH_2$ | Ph | Cl | $CH_2NH_2$ | $CONH_2$ | Cl | $CH_2NH_2$ | Cl | Cl |
| $CH_2NH_2$ | H | Et | $CH_2NH_2$ | CONHMe | Et | $CH_2NH_2$ | Et | H |
| $CH_2NH_2$ | H | nPr | $CH_2NH_2$ | CONHMs | nPr | $CH_2NH_2$ | nPr | H |
| $CH_2NH_2$ | H | Ph | $CH_2NH_2$ | NHMs | Ph | $CH_2NH_2$ | Ph | H |
| $CH_2NHMe$ | Me | Me | $CH_2NHMe$ | $NO_2$ | Me | $CH_2NHMe$ | Me | H |
| $CH_2Ph$ | Et | Et | $CH_2Ph$ | OH | Et | $CH_2Ph$ | Et | H |
| $CH_2Ph$ | nPr | nPr | $CH_2Ph$ | COMe | nPr | $CH_2Ph$ | nPr | H |
| $CH_2CH_2Ph$ | Ph | Ph | $CH_2CH_2Ph$ | COOH | Ph | $CH_2CH_2Ph$ | Ph | H |

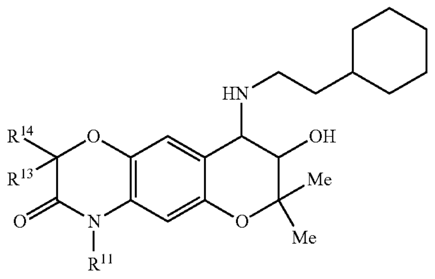

| | | | | | | | | |
|---|---|---|---|---|---|---|---|---|
| H | H | Et | H | $NO_2$ | H | H | H | $NO_2$ |
| H | H | iPr | H | CHO | H | H | H | CHO |
| H | H | nPr | H | $SO_3H$ | H | H | H | $SO_3H$ |
| H | H | nBu | H | Cl | H | H | H | Cl |
| H | H | tBu | H | Br | H | H | H | Br |
| Me | H | Ph | Me | $CH_2OH$ | H | Me | H | $CH_2OH$ |
| Me | Et | Ph | Me | $CH_2NH_2$ | H | Me | H | $CH_2NH_2$ |
| Me | iPr | H | Me | $CH_2NHMe$ | H | Me | H | $CH_2NHMe$ |
| Me | nPr | H | Me | $CH_2Ph$ | H | Me | H | $CH_2Ph$ |
| Me | nBu | H | Me | COMe | H | Me | H | COMe |
| Me | tBu | H | Me | COOH | H | Me | H | COOH |
| Et | Ph | H | Et | $CONH_2$ | H | Et | H | $CONH_2$ |
| Et | H | Et | Et | CONHMe | Et | Et | Et | CONHMe |
| Et | H | iPr | Et | CONHMs | iPr | Et | iPr | CONHMs |
| iPr | H | nPr | iPr | NHMs | nPr | iPr | nPr | NHMs |
| nPr | H | nBu | nPr | NHCOMe | nBu | nPr | nBu | NHCOMe |
| nBu | H | tBu | nBu | $NO_2$ | tBu | nBu | tBu | $NO_2$ |
| tBu | H | Ph | tBu | CHO | Ph | tBu | Ph | H |
| Ph | Cl | Et | Ph | $SO_3H$ | Et | Ph | Et | H |
| $CH_2OH$ | Cl | nPr | $CH_2OH$ | $SO_2NHMe$ | nPr | $CH_2OH$ | nPr | H |
| $CH_2OH$ | Cl | Ph | $CH_2OH$ | OH | Ph | $CH_2OH$ | Ph | H |
| $CH_2OMe$ | Et | Cl | $CH_2OMe$ | COMe | Cl | $CH_2OMe$ | Cl | Cl |
| $CH_2OMe$ | nPr | Cl | $CH_2OMe$ | COOH | Cl | $CH_2OMe$ | Cl | Cl |
| $CH_2NH_2$ | Ph | Cl | $CH_2NH_2$ | $CONH_2$ | Cl | $CH_2NH_2$ | Cl | Cl |
| $CH_2NH_2$ | H | Et | $CH_2NH_2$ | CONHMe | Et | $CH_2NH_2$ | Et | H |
| $CH_2NH_2$ | H | nPr | $CH_2NH_2$ | CONHMs | nPr | $CH_2NH_2$ | nPr | H |
| $CH_2NH_2$ | H | Ph | $CH_2NH_2$ | NHMs | Ph | $CH_2NH_2$ | Ph | H |
| $CH_2NHMe$ | Me | Me | $CH_2NHMe$ | $NO_2$ | Me | $CH_2NHMe$ | Me | H |
| $CH_2Ph$ | Et | Et | $CH_2Ph$ | OH | Et | $CH_2Ph$ | Et | H |
| $CH_2Ph$ | nPr | nPr | $CH_2Ph$ | COMe | nPr | $CH_2Ph$ | nPr | H |
| $CH_2CH_2Ph$ | Ph | Ph | $CH_2CH_2Ph$ | COOH | Ph | $CH_2CH_2Ph$ | Ph | H |

-continued

| $R^{11}$ | $R^{13}$ | $R^{14}$ | $R^{11}$ | $R^{13}$ | $R^{14}$ | $R^{11}$ | $R^{13}$ | $R^{14}$ |
|---|---|---|---|---|---|---|---|---|
| 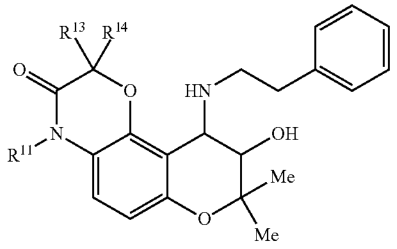 | | | | | | | | |
| H | H | Et | H | $NO_2$ | H | H | H | $NO_2$ |
| H | H | iPr | H | CHO | H | H | H | CHO |
| H | H | nPr | H | $SO_3H$ | H | H | H | $SO_3H$ |
| H | H | nBu | H | Cl | H | H | H | Cl |
| H | H | tBu | H | Br | H | H | H | Br |
| Me | H | Ph | Me | $CH_2OH$ | H | Me | H | $CH_2OH$ |
| Me | Et | Ph | Me | $CH_2NH_2$ | H | Me | H | $CH_2NH_2$ |
| Me | iPr | H | Me | $CH_2NHMe$ | H | Me | H | $CH_2NHMe$ |
| Me | nPr | H | Me | $CH_2Ph$ | H | Me | H | $CH_2Ph$ |
| Me | nBu | H | Me | COMe | H | Me | H | COMe |
| Me | tBu | H | Me | COOH | H | Me | H | COOH |
| Et | Ph | H | Et | $CONH_2$ | H | Et | H | $CONH_2$ |
| Et | H | Et | Et | CONHMe | Et | Et | Et | CONHMe |
| Et | H | iPr | Et | CONHMs | iPr | Et | iPr | CONHMs |
| iPr | H | nPr | iPr | NHMs | nPr | iPr | nPr | NHMs |
| nPr | H | nBu | nPr | NHCOMe | nBu | nPr | nBu | NHCOMe |
| nBu | H | tBu | nBu | $NO_2$ | tBu | nBu | tBu | $NO_2$ |
| tBu | H | Ph | tBu | CHO | Ph | tBu | Ph | H |
| Ph | Cl | Et | Ph | $SO_3H$ | Et | Ph | Et | H |
| $CH_2OH$ | Cl | nPr | $CH_2OH$ | $SO_2NHMe$ | Pr | $CH_2OH$ | nPr | H |
| $CH_2OH$ | Cl | Ph | $CH_2OH$ | OH | Ph | $CH_2OH$ | Ph | H |
| $CH_2OMe$ | Et | Cl | $CH_2OMe$ | COMe | Cl | $CH_2OMe$ | Cl | Cl |
| $CH_2OMe$ | nPr | Cl | $CH_2OMe$ | COOH | Cl | $CH_2OMe$ | Cl | Cl |
| $CH_2NH_2$ | Ph | Cl | $CH_2NH_2$ | $CONH_2$ | Cl | $CH_2NH_2$ | Cl | Cl |
| $CH_2NH_2$ | H | Et | $CH_2NH_2$ | CONHMe | Et | $CH_2NH_2$ | Et | H |
| $CH_2NH_2$ | H | nPr | $CH_2NH_2$ | CONHMs | nPr | $CH_2NH_2$ | nPr | H |
| $CH_2NH_2$ | H | Ph | $CH_2NH_2$ | NHMs | Ph | $CH_2NH_2$ | Ph | H |
| $CH_2NHMe$ | Me | Me | $CH_2NHMe$ | $NO_2$ | Me | $CH_2NHMe$ | Me | H |
| $CH_2Ph$ | Et | Et | $CH_2Ph$ | OH | Et | $CH_2Ph$ | Et | H |
| $CH_2Ph$ | nPr | nPr | $CH_2Ph$ | COMe | nPr | $CH_2Ph$ | nPr | H |
| $CH_2CH_2Ph$ | Ph | Ph | $CH_2CH_2Ph$ | COOH | Ph | $CH_2CH_2Ph$ | Ph | H |
| 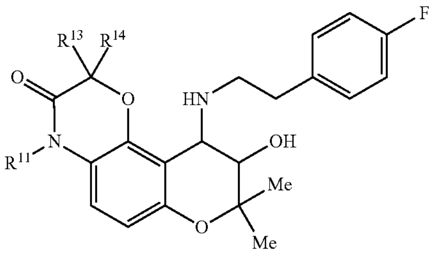 | | | | | | | | |
| H | H | Et | H | $NO_2$ | H | H | H | $NO_2$ |
| H | H | iPr | H | CHO | H | H | H | CHO |
| H | H | nPr | H | $SO_3H$ | H | H | H | $SO_3H$ |
| H | H | nBu | H | Cl | H | H | H | Cl |
| H | H | tBu | H | Br | H | H | H | Br |
| Me | H | Ph | Me | $CH_2OH$ | H | Me | H | $CH_2OH$ |
| Me | Et | Ph | Me | $CH_2NH_2$ | H | Me | H | $CH_2NH_2$ |
| Me | iPr | H | Me | $CH_2NHMe$ | H | Me | H | $CH_2NHMe$ |
| Me | nPr | H | Me | $CH_2Ph$ | H | Me | H | $CH_2Ph$ |
| Me | nBu | H | Me | COMe | H | Me | H | COMe |
| Me | tBu | H | Me | COOH | H | Me | H | COOH |
| Et | Ph | H | Et | $CONH_2$ | H | Et | H | $CONH_2$ |
| Et | H | Et | Et | CONHMe | Et | Et | Et | CONHMe |
| Et | H | iPr | Et | CONHMs | iPr | Et | iPr | CONHMs |
| iPr | H | nPr | iPr | NHMs | nPr | iPr | nPr | NHMs |
| nPr | H | nBu | nPr | NHCOMe | nBu | nPr | nBu | NHCOMe |
| nBu | H | tBu | nBu | $NO_2$ | tBu | nBu | tBu | $NO_2$ |
| tBu | H | Ph | tBu | CHO | Ph | tBu | Ph | H |
| Ph | Cl | Et | Ph | $SO_3H$ | Et | Ph | Et | H |
| $CH_2OH$ | Cl | nPr | $CH_2OH$ | $SO_2NHMe$ | nPr | $CH_2OH$ | nPr | H |

-continued

| $R^{11}$ | $R^{13}$ | $R^{14}$ | $R^{11}$ | $R^{13}$ | $R^{14}$ | $R^{11}$ | $R^{13}$ | $R^{14}$ |
|---|---|---|---|---|---|---|---|---|
| $CH_2OH$ | Cl | Ph | $CH_2OH$ | OH | Ph | $CH_2OH$ | Ph | H |
| $CH_2OMe$ | Et | Cl | $CH_2OMe$ | COMe | Cl | $CH_2OMe$ | Cl | Cl |
| $CH_2OMe$ | nPr | Cl | $CH_2OMe$ | COOH | Cl | $CH_2OMe$ | Cl | Cl |
| $CH_2NH_2$ | Ph | Cl | $CH_2NH_2$ | $CONH_2$ | Cl | $CH_2NH_2$ | Cl | Cl |
| $CH_2NH_2$ | H | Et | $CH_2NH_2$ | CONHMe | Et | $CH_2NH_2$ | Et | H |
| $CH_2NH_2$ | H | nPr | $CH_2NH_2$ | CONHMs | nPr | $CH_2NH_2$ | nPr | H |
| $CH_2NH_2$ | H | Ph | $CH_2NH_2$ | NHMs | Ph | $CH_2NH_2$ | Ph | H |
| $CH_2NHMe$ | Me | Me | $CH_2NHMe$ | $NO_2$ | Me | $CH_2NHMe$ | Me | H |
| $CH_2Ph$ | Et | Et | $CH_2Ph$ | OH | Et | $CH_2Ph$ | Et | H |
| $CH_2Ph$ | nPr | nPr | $CH_2Ph$ | COMe | nPr | $CH_2Ph$ | nPr | H |
| $CH_2CH_2Ph$ | Ph | Ph | $CH_2CH_2Ph$ | COOH | Ph | $CH_2CH_2Ph$ | Ph | H |

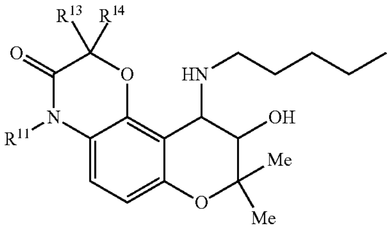

| | | | | | | | | |
|---|---|---|---|---|---|---|---|---|
| H | H | Et | H | $NO_2$ | H | H | H | $NO_2$ |
| H | H | iPr | H | CHO | H | H | H | CHO |
| H | H | nPr | H | $SO_3H$ | H | H | H | $SO_3H$ |
| H | H | nBu | H | Cl | H | H | H | Cl |
| H | H | tBu | H | Br | H | H | H | Br |
| Me | H | Ph | Me | $CH_2OH$ | H | Me | H | $CH_2OH$ |
| Me | Et | Ph | Me | $CH_2NH_2$ | H | Me | H | $CH_2NH_2$ |
| Me | iPr | H | Me | $CH_2NHMe$ | H | Me | H | $CH_2NHMe$ |
| Me | nPr | H | Me | $CH_2Ph$ | H | Me | H | $CH_2Ph$ |
| Me | nBu | H | Me | COMe | H | Me | H | COMe |
| Me | tBu | H | Me | COOH | H | Me | H | COOH |
| Et | Ph | H | Et | $CONH_2$ | H | Et | H | $CONH_2$ |
| Et | H | Et | Et | CONHMe | Et | Et | Et | CONHMe |
| Et | H | iPr | Et | CONHMs | iPr | Et | iPr | CONHMs |
| iPr | H | nPr | iPr | NHMs | nPr | iPr | nPr | NHMs |
| nPr | H | nBu | nPr | NHCOMe | nBu | nPr | nBu | NHCOMe |
| nBu | H | tBu | nBu | $NO_2$ | tBu | nBu | tBu | $NO_2$ |
| tBu | H | Ph | tBu | CHO | Ph | tBu | Ph | H |
| Ph | Cl | Et | Ph | $SO_3H$ | Et | Ph | Et | H |
| $CH_2OH$ | Cl | nPr | $CH_2OH$ | $SO_2NHMe$ | nPr | $CH_2OH$ | nPr | H |
| $CH_2OH$ | Cl | Ph | $CH_2OH$ | OH | Ph | $CH_2OH$ | Ph | H |
| $CH_2OMe$ | Et | Cl | $CH_2OMe$ | COMe | Cl | $CH_2OMe$ | Cl | Cl |
| $CH_2OMe$ | nPr | Cl | $CH_2OMe$ | COOH | Cl | $CH_2OMe$ | Cl | Cl |
| $CH_2NH_2$ | Ph | Cl | $CH_2NH_2$ | $CONH_2$ | Cl | $CH_2NH_2$ | Cl | Cl |
| $CH_2NH_2$ | H | Et | $CH_2NH_2$ | CONHMe | Et | $CH_2NH_2$ | Et | H |
| $CH_2NH_2$ | H | nPr | $CH_2NH_2$ | CONHMs | nPr | $CH_2NH_2$ | nPr | H |
| $CH_2NH_2$ | H | Ph | $CH_2NH_2$ | NHMs | Ph | $CH_2NH_2$ | Ph | H |
| $CH_2NHMe$ | Me | Me | $CH_2NHMe$ | $NO_2$ | Me | $CH_2NHMe$ | Me | H |
| $CH_2Ph$ | Et | Et | $CH_2Ph$ | OH | Et | $CH_2Ph$ | Et | H |
| $CH_2Ph$ | nPr | nPr | $CH_2Ph$ | COMe | nPr | $CH_2Ph$ | nPr | H |
| $CH_2CH_2Ph$ | Ph | Ph | $CH_2CH_2Ph$ | COOH | Ph | $CH_2CH_2Ph$ | Ph | H |

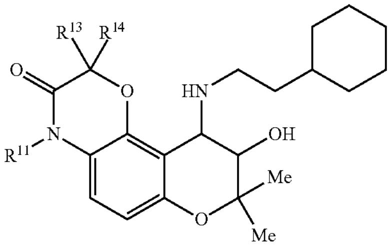

| | | | | | | | | |
|---|---|---|---|---|---|---|---|---|
| H | H | Et | H | $NO_2$ | H | H | H | $NO_2$ |
| H | H | iPr | H | CHO | H | H | H | CHO |
| H | H | nPr | H | $SO_3H$ | H | H | H | $SO_3H$ |
| H | H | nBu | H | Cl | H | H | H | Cl |
| H | H | tBu | H | Br | H | H | H | Br |
| Me | H | Ph | Me | $CH_2OH$ | H | Me | H | $CH_2OH$ |
| Me | Et | Ph | Me | $CH_2NH_2$ | H | Me | H | $CH_2NH_2$ |
| Me | iPr | H | Me | $CH_2NHMe$ | H | Me | H | $CH_2NHMe$ |
| Me | nPr | H | Me | $CH_2Ph$ | H | Me | H | $CH_2Ph$ |
| Me | nBu | H | Me | COMe | H | Me | H | COMe |

-continued

| $R^{11}$ | $R^{13}$ | $R^{14}$ | $R^{11}$ | $R^{13}$ | $R^{14}$ | $R^{11}$ | $R^{13}$ | $R^{14}$ |
|---|---|---|---|---|---|---|---|---|
| Me | tBu | H | Me | COOH | H | Me | H | COOH |
| Et | Ph | H | Et | $CONH_2$ | H | Et | H | $CONH_2$ |
| Et | H | Et | Et | CONHMe | Et | Et | Et | CONHMe |
| Et | H | iPr | Et | CONHMs | iPr | Et | iPr | CONHMs |
| iPr | H | nPr | iPr | NHMs | nPr | iPr | nPr | NHMs |
| nPr | H | nBu | nPr | NHCOMe | nBu | nPr | nBu | NHCOMe |
| nBu | H | tBu | nBu | $NO_2$ | tBu | nBu | tBu | $NO_2$ |
| tBu | H | Ph | tBu | CHO | Ph | tBu | Ph | H |
| Ph | Cl | Et | Ph | $SO_3H$ | Et | Ph | Et | H |
| $CH_2OH$ | Cl | nPr | $CH_2OH$ | $SO_2NHMe$ | nPr | $CH_2OH$ | nPr | H |
| $CH_2OH$ | Cl | Ph | $CH_2OH$ | OH | Ph | $CH_2OH$ | Ph | H |
| $CH_2OMe$ | Et | Cl | $CH_2OMe$ | COMe | Cl | $CH_2OMe$ | Cl | Cl |
| $CH_2OMe$ | nPr | Cl | $CH_2OMe$ | COOH | Cl | $CH_2OMe$ | Cl | Cl |
| $CH_2NH_2$ | Ph | Cl | $CH_2NH_2$ | $CONH_2$ | Cl | $CH_2NH_2$ | Cl | Cl |
| $CH_2NH_2$ | H | Et | $CH_2NH_2$ | CONHMe | Et | $CH_2NH_2$ | Et | H |
| $CH_2NH_2$ | H | nPr | $CH_2NH_2$ | CONHMs | nPr | $CH_2NH_2$ | nPr | H |
| $CH_2NH_2$ | H | Ph | $CH_2NH_2$ | NHMs | Ph | $CH_2NH_2$ | Ph | H |
| $CH_2NHMe$ | Me | Me | $CH_2NHMe$ | $NO_2$ | Me | $CH_2NHMe$ | Me | H |
| $CH_2Ph$ | Et | Et | $CH_2Ph$ | OH | Et | $CH_2Ph$ | Et | H |
| $CH_2Ph$ | nPr | nPr | $CH_2Ph$ | COMe | nPr | $CH_2Ph$ | nPr | H |
| $CH_2CH_2Ph$ | Ph | Ph | $CH_2CH_2Ph$ | COOH | Ph | $CH_2CH_2Ph$ | Ph | H |

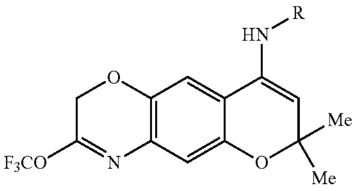

HN—R

| | | |
|---|---|---|
| 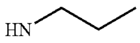 | 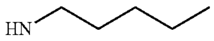 | 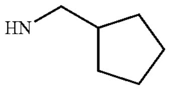 |
| 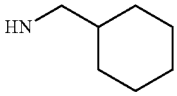 | 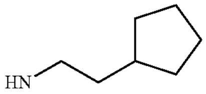 | 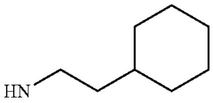 |
| 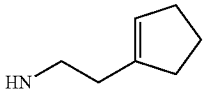 | 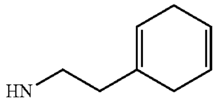 | 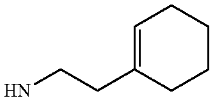 |
| 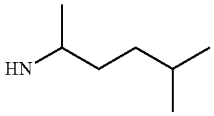 | 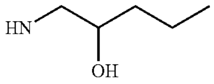 | 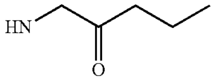 |
| 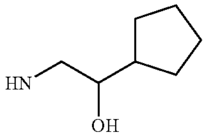 | 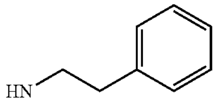 | 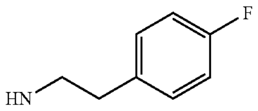 |
| 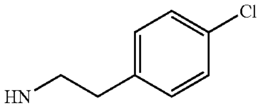 | 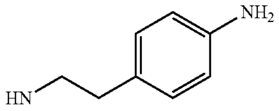 | 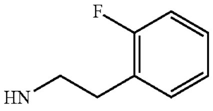 |

-continued
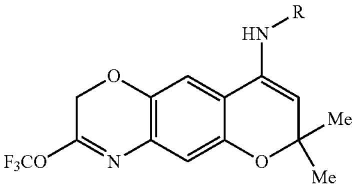
HN—R
| | | |
|---|---|---|
| 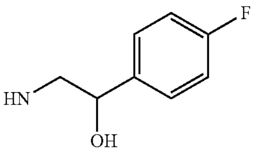 | 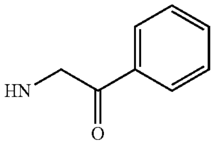 | 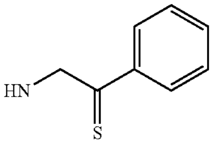 |
| 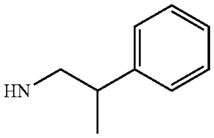 | 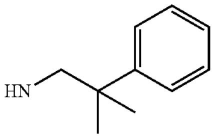 | 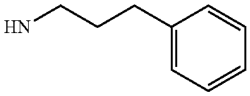 |
| 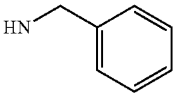 | 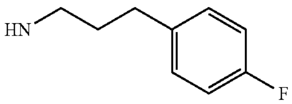 | 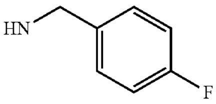 |
| 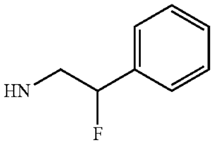 | 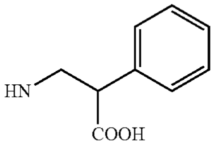 | 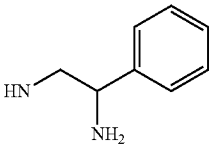 |
| 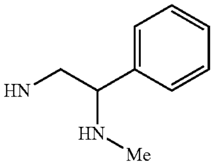 | 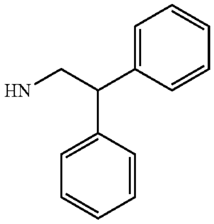 | 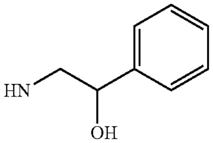 |
| 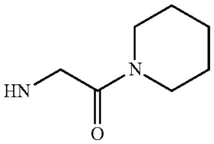 | 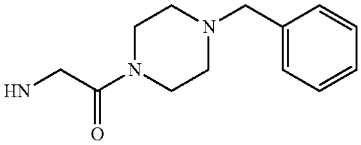 | 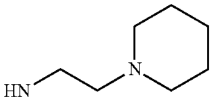 |
| 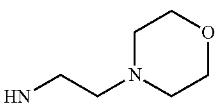 | 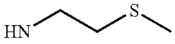 | 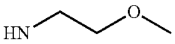 |
| 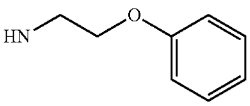 | 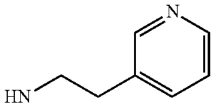 | 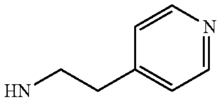 |
| 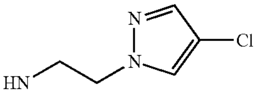 | 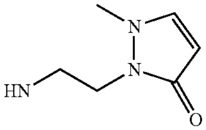 | |

The compound according to the present invention has asymmetric carbon atoms at 3-position and 4-position, thus optical isomers thereof based on the asymmetric carbon atoms are present, and optical active substances can be also used in the application of the present invention, like racemic modifications. Further, cis- and trans-isomer based on configuration at 3-position and 4-position may be included, but trans-isomer is preferred.

Further, when the compounds can form their salts, the pharmaceutically acceptable salts thereof can also be used as active ingredients.

Examples of pharmaceutically acceptable salt are such as hydrochlorides, hydrobromides, sulfates, methanesulfonates, acetates, benzoates, tartrates, phosphates, lactates, maleates, fumarates, malates, gluconates, salicylates and the like.

Preferably, hydrochlorides, maleates and methanesulfonates may be mentioned.

The compound of formulae (I-a) or (II-a) that is the compound of formula (I) or (II) wherein $R^4$ is hydrogen atom and $R^3$ is hydroxy group can be obtained by reacting the compound of formula (1) or (2) with the compound of formula (3) in an inert solvent as shown in the scheme below.

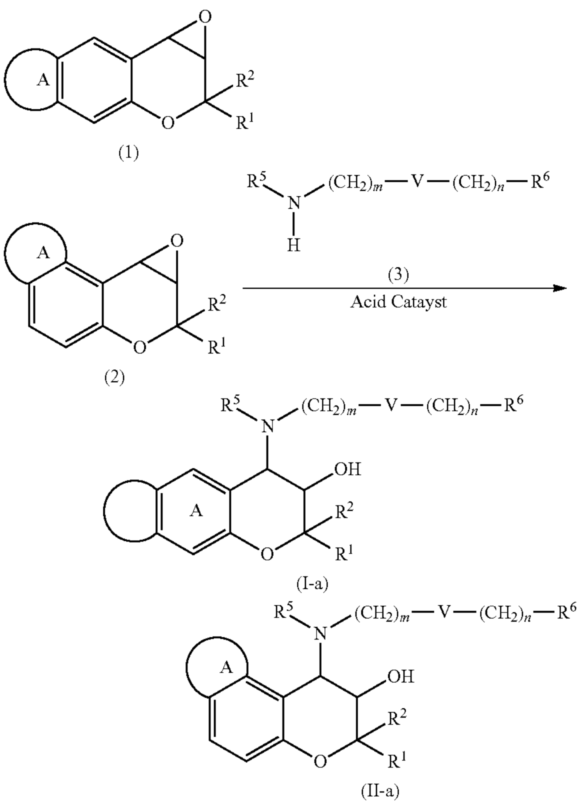

(1) (2) (3) (I-a) (II-a)

As the solvents used in the reaction of the compound of formula (1) or (2) with the compound of formula (3), the followings may be mentioned.

Sulfoxide type solvents exemplified by dimethylsulfoxide; amide type solvents exemplified by dimethylformamide and dimethylacetamide; ether type solvents exemplified by diethyl ether, dimethoxyethane, tetrahydrofuran and dioxane; halogen type solvents exemplified by dichloromethane, chloroform and dichloroethane; nitrile type solvents exemplified by acetonitrile and propionitrile; aromatic hydrocarbon type solvents exemplified by benzene and toluene; hydrocarbon type solvents exemplified by hexane and heptane; ester type solvents exemplified by ethyl acetate; alcohol type solvents exemplified by methanol, ethanol, 1-propanol, 2-propanol and ethylene glycol; and water may be mentioned. Further, the reaction can be carried out in the absence of any solvent. Preferably, ether type solvents, nitrile type solvents and alcohol type solvents may be mentioned.

The reaction temperature is generally from −80° C. to the reflux temperature of the reaction solvent, preferably from −10° C. to 100° C.

The molar ratio of the reaction materials is within the range of 0.5-4.0, preferably 1.0-2.0, for compound (3)/compound (1) or (2).

Acid catalysts may be used in the reaction.

The acid catalysts used include inorganic acids exemplified by hydrochloric acid and sulfuric acid, Lewis acids exemplified by aluminum chloride, titanium tetrachloride, boron trifluoride diethylether complex, perchloric acid, lithium perchlorate, lithium bromide and ytterbium trifluoromethanesulfonate. Preferable acid catalysts are lithium bromide and lithium perchlorate. The synthesis of optically active compounds in the compounds of formula (I) or (II) is accomplished by use of a method for optical resolution of racemate (Japanese Patent Laid-open No. Hei 3-141286, U.S. Pat. No. 5,097,037 and EP Patent No. 409165).

In addition, the synthesis of the compound of formula (1) or (2) is accomplished by use of the following synthetic process:

General Synthetic Process of Benzopyran Ring

The benzopyran ring can be synthesized according to known methods (methods described in J. M. Evans et al., J. Med. Chem. 1984, 27, 1127; J. Med. Chem. 1986, 29, 2194; J. T. North et al., J. Org. Chem. 1995, 60, 3397; as well as Japanese Patent Laid-open Nos. Sho 56-57785, Sho 56-57786, Sho 58-188880, Hei 2-141, Hei 10-87650 and Hei 11-209366 and the like);

Indole or Oxyindole

T. Sakamoto, et al., Heterocycles, 1986, 24, 31,
M. Belley, et. al., Synthesis, 2001, 222,
A. D. Cross, et al., J. Chem. Soc., 1961, 2714;

Imidazolinone

J. Kitteringham, et. al., Synthetic Commun., 2000, 30, 1937;

Quinoline

S. Imor, et al., Synthetic Commun., 1996, 26, 2197,
Y. Kitahara, et al., Tetrahedron, 1997, 53, 6001,
A. G. Osborne, et al., J. Chem. Soc. Perkin Trans. 1, 1993, 181,
R. T. Shuman, et al., J. Org. Chem., 1990, 55, 738,
T. Sakamoto, et al., Chem. Pharm. Bull., 1981, 29, 2485,
Y. Tsuji, et al., J. Org. Chem., 1987, 52, 1673,
Z. Song, et al., J. Heterocyclic Chem., 1993, 30, 17;

Quinolinone

M. R. Sabol, et al., Synthetic Commun., 2000, 30, 427,
Z-Y. Yang, et al., Tetrahedron Lett., 1999, 40, 4505,
H-B Sun, et al., Synthesis, 1997, 1249,
A. Guiotto, et al., J. Heterocyclic Chem. 1989, 26, 917,
K. Konno, et al., Heterocycles 1986, 24, 2169,
E. Fernandez, et al., Synthesis 1995, 1362;

Benzothiazole or Triazole

N. B. Ambati, et al., Synthetic Commun., 1997, 27, 1487,
D. E. Burton, et al., J. Chem. Soc (C). 1968, 1268;

Quinoxaline or Quinoxalinone

J. H. Liu, et al., J. Org. Chem., 2000, 65, 3395,
J. J. Li, et al., Tetrahedron Lett., 1999, 40, 4507,
Y. Ahmed, et al., Bull. Chem. Soc. Jpn., 1987, 60, 1145;

Benzoaxadinone

G. H. Jones, et al., J. Med. Chem., 1987, 30, 295,
J. L. Wright, et al., J. Med. Chem., 2000, 43, 3408,
M. Kluge, et al., J. Heterocyclic Chem., 1995, 32, 395.

The compound of formulae (1-a) or (2-a) that is the compound of formula (I) or (II) wherein A is the group of formula (5), $R^4$ is hydrogen atom and $R^3$ is hydroxy group can be obtained from the compound of formula (6) or (7) according to known methods (methods described in J. M. Evans et al., J. Med. Chem. 1984, 27, 1127; J. Med. Chem. 1986, 29, 2194; J. T. North et al., J. Org. Chem. 1995, 60, 3397; as well as Japanese Patent Laid-open Nos. Sho 56-57785, Sho 56-57786, Sho 58-188880, Hei 2-141, Hei 10-87650 and Hei 11-209366 and the like).

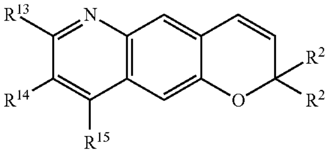

(6)

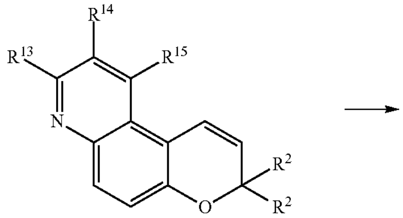

(7)

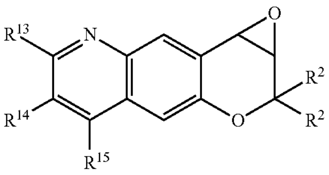

(1-a)

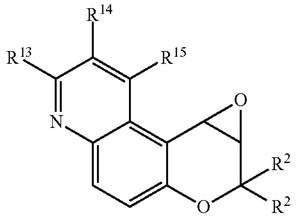

(2-a)

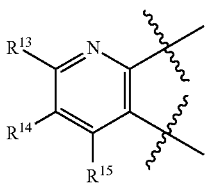

(5)

The compound of formula (6) or (7) can be obtained by reacting compound (8) with compound (9) (see, Y. Tsuji et al., J. Org. Chem., 1987, 52, 1673).

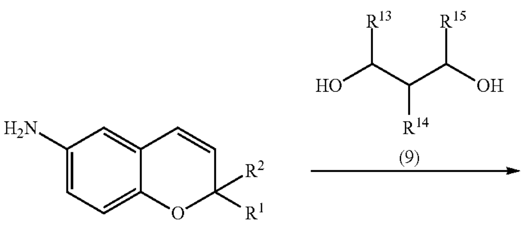

(9)

(8)

-continued

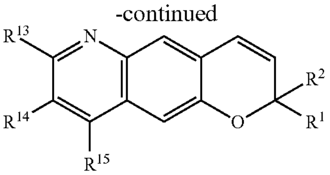

(6)

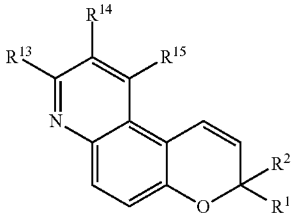

(7)

As the solvents used in the reaction of the compound of formula (8) with the compound of formula (9), the followings may be mentioned.

Sulfoxide type solvents exemplified by dimethylsulfoxide; amide type solvents exemplified by dimethylformamide and dimethylacetamide; ether type solvents exemplified by diethyl ether, dimethoxyethane, tetrahydrofuran and dioxane; halogen type solvents exemplified by dichloromethane, chloroform and dichloroethane; nitrile type solvents exemplified by acetonitrile and propionitrile; aromatic hydrocarbon type solvents exemplified by benzene and toluene; hydrocarbon type solvents exemplified by hexane and heptane; ester type solvents exemplified by ethyl acetate; alcohol type solvents exemplified by methanol, ethanol, 1-propanol, 2-propanol and ethylene glycol; and water may be mentioned. Further, the reaction can be carried out in the absence of any solvent. Preferably, ether type solvents, nitrile type solvents and alcohol type solvents may be mentioned.

The reaction temperature is generally from −80° C. to the reflux temperature of the reaction solvent, preferably from −10° C. to 200° C.

The molar ratio of the reaction materials is within the range of 0.1-4.0, preferably 0.5-2.0, for compound (8)/compound (9).

Transition metal catalysts and ligands may be used in the reaction.

The transition metal catalysts used include ruthenium chloride, dichlorotris(triphenylphosphine)ruthenium, dibromotris(triphenylphosphine)ruthenium, dihydridetetrakis(triphenylphosphine)ruthenium, (η4-cyclooctadiene)(η6-cyclooctatriene)ruthenium, dichlorotricarbonyl ruthenium dimer, dodecacarbonyl triruthenuim, (η5-pentamethylcyclopentadienyl)chloro(η4-cyclooctadiene)ruthenium, palladium acetate, palladium chloride, dichlorobis(triphenylphosphine)palladium, tetrakistriphenylphosphine palladium, bis(dibenzylideneacetone)palladium, rhodium chloride, chlorotris(triphenylphosphine)rhodium, hydridecarbonyltristriphenylphosphine rhodium, hydridetris(triphenylphosphine)rhodium, di-η-chlorotetracarbonyl dirhodium, chlorocarbonylbis(triphenylphosphine)iridium, (η5-pentamethylcyclopentadienyl)dichloroiridium dimer, nickeltetrakistriphenylphosphine, dicobaltoctacarbonyl, (η5-cycloopentadienyl)dicarbonylcobalt, and the like.

Preferably, ruthenium chloride may be mentioned.

The ligands include monodentate phosphine ligands exemplified by trimethylphosphine, triethylphosphine, tri-n-propylphosphine, tri-i-propylphosphine, tri-n-butylphosphine, tri-t-butylphosphine, tricyclohexylphosphine, triphenylphosphine and tri(o-tolyl)phosphine, didentate phosphine ligands exemplified by 1,2-bisdiphenylphosphinoethane, 1,3-bisdiphenylphosphinopropane, 1,4-bisdiphenylphosphinobutane and 1,2-diethylphosphinoethane, phosphite ligands exemplified by triethylphosphite, tributylphosphite, triphenylphosphite and tri(o-tolyl)phosphite.

Preferably, triphenylphosphine, tri-n-butylphosphine and tri-t-butylphosphine.

The compound of formula (6) or (7) can be also obtained by reacting compound (8) with compound (10) in the presence of an acid catalyst (see, Y. Kitahara et al., Tetrahedron Lett., 1997, 53, 6001, Z. Song et al., J. Heterocyclic Chem., 1993, 30, 17).

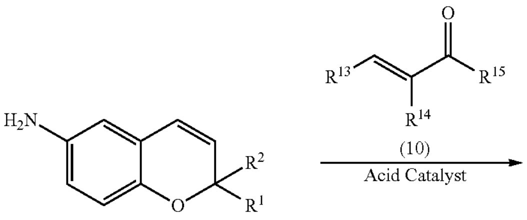

(8)

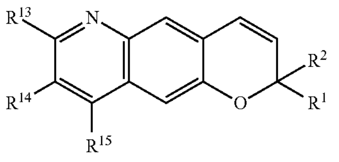

(6)

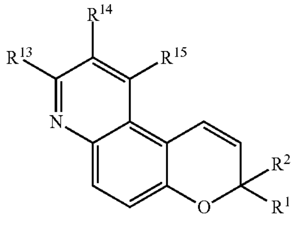

(7)

As the solvents used in the reaction of the compound of formula (8) with the compound of formula (10), the followings may be mentioned.

Sulfoxide type solvents exemplified by dimethylsulfoxide; amide type solvents exemplified by dimethylformamide and dimethylacetamide; ether type solvents exemplified by diethyl ether, dimethoxyethane, tetrahydrofuran and dioxane; halogen type solvents exemplified by dichloromethane, chloroform and dichloroethane; nitrile type solvents exemplified by acetonitrile and propionitrile; aromatic hydrocarbon type solvents exemplified by benzene and toluene; hydrocarbon type solvents exemplified by hexane and heptane; ester type solvents exemplified by ethyl acetate; alcohol type solvents exemplified by methanol, ethanol, 1-propanol, 2-propanol and ethylene glycol; organic acid type solvents exemplified by acetic acid and trifluoroacetic acid; and water may be mentioned. Further, the reaction can be carried out in the absence of any solvent. Preferably, ether type solvents, nitrile type solvents, alcohol type solvents and organic acid type solvents may be mentioned.

The acid catalysts used include inorganic acids exemplified by hydrochloric acid, sulfuric acid, nitric acid and phosphoric acid, organic sulfonic acids exemplified by methane sulfonic acid and paratoluene sulfonic acid, Lewis acids exemplified by aluminum chloride, titanium tetrachloride, boron trifluoride diethylether complex, perchloric acid, zinc chloride, zinc bromide, zinc iodide, iron(III) chloride, iron(II) chloride. copper(I) chloride and copper(II) chloride.

Preferably, hydrochloric acid and zinc chloride may be mentioned.

The reaction temperature is generally from −80° C. to the reflux temperature of the reaction solvent, preferably from −10° C. to 200° C.

The molar ratio of the reaction materials is within the range of 1-10, preferably 1-3, for compound (10)/compound (8).

Furthermore, syntheses of optically active compounds in the compounds of formula (1) or (2) can be attained by utilizing asymmetric synthetic methods (PCT Japanese Translation Patent Publication No. Hei 5-507645, Japanese Patent Laid-open Nos. Hei 5-301878 and Hei 7-285983, European Patent Laid-open No. 535377 and U.S. Pat. No. 5,420,314).

The compound of formulae (I-a) or (II-a) that is the compound of formula (I) or (II) wherein $R^4$ is hydrogen atom and $R^3$ is hydroxy group can be obtained by subjecting the compound of formula (11) or (12) and the compound of formula (13) to reductive amination reaction in an inert solvent as shown in the scheme below.

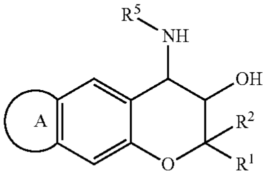

(11)

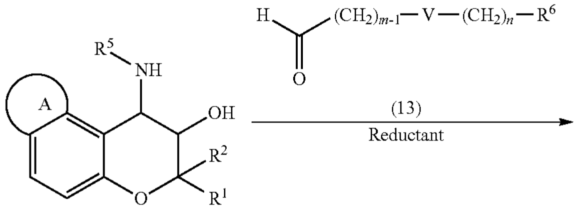

(12)

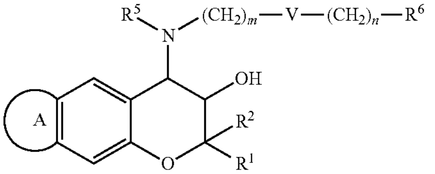

(I-a)

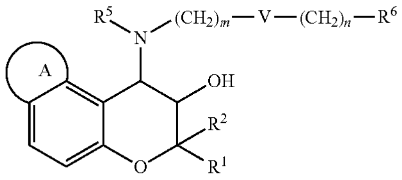

(II-a)

As the solvents used in the reaction of the compound of formula (11) or (12) with the compound of formula (13), the followings may be mentioned.

Sulfoxide type solvents exemplified by dimethylsulfoxide; amide type solvents exemplified by dimethylformamide and dimethylacetamide; ether type solvents exemplified by diethyl ether, dimethoxyethane, tetrahydrofuran and dioxane; halogen type solvents exemplified by dichloromethane, chloroform and dichloroethane; nitrile type solvents exemplified by acetonitrile and propionitrile; aromatic hydrocarbon type solvents exemplified by benzene and toluene; hydrocarbon type solvents exemplified by hexane and heptane; ester type solvents exemplified by ethyl acetate; alcohol type solvents exemplified by methanol, ethanol, 1-propanol, 2-propanol and ethylene glycol; and water may be mentioned. Further, the reaction can be carried out in the absence of any solvent. Preferably, ether type solvents and alcohol type solvents may be mentioned.

The compound of formulae (I-b) or (II-b) that is the compound of formula (I) or (II) wherein $R^4$ is hydrogen atom and $R^3$ is hydroxy group, m is 1, V is $CR^7OH$ can be obtained by reacting the compound of formula (11) or (12) with the compound of formula (14) in an inert solvent as shown in the scheme below.

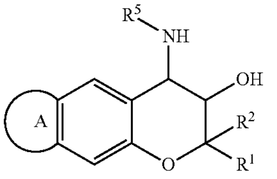

(11)

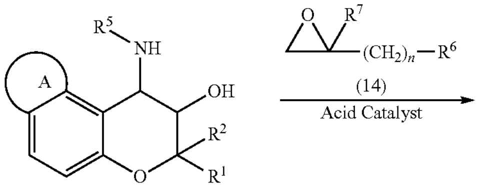

(12)

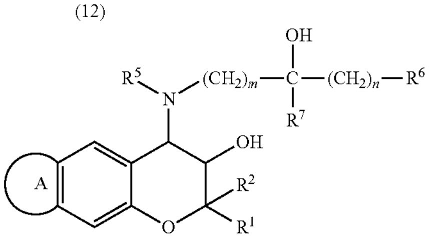

(I-b)

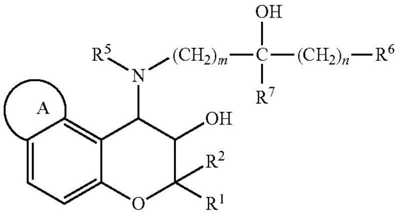

(II-b)

As the solvents used in the reaction of the compound of formula (11) or (12) with the compound of formula (14), the followings may be mentioned.

Sulfoxide type solvents exemplified by dimethylsulfoxide; amide type solvents exemplified by dimethylformamide and dimethylacetamide; ether type solvents exemplified by diethyl ether, dimethoxyethane, tetrahydrofuran and dioxane; halogen type solvents exemplified by dichloromethane, chloroform and dichloroethane; nitrile type solvents exemplified by acetonitrile and propionitrile; aromatic hydrocarbon type solvents exemplified by benzene and toluene; hydrocarbon type solvents exemplified by hexane and heptane; ester type solvents exemplified by ethyl acetate; alcohol type solvents exemplified by methanol, ethanol, 1-propanol, 2-propanol and ethylene glycol; and water may be mentioned. Further, the reaction can be carried out in the absence of any solvent. Preferably, alcohol type solvents may be mentioned.

The reaction temperature is generally from −80° C. to the reflux temperature of the reaction solvent, preferably from −10° C. to 100° C.

The molar ratio of the reaction materials is within the range of 0.5-4.0, preferably 1.0-2.0, for compound (14)/compound (11) or (12).

The acid catalysts used include inorganic acids exemplified by hydrochloric acid and sulfuric acid, Lewis acids exemplified by aluminum chloride, titanium tetrachloride, boron trifluoride diethylether complex, perchloric acid, lithium perchlorate, lithium bromide and ytterbium trifluoromethanesulfonate.

Preferable acid catalysts are lithium bromide and lithium perchlorate.

The compound of formulae (I-c) or (II-c) that is the compound of formula (I) or (II) wherein $R^4$ is hydrogen atom, $R^3$ is hydroxy group and A is the group of formula (15) can be also obtained by reacting the compound of formula (16) or (17) with the compound of formula (18) in an inert solvent as shown in the scheme below.

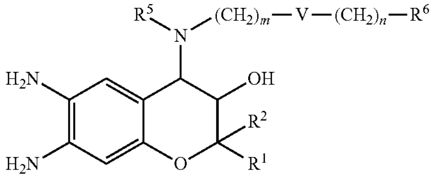

(16)

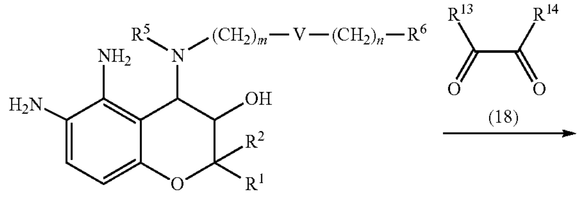

(17)

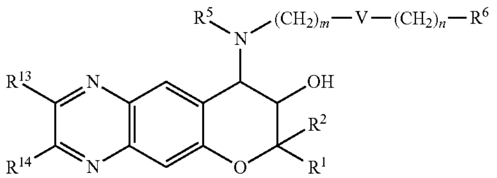

(I-c)

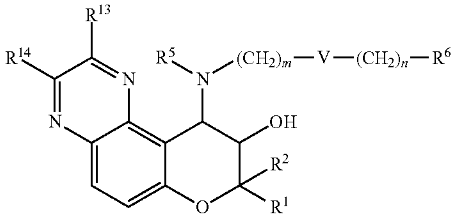

(II-c)

-continued

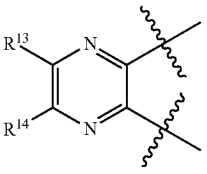

(15)

As the solvents used in the reaction of the compound of formula (16) or (17) with the compound of formula (18), the followings may be mentioned.

Sulfoxide type solvents exemplified by dimethylsulfoxide; amide type solvents exemplified by dimethylformamide and dimethylacetamide; ether type solvents exemplified by diethyl ether, dimethoxyethane, tetrahydrofuran and dioxane; halogen type solvents exemplified by dichloromethane, chloroform and dichloroethane; nitrile type solvents exemplified by acetonitrile and propionitrile; aromatic hydrocarbon type solvents exemplified by benzene and toluene; hydrocarbon type solvents exemplified by hexane and heptane; ester type solvents exemplified by ethyl acetate; alcohol type solvents exemplified by methanol, ethanol, 1-propanol, 2-propanol and ethylene glycol; and water may be mentioned. Further, the reaction can be carried out in the absence of any solvent. Preferably, alcohol type solvents may be mentioned.

The reaction temperature is generally from −80° C. to the reflux temperature of the reaction solvent, preferably from −10° C. to 50° C.

The molar ratio of the reaction materials is within the range of 0.5-4.0, preferably 0.8-2.0, for compound (18)/compound (16) or (17).

The compound of formulae (I-d) or (II-d) that is the compound of formula (I) or (II) wherein $R^4$ is hydrogen atom, $R^3$ is hydroxy group and A is the group of formula (19) can be also obtained by subjecting the compound of formula (20) or (21) to reduction reaction in an inert solvent as shown in the scheme below.

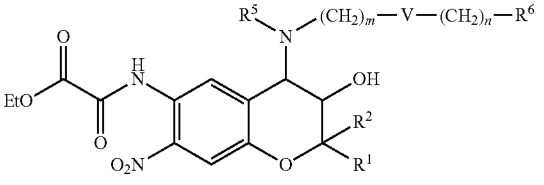

(20)

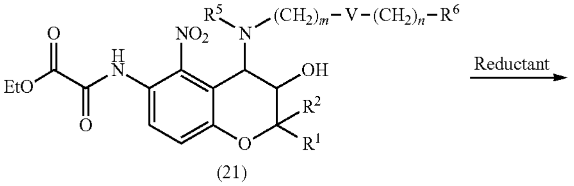

(21)

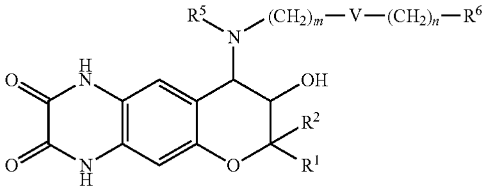

(I-d)

-continued

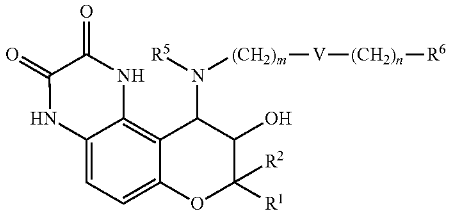

(II-d)

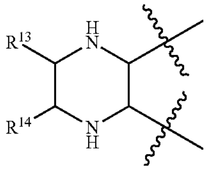

(19)

The compound of formulae (I-e) or (II-e) that is the compound of formula (I) or (II) wherein $R^4$ is hydrogen atom, $R^3$ is hydroxy group and A is the group of formula (22) (X is $SO_2$ or CO, and Y is S or O) can be also obtained by subjecting the compound of formula (23) or (24) to ring-closure reaction in an inert solvent as shown in the scheme below.

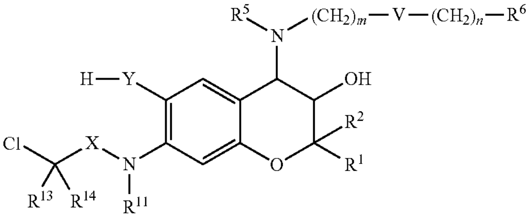

(23)

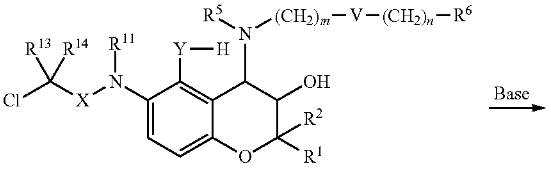

(24)

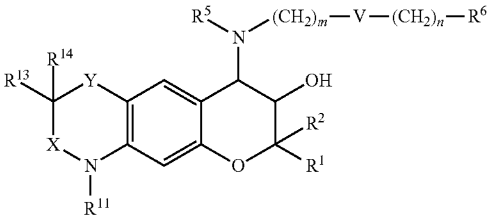

(I-e)

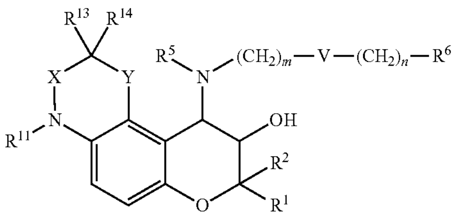

(II-e)

-continued

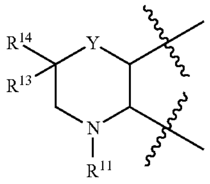

(22)

The compounds of formula (I) or (II) that are not included in the compounds of formulae (I-a to I-e) and (II-a to II-e), that is, the compounds of formula (I) or (II) wherein $R^3$ and $R^4$ are together a bond, or $R^4$ is hydrogen atom and $R^3$ is $C_{1-6}$ alkylcarbonyloxy group, can be produced by a preparation process similarly to that described in Japanese Patent Laid-open Nos. Sho 52-91866 and Hei 10-87650.

As described above, the inventors of the present invention found that the compound of formula (I) or (II) has a strong prolongation effect on the refractory period. The prolongation effect on the refractory period is one of mechanisms of anti-arrhythmic action and is an important indicator that can be taken in judging the effectiveness in clinical arrhythmia. Conventional anti-arrhythmic agents having the prolongation effect on the refractory period as the main mechanism (such as d-sotalol belonging to Class III of the antiarrhythmic agent classification according to Vaughan Williams) have been the therapeutic problems in inducing highly dangerous arrhythmia leading to the sudden death from such as torsades de pointes among others due to prolongation of action potential in ventricular muscle correlated to the prolongation effect on the refractory period, and thus becoming the therapeutic problem in arrhythmia mainly of atrial muscle (such as supraventricular tachycardia, atrial flutter, atrial fibrillation and the like).

In order to solve the problems, the inventors of the present invention carried out the investigation of compounds having the prolongation effect on the refractory period selective for atrium muscle than for ventricular muscle, and found that the compound of formula (I) or (II) has a prolongation effect on the refractory period selective for atrium muscle without any influence on the refractory period and action potential in ventricular muscle. The difference between the findings by the inventors and the prior art is in providing the prolongation effect on the refractory period selective for atrium muscle to these compound group, which may be shown by the facts that there is no influence on the action potential duration period of isolated ventricular muscle and there is no influence on QT in the electrocardiogram of anesthetized animal. From above, the compounds of the present invention show no inducing action of arrhythmia in ventricular muscle, thus they can contribute to much safer use in arrhythmia mainly of atrial muscle in comparison with the prior art. The present technical knowledge is beneficial for therapeutic or preventive uses as anti-atrial fibrillation agents, anti-atrial flutter agents and anti-atrial tachycardia agents relating to paroxysmal, chronic, preoperative, intraoperative or postoperative atrial arrhythmia, prevention in the progression leading to embolus due to arrhythmia of atrial nature, prevention in the progression leading to ventricular arrhythmia or tachycardia from atrial arrhythmia or tachycardia, and averting the life threatening prognosis due to preventive action on atrial arrhythmia or tachycardia leading to ventricular arrhythmia or tachycardia.

The present invention provides a pharmaceutical composition or a veterinary pharmaceutical composition containing a compound of formula (I) or (II) in an effective amount for these treatments.

As forms of administration for the compound according to the present invention, parenteral administration forms such as injections (subcutaneous, intravenous, intramuscular and intraperitoneal injections), ointments, suppositories, aerosols and the like, and oral administration forms such as tablets, capsules, granules, pills, syrups, solutions, emulsions, suspensions and the like can be mentioned.

The pharmaceutical or veterinary pharmaceutical composition described above contains the compound according to the present invention in an amount of about 0.01-99.5%, preferably about 0.1-30%, based on the total weight of the composition.

In addition to the compound according to the present invention or the composition containing the compound, other pharmaceutically or veterinary pharmaceutically active compounds may be contained.

Further, these compositions may contain the plurality of compounds according to the present invention.

An amount of the compound according to the present invention to be used in clinical administration may vary depending on age, weight and sensitivity of the patient, symptomatic condition and the like, but an effective amount in clinical administration is generally about 0.003-1.5 g, preferably 0.01-0.6 g, per day for adult. If necessary, however, the amount outside of the aforementioned range may be used.

The compound according to the present invention is formulated for administration by conventional pharmaceutical means.

That is, tablets, capsules, granules and pills for oral administration are prepared by using excipients such as sucrose, lactose, glucose, starch and mannitol; binders such as hydroxypropyl cellulose, syrup, gum arabic, gelatin, sorbitol, tragacanth, methyl cellulose and polyvinyl pyrrolidone; disintegrators such as starch, carboxymethyl cellulose or its calcium salt, microcrystalline cellulose and polyethylene glycol; lubricants such as talc, magnesium or calcium stearate, and silica; lubricating agents such as sodium laurate and glycerol and the like.

Injections, solutions, emulsions, suspensions, syrups and aerosols are prepared by using solvents for the active components such as water, ethyl alcohol, isopropyl alcohol, propylene glycol, 1,3-butylene glycol and polyethylene glycol; surfactants such as sorbitan fatty acid ester, polyoxyethylene sorbitan fatty acid ester, polyoxyethylene fatty acid ester, polyoxyethylene ether of hydrogenated castor oil and lecithin; suspending agents such as carboxymethyl sodium salt, cellulose derivatives such as methyl cellulose or the like, and natural rubbers such as gum arabic, tragacanth or the like; and preserves such as p-hydroxybenzoic acid esters, benzalkonium chloride, sorbic acid salts and the like.

For ointments that are transdermally adsorptive pharmaceutics, for example, white vaseline, liquid paraffin, higher alcohols, Macrogol ointments, hydrophilic ointments, aqueous gel-type bases and the like are used.

Suppositories are prepared by using, for example, cocoa fats, polyethylene glycol, lanolin, fatty acid triglyceride, coconut oil, polysorbate and the like.

EXAMPLES

The present invention is illustrated in detail by the Examples as follows, but the present invention is not limited to these Examples.

Synthesis Examples

Furthermore, Ph,Ph salen manganese complex (XX) and Cyc,Ph salen manganese complex (XY) mean optically active compounds of formulae below which were synthesized according to the method similar to one described in Japanese Patent Laid-open No. Hei 7-285983.

(XX)

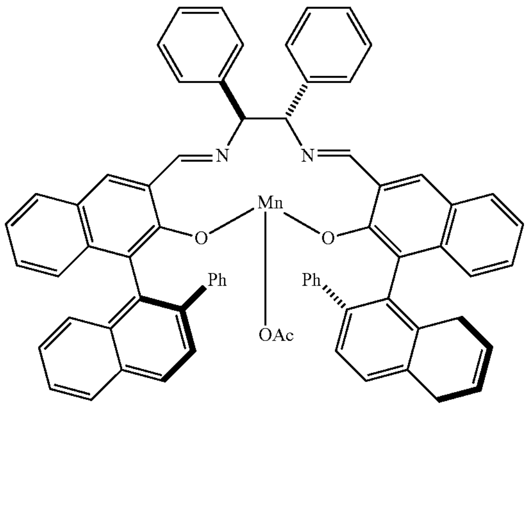

(XY)

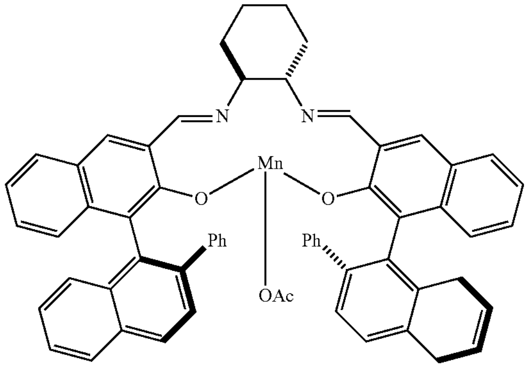

Synthesis Example 1

(±)-trans-2,2,9-Trimethyl-4-[(2-phenylethyl)amino]-3, 4-dihydro-2H-pyrano[2,3-g]quinolin-3-ol 3/2 maleate

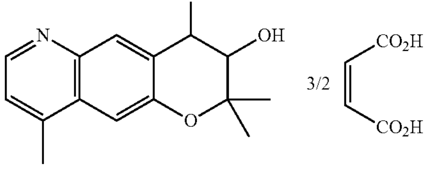

2,2,9-Trimethyl-2H-pyrano[2,3-g]quinoline

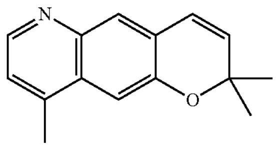

To a solution of 6-amino-2,2-dimethylchromene (10.1 g, 57.7 mmol) in ethanol (500 mL), methylvinylketone (33.0 mL, 404 mmol), m-nitrobenzenesulfonic acid (21.1 g, 104 mmol), zinc chloride (1.97 g, 14.4 mmol) and 35% hydrochloric acid (24 mL, 289 mmol) were added at room temperature and the resulting mixture was stirred at 110° C. for 5 hours. Upon the completion of the reaction, ethanol was distilled off, water was added, and the resulting solution was neutralized with sodium hydrogencarbonate and extracted with ethyl acetate. The resulting organic phase was washed with sodium chloride aqueous solution, and dried over anhydrous magnesium sulfate. After distilling off the solvent, the residue was purified by medium pressure column chromatography (hexane/ethyl acetate=3/1) and the aimed product was obtained (yield: 38%).

Brown amorphous product $^1$H-NMR ($CDCl_3$) δ; 1.51(s, 6H), 2.59(d, J=0.6 Hz, 3H), 5.90(d, J=9.9 Hz, 1H), 6.59(d, J=9.9 Hz, 1H), 7.11(d, J=3.6 Hz, 1H), 7.25(s, 1H), 7.68(s, 1H), 8.57(d, J=4.4 Hz, 1H)

MS (ESI$^+$) m/z; 226 [M+1]$^+$ (±)-trans-2,2,9-Trimethyl-4-[(2-phenylethyl)amino]-3, 4-dihydro-2H-pyrano[2,3-g]quinolin-3-ol

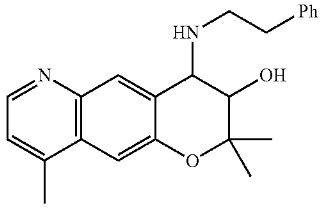

To a solution of 2,2,9-trimethyl-2H-pyrano[2,3-g]quinoline (530 mg, 2.35 mmol) in dimethylsulfoxide (8 mL), N-bromosuccinimide (920 mg, 5.17 mmol) and water (1.6 mL) were added at room temperature and the resulting mixture was stirred at room temperature for 3 hours. Upon the completion of the reaction, water was added to the reaction solution, and the resulting solution was extracted with ethyl acetate. Sodium hydrogencarbonate aqueous solution was added to the aqueous phase and the resulting solution was further extracted with ethyl acetate. The combined organic phases were was dried over anhydrous magnesium sulfate and the solvent was distilled off to obtain a crude product of 3-bromo-2,2,9-trimethyl-3,4-dihydro-2H-pyrano[2,3-g]quinolin-3-ol. At room temperature, 1,4-dioxane (30 mL) and 1 mol/L sodium hydroxide aqueous solution (5.64 mL) were added thereto, and the resulting solution was stirred at room temperature for 2.5 hours. Upon the completion of the reaction, water was added to the reaction solution, and the resulting solution was extracted with ethyl acetate, dried over anhydrous magnesium sulfate and the solvent was distilled off to obtain a crude product of 3,4-epoxy-2,2,5-trimethyl-3,4-dihydro-2H-pyrano[2,3-g]quinoline. To the residue, 1,4-dioxane (3.2 mL), lithium perchlorate (250 mg, 2.35 mmol) and 2-phenylethylamine (0.35 mL, 2.82 mmol) were added at room temperature, and the resulting mixture was stirred at 75° C. for 5 hours. Upon the completion of the reaction, sodium hydrogencarbonate aqueous solution was added to the reaction solution, and the resulting solution was extracted with ethyl acetate, the organic phase was washed with sodium hydrogencarbonate aqueous solution and then with sodium chloride aqueous solution, and dried over anhydrous magnesium sulfate. After distilling off the solvent, the residue was purified by column chromatography (hexane/ethyl acetate=1/1) and the aimed product was obtained (3-step, yield: 26%).

$^1$H-NMR ($CDCl_3$) δ; 1.26(s, 3H), 1.55(s, 3H), 2.59(s, 3H), 2.83(t, J=6.8 Hz, 2H), 2.96-3.12(m, 3H), 3.60(d, J=10.5 Hz, 1H), 3.88(dd, J=1.1 Hz, 10.5 Hz, 1H), 7.13(d, J=4.2 Hz, 1H), 7.18-7.32(m, 6H), 7.98(d, J=1.1 Hz, 1H), 8.60(d, J=4.4 Hz, 1H)

MS (ESI$^+$) m/z; 363 [M+1]$^+$

To a solution of (±)-trans-2,2,9-trimethyl-4-[(2-phenylethyl)amino]-3,4-dihydro-2H-pyrano[2,3-g]quinolin-3-ol (219 mg, 0.60 mmol) in ethyl acetate (3 mL), a solution of maleic acid (77 mg, 0.66 mmol) in ethyl acetate (1 mL) was added dropwise, the resulting reaction solution was cooled to 0° C., hexane (10 mL) was added thereto, and precipitated solid was filtered off to obtain 2,2,9-trimethyl-4-[(2-phenylethyl)amino]-3,4-dihydro-2H-pyrano[2,3-g]quinolin-3-ol 3/2 maleate (yield: 72%).

Yellow crystal mp; 172-174° C. (decomposition)

$^1$H-NMR (DMSO-$d_6$) δ; 1.17(s, 3H), 1.50(s, 3H), 2.59(s, 3H), 2.94-3.37(m, 4H), 4.10(dd, J=6.1 Hz, 9.4 Hz, 1H), 4.72 (d, J=9.4 Hz, 1H), 6.09(s, 3H), 6.33(d, J=6.1 Hz, 1H), 7.23-7.35(m, 6H), 7.42(s, 1H), 8.43(s, 1H), 8.66(d, J=4.1 Hz, 1H)

Synthesis Example 2

(±)-trans-2,2,7,9-Tetramethyl-4-[(2-phenylethyl) amino]-3, 4-dihydro-2H-pyrano[2,3-g]quinolin-3-ol

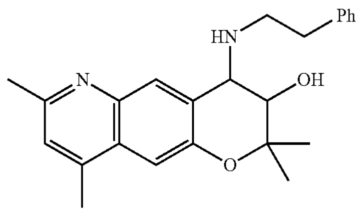

This compound was synthesized according to the process of Synthesis Example 1.

2,2,7,9-Tetramethyl-2H-pyrano[2,3-g]quinoline

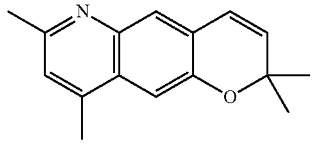

(Yield: 59%)

Black brown oily product $^1$H-NMR ($CDCl_3$) δ: 1.49(s, 6H), 2.54(s, 3H), 2.62(s, 3H), 5.86(d, J=9.9 Hz, 1H), 6.55(d, J=9.9 Hz, 1H), 7.00(s, 1H), 7.20(s, 1H), 7.60(s, 1H)

MS (ESI$^+$) m/z; 240 [M+1]$^+$ (±)-trans-3-Bromo-2,2,7,9-tetramethyl-3,4-dihydro-2H-pyrano[2,3-g]quinolin-4-ol

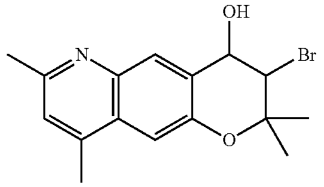

(Yield: 82%)

$^1$H-NMR ($CDCl_3$) δ; 1.47(s, 3H), 1.68(s, 3H), 2.58(s, 3H), 2.70(s, 3H), 4.28(d, J=9.6 Hz, 1H), 5.14(d, J=9.6 Hz, 1H), 7.08(s, 1H), 7.28(s, 1H), 8.37(s, 1H)

MS (ESI$^+$) m/z; 336, 338 [M+1]$^+$ (±)-trans-2,2,7,9-Tetramethyl-4-[(2-phenylethyl) amino]-3, 4-dihydro-2H-pyrano[2,3-g]quinolin-3-ol (yield: 17%)

White crystal mp; 144-147° C.

$^1$H-NMR ($CDCl_3$) δ; 1.25(s, 3H), 1.54(s, 3H), 1.90(br s, 1H), 2.55(s, 3H), 2.65(s, 3H), 2.81(t, J=6.8 Hz, 2H), 2.97-3.10(m, 2H), 3.19(br s, 1H), 3.58(d, J=10.5 Hz, 1H), 3.85(d, J=10.5 Hz, 1H), 7.04(s, 1H), 7.17-7.31(m, 6H), 7.91(s, 1H)

MS (ESI$^+$) m/z; 377 [M+1]$^+$

MS (ESI−) m/z; 421 [M+45]$^+$

Synthesis Example 3

(±)-trans-2,2,8,9-Tetramethyl-4-[(2-phenylethyl) amino]-3, 4-dihydro-2H-pyrano[2,3-g]quinolin-3-ol 1 maleate

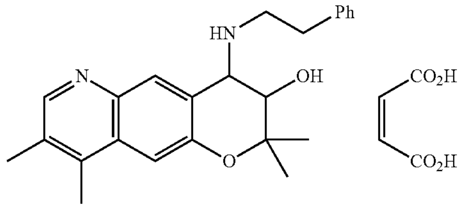

This compound was synthesized according to the process of Synthesis Example 1.

2,2,8,9-Tetramethyl-2H-pyrano[2,3-g]quinoline

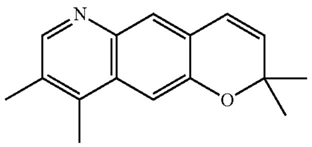

(Yield: 50%)

$^1$H-NMR ($CDCl_3$) δ; 1.50(s, 6H), 2.50(s, 3H), 2.66(s, 3H), 5.87(d, J=9.9 Hz, 1H), 6.57(d, J=9.9 Hz, 1H), 7.26(s, 1H), 7.63(s, 1H), 8.48(s, 1H)

MS (ESI$^+$) m/z; 240 [M+1]$^+$ (±)-trans-3-Bromo-2,2,7,9-tetramethyl-3,4-dihydro-2H-pyrano[2,3-g]quinolin-4-ol

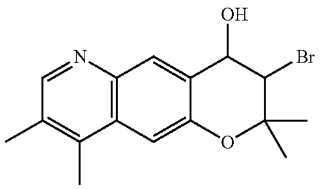

(Yield: 65%)

$^1$H-NMR ($CDCl_3$) δ; 1.48(s, 3H), 1.69(s, 3H), 1.80(br s, 1H), 2.46(s, 3H), 2.56(s, 3H), 4.28(d, J=9.6 Hz, 1H), 5.15(d, J=9.6 Hz, 1H), 7.25(s, 1H), 8.42(s, 1H), 8.57(s, 1H)

MS (ESI$^+$) m/z; 336, 338 [M+1]$^+$ (±)-trans-2,2,8,9-Tetramethyl-4-[(2-phenylethyl) amino]-3, 4-dihydro-2H-pyrano[2,3-g]quinolin-3-ol 1 maleate (Yield: 4%)

White crystal mp; 199-203° C.

$^1$H-NMR (DMSO-$d_6$) δ; 1.17(s, 3H), 1.50(s, 3H), 2.41(s, 3H), 2.49(s, 3H), 2.89-3.40(m, 4H), 4.07(dd, J=5.5 Hz, 9.4 Hz, 1H), 4.66(d, J=9.4 Hz, 1H), 6.05(s, 2H), 6.28(d, J=5.5 Hz, 1H), 7.22-7.35(m, 5H), 7.43(s, 1H), 8.36(s, 1H), 8.59(s, 1H)

MS (ESI$^+$) m/z; 377 [M+1]$^+$

MS (ESI−) m/z; 421 [M+45]$^+$

Synthesis Example 4

(±)-trans-2,2,7-Trimethyl-4-[(2-phenylethyl)amino]-3, 4-dihydro-2H-pyrano[2,3-g]quinolin-3-ol 3/2 maleate

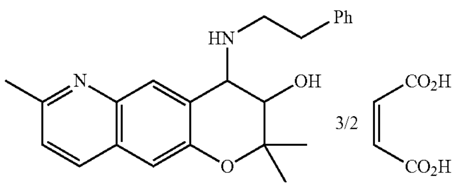

2,2,7-Trimethyl2H-pyrano[2,3-g]quinoline

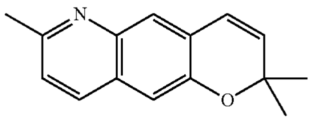

To 6-amino-2,2-dimethylchromene (1.00 g, 5.71 mmol), 35% hydrochloric acid (1.43 mL, 17.1 mmol), p-chloranil (1.40 g, 5.71 mmol) and n-butanol (1.3 mL) were added at room temperature and the temperature was increased to 120° C. A solution of crotyl aldehyde (0.567 mL, 6.84 mmol) in n-butanol (0.52 mL) was added and the resulting mixture was stirred at 120° C. for 20 minutes. A solution of zinc chloride (0.777 g, 5.71 mmol) in tetrahydrofuran (10 mL) was added, and the resulting mixture was stirred at 120° C. for 20 minutes. Upon the completion of the reaction, sodium hydrogencarbonate aqueous solution was added, and the resulting solution was extracted with ethyl acetate and dried over anhydrous magnesium sulfate. After distilling off the solvent, the residue was purified by column chromatography (hexane/ethyl acetate=2/1), and recrystallized with ethyl acetate to obtain the aimed product (yield: 22%).

Gray solid $^1$H-NMR ($CDCl_3$) δ; 1.48(s, 6H), 2.67(s, 3H), 5.87(d, J=9.9 Hz, 1H), 6.55(d, J=9.9 Hz, 1H), 7.05(s, 1H), 7.16(d, J=8.5 Hz, 1H), 7.64(s, 1H), 7.86(d, J=8.5 Hz, 1H)

MS (ESI$^+$) m/z; 226 [M+1]$^+$

MS (ESI−) m/z; 225 [M]$^+$ (±)-trans-3-Bromo-2,2,7-trimethyl-3,4-dihydro-2H-pyrano[2,3-g]quinolin-4-ol

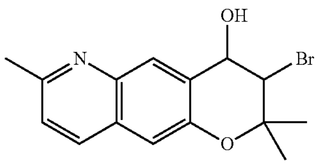

This compound was synthesized according to the process of Synthesis Example 1.

(Yield: 24%)

2,2,7-Trimethyl-4-[(2-phenylethyl)amino]-3,4-dihydro-2H-pyrano[2,3-g]quinolin-3-ol 3/2 maleate (Yield: 12%)

White crystal $^1$H-NMR (DMSO-$d_6$) δ; 1.15(s, 3H), 1.48(s, 3H), 2.63(s, 3H), 2.70-3.38(m, 4H), 4.09(dd, J=5.8 Hz, 9.4 Hz, 1H), 4.68 (d, J=9.4 Hz, 1H), 6.08(s, 3H), 6.29(d, J=5.8 Hz, 1H), 7.22-7.35(m, 6H), 7.40(s, 1H), 8.10(d, J=8.5 Hz, 1H), 8.33(s, 1H)

MS (ESI$^+$) m/z; 363 [M+1]$^+$

MS (ESI−) m/z; 407 [M+45]$^+$

Synthesis Example 5

(±)-trans-2,2,8-Trimethyl-4-[(2-phenylethyl)amino]-3, 4-dihydro-2H-pyrano[2,3-g]quinolin-3-ol 2 maleate

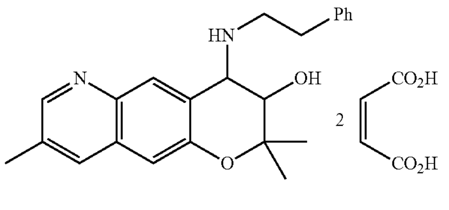

This compound was synthesized according to the process of Synthesis Example 4.

2,2,8-Trimethyl-2H-pyrano[2,3-g]quinoline

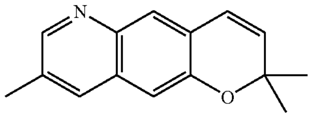

(Yield: 17%)

$^1$H-NMR ($CDCl_3$) δ; 1.48(s, 6H), 2.45(s, 3H), 5.87(d, J=9.9 Hz, 1H), 6.56(d, J=9.9 Hz, 1H), 7.00(s, 1H), 7.64(s, 1H), 7.70(s, 1H), 8.54(d, J=8.5 Hz, 1H)

MS (ESI$^+$) m/z; 226 [M+1]$^+$ (±)-trans-3-Bromo-2,2,8-trimethyl-3,4-dihydro-2H-pyrano[2,3-g]quinolin-4-ol

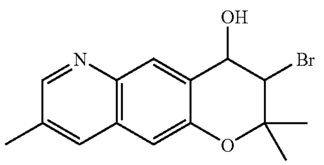

(Yield: 54%)

MS (ESI$^+$) m/z; 322, 324 [M+1]$^+$ 2,2,8-Trimethyl-4-[(2-phenylethyl)amino]-3,4-dihydro-2H-pyrano[2,3-g]quinolin-3-ol 2 maleate (Yield: 20%)

White crystal $^1$H-NMR (DMSO-$d_6$) δ; 1.15(s, 3H), 1.49(s, 3H), 2.45(s, 3H), 2.97-3.39(m, 4H), 4.09(dd, J=6.1 Hz, 9.4 Hz, 1H), 4.71 (d, J=9.1 Hz, 1H), 6.15(s, 4H), 6.32(d, J=6.3 Hz, 1H), 7.19-7.36(m, 5H), 7.97(s, 1H), 8.39(s, 1H), 8.67(s, 1H)

Synthesis Example 6

(±)-trans-7-Chloro-2,2,9-trimethyl-4-[(2-phenylethyl)amino]-3,4-dihydro-2H-pyrano[2,3-g]quinolin-3-ol 1 maleate

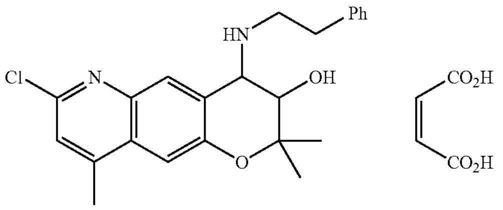

To a solution of 2,2,9-trimethyl-2H-pyrano[2,3-g]quinoline (1.56 g, 6.92 mmol) in chloroform (15.6 mL), a solution of m-chloroperbenzoic acid (2.61 g, 15.2 mmol) in chloroform (6.4 mL)-methanol (1.6 mL) was added dropwise at room temperature and the resulting mixture was stirred at room temperature for 1.5 hour. Upon the completion of the reaction, the reaction solution was extracted with sodium thiosulfate aqueous solution and the resulting organic phase was washed with sodium hydrogencarbonate aqueous solution and then with sodium chloride aqueous solution, and dried over anhydrous magnesium sulfate. After distilling off the solvent, chloroform (33 mL), p-toluenesulfonic acid chloride (1.32 g, 6.92 mmol) and potassium carbonate (0.954 g, 6.92 mmol) were added to the residue at room temperature, and the resulting mixture was stirred at 70° C. for 3 hours. Upon the completion of the reaction, water was added to the reaction solution, and it was extracted with chloroform. The resulting organic phase was washed with sodium chloride aqueous solution, and dried over anhydrous magnesium sulfate. After distilling off the solvent, the residue was purified by column chromatography (hexane/ethyl acetate=2/1) and the aimed product was obtained (yield: 67%).

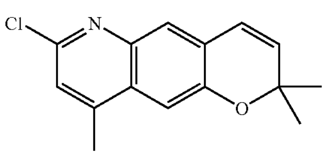

Pale yellow solid $^1$H-NMR ($CDCl_3$) δ; 1.42(s, 6H), 2.48(d, J=0.8 Hz, 3H), 5.83(d, J=9.9 Hz, 1H), 6.47(d, J=9.9 Hz, 1H), 7.03(d, J=3.6 Hz, 1H), 7.11(s, 1H), 7.50(s, 1H)

MS (ESI$^+$) m/z; 260 [M+1]$^+$ (±)-trans-3-Bromo-7-chloro-2,2,9-trimethyl-2H-pyrano[2, 3-g]quinolin-4-ol

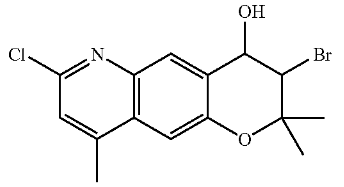

Hereinafter, the aimed compound was synthesized according to the process of Synthesis Example 1.

(Yield: 44%)

MS ($ESI^+$) m/z; 356, 358 $[M+1]^+$ (±)-trans-7-Chloro-2,2,9-trimethyl-4-[(2-phenylethyl)amino]-3,4-dihydro-2H-pyrano[2,3-g]quinolin-3-ol 1 maleate (Yield: 58%)

White crystal mp: 221-226° C. (decomposition)

$^1$H-NMR (DMSO-$d_6$) δ; 1.17(s, 3H), 1.49(s, 3H), 2.60(s, 3H), 2.93-3.32(m, 4H), 4.05(m, 1H), 4.65(d, J=9.4 Hz, 1H), 6.05(s, 2H), 6.28(br s, 1H), 7.22-7.34(m, 5H), 7.43(s, 2H), 8.32(s, 1H)

MS ($ESI^+$) m/z; 397 $[M+1]^+$

MS (ESI−) m/z; 441 $[M+45]^+$

Synthesis Example 7

(±)-trans-3-Hydroxy-2,2,9-trimethyl-4-[(2-phenylethyl)amino]-3,4-dihydro-2H-pyrano[2,3-g]quinoline-7-carbonitrile 1 maleate

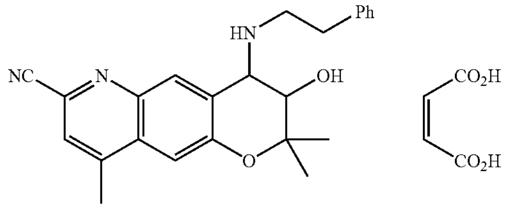

2,2,9-Trimethyl-2H-pyrano[2,3-g]quinoline-7-carbonitrile

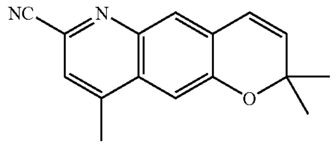

To a solution of 2,2,9-trimethyl-2H-pyrano[2,3-g]quinoline (4.36 g, 19.3 mmol) in chloroform (43.6 mL), a solution of m-chloroperbenzoic acid (7.35 g, 42.6 mmol) in chloroform (17.4 mL)-methanol (4.36 mL) was added dropwise at room temperature and the resulting mixture was stirred at room temperature for 1 hour. Upon the completion of the reaction, the reaction solution was extracted with sodium thiosulfate aqueous solution and the resulting organic phase was washed with sodium hydrogencarbonate aqueous solution and then with sodium chloride aqueous solution, and dried over anhydrous magnesium sulfate. After distilling off the solvent, acetonitrile (19.3 mL), trimethylsilylnitrile (7.27 mL, 57.9 mmol) and triethylamine (5.38 mL, 38.6 mmol) were added to the residue at room temperature, and the resulting solution was stirred at 70° C. for 3.5 hours. Upon the completion of the reaction, sodium hydrogencarbonate aqueous solution was added to the reaction solution, and it was extracted with chloroform and dried over anhydrous magnesium sulfate. After distilling off the solvent, the residue was purified by column chromatography (hexane/ethyl acetate=2/1) and the aimed product was obtained (yield: 55%).

Pale yellow solid $^1$H-NMR ($CDCl_3$) δ; 1.52(s, 6H), 2.62(d, J=0.6 Hz, 3H), 5.97(d, J=9.9 Hz, 1H), 6.58(d, J=9.9 Hz, 1H), 7.23(s, 1H), 7.40(s, 1H), 7.71(s, 1H)

MS ($ESI^+$) m/z; 251 $[M+1]^+$ (±)-trans-3-Bromo-4-hydroxy-2,2,9-trimethyl-2H-pyrano[2, 3-g]quinoline-7-carbonitrile

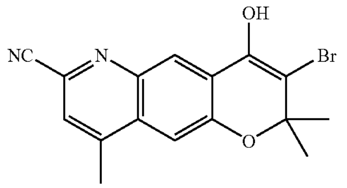

Hereinafter, the aimed compound was synthesized according to the process of Synthesis Example 1.

(Yield: 36%)

MS ($ESI^+$) m/z; 349 $[M+1]^+$ (±)-trans-3-Hydroxy-2,2,9-trimethyl-4-[(2-phenylethyl)amino]-3,4-dihydro-2H-pyrano[2,3-g]quinoline-7-carbonitrile 1 maleate White crystal mp: 218-220° C. (decomposition)

$^1$H-NMR (DMSO-$d_6$) δ; 1.20(s, 3H), 1.51(s, 3H), 2.65(s, 3H), 2.96-3.33(m, 4H), 4.04-4.06(m, 1H), 4.64(br s, 1H), 6.05(s, 2H), 6.29(br s, 1H), 7.25-7.31(m, 5H), 7.50(s, 1H), 7.85(s, 1H), 8.49(s, 1H)

MS ($ESI^+$) m/z; 388 $[M+1]^+$

MS (ESI−) m/z; 432 $[M+45]^+$

Synthesis Example 8

(±)-trans-3,3-Dimethyl-1-[(2-phenylethyl)amino]-2,3-dihydro-1H-pyrano[3,2-f]quinolin-2-ol

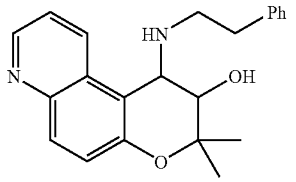

6-[(1,1-dimethyl-2-propynyl)oxy]quinoline

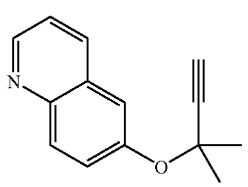

A solution of 2-methyl-3-butyn-2-ol (2.45 mL, 25.1 mmol) and 1,8-diazabicyclo-[5.4.0]-7-undecene (4.25 mL, 28.4 mmol) in acetonitrile (15.5 mL) was stirred 0° C. for 30 minutes, and anhydrous trifluoroacetic acid (3.55 mL, 25.1 mmol) was added dropwise. The resulting mixture was added dropwise to a mixed solution of 6-hydroxyquinoline (2.43 g, 16.7 mmol), copper (I) chloride (8.3 mg, 0.0835 mmol), acetonitrile (15.5 mL) and 1,8-diazabicyclo-[5.4.0]-7-undecene (4.25 mL, 28.4 mmol) at 0° C., and stirred at 0° C. for 3 hours. The resulting solution was acidified with 1 mol/L HCl and extracted with ethyl acetate, and the resulting aqueous phase was neutralized with sodium hydrogencarbonate aqueous solution, extracted with ethyl acetate, and dried over anhydrous magnesium sulfate. After distilling off the solvent, the residue was purified by column chromatography (hexane/ethyl acetate=1/1 to 1/3) and the aimed product was obtained.

Pale yellow solid mp: 65-67° C.

$^1$H-NMR ($CDCl_3$) δ; 1.86(s, 6H), 2.70(s, 1H), 7.69-7.71 (2H), 7.80(s, 1H), 8.33(d, J=8.3 Hz, 1H), 8.45(d, J=8.3 Hz 1H), 9.01(br s, 1H)

MS (EI) m/z; 211 $[M]^{30}$ 3,3-Dimethyl-3H-pyrano[3,2-f]quinoline

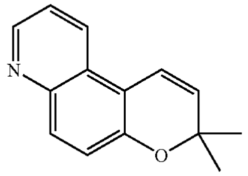

A solution of 6-[(1,1-dimethyl-2-propynyl)oxy]quinoline (16.7 mmol) in 1,2-dichlorobenzene (10 mL) was stirred at 180° C. for 1 hour. Upon the completion of the reaction, the solvent was distilled off, and the residue was recrystallized with hexane-ethyl acetate to obtain the aimed compound (2-step, quant.).

Green crystal mp: 104-107° C.

$^1$H-NMR ($CDCl_3$) δ; 1.54(s, 6H), 5.89(d, J=10.2 Hz, 1H), 6.93(d, J=10.2 Hz, 1H), 7.50(d, J=9.1 Hz, 1H), 7.73(br s, 1H), 8.31(d, J=9.1 Hz, 1H), 8.74(d, J=8.5 Hz, 1H), 9.03(br s, 1H)

MS (EI) m/z; 211 $[M]^+$ (±)-trans-3,3-dimethyl-1-[(2-phenylethyl)amino]-2,3-dihydro-1H-pyrano[3,2-f]quinolin-2-ol Hereinafter, the aimed compound was synthesized according to the process of Synthesis Example 1.

mp: 180-182° C.

$^1$H-NMR ($CDCl_3$) δ; 1.32(s, 3H), 1.44(s, 3H), 1.63(br s, 1H), 2.43(br s, 1H), 2.69-2.84(m, 3H), 2.92-2.97(m, 1H), 3.83(d, J=5.0 Hz, 1H), 4.09(d, J=5.5 Hz, 1H), 7.10-7.29(m, 6H), 7.86(d, J=9.1 Hz, 1H), 8.13(d, J=7.7 Hz, 1H), 8.71(dd, J=1.7 Hz, 4.1 Hz, 1H)

MS ($ESI^+$) m/z; 349 $[M+1]^+$

MS (ESI−) m/z; 393 $[M+45]^+$

Synthesis Example 9

(±)-trans-8-Chloro-3,3-dimethyl-1-[(2-phenylethyl)amino]-2,3-dihydro-1H-pyrano[3,2-f]quinolin-2-ol

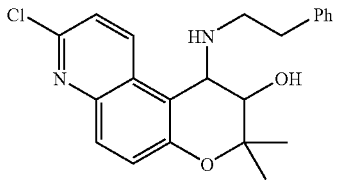

By use of 3,3-dimethyl-3H-pyrano[3,2-f]quinoline, the aimed compound was synthesized similarly to the process of Synthesis Example 6.

8-Chloro-3,3-dimethyl-3H-pyrano[3,2-f]quinoline

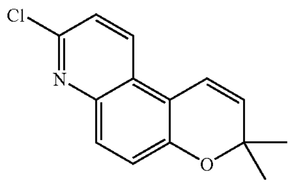

(Yield: 82%)

Red-brown oily product $^1$H-NMR ($CDCl_3$) δ; 1.49(s, 6H), 5.77(d, J=9.9 Hz, 1H), 6.87(d, J=9.9 Hz, 1H), 7.27(d, J=9.1 Hz, 1H), 7.34(d, J=8.8 Hz, 1H), 7.80(d, J=9.1 Hz, 1H), 8.19(d, J=8.8 Hz, 1H)

MS ($ESI^+$) m/z; 246 $[M+1]^+$ (±)-trans-2-Bromo-8-chloro-3,3-dimethyl-2,3-dihydro-1H-pyrano[3,2-f]quinolin-1-ol

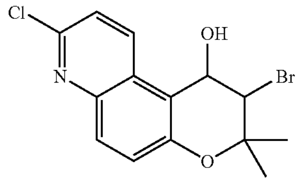

(Yield: 45%)

(±)-trans-8-Chloro-3,3-dimethyl-1-[(2-phenylethyl)amino]-2,3-dihydro-1H-pyrano[3,2-f]quinolin-2-ol (Yield: 60%)
White crystal
mp: 141-143° C.
$^1$H-NMR ($CDCl_3$) δ; 1.28(s, 3H), 1.44(s, 3H), 1.64(br s, 2H), 2.65-2.78(m, 3H), 2.86-2.96(m, 1H), 3.84(d, J=6.1 Hz, 1H), 4.06(d, J=5.8 Hz, 1H), 7.08-7.30(m, 7H), 7.98(d, J=9.1 Hz, 1H), 8.22(d, J=8.8 Hz, 1H)
MS (ESI$^+$) m/z; 383 [M+1]$^+$
MS (ESI−) m/z; 427 [M+45]$^+$ Synthesis Example 10

(±)-trans-2-Hydroxy-3,3-dimethyl-1-[(2-phenylethyl)amino]-2,3-dihydro-1H-pyrano[3,2-f]quinoline-8-carbonitrile

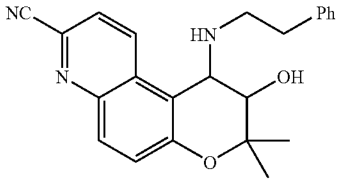

By use of 3,3-dimethyl-3H-pyrano[3,2-f]quinoline, the aimed compound was synthesized similarly to the process of Synthesis Example 7.

3,3-Dimethyl-3H-pyrano[3,2-f]quinoline-8-carbonitrile

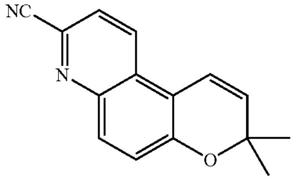

(Yield: quant.)
Yellow solid
$^1$H-NMR ($CDCl_3$) δ; 1.52(s, 6H), 5.80(d, J=9.9 Hz, 1H), 6.89(d, J=10.2 Hz, 1H), 7.37(d, J=9.4 Hz, 1H), 7.65(d, J=8.8 Hz, 1H), 7.95(d, J=9.4 Hz, 1H), 8.64(d, J=8.8 Hz, 1H)
MS (ESI$^+$) m/z; 237 [M+1]$^+$
MS (ESI−) m/z; 235 [M−1]$^+$ (±)-trans-2-Bromo-1-hydroxy-3,3-dimethyl-2,3-dihydro-1H-pyrano[3,2-f]quinoline-8-carbonitrile

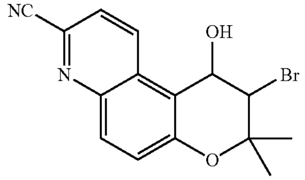

(Yield: 49%)
$^1$H-NMR ($CDCl_3$) δ; 1.50(s, 3H), 1.69(s, 3H), 2.72(d, J=4.1 Hz, 1H), 4.35(d, J=7.2 Hz, 1H), 5.43(dd, J=3.9 Hz, 7.2 Hz, 1H), 7.36(d, J=9.1 Hz, 1H), 7.70(d, J=8.8 Hz, 1H), 8.03 (d, J=9.4 Hz, 1H), 8.72(d, J=8.5 Hz, 1H)
MS (ESI$^+$) m/z; 333, 335 [M+1]$^+$
MS (ESI−) m/z; 379 [M+45]$^+$ (±)-trans-2-Hydroxy-3,3-dimethyl-1-[(2-phenylethyl)amino]-2,3-dihydro-1H-pyrano[3,2-f]quinoline-8-carbonitrile (Yield: 72%)
White crystal
mp: 93-96° C.
$^1$H-NMR ($CDCl_3$) δ; 1.30(s, 3H), 1.46(s, 3H), 1.60(br s, 3H), 2.13(br s, 1H), 2.66-2.79(m, 3H), 2.88-2.98(m, 1H), 3.87(d, J=5.8 Hz, 1H), 4.08(d, J=6.1 Hz, 1H), 7.09(d, J=6.3 Hz, 1H), 7.10(d, J=7.4 Hz, 1H), 7.23-7.27(m, 3H), 7.30(d, J=9.1 Hz, 1H), 7.41(d, J=8.8 Hz, 1H), 7.92(d, J=9.1 Hz, 1H), 8.38(d, J=8.5 Hz, 1H)
MS (ESI$^+$) m/z; 374 [M+1]$^+$
MS (ESI−) m/z; 418 [M+45]$^+$ Synthesis Example 11

(±)-trans-2-Hydroxy-3,3-dimethyl-1-[(2-phenylethyl)amino]-2,3-dihydro-1H-pyrano[3,2-f]quinoline-8-carboxamide

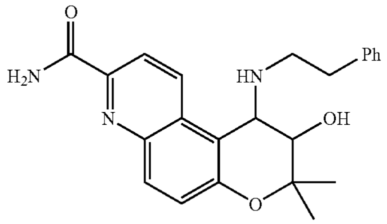

To a solution of (±)-trans-2-hydroxy-3,3-dimethyl-1-[(2-phenylethyl)amino]-2,3-dihydro-1H-pyrano[3,2-f]quinoline-8-carbonitrile (400 mg, 1.07 mmol) in t-butanol (40 mL), potassium hydroxide (800 mg, 14.3 mmol) was added at room temperature and the resulting mixture was stirred at 90° C. for 2 hour. Upon the completion of the reaction, sodium chloride aqueous solution was added to the reaction solution, and it was extracted with ethyl acetate and the resulting organic phase was dried over anhydrous magnesium sulfate. After distilling off the solvent, the residue was purified by column chromatography (hexane/ethyl acetate=1/1) and recrystallized with hexane-ethyl acetate to obtain the aimed product (yield: 54%).

White crystal mp: 197-199° C.

$^1$H-NMR ($CDCl_3$) δ; 1.32(s, 3H), 1.47(s, 3H), 1.71(br s, 2H), 2.29(br s, 1H), 2.69-2.76(m, 3H), 2.89-2.97(m, 1H), 3.86(br s, 1H), 4.13(d, J=5.8 Hz, 1H), 5.62(br s, 1H), 7.10(d, J=6.9 Hz, 1H), 7.10(d, J=7.4 Hz, 1H), 7.20-7.28(m, 4H), 7.89(d, J=9.4 Hz, 1H), 7.98(br s, 1H), 8.07(d, J=8.8 Hz, 1H), 8.31(d, J=8.8 Hz, 1H)

MS ($ESI^+$) m/z; 392 $[M+1]^+$

MS (ESI−) m/z; 436 $[M+45]^+$

Synthesis Example 12

(3R*,4S*)-2,2,7,9-tetramethyl-1-[(2-phenylethyl)amino]-3,4-dihydro-2H-pyrano[2,3-g]quinolin-3-ol 1 maleate

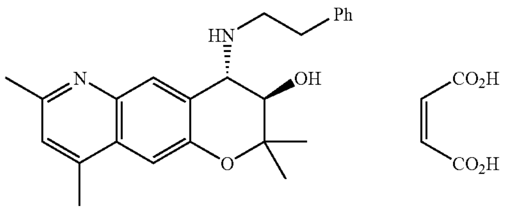

(3R*,4R*)-3,4-epoxy-2,2,7,9-tetramethyl-3,4-dihydro-2H-pyrano[2,3-g]quinoline

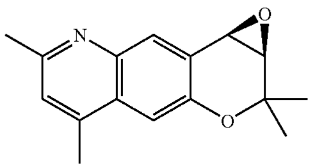

To a solution of 2,2,7,9-tetramethyl-2H-pyrano[2,3-g]quinoline (4.64 g, 19.4 mmol) in ethyl acetate (70 mL), N-methyl imidazole (0.303 mL, 3.88 mmol) and Ph,Ph salen manganese complex (201 mg, 0.194 mmol) were added at room temperature and sodium hypochlorite aqueous solution (25.6 g, 1.513 mol/kg, 38.8 mmol) was added dropwise in water bath, and the resulting mixture was stirred in water bath for 1 hour. Further, in water bath, sodium hypochlorite aqueous solution (25.6 g, 1.513 mol/kg, 38.8 mmol) was added, and the resulting mixture was stirred in water bath for 1 hour. Upon the completion of the reaction, sodium thiosulfate aqueous solution was added to the reaction solution, the resulting mixture was filtered through celite and extracted. The organic phase was washed with sodium hydrogencarbonate aqueous solution and then with sodium chloride aqueous solution, and then dried over anhydrous magnesium sulfate. After distilling off the solvent, the residue was purified by column chromatography (hexane/ethyl acetate=1/3) and the aimed product was obtained (yield: 68%).

>99.9% ee; CHIRALPAK AD-RH 20 mM phosphate buffer (pH 8.0)/acetonitrile=60/40, Retention time: 5.7 min.

$^1$H-NMR ($CDCl_3$) δ; 1.30(s, 3H), 1.64(s, 3H), 2.56(s, 3H), 2.66(s, 3H), 3.59(d, J=4.4 Hz, 1H), 4.14(d, J=4.4 Hz, 1H), 7.08(s, 1H), 7.29(s, 1H), 8.04(s, 1H)

MS ($ESI^+$) m/z; 256 $[M+1]^+$ (3R*,4S*)-2,2,7,9-tetramethyl-4-[(2-phenylethyl)amino]-3,4-dihydro-2H-pyrano[2,3-g]quinolin-3-ol 1 maleate To a solution of (3R*,4S*)-3,4-epoxy-2,2,7,9-tetramethyl-3,4-dihydro-2H-pyrano[2,3-g]quinoline (0.80 g, 3.14 mmol) in 1,4-dioxane (1.6 mL), lithium perchlorate (334 mg, 3.14 mmol) and 2-phenylethylamine (0.473 mL, 3.77 mmol) were added at room temperature and the resulting mixture was stirred at 70° C. for 1 hour. Upon the completion of the reaction, sodium hydrogencarbonate aqueous solution was added to the reaction solution, and it was extracted with ethyl acetate and the resulting organic phase was washed with sodium hydrogencarbonate aqueous solution and then with sodium chloride aqueous solution, and then dried over anhydrous magnesium sulfate. After distilling off the solvent, the residue was purified by column chromatography (ethyl acetate). Further, after distilling off the solvent, ethyl acetate (2 mL) was added and a solution of maleic acid (376 mg, 3.23 mmol) in ethyl acetate (8 mL) was added dropwise. The resulting precipitated solid was filtered to obtain the aimed product (yield: 86%).

White crystal mp: 215-219° C. (decomposition)

$^1$H-NMR (DMSO-$d_6$) δ; 1.16(s, 3H), 1.49(s, 3H), 2.55(s, 3H), 2.58(s, 3H), 2.93-3.39(m, 4H), 4.07(dd, J=6.4 Hz, 9.4 Hz, 1H), 4.64(d, J=9.4 Hz, 1H), 6.05(s, 2H), 6.27(d, J=5.8 Hz, 1H), 7.24-7.26(m, 4H), 7.30(s, 1H), 7.33(s, 1H), 7.36(s, 1H), 8.31(s, 1H)

MS ($ESI^+$) m/z; 377 $[M+1]^+$

MS (ESI−) m/z; 421 $[M+45]^+$

Synthesis Example 13

(3R*,4S*)-2,2,7-trimethyl-4-[(2-phenylethyl)amino]-3,4-dihydro-2H-pyrano[2,3-g]quinolin-3-ol 1 maleate

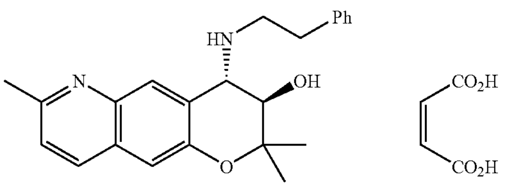

This compound was synthesized according to the process of Synthesis Example 12.

(3R*,4R*)-3,4-epoxy-2,2,7-trimethyl-3,4-dihydro-2H-pyrano[2,3-g]quinoline

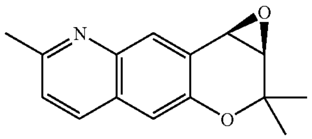

99.3% ee; CHIRALPAK AD-RH 20 mM phosphate buffer (pH 8.0)/acetonitrile=60/40, Retention time: 6.2 min.

$^1$H-NMR ($CDCl_3$) δ; 1.28(s, 3H), 1.64(s, 3H), 2.71(s, 3H), 3.59(d, J=4.4 Hz, 1H), 4.15(d, J=4.4 Hz, 1H), 7.13(s, 1H), 7.23(d, J=8.5 Hz, 1H), 7.91(d, J=8.5 Hz, 1H), 8.05(s, 1H)

MS ($ESI^+$) m/z; 242 $[M+1]^+$ (3R*,4S*)-2,2,7-trimethyl-4-[(2-phenylethyl)amino]-3,4-dihydro-2H-pyrano[2,3-g]quinolin-3-ol 1 maleate White crystal mp: 214-217° C. (decomposition)

$^1$H-NMR (DMSO-$d_6$) δ; 1.15(s, 3H), 1.48(s, 3H), 2.62(s, 3H), 2.93-3.14 (m, 4H), 4.03-4.07(m, 1H), 4.61(br s, 1H), 6.04(s, 2H), 6.23(br s, 1H), 7.23-7.39(m, 7H), 8.09(d, J=8.5 Hz, 1H), 8.31(s, 1H)

MS ($ESI^+$) m/z; 363 $[M+1]^+$

MS (ESI−) m/z; 407 $[M+45]^+$

Synthesis Example 14

(3R*,4R*)-3-hydroxy-2,2,9-trimethyl-4-[(2-phenylethyl)amino]-3,4-dihydro-2H-pyrano[2,3-g]quinoline-7-carbonitrile 1 maleate

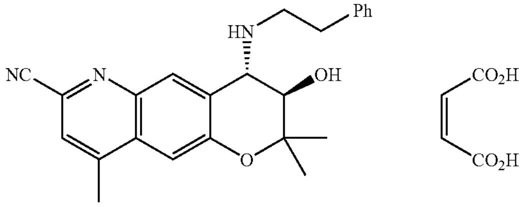

This compound was synthesized according to the process of Synthesis Example 12.

(3R*,4R*)-3,4-epoxy-3-hydroxy-2,2,9-trimethyl-3,4-dihydro-2H-pyrano[2,3-g]quinoline-7-carbonitrile

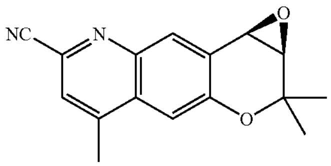

(Yield: 33%)

99.1% ee; CHIRALCEL OJ-R acetonitril/methanol/0.01 M sodium chloride aqueous solution=1/3/3, Retention time: 18.6 min.

$^1$H-NMR ($CDCl_3$) δ; 1.33(s, 3H), 1.66(s, 3H), 2.65(s, 3H), 3.64(d, J=4.1 Hz, 1H), 4.17(d, J=4.4 Hz, 1H), 7.33(s, 1H), 7.47(s, 1H), 8.18(s, 1H)

MS ($ESI^+$) m/z; 267 $[M+1]^+$

MS (ESI−) m/z; 265 $[M-1]^+$ (3R*,4S*)-3-hydroxy-2,2,9-trimethyl-4-[(2-phenylethyl)amino]-3,4-dihydro-2H-pyrano[2,3-g]quinoline-7-carbonitrile 1 maleate (Yield: 23%)

Pale brown crystal $^1$H-NMR (DMSO-$d_6$) δ; 1.20(s, 3H), 1.52(s, 3H), 2.66(s, 3H), 2.98-3.33(m, 4H), 4.09(m, 1H), 4.71(br s, 1H), 6.09(s, 2H), 6.33(br s, 1H), 7.23-7.34(m, 5H), 7.51(s, 1H), 7.86(s, 1H), 8.51(s, 1H)

MS ($ESI^+$) m/z; 388 $[M+1]^+$

MS (ESI−) m/z; 432 $[M+45]^+$

Synthesis Example 15

(3R*,4S*)-3-hydroxy-2,2,9-trimethyl-4-[(2-phenylethyl)amino]-3,4-dihydro-2H-pyrano[2,3-g]quinoline-7-carboxamide

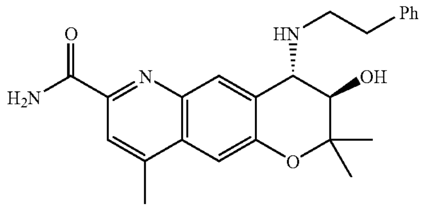

This compound was synthesized from (3R*,4S*)-3-hydroxy-2,2,9-trimethyl-4-[(2-phenylethyl)amino]-3,4-dihydro-2H-pyrano[2,3-g]quinoline-7-carbonitrile similarly to the process of Synthesis Example 11 (yield: 9%).

White crystal mp: 168-169° C.

$^1$H-NMR ($CDCl_3$) δ; 1.26(s, 3H), 1.57(s, 3H), 1.83(br s, 2.65(s, 2H), 2.90-3.16(m, 4H), 3.66(d, J=10.2 Hz, 1H), 3.95 (d, J=10.5 Hz, 1H), 5.61(br s, 1H), 7.24-7.36(m, 5H), 7.85(s, 1H), 8.00(br s, 1H), 8.04(s, 1H)

MS ($ESI^+$) m/z; 406 $[M+1]^+$

MS (ESI−) m/z; 450 $[M+45]^+$

Synthesis Example 16

(3R*,4S*)-{3-hydroxy-2,2,9-trimethyl-4-[(2-phenylethyl)amino]-3,4-dihydro-2H-pyrano[2,3-g]quinolin-7-yl}ethanone 1 maleate

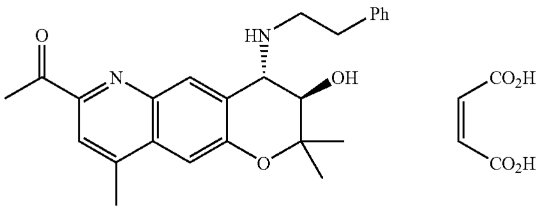

This compound was synthesized according to the process of Synthesis Example 12.

(3R*,4S*)-{3-hydroxy-2,2,9-trimethyl-4-[(2-phenylethyl)amino]-3,4-dihydro-2H-pyrano[2,3-g]quinolin-7-yl}ethanone

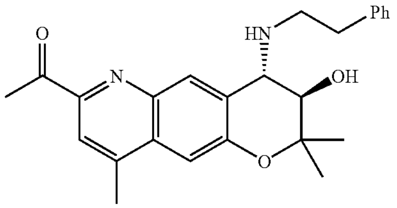

To a solution of (3R*,4S*)-3-hydroxy-2,2,9-trimethyl-4-[(2-phenylethyl)amino]-3,4-dihydro-2H-pyrano[2,3-g] quinoline-7-carbonitrile (120 mg, 0.309 mmol) in benzene (1.6 mL)-diethyl ether (1.4 mL), a solution of 3.0 M methyl magnesium bromide in diethyl ether (0.30 mL) was added dropwise in ice bath, and the resulting mixture was stirred in ice bath for 2 hours. In ice bath, a solution of 3.0 M methyl magnesium bromide in diethyl ether (0.50 mL) was added dropwise, and the resulting mixture was further stirred for 30 minutes. Upon the completion of the reaction, ammonium chloride aqueous solution was added and the resulting solution was extracted with ethyl acetate. The resulting organic phase was dried over anhydrous magnesium sulfate. After distilling off the solvent, the residue was purified by column chromatography and the aimed product was obtained (yield: 25%).

$^1$H-NMR ($CDCl_3$) δ; 1.19(s, 3H), 1.49(s, 3H), 2.53(d, J=0.83 Hz, 3H), 2.76(s, 3H), 2.77-3.06(m, 5H), 3.55(d, J=10.5 Hz, 1H), 3.81(dd, J=1.4 Hz, 10.5 Hz, 1H), 7.15-7.29 (m, 6H), 7.78(s, 1H), 7.85(d, J=1.4 Hz, 1H)

MS ($ESI^+$) m/z; 405 $[M+1]^+$ (3R*,4S*)-{3-hydroxy-2,2,9-trimethyl-4-[(2-phenylethyl)amino]-3,4-dihydro-2H-pyrano[2,3-g]quinoline-7-yl}ethanone 1 maleate To a solution of (3R*,4S*)-{3-hydroxy-2,2,9-trimethyl-4-[(2-phenylethyl)amino]-3,4-dihydro-2H-pyrano[2,3-g] quinoline-7-yl}ethanone (31.3 mg, 0.077 mmol) in ethyl acetate (2 mL), a solution of maleic acid (10.0 mg, 0.086 mmol) in ethyl acetate (2 mL) was added dropwise, and precipitated solid was filtered to obtain the aimed product (yield: 80%).

White crystal mp: 230-234° C. (decomposition)

$^1$H-NMR (DMSO-$d_6$) δ; 1.18(s, 3H), 1.51(s, 3H), 2.66(s, 3H), 2.74(s, 3H), 2.98-3.34(m, 4H), 4.10(m, 1H), 4.66(br s, 1H), 6.05(s, 2H), 6.29(br s, 1H), 7.25-7.36(m, 5H), 7.48(s, 1H), 7.87(s, 1H), 8.56(s, 1H)

Synthesis Example 17

(1R*,2R*)-3,3-dimethyl-1-[(2-phenylethyl)amino]-2,3-dihydro-1H-pyrano[3,2-f]quinolin-2-ol

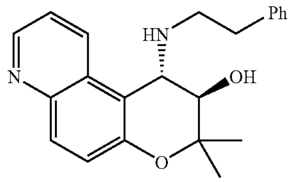

his compound was synthesized according to the process of Synthesis Example 12.

(Yield: 2-Step, 4%)

White crystal mp: 170-171° C.

$^1$H-NMR ($CDCl_3$) δ; 1.31(s, 3H), 1.45(s, 3H), 1.61(br s, 6H), 2.71-2.84(m, 3H), 2.91-2.97(m, 1H), 3.83(d, J=5.5 Hz, 1H), 4.11(d, J=5.5 Hz, 1H), 7.12(d, J=7.98 Hz, 1H), 7.18-7.25(m, 5H), 7.90(d, J=9.1 Hz, 1H), 8.15(d, J=8.5 Hz, 1H), 8.73(dd, J=1.4 Hz, 4.1 Hz, 1H)

MS ($ESI^+$) m/z; 349 $[M+1]^+$

MS (ESI−) m/z; 393 $[M+45]^+$

Epoxy form, 97.1% ee; CHIRALCEL OJ-R acetonitril/methanol/0.01 M sodium chloride aqueous solution=1/3/3, Retention time: 7.0 min.

Synthesis Example 18

(3R*,4S*)-7-hydroxymethyl-2,2,9-trimethyl-4-[(2-phenylethyl)amino]-3,4-dihydro-2H-pyrano[2,3-g] quinolin-3-ol 1 maleate

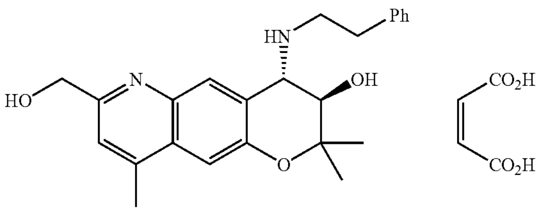

This compound was synthesized according to the process of Synthesis Example 12.

(2,2,9-trimethyl-2H-pyrano[2,3-g]quinolin-7-yl)-methyl acetate

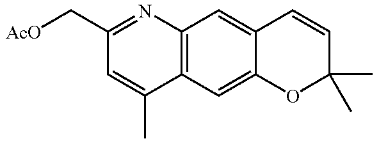

To a solution of 2,2,7,9-tetramethyl-2H-pyrano[2,3-g]quinoline (3.0 g, 12.5 mmol) in chloroform (30.0 mL), a solution of m-chloroperbenzoic acid (4.76 g, 27.6 mmol) in chloroform (12 mL)-methanol (3 mL) was added dropwise at room temperature, and the resulting mixture was stirred at room temperature for 30 minutes. Upon the completion of the reaction, sodium thiosulfate aqueous solution was added to the reaction solution, and it was extracted. The resulting organic phase was washed with sodium hydrogencarbonate and then with sodium chloride aqueous solution, and dried over anhydrous magnesium sulfate. After distilling off the solvent, acetic anhydride (12 mL) was added to the residue, and the resulting mixture was stirred at 150° C. for 1 hour. Upon the completion of the reaction, acetic anhydride was distilled off, the residue was neutralized with sodium carbonate aqueous solution, extracted with chloroform, and the resulting organic phase was washed with sodium chloride aqueous solution, and dried over anhydrous magnesium sulfate. After distilling off the solvent, the residue was purified by medium pressure column chromatography (hexane/ethyl acetate=2/1) and the aimed product was obtained (yield: 64%).

Black oily product $^1$H-NMR ($CDCl_3$) δ; 1.50(s, 6H), 2.17(s, 3H), 2.61(s, 3H), 5.30(s, 2H), 5.90(d, J=9.91 Hz, 1H), 6.57(d, J=9.9 Hz, 1H), 7.19(s, 1H), 7.24(s, 1H), 7.70(s, 1H)

MS (ESI$^+$) m/z; 298 [M+1]$^+$ (3R*,4R*)-(3,4-epoxy-2,2,9-trimethyl-3,4-dihydro-2H-pyrano[2,3-g]quinolin-7-yl)-methyl acetate

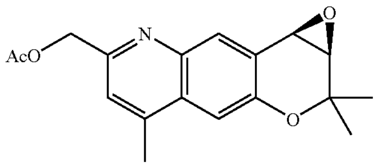

>99.9% ee; CHIRALPAK AD-RH 20 mM phosphate buffer (pH 8.0)/acetonitrile=60/40, Retention time: 5.4 min.

MS (ESI$^+$) m/z; 314 [M+1]$^+$ (3R*,4S*)-7-hydroxymethyl-2,2,9-trimethyl-4-[(2-phenylethyl)amino]-3,4-dihydro-2H-pyrano[2,3-g]quinolin-3-ol

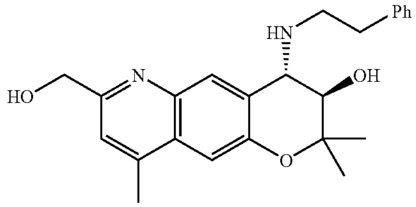

To a solution of (3R*,4R*)-(3,4-epoxy-2,2,9-trimethyl-3,4-dihydro-2H-pyrano[2,3-g]quinolin-7-yl)-methyl acetate (403 mg, 1.29 mmol) in 1,4-dioxane (1 mL), lithium perchlorate (137 mg, 1.29 mmol) and phenylethylamine (0.195 mL, 1.55 mmol) were added at room temperature and the resulting mixture was stirred at 70° C. for 1.5 hour. Upon the completion of the reaction, sodium hydrogencarbonate aqueous solution was added to the reaction solution, and it was extracted with ethyl acetate. The resulting organic phase was washed with sodium hydrogencarbonate aqueous solution and then with sodium chloride aqueous solution, and dried over anhydrous magnesium sulfate. After distilling off the solvent, the residue was purified by medium pressure column chromatography (hexane/ethyl acetate=1/1) and the aimed product was obtained (yield: 32%).

$^1$H-NMR ($CDCl_3$) δ; 1.24(s, 3H), 1.55(s, 3H), 2.58(s, 3H), 2.87-3.08(m, 5H), 3.63(d, J=10.2 Hz, 1H), 3.81(d, J=10.5 Hz, 1H), 4.82(s, 2H), 7.02(s, 1H), 7.23-7.36(m, 6H), 7.75(s, 1H) MS (ESI$^+$) m/z; 393 [M+1]$^+$

MS (ESI−) m/z; 437 [M+45]$^+$ (3R*,4S*)-7-hydroxymethyl-2,2,9-trimethyl-4-[(2-phenylethyl)amino]-3,4-dihydro-2H-pyrano[2,3-g]quinolin-3-ol 1 maleate To a solution of (3R*,4S*)-7-hydroxymethyl-2,2,9-trimethyl-4-[(2-phenylethyl)amino]-3,4-dihydro-2H-pyrano[2,3-g]quinolin-3-ol (157 mg, 0.407 mmol) in ethyl acetate (4 mL), a solution of maleic acid (52 mg, 0.448 mmol) in ethyl acetate (2 mL) was added dropwise, and precipitated solid was filtered to obtain the aimed compound (yield: 80%).

Pale yellow crystal mp: 216-221° C.

$^1$H-NMR (DMSO-$d_6$) δ; 1.17(s, 3H), 1.50(s, 3H), 2.60(s, 3H), 2.98-3.40(m, 4H), 4.06-4.11(m, 1H), 3.81(d, J=10.5 Hz, 1H), 4.66-4.69(3H), 5.50(br s, 1H), 6.06(s, 2H), 6.30(br s, 1H), 7.23-7.35(m, 5H), 7.40(s, 1H), 7.47(s, 1H), 8.35(s, 1H)

Synthesis Example 19

(3R*,4S*)-7-chloro-2,2,9-trimethyl-4-[(2-phenylethyl)amino]-3,4-dihydro-2H-pyrano[2,3-g]quinolin-3-ol 1 maleate

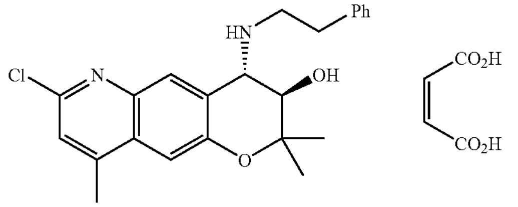

This compound was synthesized according to the process of Synthesis Example 12.

(3R*,4R*)-7-chloro-3,4-epoxy-2,2,9-trimethyl-3,4-dihydro-2H-pyrano[2,3-g]quinoline

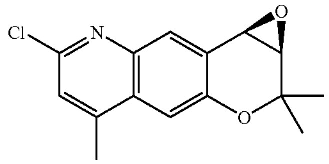

(Yield: 78%)

99.1% ee; CHIRALCEL OJ-R acetonitril/methanol/0.01 M sodium chloride aqueous solution=1/3/3, Retention time: 18.9 min.

Yellow amorphous product $^1$H-NMR ($CDCl_3$) δ; 1.28(s, 3H), 1.65(s, 3H), 2.59(d, J=0.8 Hz, 3H), 3.60(d, J=4.4 Hz, 1H), 4.13(d, J=4.4 Hz, 1H), 7.19(s, 1H), 7.29(d, 1H), 8.02(s, 1H)

MS ($ESI^+$) m/z; 276 $[M+1]^+$

(3R*,4S*)-7-chloro-2,2,9-trimethyl-4-[(2-phenylethyl)amino]-3,4-dihydro-2H-pyrano[2,3-g]quinolin-3-ol 1 maleate (2-step, yield: 34%)

Synthesis Examples 20-49

Synthesis Examples 20-49 were carried out similarly to the process of Synthesis Example 19.

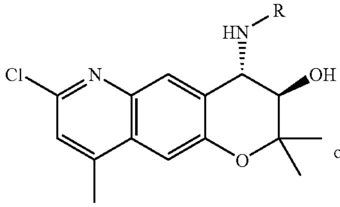

optically active

| Compound No. | 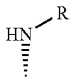 |
| --- | --- |
| Synthesis Example 20 | 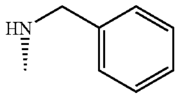 |
| Synthesis Example 21 | 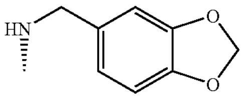 |
| Synthesis Example 22 | 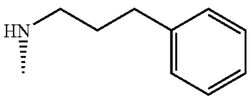 |
| Synthesis Example 23 | 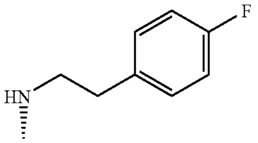 |
| Synthesis Example 24 | 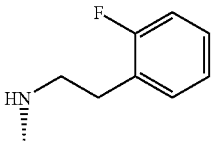 |
| Synthesis Example 25 | 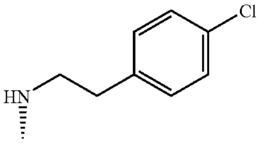 |
| Synthesis Example 26 | 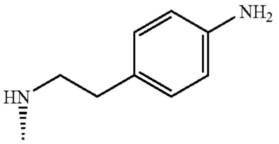 |
| Synthesis Example 27 | 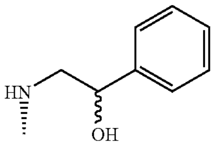 |
| Synthesis Example 28 | 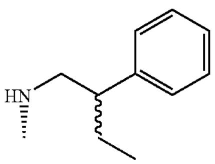 |

-continued

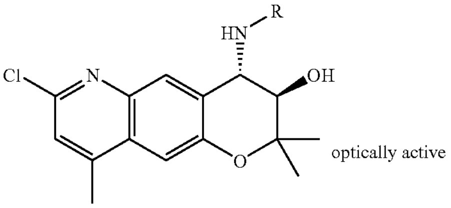

| Compound No. | 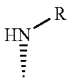 |
|---|---|
| Synthesis Example 29 | 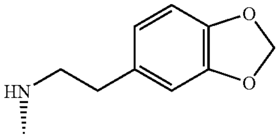 |
| Synthesis Example 30 | 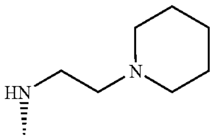 |
| Synthesis Example 31 | 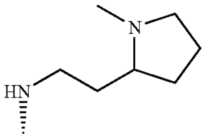 |
| Synthesis Example 32 | 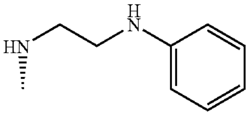 |
| Synthesis Example 33 | 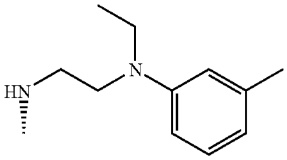 |
| Synthesis Example 34 | 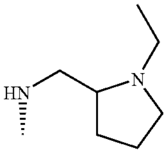 |
| Synthesis Example 35 | 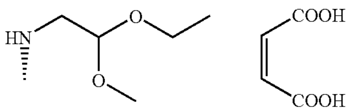 |
| Synthesis Example 36 | 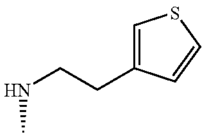 |
| Synthesis Example 37 | 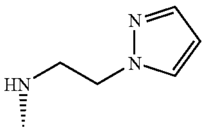 |

-continued

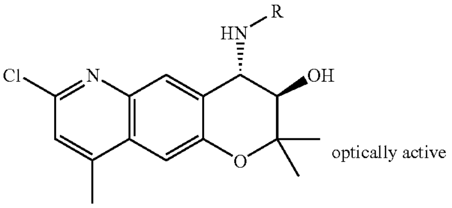

| Compound No. | 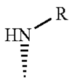 |
|---|---|
| Synthesis Example 38 | 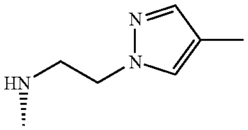 |
| Synthesis Example 39 | 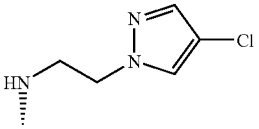 |
| Synthesis Example 40 | 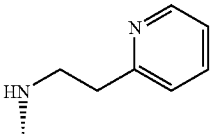 |
| Synthesis Example 41 | 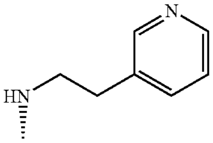 |
| Synthesis Example 42 | 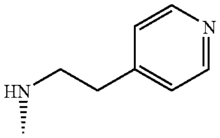 |
| Synthesis Example 43 | 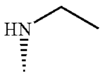 |
| Synthesis Example 44 | 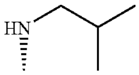 |
| Synthesis Example 45 | 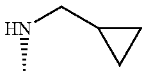 |
| Synthesis Example 46 | 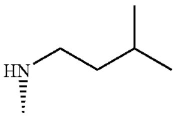 |
| Synthesis Example 47 | 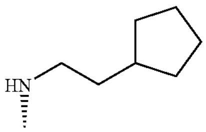 |

-continued

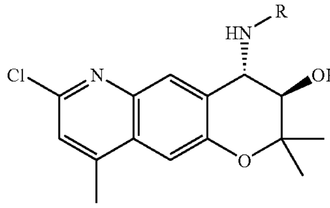

optically active

| Compound No. | 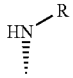 |
|---|---|
| Synthesis Example 48 | 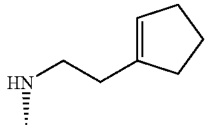 |
| Synthesis Example 49 | 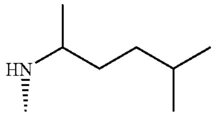 |

Synthesis Example 20

(3R*,4S*)-4-(benzylamino)-7-chloro-2,2,9-trimethyl-3, 4-dihydro-2H-pyrano[2,3-g]quinolin-3-ol (Yield: 81%)

Colorless amorphous product $^1$H-NMR ($CDCl_3$) δ: 1.28 (s, 3H), 1.58 (s, 3H), 1.60 (br s, 1H), 2.60 (s, 3H), 3.12 (s, 1H), 3.72 (d, J=10.3 Hz, 1H), 3.91 (d, J=10.3 Hz, 1H), 3.85-4.00 (m, 2H), 7.17 (s, 1H), 7.30-7.40 (m, 6H), 8.08 (s, 1H).

MS ($ESI^+$) m/z; 383 $[M+1]^+$

MS ($ESI^-$) m/z; 427 $[M+45]^+$

Synthesis Example 21

(3R*,4S*)-7-chloro-4-{[(2-(1,3-benzodioxol-5-yl) methyl]amino}-2,2,9-trimethyl-3,4-dihydro-2H-pyrano[2,3-g]quinolin-3-ol (Yield: 92%)

Pale yellow amorphous product $^1$H-NMR ($CDCl_3$) δ: 1.28 (s, 3H), 1.57 (s, 3H), 2.59 (s, 3H), 3.70 (d, J=10.3 Hz, 1H), 3.82 (Abq, J=12.8 Hz, 2H), 3.97 (dd, J=10.3, 1.2 Hz, 1H), 5.96 (s, 2H), 6.77 (d, J=8.0 Hz, 1H), 6.82 (dd, J=8.0, 1.6 Hz, 1H), 6.89 (d, J=1.6 Hz, 1H), 7.13 (s, 1H), 7.30 (s, 1H), 8.04 (s, 1H)

MS ($ESI^+$) m/z; 427 $[M+1]^+$

Synthesis Example 22

(3R*,4S*)-7-chloro-2,2,9-trimethyl-4-[(3-phenylpropyl)amino]-3,4-dihydro-2H-pyrano[2,3-g]quinolin-3-ol (Yield: 72%)

Colorless amorphous product $^1$H-NMR ($CDCl_3$) δ: 1.28 (s, 3H), 1.57 (s, 3H), 1.80-1.95 (m, 2H), 2.59 (s, 3H), 2.65-2.85 (m, 5H), 3.24 (s, 1H), 3.61 (d, J=10.4 Hz, 1H), 3.86 (d, J=10.4 Hz, 1H), 7.10-7.20 (m, 3H), 7.25-7.35 (m, 3H), 7.94 (s, 1H).

MS ($ESI^+$) m/z; 411 $[M+1]^+$

MS ($ESI^-$) m/z; 455 $[M+45]^+$

Synthesis Example 23

(3R*,4S*)-7-chloro-4-{[2-(4-fluorophenyl)ethyl] amino}-2,2,9-trimethyl-3,4-dihydro-2H-pyrano[2,3-g]quinolin-3-ol (Yield: 96%)

Colorless amorphous product $^1$H-NMR ($CDCl_3$) δ: 1.25 (s, 3H), 1.55 (s, 3H), 1.57 (br s, 1H), 2.58 (s, 3H), 2.80 (t, J=6.9 Hz, 2H), 2.90-3.10 (m, 3H), 3.58 (d, J=10.4 Hz, 1H), 3.86 (d, J=10.4 Hz, 1H), 6.95-7.05 (m, 2H), 7.15-7.20 (m, 3H), 7.26 (s, 1H), 7.89 (s, 1H).

MS ($ESI^+$) m/z; 415 $[M+1]^+$

Synthesis Example 24

(3R*,4S*)-7-chloro-4-{[2-(2-fluorophenyl)ethyl] amino}-2,2,9-trimethyl-3,4-dihydro-2H-pyrano[2,3-g]quinolin-3-ol (Yield: 79%)

Colorless amorphous product $^1$H-NMR ($CDCl_3$) δ: 1.25 (s, 3H), 1.54 (s, 3H), 1.61 (br s, 1H), 2.57 (s, 3H), 2.86 (t, J=6.9 Hz, 2H), 2.95-3.10 (m, 3H), 3.56 (d, J=10.4 Hz, 1H), 3.85 (d, J=10.4 Hz, 1H), 7.00-7.25 (m, 6H), 7.90 (s, 1H).

MS ($ESI^+$) m/z; 415 $[M+1]^+$

Synthesis Example 25

(3R*,4S*)-7-chloro-4-{[2-(4-chlorophenyl)ethyl] amino}-2,2,9-trimethyl-3,4-dihydro-2H-pyrano[2,3-g]quinolin-3-ol (Yield: 78%)

Colorless amorphous product

Synthesis Example 26

(3R*,4S*)-4-{([2-(4-aminophenyl)ethyl]amino}-7-chloro-2,2,9-trimethyl-3,4-dihydro-2H-pyrano[2,3-g] quinolin-3-ol (Yield: 40%)

Colorless amorphous product $^1$H-NMR ($CDCl_3$) δ: 1.23 (s, 3H), 1.55 (s, 3H), 1.58 (br s, 3H), 2.57 (s, 3H), 2.71 (t, J=7.4 Hz, 2H), 2.85-3.05 (m, 2H), 3.11 (br s, 1H), 3.57 (d, J=10.4 Hz, 1H), 3.84 (d, J=10.4 Hz, 1H), 6.65 (d, J=8.5 Hz, 2H), 7.01 (d, J=8.5 Hz, 2H), 7.11 (s, 1H), 7.25 (s, 1H), 7.81 (s, 1H).

MS ($ESI^+$) m/z; 412 $[M+1]^+$

MS ($ESI^-$) m/z; 456 $[M+45]^+$

Synthesis Example 27

(3R*,4S*)-7-chloro-4-[(2-hydroxy-2-phenylethyl) amino]-2,2,9-trimethyl-3,4-dihydro-2H-pyrano[2,3-g]quinolin-3-ol (Yield: 72%)

Colorless amorphous product $^1$H-NMR ($CDCl_3$) δ: 1.27 (s, 1.5H), 1.28 (s, 1.5H), 1.56 (s, 3H), 1.77 (br s, 2H), 2.57 (s, 3H), 2.85-3.15 (m, 2H), 3.68 (d, J=10.2 Hz, 1H), 3.75 (d, J=10.2 Hz, 1H), 4.75-4.85 (m, 1H), 7.25 (s, 1H), 7.27-7.40 (s, 6H), 7.99 (s, 0.5H), 8.00 (s, 0.5H).

MS ($ESI^+$) m/z; 413 $[M+1]^+$

MS ($ESI^-$) m/z; 457 $[M+45]^+$

Synthesis Example 28

(3R*,4S*)-7-chloro-2,2,9-trimethyl-4-(2-phenylbutyl)amino-3,4-dihydro-2H-pyrano[2,3-g]quinolin-3-ol (Yield: 50%)

Pale brown amorphous product $^1$H-NMR ($CDCl_3$) δ: 0.86 (t, J=7.3 Hz, 3H), 1.20 (s, 3H), 1.53 (s, 3H), 1.51-1.71 (m, 2H), 2.57 (s, 3H), 2.57-2.64 (m, 1H), 2.86 (dd, J=11.6, 9.1 Hz, 1H), 2.86 (dd, J=11.6, 5.2 Hz, 1H), 3.55 (d, J=10.2 Hz, 1H), 3.74 (d, J=10.2 Hz, 1H), 7.15 (s, 1H), 7.20-7.32 (m, 4H), 7.38 (dd, J=7.1, 7.1 Hz, 2H), 7.74 (s, 1H)

MS ($ESI^+$) m/z; 425 $[M+1]^+$

Synthesis Example 29

(3R*,4S*)-4-{[2-(1,3-benzodioxol-5-yl)ethyl]amino}-7-chloro-2,2,9-trimethyl-3,4-dihydro-2H-pyrano[2,3-g]quinolin-3-ol (Yield: 62%)

Pale brown amorphous product $^1$H-NMR ($CDCl_3$) δ: 1.26 (s, 3H), 1.56 (s, 3H), 1.66 (br, 1H), 2.57 (s, 3H), 2.74 (t, J=6.9 Hz, 2H), 2.89-3.00 (m, 2H), 3.1 (br, 1H), 3.60 (d, J=10.4 Hz, 1H), 3.86 (d, J=10.4 Hz, 1H), 5.95 (Abq, 2H), 6.66-6.77 (m, 3H), 7.15 (s, 1H), 7.26 (s, 1H), 7.83 (s, 1H)

MS ($ESI^+$) m/z; 441 $[M+1]^+$

Synthesis Example 30

(3R*,4S*)-7-chloro-2,2,9-trimethyl-4-{[2-(1-piperidinyl)ethyl]amino}-3,4-dihydro-2H-pyrano[2,3-g]quinolin-3-ol (Yield: 61%)

Pale yellow amorphous product $^1$H-NMR ($CDCl_3$) δ: 1.29 (s, 3H), 1.58 (s, 3H), 1.60 (br s, 2H), 1.50-1.70 (m, 6H), 2.30-2.60 (m, 6H), 2.58 (s, 3H), 3.06 (t, J=5.8 Hz, 2H), 3.54 (d, J=10.4 Hz, 1H), 3.80 (d, J=10.4 Hz, 1H), 7.13 (s, 1H), 7.23 (s, 1H), 8.06 (s, 1H).

MS ($ESI^+$) m/z; 404 $[M+1]^+$

MS ($ESI^-$) m/z; 448 $[M+45]^+$

Synthesis Example 31

(3R*,4S*)-7-chloro-2,2,9-trimethyl-4-{[2-(1-methyl-2-pyrrolidinyl)ethyl]amino}-3,4-dihydro-2H-pyrano[2,3-g]quinolin-3-ol (Yield: 55%)

Colorless amorphous product $^1$H-NMR ($CDCl_3$) δ: 1.29 (s, 3H), 1.58 (s, 3H), 1.49-2.00 (m, 8H), 2.10-2.25 (m, 2H), 2.34 (s, 1.5H), 2.35 (s, 1.5H), 2.58 (s, 3H), 2.65-2.85 (m, 2H), 3.00-3.15 (m, 1H), 3.62 (d, J=10.4 Hz, 0.5H), 3.70 (d, J=10.4 Hz, 0.5H), 3.85 (d, J=10.4 Hz, 0.5H), 3.88 (d, J=10.4 Hz, 0.5H), 7.15 (s, 1H), 7.27 (s, 1H), 7.96 (s, 1H).

MS ($ESI^+$) m/z; 404 $[M+1]^+$

MS ($ESI^-$) m/z; 448 $[M+45]^+$

Synthesis Example 32

(3R*,4S*)-7-chloro-4-[(2-anilinoethyl)amino]-2,2,9-trimethyl-3,4-dihydro-2H-pyrano[2,3-g]quinolin-3-ol (Yield: 78%)

Pale yellow amorphous product $^1$H-NMR ($CDCl_3$) δ: 1.27 (s, 3H), 1.56 (s, 3H), 1.77 (br s, 3H), 2.58 (s, 3H), 2.95-3.10 (m, 2H), 3.30 (t, J=5.5 Hz, 2H), 3.64 (d, J=10.2 Hz, 1H), 3.93 (d, J=10.2 Hz, 1H), 6.65-6.80 (m, 3H), 7.15-7.20 (m, 3H), 7.28 (s, 1H), 7.98 (s, 1H).

MS ($ESI^+$) m/z; 412 $[M+1]^+$

MS ($ESI^-$) m/z; 456 $[M+45]^+$

Synthesis Example 33

(3R*,4S*)-7-chloro-4-({2-[ethyl(3-methylphenyl)amino]ethyl}amino)-2,2,9-trimethyl-3,4-dihydro-2H-pyrano[2,3-g]quinolin-3-ol (Yield: 90%)

Pale yellow amorphous product $^1$H-NMR ($CDCl_3$) δ: 1.23 (t, J=6.9 Hz, 3H), 1.26 (s, 3H), 1.55 (s, 3H), 1.62 (br s, 1H), 2.27 (s, 3H), 2.57 (s, 3H), 2.80-3.00 (m, 2H), 3.30-3.50 (m, 5H), 3.61 (d, J=10.1 Hz, 1H), 3.91 (d, J=10.1 Hz, 1H), 6.60-6.70 (m, 4H), 7.05-7.15 (m, 2H), 7.96 (s, 1H).

MS ($ESI^+$) m/z; 454 $[M+1]^+$

MS ($ESI^-$) m/z; 498 $[M+45]^+$

Synthesis Example 34

(3R*,4S*)-7-chloro-2,2,9-trimethyl-4-{[(1-ethyl-(R)-2-pyrrolidinyl)methyl]amino}-3,4-dihydro-2H-pyrano[2,3-g]quinolin-3-ol (Yield: 93%)

Pale yellow amorphous product $^1$H-NMR ($CDCl_3$) δ: 1.27 (s, 1H), 1.32 (t, J=7.1 Hz, 2H), 1.56 (s, 3H), 1.95-2.12 (br, 4H), 2.56 (s, 3H), 2.71-2.81 (br, 2H), 2.98-3.37 (m, 4H), 3.64-4.01 (m, 5H), 7.12 (s, 1H), 7.22 (s, 1H), 8.01 (s, 1H)

MS ($ESI^+$) m/z; 405 $[M+1]^+$

MS ($ESI^-$) m/z; 448 $[M+45]^+$

Synthesis Example 35

(3R*,4S*)-7-chloro-2,2,9-trimethyl-4-[(2,2-diethoxyethyl)amino]-3,4-dihydro-2H-pyrano[2,3-g]quinolin-3-ol 1-maleate (Yield: 88%)

White solid $^1$H-NMR ($CD_3OD$) δ: 1.23-1.30 (m, 9H), 1.57 (s, 3H), 2.64 (s, 3H), 3.50-3.85 (m, 4H), 4.02 (d, J=10.2 Hz, 1H), 6.27 (s, 1H), 7.37 (s, 1H), 7.49 (s, 1H), 8.13 (s, 1H)

Free form (3R*,4S*)-7-chloro-2,2,9-trimethyl-4-[(2,2-diethoxyethyl)amino]-3,4-dihydro-2H-pyrano[2,3-g]quinolin-3-ol Pale yellow amorphous product MS ($ESI^+$) m/z; 410 $[M+1]^+$ MS ($ESI^-$) m/z; 453 $[M+45]^+$ Synthesis Example 36

(3R*,4S*)-7-chloro-2,2,9-trimethyl-4-{([2-(3-thienyl)ethyl]amino}-3,4-dihydro-2H-pyrano[2,3-g]quinolin-3-ol (Yield: 57%)

Pale yellow amorphous product $^1$H-NMR ($CDCl_3$) δ: 1.24 (s, 3H), 1.55 (s, 3H), 2.56 (s, 3H), 2.84 (t, J=6.8 Hz, 2H), 2.90-3.09 (m, 2H), 3.60 (d, J=10.5 Hz, 1H), 3.86 (d, J=10.5 Hz, 1H), 6.94-7.01 (m, 2H), 7.13 (s, 1H), 7.24-7.29 (m, 2H), 7.89 (s, 1H)

MS ($ESI^+$) m/z; 404 $[M+1]^+$

MS ($ESI^-$) m/z; 447 $[M+45]^+$

Synthesis Example 37

(3R*,4S*)-7-chloro-2,2,9-trimethyl-4-[2-(1-pyrazolylethyl)amino]-3,4-dihydro-2H-pyrano[2,3-g]quinolin-3-ol (Yield: 59%)

Pale yellow amorphous product $^1$H-NMR ($CDCl_3$) δ: 1.28 (s, 3H), 1.58 (s, 3H), 1.86 (br), 2.57 (s, 3H), 3.26-3.31 (m, 2H), 3.63 (d, J=10.1 Hz, 1H), 3.87 (d, J=10.1 Hz, 1H), 4.24-4.32 (m, 2H), 5.0 (br), 6.32 (dd, J=1.7, 1.7 Hz, 1H), 7.14 (s, 1H), 7.25 (s, 1H), 7.45 (d, J=1.7 Hz, 1H), 7.58 (d, J=1.7 Hz, 1H), 8.00 (s, 1H)

MS ($ESI^+$) m/z; 387 $[M+1]^+$

Synthesis Example 38

(3R*,4S*)-7-chloro-2,2,9-trimethyl-4-{[2-(4-methylpyrazol-1-yl)ethyl]amino}-3,4-dihydro-2H-pyrano[2,3-g]quinolin-3-ol (Yield: 70%)

Colorless amorphous product $^1$H-NMR ($CDCl_3$) δ: 1.28 (s, 3H), 1.58 (s, 3H), 2.0 (br), 2.10 (s, 3H), 2.57 (s, 3H), 3.16-3.31 (m, 2H), 3.64 (d, J=10.2 Hz, 1H), 3.87 (d, J=10.2 Hz, 1H), 4.11-4.30 (m, 2H), 5.2 (br), 7.13 (s, 1H), 7.21 (s, 1H), 7.24 (s, 1H), 7.36 (s, 1H), 7.98 (s, 1H)

MS ($ESI^+$) m/z; 401 $[M+1]^+$

Synthesis Example 39

(3R*,4S*)-7-chloro-2,2,9-trimethyl-4-{[2-(4-chloropyrazol-1-yl)ethyl]amino}-3,4-dihydro-2H-pyrano[2,3-g]quinolin-3-ol (Yield: 89%)

Pale yellow amorphous product $^1$H-NMR ($CDCl_3$) δ: 1.28 (s, 3H), 1.58 (s, 3H), 1.84 (br), 2.58 (s, 3H), 3.26-3.29 (m, 2H), 3.61 (d, J=10.4 Hz, 1H), 3.87 (d, J=10.4 Hz, 1H), 4.16-4.29 (m, 2H), 4.51 (br, 1H), 7.15 (s, 1H), 7.26 (s, 1H), 7.45 (s, 1H), 7.48 (s, 1H), 7.97 (s, 1H)

MS ($ESI^+$) m/z; 421 $[M+1]^+$

Synthesis Example 40

(3R*,4S*)-7-chloro-2,2,9-trimethyl-4-{[2-(2-pyridyl)ethyl]amino}-3,4-dihydro-2H-pyrano[2,3-g]quinolin-3-ol (Yield: 83%)

Yellow amorphous product $^1$H-NMR ($CDCl_3$) δ: 1.32 (s, 3H), 1.61 (s, 3H), 1.82 (br), 2.57 (s, 3H), 2.92-3.12 (m, 2H), 3.26-3.30 (m, 2H), 3.74 (d, J=10.2 Hz, 1H), 3.92 (d, J=10.2 Hz, 1H), 7.13 (s, 1H), 7.17-7.27 (m, 3H), 7.64-7.70 (m, 1H), 8.06 (s, 1H), 8.56 (d, J=5.0 Hz, 1H)

MS ($ESI^+$) m/z; 398 $[M+1]^+$

Synthesis Example 41

(3R*,4S*)-7-chloro-2,2,9-trimethyl-4-{[2-(3-pyridyl)ethyl]amino}-3,4-dihydro-2H-pyrano[2,3-g]quinolin-3-ol (Yield: 61%)

Brown amorphous product $^1$H-NMR ($CDCl_3$) δ: 1.26 (s, 3H), 1.55 (s, 3H), 1.73 (br), 2.58 (s, 3H), 2.80-2.85 (m, 2H), 2.92-3.07 (m, 2H), 3.23 (br), 3.61 (d, J=10.4 Hz, 1H), 3.89 (d, J=10.4 Hz, 1H), 7.16 (s, 1H), 7.22-7.27 (m, 2H), 7.55 (d, J=7.7 Hz, 1H), 7.93 (s, 1H), 8.47-8.48 (m, 2H)

MS ($ESI^+$) m/z; 398 $[M+1]^+$

Synthesis Example 42

(3R*,4S*)-7-chloro-2,2,9-trimethyl-4-{[2-(4-pyridyl)ethyl]amino}-3,4-dihydro-2H-pyrano[2,3-g]quinolin-3-ol (Yield: 47%)

Pale brown amorphous product $^1$H-NMR ($CDCl_3$) δ: 1.26 (s, 3H), 1.55 (s, 3H), 1.89 (br), 2.58 (s, 3H), 2.80-2.85 (m, 2H), 2.94-3.11 (m, 2H), 3.6 (br), 3.63 (d, J=10.4 Hz, 1H), 3.90 (d, J=10.4 Hz, 1H), 7.15 (d, J=5.7 Hz, 1H), 7.16 (s, 1H), 7.27 (s, 1H), 7.96 (s, 1H), 8.47 (d, J=5.7 Hz, 2H)

MS ($ESI^+$) m/z; 398 $[M+1]^+$

Synthesis Example 43

(3R*,4S*)-7-chloro-4-ethylamino-2,2,9-trimethyl-3,4-dihydro-2H-pyrano[2,3-g]quinolin-3-ol (Yield: 95%)

Pale yellow amorphous product $^1$H-NMR ($CDCl_3$) δ: 1.18 (t, J=7.1 Hz, 3H), 1.29 (s, 3H), 1.58 (s, 3H), 2.58 (s, 3H), 2.68-2.91 (m, 2H), 3.63 (d, J=10.4 Hz, 1H), 3.87 (dd, J=10.4, 1.2 Hz, 1H), 7.15 (d, J=1.1 Hz, 1H), 7.27 (s, 1H), 7.93 (d, J=1.1 Hz, 1H).

MS ($ESI^+$) m/z; 321 $[M+1]^+$

Synthesis Example 44

(3R*,4S*)-7-chloro-4-isobutylamino-2,2,9-trimethyl-3, 4-dihydro-2H-pyrano[2,3-g]quinolin-3-ol (Yield: 96%)

Pale brown amorphous product $^1$H-NMR ($CDCl_3$) δ: 0.94-0.98 (m, 6H), 1.29 (s, 3H), 1.58 (s, 3H), 1.68-1.76 (m, 1H), 2.50-2.62 (m, 2H), 2.58 (s, 3H), 3.36 (br, 1H), 3.63 (d, J=10.2 Hz, 1H), 3.88 (dd, J=10.2, 1.1 Hz, 1H), 7.15 (s, 1H), 7.28 (s, 1H), 7.93 (s, 1H)

MS ($ESI^+$) m/z; 239 $[M+1]^+$

Synthesis Example 45

(3R*,4S*)-7-chloro-4-[(cyclopropylmethyl)amino]-2,2, 9-trimethyl-3,4-dihydro-2H-pyrano[2,3-g]quinolin-3-ol (Yield: 85%)

Pale brown amorphous product $^1$H-NMR ($CDCl_3$) δ: 0.13-0.20 (m, 2H), 0.48-0.54 (m, 2H), 0.95-1.01 (m, 1H), 1.29 (s, 3H), 1.58 (s, 3H), 1.8 (br, 1H), 2.53 (m, 1H), 2.58 (s, 3H), 2.70 (m, 1H), 3.63 (d, J=10.4 Hz, 1H), 3.91 (d, J=10.4 Hz, 1H), 7.15 (s, 1H), 7.27 (s, 1H), 7.90 (s, 1H)

MS ($ESI^+$) m/z; 347 $[M+1]^+$

Synthesis Example 46

(3R*,4S*)-7-chloro-4-isopentylamylamino-2,2,9-trimethyl-3,4-dihydro-2H-pyrano[2,3-g]quinolin-3-ol (Yield: 64%)

Pale yellow amorphous product $^1$H-NMR ($CDCl_3$) δ: 0.90 (d, 6H), 1.29 (s, 3H), 1.39-1.46 (m, 2H), 1.58 (s, 3H), 1.62-1.74 (m, 2H), 2.58 (s, 3H), 2.64-2.85 (m, 2H), 3.64 (d, J=10.4 Hz, 1H), 3.87 (d, J=10.4 Hz, 1H), 7.15 (s, 1H), 7.28 (s, 1H), 7.93 (s, 1H)

MS ($ESI^+$) m/z; 363 $[M+1]^+$

Synthesis Example 47

(3R*,4S*)-7-chloro-4-[2-(cyclopentylethyl)amino]-2,2,9-trimethyl-3,4-dihydro-2H-pyrano[2,3-g]quinolin-3-ol (Yield: 78%)

Pale yellow solid $^1$H-NMR ($CDCl_3$) δ: 1.08-1.11 (m, 2H), 1.29 (s, 3H), 1.49-1.62 (m, 6H), 1.54 (s, 3H), 1.71-1.83 (m, 3H), 2.58 (s, 3H), 2.67-2.82 (m, 2H), 3.63 (d, J=10.4 Hz, 1H), 3.86 (d, J=10.4 Hz, 1H), 7.15 (s, 1H), 7.27 (s, 1H), 7.93 (s, 1H)

MS ($ESI^+$) m/z; 389 $[M+1]^+$

Synthesis Example 48

(3R*,4S*)-7-chloro-4-[2-(1-cyclopentenylethyl)amino]-2,2,9-trimethyl-3,4-dihydro-2H-pyrano[2,3-g]quinolin-3-ol (Yield: 70%)

Pale brown amorphous product $^1$H-NMR ($CDCl_3$) δ: 1.28 (s, 3H), 1.58 (s, 3H), 1.86-1.94 (m, 2H), 2.22-2.34 (m, 7H), 2.58 (s, 3H), 2.79-2.96 (m, 2H), 3.63 (d, J=10.5 Hz, 1H), 3.87 (dd, J=10.5, 1.2 Hz, 1H), 5.44 (s, 1H), 7.15 (s, 1H), 7.27 (s, 1H), 7.92 (s, 1H)

MS ($ESI^+$) m/z; 387 $[M+1]^+$

Synthesis Example 49

(3R*,4S*)-7-chloro-2,2,9-trimethyl-4-[(5-methylhexane-2-yl)amino]-3,4-dihydro-2H-pyrano[2,3-g]quinolin-3-ol (Yield: 83%)

Pale yellow amorphous product $^1$H-NMR ($CDCl_3$) δ: 0.91 (dd, J=6.6 Hz, 9.6 Hz, 6H), 1.13-1.34 (m, 9H), 1.56 (s, 6H), 2.57 (s, 3H), 3.22-3.44 (m, 2H), 3.80-3.85 (br, 1H), 7.14 (s, 1H), 7.26 (s, 1H), 7.96-7.98 (br, 1H)

MS ($ESI^+$) m/z; 392 $[M+2]^+$

MS ($ESI^-$) m/z; 435 $[M+45]^+$

Synthesis Example 50

(3R*,4R*)-7-chloro-2,2,9-trimethyl-4-[(2-phenylethyl)amino]-3,4-dihydro-2H-pyrano[2,3-g]quinolin-3-ol 1 maleate

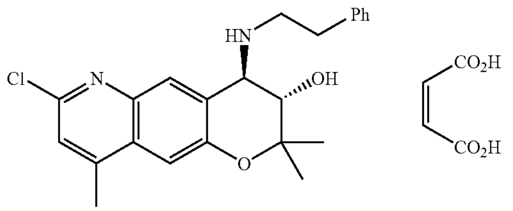

This compound was synthesized by using the enantiomer of Ph,Ph salen manganese complex (XX) (hereinafter, referred to as ent-Ph,Ph salen manganese complex).

(3S*,4S*)-7-chloro-3,4-epoxy-2,2,9-trimethyl-3,4-dihydro-2H-pyrano[2,3-g]quinoline

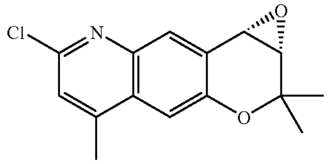

To a solution of 7-chloro-2,2,9-trimethyl-2H-pyrano[2,3-g]quinoline (200 mg, 0.77 mmol) in ethyl acetate (3.0 mL), N-methyl imidazole (0.012 mL, 0.154 mmol) and ent-Ph,Ph salen manganese complex (8.0 mg, 0.0077 mmol) were added at room temperature and sodium hypochlorite aqueous solution (1.0 g, 1.513 mol/kg, 1.54 mmol) was added dropwise in water bath, and the resulting mixture was stirred in water bath for 40 minutes. In water bath, sodium hypochlorite aqueous solution (1.0 g, 1.513 mol/kg, 1.54 mmol) was added dropwise, and the resulting mixture was further stirred in water bath for 30 minutes. Upon the completion of the reaction, sodium thiosulfate aqueous solution was added to the reaction solution, the resulting solution was filtered through celite and extracted. The organic phase was washed with sodium hydrogencarbonate aqueous solution and then with sodium chloride aqueous solution, and then dried over anhydrous magnesium sulfate. After distilling off the solvent, the residue was purified by column chromatography (hexane/ethyl acetate=10/1) to obtain (3S*,4S*)-7-chloro-3,4-epoxy-2,2,9-trimethyl-3,4-dihydro-2H-pyrano[2,3-g]quinoline (yield: 94%).

>99.9% ee; CHIRALCEL OJ-R acetonitrile/methanol/0.01 M sodium chloride aqueous solution=1/3/3, Retention time: 44.3 min.

(3S*,4R*)-7-chloro-2,2,9-trimethyl-4-[(2-phenylethyl)amino]-3,4-dihydro-2H-pyrano[2,3-g]quinolin-3-ol 1 maleate To a solution of (3S*,4S*)-7-chloro-3,4-epoxy-2,2,9-trimethyl-3,4-dihydro-2H-pyrano[2,3-g]quinoline (199 mg, 0.72 mmol) in 1,4-dioxane (0.4 mL), lithium perchlorate (77.0 mg, 0.72 mmol) and phenethylamine (0.11 mL, 0.87 mmol) were added at room temperature and the resulting mixture was stirred at 70° C. for 3 hours. Upon the completion of the reaction, sodium hydrogencarbonate aqueous solution was added to the reaction solution, and it was extracted with ethyl acetate and the resulting organic phase was washed with sodium chloride aqueous solution, and then dried over anhydrous magnesium sulfate. After distilling off the solvent, the residue was purified by medium pressure column chromatography (hexane/ethyl acetate=3/1). Further, after distilling off the solvent, ethyl acetate (2 mL) was added and a solution of maleic acid (50.3 mg, 0.43 mmol) in ethyl acetate (2 mL) was added dropwise. The precipitated solid was filtered to obtain (3S*,4R*)-7-chloro-2,2,9-trimethyl-4-[(2-phenylethyl)amino]-3,4-dihydro-2H-pyrano[2,3-g]quinolin-3-ol 1 maleate (yield: 41%).

White crystal mp: 240-242° C.

$^1$H-NMR (DMSO-$d_6$): 1.18(s, 3H), 1.50(s, 3H), 2.60(s, 3H), 2.97-3.32(m, 4H), 4.04-4.09(m, 1H), 4.65(d, J=9.6 Hz, 1H), 6.05(s, 2H), 6.29(br s, 1H), 7.23-7.35(m, 5H), 7.44(s, 2H), 8.32(s, 1H)

MS (ESI$^+$) m/z; 397 [M+1]$^+$

MS (ESI−) m/z; 441 [M+45]$^+$

Synthesis Example 51

(3R*,4R*)-2,2,7,9-tetramethyl-4-[(2-phenethyl)amino]-3,4-dihydro-2H-pyrano[2,3-g]quinolin-3-ol 1 maleate

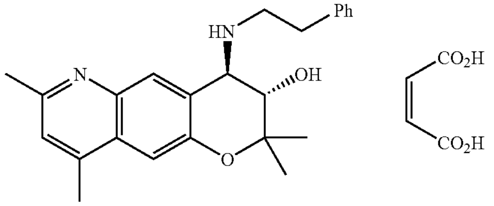

This compound was synthesized according to the process of Synthesis Example 50.

(2-step yield: 25%)

epoxide 99.1% ee CHIRALPAK AD-RH 20 mM phosphate buffer (pH 8.0)/acetonitrile=60/40, Retention time: 10.3 min.

White crystal mp: 215-216° C. (decomposition)

$^1$H-NMR (DMSO-$d_6$); 1.16(s, 3H), 1.49(s, 3H), 2.55(s, 3H), 2.58(s, 3H), 2.97-3.32 (m, 4H), 4.02-4.04(m, 1H), 4.62 (br s, 1H), 6.04(s, 2H), 6.25(br s, 1H), 7.24-7.36 (m, 7H), 8.31 (s, 1H)

MS (ESI$^+$) m/z; 377 [M+1]$^+$

Synthesis Example 52

(3R*,4S*)-7-chloro-2,2,9-trimethyl-4-(pentylamino)-3, 4-dihydro-2H-pyrano[2,3-g]quinolin-3-ol hydrochloride

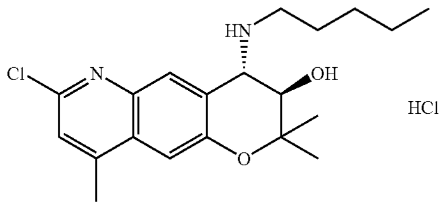

(3R*,4S*)-4-amino-7-chloro-2,2,9-trimethyl-3,4-dihydro-2H-pyrano[2,3-g]quinolin-3-ol

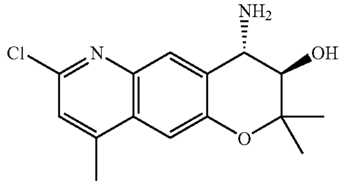

To a solution of (3R*,4R*)-7-chloro-3,4-epoxy-2,2,9-trimethyl-3,4-dihydro-2H-pyrano[2,3-g]quinoline (2.0 g, 7.25 mmol) in ethanol (20 mL), ammonia water (10 mL) was added, and the resulting mixture was stirred in a sealed tube at 90° C. for 3 hours. Upon the completion of the reaction, the reaction solution was concentrated, and ethyl acetate was added thereto, The resulting solution was washed with water and then with saturated sodium chloride solution, and dried over magnesium sulfate and concentrated. The resulting mixture was purified by silica gel column (hexane/ethyl acetate=1/2) to obtain the aimed product (yield: 86%).

White crystal $^1$H-NMR ($CDCl_3$) δ; 1.30 (s, 3H), 1.58 (s, 3H), 1.67 (br s, 2H), 2.59 (s, 3H), 3.28 (br s, 1H), 3.45 (d, J=10.4 Hz, 1H), 3.85 (d, J=10.4 Hz, 1H), 7.15 (s, 1H), 7.26 (s, 1H), 8.02 (s, 1H).

(3R*,4S*)-7-chloro-2,2,9-trimethyl-4-(pentylamino)-3, 4-dihydro-2H-pyrano[2,3-g]quinolin-3-ol

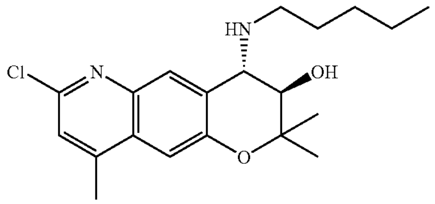

To a solution of (3R*,4S*)-4-amino-7-chloro-2,2,9-trimethyl-3,4-dihydro-2H-pyrano[2,3-g]quinolin-3-ol (60 mg, 0.205 mmol) in methanol (1.2 mL), butyl aldehyde (35 mg, 0.041 mmol) was added, and the resulting mixture was stirred at room temperature for 20 minutes. Sodium cyanoborohydride (52 mg, 0.82 mmol) was added thereto, and the resulting mixture was stirred at room temperature for 1 hour. Upon the completion of the reaction, saturated sodium hydrogencarbonate aqueous solution was added thereto, and the resulting solution was extracted with ethyl acetate, washed with saturated sodium chloride solution, and dried over magnesium sulfate and concentrated. The resulting mixture was purified by silica gel column (hexane/ethyl acetate=3/1) to obtain the aimed product (yield: 41%).

Colorless amorphous product $^{1}$H-NMR ($CDCl_3$) δ: 0.90 (t, J=6.9 Hz, 3H), 1.29 (s, 3H), 1.20-1.45 (m, 4H), 1.55-1.70 (m, 4H), 2.58 (s, 3H), 2.60-2.82 (m, 2H), 3.63 (d, J=10.4 Hz, 1H), 3.86 (d, J=10.4 Hz, 1H), 7.15 (s, 1H), 7.28 (s, 1H), 7.93 (s, 1H).

MS ($ESI^+$) m/z; 363 $[M+1]^+$

MS ($ESI^-$) m/z; 407 $[M+45]^+$ (3R*,4S*)-7-chloro-2,2,9-trimethyl-4-pentylamino-3, 4-dihydro-2H-pyrano[2,3-g]quinolin-3-ol hydrochloride To a solution of (3R*,4S*)-7-chloro-2,2,9-trimethyl-4-(pentylamino)-3, 4-dihydro-2H-pyrano[2,3-g]quinolin-3-ol (28 mg, 0.77 mmol) in ether (560 δL), 4 M hydrogen chloride solution in ether (56 δL) was added dropwise, and the resulting mixture was stirred at 0° C. for 15 minutes. Solid product was filtered off, washed with ether and dried to obtain the aimed product (yield: 88%).

Colorless crystal mp: 291-294° C. (decomposition)

Synthesis Examples 53-57

The compounds of Synthesis Examples 53-57 were synthesized according to the process of Synthesis Example 52.

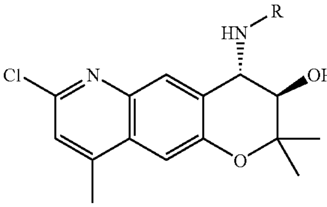

optically active

| Compound No. | 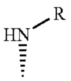 |
|---|---|
| Synthesis Example 53 | 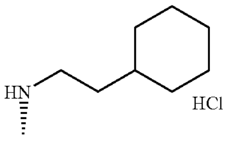 |

-continued

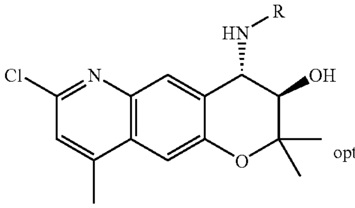

optically active

| Compound No. | 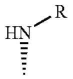 |
|---|---|
| Synthesis Example 54 | 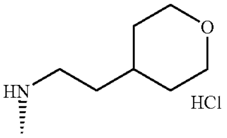 |
| Synthesis Example 55 | 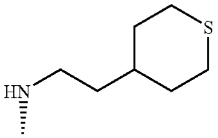 |
| Synthesis Example 56 | 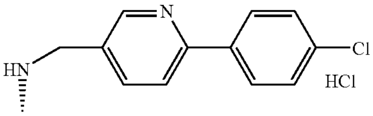 |
| Synthesis Example 57 | 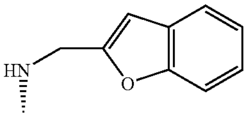 |

Synthesis Example 53

(3R*,4S*)-7-chloro-2,2,9-trimethyl-4-[(2-cyclohexylethyl)amino]-3,4-dihydro-2H-pyrano[2,3-g]quinolin-3-ol hydrochloride Free form (3R*,4S*)-7-chloro-2,2,9-trimethyl-4-[(2-cyclohexylethyl)amino]-3,4-dihydro-2H-pyrano[2,3-g]quinolin-3-ol (Yield: 31%)

Colorless amorphous product $^{1}$H-NMR ($CDCl_3$) δ: 0.90-1.00 (m, 2H), 1.05-1.25 (m, 6H), 1.29 (s, 3H), 1.58 (s, 3H) 1.60-1.70 (m, 7H), 2.58 (s, 3H), 2.75-2.85 (m, 2H), 3.63 (d, J=10.4 Hz, 1H), 3.86 (d, J=10.4 Hz, 1H), 7.15 (s, 1H), 7.27 (s, 1H), 7.93 (s, 1H)

Hydrochloride (3R*,4S*)-7-chloro-2,2,9-trimethyl-4-[(2-cyclohexylethyl)amino]-3,4-dihydro-2H-pyrano[2,3-g]quinolin-3-ol hydrochloride (Yield: 76%)

Colorless crystal mp: 294-295° C. (decomposition)

MS ($ESI^+$) m/z; 403 $[M+1]^+$

MS ($ESI^-$) m/z; 447 $[M+45]^+$

Synthesis Example 54

(3R*,4S*)-7-chloro-2,2,9-trimethyl-4-{[2-(tetrahydropyran-4-yl)ethyl]amino}-3,4-dihydro-2H-pyrano[2,3-g]quinolin-3-ol hydrochloride Free form (3R*,4S*)-7-chloro-2,2,9-trimethyl-4-[(2-tetrahydro-2H-pyran-4-ylethyl)amino]-3,4-dihydro-2H-pyrano[2,3-g]quinolin-3-ol (Yield: 65%)

Colorless amorphous product $^1$H-NMR ($CDCl_3$) δ: 1.29 (s, 3H), 1.20-1.40 (m, 4H), 1.58 (s, 3H), 1.50-1.80 (m, 4H), 2.59 (s, 3H), 2.65-2.90 (s, 2H), 3.20-3.40 (m, 3H), 3.64 (d, J=10.4 Hz, 1H), 3.70-3.75 (m, 1H), 3.85 (d, J=10.4 Hz, 1H), 3.80-4.00 (m, 3H), 7.16 (s, 1H), 7.28 (s, 1H), 7.92 (s, 1H).

MS (ESI$^+$) m/z; 405 [M+1]$^+$

MS (ESI$^-$) m/z; 449 [M+45]$^+$

Hydrochloride (3R*,4S*)-7-chloro-2,2,9-trimethyl-4-{[2-(tetrahydropyran-4-yl)ethyl]amino}-3,4-dihydro-2H-pyrano[2,3-g]quinolin-3-ol hydrochloride (Yield: 72%)

Colorless crystal mp: 318-320° C. (decomposition)

Synthesis Example 55

(3R*,4S*)-7-chloro-2,2,9-trimethyl-4-{[2-tetrahydro-2H-thiopyran-4-ylethyl]amino}-3,4-dihydro-2H-pyrano[2,3-g]quinolin-3-ol (Yield: 63%)

Colorless amorphous product $^1$H-NMR ($CDCl_3$) δ: 1.28 (s, 3H), 1.40-1.60 (m, 5H), 1.56 (s, 1H), 1.90-2.00 (m, 2H), 2.59 (s, 3H), 2.50-2.85 (m, 6H), 3.23 (s, 1H), 3.63 (d, J=10.4 Hz, 1H), 3.87 (d, J=10.4 Hz, 1H), 7.16 (s, 1H), 7.28 (s, 1H), 7.91 (s, 1H).

MS (ESI$^+$) m/z; 421 [M+1]$^+$

MS (ESI$^-$) m/z; 465 [M+45]$^+$

Synthesis Example 56

(3R*,4S*)-7-chloro-4-({[6-(4-chlorophenyl)-3-pyridinyl]methyl}amino)-2,2,9-trimethyl-3,4-dihydro-2H-pyrano[2,3-g]quinolin-3-ol hydrochloride Free form (3R*,4S*)-7-chloro-4-({[6-(4-chlorophenyl)-3-pyridinyl]methyl}amino)-2,2,9-trimethyl-3,4-dihydro-2H-pyrano[2,3-g]quinolin-3-ol (Yield: 16%)

$^1$H-NMR ($CDCl_3$) δ: 1.30 (s, 3H), 1.59 (s, 3H), 1.60 (br s, 1H), 2.60 (s, 3H), 2.98 (s, 1H), 3.75-4.10 (m, 4H), 7.19 (s, 1H), 7.34 (s, 1H), 7.45 (d, J=8.8 Hz, 2H), 7.71 (d, J=9.0 Hz, 1H), 7.80 (dd, J=9.0, 2.2 Hz, 1H), 7.96 (d, J=8.8 Hz, 2H), 8.09 (s, 1H), 8.66 (d, J=2.2 Hz, 1H).

MS (ESI$^+$) m/z; 494 [M+1]$^+$

MS (ESI$^-$) m/z; 538 [M+45]$^+$

Hydrochloride (3R*,4S*)-7-chloro-4-({[6-(4-chlorophenyl)-3-pyridinyl]methyl}amino)-2,2,9-trimethyl-3,4-dihydro-2H-pyrano[2,3-g]quinolin-3-ol hydrochloride (Yield: 67%)

Pale yellow solid

Synthesis Example 57

(3R*,4S*)-4-[(2-benzofuranylmethyl)amino]-7-chloro-2,2,9-trimethyl-3,4-dihydro-2H-pyrano[2,3-g]quinolin-3-ol (Yield: 74%)

Colorless amorphous product $^1$H-NMR ($CDCl_3$) δ: 1.28 (s, 3H), 1.58 (s, 3H), 2.0 (br), 2.59 (s, 3H), 3.35 (br, 1H), 3.75 (d, J=10.2 Hz, 1H), 4.04 (dd, J=10.2, 1.1 Hz, 1H), 4.06 (s, 2H), 6.60 (s, 1H), 7.16 (s, 1H), 7.18-7.27 (m, 2H), 7.30 (s, 1H), 7.46 (d, J=8.3 Hz, 1H), 7.49-7.52 (m, 1H), 8.08 (d, J=1.1 Hz, 1H)

MS (ESI$^+$) m/z; 423 [M+1]$^+$

Synthesis Example 58

(3R*,4S*)-7-chloro-4-[(2-hydroxypentyl)amino]-2,2,9-trimethyl-3,4-dihydro-2H-pyrano[2,3-g]quinolin-3-ol

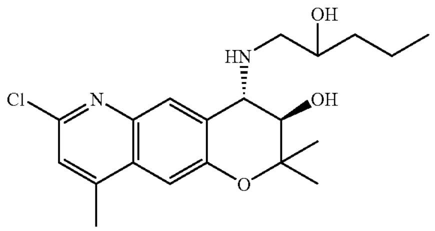

Under nitrogen stream, 1,2-epoxypentane (71 δL, 0.682 mmol) was added to a solution of (3R*,4S*)-4-amino-7-chloro-2,2,9-trimethyl-3,4-dihydro-2H-pyrano[2,3-g]quinolin-3-ol (100 mg, 0.343 mmol) and lithium perchlorate (36 mg, 0.343 mmol) in dioxane (0.50 mL) at room temperature, and the resulting mixture was stirred at 70° C. for 25 hours. Upon the completion of the reaction, ethyl acetate was added thereto, the resulting reaction solution was washed with saturated sodium hydrogencarbonate aqueous solution and then with saturated sodium chloride aqueous solution, and then dried over magnesium sulfate and concentrated. The resulting mixture was purified by silica gel column (hexane/ethyl acetate=1/1) to obtain the aimed product (yield: 59%).

Pale yellow amorphous product $^1$H-NMR ($CDCl_3$) δ: 0.93 (t, J=6.9 Hz, 3H), 1.28 (s, 3H), 1.30-1.50 (m, 4H), 1.57 (s, 3H), 1.91 (br s, 3H), 2.59 (s, 3H), 2.60-2.70 (m, 1H), 2.85-3.00 (m, 1H), 3.60-3.75 (m, 2H), 3.90-4.00 (m, 1H), 7.16 (s, 1H), 7.28 (s, 1H), 7.99 (s, 0.5H), 8.00 (s, 0.5H).

MS (ESI$^+$) m/z; 379 [M+1]$^+$

MS (ESI$^-$) m/z; 423 [M+45]$^+$

Synthesis Example 59

(3R*,4S*)-7,7-dimethyl-9-[(2-phenylethyl)amino]-8, 9-dihydro-7H-pyrano[2,3-g]quinoxalin-8-ol 1 maleate

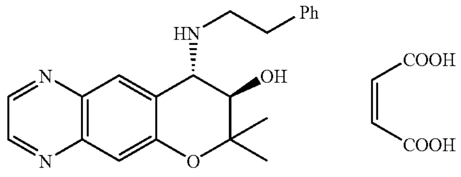

(3R*,4S*)-6,7-dimethyl-3,4-dihydro-2,2-dimethyl-4-(2'-phenylethylamino)-2H-1-benzopyran-3-ol

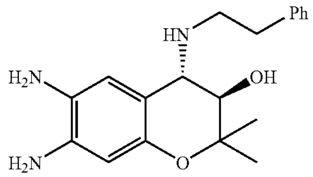

Under hydrogen stream at 1 atm, a solution of (3R*,4S*)-6-amino-3,4-dihydro-2,2-dimethyl-7-nitro-4-(2'-phenylethylamino)-2H-benzopyran-3-ol (10.0 g, 28.0 mmol) and 5% palladium carbon (AER type, 1 g) in ethanol (200 mL) was stirred at room temperature for 6 hours. Upon the completion of the reaction, the reaction solution was filtered through celite and concentrated to obtain the aimed product (yield: 98%).

Black amorphous product $^1$H-NMR ($CDCl_3$) δ: 1.13 (s, 3H), 1.43 (s, 3H), 2.60-3.00 (m, 4H), 2.5-3.5 (br 6H), 3.47 (d, J=9.6 Hz, 1H), 3.51 (d, J=9.6 Hz, 1H), 6.12 (s, 1H), 6.14 (s, 1H), 7.15-7.50 (m, 5H)

MS (ESI) m/z; 400 $[M+1]^+$, 327 (bp).

(3R*,4S*)-7,7-dimethyl-9-[(2-phenylethyl)amino]-8, 9-dihydro-7H-pyrano[2,3-g]quinoxalin-8-ol

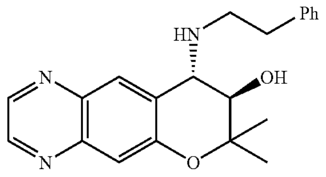

To a solution of (3R*,4S*)-6,7-diamino-3,4-dihydro-2,2-dimethyl-4-(2'-phenylethylamino)-2H-benzopyran-3-ol (1.5 g, 4.58 mmol) in ethanol (30 mL), 40% glyoxal aqueous solution (997 mg, 6.87 mmol) was added, and the resulting mixture was stirred at room temperature for 30 minutes. Upon the completion of the reaction, ethyl acetate was added thereto, the resulting solution was washed with saturated sodium hydrogencarbonate aqueous solution and then with saturated sodium chloride solution, and then dried over magnesium sulfate and concentrated. The resulting mixture was purified by silica gel column (hexane/ethyl acetate=1/1) to obtain the aimed product (yield: 74%).

$^1$H-NMR ($CDCl_3$) δ: 1.26 (s, 3H), 1.56 (s, 3H), 1.60 (br s, 1H), 2.86 (t, J=6.9 Hz, 1H), 2.90-3.10 (m, 3H), 3.62 (d, J=10.4 Hz, 1H), 3.90 (d, J=10.4 Hz, 1H), 7.24-7.40 (m, 5H), 7.42 (s, 1H), 7.94 (s, 1H), 8.05 (d, J=1.7 Hz, 1H), 8.72 (d, J=1.7 Hz, 1H)

MS ($ESI^+$) m/z; 350 $[M+1]^+$

MS ($ESI^-$) m/z; 349 $[M-1]^+$ (3R*,4S*)-7,7-dimethyl-9-[(2-phenylethyl)amino]-8, 9-dihydro-7H-pyrano[2,3-g]quinoxalin-8-ol 1 maleate To a solution of (3R*,4S*)-7,7-dimethyl-9-[(2-phenylethyl)amino]-8, 9-dihydro-7H-pyrano[2,3-g]quinoxalin-8-ol (1.18 g, 3.38 mmol) in ethyl acetate (22 mL), maleic acid (471 mg, 4.06 mmol) was added at room temperature, and the resulting mixture was stirred for 10 minutes. Upon the completion of the reaction, solid product was filtered off, washed with ethyl acetate and dried to obtain the aimed product (yield: 61%).

Pale gray crystal mp: 176-179° C. (decomposition)

$^1$H-NMR (DMSO-$d_6$) δ: 1.20 (s, 3H), 1.52 (s, 3H), 2.90-3.70 (m, 6H), 4.00-4.15 (m, 1H), 4.71 (d, J=9.1 Hz, 1H), 6.07 (s, 2H), 6.34 (br s, 1H), 7.15-7.45 (m, 5H), 7.43 (s, 1H), 8.50 (s, 1H), 8.84 (s, 1H), 8.88 (s, 1H).

Synthesis Example 60

(3R*,4S*)-4-{[2-(2-fluorophenyl)ethyl]amino}-2,2-dimethyl-3,4-dihydro-2H-pyrano[2,3-g]quinoxalin-3-ol hydrochloride

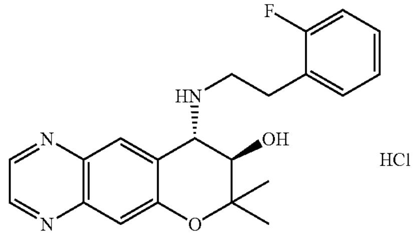

HCl

Synthesis Example 60 was carried out similarly to the process of Synthesis Example 59.

(3R*,4S*)-6,7-diamino-4-{[2-(2-fluorophenyl)ethyl] amino}-2,2-dimethyl-3,4-dihydro-2H-1-benzopyran-3-ol

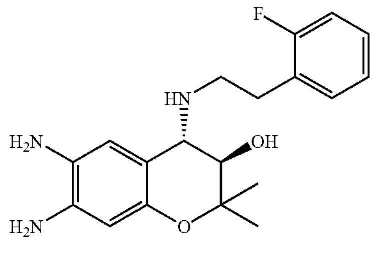

mp: 191-197° C. (decomposition)

(Yield: 87%)

Black amorphous product

MS ($ESI^+$) m/z; 346 $[M+1]^+$

MS ($ESI^-$) m/z; 380 $[M+45]^+$ (3R*,4S*)-4-{([2-(2-fluorophenyl)ethyl]amino}-2,2-dimethyl-3,4-dihydro-2H-pyrano[2,3-g]quinoxalin-3-ol

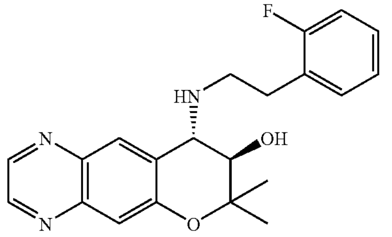

(Yield: 25%)

Gray amorphous product $^1$H-NMR ($CDCl_3$) δ: 1.26 (s, 3H), 1.57 (s, 3H), 1.74 (br s, 2H), 2.85-3.15 (m, 4H), 3.61 (d, J=10.4 Hz, 1H), 3.91 (d, J=10.4 Hz, 1H), 7.00-7.15 (m, 3H), 7.15-7.35 (m, 2H), 7.42 (s, 1H), 7.98 (s, 1H), 8.66 (d, J=1.7 Hz, 1H), 8.72 (d, J=1.7 Hz, 1H).

MS ($ESI^+$) m/z; 368 $[M+1]^+$

MS ($ESI^-$) m/z; 412 $[M+45]^+$ (3R*,4S*)-4-{([2-(2-fluorophenyl)ethyl]amino}-2,2-dimethyl-3,4-dihydro-2H-pyrano[2,3-g]quinoxalin-3-ol hydrochloride (Yield: 95%)

Colorless crystal mp: 265-268° C. (decomposition)

Synthesis Example 61

(3R*,4S*)-9-{[2-(4-fluorophenyl)ethyl]amino}-7,7-dimethyl-8,9-dihydro-7H-pyrano[2,3-g]quinoxalin-8-ol hydrochloride

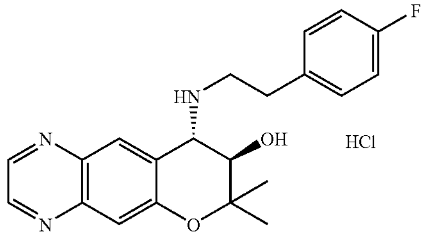

Synthesis Example 61 was carried out similarly to the process of Synthesis Example 59.

(3R*,4S*)-6,7-diamino-4-{[2'-(4-fluorophenyl)ethyl]amino}-2,2-dimethyl-3,4-dihydro-2H-1-benzopyran-3-ol

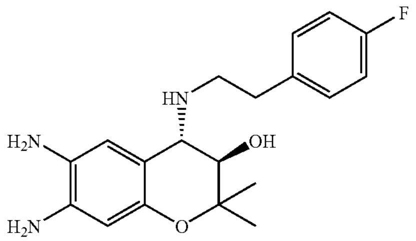

(Yield: 87%)

Black amorphous product $^1$H-NMR ($CDCl_3$) δ: 1.13 (s, 3H), 1.45 (s, 3H), 1.90 (br s, 4H), 2.75-3.00 (m, 6H), 3.50-3.70 (m, 2H), 6.16 (s, 1H), 6.29 (s, 1H), 7.02 (t, J=8.5 Hz, 2H), 7.17 (t, J=8.5 Hz, 2H).

(3R*,4S*)-9-{([2-(4-fluorophenyl)ethyl]amino}-7,7-dimethyl-8,9-dihydro-7H-pyrano[2,3-g]quinoxalin-8-ol

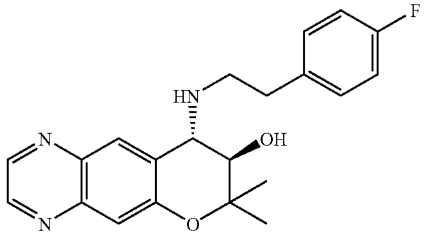

(Yield: 23%)

Pink oily product $^1$H-NMR ($CDCl_3$) δ: 1.27 (s, 3H), 1.57 (s, 3H), 1.69 (br s, 2H), 2.83 (t, J=6.9 Hz, 2H), 2.90-3.10 (m, 4H), 3.64 (d, J=10.4 Hz, 1H), 3.92 (d, J=10.4 Hz, 1H), 6.95-7.05 (m, 2H), 7.15-7.25 (m, 2H), 7.42 (s, 1H), 7.94 (s, 1H), 8.66 (d, J=1.7 Hz, 1H), 8.73 (d, J=1.7 Hz, 1H).

(8R*,9S*)-9-{[2-(4-fluorophenyl)ethyl]amino}-7,7-dimethyl-8,9-dihydro-7H-pyrano[2,3-g]quinoxalin-8-ol hydrochloride (Yield: 95%)

Brown crystal

Synthesis Example 62

(3R*,4S*)-4-[(2-hydroxy-2-phenylethyl)amino]-2,2-dimethyl-3,4-dihydro-2H-pyrano[2,3-g]quinoxalin-3-ol

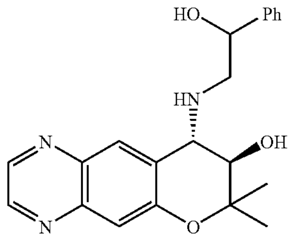

Synthesis Example 62 was carried out similarly to the process of Synthesis Example 59.

(3R*,4S*)-6,7-diamino-4-[(2-hydroxy-2-phenylethyl)amino]-2,2-dimethyl-3,4-dihydro-2H-1-benzopyran-3-ol

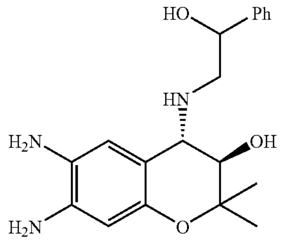

(Yield: 92%)

Two diastereomers that cannot be separated

Black amorphous product

$^1$H-NMR ($CDCl_3$) δ: 1.16 (s, 3H), 1.43 (s, 3H), 2.31 (br s, 7H), 2.70-3.05 (m, 3H), 3.50-3.70 (m, 2H), 4.70-4.80 (m, 1H), 6.16 (s, 1H), 6.53 (s, 0.5H), 6.58 (s, 0.5H), 7.20-7.40 (s, 5H).

(3R*,4S*)-4-[(2-hydroxy-2-phenylethyl)amino]-2,2-dimethyl-3,4-dihydro-2H-pyrano[2,3-g]quinoxalin-3-ol (Yield: 66%)

Two diastereomers that cannot be separated

Gray amorphous product

$^1$H-NMR ($CDCl_3$) δ: 1.30 (s, 3H), 1.58 (s, 1.5H), 1.59 (s, 1.5H), 1.70 (br s, 3H), 2.90-3.10 (m, 2H), 3.71 (d, J=10.5 Hz, 1H), 3.95-4.05 (m, 1H), 7.20-7.45 (m, 6H), 8.10 (s, 0.5H), 8.12 (s, 0.5H), 8.64 (d, J=1.9 Hz, 1H), 8.73 (d, J=1.9 Hz, 1H).

MS ($ESI^+$) m/z; 366 $[M+1]^+$

MS ($ESI^-$) m/z; 410 $[M+45]^+$

Synthesis Example 63

(3R*,4S*)-2,2-dimethyl-4-pentylamino-3,4-dihydro-2H-pyrano[2,3-g]quinoxalin-3-ol hydrochloride

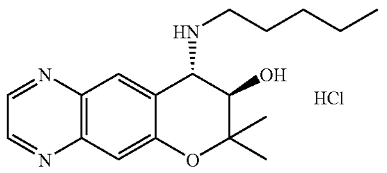

Synthesis Example 63 was carried out similarly to the process of Synthesis Example 59.

(3R*,4S*)-6,7-diamino-2,2-dimethyl-4-pentylamino-3, 4-dihydro-2H-1-benzopyran-3-ol

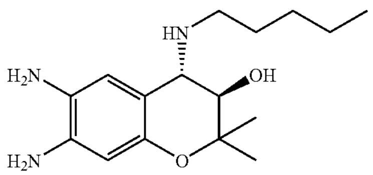

(Yield: 98%)

Brown amorphous product

$^1$H-NMR ($CDCl_3$) δ: 0.80-0.90 (m, 3H), 0.99 (s, 3H), 1.26 (s, 3H), 1.30-1.50 (m, 5H), 2.20-2.30 (m, 1H), 2.40-2.50 (m, 4H), 3.30-3.60 (m, 4H), 3.90 (br s, 2H), 4.34 (br s, 2H), 4.93 (d, J=4.4 Hz, 1H), 5.89 (s, 1H), 6.59 (s, 1H).

(3R*,4S*)-2,2-dimethyl-4-pentylamino-3,4-dihydro-2H-pyrano[2,3-g]quinoxalin-3-ol

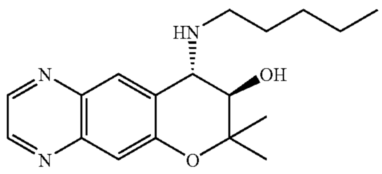

(Yield: 36%)

Orange amorphous product

$^1$H-NMR ($CDCl_3$) δ: 0.90 (t, J=7.4 Hz, 3H), 1.32 (s, 3H), 1.20-1.40 (m, 3H), 1.60-1.70 (m, 3H), 1.61 (s, 3H), 1.81 (br s, 2H), 2.60-2.90 (m, 2H), 3.68 (d, J=10.2 Hz, 1H), 3.93 (d, J=10.2 Hz, 1H), 7.44 (s, 1H), 8.04 (s, 1H), 8.66 (d, J=1.9 Hz, 1H), 8.74 (d, J=1.9 Hz, 1H).

(3R*,4S*)-2,2-dimethyl-4-pentylamino-3,4-dihydro-2H-pyrano[2,3-g]quinoxalin-3-ol hydrochloride (Yield: 96%)

Pale yellow crystal mp: 209-212° C. (decomposition)

MS ($ESI^+$) m/z; 316 $[M+1]^+$

Synthesis Example 64

(3R*,4S*)-2,2,7,8-tetramethyl-4-[(2-phenylethyl)amino]-3,4-dihydro-2H-pyrano[2,3-g]quinoxalin-3-ol 1-maleate

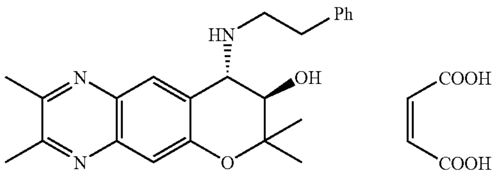

Synthesis Example 64 was carried out similarly to the process of Synthesis Example 59.

(3R*,4S*)-2,2,7,8-tetramethyl-4-[(2-phenylethyl)amino]-3,4-dihydro-2H-pyrano[2,3-g]quinoxalin-3-ol 1-maleate

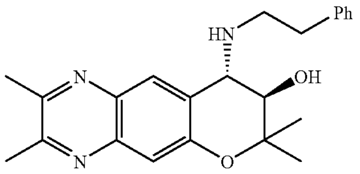

(Yield: 80%)

White amorphous product $^1$H-NMR ($CDCl_3$) δ: 1.24 (s, 3H), 1.54 (s, 3H), 2.68 (s, 6H), 2.84 (t, J=6.9 Hz, 2H), 2.90-3.10 (m, 4H), 3.59 (d, J=10.2 Hz, 1H), 3.86 (d, J=10.2 Hz, 1H), 7.20-7.40 (m, 6H), 7.82 (s, 1H).

MS (ESI$^+$) m/z; 378 [M+1]$^+$

MS (ESI$^-$) m/z; 380 [M+45]$^+$

Synthesis Example 65

(3R*,4S*)-7,8-diethyl-2,2-dimethyl-4-[(2-phenylethyl)amino]-3,4-dihydro-2H-pyrano[2,3-g]quinoxalin-3-ol

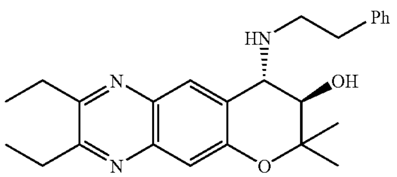

Synthesis Example 65 was carried out similarly to the process of Synthesis Example 59.

(Yield: 79%)

White solid $^1$H-NMR ($CDCl_3$) δ: 1.23 (s, 3H), 1.39 (q, J=6.6 Hz, 6H), 1.54 (s, 3H), 2.80-2.90 (m, 2H), 2.95-3.10 (m, 10H), 3.60 (d, J=10.4 Hz, 1H), 3.85 (d, J=10.4 Hz, 1H), 7.20-7.40 (m, 6H), 7.81 (s, 1H).

MS (ESI$^+$) m/z; 406 [M+1]$^+$

Synthesis Example 66

(3R*,4S*)-2,2,8-trimethyl-7-phenyl-4-[(2-phenylethyl)amino]-3,4-dihydro-2H-pyrano[2,3-g]quinoxalin-3-ol

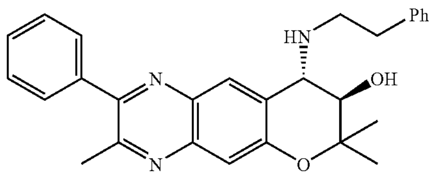

Synthesis Example 66 was carried out similarly to the process of Synthesis Example 59.

(Yield: 33%, law polar component)

White amorphous product $^1$H-NMR ($CDCl_3$) δ: 1.27 (s, 3H), 1.57 (s, 3H), 1.66 (br s. 2H), 2.72 (s, 3H), 2.83 (t, J=6.9 Hz, 2H), 2.90-3.15 (m, 4H), 3.61 (d, J=10.2 Hz, 1H), 3.88 (d, J=10.2 Hz, 1H), 7.15-7.35 (m, 5H), 7.36 (s, 1H), 7.50-7.60 (m, 3H), 7.60-7.70 (m, 2H), 7.97 (s, 1H).

MS (ESI$^+$) m/z; 440 [M+1]$^+$

Synthesis Example 67

(3R*,4S*)-2,2,7-trimethyl-8-phenyl-4-[(2-phenylethyl)amino]-3,4-dihydro-2H-pyrano[2,3-g]quinoxalin-3-ol

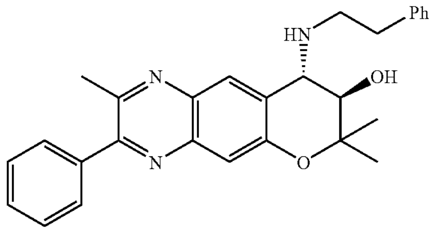

Synthesis Example 67 was carried out similarly to the process of Synthesis Example 59.

(Yield: 29%, high polar component)

$^1$H-NMR ($CDCl_3$) δ: 1.26 (s, 3H), 1.55 (s, 3H), 2.72 (s, 3H), 2.86 (t, J=6.9 Hz, 2H), 2.95-3.12 (m, 4H), 3.62 (d, J=10.2 Hz, 1H), 3.91 (d, J=10.2 Hz, 1H), 7.20-7.35 (m, 5H), 7.42 (s, 1H), 7.45-7.55 (m, 3H), 7.60-7.70 (m, 2H), 7.90 (s, 1H)

MS (ESI$^+$) m/z; 440 [M+1]$^+$ .

Synthesis Example 68

(3R*,4S*)-2,2,8-trimethyl-4-[(2-phenylethyl)amino]-3,4-dihydro-2H-pyrano[2,3-g]quinoxalin-3-ol 1 maleate

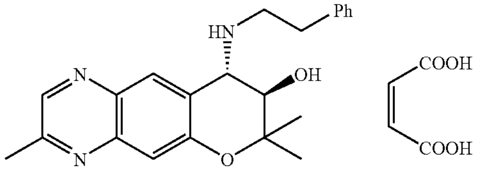

Synthesis Example 68 was carried out similarly to the process of Synthesis Example 59.

(3R*,4S*)-2,2,8-trimethyl-4-[(2-phenylethyl)amino]-3,4-dihydro-2H-pyrano[2,3-g]quinoxalin-3-ol 1 maleate

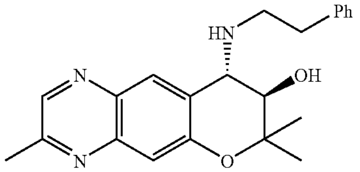

(Yield: 52%)

White amorphous product

$^1$H-NMR ($CDCl_3$) δ: 1.25 (s, 3H), 1.55 (s, 3H), 2.72 (s, 3H), 2.84 (t, J=6.9 Hz, 2H), 2.90-3.10 (m, 4H), 3.61 (d, J=10.4 Hz, 1H), 3.87 (d, J=10.4 Hz, 1H), 7.15-7.40 (m, 6H), 7.89 (s, 1H), 8.54 (s, 1H).

(3R*,4S*)-2,2,8-trimethyl-4-[(2-phenylethyl)amino]-3,4-dihydro-2H-pyrano[2,3-g]quinoxalin-3-ol 1 maleate Colorless crystal mp: 189-192° C. (decomposition)

Synthesis Example 69

(3R*,4S*)-4-[(2-cyclohexylethyl)amino)]-2,2-dimethyl-3,4-dihydro-2H-pyrano[2,3-g]quinoxalin-3-ol hydrochloride

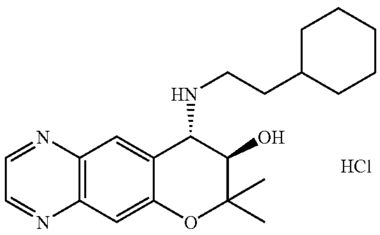

HCl (3R*,4S*)-4-amino-2,2-dimethyl-3,4-dihydro-2H-pyrano[2,3-g]quinoxalin-3-ol

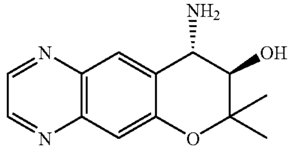

To a solution of (3R*,4S*)-4,6,7-triamino-2,2-dimethyl-3,4-dihydro-2H-1-benzopyran-3-ol (280 mg, 1.25 mmol) in ethanol (5.6 mL), 40% glyoxal aqueous solution (226 mg, 1.56 mmol) was added, and the resulting mixture was stirred at room temperature for 1 hour. Upon the completion of the reaction, 1 mol/L hydrochloric acid was added thereto, the resulting solution was washed with ethyl acetate, the resulting aqueous phase was adjusted to pH 14 with 1 mol/L sodium hydroxide aqueous solution. Then, the resulting solution was extracted with ethyl acetate, washed with saturated sodium chloride solution, and dried over magnesium sulfate and concentrated. The resulting mixture was purified by silica gel column (ethyl acetate/methanol=10/1) to obtain the aimed product (yield: 35%).

Pale brown amorphous product

$^1$H-NMR ($CDCl_3$) δ: 1.26 (s, 3H), 1.58 (s, 3H), 2.17 (br s, 3H), 3.49 (d, J=10.7 Hz, 1H), 3.92 (d, J=10.7 Hz, 1H), 7.41 (s, 1H), 8.13 (s, 1H), 8.65 (s, 1H), 8.72 (s, 1H).

MS (ESI$^+$) m/z: 246 $[M+1]^+$ (3R*,4S*)-4-[(2-cyclohexylethyl)amino)]-2,2-dimethyl-3,4-dihydro-2H-pyrano[2,3-g]quinoxalin-3-ol

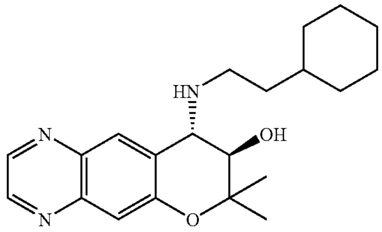

To a solution of (4R*,4S*)-4-amino-2,2-dimethyl-3,4-dihydro-2H-pyrano[2,3-g]quinoxalin-3-ol (100 mg, 0.408 mmol) in methanol (2 mL), cyclohexylmethyl aldehyde (103 mg, 0.816 mmol) was added, and the resulting mixture was stirred at room temperature for 20 minutes. Sodium cyanoborohydride (51 mg, 0.816 mmol) was added thereto, and the resulting mixture was stirred at room temperature for 1 hour. Upon the completion of the reaction, saturated sodium hydrogencarbonate aqueous solution was added thereto, the resulting solution was extracted with ethyl acetate, washed with saturated sodium chloride solution, and dried over magnesium sulfate and concentrated. The resulting mixture was purified by silica gel column (hexane/ethyl acetate=2/1) to obtain the aimed product (yield: 48%).

Yellow oily product

$^1$H-NMR ($CDCl_3$) δ: 0.80-1.00 (m, 2H), 1.10-1.40 (m, 4H), 1.31 (s, 3H), 1.44 (t, J=7.1 Hz, 1H), 1.60 (s, 3H), 1.65-1.80 (m, 6H), 2.65-2.90 (m, 2H), 3.68 (d, J=10.4 Hz, 1H), 3.93 (d, J=10.4 Hz, 1H), 7.44 (s, 1H), 8.04 (s, 1H), 8.67 (d, J=1.9 Hz, 1H), 8.73 (d, J=1.9 Hz, 1H).

(3R,4S*)-4-amino-2,2-dimethyl-3,4-dihydro-2H-pyrano[2,3-g]quinoxalin-3-ol hydrochloride (Yield: 89%)

Yellow crystal mp: 258-259° C. (decomposition)

MS ($ESI^+$) m/z; 356 $[M+1]^+$

MS ($ESI^-$) m/z; 400 $[M+45]^+$

Synthesis Example 70

(±)-trans-3-hydroxy-2,2-dimethyl-4-[(2-phenylethyl)amino]-2,3,4,6-tetrahydro-pyrano[2,3-f]benzimidazol-7one,

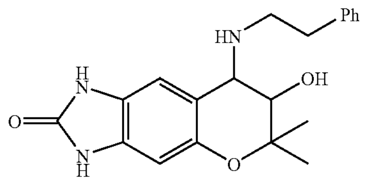

To a solution of (±)-trans-6,7-diamino-3,4-dihydro-2,2-dimethyl-4-(2'-phenylethylamino)-2H-1-benzopyran-3-ol (500 mg, 1.53 mmol) in dioxane (7 mL), 4 mol/L hydrochloric acid/dioxane solution (0.38 mL) was added, and the resulting mixture was stirred at room temperature for 15 minutes. Then, phenyl chloroformate (0.21 mL, 1.53 mmol) and triethylamine (0.21 mL, 1.53 mmol) were added thereto, and the resulting mixture was stirred at room temperature for 1 hour. Further, triethylamine (0.63 mL, 4.58 mmol) was added thereto, and the resulting mixture was stirred at room temperature for 2 hours. Upon the completion of the reaction, 1 mol/L hydrochloric acid was added thereto and thereby adjusted to pH 7-8. Thereafter, the resulting reaction solution was extracted with ethyl acetate, washed with saturated sodium chloride aqueous solution, and then dried over sodium sulfate and concentrated. The resulting mixture was purified by silica gel column (methanol/chloroform=1/20) to obtain the aimed product (yield: 4%).

Yellow amorphous product $^1H$-NMR ($CDCl_3$) δ: 1.15 (s, 3H), 1.30-1.41 (br, 1H), 1.45 (s, 3H), 2.71-3.96 (m, 4H), 3.51 (d, J=9.9 Hz, 1H), 3.67 (d, J=9.9 Hz, 1H), 6.51 (s, 1H), 7.12-7.48 (m, 7H), 7.76 (s, 1H)

MS ($ESI^+$) m/z; 354 $[M+1]^+$

Synthesis Example 71

(7R*,8S*)-7-hydroxy-6,6-dimethyl-8-(2-phenylethyl)amino]-4,6,7,8-tetrahydro-1,5-dioxa-4-aza-anthracene-3-one

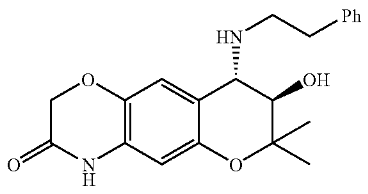

4-(1,1-dimethyl-2-propynyloxy)anisole

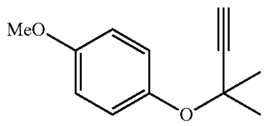

To a solution of 4-methoxyphenol (15.0 g, 121 mmol) in acetonitrile (75 mL), 1,8-diazabicyclo[5.4.0]undecene (23.9 g, 157 mmol) was added under ice cooling and the resulting mixture was stirred at 0° C. for 30 minutes (Solution 1). To a solution of 2-methyl-3-butyn-2-ol (11.7 g, 139 mmol) in acetonitrile (75 mL), 1,8-diazabicyclo[5.4.0]undecene (23.9 g, 157 mmol) was added under ice cooling, the resulting mixture was stirred at 0° C. for 30 minutes, then trifluoroacetic anhydride (25.4 g, 121 mmol) was added and the resulting mixture was stirred at 0° C. for 30 minutes (Solution 2). Copper (I) chloride (36 mg, 0.36 mmol) was added to Solution 1, and then Solution 2 was added dropwise thereto over 15 minutes. Upon the conclusion of dropwise addition, the temperature was raised to room temperature, and the mixture was stirred overnight. Upon the completion of the reaction, an aqueous solution of ammonium chloride was added to the reaction solution, and the solvent was distilled off under a reduced pressure. An aqueous solution of 1 mol/L hydrochloric acid was added to the residue, the resulting mixture was extracted with ethyl acetate, the organic phase was washed once with an aqueous solution of 1 mol/L hydrochloric acid, twice with an aqueous solution of saturated sodium hydrogen carbonate and once with saturated sodium chloride solution. Then, the organic phase was dried over anhydrous magnesium sulfate. After distilling off the solvent, the residue was directly used for the subsequent reaction.

6-methoxy-2,2-dimethyl-2H-1-benzopyran

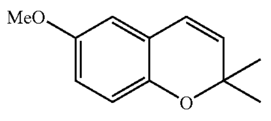

A solution of 4-(1,1-dimethyl-2-propynyloxy)anisole in 1,2-dichlorobenzene (50 mL) was stirred at 190° C. for 2 hours. Upon the completion of the reaction, the solvent was distilled off under a reduced pressure. The residue was purified by column chromatography (hexane/chloroform=3/1) and the aimed product was obtained as red oily substance (2-step, yield: 61%).

$^1$H-NMR ($CDCl_3$) δ: 1.41 (s, 6H), 3.75 (s, 3H), 5.64 (d, J=9.9 Hz, 1H), 6.28 (d, J=9.9 Hz, 1H), 6.55 (d, J=2.7 Hz, 1H), 6.64-6.73 (m, 2H)

LC/MS (ESI$^+$) m/z: 191 [M$^+$+1]

6-methoxy-2,2-dimethyl-7-nitro-2H-1-benzopyran

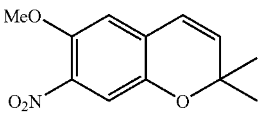

A mixed solution of acetic acid (6.2 mL) and acetic anhydride (6.2 mL) containing 6-methoxy-2,2-dimethyl-2H-1-benzopyran (3.1 g, 16.4 mmol) was cooled with ice, nitric acid (1.37 mL, 18.0 mmol) was added dropwise and then the mixture was stirred at 0° C. for 1 hour. Upon the completion of the reaction, an aqueous solution of 1 mol/L sodium hydroxide was added to the reaction solution, the resulting solution was extracted with ethyl acetate (150 mL). The organic phase was washed twice with 1 mol/L sodium hydroxide aqueous solution and once with saturated sodium chloride solution. Then, the organic phase was dried over anhydrous magnesium sulfate. After distilling off the solvent, the residue was purified by column chromatography (hexane/ethyl acetate=6/1) and the aimed product was obtained as yellow crystal (yield: 79%).

$^1$H-NMR ($CDCl_3$) δ: 1.44 (s, 6H), 3.91 (s, 3H), 5.85 (d, J=9.6 Hz, 1H), 6.33 (d, J=9.6 Hz, 1H), 6.69 (s, 1H), 7.34 (s, 1H)

LC/MS (ESI$^+$) m/z: 236 [M$^+$+1]

(3R*,4R*)-3,4-epoxy-6-methoxy-2,2-dimethyl-7-nitro-3,4-dihydro-2H-1-benzopyran

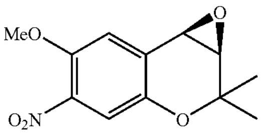

To a solution (300 mL) of acetonitrile containing 6-methoxy-2,2-dimethyl-7-nitro-2H-1-benzopyran (10.0 g, 42.5 mmol), N-methyl imidazole (0.678 mL, 8.50 mmol), (R,R,S,S)-Ph,Ph salen manganese complex (XX) (880 mg, 0.850 mmol) and iodosobenzene (18.7 mg, 85.0 mmol) were added at room temperature and the mixture was stirred for 2 hours. Upon the completion of the reaction, an aqueous solution of sodium thiosulfate was added to the reaction solution, the resulting solution was filtered through celite. The resulting filtrate extracted with ethyl acetate. The organic phase was washed with water and sodium chloride solution, and then dried over anhydrous magnesium sulfate. After distilling off the solvent, the residue was purified by column chromatography (hexane/ethyl acetate=4/1) and the aimed product was obtained as yellow crystal (yield: 75%, optical purity: 99.7% ee).

$^1$H-NMR ($CDCl_3$) δ: 1.26 (s, 3H), 1.58 (s, 3H), 3.53 (d, J=4.3 Hz, 1H), 3.90 (d, J=4.3 Hz, 1H), 3.95 (s, 3H), 7.08 (s, 1H), 7.33 (s, 1H)

MS (EI) m/z: 251 [M$^{+}$]

HPLC: 18.6 min (enantiomer 24.1 min)

HPLC condition: chiralcel OJ-RH, MeCN/MeOH/0.01 M NaCl aq.=1/3/5, 1.0 ml/min, 40° C., 256 nm (3R*,4S*)-6-methoxy-2,2-dimethyl-7-nitro-4-[(2-phenylethyl)amino]-3,4-dihydro-2H-1-benzopyran-3-ol

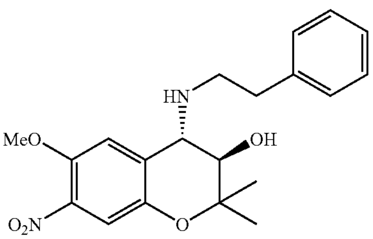

To a solution of (3R*,4S*)-3,4-epoxy-6-methoxy-2,2-dimethyl-7-nitro-3, 4-dihydro-2H-1-benzopyran (2.50 g, 9.95 mmol) in 1,4-dioxane (5.0 mL), lithium perchlorate (1.06 g, 9.95 mmol) and 4-(phenylethyl)amine (1.50 mL, 11.9 mmol) were added at room temperature and the mixture was stirred at 80° C. for 1 hour. Upon the completion of the reaction, an aqueous solution of saturated ammonium chloride was added to the reaction solution, and the resulting solution was extracted with ethyl acetate. The organic phase was washed with saturated sodium chloride solution, and then dried over anhydrous sodium sulfate. After distilling off the solvent, the residue was purified by column chromatography (hexane/ethyl acetate=6/4) and the aimed product was obtained as orange amorphous substance (quantitative yield).

$^1$H-NMR ($CDCl_3$) δ: 1.15 (s, 3H), 1.47 (s, 3H), 2.73-2.95 (m, 4H), 3.60 (d, J=10.0 Hz, 1H), 3.68 (d, J=10.0 Hz, 1H), 3.73 (s, 3H), 6.78 (s, 1H), 7.21-7.35 (m, 6H)

MS (EI): 372 [M$^{+}$]

t-Butyl (2-phenylethyl)(3R*,4S*)-3-hydroxy-6-methoxy-2, 2-dimethyl-7-nitro-3,4-dihydro-2H-1-benzopyran-4-yl carbamate

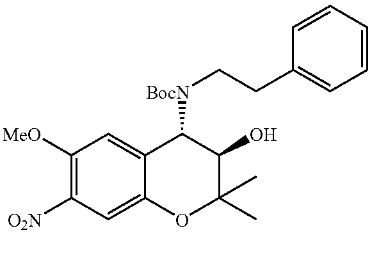

To a solution of (3R*,4S*)-6-methoxy-2,2-dimethyl-7-nitro-4-[(2-phenylethyl)amino]-3,4-dihydro-2H-1-benzopyran-3-ol (407 mg, 1.09 mmol) and di-t-butyl carbonate (477 mg, 2.19 mmol) in tetrahydrofuran (6.0 mL), triethylamine (305 mL, 2.19 mmol) was added at 0° C. and the mixture was stirred at room temperature overnight. Upon the completion of the reaction, an aqueous solution of saturated sodium carbonate was added to the reaction solution, and the resulting solution was extracted with ethyl acetate. The organic phase was washed with 1 mol/L hydrochloric acid aqueous solution and saturated sodium chloride solution, and then dried over anhydrous sodium sulfate. After distilling off the solvent, the residue was purified by column chromatography (hexane/ethyl acetate=4/1) and the aimed product was obtained as yellow amorphous substance (yield: 88%).

MS (EI) m/z: 473 [$M^+$+1]

t-Butyl (2-phenylethyl)(3R*,4S*)-7-amino-3-hydroxy-6-methoxy-2,2-dimethyl-3, 4-dihydro-2H-1-benzopyran-4-ylcarbamate

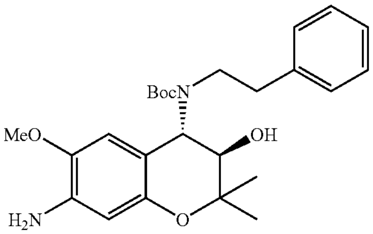

A solution of t-butyl (2-phenylethyl)(3R*,4S*)-3-hydroxy-6-methoxy-2,2-dimethyl-7-nitro-3,4-dihydro-2H-1-benzopyran-4-ylcarbamate (1.32 g, 2.80 mmol) and 5% palladium-carbon (132 mg) in methanol (26 mL) was stirred under hydrogen atmosphere at room temperature overnight. Upon the completion of the reaction, the reaction solution was filtered through celite. After distilling off the solvent, the residue was purified by column chromatography (hexane/ethyl acetate=4/1) and the aimed product was obtained (yield: 94%).

Colorless solid

LC/MS ($ESI^+$) m/z: 443 [$M^+$+1]

t-Butyl (2-phenylethyl)(3R*,4S*)-[7-(2-chloro-chloroacetamide)-3-hydroxy-6-methoxy-2, 2-dimethyl-3, 4-dihydro-2H-1-benzopyran-4-yl]carbamate

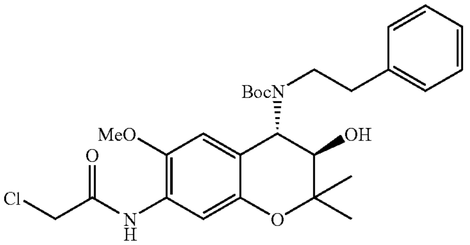

To a solution of t-butyl (2-phenylethyl)(3R*,4S*)-7-amino-3-hydroxy-6-methoxy-2,2-dimethyl-3,4-dihydro-2H-1-benzopyran-4-yl carbamate (270 mg, 0.61 mmol) in tetrahydrofuran, triethylamine (128 δL, 0.92 mmol) and chloroacetyl chloride (73 δL, 0.92 mmol) were added at room temperature and the resulting mixture was stirred at room temperature for 2.5 hours. Upon the completion of the reaction, ethanol (1 mL) and saturated ammonium chloride aqueous solution were added to the reaction solution, and the resulting solution was extracted with ethyl acetate, washed with saturated sodium chloride solution, dried over magnesium sulfate, and concentrated. The resulting mixture was purified by silica gel column (hexane/ethyl acetate=5/1) and the aimed product was obtained (yield: 91%).

Colorless oily product

2-Chloro-N-[(3R*,4S*)-3,6-dihydroxy-2,2-dimethyl-4-(2-phenylethylamino)-3, 4-dihydro-2H-1-benzopyran-7-yl]-acetamide

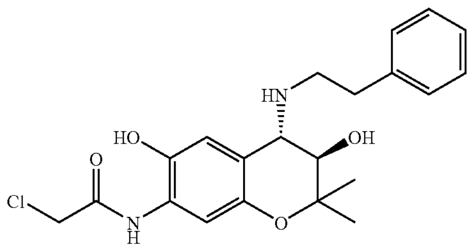

To a solution of t-butyl (2-phenylethyl)(3R*,4S*)-[7-(2-chloro-acetamide)-3-hydroxy-6-methoxy-2,2-dimethyl-3,4-dihydro-2H-1-benzopyran-4-yl carbamate (251 mg, 0.48 mmol) in methylene chloride (5 mL), borane tribromide (1M solution in methylene chloride, 2.42 mL, 2.42 mmol) was added at 0° C., and the resulting mixture was stirred for 2 hours. Upon the completion of the reaction, water was added thereto, the resulting solution was extracted with ethyl acetate, washed with saturated sodium hydrogencarbonate aqueous solution and then with saturated sodium chloride solution, dried over magnesium sulfate, and concentrated. The resulting mixture was purified by silica gel column (hexane/ethyl acetate=2/1) and the aimed product was obtained (yield: 70%).

Pale pink amorphous product $^1$H-NMR ($CDCl_3$) δ: 1.33 (s, 3H), 1.44 (s, 3H), 2.75-3.00 (m, 4H), 3.50 (d, J=9.6 Hz, 1H), 3.60 (d, J=9.6 Hz, 1H), 4.23 (s, 2H), 6.58 (s, 1H), 6.83 (s, 1H), 7.20-7.35 (m, 5H), 8.47 (s, 1H).

MS ($ESI^+$) m/z: 405 $[M+1]^+$

MS ($ESI^-$) m/z: 403 $[M-1]^+$ (7R*,8S*)-7-hydroxy-6,6-dimethyl-8-(2-phenylethyl)amino]-4,6,7,8-tetrahydro-1,5-dioxa-4-aza-anthracene-3-one

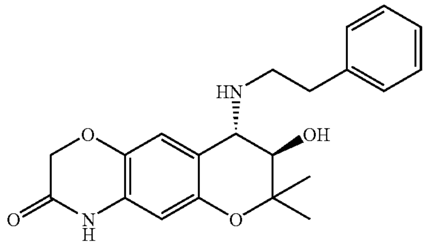

To a solution of 2-chloro-N-[(3R*,4S*)-3,6-dihydroxy-2,2-dimethyl-4-(2-phenylethylamino)-3, 4-dihydro-2H-1-benzopyran-7-yl]-acetamide (120 mg, 0.30 mmol) in methanol (1.2 mL), sodium hydroxide aqueous solution (1 mol/L, 1.5 mL) was added at room temperature, and the resulting mixture was stirred for 4 hours. Upon the completion of the reaction, saturated ammonium chloride aqueous solution was added thereto, the resulting solution was extracted with ethyl acetate, washed with saturated sodium hydroxide aqueous solution (1 mol/L) and then with saturated sodium chloride solution, dried over magnesium sulfate, and concentrated. The resulting mixture was purified by silica gel column (hexane/ethyl acetate=1/1) and the aimed product was obtained (yield: 72%).

Colorless solid $^1$H-NMR ($CDCl_3$) δ: 1.14 (s, 3H), 1.44 (s, 3H), 2.75-3.00 (m, 4H), 3.47 (d, J=9.9 Hz, 1H), 3.56 (d, J=9.9 Hz, 1H), 4.50 (d, J=15.4 Hz, 1H), 4.55 (d, J=15.4 Hz, 1H), 6.27 (s, 1H), 6.68 (s, 1H), 7.20-7.35 (m, 5H), 7.74 (s, 1H).

MS (ESI$^+$) m/z: 369 [M+1]$^+$

MS (ESI$^-$) m/z: 367 [M−1]$^+$

Synthesis Example 72

(7R*,8S*)-6,6-dimethyl-8-(2-phenylethyl)amino]-2,3,4,6,7,8-hexahydro-1,5-dioxa-4-aza-anthracene-7-ol maleate

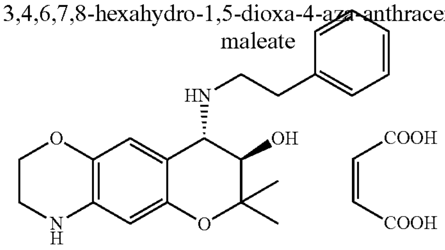

To a solution of (7R*,8S*)-7-hydroxy-6,6-dimethyl-8-(2-phenylethylamino)-4,6,7,8-tetrahydro-1,5-dioxa-4-aza-anthracene-3-one (42 mg, 0.11 mmol) in tetrahydrofuran (1.2 mL), lithium aluminum hydride (1M solution in tetrahydrofuran, 570 δL, 0.57 mmol) was added at room temperature, and the resulting mixture was stirred at 90° C. for 1.5 hour. Upon the completion of the reaction, saturated sodium hydrogencarbonate aqueous solution was added thereto, the resulting solution was extracted with ethyl acetate, washed with saturated sodium chloride solution, dried over magnesium sulfate, and concentrated. Maleic acid (13 mg, 0.11 mmol) and hexane (1 mL) were added to the solution of the resulting mixture in ethyl acetate (600 δL) at room temperature, and the resulting mixture was stirred at room temperature for 15 minutes. The resulting crystal was filtered off and the aimed product was obtained (yield: 60%).

Pale brown solid $^1$H-NMR (DMSO-$d_6$) δ: 1.04 (s, 3H), 1.36 (s, 3H), 2.85-3.30 (m, 6H), 3.80-3.85 (m, 1H), 4.11 (d, J=4.2 Hz, 2H), 4.15-4.20 (m, 1H), 6.05 (s, 2H), 6.18 (s, 1H), 6.76 (s, 1H), 7.20-7.40 (m, 5H).

Synthesis Example 73

(7R*,8S*)-7-hydroxy-4,6,6-trimethyl-8-(2-phanyl-ethylamino)-4,6,7, 8-tetrahydro-1,5-dioxa-4-aza-anthracene-3-one hydrochloride

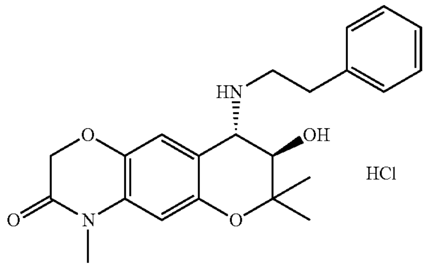

t-Butyl (2-phenylethyl)(7R*,8S*)-[7-hydroxy-6,6-dimethyl-3-oxo-2,3,4,6,7,8-hexahydro-1, 5-dioxa-4-aza-anthracene-8-yl]carbamate

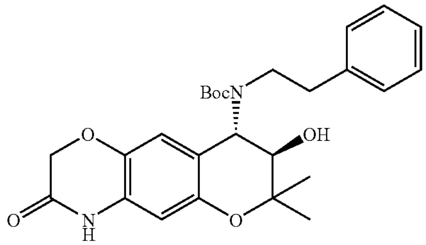

To a solution of (7R*,8S*)-7-hydroxy-6,6-dimethyl-8-(2-phenylethyl)amino]-4,6,7,8-tetrahydro-1,5-dioxa-4-aza-anthracene-3-one (150 mg, 0.41 mmol) in tetrahydrofuran (3 mL), triethylamine (85 δL, 0.61 mmol) and di-t-butyl carbonate (178 mg, 0.81 mmol) were added at room temperature, and the resulting mixture was stirred at 90° C. for 1.5 hour. Upon the completion of the reaction, saturated ammonium chloride aqueous solution was added thereto, the resulting solution was extracted with ethyl acetate, washed with saturated sodium chloride solution, dried over magnesium sulfate, and concentrated. The resulting mixture was purified by silica gel column (hexane/ethyl acetate=3/1) and the aimed product was obtained (yield: 85%).

MS (ESI$^+$) m/z: 469 [M+1]$^+$

MS (ESI$^-$) m/z: 467 [M−1]$^+$ t-Butyl (2-phenylethyl)(7R*,8S*)-[7-hydroxy-4,6,6-trimethyl-3-oxo-2,3,4,6,7,8-hexahydro-1,5-dioxa-4-aza-anthracene-8-yl]carbamate

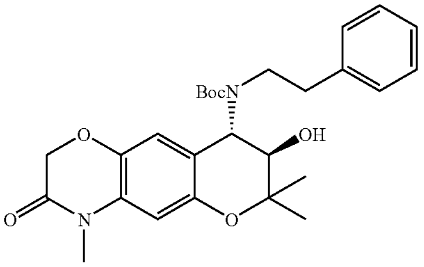

To a solution of t-butyl (2-phenylethyl)(7R*,8S*)-[7-hydroxy-6,6-dimethyl-3-oxo-2,3,4,6,7,8-hexahydro-1,5-dioxa-4-aza-anthracene-8-yl]carbamate (106 mg, 0.23 mmol) in dimethylformamide (2 mL), potassium carbonate (79 mg, 0.57 mmol) and methyl iodide (28 δL, 0.46 mmol) were added at room temperature, and the resulting mixture was stirred at room temperature for 4 hours. Upon the completion of the reaction, saturated ammonium chloride aqueous solution was added thereto, the resulting solution was extracted with ethyl acetate, washed with saturated sodium chloride solution, dried over magnesium sulfate, and concentrated. The resulting mixture was purified by silica gel column (hexane/ethyl acetate=2/1) and the aimed product was obtained (yield: 100%).

MS ($ESI^+$) m/z: 505 $[M+23]^+$

MS ($ESI^-$) m/z: 527 $[M+45]^+$ (7R*,8S*)-7-hydroxy-4,6,6-trimethyl-8-(2-phenylethyl)amino]-4,6,7,8-tetrahydro-1,5-dioxa-4-aza-anthracene-3-one

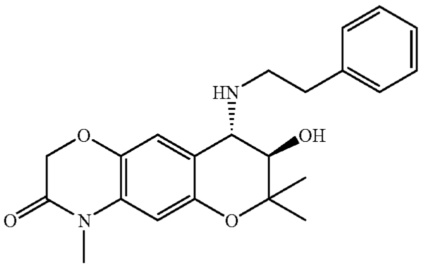

To a solution of t-butyl (2-phenylethyl)(7R*,8S*)-[7-hydroxy-4,6,6-trimethyl-3-oxo-2,3,4,6,7,8-hexahydro-1,5-dioxa-4-aza-anthracene-8-yl]carbamate (115 mg, 0.24 mmol) in ether (2.2 mL), 4 mol/L hydrogen chloride-dioxane (500 δL) was added at room temperature, and the resulting mixture was stirred at room temperature for 5 hours and then at 50° C. for 30 minutes. Upon the completion of the reaction, saturated sodium hydrogencarbonate aqueous solution was added thereto, the resulting solution was extracted with ethyl acetate, washed with saturated sodium chloride solution, dried over magnesium sulfate, and concentrated. The resulting mixture was purified by silica gel column (hexane/ethyl acetate=1/2) and the aimed product was obtained (yield: 76%).

Colorless oily product $^1$H-NMR ($CDCl_3$) δ: 1.17 (s, 3H), 1.47 (s, 3H), 2.75-3.00 (m, 4H), 3.29 (s, 3H), 3.49 (d, J=9.9 Hz, 1H), 3.58 (d, J=9.9 Hz, 1H), 4.52 (d, J=15.1 Hz, 1H), 4.58 (d, J=15.1 Hz, 1H), 6.42 (s, 1H), 6.68 (s, 1H), 7.20-7.35 (m, 5H).

MS ($ESI^+$) m/z: 383 $[M+1]^+$

MS ($ESI^-$) m/z: 427 $[M+45]^+$ (7R*,8S*)-7-hydroxy-4,6,6-trimethyl-8-(2-phanylethylamino)-4,6,7,8-tetrahydro-1,5-dioxa-4-aza-anthracene-3-one hydrochloride To a solution of (7R*,8S*)-7-hydroxy-4,6,6-trimethyl-8-(2-phenylethyl)amino]-4,6,7,8-tetrahydro-1,5-dioxa-4-aza-anthracene-3-one (65 mg, 0.17 mmol) in ether (2.2 mL), 4 mol/L hydrogen chloride-dioxane (200 δL) was added at room temperature, and the resulting mixture was stirred at room temperature for 10 minutes. Upon the completion of the reaction, the resulting crystal was filtered off and the aimed product was obtained (yield: 93%).

Pale pink solid

Synthesis Example 74

7-Hydroxy-6,6-dimethyl-8-(2-phenylethylamino)-7,8-dihydro-1H,6H-4,5-dioxa-1-aza-anthracene-2-one

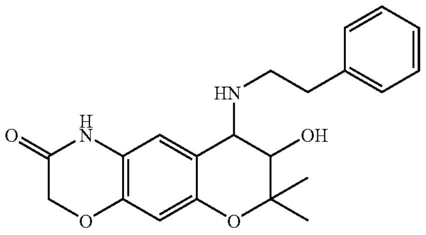

2-methoxymethoxy-4-(1,1-dimethyl-2-propynyloxy)-1-nitro-benzene

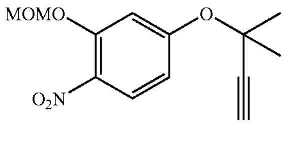

To a solution of 2-nitro-4-fluorophenol (1.6 g, 10.2 mmol) in tetrahydrofuran (32 mL), chloromethyl methyl ether (1.23 g, 15.3 mmol) and di-isopropyl ethyl amine (2.66 mL, 15.3 mmol) were added at room temperature, and the resulting mixture was stirred at room temperature for 1 hour. Upon the completion of the reaction, saturated ammonium chloride aqueous solution was added thereto, the resulting solution was extracted with ethyl acetate, washed with saturated sodium chloride solution, dried over magnesium sulfate, and concentrated. Sodium hydride (553 mg, 12.3 mmol) and 1-methyl-2-butyn-1-ol (1.23 mL, 12.7 mmol) were added to the solution of the resulting mixture in dimethylacetamide (17 mL) at 0° C., and the resulting mixture was stirred for 7 hours. Upon the completion of the reaction, saturated ammonium chloride aqueous solution was added thereto, the resulting solution was extracted with ethyl acetate, washed with saturated sodium chloride solution, dried over magnesium sulfate, and concentrated. The resulting mixture was purified by silica gel column (hexane/ethyl acetate=5/1) and the aimed product was obtained (yield: 94%).

Yellow oily product

7-Methoxymethoxy-2,2-dimethyl-6-nitro-2H-1-benzopyrane

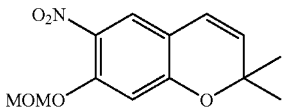

A solution of 2-methoxymethoxy-4-(1,1-dimethyl-2-propynyloxy)-1-nitro-benzene (2.1 g, 7.92 mmol) in 1,2-dichlorobenzene (21 mL) was stirred at 20° C. for 0.5 hour. Upon the completion of the reaction, the resulting mixture was concentrated and purified by silica gel column (hexane/ethyl acetate=5/1). Thereby, a mixture (1:1) of the aimed product and the regioisomer was obtained (yield: 77%).

Yellow oily product $^1$H-NMR ($CDCl_3$) δ: 1.46 (s, 6H), 3.53 (s, 1.5H), 3.58 (s, 1.5H), 5.10 (s, 1H), 5.27 (s, 1H), 5.64 (d, J=10.4 Hz, 0.5H), 5.74 (d, J=10.4 Hz, 0.5H), 6.27 (d, J=10.4 Hz, 0.5H), 6.60-6.70 (m, 1.5H), 7.67 (s, 0.5H), 7.77 (d, J=9.1 Hz, 0.5H).

3-Bromo-7-methoxymethoxy-2,2-dimethyl-6-nitro-1-benzopyran-4-ol

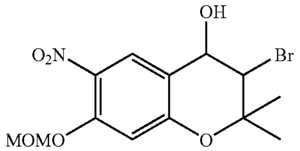

To an aqueous solution of a mixture of 7-methoxymethoxy-2,2-dimethyl-6-nitro-2H-1-benzopyrane and the regioisomer (1.5 g, 5.65 mmol) in dimethylsulfoxide (17 mL), N-bromosuccinimide (1.21 g, 6.78 mmol) was added at room temperature, and the resulting mixture was stirred for 3 hours. Upon the completion of the reaction, saturated ammonium chloride aqueous solution was added thereto, the resulting solution was extracted with ethyl acetate, washed with saturated sodium hydrogencarbonate aqueous solution and then with saturated sodium chloride solution, dried over magnesium sulfate, and concentrated. The resulting mixture was purified by silica gel column (hexane/ethyl acetate=7/1) and the aimed product was obtained (yield: 27%).

Yellow solid $^1$H-NMR ($CDCl_3$) δ: 1.45 (s, 3H), 1.63 (s, 3H), 2.73 (d, J=4.4 Hz, 1H), 3.52 (s, 3H), 4.08 (d, J=9.4 Hz, 1H), 4.88 (dd, J=9.4, 4.4 Hz, 1H), 6.71 (s, 1H), 8.16 (s, 1H).

3,4-Epoxy-7-methoxymethoxy-2,2-dimethyl-6-nitro-3,4-dihydro-2H-1-benzopyrane

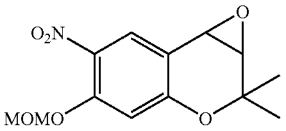

To a solution of 3-bromo-7-methoxymethoxy-2,2-dimethyl-6-nitro-1-benzopyran-4-ol (550 mg, 1.52 mmol) in dioxane (5.5 mL), 1 mol/L sodium hydroxide aqueous solution (1.82 mL, 1.82 mmol) was added at room temperature, and the resulting mixture was stirred for 2 hours. Upon the completion of the reaction, water was added thereto, the resulting solution was extracted with ethyl acetate, washed with saturated sodium thiosulfate aqueous solution and then with saturated sodium chloride solution, dried over magnesium sulfate, and concentrated. The resulting mixture was purified by silica gel column (hexane/ethyl acetate=4/1) and the aimed product was obtained (yield: 78%).

Yellow oily product $^1$H-NMR ($CDCl_3$) δ: 1.32 (s, 3H), 1.59 (s, 3H), 3.51 (s, 3H), 3.52 (d. J=3.9 Hz, 1H), 3.91 (d, J=3.9 Hz, 1H), 5.26 (s, 2H), 6.73 (s, 1H), 8.05 (s, 1H).

7-Methoxymethoxy-2,2-dimethyl-6-nitro-4-(2-phenylethylamino)-3,4-dihydro-2H-1-benzopyrane

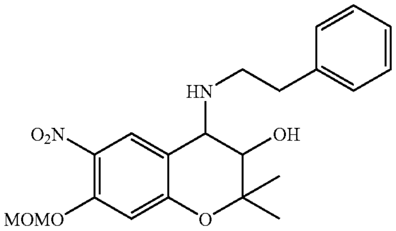

To a solution of 3,4-epoxy-7-methoxymethoxy-2,2-dimethyl-6-nitro-3,4-dihydro-2H-1-benzopyrane (332 mg, 1.18 mmol) in dioxane (1.3 mL), lithium perchlorate (126 mg, 1.18 mmol) and phenylethylamine (214 mg, 1.77 mmol) were added at room temperature, and the resulting mixture was stirred for 2 hours. Upon the completion of the reaction, saturated sodium hydrogencarbonate aqueous solution was added thereto, the resulting solution was extracted with ethyl acetate, washed with saturated sodium chloride solution, dried over magnesium sulfate, and concentrated. The resulting mixture was purified by silica gel column (hexane/ethyl acetate=3/1) and the aimed product was obtained (yield: 73%).

Yellow oily product $^1$H-NMR ($CDCl_3$) δ: 1.19 (s, 3H), 1.47 (s, 3H), 2.75-3.00 (m, 4H), 3.45-3.55 (m, 2H), 3.50 (s, 3H), 5.24 (s, 2H), 6.66 (s, 1H), 7.15-7.40 (m, 5H), 7.72 (s, 1H)

(±)-trans-6-Amino-7-Methoxymethoxy-2,2-dimethyl-4-[(2-phenylethyl)amino]-3,4-dihydro-2H-1-benzopyran-3-ol

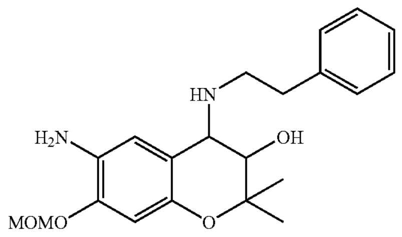

To a solution of 7-methoxymethoxy-2,2-dimethyl-6-nitro-4-(2-phenylethylamino)-3,4-dihydro-2H-1-benzopyrane (265 mg, 0.66 mmol) in ethanol (5 mL), 5% palladium-carbon (AER type, 13 mg) was added at room temperature, and the resulting mixture was stirred under hydrogen stream overnight. Upon the completion of the reaction, the resulting solution was filtered through celite, concentrated, and the aimed product was obtained (yield: 98%).

Brown oily product $^1$H-NMR ($CDCl_3$) δ: 1.13 (s, 3H), 1.43 (s, 3H), 2.70-3.05 (m, 8H), 3.51 (s, 3H), 3.52-3.60 (m, 2H), 5.12 (s, 2H), 6.21 (s, 1H), 6.51 (s, 1H), 7.20-7.50 (m, 5H).

2-Chloro-N-{(±)-trans-3-hydroxy-7-methoxymethoxy-2,2-dimethyl-4-(2-phenylethylamino)-3,4-dihydro-2H-1-benzopyran-6-yl}-acetamide

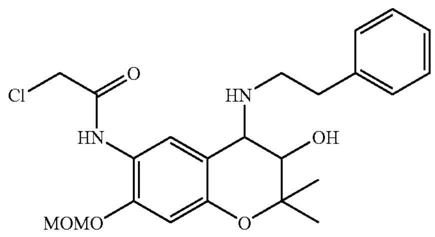

To trans-6-amino-7-methoxymethoxy-2,2-dimethyl-6-amino-4-(2-phenylethylamino)-3,4-dihydro-2H-1-benzopyran (242 mg, 0.65 mmol) in ethyl acetate-dimethylformamide mixed solution (5 mL), 4 M hydrogen chloride-dioxane solution (194 δL, 0.78 mmol) was added at 0° C., and the resulting mixture was stirred for 5 minutes. Chloroacetyl chloride (88 mg, 0.78 mmol) was added thereto, and the resulting mixture was stirred for 15 minutes. Upon the completion of the reaction, ethanol and saturated sodium hydrogencarbonate aqueous solution were added thereto, the resulting solution was extracted with ethyl acetate, washed with saturated sodium chloride solution, dried over magnesium sulfate and concentrated. The resulting mixture was purified by silica gel column (hexane/ethyl acetate=1/1) and the aimed product was obtained (yield: 79%).

Pale pink oily product $^1$H-NMR ($CDCl_3$) δ: 1.17 (s, 3H), 1.45 (s, 3H), 2.75-3.00 (m, 4H), 3.43 (d, J=9.9 Hz, 1H), 3.50 (s, 3H), 3.59 (d, J=9.9 Hz, 1H), 4.20 (s, 2H), 5.19 (s, 2H), 6.61 (s, 1H), 7.15-7.30 (m, 5H), 8.14 (s, 1H), 8.73 (s, 1H).

MS (ESI$^+$) m/z: 449 [M+1]$^+$

MS (ESI$^-$) m/z: 447 [M−1]$^+$

2-Chloro-N-{(±)-trans-3,7-dihydroxy-2,2-dimethyl-4-[(2-phenylethyl)amino]-3,4-dihydro-2H-1-benzopyran-6-yl}-acetamide

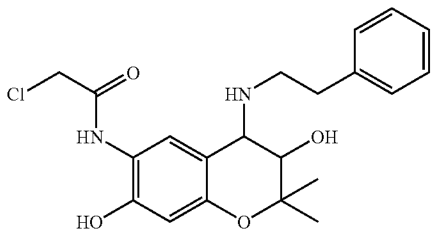

To a solution of 2-chloro-N-{(±)-trans-3-hydroxy-7-methoxymethoxy-2,2-dimethyl-4-[(2-phenylethyl)amino]-3,4-dihydro-2H-1-benzopyran-6-yl}-acetamide (228 mg, 0.51 mmol) in methylene chloride (6 mL), boron tribromide (1 M solution in methylene chloride, 2.42 mL, 2.42 mmol) was added at 0° C., and the resulting mixture was stirred for 2 hours. Upon the completion of the reaction, methanol and saturated sodium hydrogencarbonate aqueous solution were added thereto, and the resulting solution was extracted with ethyl acetate, washed with saturated sodium hydrogencarbonate aqueous solution and then with saturated sodium chloride solution, dried over magnesium sulfate and concentrated to obtain the aimed product (yield: 100%).

Colorless amorphous product

MS (ESI$^+$) m/z: 405 [M+1]$^+$

MS (ESI$^-$) m/z: 403 [M−1]$^+$

7-Hydroxy-6,6-dimethyl-8-(2-phenylethyl)amino]-7,8-dihydro-1H,6H-4,5-dioxa-1-aza-anthracene-2-one

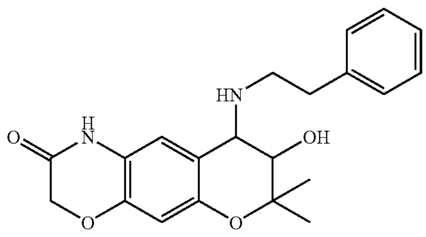

To a solution of 2-chloro-N-{(±)-trans-3,7-dihydroxy-2,2-dimethyl-4-[(2-phenylethy')amino]-3,4-dihydro-2H-1-benzopyran-6-yl}-acetamide (187 mg, 0.46 mmol) in methanol (2 mL), sodium hydroxide aqueous solution (1 mol/L, 1.8 mL) was added at room temperature, and the resulting mixture was stirred for 3 hours. Upon the completion of the reaction, saturated ammonium chloride aqueous solution was added thereto, the resulting solution was extracted with ethyl acetate, washed with 1 mol/L sodium hydroxide aqueous solution and then with saturated sodium chloride solution, dried over magnesium sulfate, and concentrated. The resulting mixture was purified by silica gel column (hexane/ethyl acetate=1/3) and the aimed product was obtained (yield: 61%).

Colorless oily product $^1$H-NMR ($CDCl_3$) δ: 1.14 (s, 3H), 1.45 (s, 3H), 2.65-3.00 (m, 4H), 3.53 (d. J=9.9 Hz, 1H), 3.57 (d, J=9.9 Hz, 1H), 4.50 (d, J=15.4 Hz, 1H), 4.56 (d, J=15.4 Hz, 1H), 5.99 (s, 1H), 6.40 (s, 1H), 7.15-7.40 (m, 5H).

MS ($ESI^+$) m/z: 369 $[M+1]^+$

Synthesis Example 75

6,6-Dimethyl-8-(2-phenylethyl)amino]-2,3,7,8-tetrahydro-1H,6H-4,5-dioxa-1-aza-anthracene-7-ol maleate

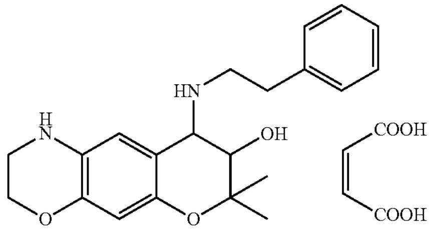

6,6-dimethyl-8-(2-phenylethylamino)-2,3,7,8-tetrahydro-1H,6H-4,5-dioxa-1-aza-anthracene-7-ol 1-maleate

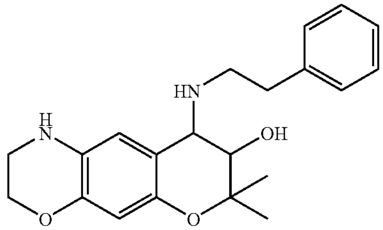

To (±)-trans-7-hydroxy-6,6-dimethyl-8-(2-phenylethylamino)-7, 8-dihydro-1H,6H-4,5-dioxa-1-aza-anthracene-2-one (67 mg, 0.18 mmol), lithium aluminum hydride (1M solution in tetrahydrofuran, 910 δL, 0.91 mmol) was added at room temperature, and the resulting mixture was stirred at 90° C. for 0.5 hour. Upon the completion of the reaction, saturated sodium hydrogencarbonate aqueous solution was added thereto, the resulting solution was extracted with ethyl acetate, washed with saturated sodium chloride solution, dried over magnesium sulfate, and concentrated. The resulting mixture was purified by silica gel column (ethyl acetate) and the aimed product was obtained (yield: 59%).

Colorless oily product $^1$H-NMR ($CDCl_3$) δ: 1.13 (s, 3H), 1.43 (s, 3H), 2.75-3.00 (m, 4H), 3.30-3.35 (m, 2H), 3.50-3.70 (m, 2H), 4.15-4.25 (m, 2H), 6.12 (s, 1H), 6.25 (s, 1H), 7.20-7.35 (m, 5H).

MS ($ESI^+$) m/z: 355 $[M+1]^+$

MS ($ESI^-$) m/z: 389 $[M+45]^+$ (±)-trans-6,6-dimethyl-8-(2-phenylethylamino)-2,3,7,8-tetrahydro -1H,6H-4,5-dioxa-1-aza-anthracene-7-ol 1-maleate To a solution of (±)-trans-6,6-dimethyl-8-(2-phenylethylamino)-2,3,7,8-tetrahydro-1H,6H-4,5-dioxa-1-aza-anthracene-7-ol in ethyl acetate (800 δL) maleic acid (14 mg, 0.12 mmol) was added at room temperature, and the resulting mixture was stirred for 10 minutes. Hexane (1 mL) was added thereto, and the resulting mixture was stirred at 0° C. for 30 minutes. The resulting crystal was filtered off and the aimed product was obtained (yield: 73%).

Pale gray crystal mp; 160-162° C. (decomposition)

$^1$H-NMR (DMSO-$d_6$) δ: 1.04 (s, 3H), 1.36 (s, 3H), 2.85-3.30 (m, 6H), 3.80-3.85 (m, 1H), 4.11 (d, J=4.2 Hz, 2H), 4.15-4.20 (m, 1H), 6.05 (s, 2H), 6.18 (s, 1H), 6.76 (s, 1H), 7.20-7.40 (m, 5H).

Synthesis Example 76

(3R*,4S*)-4-{[2-(4-fluorophenyl)ethyl]amino}-7-hydroxymethyl-2,2,9-trimethyl-3,4-dihydro-2H-pyrano[2,3-g]quinolin-3-ol

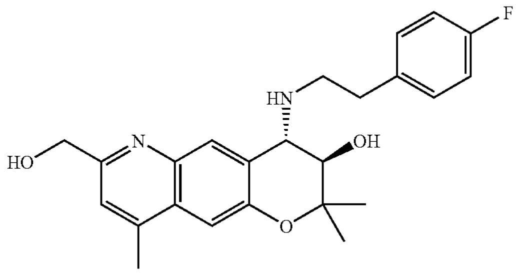

This compound was synthesized according to the process of Synthesis Example 18 (Yield: 42%)

White crystal mp; 147-152° C.

$^1$H-NMR ($CDCl_3$); 1.26(s, 3H), 1.56(s, 3H), 2.59(s, 3H), 2.84-2.86(m, 2H), 2.92-3.09(m, 2H), 3.64(d, J=10.5 Hz, 1H), 3.89(d, J=10.2 Hz, 1H), 4.83(s, 2H), 6.99-7.05(m, 3H), 7.12-7.23(m, 2H), 7.29(s, 1H), 7.81(s, 1H)

MS (ESI+) m/z; 411 [M+1]+

MS (ESI−) m/z; 455 [M+45]+

Synthesis Example 77

(3R*,4S*)-2,2-dimethyl-4-[(2-phenylethyl)amino]-3,4-dihydro-2H-pyrano[2,3-g]quinolin-3-ol 1 maleate

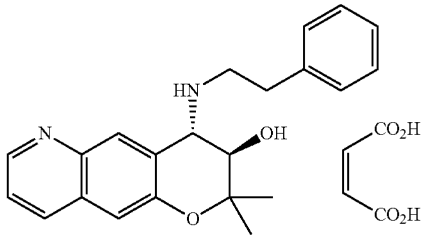

2,2-dimethyl-2H-pyrano[2,3-g]quinoline

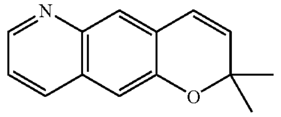

Under nitrogen atmosphere, to a solution of 6-amino-2,2-dimethylchromene (3.88 g, 22.1 mmol) and ruthenium trichloride (55.0 mg, 0.265 mmol) in dimethylene glycol dimethyl ether (8 mL), 1,3-propanediol (0.639 mL, 8.84 mmol) and tri-n-butyl phosphine (0.132 mL, 0.530 mmol) were added at room temperature, and the resulting mixture was stirred at 180° C. for 5 hours. Upon the completion of the reaction, ruthenium complex was removed by florisil column, and solvent was distilled off. The residue was purified by medium pressure column chromatography (hexane/ethyl acetate=5/1) and the aimed product was obtained (yield: 59%).

Brown amorphous product $^1$H-NMR ($CDCl_3$); 1.49(s, 6H), 5.91(d, J=9.9 Hz, 1H), 6.59(d, J=9.9 Hz, 1H), 7.08(s, 1H), 7.24-7.28(m, 1H), 7.67(s, 1H), 7.93 (d, J=8.0 Hz, 1H), 8.70(dd, J=4.1 Hz, 1.7 Hz, 1H)

MS (ESI+) m/z; 212 [M+1]+

(3R*,4S*)-3,4-epoxy-2,2-dimethyl-3,4-dihydro-2H-pyrano[2,3-g]quinoline

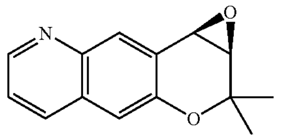

This compound was synthesized according to the process of Synthesis Example 12.

(Yield: 65%)

CHIRALPAK AD-RH 20 mM phosphate buffer (pH 8.0)/acetonitrile=60/40, Retention time: 7.3 min.

Brown solid $^1$H-NMR ($CDCl_3$); 1.30(s, 3H), 1.65(s, 3H), 3.61(d, J=4.4 Hz, 1H), 4.18(d, J=4.4 Hz, 1H), 7.17(s, 1H), 7.34(dd, J=8.5 Hz, 4.4 Hz, 1H), 8.01(d, J=7.7 Hz, 1H), 8.12(s, 1H), 8.79(dd, J=4.1 Hz, 1.7 Hz, 1H)

MS (ESI+) m/z; 228 [M+1]+

(3R*,4S*)-2,2-dimethyl-4-[(2-phenylethyl)amino]-3,4-dihydro-2H-pyrano[2,3-g]quinolin-3-ol

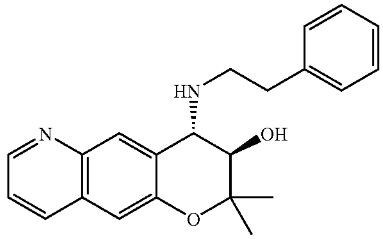

(Yield: 58%)

MS (ESI+) m/z; 349 [M+1]+

MS (ESI−) m/z; 393 [M+45]+

(3R*,4S*)-2,2-dimethyl-4-[(2-phenylethyl)amino]-3,4-dihydro-2H-pyrano[2,3-g]quinolin-3-ol 1 maleate (Yield: 79%)

White crystal mp; 187-192° C. (decomposition)

$^1$H-NMR (DMSO-d6); 1.16(s, 3H), 1.50(s, 3H), 2.94-3.00 (m, 1H), 3.09-3.20(m, 2H), 3.34-3.37(m, 1H), 4.07-4.11(m, 1H), 4.69(d, J=9.4 Hz, 1H), 6.05(s, 2H), 6.32(br s, 1H), 7.23-7.39(m, 6H), 7.49(dd, J=8.3 Hz, 4.1 Hz, 1H), 8.22(d, J=8.3 Hz, 1H), 8.44(s, 1H), 8.80(d, J=3.9 Hz, 1H)

Synthesis Example 78

(3R*,4S*)-7-chloro-2,2,9-trimethyl-4-{[2-(1-pyrrolidinyl)ethyl]amino}-3,4-dihydro-2H-pyrano[2,3-g]quinolin-3-ol

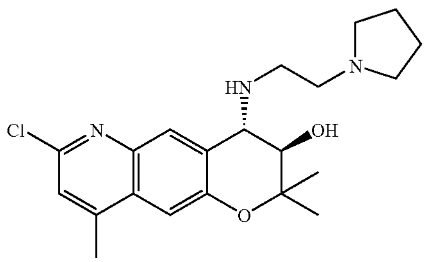

This compound was synthesized according to the process of Synthesis Example 19.

(Yield: 30%)

Orange amorphous product $^1$H-NMR ($CDCl_3$) δ: 1.19 (s, 3H), 1.50 (s, 3H), 2.05-2.15 (br, 2H), 2.49 (s, 3H), 3.09-3.32 (m, 10H), 4.60-5.20 (br, 2H), 7.06 (s, 1H), 7.11 (s, 1H), 7.88 (s, 1H)

MS ($ESI^+$) m/z; 390 $[M+1]^+$

Synthesis Example 79

(3R*,4S*)-7-chloro-4-[2-(1-triazolylethyl)amino]-2,2,9-trimethyl-3,4-dihydro-2H-pyrano[2,3-g]quinolin-3-ol

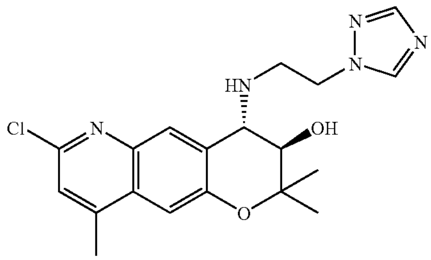

This compound was synthesized according to the process of Synthesis Example 19.

(Yield: 32%)

Pale yellow solid $^1$H-NMR ($CDCl_3$) δ: 1.28 (s, 3H), 1.57 (s, 3H), 2.00 (br), 2.58 (s, 3H), 3.23-3.35 (m, 2H), 3.63 (d, J=10.2 Hz, 1H), 3.90 (d, J=10.2 Hz, 1H), 4.29-4.38 (m, 2H), 7.15 (s, 1H), 7.27 (s, 1H), 7.99 (m, 2H), 8.18 (s, 1H)

MS (ESI$^+$) m/z; 388 [M+1]$^+$

Synthesis Example 80

(3R*,4S*)-7-hydroxymethyl-4-(n-pentylamino)-2,2,9-trimethyl-3,4-dihydro-2H-pyrano[2,3-g]quinolin-3-ol

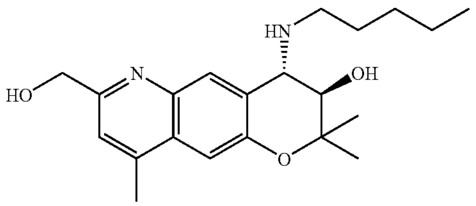

This compound was synthesized according to the process of Synthesis Example 18.

(Yield: 38%)

Pale yellow crystal $^1$H-NMR ($CDCl_3$) δ: 0.88-0.93 (m, 3H), 1.29 (s, 3H), 1.33-1.37 (m, 4H), 1.59 (s, 3H), 1.60 (m, 2H), 2.60 (s, 3H), 2.66-2.84 (m, 2H), 3.68 (d, J=10.5 Hz, 1H), 3.94 (d, J=10.5 Hz, 1H), 4.83 (s, 2H), 7.04 (s, 1H), 7.31 (s, 1H), 7.99 (s, 1H)

MS (ESI$^+$) m/z; 359 [M+1]$^+$

Synthesis Example 81

(8R*,9S*)-7,7-dimethyl-9-[(2-cyclopentyl)amino)-8,9-dihydro-7H-pyrano[2,3-g]quinoxalin-8-ol

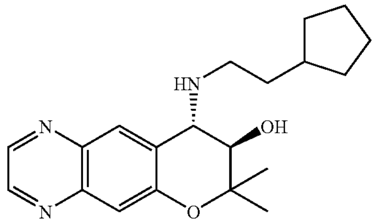

This compound was synthesized according to the process of Synthesis Example 59.

(3R*,4S*)-6,7-diamino-3,4-dihydro-2,2-dimethyl-4-(2-cyclopentylamino)-2H-1-benzopyran-3-ol

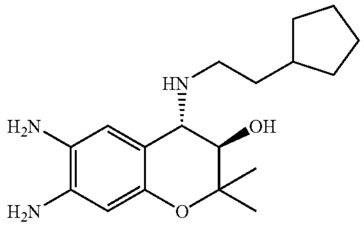

Black amorphous product (8R*,9S*)-7,7-dimethyl-9-[(2-cyclopentyl)amino)-8,9-dihydro-7H-pyrano[2,3-g]quinoxalin-8-ol $^1$H-NMR ($CDCl_3$) δ: 1.05(m, 2H), 1.31(s, 3H), 1.50-1.90 (m, 9H), 1.59(s, 3H), 2.60-2.90(m, 2H), 3.37(brs, 1H), 3.68 (d, J=10.4 Hz, 1H), 3.93(d, J=10.4 Hz, 1H), 7.44(s, 1H), 8.03(s, 1H), 8.66(d, J=1.7 Hz, 1H), 8.74(d, J=1.7 Hz, 1H).

Synthesis Example 82

(3R*,4S*)-3-hydroxy-2,2,9-trimethyl-4-[(2-phenylethyl)amino]-3,4-dihydro-2H-pyrano[2,3-g]quinolin-7-carboxylic acid

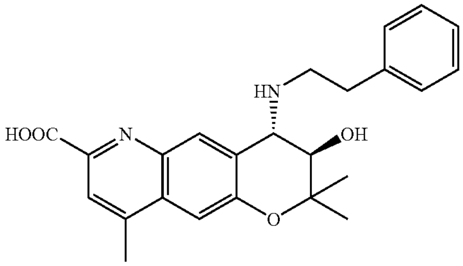

To a solution of (3R*,4R*)-3-hydroxy-2,2,9-trimethyl-4-[(2-phenylethyl)amino]-3,4-dihydro-2H-pyrano[2,3-g]quinoline-7-carbonitrile described in Synthesis Example 14 (465 mg, 1.20 mmol) in ethanol (5 mL), sodium hydroxide aqueous solution (3 mol/L, 5 mL) was added at room temperature, and the resulting mixture was stirred for 2 hours with reflux under heating. After cooling to room temperature, the resulting solution was neutralized with 1 mol/L hydrochloric acid, precipitated brown solid was filtered off and the aimed product was obtained (yield: 90%).

Brown solid $^1$H-NMR ($CDCl_3$) δ: 1.07 (s, 3H), 1.41 (s, 3H), 2.46 (s, 3H), 2.89-3.08 (br, 2H), 3.10-3.28 (br, 2H), 4.03-4.22 (br, 1H), 4.30-4.44 (br, 1H), 7.01-7.54 (m, 7H), 7.86 (s, 1H), 8.51-8.73 (br, 1H)

MS (ESI$^+$) m/z; 407 [M+1]$^+$

Synthesis Example 83

(3R*,4S*)-7-aminomethyl-2,2,9-trimethyl-4-[(2-phenylethyl)amino]-3,4-dihydro-2H-pyrano[2,3-g]quinolin-3-ol 2 maleate

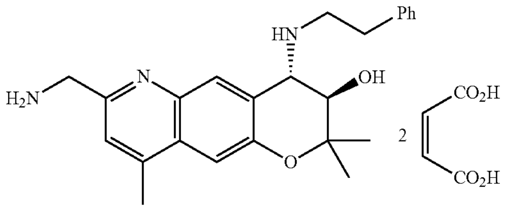

(3R*,4S*)-7-aminomethyl-2,2,9-trimethyl-4-[(2-phenylethyl)amino]-3,4-dihydro-2H-pyrano[2,3-g]quinolin-3-ol

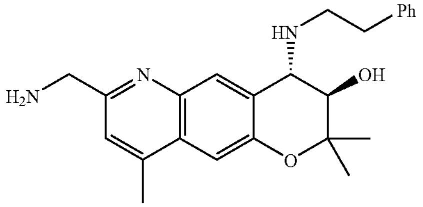

To a solution of (3R*,4R*)-3-hydroxy-2,2,9-trimethyl-4-[(2-phenylethyl)amino]-3,4-dihydro-2H-pyrano[2,3-g]quinoline-7-carbonitrile described in Synthesis Example 14 (110 mg, 0.283 mmol) in acetic acid (5 mL), 10% Pd/C (22 mg) was added at room temperature, and the resulting mixture was stirred for 2 hours under hydrogen atmosphere. Upon the completion of the reaction, the resulting solution was filtered through celite, the solvent was distilled off and then sodium carbonate aqueous solution was added to the residue, and the resulting solution was extracted with chloroform, dried over anhydrous magnesium sulfate, and the solvent was distilled off to obtain crude product of (3R*,4S*)-7-aminomethyl-2,2,9-trimethyl-4-[(2-phenylethyl)amino]-3,4-dihydro-2H-pyrano[2,3-g]quinolin-3-ol (75.1 mg).

$^1$H-NMR ($CDCl_3$) δ; 1.14(s, 3H), 1.46(s, 3H), 2.48(s, 3H), 2.73(t, J=6.6 Hz, 2H), 2.88-2.95(m, 2H), 3.53(d, J=10.5 Hz, 1H), 3.77(d, J=10.2 Hz, 1H), 3.98(s, 2H), 7.04(s, 1H), 7.12-7.23(m, 6H), 7.84(s, 1H)

MS (ESI$^+$) m/z; 392 [M+1]$^+$ (3R*,4S*)-7-aminomethyl-2,2,9-trimethyl-4-[(2-phenylethyl)amino]-3,4-dihydro-2H-pyrano[2,3-g]quinolin-3-ol 2 maleate (2-step yield: 14%)

Brown crystal mp; 136-140° C.

$^1$H-NMR (DMSO-$d_6$) δ; 1.18(s, 3H), 1.49(s, 3H), 2.60(s, 3H), 2.90-3.00(m, 2H), 3.24-3.35(m, 2H), 4.02(brs, 1H), 4.33 (s, 2H), 4.51(brs, 1H), 6.04(s, 4H), 7.21-7.42(m, 7H), 8.32 (brs, 2H), 8.36(s, 1H)

Synthesis Example 84

(3R*,4S*)-9-hydroxymethyl-2,2-dimethyl-4-[(2-phenylethyl)amino)]-3,4-dihydro-2H-pyrano[2,3-g]quinolin-3-ol 1 maleate

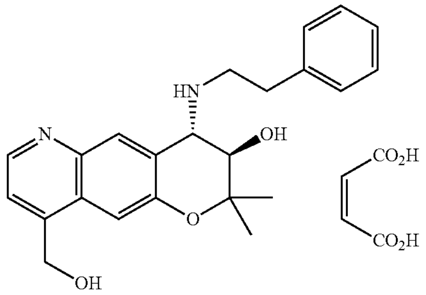

This compound was synthesized according to the process of Synthesis Example 18.

(2,2-Dimethyl-2H-pyrano[2,3-g]quinolin-9-yl)-methylacetate

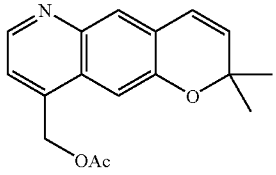

To a solution of 2,2,9-trimethyl-2H-pyrano[2,3-g]quinoline described in Synthesis Example 1 (3.30 mg, 14.6 mmol) in chloroform (33 mL), a solution of m-chloroperbenzoic acid (5.54 g, 19.5 mmol) in chloroform (13.2 mL)-methanol (3.3 mL) was added dropwise at room temperature, and the resulting mixture was stirred at room temperature for 1 hour. Upon the completion of the reaction, sodium thiosulfate aqueous solution was added thereto and the resulting solution was extracted therewith. The resulting organic phase was washed with sodium hydrogencarbonate aqueous solution and then with sodium chloride aqueous solution, and dried over anhydrous magnesium sulfate. After distilling off the solvent, acetic anhydride (46 mL) was added to the residue at room temperature, and the resulting mixture was stirred at 150° C. for 1 hour. Upon the completion of the reaction, acetic anhydride was distilled off, the residue was neutralized with sodium carbonate aqueous solution, extracted with chloroform, and the resulting organic phase was washed with sodium chloride aqueous solution, and dried over anhydrous magnesium sulfate. After distilling off the solvent, the residue was purified by medium pressure column chromatography (hexane/ethyl acetate=1/1) and the aimed product was obtained (yield: 34%).

$^1$H-NMR ($CDCl_3$) δ; 1.41(s, 6H), 2.09(s, 3H), 5.37(s, 2H), 5.84(d, J=9.9 Hz, 1H), 6.49(d, J=9.9 Hz, 1H), 7.09(s, 1H), 7.24(d, J=4.4 Hz, 1H), 7.66(s, 1H), 8.61(d, J=4.4 Hz, 1H)

MS (ESI$^+$) m/z; 284 [M+1]$^+$ (3R*,4S*)-(3,4-epoxy-2,2-dimethyl-3,4-dihydro-2H-pyrano[2,3-g]quinolin-9-yl)-methylacetate

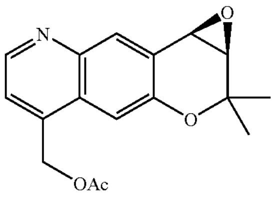

(Yield: 58%)

99.5% ee; CHIRALPAK AD-RH 20 mM phosphate buffer (pH 8.0)/acetonitrile=60/40, Retention time: 9.5 min.

Pale yellow solid $^1$H-NMR ($CDCl_3$) δ1.31(s, 3H), 1.66(s, 3H), 2.18(s, 3H), 3.62(d, J=4.4 Hz, 1H), 4.18(d, J=4.4 Hz, 1H), 5.47(d, J=2.2 Hz, 2H), 7.28(s, 1H), 7.38(d, J=4.1 Hz, 1H), 8.16(s, 1H), 8.78(d, J=4.4 Hz, 1H)

MS (ESI$^+$) m/z; 300 [M+1]$^+$ (3R*,4S*)-9-hydroxymethyl-2,2-dimethyl-4-[(2-phenylethyl)amino)]-3,4-dihydro-2H-pyrano[2,3-g]quinolin-3-ol

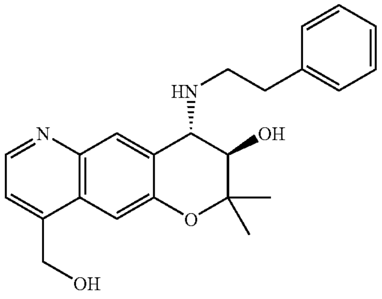

(Yield: 80%)

Brown amorphous product $^1$H-NMR ($CDCl_3$) δ; 1.23(s, 3H), 1.52(s, 3H), 2.77-2.81 (m, 2H), 2.90-3.04(m, 2H), 3.58(d, J=10.5 Hz, 1H), 3.83(d, J=10.4 Hz, 1H), 5.08(s, 2H), 7.17-7.21(m, 4H), 7.26-7.31(m, 2H), 7.44(d, J=4.4 Hz, 1H), 7.98(s, 1H), 8.65(t, J=4.7 Hz, 1H)

MS (ESI$^+$) m/z; 379 [M+1]$^+$

MS (ESI$^-$) m/z; 423 [M+45]$^+$ (3R*,4S*)-9-hydroxymethyl-2,2-dimethyl-4-[(2-phenylethyl)amino)]-3,4-dihydro-2H-pyrano[2,3-g]quinolin-3-ol 1 maleate (Yield: 88%)

White crystal mp; 163-169° C. (decomposition)

$^1$H-NMR (DMSO-$d_6$) δ; 1.17(s, 3H), 1.50(s, 3H), 2.94-3.01(m, 1H), 3.09-3.21(m, 2H), 3.35-3.38(m, 2H), 4.09(dd, J=9.6 Hz, 6.3 Hz, 1H), 4.72(d, J=9.4 Hz, 1H), 4.91(s, 2H), 5.57(brs, 1H), 6.08(s, 2H), 6.34(d, J=5.5 Hz, 1H), 7.23-7.39 (m, 6H), 7.52(d, J=4.4 Hz, 1H), 8.45(s, 1H), 8.77(d, J=4.4 Hz, 1H)

Synthesis Example 85

(3R*,4S*)-2,2,9-trimethyl-4-[(2-phenylethyl) amino)]-3,4-dihydro-2H-pyrano[2,3-g]quinolin-3,7-diol 3/2 maleate

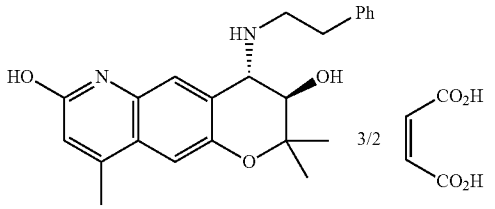

This compound was synthesized according to the process of Synthesis Example 18.

2,2,9-Trimethyl-2H-pyrano[2,3-g]quinolin-7-yl-acetate

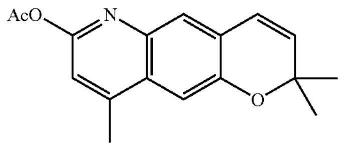

To a solution of 2,2,9-trimethyl-2H-pyrano[2,3-g]quinoline described in Synthesis Example 1 (3.30 mg, 14.6 mmol) in chloroform (33 mL), a solution of m-chloroperbenzoic acid (5.54 g, 19.5 mmol) in chloroform (13.2 mL)-methanol (3.3 mL) was added dropwise at room temperature, and the resulting mixture was stirred at room temperature for 1 hour. Upon the completion of the reaction, sodium thiosulfate aqueous solution was added thereto and the resulting solution was extracted therewith. The resulting organic phase was washed with sodium hydrogencarbonate aqueous solution and then with sodium chloride aqueous solution, and dried over anhydrous magnesium sulfate. After distilling off the solvent, acetic anhydride (46 mL) was added to the residue at room temperature, and the resulting mixture was stirred at 150° C. for 1 hour. Upon the completion of the reaction, acetic anhydride was distilled off, the residue was neutralized with sodium carbonate aqueous solution, extracted with chloroform, and the resulting organic phase was washed with sodium chloride aqueous solution, and dried over anhydrous magnesium sulfate. After distilling off the solvent, the residue was purified by medium pressure column chromatography (hexane/ethyl acetate=1/1) and the aimed product was obtained (yield: 23%).

Red oily product $^1$H-NMR ($CDCl_3$) δ; 1.49(s, 6H), 2.395(s, 3H), 2.404(s, 3H), 5.90(d, J=9.9 Hz, 1H), 6.58(d, J=9.9 Hz, 1H), 7.23(s, 1H), 7.74(s, 1H), 8.48(s, 1H)

MS (ESI$^+$) m/z; 284 [M+1]$^+$ (3R*,4S*)-(3,4-epoxy-2,2,9-trimethyl-3,4-dihydro-2H-pyrano[2,3-g]quinolin-7-yl-acetate

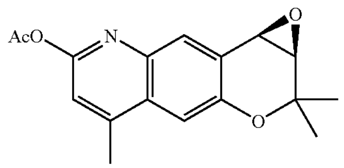

(Yield: 37%)

CHIRALPAK AD-RH 20 mM phosphate buffer (pH 8.0)/acetonitrile=60/40, Retention time: 6.6 min.

Brown amorphous product $^1$H-NMR ($CDCl_3$) δ; 1.29(s, 3H), 1.64(s, 3H), 2.41(s, 6H), 3.60(d, J=4.4 Hz, 1H), 4.15(d, J=4.1 Hz, 1H), 7.31(s, 1H), 8.10(s, 1H), 8.47(s, 1H)

MS (ESI$^+$) m/z; 300 [M+1]$^+$ (3R*,4S*)-2,2,9-trimethyl-4-[(2-phenylethyl)amino)]-3,4-dihydro-2H-pyrano[2,3-g]quinolin-3,7-diol

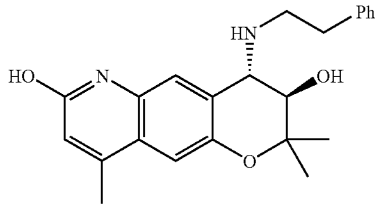

(Yield: 46%)

Brown amorphous product $^1$H-NMR ($CDCl_3$) δ; 1.25(s, 3H), 2.05(s, 3H), 2.48(s, 3H), 2.80(t, J=6.6 Hz, 2H), 2.93-3.12(m, 2H), 3.58(d, J=10.2 Hz, 1H), 3.84(d, J=10.2 Hz, 1H), 7.12-7.25(m, 6H), 8.02(s, 1H), 8.66(s, 1H)

MS (ESI$^+$) m/z; 379 [M+1]$^+$

MS (ESI$^-$) m/z; 377 [M−1]$^+$ (3R*,4S*)-2,2,9-trimethyl-4-[(2-phenylethyl)amino)]-3,4-dihydro-2H-pyrano[2,3-g]quinolin-3,7-diol 3/2 maleate (Yield: 70%)

White crystal mp; 184-188° C. (decomposition)

$^1$H-NMR (DMSO-$d_6$) δ; 1.16(s, 3H), 1.49(s, 3H), 2.35(s, 3H), 2.94-3.00(m, 1H), 3.10-3.22(m, 2H), 3.36-3.42(m, 1H), 4.04-4.10(m, 1H), 4.66(d, J=9.4 Hz, 1H), 6.12(s, 3H), 6.33(d, J=5.8 Hz, 1H), 7.23-7.36(m, 6H), 8.30(s, 1H), 8.49(s, 1H), 10.12(s, 1H)

Synthesis Example 86

(3R*,4S*)-7-chloro-2,2,9-trimethyl-6-oxy-4-[(2-phenylethyl)amino]-3,4-dihydro-2H-pyrano[2,3-g]quinolin-3-ol hydrochloride

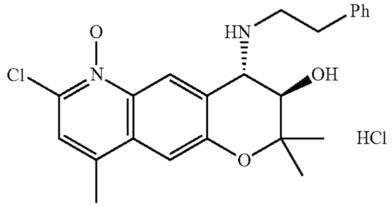

(3/R*,4S*)-t-butyl-7-chloro-3-hydroxy-2,2,9-trimethyl-3,4-dihydro-2H-pyrano[2,3-g]quinolin-4-yl (2-phenylethyl)carbamate

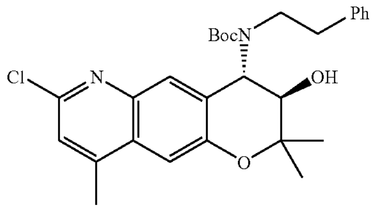

To a solution of (3R*,4S*)-7-chloro-2,2,9-trimethyl-4-[(2-phenylethyl)amino]-3,4-dihydro-2H-pyrano[2,3-g]quinoline-3-ol described in Synthesis Example 19 (391 mg, 0.99 mmol) and di-t-butyl dicarbonate (430 mg, 1.97 mmol) in tetrahydrofuran (8 mL), triethylethylamine (600 δL, 4.29 mmol) was added dropwise, and the resulting mixture was stirred at room temperature for 2 hours. Further, di-t-butyl dicarbonate (430 mg, 1.97 mmol) was added thereto at room temperature, and the resulting mixture was stirred overnight. Upon the completion of the reaction, sodium carbonate aqueous solution was added thereto and the resulting solution was extracted with ethyl acetate. The resulting organic phase was washed with sodium chloride aqueous solution, and dried over anhydrous magnesium sulfate. After distilling off the solvent, the residue was purified by medium pressure column chromatography (hexane/ethyl acetate=10/1) and the aimed product was obtained (yield: 87%).

MS (ESI$^+$) m/z; 497 [M+1]$^+$

MS (ESI$^-$) m/z; 541 [M+45]$^+$ (3R*,4S*)-t-butyl-7-chloro-3-hydroxy-2,2,9-trimethyl-6-oxy-3,4-dihydro-2H-pyrano[2,3-g]quinolin-4-yl (2-phenylethyl)carbamate

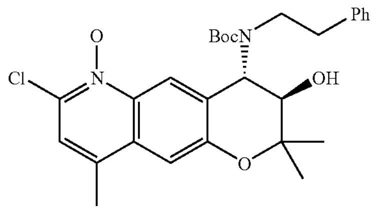

To a solution of ((3R*,4S*)-t-butyl-7-chloro-3-hydroxy-2,2,9-trimethyl-3, 4-dihydro-2H-pyrano[2,3-g]quinolin-4-yl (2-phenylethyl)carbamate (100 mg, 0.20 mmol) in chloroform (1 mL), a solution of m-chloroperbenzoic acid (75.9 mg, 0.44 mmol) in chloroform (0.4 mL)-methanol (0.1 mL) was added dropwise at room temperature, and the resulting mixture was stirred at room temperature for 30 minutes. At room temperature, a solution of m-chloroperbenzoic acid (75.9 mg, 0.44 mmol) in chloroform (0.4 mL) was further added thereto and the resulting mixture was stirred overnight. Upon the completion of the reaction, sodium thiosulfate aqueous solution was added thereto and the resulting solution was extracted therewith. The resulting organic phase was washed with sodium hydrogencarbonate aqueous solution and then with sodium chloride aqueous solution, and dried over anhydrous magnesium sulfate. After distilling off the solvent, the residue was purified by medium pressure column chromatography (hexane/ethyl acetate=3/1 to 1/1) and the aimed product was obtained (yield: 41%).

MS ($ESI^+$) m/z; 513 $[M+1]^+$

MS ($ESI^-$) m/z; 557 $[M+45]^+$ (3R*,4S*)-7-chloro-2,2,9-trimethyl-6-oxy-4-[(2-phenylethyl)amino)]-3,4-dihydro-2H-pyrano[2,3-g]quinolin-3-ol hydrochloride To a solution of (3R*,4S*)-t-butyl-7-chloro-3-hydroxy-2,2,9-trimethyl-6-oxy-3,4-dihydro-2H-pyrano[2,3-g]quinolin-4-yl (2-phenylethyl)carbamate (41.7 mg, 0.081 mmol) in 1,4-dioxane (0.2 mL), 4 mol/L hydrochloric acid-dioxane solution (0.42 mL) was added at room temperature, and the resulting mixture was stirred at 80° C. for 1 hour. Upon the completion of the reaction, precipitated solid was filtered off and washed with di-isopropyl ether to obtain the aimed product (yield: 72%).

White crystal mp; 174-179° C. (decomposition)

$^1$H-NMR (DMSO-$d_6$) δ; 1.14(s, 3H), 1.49(s, 3H), 2.53(s, 3H), 3.00-3.55(m, 4H), 4.21(d, J=9.1 Hz, 1H), 4.76(brs, 1H), 7.23-7.31(m, 6H), 7.45(s, 1H), 7.65(s, 1H), 9.08(s, 1H), 9.37 (brs, 1H), 10.16(brs, 1H)

MS ($ESI^+$) m/z; 413, 415 $[M+1]^+$

MS ($ESI^-$) m/z; 457, 459 $[M+45]^+$

Synthesis Example 87

(3R*,4S*)-7-chloro-4-{([2-(4-fluorophenyl)ethyl] amino}-2,2,9-trimethyl-6-oxy3,4-dihydro-2H-pyrano [2,3-g]quinolin-3-ol hydrochloride

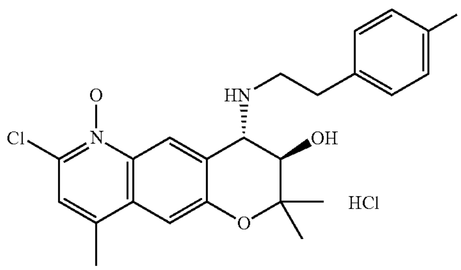

This compound was synthesized by using the compound of Synthesis Example 23 similarly to the process of Synthesis Example 86.

(3R*,4S*)-t-butyl-7-chloro-3-hydroxy-2,2,9-trimethyl-3, 4-dihydro-2H-pyrano[2,3-g]quinolin-4-yl[2-(4-fluorophenyl)ethyl]carbamate

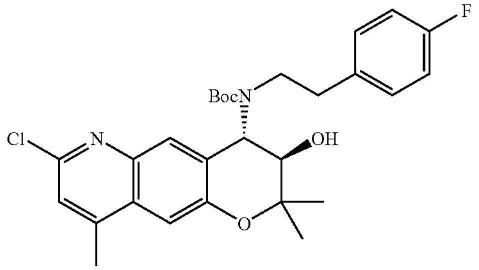

MS ($ESI^+$) m/z; 515, 517 $[M+1]^+$

MS ($ESI^-$) m/z; 559, 561 $[M+45]^+$ (3R*,4S*)-t-butyl-7-chloro-3-hydroxy-2,2,9-trimethyl-6-oxy-3,4-dihydro-2H-pyrano[2,3-g]quinolin-4-yl[2-(4-fluorophenyl)ethyl]carbamate

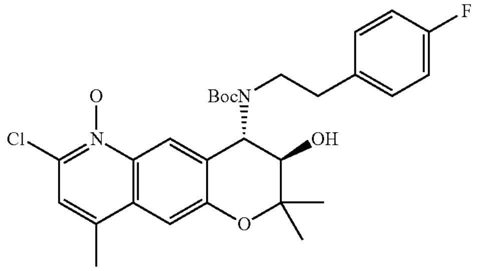

(2-step yield: 30%).

MS ($ESI^+$) m/z; 531, 533 $[M+1]^+$

MS ($ESI^-$) m/z; 575, 577 $[M+45]^+$ (3R*,4S*)-7-chloro-4-{[2-(4-fluorophenyl)ethyl]amino}-2,2,9-trimethyl-6-oxy-3,4-dihydro-2H-pyrano[2,3-g]quinolin-3-ol hydrochloride (yield: 71%).

Pale yellow crystal mp; 193-198° C. (decomposition)

$^1$H-NMR (DMSO-$d_6$) δ; 1.14(s, 3H), 1.49(s, 3H), 2.53(s, 3H), 2.96-3.06(m, 1H), 3.16-3.18(m, 2H), 3.36(brs, 1H), 4.19-4.22(m, 1H), 4.75-4.78(m, 1H), 7.13(t, J=9.08 Hz, 2H), 7.26-7.31(m, 2H), 7.45(s, 1H), 7.65(s, 1H), 9.06(s, 1H), 9.37 (brs, 1H), 10.16(brs, 1H)

MS (ESI$^+$) m/z, 431, 433 [M+1]$^+$

MS (ESI$^-$) m/z; 475, 477 [M+45]$^+$

Synthesis Example 88

(3R*,4S*)-7-chloro-2,2,9-trimethyl-6-oxy-4-(pentylamino) -3,4-dihydro-2H-pyrano[2,3-g]quinolin-3-ol hydrochloride

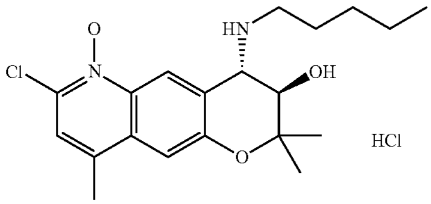

This compound was synthesized by using the compound of Synthesis Example 52 similarly to the process of Synthesis Example 86.

(3R*,4S*)-t-butyl-7-chloro-3-hydroxy-2,2,9-trimethyl-3, 4-dihydro-2H-pyrano[2,3-g]quinolin-4-yl pentyl carbamate

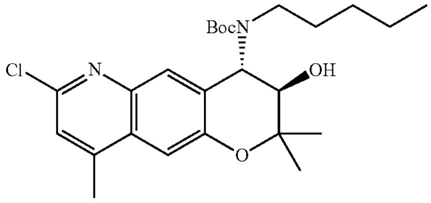

MS (ESI$^+$) m/z; 463, 465 [M+1]$^+$

MS (ESI$^-$) m/z; 507, 509 [M+45]$^+$ (3R*,4S*)-t-butyl-7-chloro-3-hydroxy-2,2,9-trimethyl-6-oxy-3,4-dihydro-2H-pyrano[2,3-g]quinolin-4-yl pentyl carbamate

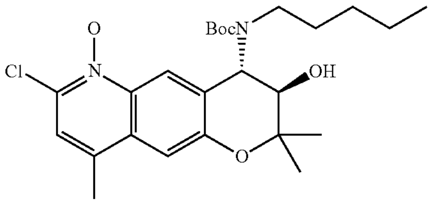

(2-step yield: 23%).

MS (ESI$^+$) m/z; 479, 481 [M+1]$^+$

MS (ESI$^-$) m/z; 523, 525 [M+45]$^+$ (3R*,4S*)-7-Chloro-2,2,9-trimethyl-6λ5-oxy-4-(pentylamino)-3,4-dihydro-2H-pyrano[2,3-g]quinolin-3-ol hydrochloride (yield: 60%).

Pale yellow crystal mp; 226-230° C. (decomposition)

$^1$H-NMR (DMSO-$d_6$) δ; 0.86(t, J=6.3 Hz, 3H), 1.16(s, 3H), 1.27-1.29(m, 4H), 1.50(s, 3H), 1.60-1.72(m, 2H), 2.54 (s, 3H), 2.86(brs, 1H), 3.07(brs, 1H), 4.07-4.10(m, 1H), 4.71 (d, J=8.5 Hz, 1H), 6.51(d, J=4.7 Hz, 1H), 7.47(s, 1H), 7.67(s, 1H), 9.04(s, 1H), 9.19(brs, 1H), 9.74(brs, 1H)

MS (ESI$^+$) m/z; 379, 381 [M+1]$^+$

MS (ESI$^-$) m/z; 423, 425 [M+45]$^+$

Synthesis Example 89

8,8-Dimethyl-6-[(2-phenylethyl)amino)]-1,6,7, 8-tetrahydrochromeno[7,6-e][1,3,4]oxathiazin-7-ol 2,2-dioxide

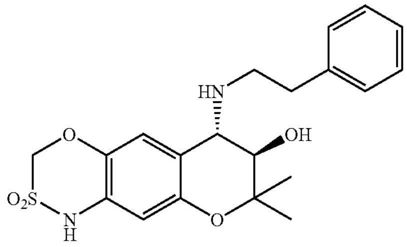

t-Butyl (3R*,4S*)-7-{[(chloromethyl)sulfonyl]amino}-3-hydroxy-6-methoxy-2,2-dimethyl-3,4-dihydro-2H-1-benzopyran-4-yl (2-phenylethyl)carbamate

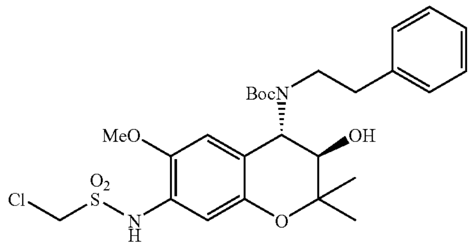

To a solution of t-butyl (2-phenylethyl)(3R*,4S*)-7-amino-3-hydroxy-6-methoxy-2,2-dimethyl-3, 4-dihydro-2H-1-benzopyran-4-yl carbamate described in Synthesis Example 71 (1.04 g, 2.35 mmol) in pyridine (1.90 mL, 23.5 mmol), chloromethanesulfonylchloride (0.31 mL, 3.52 mmol) was added, and the resulting mixture was stirred at room temperature for 10 hours. Upon the completion of the reaction, 1 mol/L hydrochloric acid aqueous solution (ca. 30 mL) was added thereto to adjust pH to about 7, and then the resulting solution was extracted with ethyl acetate, washed with saturated sodium chloride aqueous solution, and dried over anhydrous sodium sulfate and concentrated. The resulting mixture was purified by column chromatography (hexane/ethyl acetate=3/1) and the aimed product was obtained (yield: 81%).

Colorless oily product

LC/MS ($ES^+$) m/z: 555 $[M+1]^+$

LC/MS ($ES^-$) m/z: 553 $[M-1]^+$

1-Chloro-N-{(3R*,4S*)-3,6-dihydroxy-2,2-dimethyl-4-[(2-phenylethyl)amino]-3,4-dihydro-2H-1-benzopyran-7-yl}methanesulfonamide

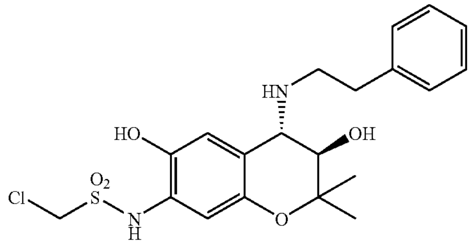

To a solution of (t-butyl (3R*,4S*)-7-{[(chloromethyl)sulfonyl]amino}-3-hydroxy-6-methoxy-2,2-dimethyl-3,4-dihydro-2H-1-benzopyran-4-yl (2-phenylethyl)carbamate (400 mg, 0.72 mmol) in dichloromethane (4.0 mL), 1 mol/L solution of boron tribromide in dichloromethane (3.61 mL, 3.61 mmol) was added below freezing point, and the resulting mixture was stirred at 0° C. for 1 hour. Water was added, and the resulting mixture was further stirred for 30 minutes. The resulting solid was filtered off, washed with water and then with chloroform. The solid was dried at 60° C. for 3 hours under reduced pressure, and the aimed product was quantitatively obtained.

LC/MS ($ES^+$) m/z: 441 $[M+1]^+$

LC/MS ($ES^-$) m/z: 439 $[M-1]^+$ 8,8-Dimethyl-6-[(2-phenylethyl)amino]-1,6,7, 8-tetrahydrochromeno[7,6-e][1,3,4]oxathiazine-7-ol 2,2-dioxide To a solution of 1-Chloro-N-{(3R*,4S*)-3,6-dihydroxy-2,2-dimethyl-4-[(2-phenylethyl)amino]-3,4-dihydro-2H-1-benzopyran-7-yl}methanesulfonamide (220 mg, 0.50 mmol) in methanol (2.2 mL), 1 mol/L sodium hydroxide aqueous solution (1.00 mL, 1.00 mmol) was added, and the resulting mixture was stirred at room temperature for 3 hours. Then, the temperature was raised to 50° C., and the mixture was further stirred for 2 hours. Upon the completion of the reaction, the solution was cooled on standing, neutralized with saturated ammonium chloride aqueous solution, extracted 4 times with chloroform, and dried over anhydrous sodium sulfate. The solvent was distilled off and the aimed product was obtained (yield: 37%).

Yellow solid $^1$H-NMR ($CDCl_3$) δ: 1.13 (s, 3H), 1.44 (s, 3H), 2.54 (brs, 3H), 2.79-3.02 (m, 4H), 3.49 (d, J=10.0 Hz, 1H), 3.59 (d, J=10.0 Hz, 1H), 4.86 (s, 2H), 6.23 (s, 1H), 6.78 (s, 1H), 7.21-7.35 (m, 5H)

LC/MS ($ES^+$) m/z: 405 $[M+1]^+$

LC/MS ($ES^-$) m/z: 403 $[M-1]^+$

Synthesis Example 90

1-Benzyl-7-hydroxy-6,6-dimethyl-8-phenetylamino-3,6,7, 8-tetrahydro-1H-pyrano[2,3-f]indole-2-one

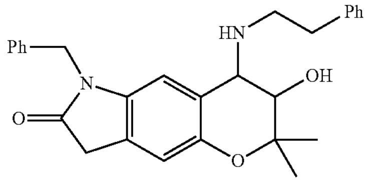

N-Benzyl-5-methoxyisatin

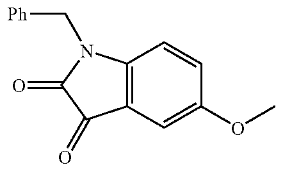

To a solution of 5-methoxyisatin (15.0 g, 84.7 mmol) in DMF (100 mL), sodium hydride (5.1 g, 127 mmol) and benzyl bromide (12.1 mL, 101.6 mmol) were added at 0° C., and the resulting mixture was stirred for 1 hour. Water was added thereto, and the resulting solution was extracted with ethyl acetate. The resulting organic phase was washed with saturated ammonium chloride aqueous solution and then with saturated sodium chloride solution, dried over anhydrous sodium sulfate, and concentrated to obtain the aimed product (yield: 96%).

Brown solid $^1$H-NMR ($CDCl_3$) δ; 3.77(s, 3H), 4.91(s, 2H), 6.67(d, J=8.5 Hz, 1H), 7.0-7.1(m, 1H), 7.15(m, 1H), 7.25-7.45(m, 5H)

N-Benzyl-5-hydroxyisatin

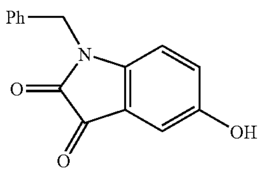

To a solution of N-benzyl-5-methoxyisatin (3.0 g, 11.2 mmol) in dichloromethane (60 mL), aluminum chloride (3.7 g, 28.1 mmol) was added, and the resulting mixture was stirred at 100° C. for 1 hour. Water was added thereto, and the resulting solution was extracted with ethyl acetate. The resulting organic phase was washed with saturated sodium hydrogencarbonate aqueous solution and then with saturated sodium chloride solution, dried over anhydrous sodium sulfate, and concentrated to obtain the aimed product (yield: 78%).

Red solid

MS ($ESI^+$) m/z; 254 $[M+1]^+$

MS ($ESI^-$) m/z; 252 $[M-1]^+$

N-Benzyl-6,6-dimethyl-1H-pyrano[2,3-f]indole-2,3-dione

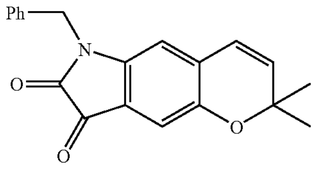

Under nitrogen stream, a solution of N-benzyl-5-hydroxyisatin (4.74 g, 18.7 mmol), potassium iodide (5.09 g, 31.8 mmol), potassium carbonate (5.17 g, 37.4 mmol), copper iodide (71 mg, 0.37 mmol) and 3-chloro-3-methyl-1-butyne (4.83 mL, 43.0 mmol) in DMF (47 mL) was stirred at 70° C. for 2 hours. Upon the completion of the reaction, saturated ammonium chloride aqueous solution was added thereto, the resulting solution was extracted with ethyl acetate. The resulting organic phase was washed with saturated sodium chloride solution, dried over anhydrous sodium sulfate, concentrated and purified by silica gel short column (chloroform). 1,2-Dichlorobenzene (9 mL) was added and the resulting mixture was stirred at 200° C. for 30 minutes. After concentrating the reaction solution, the residue was purified by silica gel column (hexane/ethyl acetate=5/1) to obtain the aimed product (yield: 8%).

Red oily product

MS ($ESI^+$) m/z; 320 $[M+1]^+$

N-Benzyl-6,6-dimethyl-1H-pyrano[2,3-f]indole-2-one

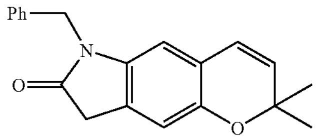

To a solution of N-benzyl-6,6-dimethyl-1H-pyrano[2,3-f]indole-2,3-dione (500 mg, 1.57 mmol) in DMF (5 mL), hydrazine monohydrate (2.5 mL) was added, and the resulting mixture was stirred at 100° C. for 1.5 hour. Water was added thereto, and the resulting solution was extracted with ethyl acetate. The resulting organic phase was washed with saturated ammonium chloride aqueous solution and then with saturated sodium chloride solution, dried over anhydrous sodium sulfate, concentrated and purified by silica gel column (hexane/ethyl acetate=3/1) to obtain the aimed product (yield: 65%).

Yellow amorphous product

MS ($ESI^+$) m/z; 306 $[M+1]^+$

1-Benzyl-7-hydroxy-6,6-dimethyl-8-phenetylamino-3,6,7, 8-tetrahydro-1H-pyrano[2,3-f]indole-2-one To 1-benzyl-6,6-dimethyl-1H-pyrano[2,3-f]indole-2-one (210 mg, 0.69 mmol) in chloroform-water mixed solution, sodium hydrogencarbonate (115 mg, 1.38 mmol) and m-chloroperbenzoic acid (237 mg, 1.38 mmol) were added, and the resulting mixture was stirred at room temperature for 3.5 hours. Sodium hydrogencarbonate aqueous solution and saturated sodium thiosulfate aqueous solution were added to the reaction solution, the resulting solution was extracted with chloroform, washed with saturated sodium chloride, dried over anhydrous sodium sulfate and concentrated. Phenethylamine (173 □L, 1.38 mmol), lithium perchlorate (73 mg, 0.69 mmol) and dioxane (1 mL) were added to the resulting residue, and the resulting mixture was stirred at 70° C. for 2 hours. Water was added to the reaction solution, and the resulting solution was extracted with ethyl acetate. The resulting organic phase was washed with saturated sodium hydrogencarbonate aqueous solution and then with saturated sodium chloride solution, dried over anhydrous sodium sulfate, concentrated, purified by silica gel column (hexane/ethyl acetate=1/1) and recrystallized with ethyl acetate to obtain the aimed product (2-step yield: 16%).

Pale pink crystal mp: 195° C. (decomposition)

$^1$H-NMR ($CDCl_3$) δ; 1.16(s, 3H), 1.45(s, 3H), 2.8-3.2(m, 4H), 3.51(s, 2H), 3.59(d, J=4.4 Hz, 1H), 3.73(m, 1H), 4.75(d, J=15.7 Hz, 1H), 4.84(d, J=15.7 Hz, 1H), 6.51(s, 1H), 6.73(s, 1H), 7.2-7.4(m, 10H).

MS ($ESI^+$) m/z; 443 $[M+1]^+$

MS ($ESI^-$) m/z; 441 $[M-1]^+$

Synthesis Example 91

8-(2-Cyclohexa-1,5-dienyl-ethylamino)-7-hydroxy-6,6-dimethyl-3,6,7,8-tetrahydro-1H-pyrano[2,3-f]indole-2-one

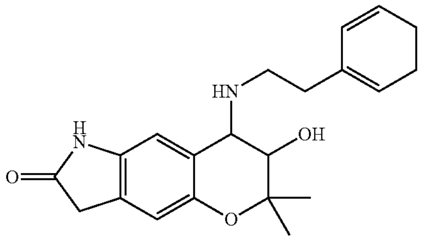

Under nitrogen stream, sodium (90 mg, 3.91 mmol) was added to liquid ammonia (5 mL) at −78° C., and the resulting mixture was stirred. A solution of 1-benzyl-7-hydroxy-6,6-dimethyl-8-phenetylamino-3,6,7,8-tetrahydro-1H-pyrano[2,3-f]indole-2-one (173 mg, 0.39 mmol) in THF (2 mL) was added dropwise at −45° C., and the resulting mixture was stirred for 15 minutes. Upon the completion of the reaction, saturated ammonium chloride aqueous solution was added thereto, the resulting solution was extracted with ethyl acetate. The resulting organic phase was washed with water and then with saturated sodium chloride solution, dried over anhydrous magnesium sulfate, concentrated and purified by silica gel column (ethyl acetate) to obtain the aimed product (yield: 19%).

White solid $^1$H-NMR ($CDCl_3$) δ; 1.21(s, 3H), 1.49(s, 3H), 2.27(t, J=6.9 Hz, 2H), 2.6-2.8(m, 4H), 2.82-3.02(m, 2H), 3.44(m, 2H), 3.63(d, J=4.4 Hz, 1H), 3.81(d, J=4.4 Hz, 1H), 5.54(s, 1H), 5.74(s, 2H), 6.72(s, 1H), 6.86(s, 1H), 8.78(s, 1H).

Preparation Examples

Preparation Example 1

Tablet

| | |
|---|---|
| A compound according to the invention | 10 g |
| Lactose | 260 g |
| Microcrystalline cellulose | 600 g |
| Corn starch | 350 g |
| Hydroxypropyl cellulose | 100 g |
| CMC—Ca | 150 g |
| Magnesium stearate | 30 g |
| Total weight | 1,500 g |

The aforementioned ingredients were mixed by a conventional method and then 10,000 sugar-coated tablets each containing 1 mg of the active ingredient per tablet were prepared.

Preparation Example 2

Capsule

| | |
|---|---|
| A compound according to the invention | 10 g |
| Lactose | 440 g |
| Microcrystalline cellulose | 1,000 g |
| Magnesium stearate | 50 g |
| Total weight | 1,500 g |

The aforementioned ingredients were mixed by a conventional method and then filled into gelatin capsules to prepare 10,000 capsules each containing 1 mg of the active ingredient per capsule.

Preparation Example 3

Soft Capsule

| | |
|---|---|
| A compound according to the invention | 10 g |
| PEG 400 | 479 g |
| Saturated fatty acid triglyceride | 1,500 g |
| Peppermint oil | 1 g |
| Polysorbate 80 | 10 g |
| Total weight | 2,000 g |

The aforementioned ingredients were mixed by a conventional method and then filled into No. 3 soft gelatin capsules to prepare 10,000 soft capsules each containing 1 mg of the active ingredient per capsule.

Preparation Example 4

Ointment

| | |
|---|---|
| A compound according to the invention | 1.0 g |
| Liquid paraffin | 10.0 g |
| Cetanol | 20.0 g |
| White vaseline | 68.4 g |
| Ethylparaben | 0.1 g |
| 1-menthol | 0.5 g |
| Total weight | 100.0 g |

The aforementioned ingredients were mixed by a conventional method to obtain 1% ointment.

Preparation Example 5

Suppository

| | |
|---|---|
| A compound according to the invention | 1 g |
| Witepsol H15* | 478 g |
| Witepsol W35* | 520 g |
| Polysorbate 80 | 1 g |
| Total weight | 1,000 g |

(*trade name for triglyceride type compounds)

The aforementioned ingredients were melt-mixed by a conventional method, poured into suppository containers and cooled to solidify, and 1,000 suppositories (1 g) each containing 1 mg of the active ingredient per suppository were prepared.

Preparation Example 6

Injection

| | |
|---|---|
| A compound according to the invention | 1 mg |
| Distilled water for injection | 5 mL |

It is used by dissolving when applied.

Pharmacological Test Example

Effects on the Effective Refractory Period

Method

Beagles were anesthetized with pentobarbital sodium and thoracotomy was done along the median line under a respirator and the incision was made on the pericardium to expose the heart. An electrocardiogram (ECG) was recorded using bipolar electrodes attached to the surface of the right atrial free wall, right atrial auricle, and right ventricular free wall. The vagal nerves were stimulated using an electrostimulation device with Nichrome wires inserted into the vagal nerves in the neck bilaterally. The conditions for electrostimulation to the vagal nerves were set such that the RR intervals on ECG were prolonged by about 100 msec compared with those before the stimulation was started.

Atrial and ventricular effective refractory periods were determined by S1-S2 extrastimulus technique at basic cycle length of 300 msec during bilateral vagal nerve stimulation, using programmable electric stimulator. A train of 10 basic stimuli (S1) was followed by a premature extrastimulus (S2) at 2 times diastolic threshold. The S1-S2 interval was successively decreased by 2 msec, and the effective refractory period was defined as the point at which S2 failed to produced a propagated response.

For evaluation of drug effects, the atrial and ventricular effective refractory periods were determined before drug administration, then respective compound was administrated intravenously at the dose of 0.3 mg/kg or 0.6 mg/kg, and the atrial and ventricular effective refractory periods were determined from 5 minutes after the administration.

The results were shown as the prolongation time on the atrial and ventricular effective refractory periods, i.e. [effective refractory period after drug administration]−[effective refractory period before drug administration] (msec).

Results

The compounds of the present invention exhibited the prolongation effect on the effective refractory period selective for atrium as shown in Table below.

TABLE

| Synthesis Example No. | Dose (mg/kg) (mg/kg) | Atrial Refractory Period (msec) |
|---|---|---|
| 2 | 0.6 | 21 |
| 4 | 0.6 | 30 |
| 6 | 0.6 | 20 |
| 7 | 0.6 | 25 |
| 8 | 0.6 | 23 |
| 14 | 0.3 | 27 |
| 18 | 0.3 | 27 |
| 19 | 0.3 | 26 |
| 23 | 0.3 | 22 |
| 24 | 0.3 | 23 |
| 25 | 0.3 | 27 |
| 26 | 0.3 | 24 |
| 27 | 0.3 | 32 |
| 41 | 0.3 | 31 |
| 47 | 0.3 | 24 |
| 48 | 0.3 | 23 |
| 52 | 0.3 | 28 |
| 53 | 0.3 | 30 |
| 58 | 0.3 | 28 |
| 59 | 0.3 | 22 |
| 60 | 0.3 | 22 |
| 61 | 0.3 | 20 |
| 63 | 0.3 | 23 |
| 69 | 0.3 | 37 |
| 71 | 0.3 | 31 |
| 73 | 0.3 | 31 |
| 74 | 0.6 | 25 |
| 77 | 0.3 | 25 |

EFFECTS OF THE INVENTION

The compounds according to the present invention exhibit the prolongation effect on the effective refractory period selective for atrium, thus can be used as an anti-atrial fibrillation agents and an supraventricular antiarrhythmic agent, and are useful as pharmaceuticals. Further, since the compounds according to the present invention have small influence on ventricle, they can contribute to safe treatments of aforementioned arrhythmic conditions.

The invention claimed is:

1. A benzopyran derivative of formula (I) or (II), or pharmaceutically acceptable salt thereof (I)

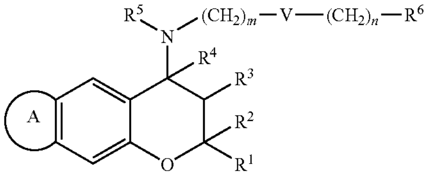

(II)

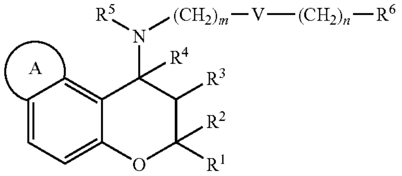

wherein $R^1$ and $R^2$ are independently of each other
(i) hydrogen atom,
(ii) $C_{1-6}$ alkyl group, wherein the alkyl group may be substituted with:
(1) halogen atom,
(2) $C_{1-6}$ alkoxy group wherein the alkoxy group may be substituted with halogen atom or
(3) hydroxy group, or
(iii) $C_{6-14}$ aryl group, wherein the aryl group may be substituted with:
(1) halogen atom,
(2) hydroxy group,
(3) nitro group,
(4) cyano group,
(5) $C_{1-6}$ alkyl group, wherein the alkyl group may be substituted with:

(a) halogen atom, (b) $C_{1-6}$ alkoxy group wherein the alkoxy group may be substituted with a halogen atom or (c) hydroxy group or (6) $C_{1-6}$ alkoxy group wherein the alkoxy group may be substituted with halogen atom;

$R^3$ is hydroxy group or $C_{1-6}$ alkylcarbonyloxy group, or $R^3$ forms a bond together with $R^4$;

$R^4$ is hydrogen atom, or $R^4$ forms a bond together with $R^3$;

m is an integer of 0 to 4;

n is an integer of 0 to 4;

V is a single bond, $CR^7$—R8 wherein $R^7$ is:

(i) $C_{1-6}$ alkyl group, wherein the alkyl group may be substituted with:

(1) halogen atom, (2) hydroxy group, (3) $C_{1-6}$ alkoxy group wherein the $C_{1-6}$ alkoxy group may be substituted with halogen atom, (4) $C_{6-14}$ aryl group or $C_{2-9}$ heteroaryl group, wherein each of the aryl group or heteroaryl group may be substituted with 1 to 3 $R^{10}$, wherein $R^{10}$ is (a) halogen atom;

(b) hydroxy group;

(c) $C_{1-6}$ alkyl group, wherein the alkyl group may be substituted with halogen atom, hydroxy group or $C_{1-6}$ alkoxy group, wherein the alkoxy group may be substituted with halogen atom;

(d) $C_{1-6}$ alkoxy group wherein the alkoxy group may be substituted with halogen atom;

(e) nitro group; cyano group; formyl group; formamide group; sulfonylamino group; sulfonyl group; amino group; $C_{1-6}$ alkylamino group; di-$C_{1-6}$ alkylamino group; $C_{1-6}$ alkylcarbonylamino group; $C_{1-6}$ alkylsulfonylamino group; aminocarbonyl group; $C_{1-6}$ alkylaminocarbonyl group; di-$C_{1-6}$ alkylaminocarbonyl group; $C_{1-6}$ alkylcarbonyl group; $C_{1-6}$ alkoxycarbonyl group; aminosulfonyl group; $C_{1-6}$ alkylsulfonyl group; carboxy group or $C_{6-14}$ arylcarbonyl group, and when a plurality of $R^{10}$ are present, they may be identical or different from each other;

(5) $C_{1-6}$ alkylcarbonyloxy group; nitro group; cyano group; formyl group; formamide group; amino group; $C_{1-6}$ alkylamino group; alkylamino group; $C_{1-6}$ alkylcarbonylamino group; $C_{1-6}$ alkylsulfonylamino group; aminocarbonyl group; $C_{1-6}$ alkylaminocarbonyl group; di-$C_{1-6}$alkylaminocarbonyl group; $C_{1-6}$ alkylcarbonyl group; $C_{1-6}$ alkoxycarbonyl group; aminosulfonyl group; $C_{1-6}$ alkylsulfonyl group; carboxy group or sulfonyl group;

(ii) $C_{6-14}$ aryl group or $C_{2-9}$ heteroaryl group, wherein each of the aryl group or heteroaryl group may be substituted with 1 to 3 $R^{10}$, wherein $R^{10}$ has the above-mentioned meaning;

(iii) hydroxy group;

(iv) $C_{1-6}$ alkoxy group, wherein the alkoxy group may be substituted with halogen atom; or (v) nitro group; cyano group; formyl group; formamide group; sulfonylamino group; sulfonyl group; amino group; $C_{1-6}$ alkylamino group; di-$C_{1-6}$ alkylamino group; $C_{1-6}$ alkylcarbonylamino group; $C_{1-6}$ alkylsulfonylamino group; aminocarbonyl group; $C_{1-6}$ alkylaminocarbonyl group; di-$C_{1-6}$ alkylaminocarbonyl group; $C_{1-6}$ alkylcarbonyl group; $C_{1-6}$ alkoxycarbonyl group; aminosulfonyl group; $C_{1-6}$ alkylsulfonyl group; carboxy group, (vi) $C_{6-14}$ arylcarbonyl group or $C_{2-9}$ heteroarylcarbonyl group, wherein each of the arylcarbonyl group or heteroarylcarbonyl group may be substituted with 1 to 3 $R^{10}$ wherein $R^{10}$ has the above-mentioned meaning, and wherein $R^8$ is:

(i) hydrogen atom, (ii) $C_{1-6}$ alkyl group, wherein the $C_{1-6}$ alkyl group may be substituted with:

(1) halogen atom, (2) hydroxy group, (3) $C_{1-6}$ alkoxy group, wherein the alkoxy group may be substituted with halogen atom, (4) $C_{6-14}$ aryl group of $C_{2-9}$ heteroaryl group, wherein each of the aryl group or heteroaryl group may be substituted with 1 to 3 $R^{17}$, wherein $R^{17}$ has the same meaning as $R^{10}$, (5) $C_{1-6}$ alkylcarbonyloxy group; nitro group; cyano group; formyl group; formamide group; amino group; $C_{1-6}$ alkylamino group; di-$C_{1-6}$ alkylamino group; $C_{1-6}$ alkylcarbonylamino group; $C_{1-6}$ alkylsulfonylamino group; aminocarbonyl group; $C_{1-6}$ alkylaminocarbonyl group; di-$C_{1-6}$ alkylaminocarbonyl group; $C_{1-6}$ alkylcarbonyl group; $C_{1-6}$ alkoxycarbonyl group; aminosulfonyl group; $C_{1-6}$ alkylsulfonyl group; carboxy group or sulfonyl group;

(iii) $C_{6-14}$ aryl group or $C_{2-9}$ heteroaryl group, wherein each of the aryl group or heteroaryl group may be substituted with 1 to 3 $R^{17}$, wherein $R^{17}$ has the same meaning as $R^{10}$;

(iv) hydroxy group;

(v) $C_{1-6}$ alkoxy group, wherein the alkoxy group may be substituted with halogen atom, or (vi) nitro group; cyano group; formyl group; formamide group; sulfonylamino group; sulfonyl group; amino group; $C_{1-6}$ alkylamino group; alkylamino group; $C_{1-6}$ alkylcarbonylamino group; $C_{1-6}$ alkylsulfonylamino group; aminocarbonyl group; $C_{1-6}$ alkylaminocarbonyl group; di-$C_{1-6}$ alkylaminocarbonyl group; $C_{1-6}$ alkylcarbonyl group; $C_{1-6}$ alkoxycarbonyl group; aminosulfonyl group; $C_{1-6}$ alkylsulfonyl group; carboxy group, $C_{6-14}$ arylcarbonyl group or $C_{2-9}$ heteroarylcarbonyl group, wherein each of the arylcarbonyl group or heteroarylcarbonyl group may be substituted with 1 to 3 $R^{17}$, wherein $R^{17}$ has the same meaning as $R^{10}$, or $R^7$ together with $R^8$ may represent ═O or ═S, or V is $NR^9$ wherein $R^9$ is (i) hydrogen atom, (ii) $C_{1-6}$ alkyl group, wherein the alkyl group may be substituted with:

(1) halogen atom, (2) $C_{1-6}$ alkoxy group, wherein the alkoxy group may be substituted with a halogen atom, (3) hydroxy group, (4) $C_{6-14}$ aryl group or $C_{2-9}$ heteroaryl group, wherein each of the aryl group or heteroaryl group may be substituted with 1 to 3 $R^{17}$, wherein $R^{17}$ has the same meaning as $R^{10}$, (5) $C_{1-6}$ alkylaminocarbonyl group, di-$C_{1-6}$ alkylaminocarbonyl group, $C_{1-6}$ alkylcarbonyl group, $C_{3-8}$ cycloalkylcarbonyl group, $C_{1-6}$ alkoxycarbonyl group, $C_{1-6}$ alkylsulfonyl group, carboxy group, $C_{6-14}$ arylsulfonyl group or $C_{2-9}$ heteroarylsulfonyl group, (iii) $C_{1-6}$ alkylaminocarbonyl group, di-$C_{1-6}$ alkylaminocarbonyl group, $C_{1-6}$ alkylcarbonyl group, $C_{3-8}$ cycloalkylcarbonyl group, $C_{1-6}$ alkoxycarbonyl group, $C_{1-6}$ alkylsulfonyl group, (iv) $C_{6-14}$ arylsulfonyl group or $C_{2-9}$ heteroarylsulfonyl group, wherein each of the arylsulfonyl group or heteroarylsulfonyl group may be substituted with 1 to 3 $R^{17}$, wherein $R^{17}$ has the same meaning as $R^{10}$, (v) carboxy group;

(vi) $C_{6-14}$ arylcarbonyl group or $C_{2-9}$ heteroarylcarbonyl group, wherein each of the arylcarbonyl group or heteroarylcarbonyl group may be substituted with 1 to 3 $R^{17}$, wherein $R^{17}$ has the same meaning as $R^{10}$;

(vii) or O, S, SO or $SO_2$;

$R^5$ is hydrogen atom or $C_{1-6}$ alkyl group, wherein the alkyl group may be substituted with (i) halogen atom, (ii) $C_{1-6}$ alkoxy group, wherein the alkoxy group may be substituted with halogen atom, or (iii) hydroxy group; and $R^6$ is (i) hydrogen atom, (ii) $C_{1-6}$ alkyl group, wherein the alkyl group may be substituted with:

(1) halogen atom, (2) $C_{1-6}$ alkoxy group, wherein the alkoxy group may be substituted with halogen atom, (3) amino group, (4) carboxy group or (5) hydroxy group, (iii) $C_{3-8}$ cycloalkyl group or $C_{3-8}$ cycloalkenyl group, wherein the cycloalkyl group or cycloalkenyl group may be substituted with:

(1) halogen atom, (2) $C_{1-6}$ alkyl group, wherein the alkyl group may be substituted with:

(a) halogen atom, (b) $C_{1-6}$ alkoxy group, wherein the alkoxy group may be substituted with halogen atom, (c) amino group, (d) carboxy group or (e) hydroxy group, (3) $C_{1-6}$ alkoxy group, wherein the alkoxy group may be substituted with halogen atom, (4) amino, (5) carboxy group or (6) hydroxy group, (iv) amino group, $C_{1-6}$ alkylamino group, di-$C_{1-6}$ alkylamino group, (v) $C_{6-14}$ arylamino group or $C_{2-9}$ heteroarylamino group, wherein each of the arylamino group or heteroarylamino group may be substituted with 1 to 3 $R^{18}$, wherein $R^{18}$ has the same meaning as $R^{10}$;

(v) $C_{6-14}$ aryl group or $C_{2-9}$ heteroaryl group, wherein each of the aryl group or heteroaryl group may be substituted with 1 to 3 $R^{18}$, wherein $R^{18}$ has the same meaning as $R^{10}$; or (vi) $C_{2-9}$ heterocyclyl group, wherein the heterocyclyl group may be substituted with:

(1) halogen atom, (2) $C_{1-6}$ alkyl group, wherein the alkyl group may be substituted with:

(a) halogen atom, (b) $C_{1-6}$ alkoxy group, wherein the alkoxy group may be substituted with halogen atom, (c) amino group, (d) carboxy group or (e) hydroxy group, (3) $C_{1-6}$ alkoxy group, wherein the alkoxy group may be substituted with halogen atom, (4) $C_{6-14}$ aryl group or $C_{2-9}$ heteroaryl group, wherein each of the aryl group or heteroaryl group may be substituted with 1 to 3 $R^{18}$, wherein $R^{18}$ has the same meaning as $R^{10}$, (5) hydroxy group, nitro group, cyano group, formyl group, formamide group, amino group, $C_{1-6}$ alkylamino group, di-$C_{1-6}$ alkylamino group, $C_{1-6}$ alkylcarbonylamino group, $C_{1-6}$ alkylsulfonylamino group, aminocarbonyl group, $C_{1-6}$ alkylaminocarbonyl group, di-$C_{1-6}$ alkylaminocarbonyl group, $C_{1-6}$ alkylcarbonyl group, $C_{1-6}$ alkoxycarbonyl group; aminosulfonyl group, $C_{1-6}$ alkylsulfonyl group, carboxy group or $C_{6-14}$ arylcarbonyl group;

A is:

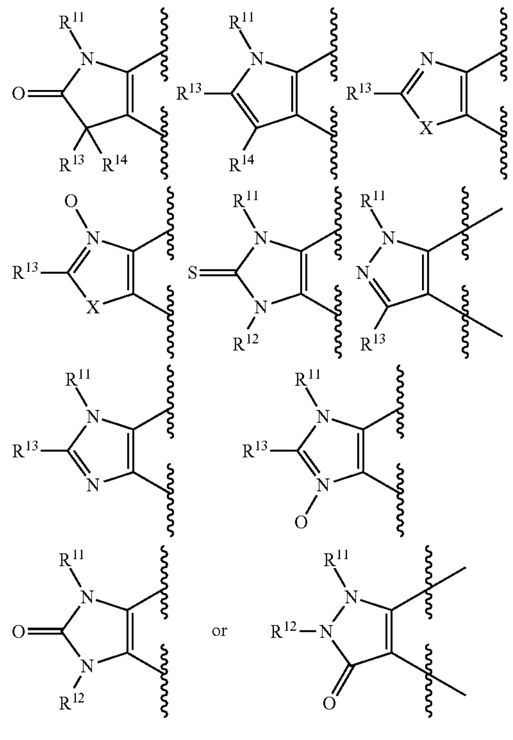

or wherein $R^{11}$ and $R^{12}$ are independently of each other:

(i) hydrogen atom, (ii) $C_{1-6}$ alkyl group, wherein the alkyl group may be substituted with:

(1) halogen atom, (2) $C_{1-6}$ alkoxy group, wherein the alkoxy group may be substituted with halogen atom, (3) hydroxy group, (4) $C_{6-14}$ aryl group or $C_{2-9}$ heteroaryl group, wherein each of the aryl group or heteroaryl group may be substituted with 1 to 3 $R^{19}$, wherein $R^{19}$ has the same meaning as $R^{10}$, (5) $C_{1-6}$ alkylaminocarbonyl group, di-$C_{1-6}$ alkylaminocarbonyl group, $C_{1-6}$ alkylcarbonyl group, $C_{3-8}$ cycloalkylcarbonyl group, $C_{1-6}$ alkoxycarbonyl group, $C_{1-6}$ alkylsulfonyl group, carboxy group, $C_{6-14}$ arylcarbonyl group or $C_{2-9}$ heteroarylcarbonyl group, (iii) $C_{6-14}$ aryl group or $C_{2-9}$ heteroaryl group, wherein each of the aryl group or heteroaryl group may be substituted with 1 to 3 $R^{19}$, wherein $R^{19}$ has the same meaning as $R^{10}$, (iv) $C_{1-6}$ alkylaminocarbonyl group, di-$C_{1-6}$ alkylaminocarbonyl group, $C_{1-6}$ alkylcarbonyl group, $C_{3-8}$ cycloalkylcarbonyl group, $C_{1-6}$ alkoxycarbonyl group, $C_{1-6}$ alkylsulfonyl group, (v) $C_{6-14}$ arylsulfonyl group or $C_{2-9}$ heteroarylsulfonyl group, wherein each of the arylsulfonyl group or heteroarylsulfonyl group may be substituted with 1 to 3 $R^{19}$ wherein $R^{19}$ has the same meaning as $R^{10}$, (vi) carboxy group;

(vii) $C_{6-14}$ arylcarbonyl group or $C_{2-9}$ heteroarylcarbonyl group, wherein each of the arylcarbonyl group or heteroarylcarbonyl group may be substituted with 1 to 3 $R^{19}$ wherein $R^{19}$ has the same meaning as $R^{10}$, $R^{13}$, $R^{14}$, $R^{15}$ and $R^{16}$ are, independently of each other, (i) hydrogen atom, (ii) halogen atom, (iii) $C_{1-6}$ alkyl group, wherein the alkyl group may be substituted with:

(1) halogen atom, (2) $C_{1-6}$ alkoxy group, wherein the alkoxy group may be substituted with halogen atom, (3) amino group, hydroxy group, (4) $C_{6-14}$ aryl group or $C_{2-9}$ heteroaryl group, wherein each of the aryl group or heteroaryl group may be substituted with 1 to 3 $R^{20}$, wherein $R^{20}$ has the same meaning as $R^{10}$, (5) $C_{1-6}$ alkylaminocarbonyl group, di-$C_{1-6}$ alkylaminocarbonyl group, $C_{1-6}$ alkylcarbonyl group, $C_{3-8}$ cycloalkylcarbonyl group, $C_{1-6}$ alkoxycarbonyl group, $C_{1-6}$ alkylsulfonyl group, carboxy group, $C_{6-14}$ arylcarbonyl group or $C_{2-9}$ heteroarylcarbonyl group, (iv) $C_{1-6}$ alkoxy group, wherein the alkoxy group may be arbitrarily substituted with halogen atom, (v) carboxy group, (vi) amino group, (vii) hydroxy group, (viii) $C_{6-14}$ aryl group or $C_{2-9}$ heteroaryl group, wherein each of the aryl group or heteroaryl group may be substituted with 1 to 3 $R^{20}$, wherein $R^{20}$ has the same meaning as $R^{10}$, (ix) $C_{1-6}$ thioalkoxy group, wherein the thioalkoxy group may be substituted with:

(1) halogen atom, (2) $C_{1-6}$ alkoxy group, wherein the alkoxy group may be substituted with halogen atom, (3) carboxy group, (4) hydroxy group, (5) $C_{6-14}$ aryl group or $C_{2-9}$ heteroaryl group, wherein each of the aryl group or heteroaryl group may be substituted with 1 to 3 $R^{20}$, wherein $R^{20}$ has the same meaning as $R^{10}$, (6) $C_{1-6}$ alkylcarbonyloxy group, nitro group, cyano group, formyl group, formamide group, amino group, sulfonyl group, $C_{1-6}$ alkylamino group, di-$C_{1-6}$ alkylamino group, (7) $C_{6-14}$ arylamino group or $C_{2-9}$ heteroarylamino group, wherein each of the arylamino group or heteroarylamino group may be substituted with 1 to 3 $R^{20}$, wherein $R^{20}$ has the same meaning as $R^{10}$, (8) $C_{1-6}$ alkylcarbonyloxyamino group, $C_{1-6}$ alkylsulfonylamino group, aminocarbonyl group, $C_{1-6}$ alkylaminocarbonyl group, di-$C_{1-6}$ alkylaminocarbonyl group, $C_{1-6}$ alkylcarbonyl group, (9) $C_{6-14}$ arylcarbonyl group or $C_{2-9}$ heteroarylcarbonyl group, wherein each of the arylcarbonyl group or heteroarylcarbonyl group may be substituted with 1 to 3 $R^{20}$, wherein $R^{20}$ has the same meaning as $R^{10}$,

(10) $C_{1-6}$ alkoxycarbonyl group, aminosulfonyl group, $C_{1-6}$ alkylsulfonyl group,

(11) $C_{6-14}$ arylsulfonyl group or $C_{2-9}$ heteroarylsulfonyl group, wherein each of the arylsulfonyl group or heteroarylsulfonyl group may be substituted with 1 to 3 $R^{20}$, wherein $R^{20}$ has the same meaning as $R^{10}$,

(12) carboxy group,

(13) sulfonyl group or

(14) $C_{2-9}$ heterocyclyl group, wherein the heterocyclyl group may be substituted with:

(a) halogen atom, (b) $C_{1-6}$ alkyl group, wherein the alkyl group may be substituted with:

(A) halogen atom, (B) $C_{1-6}$ alkoxy group, wherein the alkoxy group may be substituted with halogen atom, (C) amino group, (D) carboxy group or (E) hydroxy group), (c) $C_{1-6}$ alkoxy group, wherein the alkoxy group may be substituted with halogen atom, (d) $C_{6-14}$ aryl group or $C_{2-9}$ heteroaryl group, wherein each of the aryl group or heteroaryl group may be substituted with 1 to 3 $R^{20}$, wherein $R^{20}$ has the same meaning as $R^{10}$, (e) hydroxy group, nitro group, cyano group, formyl group, formamide group, amino group, $C_{1-6}$ alkylamino group, di-$C_{1-6}$ alkylamino group, $C_{1-6}$ alkylcarbonylamino group, $C_{1-6}$ alkylsulfonylamino group, aminocarbonyl group, $C_{1-6}$ alkylaminocarbonyl group, di-$C_{1-6}$ alkylaminocarbonyl group, $C_{1-6}$ alkylcarbonyl group, $C_{1-6}$ alkoxycarbonyl group, aminosulfonyl group, $C_{1-6}$ alkylsulfonyl group, carboxy group or $C_{6-14}$ arylcarbonyl group, and X is O, S, SO or $SO_2$.

2. The benzopyran derivative or pharmaceutically acceptable salt thereof according to claim 1, wherein $R^1$ and $R^2$ are methyl group, $R^3$ is hydroxy group, and $R^4$ is hydrogen atom.

3. The benzopyran derivative or pharmaceutically acceptable salt thereof according to claim 2, wherein $R^5$ is hydrogen atom, m is an integer of 0 to 3 and n is an integer of 0 to 2.

4. The benzopyran derivative or pharmaceutically acceptable salt thereof according to claim 3, wherein V is a single bond.

5. The benzopyran derivative or pharmaceutically acceptable salt thereof according to claim 4, wherein m is an integer of 1 to 3, n is 0, and $R^6$ is $C_{6-14}$ aryl group wherein the aryl group may be substituted with 1 to 3 $R^{18}$ wherein $R^{18}$ has the same meaning as $R^{13}$.

6. The benzopyran derivative or pharmaceutically acceptable salt thereof according to claim 5, wherein m is 2.

7. The benzopyran derivative or pharmaceutically acceptable salt thereof according to claim 6, wherein $R^6$ is $C_{6-14}$ aryl group wherein the aryl group may be substituted with 1 to 3 halogen atom or amino group, and when a plurality of substituents are present, they may be identical or different from each other.

8. The benzopyran derivative or pharmaceutically acceptable salt thereof according to claim 4, wherein m is an integer of 1 to 3, n is 0, and $R^6$ is $C_{2-9}$ heteroaryl group wherein the heteroaryl group may be substituted with 1 to 3 $R^{18}$ wherein $R^{18}$ has the same meaning as $R^{10}$.

9. The benzopyran derivative or pharmaceutically acceptable salt thereof according to claim 8, wherein m is 2.

10. The benzopyran derivative or pharmaceutically acceptable salt thereof according to claim 9, wherein $R^6$ is 2-pyridyl group, 3-pyridyl group or 4-pyridyl group.

11. The benzopyran derivative or pharmaceutically acceptable salt thereof according to claim 4, wherein m is an integer of 1 to 3, n is 0, and $R^6$ is:

(i) $C_{2-4}$ alkyl group, wherein the alkyl group may be substituted with:
(1) halogen atom,
(2) $C_{1-6}$ alkoxy group, wherein the alkoxy group may be substituted with halogen atom,
(3) amino group,
(4) carboxy group or
(5) hydroxy group,
(ii) $C_{1-6}$ alkoxy group, wherein the alkoxy group may be substituted with halogen atom,
(iii) amino group,
(iv) carboxy group,
(v) hydroxy group,
(vi) $C_{3-8}$ cycloalkyl group or $C_{3-8}$ cycloalkenyl group, wherein the cycloalkyl group or cycloalkenyl group may be substituted with:
(1) halogen atom,
(2) $C_{1-6}$ alkyl group, wherein the alkyl group may be substituted with:
(a) halogen atom,
(b) $C_{1-6}$ alkoxy group, wherein the alkoxy group may be substituted with halogen atom,
(c) amino group,
(d) carboxy group or
(e) hydroxy group
(3) $C_{1-6}$ alkoxy group wherein the alkoxy group may be substituted with halogen atom,
(4) amino group,
(5) carboxy group or
(6) hydroxy group,
(vii) or $C_{2-9}$ hetecyclyl group, wherein the heterocyclyl group may be substituted with:
(1) halogen atom,
(2) $C_{1-6}$ alkyl group, wherein the alkyl group may be substituted with:
(a) halogen atom,
(b) $C_{1-6}$ alkoxy group, wherein the alkoxy group may be substituted with halogen atom,
(c) amino group,
(d) carboxy group or
(e) hydroxy group,
(3) $C_{1-6}$ alkoxy group, wherein the alkoxy group may be substituted with halogen atom,
(4) hydroxy group or
(5) amino group.

12. The benzopyran derivative or pharmaceutically acceptable salt thereof according to claim 11, wherein m is 2.

13. The benzopyran derivative or pharmaceutically acceptable salt thereof according to claim 12, wherein $R^6$ is n-propyl group, i-propyl group, c-pentyl group, c-hexyl group, 1-c-pentenyl group, 2-c-pentenyl group, 3-c-pentenyl group, 1-c-hexenyl group, 2-c-hexenyl group or 3-c-hexenyl group.

14. The benzopyran derivative or pharmaceutically acceptable salt thereof according to claim 3, wherein V is $CR^7R^8$.

15. The benzopyran derivative or pharmaceutically acceptable salt thereof according to claim 14, wherein $R^7$ is:

(i) hydroxy group,
(ii) $C_{1-6}$ alkyl group, wherein the alkyl group may be substituted with;
(1) halogen atom,
(2) $C_{1-6}$ alkoxy group, wherein the alkoxy group may be substituted with halogen atom,
(3) amino group,
(4) carboxy group or
(5) hydroxy group,
(iii) $C_{1-6}$ alkoxy group, wherein the alkoxy group may be substituted with halogen atom,
(iv) $C_{1-6}$ alkylamino group,
(v) di-$C_{1-6}$ alkylamino group, or
(vi) carboxy group, and $R^8$ is hydrogen atom or $C_{1-6}$ alkyl group, wherein the alkyl group may be substituted with:

(i) halogen atom,
(ii) $C_{1-6}$ alkoxy group, wherein the alkoxy group may be substituted with halogen atom,
(iii) amino group,
(iv) carboxy group or
(v) hydroxy group, or $R^7$ and $R^8$ together are =O or =S.

16. The benzopyran derivative or pharmaceutically acceptable salt thereof according to claim 15, wherein $R^7$ is:

(i) hydroxy group,
(ii) $C_{1-6}$ alkyl group, wherein the alkyl group may be substituted with halogen atom, hydroxy group or carboxy group or
(iii) carboxy group, and $R^8$ is hydrogen atom or $C_{1-6}$ alkyl group, wherein the alkyl group may be substituted with halogen atom, hydroxy group or carboxy group, or $R^7$ and $R^8$ together are =O.

17. The benzopyran derivative or pharmaceutically acceptable salt thereof according to claim 16, wherein $R^7$ is hydroxy group, and $R^8$ is hydrogen atom.

18. The benzopyran derivative or pharmaceutically acceptable salt thereof according to claim 14, wherein m is an integer of 1 to 2, n is 0, and $R^6$ is $C_{6-14}$ aryl group or $C_{2-9}$ heteroaryl wherein each of the aryl group or heteroaryl group may be substituted with 1 to 3 $R^{18}$ wherein $R^{18}$ has the same meaning as $R^{10}$.

19. The benzopyran derivative or pharmaceutically acceptable salt thereof according to claim 18, wherein $R^7$ is:

(i) hydroxy group,
(ii) $C_{1-6}$ alkyl group, wherein the alkyl group may be substituted with:
(1) halogen atom,
(2) $C_{1-6}$ alkoxy group, wherein the alkoxy group may be substituted with halogen atom,
(3) amino group,
(4) carboxy group or
(5) hydroxy group,
(iv) $C_{1-6}$ alkoxy group, wherein the alkoxy group may be substituted with halogen atom,
(v) $C_{1-6}$ alkylamino group,
(vi) di-$C_{1-6}$ alkylamino group, or
(vii) carboxy group, and $R^8$ is hydrogen atom or $C_{1-6}$ alkyl group, wherein the alkyl group may be substituted with:
(i) halogen atom,
(ii) $C_{1-6}$ alkoxy group, wherein the alkoxy group may be substituted with halogen atom,
(iii) amino group,
(iv) carboxy group or
(v) hydroxy group, or
$R^7$ and $R^8$ together are =O or =S.

20. The benzopyran derivative or pharmaceutically acceptable salt thereof according to claim 19, wherein $R^7$ is:
(i) hydroxy group,
(ii) $C_{1-6}$ alkyl group, wherein the alkyl group may be substituted with halogen atom, hydroxy group or carboxy group or
(iii) carboxy group, and
$R^8$ is hydrogen atom or $C_{1-6}$ alkyl group, wherein the alkyl group may be substituted with halogen atom, hydroxy group or carboxy group, or $R^7$ and $R^8$ together are =O.

21. The benzopyran derivative or pharmaceutically acceptable salt thereof according to claim 20, wherein $R^7$ is hydroxy group, and $R^8$ is hydrogen atom.

22. The benzopyran derivative or pharmaceutically acceptable salt thereof according to claim 21, wherein m is 1, n is 0, and $R^6$ is $C_{6-14}$ aryl group, wherein the aryl group may be substituted with 1 to 3 halogen atom or amino group, and when a plurality of substituents are present, they may be identical or different from each other.

23. The benzopyran derivative or pharmaceutically acceptable salt thereof according to claim 14, wherein m is an integer of 1 to 2, n is 0, and $R^6$ is:
(i) $C_{1-4}$ alkyl group, wherein the alkyl group may be substituted with;
(1) halogen atom,
(2) $C_{1-6}$ alkoxy group, wherein the alkoxy group may be substituted with halogen atom,
(3) amino group,
(4) carboxy group or
(5) hydroxy group,
(ii) $C_{3-8}$ cycloalkyl group or $C_{3-8}$ cycloalkenyl group, wherein the cycloalkyl group or cycloalkenyl group may be substituted with:
(1) halogen atom,
(2) $C_{1-6}$ alkyl group (wherein the alkyl group may be substituted with:
(a) halogen atom,
(b) $C_{1-6}$ alkoxy group, wherein the alkoxy group may be substituted with halogen atom,
(c) amino group,
(d) carboxy group or
(e) hydroxy group,
(3) $C_{1-6}$ alkoxy group, wherein the alkoxy group may be substituted with halogen atom,
(3) amino group,
(4) carboxy group or
(5) hydroxy group, or
(iii) $C_{2-9}$ heterocyclyl group, wherein the heterocyclyl group may be substituted with:
(1) halogen atom,
(2) $C_{1-6}$ alkyl group, wherein the alkyl group may be substituted with:
(a) halogen atom,
(b) $C_{1-6}$ alkoxy group, wherein the alkoxy group may be substituted with halogen atom,
(c) amino group,
(d) carboxy group or hydroxy group,
(3) $C_{1-6}$ alkoxy group, wherein the alkoxy group may be substituted with halogen atom,
(4) amino group,
(5) carboxy group or
(6) hydroxy group.

24. The benzopyran derivative or pharmaceutically acceptable salt thereof according to claim 23, wherein $R^7$ is;
(i) hydroxy group,
(ii) $C_{1-6}$ alkyl group, wherein the alkyl group may be substituted with:
(1) halogen atom,
(2) $C_{1-6}$ alkoxy group, wherein $C_{1-6}$ alkoxy group may be substituted with halogen atom,
(3) amino group,
(4) carboxy group or
(5) hydroxy group,
(iii) $C_{1-6}$ alkoxy group, wherein $C_{1-6}$ alkoxy group may be substituted with halogen atom,
(iv) $C_{1-6}$ alkylamino group,
(v) di-$C_{1-6}$ alkylamino group, or
(vi) carboxy group, and
$R^8$ is
(i) hydrogen atom or
(ii) $C_{1-6}$ alkyl group, wherein the alkyl group may be substituted with:
(iii) halogen atom,
(iv) $C_{1-6}$ alkoxy group, wherein $C_{1-6}$ alkoxy group may be substituted with halogen atom,
(v) amino group,
(vi) carboxy group or
(vii) hydroxy group), or
$R^7$ and $R^8$ together are =O or =S.

25. The benzopyran derivative or pharmaceutically acceptable salt thereof according to claim 24, wherein $R^7$ is:
(i) hydroxy group,
(ii) $C_{1-6}$ alkyl group, wherein the alkyl group may be substituted with:
(1) halogen atom,
(2) hydroxy group or
(3) carboxy group) or
(iii) carboxy group, and
$R^8$ is hydrogen atom or $C_{1-6}$ alkyl group, wherein the alkyl group may be substituted with halogen atom, hydroxy group or carboxy group, or $R^7$ and $R^8$ together are =O.

26. The benzopyran derivative or pharmaceutically acceptable salt thereof according to claim 25, wherein $R^7$ is hydroxy group, and $R^8$ is hydrogen atom.

27. The benzopyran derivative or pharmaceutically acceptable salt thereof according to claim 26, wherein $R^6$ is n-propyl group, i-propyl group, c-pentyl group, c-hexyl group, 1-c-pentenyl group, 2-c-pentenyl group, 3-c-pentenyl group, 1-c-hexenyl group, 2-c-hexenyl group or 3-c-hexenyl group.

28. The benzopyran derivative or pharmaceutically acceptable salt thereof according to claim 14, wherein $R^7$ and $R^8$ together are =O or =S, and $R^6$ is:
(i) amino group,
(ii) $C_{1-6}$ alkylamino group,
(iii) di-$C_{1-6}$ alkylamino group,
(iv) $C_{6-14}$ arylamino group or $C_{2-9}$ heteroarylamino group, wherein each of the arylamino group or heteroarylamino group may be substituted with:
(1) 1 to 3 $R^{18}$, wherein $R^{18}$ has the same meaning as $R^{10}$, or
(2) $C_{2-9}$ heterocyclyl group, wherein the heterocyclyl group may be substituted with:
(a) halogen atom, (b) $C_{1-6}$ alkyl group, wherein the alkyl group may be substituted with:
(A) halogen atom,
(B) $C_{1-6}$ alkoxy group, wherein the alkoxy group may be substituted with halogen atom,
(C) amino group,
(D) carboxy group or
(E) hydroxy group),
(c) $C_{1-6}$ alkoxy group, wherein the alkoxy group may be substituted with halogen atom,
(d) amino group,
(e) carboxy group or
(f) hydroxy group.

29. The benzopyran derivative or pharmaceutically acceptable salt thereof according to claim 3, wherein V is $NR^9$.

30. The benzopyran derivative or pharmaceutically acceptable salt thereof according to claim 29, wherein m is an integer of 1 to 3, n is 0, and $R^6$ is $C_{6-14}$ aryl group or $C_{2-9}$ heteroaryl group, wherein each of the aryl group or heteroaryl group may be substituted with 1 to 3 $R^{18}$, wherein $R^{18}$ has the same meaning as $R^{10}$.

31. The benzopyran derivative or pharmaceutically acceptable salt thereof according to claim 30, wherein m is 2.

32. The benzopyran derivative or pharmaceutically acceptable salt thereof according to claim 29, wherein m is an integer of 1 to 3, n is 0 and $R^6$ is:
(i) hydrogen atom,
(ii) $C_{2-4}$ alkyl group, wherein the alkyl group may be substituted with:
(1) halogen atom,
(2) $C_{1-6}$ alkoxy group, wherein the alkoxy group may be substituted with halogen atom,
(3) amino group,
(4) carboxy group or
(5) hydroxy group,
(iii) $C_{3-8}$ cycloalkyl group or $C_{3-8}$ cycloalkenyl group, wherein the cycloalkyl group or cycloalkenyl group may be substituted with:
(1) halogen atom,
(2) $C_{1-6}$ alkyl group, wherein the alkyl group may be substituted with:
(a) halogen atom,
(b) $C_{1-6}$ alkoxy group, wherein the alkoxy group may be substituted with halogen atom,
(c) amino group,
(d) carboxy group or
(e) hydroxy group,
(3) $C_{1-6}$ alkoxy group, wherein the alkoxy group may be substituted with halogen atom,
(4) amino,
(5) carboxy group or
(6) hydroxy group, or
(iv) $C_{2-9}$ hetecyclyl group, wherein the heterocyclyl may be substituted with:
(1) halogen atom,
(2) $C_{1-6}$ alkyl group, wherein the alkyl group may be substituted with:
(a) halogen atom,
(b) $C_{1-6}$ alkoxy group, wherein the alkoxy group may be substituted with halogen atom,
(c) amino group,
(d) carboxy group or
(e) hydroxy group),
(3) $C_{1-6}$ alkoxy group, wherein the alkoxy group may be substituted with halogen atom,
(4) amino group,
(5) carboxy group or
(6) hydroxy group.

33. The benzopyran derivative or pharmaceutically acceptable salt thereof according to claim 32, wherein m is 2.

34. The benzopyran derivative or pharmaceutically acceptable salt thereof according to claim 2, which is the compound of formula (I).

35. The benzopyran derivative or pharmaceutically acceptable salt thereof according to claim 2, which is the compound of formula (II).

36. The benzopyran derivative or pharmaceutically acceptable salt thereof according to claim 7, wherein the ring structure of A is

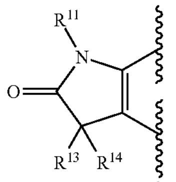
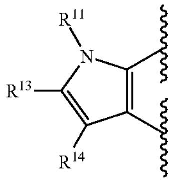
or
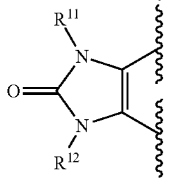

wherein $R^{11}$, $R^{12}$, $R^{13}$ and $R^{14}$ have the above-mentioned meanings.

37. The benzopyran derivative or pharmaceutically acceptable salt thereof according to claim 36, wherein $R^{11}$ and $R^{12}$ are independently of each other:
(i) hydrogen atom or
(ii) $C_{1-6}$ alkyl group, wherein the alkyl group may be substituted with:
(1) halogen atom,
(2) $C_{1-6}$ alkoxy group, wherein the alkoxy group may be substituted with halogen atom,
(3) $C_{1-6}$ aryl group, wherein the aryl group may be substituted with:
(a) halogen atom,
(b) hydroxy group or
(c) $C_{1-6}$ alkoxy group, wherein the alkoxy group may be substituted with halogen atom,
(iii) amino group or
(iv) hydroxy group, and
$R^{13}$ and $R^{14}$ are independently of each other:
(i) hydrogen atom,
(ii) halogen atom,
(iii) $C_{1-6}$ alkyl group, wherein the alkyl group may be substituted with:
(1) halogen atom,
(2) amino group,
(3) $C_{1-6}$ alkoxy group, wherein the alkoxy group may be substituted with halogen atom or
(4) hydroxy group,
(iv) $C_{1-6}$ alkoxy group, wherein the alkoxy group may be substituted with;
(1) halogen atom,
(2) amino group,
(3) $C_{1-6}$ alkoxy group, wherein the alkoxy group may be substituted with halogen atom, or
(4) hydroxy group, (v) amino group or (vi) cyano group.

38. The benzopyran derivative or pharmaceutically acceptable salt thereof according to claim 37, wherein $R^{11}$ and $R^{12}$ are independently of each other hydrogen atom or $C_{1-6}$ alkyl group, wherein the alkyl group may be substituted with halogen atom, amino group or hydroxy group, and $R^{13}$ and $R^{14}$ are hydrogen atom.

39. A pharmaceutical for treating arrhythmia comprising the benzopyran derivative or pharmaceutically acceptable salt thereof according to claim 1 as an active ingredient.

40. A method for treating arrhythmia comprising the step of administering to a patient an effective dose of a pharmaceutical compound, wherein the pharmaceutical compound comprises the benzopyran derivative or pharmaceutically acceptable salt thereof according to claim 1.

* * * * *